(12) United States Patent
Chrovian et al.

(10) Patent No.: US 9,963,447 B2
(45) Date of Patent: May 8, 2018

(54) SUBSTITUTED 4-AZAINDOLES AND THEIR USE AS GLUN2B RECEPTOR MODULATORS

(71) Applicant: JANSSEN PHARMACEUTICA NV, Beerse (BE)

(72) Inventors: Christa C. Chrovian, La Jolla, CA (US); Michael A. Letavic, San Diego, CA (US); Jason C. Rech, San Diego, CA (US); Akinola Soyode-Johnson, San Diego, CA (US); Jessica L. Wall, San Diego, CA (US)

(73) Assignee: Janssen Pharmaceutica NV (BE)

( * ) Notice: Subject to any disclaimer, the term of this patent is extended or adjusted under 35 U.S.C. 154(b) by 0 days. days.

(21) Appl. No.: 15/205,632

(22) Filed: Jul. 8, 2016

(65) Prior Publication Data
US 2017/0008890 A1  Jan. 12, 2017

Related U.S. Application Data

(60) Provisional application No. 62/190,416, filed on Jul. 9, 2015.

(51) Int. Cl.
C07D 471/04 (2006.01)
(52) U.S. Cl.
CPC .................. C07D 471/04 (2013.01)
(58) Field of Classification Search
CPC .................................... C07D 471/04
USPC .................................... 514/210.18
See application file for complete search history.

(56) References Cited

U.S. PATENT DOCUMENTS

| | | |
|---|---|---|
| 2007/0275965 A1 | 11/2007 | Thomas et al. |
| 2008/0300239 A1 | 12/2008 | Adams et al. |
| 2014/0275011 A1* | 9/2014 | Mastracchio ........ C07D 401/04 514/210.18 |

FOREIGN PATENT DOCUMENTS

| | | |
|---|---|---|
| EP | 2194045 A1 | 6/2010 |
| WO | WO 03/082868 A1 | 10/2003 |
| WO | WO 2005/080379 | 9/2005 |
| WO | 2008145616 A1 | 12/2008 |
| WO | WO 2009/05821 A1 | 5/2009 |
| WO | 2009118187 A1 | 10/2009 |
| WO | WO 2010/043396 A1 | 4/2010 |
| WO | 2013130855 A1 | 9/2013 |
| WO | WO 2014/124651 A1 | 8/2014 |
| WO | WO 2016/025917 | 2/2016 |

OTHER PUBLICATIONS

M. H. Buonarati et. al.: "Role of Sulfation and Acetylation in the Activation of2-Hydroxyamino-L-Methyl-6-Phenyl-Imidazo[4,5-B]Pyridine to Intermeidates Which Bind DNA", Mutation Research, Vol. 245, Sep. 1, 1990 (Sep. 1, 1990), pp. 185-190.
International Search Report and Written Opinion for International Application No. PCT/US2016/041339 Mailed September 27, 2016.
Addy et al., "Single-Dose Administration of MK-0657, an NR2B-Selective NMDA Antagonist, Does Not Result in Clinically Meaningful Improvement in Motor Function in Patients With Moderate Parkinson's Disease.", J. Clin. Pharmacal., 2009, pp. 856-864, vol. 49(7).
Arnold et al., "Glutamate receptor gene (GRIN2B) associated with reduced anterior cingulate glutamatergic concentration in pediatric obsessive-compulsive disorder.", Psychiatry Research: Neuroimaging, 2009, pp. 136-139, vol. 172(2).
Bagshawe, K.D., "Antibody-Directed Enzyme Prodrug Therapy: A Review.", Drug Dev. Research, 1995, pp. 220-230, vol. 34.
Berberich et al., "The role of NMDAR subtypes and charge transfer during hippocampal LTP induction.", Neuropharmacology, 2007, pp. 77-76, vol. 52(1).
Berge et al., "Pharmaceutical Salts.", J. Pharm. Sci., 1977, pp. 1-19, vol. 66(1).
Bertolini et al., "A New Rational Hypothesis for the Pharmacophore of the Active Metabolite of Leflunomide, a Potent Immunosuppressive Drug,", J Med Chem.,1997, pp. 2011-2016, vol. 40.
Bodor, N., "Novel Approaches to the Design of Safer Drugs: Soft Drugs and Site-Specific Chemical Delivery Systems.", Adv. Drug Res., 1984, pp. 255-331, vol. 13.
Bullock et al., "An Open-Label Study of CP-101,606 in Subjects with a Severe Traumatic Head Injury or Spontaneous Intracerebral Hemorrhage.", Annals New York Academy of Sciences, 1999, pp. 51-58, vol. 890.
Cull-Candy et al., "NMDA receptor subunits: diversity, development and disease.", Current Opin. Neurobiol., 2001, pp. 327-335, vol. 11(3).
Dalmau et al., "Anti-NMDA-receptor encephalitis: case series and analysis of the effects of antibodies.", Lancet Neural., Dec. 2008, pp. 1091-1098, vol. 7(12).
Dorval et al., "Association of the glutamate receptor subunit gene GRIN2B with attention-deficit/hyperactivity disorder.", Genes Brain Behav., 2007, pp. 444-452, vol. 6(5).
Duty, S., "Targeting Glutamate Receptors to Tackle the Pathogenesis, Clinical Symptoms and Levodopa-Induced Dyskinesia Associated with Parkinson's Disease.", CNS Drugs, 2012, pp. 1017-1032, vol. 26 (12).
Farjam et al., "Inhibition of NR2B-Containing N-methyl-D-Aspartate Receptors (NMDARs) in Experimental Autoimmune Encephalomyelitis, a Model of Multiple Sclerosis", Iranian Journal of Pharmaceutical Research, 2014, pp. 695-705, vol. 13(2).
Fleisher et al., "Improved oral drug delivery: solubility limitations overcome by the use of prodrugs.", Adv. Drug Delivery Rev., 1996, pp. 115-130, vol. 19.
Fuller et al., "Differential expression of the NMDA NR2B receptor subunit in motoneuron populations susceptible and resistant to amyotrophic lateral sclerosis.", Neuroscience Letters, 2006, pp. 157-161, vol. 399(1-2).
Grasselli et al., "Abnormal NMDA receptor function exacerbates experimental autoimmune encephalomyelitis.", British Journal of Pharmacology, 2013, pp. 502-517, vol. 168(2).

(Continued)

Primary Examiner — Yong Chu

(57) ABSTRACT

Substituted 4-azaindoles as NR2B receptor ligands. Such compounds may be used in NR2B receptor modulation and in pharmaceutical compositions and methods for the treatment of disease states, disorders, and conditions mediated by NR2B receptor activity.

26 Claims, No Drawings

(56) References Cited

OTHER PUBLICATIONS

Grimwood et al., "NR2B-containing NMDA receptors are up-regulated in temporal cortex in schizophrenia.", *NeuroReport*, 1999, pp. 461-465, vol. 10(3).
Guitton et al., "Blockade of Cochlear NMDA Receptors Prevents Long-Term Tinnitus during a Brief Consolidation Window after Acoustic Trauma.", *Neural Plasticity*, 2007, pp. 1-11, vol. 2007.
Haller et al., "NR2B subunit-specific NMDA antagonist Ro25-6981 inhibits the expression of conditioned fear: a comparison with the NMDA antagonist MK-801 and fluoxetine.", *Behavioural Pharmacology*, 2011, pp. 113-121, vol. 22(2).
Hanson et al., "Altered GluN2B NMDA receptor function and synaptic plasticity during early pathology in the PS2APP mouse model of Alzheimer's disease.", *Neurobiology of Diseases*, 2015, pp. 254-262, vol. 74.
Hu et al., "Expression of immediate-early genes in the dorsal cochlear nucleus in salicylate-induced tinnitus.", *Otology*, 2016, pp. 325-332, vol. 273(2).
Kowal et al., "Human lupus autoantibodies against NMDA receptors mediate cognitive impairment.", *Proc. Natl. Acad. Sci.*, Dec. 26, 2006, pp. 19854-19859, vol. 103(52).
Leaderbrand et al., "Co-activation of NR2A and NR2B subunits induces resistance to fear extinction.", *Neurobiology Learn Mem.*, 2014, pp. 1-16, vol. 113.
Leaver et al., "Neuroprotective Effects of a Selective N-Methyl-D-Aspartate NR2B Receptor Antagonist in the 6-Hydroxydopamine Rat Model of Parkinson's Rats.", Clin. Exp. *Pharmaca. Physiol.*, 2008; pp. 1388-1394, vol. 35(11).
Li et al., "Enhanced Striatal NR2B-Containing N-Methyl-D-Aspartate Receptor-Mediated Synaptic Currents in a Mouse Model of Huntington Disease.", *J. Neurophysiol.*, 2004, pp. 2738-2746, vol. 92(5).
Li et al., "Glutamate N-methyl-D-aspartate Receptor Antagonists Rapidly Reverse Behavioral and Synaptic Deficits Caused by Chronic Stress Exposure.", *Biol. Psychiatry*, 2011, pp. 754-761, vol. 69(8).
Li et al., "Soluble $\alpha\beta$ Oligomers Inhibit Long-Term Potentiation through a Mechanism Involving Excessive Activation of Extrasynaptic NR2B—Containing NMDA Receptors.", *Journal of Neuroscience*, May 4, 2011, pp. 6627-6238, vol. 31(18).
Lima-Ojeda et al., "Pharmacological blockade of GluN2B-containing NMDA receptors induces antidepressant-like effects lacking psychotomimetic action and neurotoxicity in the perinatal and adult rodent brain.", *Progress in Neuro-Psychopharmacology & Biological Psychiatry*, 2013, pp. 28-33, vol. 45.
Martucci et al., "N-methyl-D-aspartate receptor NR2B subunit gene GRIN2B in schizophrenia and bipolar disorder: Polymorphisms and mRNA levels.", *Schizophrenia Research*, 2006, pp. 214-221, vol. 84(2-3).
Massey et al., "Differential Roles of NR2A and NR2B—Containing NMDA Receptors in Cortical Long-Term Potentiation and Long-Term Depression.", *Journal of Neuroscience*, Sep. 8, 2004, pp. 7821-7828, vol. 24(36).
Miller et al., "GluN2B—containing NMDA receptors regulate depression-like behavior and are critical for the rapid antidepressant actions of ketamine.", *eLife*, 2014, pp. 1-22, vol. 3:e03581.
Morissette et al., "Prevention of Levodopa-Induced Dyskinesias by a Selective NR1A/2B N-Methyl-D-aspartate Receptor Antagonist in Parkinsonian Monkeys: Implication of Preproenkephalin.", *Movement Disorders*, 2006, pp. 9-17, vol. 21(1).
Nagy, J., The NR2B Subtype of NMDA Receptor: A Potential Target for the Treatment of Alcohol Dependence., *Current Drug Targets—CNS Neurological Disorders*, 2004, pp. 169-179, vol. 3(3).
Naskar et al., "Saving the Nerve from Glaucoma: Memantine to Caspaces.", *Seminars in Ophthalmology*, Sep. 1999, pp. 152-158, vol. 14(3).
Naspolini et al., "Traxoprodil decreases pentylenetetrazol-induced seizures.", *Epilepsy Research*, 2012, pp. 12-19, vol. 100(1-2).
Nutt et al., "Effects of a NR2B Selective NMDA Glutamate Antagonist, CP-101,606, on Dyskinesia and Parkinsonism.", *Movement Disorders*, 2008, pp. 1860-1866, vol. 23(13).
Orgogozo et al., "Efficacy and Safety of Memantine in Patients With Mild to Moderate Vascular Dementia. A Randomized, Placebo-Controlled Trial (MMM 300).", *Stroke*, 2002, pp. 1834-1839, vol. 33.
Paoletti et al., "NMDA receptor subunit diversity: impact on receptor properties, synaptic plasticity and disease.", *Nature Reviews Neuroscience*, Jun. 2013, pp. 383-400, vol. 14(6).
Paulekuhn et al., "Trends in Active Pharmaceutical Ingredient Salt Selection based on Analysis of the Orange Book Database.", *J. Med. Chem.*, 2007, pp. 6665-6671, vol. 50.
Peeters et al., "Effects of Pan- and Subtype-Selective N-Methyl-D-aspartate Receptor Antagonists on Cortical Spreading Depression in the Rat: Therapeutic Potential for Migraine.", *J. Pharmacal. Exp. Ther.*, 2007, pp. 564-572, vol. 321(2).
Preskorn et al., "An Innovative Design to Establish Proof of Concept of the Antidepressant Effects of the NR2B Subunit Selective N-Methyl-D-Aspartate Antagonist CP-101,606, in Patients With Treatment-Refractory Major Depressive Disorder.", *J. Clinical Psychopharmacalogy*, 2008, pp. 631-637, vol. 28(6).
Robinson et al., "Discovery of the Hemifumarate and ($\alpha$-L-Alanyloxy)methyl Ether as Prodrugs of an Antirheumatic Oxindole: Prodrugs for the Enolic OH Group.", *J. Med. Chem.*, 1996, pp. 10-18, vol. 39 (1).
Shan et al., "Prodrug Strategies Based on Intramolecular Cyclization Reactions.", *Journal of Pharmaceutical Sciences*, Jul. 1997, pp. 765-767, vol. 86 (7).
Shen et al., "Heroin relapse requires long-term potentiation-like plasticity mediated by NMDA2b-containing receptors.", *Proc. Natl. Acad. Sc.*, Nov. 29, 2011, pp. 19407-19412, vol. 108(48).
Starck et al., "Drug therapy for acquired pendular nystagmus in multiple sclerosis.", *J. Neurol.*, 1997, pp. 9-16, vol. 244(1).
Steece-Collier et al., "Antiparkinsonian Actions of CP-101,606, an Antagonist of NR2B Subunit-Containing N-Methyl-D-Aspartate Receptors.", *Experimental Neurology*, 2000, pp. 239-243, vol. 163(1).
Straube A., "Pharmacology of vertigo/nystagmus/oscillopsia.", *Current Opinion in Neurology*, 2005, pp. 11-14, vol. 18(1).
Tang et al., "Disturbed $Ca^{2+}$ signaling and apoptosis of medium spiny neurons in Huntington's disease.", *Proc. Natl. Acad. Sci.*, Feb. 15, 2005, pp. 2602-2607, vol. 102(7).
Tang et al., "Genetic enhancement of learning and memory in mice.", *Nature*, Sep. 2, 1999, pp. 63-69, vol. 401.
Traynelis et al., "Glutamate Receptor Ion Channels: Structure, Regulation, and Function.", *Pharmacological Reviews*, 2010, pp. 405-409, vol. 62(3).
Wang et al., "Targeting the NMDA receptor subunit NR2B for treating or preventing age-related memory decline.", *Expert Opinion on Therapeutic Targets*, Aug. 24, 2014, pp. 1121-1130, vol. 18(10).
Watanabe et al., "Distinct Distributions of Five N-Methyl-D-Aspartate Receptor Channel Subunit mRNAs in the Forebrain.", *J. Camp. Neural.*, 1993, pp. 377-390, vol. 338(3).
Weickert et al., "Molecular evidence of N-Methyl-D-Aspartate Receptor hypofunction in schizophrenia.", *Molecular Psychiatry*, 2013, pp. 1185-1192, vol. 18.
Won et al., "Autistic-like social behaviour in *Shank2*-mutant mice improved by restoring NMDA receptor function.", *Nature*, Jun. 14, 2012, pp. 261-265, vol. 486.
Wu, L.J. and Zhuo, M., "Targeting the NMDA Receptor Subunit NR2B for the Treatment of Neuropathic Pain.", *Neurotherapeutics*, Oct. 2009, pp. 693-702, vol. 6(4).
Yang et al., "Reduced brain infarct volume and improved neurological outcome by inhibition of the NR2B subunit of NMDA receptors by using CP101,606-27 alone and in combination with rt-PA in a thromboembolic stroke model in rats.", *J. Neurosurg.*, 2003, pp. 397-403, vol. 98(2).
Yuan et al., "Context-Dependent GluN2B—Selective Inhibitors of NMDA Receptor Function Are Neuroprotective with Minimal Side Effects.", *Neuron*, Mar. 18, 2015; pp. 1305-1318, vol. 85(6).

(56) References Cited

OTHER PUBLICATIONS

Zarate et al., "A Randomized Trial of an N-methyl-D-aspartate Antagonist in Treatment-Resistant Major Depression.", *Arch. Gen. Psychiatry*, Aug. 2006, pp. 856-864, vol. 63(8).
STN Registry database entry for CAS RN 1394745-67-5, Entered STN Sep. 18, 2012, Accessed Sep. 8, 2017.
Ito, et al., "A Medium-term Rat Liver Bioassay For Rapid In Vivo Detection of Carcinogenic Potential of Chemicals" Cancer Science, vol. 94(1), pp. 3-8, 2003.
Berge, et al, Pharmaceutical Salts, Journal of Pharmaceutical Sciences, 1977, pp. 1-19, vol. 66 Issue 1.
Chattopadhyay, et al., Fused Tetrazoles as Azide Surrogates in Click Reaction: Efficient Synthesis of N-Heterocycle-Substituted 1,2,3-Triazoles, Organic Letters, Mar. 30, 2010, pp. 2166-2169, vol. 12 Issue 9.
Glenn D. Considine., Van Nostrand's Encyclopedia of Chemistry, Encyclopedia of Chemistry, 2005, pp. 261, Chapter 5.
Kolb, et al., Click Chemistry: Diverse Chemical Function from a Few Good Reactions, Angew. Chem. Int. Ed, 2001, pp. 2004-2021, vol. 40.
Leyva, et al., Photochemistry of Fluorinated Aryl Azides in Toluene Solution and in Frozen Poiycrystals, J. Org. Chem, May 8, 1989, pp. 5938-5945, vol. 54 Issue 25, American Chemical Society.
Porsolt, Etal., Behavioural Despair in Mice: A Primary Screening Test for Antidepressants, Arch int Pharmacodyn, 1977, pp. 327-336, vol. 229.
Remington., Remington Pharmaceutical Sciences., Pharmaceutical Sciences., 1985, pp. 1418 vol. 76.
U.S. Appl. No. 15/503,875.
U.S. Appl. No. 15/503,864.
U.S. Appl. No. 15/428,710.
U.S. Appl. No. 62/404,798.
PCT ISR PCT/US2017/017093, dated Mar. 20, 2017 (JPI-5007USNP).
PCT ISR PCT/US2015/045413, dated Nov. 27, 2015 (JPI-5005USPCT).
PCT ISR PCT/US2015/045412, dated Nov. 15, 2015 (JPI-5003USPCT).

* cited by examiner

SUBSTITUTED 4-AZAINDOLES AND THEIR USE AS GLUN2B RECEPTOR MODULATORS

CROSS REFERENCE TO RELATED APPLICATION

This application claims the benefit of U.S. Provisional Application No. 62/190,416, filed on Jul. 9, 2015, which is incorporated herein by reference in its entirety.

FIELD OF THE INVENTION

The present invention is related to compounds having NR2B modulating properties, pharmaceutical compositions comprising these compounds, chemical processes for preparing these compounds and their use in the treatment of diseases associated with NR2B receptor activity in animals, in particular humans.

BACKGROUND OF THE INVENTION

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., Pharmacol Rev. 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., Neuropharmacology 2007; 52(1):77-86) and long-term depression (LTD) (Massey, P V et al., J Neurosci. 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluNR2 subunits play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., Nat Rev Neurosci. 2013; 14(6):383-400; Watanabe M et al., J Comp Neurol. 1993; 338(3):377-90) and are implicated in learning, memory processing, mood, attention, emotion and pain perception (Cull-Candy S et al., Curr Opin Neurobiol. 2001; 11(3):327-35).

Compounds that modulate GluN2B-containing NMDA receptor function can be useful in treatment of many neurological and psychiatric disorders including but not limited to bipolar disorder (Martucci L et al., Schizophrenia Res, 2006; 84(2-3):214-21) major depressive disorder (Miller O H et al., eLife. 2014; 3:e03581; Li N et al., Biol Psychiatry. 2011; 69(8):754-61), treatment-resistant depression (Preskorn S H et al. J Clin Psychopharmacol. 2008; 28(6): 631-7) and ther mood disorders (including schizophrenia (Grimwood S et al., Neuroreport. 1999, 10(3):461-5, Weickert C S et al. Molecular Psychiatry (2013) 18, 1185-1192), ante- and postpartum depression, seasonal affective disorder and the like), Alzheimer's disease (Hanson J E et al., Neurobiol Dis. 2015; 74:254-62; Li S et al., J Neurosci. 2011; 31(18):6627-38) and other dementias (Orgogozo J M et al. Stroke 2002, 33: 1834-1839), Parkinson's disease (Duty S, CNS Drugs. 2012; 26(12):1017-32, Steece-Collier K et al., Exp Neurol. 2000; 163(1):239-43, Leaver K R et al. Clin Exp Pharmacol Physiol. 2008; 35(11):1388-94), Huntington's chorea (Tang T S et al., Proc Natl Acad Sci USA. 2005; 102(7):2602-7; Li L et al., J Neurophysiol. 2004; 92(5):2738-46), multiple sclerosis (Grasselli G et al., Br J Pharmacol. 2013; 168(2):502-17; Farjam M et al., Iran J Pharm Res. 2014; 13(2):695-705), cognitive impairment (Wang D et al. 2014, Expert Opin Ther Targets Expert Opin Ther Targets. 2014; 18(10):1121-30), head injury (Bullock M R et al., Ann N Y Acad Sci. 1999; 890:51-8), spinal cord injury, stroke (Yang Y et al., J Neurosurg. 2003; 98(2):397-403), epilepsy (Naspolini A P et al., Epilepsy Res. 2012 June; 100(1-2):12-9), movement disorders (e.g. dyskinesias) (Morissette M et al., Mov Disord. 2006; 21(1):9-17), various neurodegenerative diseases (e.g. amyotrophic lateral sclerosis (Fuller P I et al., Neurosci Lett. 2006; 399(1-2):157-61) or neurodegeneration associated with bacterial or chronic infections), glaucoma (Naskar R et al. Semin Ophthalmol. 1999 September, 14(3):152-8), pain (e.g. chronic, cancer, post-operative and neuropathic pain (Wu L J and Zhuo M, Neurotherapeutics. 2009; 6(4):693-702), diabetic neuropathy, migraine (Peeters M et al., J Pharmacol Exp Ther. 2007; 321(2):564-72), cerebral ischemia (Yuan H et al., Neuron. 2015; 85(6):1305-18), encephalitis (Dalmau J. et al., Lancet Neurol. 2008; 7(12):1091-8.), autism and autism spectrum disorders (Won H. et al., Nature. 2012; 486(7402):261-5), memory and learning disorders (Tang, Y. P. et al., Nature. 1999; 401(6748):63-9), obsessive compulsive disorder (Arnold P D et al., Psychiatry Res. 2009; 172(2):136-9.), attention deficit hyperactivity disorder (ADHD) (Dorval K M et al., Genes Brain Behav. 2007; 6(5):444-52), PTSD (Haller J et al. Behav Pharmacol. 2011; 22(2):113-21; Leaderbrand K et al. Neurobiol Learn Mem. 2014; 113:35-40), tinnitus (Guitton M J, and Dudai Y, Neural Plast. 2007; 80904; Hu S S et al. 2016; 273(2): 325-332), sleep disorders (like narcolepsy or excessive daytime sleepiness, patent WO 2009058261 A1), vertigo and nystagmus (Straube A. et al., Curr Opin Neurol. 2005, 18(1):11-4, Starck M et al. J Neurol. 1997 January; 244(1):9-16), anxiety autoimmunological disorders like neuropsychiatric systemic lupus erythematosus (Kowal C et al. *Proc. Natl. Acad. Sci. U.S.A.* 2006; 103, 19854-19859) and addictive illnesses (e.g. alcohol addiction, drug addiction) (Nagy J, 2004, *Curr Drug Targets CNS Neurol Disord.* 2004; 3(3):169-79; Shen H et al., *Proc Natl Acad Sci USA.* 2011, 108(48):19407-12).

In view of the clinical importance of NR2B, the identification of compounds that modulate NR2B receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

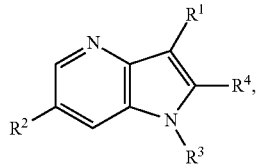

wherein:
$R^1$ is selected from the group consisting of: H, $^3$H, halo, $C_{1-3}$alkyl, and $C_{1-3}$haloalkyl;
$R^2$ is selected from the group consisting of: phenyl optionally substituted with one, two, or three members independently selected from: halo, $C_{1-5}$alkyl, and $C_{1-5}$haloalkyl; pyridinyl optionally substituted with halo, $C_{1-5}$alkyl, $C_{1-5}$haloalkyl, and —CN, thiazolyl optionally substituted with $C_{1-5}$alkyl; benzothiophenyl; and thienyl optionally substituted with one, two or three members independently selected from: halo, $C_{1-5}$alkyl, and $C_{1-5}$haloalkyl;
$R^3$ is selected from the group consisting of:
(a)

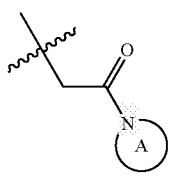

wherein ring A is a 4-7 membered heterocycloalkyl optionally containing an additional oxygen heteroatom selected from the group consisting of: azetidinyl optionally substituted with one or two members independently selected from the group consisting of: halo, $C_{1-5}$alkyl, $C_{1-5}$haloalkyl, $CH_2OH$, $C_{1-5}$alkoxy, OH, and CN; pyrrolidinyl optionally substituted one or two members independently selected from the group consisting of: halo, $C_{1-5}$alkyl, $C_{1-5}$alkoxy, and OH; morpholino optionally substituted one or two $C_{1-5}$alkyl members; piperidinyl optionally substituted with one or two members independently selected from the group consisting of: halo, $C_{1-5}$alkyl, $C_{1-5}$haloalkyl, $C_{1-5}$alkoxy, and OH; 3-azabicyclo[3.1.0]hexan-3-yl; 5-azaspiro[2.3]hexan-5-yl; and pyrrolidin-3-one; or (b)

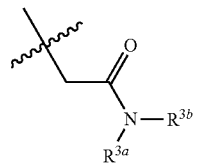

wherein $R^{3a}$ is H, or $C_{1-5}$alkyl;
and $R^{3b}$ is selected from the group consisting of: $C_{1-5}$alkyl optionally substituted with OH, halo, or $OCH_3$; $C_{1-5}$haloalkyl; benzyl; $CH_2$cyclopropyl; cyclopropyl optionally substituted with $C_{1-5}$alkyl; and cyclobutyl; or (c)

wherein $R^{3c}$ is selected from the group consisting of: cyclopropyl; cyclobutyl; pyrimidinyl optionally substituted with halo; pyridinyl; pyridazinyl; furanyl optionally substituted with $C_{1-5}$haloalkyl; oxazolyl; isoxazolyl optionally substituted with $C_{1-5}$alkyl; oxadiazolyl optionally substituted with $C_{1-5}$alkyl; pyrazolyl optionally substituted with $C_{1-5}$alkyl; triazolyl optionally substituted with $C_{1-5}$alkyl; tetrahydrofuranyl; tetrahydropyranyl; oxetanyl; and oxiranyl; or (d)

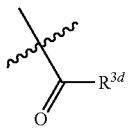

wherein $R^{3d}$ is $CH_2$-cyclopropyl or cyclobutyl; or (e)

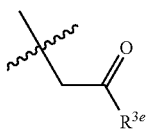

wherein $R^{3e}$ is selected from the group consisting of: OH, $C_{1-5}$alkyl, cyclopropyl, cyclobutyl, and phenyl optionally substituted with one halo substituent; or (f) $C_{1-5}$alkyl optionally substituted with OH or $C_{1-5}$alkoxy; $CH_2S(CH_3)$; $CH_2(S=O)CH_3$; $CH_2(SO_2)CH_3$; and $CH_2CH_2(C=O)CH_3$; or (g)

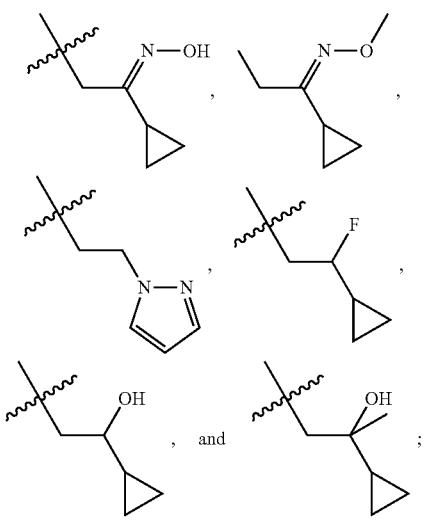

and $R^4$ is H, $^2H$ or $C_{1-3}$alkyl and pharmaceutically acceptable salts of compounds of Formula (I).

Further embodiments are provided by pharmaceutically acceptable salts of compounds of Formulas (I), pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as the pharmaceutically acceptable salts.

In a further aspect, the invention relates to pharmaceutical compositions for treating a disease, disorder, or medical condition mediated by NR2B receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as NR2B receptor modulators. Thus, the invention is directed to a method for modulating NR2B receptor activity, including when such receptor is in a subject, comprising exposing NR2B receptor to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by NR2B receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION

In one aspect, provided herein are compounds of Formula (I), and pharmaceutically acceptable salts, N-oxides, or solvates thereof,

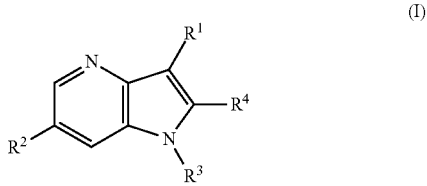

(I)

wherein:
R$^1$ is selected from the group consisting of: H, $^3H$, halo, $C_{1-3}$alkyl, and $C_{1-3}$haloalkyl;
R$^2$ is selected from the group consisting of: phenyl optionally substituted with one, two, or three members independently selected from: halo, $C_{1-5}$alkyl, and $C_{1-5}$haloalkyl; pyridinyl optionally substituted with halo, $C_{1-5}$alkyl, $C_{1-5}$haloalkyl; and —CN; thiazolyl optionally substituted with $C_{1-5}$alkyl; benzothiophenyl; and thienyl optionally substituted with one, two or three members independently selected from: halo, $C_{1-5}$alkyl; and $C_{1-5}$haloalkyl;
R$^3$ is selected from the group consisting of:
(a)

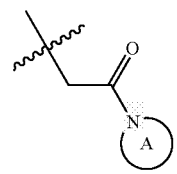

wherein ring A is a 4-7 membered heterocycloalkyl optionally containing an additional oxygen heteroatom selected from the group consisting of: azetidinyl optionally substituted with one or two members independently selected from the group consisting of: halo, $C_{1-5}$alkyl, $C_{1-5}$haloalkyl, $CH_2OH$, $C_{1-5}$alkoxy, OH, and CN; pyrrolidinyl optionally substituted one or two members independently selected from the group consisting of: halo, $C_{1-5}$alkyl, $C_{1-5}$alkoxy, and OH; morpholino optionally substituted one or two $C_{1-5}$alkyl members; piperidinyl optionally substituted with one or two members independently selected from the group consisting of: halo, $C_{1-5}$alkyl, $C_{1-5}$haloalkyl, $C_{1-5}$alkoxy, and OH; 3-azabicyclo[3.1.0]hexan-3-yl; 5-azaspiro[2.3]hexan-5-yl; and pyrrolidin-3-one; or
(b)

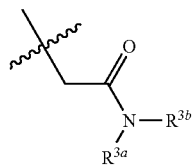

wherein $R^{3a}$ is H, or $C_{1-5}$alkyl;
and $R^{3b}$ is selected from the group consisting of: $C_{1-5}$alkyl optionally substituted with OH, halo, or $OCH_3$; $C_{1-5}$haloalkyl; benzyl; $CH_2$cyclopropyl; cyclopropyl optionally substituted with $C_{1-5}$alkyl; and cyclobutyl; or
(c)

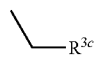

wherein $R^{3c}$ is selected from the group consisting of: cyclopropyl; cyclobutyl; pyrimidinyl optionally substituted with halo; pyridinyl; pyridazinyl; furanyl optionally substituted with $C_{1-5}$haloalkyl; oxazolyl; isoxazolyl optionally substituted with $C_{1-5}$alkyl; oxadiazolyl optionally substituted with $C_{1-5}$alkyl; pyrazolyl optionally substituted with $C_{1-5}$alkyl; triazolyl optionally substituted with $C_{1-5}$alkyl; tetrahydrofuranyl; tetrahydropyranyl; oxetanyl; and oxiranyl; or
(d)

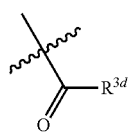

wherein $R^{3d}$ is $CH_2$-cyclopropyl or cyclobutyl; or
(e)

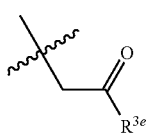

wherein $R^{3e}$ is selected from the group consisting of: OH, $C_{1-5}$alkyl, cyclopropyl, cyclobutyl, and phenyl optionally substituted with one halo substituent; or
(f) $C_{1-5}$alkyl optionally substituted with OH or $C_{1-5}$alkoxy; $CH_2S(CH_3)$; $CH_2(S=O)CH_3$; $CH_2(SO_2)CH_3$; and $CH_2CH_2(C=O)CH_3$; or
(g)

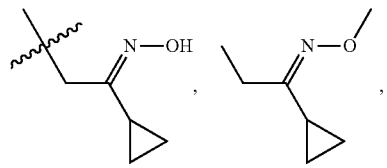

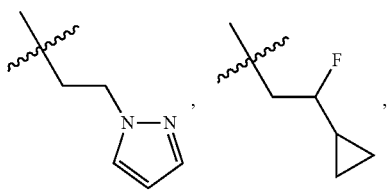

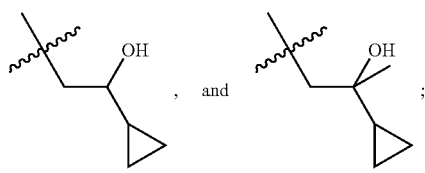

and
$R^4$ is H, $^2H$ or $C_{1-3}$alkyl.

An additional embodiment of the invention is a compound of Formula (I) wherein $R^1$ is H, Cl, Br, F, or $CH_3$.
An additional embodiment of the invention is a compound of Formula (I) wherein $R^1$ is H.
An additional embodiment of the invention is a compound of Formula (I) wherein $R^1$ is Cl.
An additional embodiment of the invention is a compound of Formula (I) wherein $R^1$ is $CH_3$.
An additional embodiment of the invention is a compound of Formula (I) wherein $R^2$ is phenyl optionally substituted with one, two, or three members independently selected from: Cl, F, $CH_3$, $CH_2CH_3$, $CF_2H$, and $CF_3$, pyridinyl optionally substituted with F, CN, $CH_3$ and $CF_3$, thiazolyl optionally substituted with $CH_3$, benzothiophenyl; and thienyl optionally substituted with one, two or three members independently selected from: Cl, $CH_3$, $CH_2CH_3$, $CHF_2$ and $CF_3$.
An additional embodiment of the invention is a compound of Formula (I) wherein $R^2$ is phenyl, 2-methylphenyl, 3-methylphenyl, 4-methylphenyl, 3-ethylphenyl, 3-(difluoromethyl)phenyl, 3-(trifluoromethyl)phenyl, 3,5-dimethylphenyl, 2,3-dimethylphenyl, 2-fluorophenyl, 3-fluorophenyl, 3-chlorophenyl, 4-fluorophenyl, 2,3-difluorophenyl, 2,4-difluorophenyl, 3,4-difluorophenyl, 3,4-dichlorophenyl, 2,5-difluorophenyl, 3,5-difluorophenyl, 3-chloro-2-fluorophenyl, 3-chloro-4-fluoro-phenyl, 2-fluoro-3-methyl-phenyl, 4-fluoro-2-methyl-phenyl, 2-methyl-3-(trifluoromethyl) phenyl, 2-fluoro-3-(trifluoromethyl)phenyl, 4-fluoro-3-(trifluoromethyl)phenyl, 4-fluoro-3-methyl-phenyl, 2-fluoro-5-methyl-phenyl, 4-fluoro-2,3-dimethyl-phenyl, 2,4-difluoro-3-methyl-phenyl, 2,6-difluoro-3-methyl-phenyl, 2,3,4-trifluorophenyl, 3,4,5-trifluorophenyl, 2-thienyl, 3-thienyl, 5-methyl-2-thienyl, 4-methyl-2-thienyl, 5-ethyl-2-thienyl, 5-chloro-2-thienyl, 3-chloro-2-thienyl, 4-chloro-2-thienyl, 5-chloro-3-thienyl, 5-(difluoromethyl)-2-thienyl, 5-(trifluoromethyl)-2-thienyl, 2,5-dimethyl-3-thienyl, 2,5-dichloro-3-thienyl, 5-chloro-4-methyl-2-thienyl, 2,4,5-trimethyl-3-thienyl, 6-thiazol-5-yl, 2-methylthiazol-5-yl, 6-methyl-3-pyridyl, 6-fluoro-3-pyridyl, pyridine-2-carbonitrile, 2-(trifluoromethyl)-4-pyridyl, 5-(trifluoromethyl)-3-pyridyl, 6-(trifluoromethyl)-2-pyridyl, or benzothiophen-2-yl.

An additional embodiment of the invention is a compound of Formula (I) $R^2$ is phenyl or thienyl, wherein the phenyl or thienyl is optionally substituted with one, two, or three members independently selected from: halo, $C_{1-5}$alkyl, and $C_{1-5}$haloalkyl.

An additional embodiment of the invention is a compound of Formula (I) wherein $R^3$ is

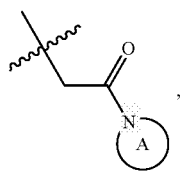

wherein ring A is

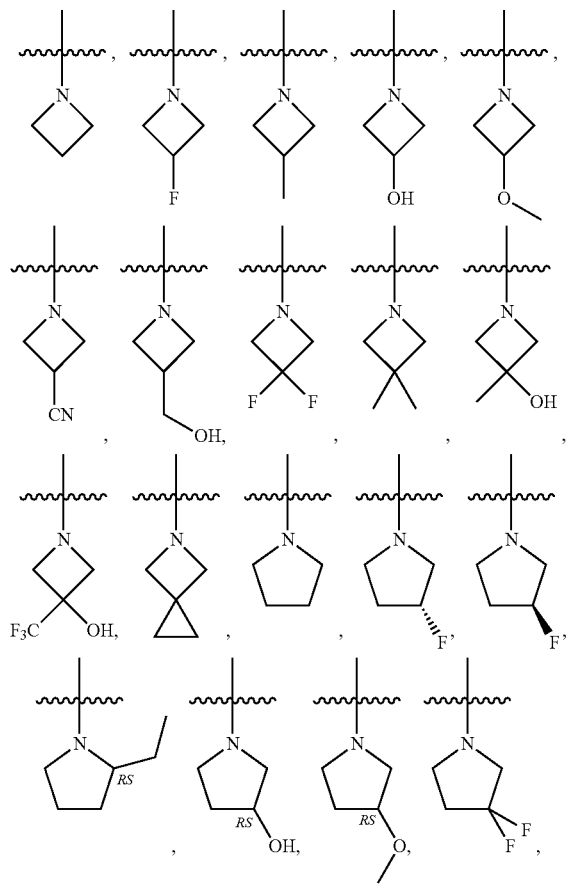

-continued

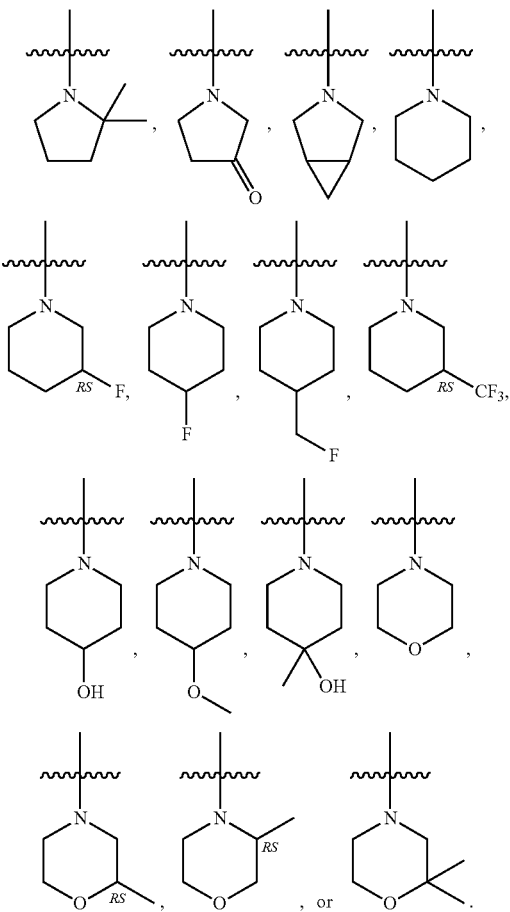

or

An additional embodiment of the invention is a compound of Formula (I) wherein $R^3$ is

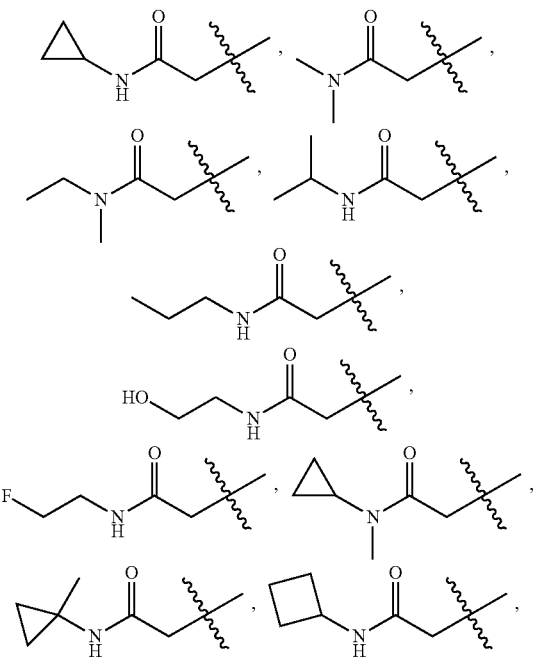

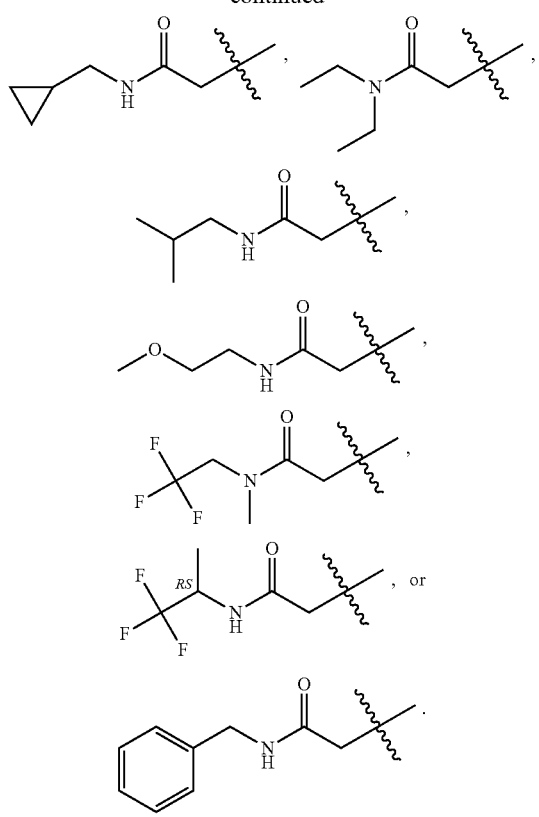

An additional embodiment of the invention is a compound of Formula (I) wherein R³ is

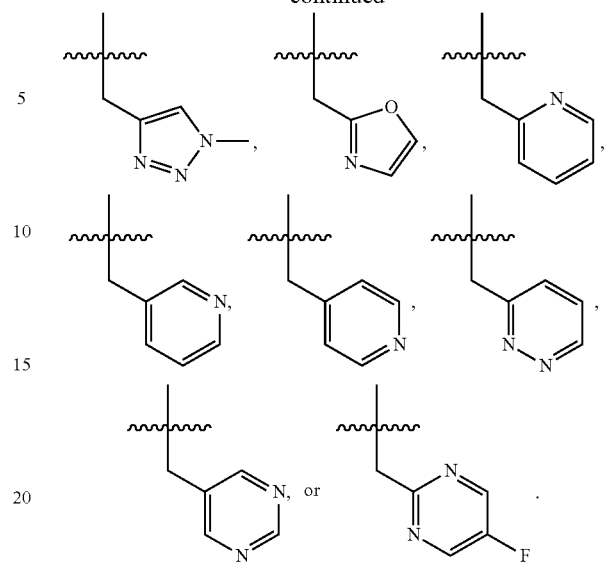

An additional embodiment of the invention is a compound of Formula (I) wherein R³ is

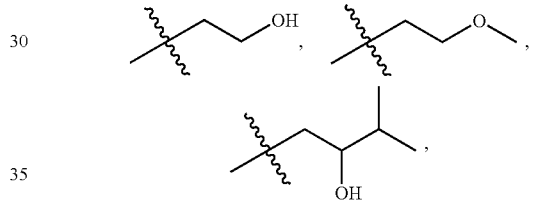

$CH_2S(CH_3)$, $CH_2(S=O)CH_3$, $CH_2(SO_2)CH_3$, or $CH_2CH_2(C=O)CH_3$.

An additional embodiment of the invention is a compound of Formula (I) R³ is

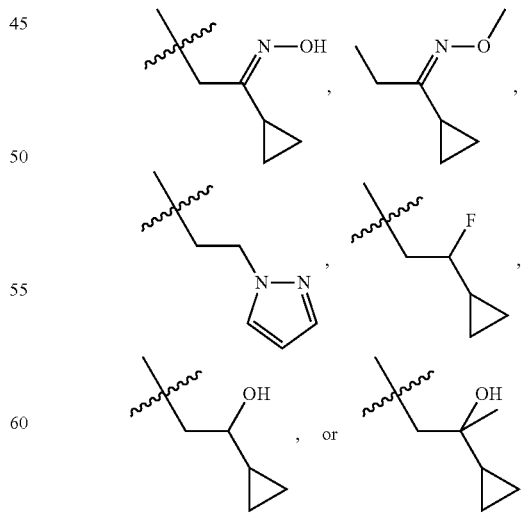

An additional embodiment of the invention is a compound of Formula (I) wherein R³ is

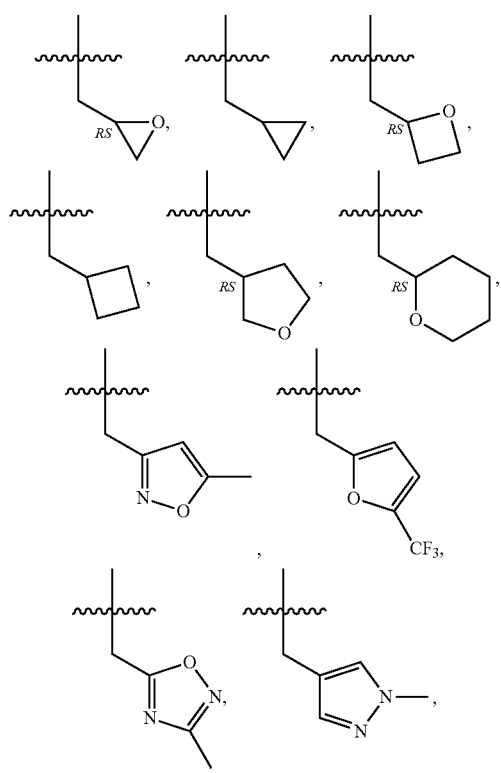

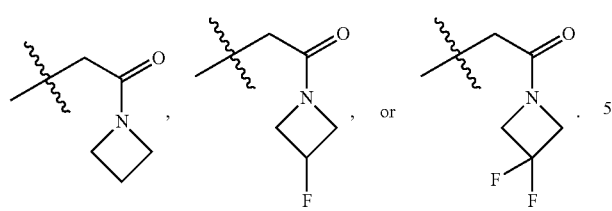

An additional embodiment of the invention is a compound of Formula (I) R⁴ is H.

An additional embodiment of the invention is a compound of Formula (I) wherein R⁴ is CH₃.

An additional embodiment of the invention is a compound of Formula (I) having the Formula (II):

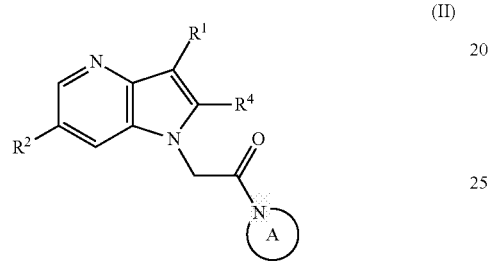

wherein
R¹ is selected from the group consisting of: H, ³H, halo and C₁₋₃alkyl;
R² is selected from the group consisting of: phenyl optionally substituted with one, two, or three members independently selected from: halo, C₁₋₅alkyl, and C₁₋₅haloalkyl; pyridinyl optionally substituted with halo, C₁₋₅alkyl, C₁₋₅haloalkyl, and CN; thiazolyl optionally substituted with C₁₋₅alkyl; and thienyl optionally substituted with halo, or C₁₋₅alkyl; ring A is selected from the group consisting of:

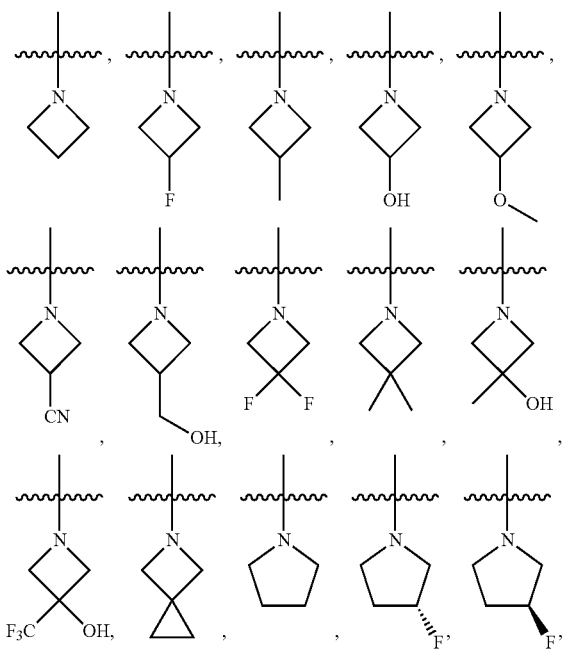

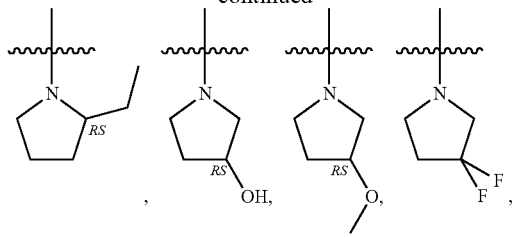

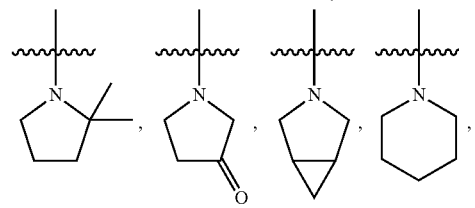

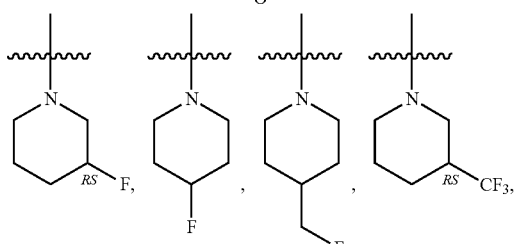

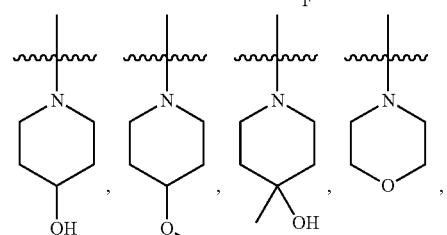

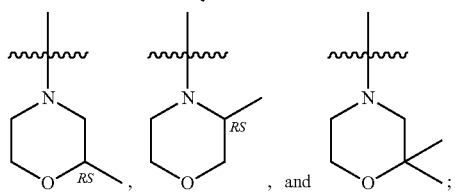

and R⁴ is H, ²H, or CH₃;
and pharmaceutically acceptable salts, N-oxides or solvates of compounds of Formula (II).

An additional embodiment of the invention is a compound of Formula (I) having the Formula (IIA):

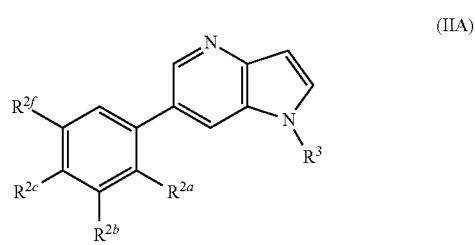

wherein
R²ᵃ is H, or F;
R²ᵇ is H, F, CH₃ or CH₂CH₃;

$R^{2c}$ is H, F or $CH_3$;
$R^{2f}$ is H, F, or $CH_3$; and
$R^3$ is

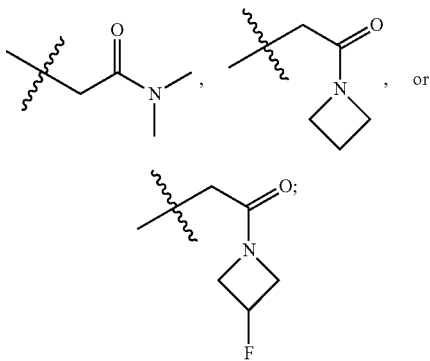

and pharmaceutically acceptable salts, N-oxides or solvates of compounds of Formula (IIA).

An additional embodiment of the invention is a compound of Formula (I) having the structure of Formula (IIB):

(IIB)

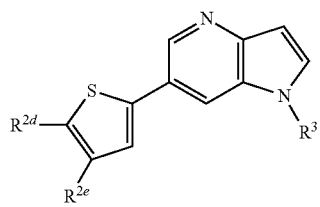

wherein
$R^{2d}$ is H, Cl, $CH_3$ or $CF_3$;
$R^{2e}$ is H or $CH_3$; and
$R^3$ is

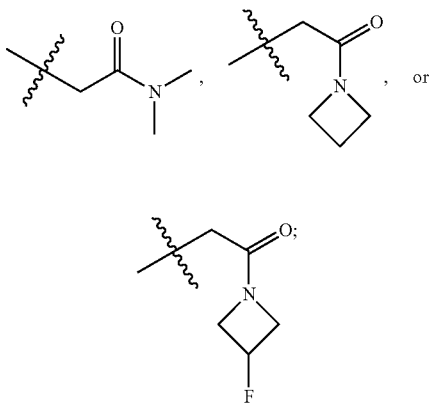

and pharmaceutically acceptable salts, N-oxides or solvates of compounds of Formula (IIB).

An additional embodiment of the invention is a compound of Formula (I) having the structure of Formula (III):

(III)

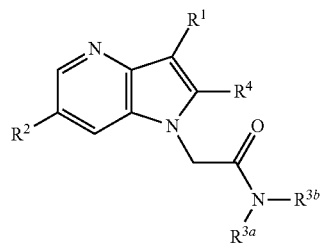

wherein
$R^1$ is H, $^3$H, halo, $C_{1-3}$alkyl, or $C_{1-3}$haloalkyl;
$R^2$ is selected from the group consisting of: phenyl optionally substituted with one, two, or three members independently selected from: halo, $C_{1-5}$alkyl, and $C_{1-5}$haloalkyl; pyridinyl optionally substituted with $C_{1-5}$haloalkyl; benzothiophenyl; and thienyl optionally substituted with one, two, or three members independently selected from halo, $C_{1-5}$alkyl, or $C_{1-5}$haloalkyl;
$R^{3a}$ is H, or $C_{1-5}$alkyl;
$R^{3b}$ is selected from the group consisting of: $C_{1-5}$alkyl optionally substituted with OH or $OCH_3$; $C_{1-5}$haloalkyl; benzyl; $CH_2$cyclopropyl; cyclopropyl optionally substituted with $C_{1-5}$alkyl; and cyclobutyl; and
$R^4$ is H, $H^2$, or $CH_3$;
and pharmaceutically acceptable salts, N-oxides or solvates of compounds of Formula (III).

An additional embodiment of the invention is a compound of Formula (I) having the structure of Formula (IV):

(IV)

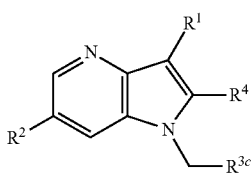

$R^1$ is H, or halo;
$R^2$ is phenyl optionally substituted with one, or two members independently selected from: halo, $C_{1-5}$alkyl, and $C_{1-5}$haloalkyl; or thienyl substituted with $C_{1-5}$alkyl;
$R^{3c}$ is

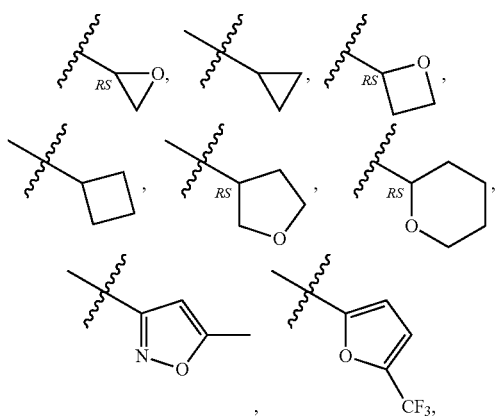

-continued

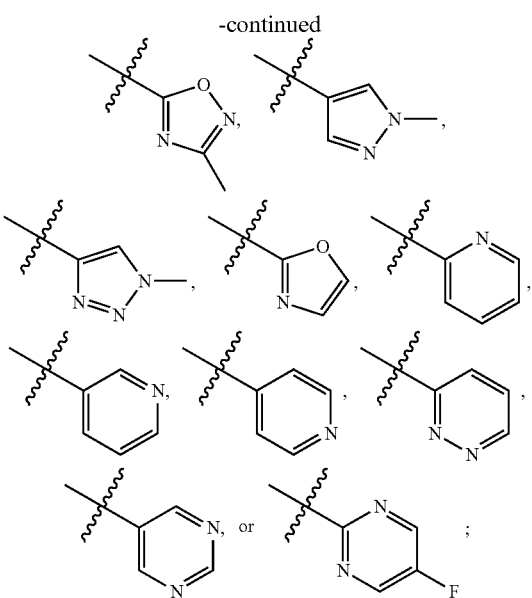

and R⁴ is H;
and pharmaceutically acceptable salts, N-oxides or solvates of compounds of Formula (IV).

An additional embodiment of the invention is a compound of Formula (I) having the structure of Formula (V):

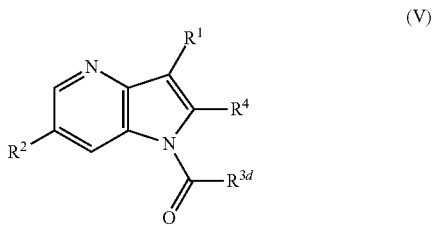

(V)

wherein
R¹ and R⁴ are H;
R² is phenyl optionally substituted with two halo; and
R$^{3d}$ is cyclobutyl, or CH$_2$-cyclopropyl;
and pharmaceutically acceptable salts, N-oxides or solvates of compounds of Formula (V).

An additional embodiment of the invention is a compound of Formula (I) having the structure of Formula (VI):

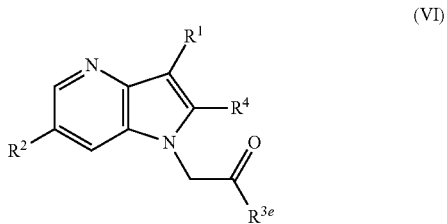

(VI)

R¹ is H or halo;
R² is phenyl optionally substituted with one, two, or three members independently selected from: halo, C$_{1-5}$alkyl, and C$_{1-5}$haloalkyl; or thienyl substituted with halo or C$_{1-5}$alkyl;

R$^{3e}$ is selected from the group consisting of: OH, C$_{1-5}$alkyl, cyclopropyl, cyclobutyl, and phenyl optionally substituted with one halo substituent;
and
R⁴ is H or CH$_3$;
and pharmaceutically acceptable salts, N-oxides or solvates of compounds of Formula (VI).

A further embodiment of the current invention is a compound as shown below in Table 1.

| Example # | Compound Name |
|---|---|
| 1 | 2-(3-Chloro-6-phenyl-pyrrolo[3,2-b]pyridin-1-yl)-N-cyclopropyl-acetamide; |
| 2 | 2-[3-Chloro-6-(4-fluorophenyl)pyrrolo[3,2-b]pyridin-1-yl]-N-cyclopropyl-acetamide; |
| 3 | 1-(Azetidin-1-yl)-2-[3-chloro-6-(4-fluorophenyl)pyrrolo[3,2-b]pyridin-1-yl]ethanone; |
| 4 | 2-(3-Chloro-6-phenyl-pyrrolo[3,2-b]pyridin-1-yl)-1-pyrrolidin-1-yl-ethanone; |
| 5 | 2-(3-Chloro-6-phenyl-pyrrolo[3,2-b]pyridin-1-yl)-1-morpholino-ethanone; |
| 6 | 1-(Azetidin-1-yl)-2-(3-chloro-6-phenyl-pyrrolo[3,2-b]pyridin-1-yl)ethanone; |
| 7 | 2-[3-Chloro-6-(4-fluorophenyl)pyrrolo[3,2-b]pyridin-1-yl]-1-morpholino-ethanone; |
| 8 | 1-(Azetidin-1-yl)-2-[3-chloro-6-(m-tolyl)pyrrolo[3,2-b]pyridin-1-yl]ethanone; |
| 9 | 2-[3-Chloro-6-(4-fluorophenyl)pyrrolo[3,2-b]pyridin-1-yl]-1-pyrrolidin-1-yl-ethanone; |
| 10 | 2-[3-Chloro-6-(m-tolyl)pyrrolo[3,2-b]pyridin-1-yl]-N-cyclopropyl-acetamide; |
| 11 | 1-(Azetidin-1-yl)-2-(3-bromo-6-phenyl-pyrrolo[3,2-b]pyridin-1-yl)ethanone; |
| 12 | 2-[3-Chloro-6-(m-tolyl)pyrrolo[3,2-b]pyridin-1-yl]-1-pyrrolidin-1-yl-ethanone; |
| 13 | 2-[3-Chloro-6-(m-tolyl)pyrrolo[3,2-b]pyridin-1-yl]-1-morpholino-ethanone; |
| 14 | 2-(3-Bromo-6-phenyl-pyrrolo[3,2-b]pyridin-1-yl)-N-cyclopropyl-acetamide; |
| 15 | 2-(3-Bromo-6-phenyl-pyrrolo[3,2-b]pyridin-1-yl)-1-pyrrolidin-1-yl-ethanone; |
| 16 | 2-(3-Bromo-6-phenyl-pyrrolo[3,2-b]pyridin-1-yl)-1-morpholino-ethanone; |
| 17 | 2-[3-Bromo-6-(4-fluorophenyl)pyrrolo[3,2-b]pyridin-1-yl]-N-cyclopropyl-acetamide; |
| 18 | 1-(Azetidin-1-yl)-2-[3-bromo-6-(4-fluorophenyl)pyrrolo[3,2-b]pyridin-1-yl]ethanone; |
| 19 | 2-[3-Bromo-6-(4-fluorophenyl)pyrrolo[3,2-b]pyridin-1-yl]-1-pyrrolidin-1-yl-ethanone; |
| 20 | 2-[3-Bromo-6-(4-fluorophenyl)pyrrolo[3,2-b]pyridin-1-yl]-1-morpholino-ethanone; |
| 21 | 2-[3-Bromo-6-(m-tolyl)pyrrolo[3,2-b]pyridin-1-yl]-N-cyclopropyl-acetamide; |
| 22 | 1-(Azetidin-1-yl)-2-[3-bromo-6-(m-tolyl)pyrrolo[3,2-b]pyridin-1-yl]ethanone; |
| 23 | 2-[3-Bromo-6-(m-tolyl)pyrrolo[3,2-b]pyridin-1-yl]-1-pyrrolidin-1-yl-ethanone; |
| 24 | 2-[3-Bromo-6-(m-tolyl)pyrrolo[3,2-b]pyridin-1-yl]-1-morpholino-ethanone; |
| 25 | 2-[3-Chloro-6-(4-fluoro-3-methyl-phenyl)pyrrolo[3,2-b]pyridin-1-yl]-1-(3,3-difluoroazetidin-1-yl)ethanone; |
| 26 | 2-[3-Chloro-6-(4-fluoro-3-methyl-phenyl)pyrrolo[3,2-b]pyridin-1-yl]-1-(3-fluoroazetidin-1-yl)ethanone; |
| 27 | 2-[6-(4-Fluorophenyl)-3-methyl-pyrrolo[3,2-b]pyridin-1-yl]-1-pyrrolidin-1-yl-ethanone; |
| 28 | 2-[6-(4-Fluorophenyl)-3-methyl-pyrrolo[3,2-b]pyridin-1-yl]-1-morpholino-ethanone; |
| 29 | 1-(Azetidin-1-yl)-2-[3-chloro-6-(3,4-difluorophenyl)pyrrolo[3,2-b]pyridin-1-yl]ethanone; |
| 30 | 2-[3-Chloro-6-(3,4-difluorophenyl)pyrrolo[3,2-b]pyridin-1-yl]-1-(3-fluoroazetidin-1-yl)ethanone; |
| 31 | 2-[6-(4-Fluorophenyl)-2-methyl-pyrrolo[3,2-b]pyridin-1-yl]-1-morpholino-ethanone; |
| 32 | N-Cyclopropyl-2-[6-(4-fluorophenyl)-3-methyl-pyrrolo[3,2-b]pyridin-1-yl]acetamide; |
| 33 | 1-(Azetidin-1-yl)-2-[6-(4-fluorophenyl)-3-methyl-pyrrolo[3,2-b]pyridin-1-yl]ethanone; |

| Example # | Compound Name |
|---|---|
| 34 | 2-[3-Chloro-6-(3,4-difluorophenyl)pyrrolo[3,2-b]pyridin-1-yl]-1-(3,3-difluoroazetidin-1-yl)ethanone; |
| 35 | 2-[3-Chloro-6-[4-fluoro-3-(trifluoromethyl)phenyl]pyrrolo[3,2-b]pyridin-1-yl]-1-(3-fluoroazetidin-1-yl)ethanone; |
| 36 | 2-[3-Chloro-6-[3-(trifluoromethyl)phenyl]pyrrolo[3,2-b]pyridin-1-yl]-1-(3,3-difluoroazetidin-1-yl)ethanone; |
| 37 | 2-[6-(4-Fluorophenyl)-2-methyl-pyrrolo[3,2-b]pyridin-1-yl]-1-pyrrolidin-1-yl-ethanone; |
| 38 | N-Cyclopropyl-2-[6-(4-fluorophenyl)-2-methyl-pyrrolo[3,2-b]pyridin-1-yl]acetamide; |
| 39 | 2-[3-Chloro-6-(3,4,5-trifluorophenyl)pyrrolo[3,2-b]pyridin-1-yl]-1-(3-fluoroazetidin-1-yl)ethanone; |
| 40 | 2-[3-Chloro-6-[4-fluoro-3-(trifluoromethyl)phenyl]pyrrolo[3,2-b]pyridin-1-yl]-1-(3,3-difluoroazetidin-1-yl)ethanone; |
| 41 | 1-(Azetidin-1-yl)-2-[2-methyl-6-(m-tolyl)pyrrolo[3,2-b]pyridin-1-yl]ethanone; |
| 42 | 2-(2-Methyl-6-phenyl-pyrrolo[3,2-b]pyridin-1-yl)-1-pyrrolidin-1-yl-ethanone; |
| 43 | N-Cyclopropyl-2-(2-methyl-6-phenyl-pyrrolo[3,2-b]pyridin-1-yl)acetamide; |
| 44 | 2-[2-Methyl-6-(m-tolyl)pyrrolo[3,2-b]pyridin-1-yl]-1-pyrrolidin-1-yl-ethanone; |
| 45 | 2-[2-Methyl-6-(m-tolyl)pyrrolo[3,2-b]pyridin-1-yl]-1-morpholino-ethanone; |
| 46 | 1-(Azetidin-1-yl)-2-[6-(4-fluorophenyl)-2-methyl-pyrrolo[3,2-b]pyridin-1-yl]ethanone; |
| 47 | 1-(Azetidin-1-yl)-2-(2-methyl-6-phenyl-pyrrolo[3,2-b]pyridin-1-yl)ethanone; |
| 48 | 2-[3-Chloro-6-[3-(trifluoromethyl)phenyl]pyrrolo[3,2-b]pyridin-1-yl]-1-(3-fluoroazetidin-1-yl)ethanone; |
| 49 | 2-[3-Chloro-6-(3,4,5-trifluorophenyl)pyrrolo[3,2-b]pyridin-1-yl]-1-(3,3-difluoroazetidin-1-yl)ethanone; |
| 50 | 2-[3-Chloro-6-(2,3,4-trifluorophenyl)pyrrolo[3,2-b]pyridin-1-yl]-1-(3,3-difluoroazetidin-1-yl)ethanone; |
| 51 | N-Cyclopropyl-2-[2-methyl-6-(m-tolyl)pyrrolo[3,2-b]pyridin-1-yl]acetamide; |
| 52 | 2-(2-Methyl-6-phenyl-pyrrolo[3,2-b]pyridin-1-yl)-1-morpholino-ethanone; |
| 53 | 2-[3-Chloro-6-(m-tolyl)pyrrolo[3,2-b]pyridin-1-yl]-1-(3,3-difluoroazetidin-1-yl)ethanone; |
| 54 | 2-[3-Chloro-6-(m-tolyl)pyrrolo[3,2-b]pyridin-1-yl]-1-(3-fluoroazetidin-1-yl)ethanone; |
| 55 | 2-(3-Chloro-6-phenyl-pyrrolo[3,2-b]pyridin-1-yl)-1-(3,3-difluoroazetidin-1-yl)ethanone; |
| 56 | 2-(3-Chloro-6-phenyl-pyrrolo[3,2-b]pyridin-1-yl)-1-(3-fluoroazetidin-1-yl)ethanone; |
| 57 | 2-[3-Chloro-6-(4-fluorophenyl)pyrrolo[3,2-b]pyridin-1-yl]-1-(3,3-difluoroazetidin-1-yl)ethanone; |
| 58 | 2-[3-Chloro-6-(4-fluorophenyl)pyrrolo[3,2-b]pyridin-1-yl]-1-(3-fluoroazetidin-1-yl)ethanone; |
| 59 | 3-[[6-(4-Fluoro-2-methyl-phenyl)pyrrolo[3,2-b]pyridin-1-yl]methyl]-5-methyl-isoxazole; |
| 60 | 5-Methyl-3-[[6-[3-(trifluoromethyl)phenyl]pyrrolo[3,2-b]pyridin-1-yl]methyl]isoxazole; |
| 61 | 5-Methyl-3-[[6-(m-tolyl)pyrrolo[3,2-b]pyridin-1-yl]methyl]isoxazole trifluoroacetate salt; |
| 62 | 5-Methyl-3-[[6-(o-tolyl)pyrrolo[3,2-b]pyridin-1-yl]methyl]isoxazole trifluoroacetate salt; |
| 63 | 3-[[6-(4-Fluoro-2-methyl-phenyl)pyrrolo[3,2-b]pyridin-1-yl]methyl]-5-methyl-isoxazole trifluoroacetate salt; |
| 64 | 3-[[6-(3,5-Difluorophenyl)pyrrolo[3,2-b]pyridin-1-yl]methyl]-5-methyl-isoxazole trifluoroacetate salt; |
| 65 | 3-[[6-(4-Fluorophenyl)pyrrolo[3,2-b]pyridin-1-yl]methyl]-5-methyl-isoxazole trifluoroacetate salt; |
| 66 | N-Cyclobutyl-2-[6-(4-fluoro-3-methyl-phenyl)pyrrolo[3,2-b]pyridin-1-yl]acetamide trifluoroacetate salt; |
| 67 | 2-[6-(4-Fluoro-3-methyl-phenyl)pyrrolo[3,2-b]pyridin-1-yl]-1-pyrrolidin-1-yl-ethanone trifluoroacetate salt; |
| 68 | 1-(Azetidin-1-yl)-2-[3-bromo-6-(4-fluoro-3-methyl-phenyl)pyrrolo[3,2-b]pyridin-1-yl]ethanone; |
| 69 | 1-(Azetidin-1-yl)-2-[3-fluoro-6-(4-fluoro-3-methyl-phenyl)pyrrolo[3,2-b]pyridin-1-yl]ethanone; |
| 70 | 2-[6-(4-Fluoro-3-methyl-phenyl)pyrrolo[3,2-b]pyridin-1-yl]acetic acid; |
| 71 | 1-(Azetidin-1-yl)-2-[6-(2-fluorophenyl)pyrrolo[3,2-b]pyridin-1-yl]ethanone; |
| 72 | 1-(Azetidin-1-yl)-2-[6-(3-fluorophenyl)pyrrolo[3,2-b]pyridin-1-yl]ethanone; |
| 73 | 1-(Azetidin-1-yl)-2-[6-(p-tolyl)pyrrolo[3,2-b]pyridin-1-yl]ethanone; |
| 74 | 1-(Azetidin-1-yl)-2-[6-(3-ethylphenyl)pyrrolo[3,2-b]pyridin-1-yl]ethanone; |
| 75 | N-Cyclopropyl-2-[6-(2-fluorophenyl)pyrrolo[3,2-b]pyridin-1-yl]acetamide; |
| 76 | N-Cyclopropyl-2-[6-(3-fluorophenyl)pyrrolo[3,2-b]pyridin-1-yl]acetamide; |
| 77 | N-Cyclopropyl-2-[6-(p-tolyl)pyrrolo[3,2-b]pyridin-1-yl]acetamide; |
| 78 | 2-(6-Phenylpyrrolo[3,2-b]pyridin-1-yl)-1-pyrrolidin-1-yl-ethanone; |
| 79 | 2-[6-(2-Fluorophenyl)pyrrolo[3,2-b]pyridin-1-yl]-1-pyrrolidin-1-yl-ethanone; |
| 80 | 2-[6-(4-Fluorophenyl)pyrrolo[3,2-b]pyridin-1-yl]-1-pyrrolidin-1-yl-ethanone; |
| 81 | 2-[6-(m-Tolyl)pyrrolo[3,2-b]pyridin-1-yl]-1-pyrrolidin-1-yl-ethanone; |
| 82 | 2-[6-(p-Tolyl)pyrrolo[3,2-b]pyridin-1-yl]-1-pyrrolidin-1-yl-ethanone; |
| 83 | 2-[6-(3-Ethylphenyl)pyrrolo[3,2-b]pyridin-1-yl]-1-pyrrolidin-1-yl-ethanone; |
| 84 | 2-[6-(3-Fluorophenyl)pyrrolo[3,2-b]pyridin-1-yl]-1-pyrrolidin-1-yl-ethanone; |
| 85 | 1-Morpholino-2-(6-phenylpyrrolo[3,2-b]pyridin-1-yl)ethanone; |
| 86 | 2-[6-(2-Fluorophenyl)pyrrolo[3,2-b]pyridin-1-yl]-1-morpholino-ethanone; |
| 87 | 2-[6-(3-Fluorophenyl)pyrrolo[3,2-b]pyridin-1-yl]-1-morpholino-ethanone; |
| 88 | 2-[6-(4-Fluorophenyl)pyrrolo[3,2-b]pyridin-1-yl]-1-morpholino-ethanone; |
| 89 | 1-Morpholino-2-[6-(m-tolyl)pyrrolo[3,2-b]pyridin-1-yl]ethanone; |
| 90 | 1-Morpholino-2-[6-(p-tolyl)pyrrolo[3,2-b]pyridin-1-yl]ethanone; |
| 91 | 2-[6-(3-Ethylphenyl)pyrrolo[3,2-b]pyridin-1-yl]-1-morpholino-ethanone; |
| 92 | 2-[3-Fluoro-6-(4-fluoro-3-methyl-phenyl)pyrrolo[3,2-b]pyridin-1-yl]-N,N-dimethyl-acetamide; |
| 93 | 2-[6-(3,4-Difluorophenyl)-3-fluoro-pyrrolo[3,2-b]pyridin-1-yl]-N,N-dimethyl-acetamide; |
| 94 | 2-[3-Fluoro-6-(3,4,5-trifluorophenyl)pyrrolo[3,2-b]pyridin-1-yl]-N,N-dimethyl-acetamide; |
| 95 | 2-[6-[3-(Difluoromethyl)phenyl]-3-fluoro-pyrrolo[3,2-b]pyridin-1-yl]-N,N-dimethyl-acetamide; |
| 96 | 2-[3-Fluoro-6-(4-methyl-2-thienyl)pyrrolo[3,2-b]pyridin-1-yl]-N,N-dimethyl-acetamide; |
| 97 | 2-[6-(5-Chloro-2-thienyl)-3-fluoro-pyrrolo[3,2-b]pyridin-1-yl]-N,N-dimethyl-acetamide; |
| 98 | 2-[3-Fluoro-6-(4-fluorophenyl)pyrrolo[3,2-b]pyridin-1-yl]-N,N-dimethyl-acetamide; |
| 99 | N-Cyclopropyl-2-[6-[5-(trifluoromethyl)-3-pyridyl]pyrrolo[3,2-b]pyridin-1-yl]acetamide; |
| 100 | N-Cyclopropyl-2-[6-(3,4-difluorophenyl)pyrrolo[3,2-b]pyridin-1-yl]acetamide; |
| 101 | N-Cyclopropyl-2-[6-[4-fluoro-3-(trifluoromethyl)phenyl]pyrrolo[3,2-b]pyridin-1-yl]acetamide; |
| 102 | 1-(Azetidin-1-yl)-2-[6-[5-(trifluoromethyl)-3-pyridyl]pyrrolo[3,2-b]pyridin-1-yl]ethanone; |
| 103 | 1-(Azetidin-1-yl)-2-[6-(3,4-difluorophenyl)pyrrolo[3,2-b]pyridin-1-yl]ethanone; |
| 104 | 1-(Azetidin-1-yl)-2-[6-[4-fluoro-3-(trifluoromethyl)phenyl]pyrrolo[3,2-b]pyridin-1-yl]ethanone; |
| 105 | 2-[6-[4-fluoro-3-(trifluoromethyl)phenyl]pyrrolo[3,2-b]pyridin-1-yl]-1-pyrrolidin-1-yl-ethanone; |
| 106 | 1-(3,3-Difluoroazetidin-1-yl)-2-[6-[4-fluoro-3-(trifluoromethyl)phenyl]pyrrolo[3,2-b]pyridin-1-yl]ethanone; |
| 107 | 2-[6-(3,4-Difluorophenyl)pyrrolo[3,2-b]pyridin-1-yl]-1-morpholino-ethanone; |

| Example # | Compound Name |
|---|---|
| 108 | 2-[6-[4-Fluoro-3-(trifluoromethyl)phenyl]pyrrolo[3,2-b]pyridin-1-yl]-1-morpholino-ethanone; |
| 109 | 1-(Azetidin-1-yl)-2-[6-[2-(trifluoromethyl)-4-pyridyl]pyrrolo[3,2-b]pyridin-1-yl]ethanone; |
| 110 | N-Cyclopropyl-2-[6-[2-(trifluoromethyl)-4-pyridyl]pyrrolo[3,2-b]pyridin-1-yl]acetamide; |
| 111 | N-Cyclopropyl-2-[6-[6-(trifluoromethyl)-2-pyridyl]pyrrolo[3,2-b]pyridin-1-yl]acetamide; |
| 112 | 1-(Azetidin-1-yl)-2-[6-(6-methyl-3-pyridyl)pyrrolo[3,2-b]pyridin-1-yl]ethanone; |
| 113 | 5-[1-[2-(Azetidin-1-yl)-2-oxo-ethyl]pyrrolo[3,2-b]pyridin-6-yl]pyridine-2-carbonitrile; |
| 114 | 6-(3,4-Difluorophenyl)-1-(pyrimidin-5-ylmethyl)pyrrolo[3,2-b]pyridine; |
| 115 | 6-(3,4-Difluorophenyl)-1-[(5-fluoropyrimidin-2-yl)methyl]pyrrolo[3,2-b]pyridine; |
| 116 | Cyclobutyl-[6-(3,4-difluorophenyl)pyrrolo[3,2-b]pyridin-1-yl]methanone; |
| 117 | 1-(3,3-Difluoroazetidin-1-yl)-2-[6-[6-(trifluoromethyl)-2-pyridyl]pyrrolo[3,2-b]pyridin-1-yl]ethanone; |
| 118 | 1-(Azetidin-1-yl)-2-[6-(2,3,4-trifluorophenyl)pyrrolo[3,2-b]pyridin-1-yl]ethanone; |
| 119 | 2-Cyclopropyl-1-[6-(3,4-difluorophenyl)pyrrolo[3,2-b]pyridin-1-yl]ethanone; |
| 120 | 1-Pyrrolidin-1-yl-2-[6-(2,3,4-trifluorophenyl)pyrrolo[3,2-b]pyridin-1-yl]ethanone; |
| 121 | 1-(3,3-Difluoroazetidin-1-yl)-2-[6-(3,5-difluorophenyl)pyrrolo[3,2-b]pyridin-1-yl]ethanone; |
| 122 | 2-[6-(3,5-Difluorophenyl)pyrrolo[3,2-b]pyridin-1-yl]-1-pyrrolidin-1-yl-ethanone; |
| 123 | 1-Pyrrolidin-1-yl-2-[6-(3,4,5-trifluorophenyl)pyrrolo[3,2-b]pyridin-1-yl]ethanone; |
| 124 | 1-(3,3-Difluoroazetidin-1-yl)-2-[6-(3,4,5-trifluorophenyl)pyrrolo[3,2-b]pyridin-1-yl]ethanone; |
| 125 | 2-[6-(3,5-Difluorophenyl)pyrrolo[3,2-b]pyridin-1-yl]-1-morpholino-ethanone; |
| 126 | 1-Morpholino-2-[6-(2,3,4-trifluorophenyl)pyrrolo[3,2-b]pyridin-1-yl]ethanone; |
| 127 | 1-Morpholino-2-[6-(3,4,5-trifluorophenyl)pyrrolo[3,2-b]pyridin-1-yl]ethanone; |
| 128 | 2-[6-(3,4-Difluorophenyl)pyrrolo[3,2-b]pyridin-1-yl]-1-(3-fluoroazetidin-1-yl)ethanone; |
| 129 | 2-[6-(3,5-Difluorophenyl)pyrrolo[3,2-b]pyridin-1-yl]-1-(3-fluoroazetidin-1-yl)ethanone; |
| 130 | 6-(4-Methyl-2-thienyl)-1-(pyridazin-3-ylmethyl)pyrrolo[3,2-b]pyridine; |
| 131 | 6-(3,4-Difluorophenyl)-1-(pyridazin-3-ylmethyl)pyrrolo[3,2-b]pyridine; |
| 132 | 2-[6-(4-Methyl-2-thienyl)pyrrolo[3,2-b]pyridin-1-yl]-1-morpholino-ethanone; |
| 133 | 1-(Azetidin-1-yl)-2-[6-(2,4-difluorophenyl)pyrrolo[3,2-b]pyridin-1-yl]ethanone; |
| 134 | 1-(Azetidin-1-yl)-2-[6-(2,3-difluorophenyl)pyrrolo[3,2-b]pyridin-1-yl]ethanone; |
| 135 | 1-(Azetidin-1-yl)-2-[6-(2,5-difluorophenyl)pyrrolo[3,2-b]pyridin-1-yl]ethanone; |
| 136 | 1-Cyclopropyl-2-[6-(3,4-difluorophenyl)-3-fluoro-pyrrolo[3,2-b]pyridin-1-yl]ethanone; |
| 137 | 6-(4-Methyl-2-thienyl)-1-[[5-(trifluoromethyl)-2-furyl]methyl]pyrrolo[3,2-b]pyridine; |
| 138 | 6-(3,4-Difluorophenyl)-1-[[5-(trifluoromethyl)-2-furyl]methyl]pyrrolo[3,2-b]pyridine; |
| 139 | N,N-Dimethyl-2-[6-(4-methyl-2-thienyl)pyrrolo[3,2-b]pyridin-1-yl]acetamide; |
| 140 | 1-[6-(3,4-Difluorophenyl)pyrrolo[3,2-b]pyridin-1-yl]-3,3-dimethyl-butan-2-one; |
| 141 | 1-[6-(4-Fluoro-3-methyl-phenyl)pyrrolo[3,2-b]pyridin-1-yl]-3,3-dimethyl-butan-2-one; |
| 142 | 1-[6-(3,5-Difluorophenyl)pyrrolo[3,2-b]pyridin-1-yl]-3,3-dimethyl-butan-2-one; |
| 143 | 3,3-Dimethyl-1-[6-(4-methyl-2-thienyl)pyrrolo[3,2-b]pyridin-1-yl]butan-2-one; |
| 144 | 1-[6-[3-(Difluoromethyl)phenyl]pyrrolo[3,2-b]pyridin-1-yl]-3,3-dimethyl-butan-2-one; |
| 145 | 1-[6-(3-Ethylphenyl)pyrrolo[3,2-b]pyridin-1-yl]-3,3-dimethyl-butan-2-one; |
| 146 | 2-[3-Chloro-6-(4-fluoro-3-methyl-phenyl)pyrrolo[3,2-b]pyridin-1-yl]-N,N-dimethyl-acetamide; |
| 147 | 2-[3-Chloro-6-(3,4-difluorophenyl)pyrrolo[3,2-b]pyridin-1-yl]-N,N-dimethyl-acetamide; |
| 148 | 2-[3-Chloro-6-(3,5-difluorophenyl)pyrrolo[3,2-b]pyridin-1-yl]-N,N-dimethyl-acetamide; |
| 149 | 2-[3-Chloro-6-(4-methyl-2-thienyl)pyrrolo[3,2-b]pyridin-1-yl]-N,N-dimethyl-acetamide; |
| 150 | 2-[3-Chloro-6-[3-(difluoromethyl)phenyl]pyrrolo[3,2-b]pyridin-1-yl]-N,N-dimethyl-acetamide; |
| 151 | 2-[3-Chloro-6-(3-ethylphenyl)pyrrolo[3,2-b]pyridin-1-yl]-N,N-dimethyl-acetamide; |
| 152 | 2-[3-Chloro-6-(3,4,5-trifluorophenyl)pyrrolo[3,2-b]pyridin-1-yl]-N,N-dimethyl-acetamide; |
| 153 | N-Cyclopropyl-2-[6-(4-methyl-2-thienyl)pyrrolo[3,2-b]pyridin-1-yl]acetamide trifluoroacetate salt; |
| 154 | N-Cyclopropyl-2-[6-(2,3-dimethylphenyl)pyrrolo[3,2-b]pyridin-1-yl]acetamide trifluoroacetate salt; |
| 155 | N-Cyclopropyl-2-[6-(m-tolyl)pyrrolo[3,2-b]pyridin-1-yl]acetamide trifluoroacetate salt; |
| 156 | N-Cyclopropyl-2-[6-(3,4-dichlorophenyl)pyrrolo[3,2-b]pyridin-1-yl]acetamide trifluoroacetate salt; |
| 157 | N-Cyclopropyl-2-[6-[2-methyl-3-(trifluoromethyl)phenyl]pyrrolo[3,2-b]pyridin-1-yl]acetamide trifluoroacetate salt; |
| 158 | N-Cyclopropyl-2-(6-phenylpyrrolo[3,2-b]pyridin-1-yl)acetamide trifluoroacetate salt; |
| 159 | N-Cyclopropyl-2-[6-(4-fluoro-2,3-dimethyl-phenyl)pyrrolo[3,2-b]pyridin-1-yl]acetamide trifluoroacetate salt; |
| 160 | N-Cyclopropyl-2-[6-(o-tolyl)pyrrolo[3,2-b]pyridin-1-yl]acetamide; |
| 161 | N-Cyclopropyl-2-[6-(4-fluoro-2-methyl-phenyl)pyrrolo[3,2-b]pyridin-1-yl]acetamide trifluoroacetate salt; |
| 162 | 1-(Azetidin-1-yl)-2-[6-(o-tolyl)pyrrolo[3,2-b]pyridin-1-yl]ethanone trifluoroacetate salt; |
| 163 | 1-(Azetidin-1-yl)-2-[6-(4-fluoro-2-methyl-phenyl)pyrrolo[3,2-b]pyridin-1-yl]ethanone trifluoroacetate salt; |
| 164 | 1-(Azetidin-1-yl)-2-[6-(4-fluoro-2,3-dimethyl-phenyl)pyrrolo[3,2-b]pyridin-1-yl]ethanone trifluoroacetate salt; |
| 165 | 1-(Azetidin-1-yl)-2-[6-(2,3-dimethylphenyl)pyrrolo[3,2-b]pyridin-1-yl]ethanone trifluoroacetate salt; |
| 166 | 1-(Azetidin-1-yl)-2-[6-[3-(trifluoromethyl)phenyl]pyrrolo[3,2-b]pyridin-1-yl]ethanone trifluoroacetate salt; |
| 167 | 1-(Azetidin-1-yl)-2-[6-[2-methyl-3-(trifluoromethyl)phenyl]pyrrolo[3,2-b]pyridin-1-yl]ethanone trifluoroacetate salt; |
| 168 | N-Cyclopropyl-2-[6-(4-fluorophenyl)pyrrolo[3,2-b]pyridin-1-yl]acetamide; |
| 169 | 1-(Azetidin-1-yl)-2-[6-(4-fluoro-3-methyl-phenyl)-3-methyl-pyrrolo[3,2-b]pyridin-1-yl]ethanone trifluoroacetate salt; |
| 170 | 1-Butyl-6-(4-fluoro-3-methyl-phenyl)pyrrolo[3,2-b]pyridine trifluoroacetate salt; |
| 171 | 6-(4-Fluoro-3-methyl-phenyl)-1-isopentyl-pyrrolo[3,2-b]pyridine trifluoroacetate salt; |
| 172 | 6-(4-Fluoro-3-methyl-phenyl)-1-(3-pyridylmethyl)pyrrolo[3,2-b]pyridine trifluoroacetate salt; |
| 173 | 1-(Cyclobutylmethyl)-6-(4-fluoro-3-methyl-phenyl)pyrrolo[3,2-b]pyridine trifluoroacetate salt; |
| 174 | 1-(Cyclopropylmethyl)-6-(4-fluoro-3-methyl-phenyl)pyrrolo[3,2-b]pyridine trifluoroacetate salt; |
| 175 | 2-[6-(4-Fluoro-3-methyl-phenyl)pyrrolo[3,2-b]pyridin-1-yl]-N,N-dimethyl-acetamide trifluoroacetate salt; |
| 176 | 2-[3-Chloro-6-(4-fluoro-3-methyl-phenyl)pyrrolo[3,2-b]pyridin-1-yl]-N-cyclopropyl-acetamide trifluoroacetate salt; |
| 177 | 6-(4-Fluoro-3-methyl-phenyl)-1-(2-pyridylmethyl)pyrrolo[3,2-b]pyridine trifluoroacetate salt; |

| Example # | Compound Name |
|---|---|
| 178 | (R/S)-6-(4-Fluoro-3-methyl-phenyl)-1-(tetrahydrofuran-3-ylmethyl)pyrrolo[3,2-b]pyridine trifluoroacetate salt; |
| 179 | 6-(4-Fluoro-3-methyl-phenyl)-1-(4-pyridylmethyl)pyrrolo[3,2-b]pyridine trifluoroacetate salt; |
| 180 | (R/S)-6-(4-Fluoro-3-methyl-phenyl)-1-(oxiran-2-ylmethyl)pyrrolo[3,2-b]pyridine trifluoroacetate salt; |
| 181 | 6-(4-Fluoro-3-methyl-phenyl)-1-(2-pyrazol-1-ylethyl)pyrrolo[3,2-b]pyridine trifluoroacetate salt; |
| 182 | 1-(Azetidin-1-yl)-2-[6-(5-chloro-2-thienyl)-3-fluoro-pyrrolo[3,2-b]pyridin-1-yl]ethanone; |
| 183 | 6-(4-Fluoro-3-methyl-phenyl)-1-(pyrimidin-2-ylmethyl)pyrrolo[3,2-b]pyridine trifluoroacetate salt; |
| 184 | (R/S)-6-(4-Fluoro-3-methyl-phenyl)-1-(oxetan-2-ylmethyl)pyrrolo[3,2-b]pyridine trifluoroacetate salt; |
| 185 | 1-(3,3-Difluoroazetidin-1-yl)-2-[3-fluoro-6-(4-fluoro-3-methyl-phenyl)pyrrolo[3,2-b]pyridin-1-yl]ethanone; |
| 186 | 1-Cyclopropyl-2-[6-(4-fluoro-3-methyl-phenyl)pyrrolo[3,2-b]pyridin-1-yl]ethanone trifluoroacetate salt; |
| 187 | 1-[6-(4-Fluoro-3-methyl-phenyl)pyrrolo[3,2-b]pyridin-1-yl]-3-methyl-butan-2-one trifluoroacetate salt; |
| 188 | 2-[6-(4-Fluoro-3-methyl-phenyl)pyrrolo[3,2-b]pyridin-1-yl]-1-(4-hydroxy-1-piperidyl)ethanone trifluoroacetate salt; |
| 189 | (R/S)-1-(3-Azabicyclo[3.1.0]hexan-3-yl)-2-[6-(4-fluoro-3-methyl-phenyl)pyrrolo[3,2-b]pyridin-1-yl]ethanone trifluoroacetate salt; |
| 190 | 2-[6-(4-Fluoro-3-methyl-phenyl)pyrrolo[3,2-b]pyridin-1-yl]-1-(4-methoxy-1-piperidyl)ethanone trifluoroacetate salt; |
| 191 | 2-[6-(4-Fluoro-3-methyl-phenyl)pyrrolo[3,2-b]pyridin-1-yl]-1-(4-fluoro-1-piperidyl)ethanone trifluoroacetate salt; |
| 192 | 2-[6-(4-Fluoro-3-methyl-phenyl)pyrrolo[3,2-b]pyridin-1-yl]-1-[4-(fluoromethyl)-1-piperidyl]ethanone trifluoroacetate salt; |
| 193 | 2-[6-(4-Fluoro-3-methyl-phenyl)pyrrolo[3,2-b]pyridin-1-yl]-1-(1-piperidyl)ethanone trifluoroacetate salt; |
| 194 | (R/S)-2-[6-(4-Fluoro-3-methyl-phenyl)pyrrolo[3,2-b]pyridin-1-yl]-1-(2-methylmorpholin-4-yl)ethanone trifluoroacetate salt; |
| 195 | (R/S)-2-[6-(4-Fluoro-3-methyl-phenyl)pyrrolo[3,2-b]pyridin-1-yl]-1-[3-(trifluoromethyl)-1-piperidyl]ethanone trifluoroacetate salt; |
| 196 | (R/S)-1-(2-Ethylpyrrolidin-1-yl)-2-[6-(4-fluoro-3-methyl-phenyl)pyrrolo[3,2-b]pyridin-1-yl]ethanone trifluoroacetate salt; |
| 197 | 1-(2,2-Dimethylmorpholin-4-yl)-2-[6-(4-fluoro-3-methyl-phenyl)pyrrolo[3,2-b]pyridin-1-yl]ethanone trifluoroacetate salt; |
| 198 | (R/S)-2-[6-(4-Fluoro-3-methyl-phenyl)pyrrolo[3,2-b]pyridin-1-yl]-1-(3-methoxypyrrolidin-1-yl)ethanone trifluoroacetate salt; |
| 199 | (R/S)-2-[6-(4-Fluoro-3-methyl-phenyl)pyrrolo[3,2-b]pyridin-1-yl]-1-(3-fluoro-1-piperidyl)ethanone trifluoroacetate salt; |
| 200 | 1-(2,2-Dimethylpyrrolidin-1-yl)-2-[6-(4-fluoro-3-methyl-phenyl)pyrrolo[3,2-b]pyridin-1-yl]ethanone trifluoroacetate salt; |
| 201 | 2-[6-(4-Fluoro-3-methyl-phenyl)pyrrolo[3,2-b]pyridin-1-yl]-1-[(3R)-3-fluoropyrrolidin-1-yl]ethanone trifluoroacetate salt; |
| 202 | 2-[6-(4-Fluorophenyl)pyrrolo[3,2-b]pyridin-1-yl]-1-(3-hydroxy-3-methyl-azetidin-1-yl)ethanone; |
| 203 | 2-[6-(4-Fluorophenyl)pyrrolo[3,2-b]pyridin-1-yl]-1-[3-hydroxy-3-(trifluoromethyl)azetidin-1-yl]ethanone; |
| 204 | 1-(3-Fluoroazetidin-1-yl)-2-[6-(4-fluorophenyl)pyrrolo[3,2-b]pyridin-1-yl]ethanone; |
| 205 | N-Cyclopropyl-2-[6-(4-fluorophenyl)pyrrolo[3,2-b]pyridin-1-yl]-N-methyl-acetamide; |
| 206 | 2-[6-(4-Fluorophenyl)pyrrolo[3,2-b]pyridin-1-yl]-1-[3-(hydroxymethyl)azetidin-1-yl]ethanone; |
| 207 | 2-[6-(4-Fluorophenyl)pyrrolo[3,2-b]pyridin-1-yl]-1-(3-methoxyazetidin-1-yl)ethanone; |
| 208 | 1-(5-Azaspiro[2.3]hexan-5-yl)-2-[6-(4-fluoro-3-methyl-phenyl)pyrrolo[3,2-b]pyridin-1-yl]ethanone trifluoroacetate salt; |
| 209 | 2-[6-(4-Fluoro-3-methyl-phenyl)pyrrolo[3,2-b]pyridin-1-yl]-1-(4-hydroxy-4-methyl-1-piperidyl)ethanone trifluoroacetate salt; |
| 210 | (R/S)-2-[6-(4-Fluoro-3-methyl-phenyl)pyrrolo[3,2-b]pyridin-1-yl]-1-(3-methylmorpholin-4-yl)ethanone trifluoroacetate salt; |
| 211 | 2-[6-(4-Fluorophenyl)pyrrolo[3,2-b]pyridin-1-yl]-1-(3-hydroxyazetidin-1-yl)ethanone; |
| 212 | 1-[2-[6-(4-Fluorophenyl)pyrrolo[3,2-b]pyridin-1-yl]acetyl]azetidine-3-carbonitrile; |
| 213 | 1-(3,3-Difluoroazetidin-1-yl)-2-[6-(4-fluorophenyl)pyrrolo[3,2-b]pyridin-1-yl]ethanone; |
| 214 | 2-[6-(4-Fluorophenyl)pyrrolo[3,2-b]pyridin-1-yl]-1-(3-methylazetidin-1-yl)ethanone; |
| 215 | 1-(3,3-Dimethylazetidin-1-yl)-2-[6-(4-fluorophenyl)pyrrolo[3,2-b]pyridin-1-yl]ethanone; |
| 216 | 1-[2-[6-(4-Fluorophenyl)pyrrolo[3,2-b]pyridin-1-yl]acetyl]pyrrolidin-3-one trifluoroacetate salt; |
| 217 | 1-(3,3-Difluoropyrrolidin-1-yl)-2-[6-(4-fluorophenyl)pyrrolo[3,2-b]pyridin-1-yl]ethanone; |
| 218 | (R/S)-2-[6-(4-Fluorophenyl)pyrrolo[3,2-b]pyridin-1-yl]-1-(3-hydroxypyrrolidin-1-yl)ethanone; |
| 219 | 1-Cyclopropyl-2-[6-(m-tolyl)pyrrolo[3,2-b]pyridin-1-yl]ethanone; |
| 220 | 1-Cyclopropyl-2-(6-phenylpyrrolo[3,2-b]pyridin-1-yl)ethanone; |
| 221 | 1-Cyclopropyl-2-[6-(3-fluorophenyl)pyrrolo[3,2-b]pyridin-1-yl]ethanone; |
| 222 | 1-Cyclopropyl-2-[6-(4-fluorophenyl)pyrrolo[3,2-b]pyridin-1-yl]ethanone; |
| 223 | 1-[6-(4-Fluoro-2,3-dimethyl-phenyl)pyrrolo[3,2-b]pyridin-1-yl]-3-methyl-butan-2-one; |
| 224 | 1-[6-(3-Ethylphenyl)pyrrolo[3,2-b]pyridin-1-yl]-3-methyl-butan-2-one; |
| 225 | 1-[6-(2,3-Dimethylphenyl)pyrrolo[3,2-b]pyridin-1-yl]-3-methyl-butan-2-one; |
| 226 | 2-[6-(4-Fluorophenyl)pyrrolo[3,2-b]pyridin-1-yl]-1-phenyl-ethanone; |
| 227 | 1-(4-Fluorophenyl)-2-[6-(4-fluorophenyl)pyrrolo[3,2-b]pyridin-1-yl]ethanone; |
| 228 | (R/S)-6-(4-Fluorophenyl)-1-(tetrahydropyran-2-ylmethyl)pyrrolo[3,2-b]pyridine trifluoroacetate salt; |
| 229 | 2-[6-(4-Fluorophenyl)pyrrolo[3,2-b]pyridin-1-yl]-N-isopropyl-acetamide; |
| 230 | 2-[6-(4-Fluorophenyl)pyrrolo[3,2-b]pyridin-1-yl]-N-propyl-acetamide; |
| 231 | (R/S)-2-[6-(4-Fluorophenyl)pyrrolo[3,2-b]pyridin-1-yl]-N-(2,2,2-trifluoro-1-methyl-ethyl)acetamide; |
| 232 | 2-[6-(4-Fluorophenyl)pyrrolo[3,2-b]pyridin-1-yl]-N-(1-methylcyclopropyl)acetamide; |
| 233 | N-(2-Fluoroethyl)-2-[6-(4-fluorophenyl)pyrrolo[3,2-b]pyridin-1-yl]acetamide; |
| 234 | 2-[6-(4-Fluorophenyl)pyrrolo[3,2-b]pyridin-1-yl]-N-isobutyl-acetamide; |
| 235 | 5-[[6-(4-Fluoro-3-methyl-phenyl)pyrrolo[3,2-b]pyridin-1-yl]methyl]-3-methyl-1,2,4-oxadiazole; |
| 236 | 6-(4-Fluoro-3-methyl-phenyl)-1-[(1-methylpyrazol-4-yl)methyl]pyrrolo[3,2-b]pyridine; |
| 237 | N-(Cyclopropylmethyl)-2-[6-(4-fluorophenyl)pyrrolo[3,2-b]pyridin-1-yl]acetamide; |
| 238 | 6-(4-Fluoro-3-methyl-phenyl)-1-[(1-methyltriazol-4-yl)methyl]pyrrolo[3,2-b]pyridine; |
| 239 | 5-[[3-Chloro-6-(4-fluoro-3-methyl-phenyl)pyrrolo[3,2-b]pyridin-1-yl]methyl]-3-methyl-1,2,4-oxadiazole; |
| 240 | 3-Chloro-6-(4-fluoro-3-methyl-phenyl)-1-[(1-methylpyrazol-4-yl)methyl]pyrrolo[3,2-b]pyridine; |
| 241 | 2-[3-Chloro-6-(4-fluoro-3-methyl-phenyl)pyrrolo[3,2-b]pyridin-1-yl]-1-cyclobutyl-ethanone; |
| 242 | 1-Cyclobutyl-2-[6-(4-fluoro-3-methyl-phenyl)pyrrolo[3,2-b]pyridin-1-yl]ethanone; |
| 243 | 1-(Azetidin-1-yl)-2-[3-chloro-6-[5-(trifluoromethyl)-3-pyridyl]pyrrolo[3,2-b]pyridin-1-yl]ethanone trifluoroacetate salt; |

| Example # | Compound Name |
|---|---|
| 244 | 2-[3-Chloro-6-[5-(trifluoromethyl)-3-pyridyl]pyrrolo[3,2-b]pyridin-1-yl]-N-cyclopropyl-acetamide trifluoroacetate salt; |
| 245 | 1-(Azetidin-1-yl)-2-[3-chloro-6-[6-(trifluoromethyl)-2-pyridyl]pyrrolo[3,2-b]pyridin-1-yl]ethanone; |
| 246 | 2-[3-Chloro-6-[6-(trifluoromethyl)-2-pyridyl]pyrrolo[3,2-b]pyridin-1-yl]-N-cyclopropyl-acetamide; |
| 247 | 2-[3-Chloro-6-[6-(trifluoromethyl)-2-pyridyl]pyrrolo[3,2-b]pyridin-1-yl]-1-(3-fluoroazetidin-1-yl)ethanone; |
| 248 | N-Cyclopropyl-2-[6-(3,4,5-trifluorophenyl)pyrrolo[3,2-b]pyridin-1-yl]acetamide; |
| 249 | N-Cyclopropyl-2-[6-(2,3,4-trifluorophenyl)pyrrolo[3,2-b]pyridin-1-yl]acetamide; |
| 250 | N-Cyclopropyl-2-[6-[3-(difluoromethyl)phenyl]pyrrolo[3,2-b]pyridin-1-yl]acetamide; |
| 251 | N-Benzyl-2-[6-(4-fluorophenyl)pyrrolo[3,2-b]pyridin-1-yl]acetamide; |
| 252 | 2-[[6-(4-Fluoro-3-methyl-phenyl)pyrrolo[3,2-b]pyridin-1-yl]methyl]oxazole; |
| 253 | 2-[6-(4-Fluorophenyl)pyrrolo[3,2-b]pyridin-1-yl]-N-(2-hydroxyethyl)acetamide; |
| 254 | 2-[6-(4-Fluorophenyl)pyrrolo[3,2-b]pyridin-1-yl]-N-(2-methoxyethyl)acetamide; |
| 255 | 1-(3,3-Difluoroazetidin-1-yl)-2-[6-[2-fluoro-3-(trifluoromethyl)phenyl]pyrrolo[3,2-b]pyridin-1-yl]ethanone trifluoroacetate salt; |
| 256 | 1-(3,3-Difluoroazetidin-1-yl)-2-[6-(3-fluorophenyl)pyrrolo[3,2-b]pyridin-1-yl]ethanone trifluoroacetate salt; |
| 257 | 1-(3,3-Difluoroazetidin-1-yl)-2-(6-phenylpyrrolo[3,2-b]pyridin-1-yl)ethanone trifluoroacetate salt; |
| 258 | 1-(3,3-Difluoroazetidin-1-yl)-2-[6-(3-ethylphenyl)pyrrolo[3,2-b]pyridin-1-yl]ethanone trifluoroacetate salt; |
| 259 | 1-(3,3-Difluoroazetidin-1-yl)-2-[6-(4-fluoro-3-methyl-phenyl)pyrrolo[3,2-b]pyridin-1-yl]ethanone trifluoroacetate salt; |
| 260 | 1-(3,3-Difluoroazetidin-1-yl)-2-[6-[3-(trifluoromethyl)phenyl]pyrrolo[3,2-b]pyridin-1-yl]ethanone trifluoroacetate salt; |
| 261 | 1-(3,3-Difluoroazetidin-1-yl)-2-[6-(4-fluoro-2-methyl-phenyl)pyrrolo[3,2-b]pyridin-1-yl]ethanone trifluoroacetate salt; |
| 262 | 1-(3-Fluoroazetidin-1-yl)-2-[6-[4-fluoro-3-(trifluoromethyl)phenyl]pyrrolo[3,2-b]pyridin-1-yl]ethanone trifluoroacetate salt; |
| 263 | 1-(3-Fluoroazetidin-1-yl)-2-[6-(3-fluorophenyl)pyrrolo[3,2-b]pyridin-1-yl]ethanone trifluoroacetate salt; |
| 264 | 1-(3-Fluoroazetidin-1-yl)-2-[6-(4-fluoro-2-methyl-phenyl)pyrrolo[3,2-b]pyridin-1-yl]ethanone trifluoroacetate salt; |
| 265 | 1-(3-Fluoroazetidin-1-yl)-2-[6-[3-(trifluoromethyl)phenyl]pyrrolo[3,2-b]pyridin-1-yl]ethanone trifluoroacetate salt; |
| 266 | 1-(3-Fluoroazetidin-1-yl)-2-[6-(m-tolyl)pyrrolo[3,2-b]pyridin-1-yl]ethanone trifluoroacetate salt; |
| 267 | 1-(3-Fluoroazetidin-1-yl)-2-[6-[2-fluoro-3-(trifluoromethyl)phenyl]pyrrolo[3,2-b]pyridin-1-yl]ethanone trifluoroacetate salt; |
| 268 | 2-[6-(3-Ethylphenyl)pyrrolo[3,2-b]pyridin-1-yl]-1-(3-fluoroazetidin-1-yl)ethanone trifluoroacetate salt; |
| 269 | 1-(3,3-Difluoroazetidin-1-yl)-2-[6-(m-tolyl)pyrrolo[3,2-b]pyridin-1-yl]ethanone; |
| 270 | 1-(3-Fluoroazetidin-1-yl)-2-(6-phenylpyrrolo[3,2-b]pyridin-1-yl)ethanone; |
| 271 | 1-(3,3-Difluoroazetidin-1-yl)-2-[6-(2,4-difluoro-3-methyl-phenyl)-3-fluoro-pyrrolo[3,2-b]pyridin-1-yl]ethanone; |
| 272 | (R/S)-1-[6-(3,5-Difluorophenyl)pyrrolo[3,2-b]pyridin-1-yl]-3-methyl-butan-2-ol; |
| 273 | 2-[6-(4-Fluoro-3-methyl-phenyl)pyrrolo[3,2-b]pyridin-1-yl]-1-(3-hydroxyazetidin-1-yl)ethanone; |
| 274 | (R/S)-1-Cyclopropyl-2-[6-(4-fluoro-3-methyl-phenyl)pyrrolo[3,2-b]pyridin-1-yl]ethanol; |
| 275 | (R/S)-2-Cyclopropyl-1-[6-(4-fluoro-3-methyl-phenyl)pyrrolo[3,2-b]pyridin-1-yl]propan-2-ol trifluoroacetate salt; |
| 276 | 1-Cyclopropyl-2-[6-(4-fluoro-3-methyl-phenyl)pyrrolo[3,2-b]pyridin-1-yl]-N-methoxy-ethanimine; |
| 277 | 1-(3-Fluoroazetidin-1-yl)-2-[6-(2-thienyl)pyrrolo[3,2-b]pyridin-1-yl]ethanone; |
| 278 | 1-Pyrrolidin-1-yl-2-[6-(2-thienyl)pyrrolo[3,2-b]pyridin-1-yl]ethanone; |
| 279 | 1-(3,3-Difluoroazetidin-1-yl)-2-[6-(5-methyl-2-thienyl)pyrrolo[3,2-b]pyridin-1-yl]ethanone; |
| 280 | 1-(3-Fluoroazetidin-1-yl)-2-[6-(5-methyl-2-thienyl)pyrrolo[3,2-b]pyridin-1-yl]ethanone; |
| 281 | 2-[6-(5-Ethyl-2-thienyl)pyrrolo[3,2-b]pyridin-1-yl]-1-(3-fluoroazetidin-1-yl)ethanone; |
| 282 | 2-[6-(5-Ethyl-2-thienyl)pyrrolo[3,2-b]pyridin-1-yl]-1-pyrrolidin-1-yl-ethanone; |
| 283 | 2-[6-(5-Methyl-2-thienyl)pyrrolo[3,2-b]pyridin-1-yl]-1-pyrrolidin-1-yl-ethanone; |
| 284 | 1-(3,3-Difluoroazetidin-1-yl)-2-[6-(5-ethyl-2-thienyl)pyrrolo[3,2-b]pyridin-1-yl]ethanone; |
| 285 | 2-[6-(4-Chloro-2-thienyl)pyrrolo[3,2-b]pyridin-1-yl]-1-(3-fluoroazetidin-1-yl)ethanone; |
| 286 | 1-Cyclopropyl-2-[6-(4-fluoro-3-methyl-phenyl)pyrrolo[3,2-b]pyridin-1-yl]ethanone oxime trifluoroacetate salt; |
| 287 | 2-[6-(5-Chloro-2-thienyl)pyrrolo[3,2-b]pyridin-1-yl]-1-pyrrolidin-1-yl-ethanone; |
| 288 | 2-[6-(4-Chloro-2-thienyl)pyrrolo[3,2-b]pyridin-1-yl]-1-pyrrolidin-1-yl-ethanone; |
| 289 | (R/S)-1-(2-Cyclopropyl-2-fluoro-ethyl)-6-(4-fluoro-3-methyl-phenyl)pyrrolo[3,2-b]pyridine; |
| 290 | 2-[6-(4-Fluoro-3-methyl-phenyl)pyrrolo[3,2-b]pyridin-1-yl]-1-(3-methoxyazetidin-1-yl)ethanone; |
| 291 | 6-(4-Fluoro-3-methyl-phenyl)-1-(2-methoxyethyl)pyrrolo[3,2-b]pyridine trifluoroacetate salt; |
| 292 | 1-Cyclobutyl-2-[6-(3-fluorophenyl)pyrrolo[3,2-b]pyridin-1-yl]ethanone; |
| 293 | 2-[6-(4-Fluorophenyl)pyrrolo[3,2-b]pyridin-1-yl]-1-[(3R)-3-fluoropyrrolidin-1-yl]ethanone trifluoroacetate salt; |
| 294 | 2-[6-(4-Fluorophenyl)pyrrolo[3,2-b]pyridin-1-yl]-1-[(3S)-3-fluoropyrrolidin-1-yl]ethanone trifluoroacetate salt; |
| 295 | 1-[6-(4-Fluoro-3-methyl-phenyl)pyrrolo[3,2-b]pyridin-1-yl]butan-2-one trifluoroacetate salt; |
| 296 | N-Ethyl-2-[6-(4-fluoro-3-methyl-phenyl)pyrrolo[3,2-b]pyridin-1-yl]-N-methyl-acetamide; |
| 297 | N,N-Diethyl-2-[6-(4-fluoro-3-methyl-phenyl)pyrrolo[3,2-b]pyridin-1-yl]acetamide; |
| 298 | 1-(Azetidin-1-yl)-2-[3-chloro-6-[3-(trifluoromethyl)phenyl]pyrrolo[3,2-b]pyridin-1-yl]ethanone; |
| 299 | 2-[3-Chloro-6-(m-tolyl)pyrrolo[3,2-b]pyridin-1-yl]-1-cyclopropyl-ethanone; |
| 300 | 2-(3-Chloro-6-phenyl-pyrrolo[3,2-b]pyridin-1-yl)-1-cyclopropyl-ethanone; |
| 301 | 1-(Azetidin-1-yl)-2-[3-chloro-6-(3,4,5-trifluorophenyl)pyrrolo[3,2-b]pyridin-1-yl]ethanone; |
| 302 | 1-(Azetidin-1-yl)-2-[3-fluoro-6-(4-fluorophenyl)pyrrolo[3,2-b]pyridin-1-yl]ethanone; |
| 303 | 1-(Azetidin-1-yl)-2-[3-chloro-6-(3,5-dimethylphenyl)pyrrolo[3,2-b]pyridin-1-yl]ethanone; |
| 304 | 2-[3-Fluoro-6-(4-fluoro-3-methyl-phenyl)pyrrolo[3,2-b]pyridin-1-yl]-1-morpholino-ethanone; |
| 305 | 2-[3-Fluoro-6-(4-fluorophenyl)pyrrolo[3,2-b]pyridin-1-yl]-1-morpholino-ethanone; |
| 306 | 1-(3-Fluoroazetidin-1-yl)-2-[3-fluoro-6-(3,4,5-trifluorophenyl)pyrrolo[3,2-b]pyridin-1-yl]ethanone; |
| 307 | 1-(3-Fluoroazetidin-1-yl)-2-[3-fluoro-6-(4-fluoro-3-methyl-phenyl)pyrrolo[3,2-b]pyridin-1-yl]ethanone; |
| 308 | 1-(3-Fluoroazetidin-1-yl)-2-[3-fluoro-6-(4-fluorophenyl)pyrrolo[3,2-b]pyridin-1-yl]ethanone; |

| Example # | Compound Name |
|---|---|
| 309 | 1-(3-Fluoroazetidin-1-yl)-2-[3-fluoro-6-(4-methyl-2-thienyl)pyrrolo[3,2-b]pyridin-1-yl]ethanone; |
| 310 | 2-[6-[3-(Difluoromethyl)phenyl]-3-fluoro-pyrrolo[3,2-b]pyridin-1-yl]-1-(3-fluoroazetidin-1-yl)ethanone; |
| 311 | 2-[6-(3,4-Difluorophenyl)-3-fluoro-pyrrolo[3,2-b]pyridin-1-yl]-1-(3-fluoroazetidin-1-yl)ethanone; |
| 312 | 1-(Azetidin-1-yl)-2-[3-chloro-6-(2,3,4-trifluorophenyl)pyrrolo[3,2-b]pyridin-1-yl]ethanone; |
| 313 | 2-[3-Fluoro-6-(4-fluoro-3-methyl-phenyl)pyrrolo[3,2-b]pyridin-1-yl]-1-pyrrolidin-1-yl-ethanone; |
| 314 | 2-[3-Fluoro-6-(4-fluorophenyl)pyrrolo[3,2-b]pyridin-1-yl]-1-pyrrolidin-1-yl-ethanone; |
| 315 | 2-[3-Fluoro-6-(3,4,5-trifluorophenyl)pyrrolo[3,2-b]pyridin-1-yl]-1-pyrrolidin-1-yl-ethanone; |
| 316 | 1-Cyclopropyl-2-[3-fluoro-6-(4-fluoro-3-methyl-phenyl)pyrrolo[3,2-b]pyridin-1-yl]ethanone; |
| 317 | 1-Cyclopropyl-2-[3-fluoro-6-(4-methyl-2-thienyl)pyrrolo[3,2-b]pyridin-1-yl]ethanone; |
| 318 | 2-[6-(5-Chloro-2-thienyl)-3-fluoro-pyrrolo[3,2-b]pyridin-1-yl]-1-cyclopropyl-ethanone; |
| 319 | 1-Cyclopropyl-2-[3-fluoro-6-(4-fluorophenyl)pyrrolo[3,2-b]pyridin-1-yl]ethanone; |
| 320 | 1-Cyclopropyl-2-[3-fluoro-6-(3,4,5-trifluorophenyl)pyrrolo[3,2-b]pyridin-1-yl]ethanone; |
| 321 | 1-Cyclopropyl-2-[6-[3-(difluoromethyl)phenyl]-3-fluoro-pyrrolo[3,2-b]pyridin-1-yl]ethanone; |
| 322 | 1-(Azetidin-1-yl)-2-[3-fluoro-6-(4-methyl-2-thienyl)pyrrolo[3,2-b]pyridin-1-yl]ethanone; |
| 323 | 1-(Azetidin-1-yl)-2-[6-[3-(difluoromethyl)phenyl]-3-fluoro-pyrrolo[3,2-b]pyridin-1-yl]ethanone; |
| 324 | 1-[3-Fluoro-6-(4-fluoro-3-methyl-phenyl)pyrrolo[3,2-b]pyridin-1-yl]-3-methyl-butan-2-one; |
| 325 | 1-[6-(3-Ethylphenyl)-3-fluoro-pyrrolo[3,2-b]pyridin-1-yl]-3-methyl-butan-2-one; |
| 326 | 1-[6-(3,4-Difluorophenyl)-3-fluoro-pyrrolo[3,2-b]pyridin-1-yl]-3-methyl-butan-2-one; |
| 327 | 1-[3-Fluoro-6-(3-fluorophenyl)pyrrolo[3,2-b]pyridin-1-yl]-3-methyl-butan-2-one; |
| 328 | 1-[3-Fluoro-6-[3-(trifluoromethyl)phenyl]pyrrolo[3,2-b]pyridin-1-yl]-3-methyl-butan-2-one; |
| 329 | 1-[3-Fluoro-6-(m-tolyl)pyrrolo[3,2-b]pyridin-1-yl]-3-methyl-butan-2-one; |
| 330 | 6-(4-Fluoro-3-methyl-phenyl)-1-(methylsulfanylmethyl)pyrrolo[3,2-b]pyridine; |
| 331 | (R/S)-6-(4-Fluoro-3-methyl-phenyl)-1-(methylsulfinylmethyl)pyrrolo[3,2-b]pyridine; |
| 332 | 6-(4-Fluoro-3-methyl-phenyl)-1-(methylsulfonylmethyl)pyrrolo[3,2-b]pyridine; |
| 333 | 1-[3-Fluoro-6-(4-fluorophenyl)pyrrolo[3,2-b]pyridin-1-yl]butan-2-one; |
| 334 | 1-[3-Fluoro-6-(3,4,5-trifluorophenyl)pyrrolo[3,2-b]pyridin-1-yl]butan-2-one; |
| 335 | 1-[3-Fluoro-6-(4-fluoro-3-methyl-phenyl)pyrrolo[3,2-b]pyridin-1-yl]butan-2-one; |
| 336 | 1-[6-(3,4-Difluorophenyl)-3-fluoro-pyrrolo[3,2-b]pyridin-1-yl]butan-2-one; |
| 337 | 1-[6-[3-(Difluoromethyl)phenyl]-3-fluoro-pyrrolo[3,2-b]pyridin-1-yl]butan-2-one; |
| 338 | 1-[6-(5-Chloro-2-thienyl)-3-fluoro-pyrrolo[3,2-b]pyridin-1-yl]butan-2-one; |
| 339 | 1-[3-Fluoro-6-(4-methyl-2-thienyl)pyrrolo[3,2-b]pyridin-1-yl]butan-2-one; |
| 340 | 4-[6-(4-Fluorophenyl)pyrrolo[3,2-b]pyridin-1-yl]butan-2-one; |
| 341 | 1-[3-Fluoro-6-(4-fluorophenyl)pyrrolo[3,2-b]pyridin-1-yl]-3-methyl-butan-2-one; |
| 342 | 1-[6-[3-(Difluoromethyl)phenyl]-3-fluoro-pyrrolo[3,2-b]pyridin-1-yl]-3-methyl-butan-2-one; |
| 343 | 1-[3-Fluoro-6-(4-methyl-2-thienyl)pyrrolo[3,2-b]pyridin-1-yl]-3-methyl-butan-2-one; |
| 344 | 1-[3-Fluoro-6-(3,4,5-trifluorophenyl)pyrrolo[3,2-b]pyridin-1-yl]-3-methyl-butan-2-one; |
| 345 | 1-[6-(5-Chloro-2-thienyl)-3-fluoro-pyrrolo[3,2-b]pyridin-1-yl]-3-methyl-butan-2-one; |
| 346 | 2-[6-(4-Fluoro-3-methyl-phenyl)pyrrolo[3,2-b]pyridin-1-yl]-1-morpholino-ethanone; |
| 347 | 1-(3-Fluoroazetidin-1-yl)-2-[6-(4-fluoro-3-methyl-phenyl)pyrrolo[3,2-b]pyridin-1-yl]ethanone; |
| 348 | N-Cyclopropyl-2-[6-(4-fluoro-3-methyl-phenyl)pyrrolo[3,2-b]pyridin-1-yl]acetamide; |
| 349 | 1-(Azetidin-1-yl)-2-[6-(4-fluoro-3-methyl-phenyl)pyrrolo[3,2-b]pyridin-1-yl]ethanone; |
| 350 | N-Cyclopropyl-2-[6-(3,5-difluorophenyl)pyrrolo[3,2-b]pyridin-1-yl]acetamide trifluoroacetate salt; |
| 351 | N-Cyclopropyl-2-[6-[3-(trifluoromethyl)phenyl]pyrrolo[3,2-b]pyridin-1-yl]acetamide trifluoroacetate salt; |
| 352 | N-Cyclopropyl-2-[6-[2-fluoro-3-(trifluoromethyl)phenyl]pyrrolo[3,2-b]pyridin-1-yl]acetamide trifluoroacetate salt; |
| 353 | 1-(Azetidin-1-yl)-2-[6-(4-fluorophenyl)pyrrolo[3,2-b]pyridin-1-yl]ethanone; |
| 354 | 1-(Azetidin-1-yl)-2-(6-phenylpyrrolo[3,2-b]pyridin-1-yl)ethanone; |
| 355 | 1-(Azetidin-1-yl)-2-[6-(3,5-difluorophenyl)pyrrolo[3,2-b]pyridin-1-yl]ethanone; |
| 356 | 1-(Azetidin-1-yl)-2-[6-(m-tolyl)pyrrolo[3,2-b]pyridin-1-yl]ethanone trifluoroacetate salt; |
| 357 | 1-(Azetidin-1-yl)-2-[6-(3,4-dichlorophenyl)pyrrolo[3,2-b]pyridin-1-yl]ethanone trifluoroacetate salt; |
| 358 | 1-(Azetidin-1-yl)-2-[6-[2-fluoro-3-(trifluoromethyl)phenyl]pyrrolo[3,2-b]pyridin-1-yl]ethanone trifluoroacetate salt; |
| 359 | 1-(Azetidin-1-yl)-2-[6-(4-methyl-2-thienyl)pyrrolo[3,2-b]pyridin-1-yl]ethanone trifluoroacetate salt; |
| 360 | 1-(Azetidin-1-yl)-2-[3-chloro-6-(4-fluoro-3-methyl-phenyl)pyrrolo[3,2-b]pyridin-1-yl]ethanone; |
| 361 | 1-(3,3-Difluoroazetidin-1-yl)-2-[6-(3,4-difluorophenyl)pyrrolo[3,2-b]pyridin-1-yl]ethanone; |
| 362 | 1-(Azetidin-1-yl)-2-[6-[6-(trifluoromethyl)-2-pyridyl]pyrrolo[3,2-b]pyridin-1-yl]ethanone; |
| 363 | 1-(Azetidin-1-yl)-2-[6-(3,4,5-trifluorophenyl)pyrrolo[3,2-b]pyridin-1-yl]ethanone; |
| 364 | 1-[6-(3,5-Difluorophenyl)pyrrolo[3,2-b]pyridin-1-yl]-3-methyl-butan-2-one; |
| 365 | 1-Cyclobutyl-2-[6-(4-fluorophenyl)pyrrolo[3,2-b]pyridin-1-yl]ethanone; |
| 366 | N-Cyclopropyl-2-[6-(3-ethylphenyl)pyrrolo[3,2-b]pyridin-1-yl]acetamide; |
| 367 | 2-[6-(3,4-Difluorophenyl)pyrrolo[3,2-b]pyridin-1-yl]-1-pyrrolidin-1-yl-ethanone; |
| 368 | 1-(3,3-Difluoroazetidin-1-yl)-2-[6-(4-methyl-2-thienyl)pyrrolo[3,2-b]pyridin-1-yl]ethanone; |
| 369 | 2-[6-(4-Methyl-2-thienyl)pyrrolo[3,2-b]pyridin-1-yl]-1-pyrrolidin-1-yl-ethanone; |
| 370 | 1-(3-Fluoroazetidin-1-yl)-2-[6-(4-methyl-2-thienyl)pyrrolo[3,2-b]pyridin-1-yl]ethanone; |
| 371 | 1-(3-Fluoroazetidin-1-yl)-2-[6-(3,4,5-trifluorophenyl)pyrrolo[3,2-b]pyridin-1-yl]ethanone; |
| 372 | 2-[6-(5-Chloro-2-thienyl)pyrrolo[3,2-b]pyridin-1-yl]-1-(3-fluoroazetidin-1-yl)ethanone; |
| 373 | 1-(Azetidin-1-yl)-2-[6-(5-chloro-2-thienyl)pyrrolo[3,2-b]pyridin-1-yl]ethanone; |
| 374 | 2-[3-Chloro-6-(2,3,4-trifluorophenyl)pyrrolo[3,2-b]pyridin-1-yl]-1-(3-fluoroazetidin-1-yl)ethanone; |
| 375 | N,N-Dimethyl-2-[6-(3,4,5-trifluorophenyl)pyrrolo[3,2-b]pyridin-1-yl]acetamide; |
| 376 | 2-[6-(3,5-Difluorophenyl)pyrrolo[3,2-b]pyridin-1-yl]-N,N-dimethyl-acetamide; |
| 377 | 2-[6-[3-(Difluoromethyl)phenyl]pyrrolo[3,2-b]pyridin-1-yl]-N,N-dimethyl-acetamide; |
| 378 | 2-[6-(5-Chloro-2-thienyl)pyrrolo[3,2-b]pyridin-1-yl]-N,N-dimethyl-acetamide; |
| 379 | 2-[6-(3,4-Difluorophenyl)pyrrolo[3,2-b]pyridin-1-yl]-N,N-dimethyl-acetamide; |
| 380 | 1-(Azetidin-1-yl)-2-[6-(5-methyl-2-thienyl)pyrrolo[3,2-b]pyridin-1-yl]ethanone; |
| 381 | 1-(Azetidin-1-yl)-2-[3-chloro-6-(5-chloro-2-thienyl)pyrrolo[3,2-b]pyridin-1-yl]ethanone; |
| 382 | 1-(Azetidin-1-yl)-2-[6-(3,4-difluorophenyl)-3-fluoro-pyrrolo[3,2-b]pyridin-1-yl]ethanone; |
| 383 | 1-(Azetidin-1-yl)-2-[3-fluoro-6-(3,4,5-trifluorophenyl)pyrrolo[3,2-b]pyridin-1-yl]ethanone; |

| Example # | Compound Name |
|---|---|
| 384 | 2-[3-Chloro-6-(4-fluorophenyl)pyrrolo[3,2-b]pyridin-1-yl]-1-cyclopropyl-ethanone; |
| 385 | 1-(Azetidin-1-yl)-2-[6-(3-thienyl)pyrrolo[3,2-b]pyridin-1-yl]ethanone trifluoroacetate salt; |
| 386 | N,N-Dimethyl-2-[6-(5-methyl-2-thienyl)pyrrolo[3,2-b]pyridin-1-yl]acetamide trifluoroacetate salt; |
| 387 | 2-[3-Fluoro-6-(2-thienyl)pyrrolo[3,2-b]pyridin-1-yl]-N,N-dimethyl-acetamide; |
| 388 | 2-[6-(5-Ethyl-2-thienyl)pyrrolo[3,2-b]pyridin-1-yl]-N,N-dimethyl-acetamide trifluoroacetate salt; |
| 389 | 1-(Azetidin-1-yl)-2-[3-fluoro-6-(2-thienyl)pyrrolo[3,2-b]pyridin-1-yl]ethanone trifluoroacetate salt; |
| 390 | 2-[3-Fluoro-6-(5-methyl-2-thienyl)pyrrolo[3,2-b]pyridin-1-yl]-N,N-dimethyl-acetamide; |
| 391 | 2-[6-(4-Chloro-2-thienyl)pyrrolo[3,2-b]pyridin-1-yl]-N,N-dimethyl-acetamide trifluoroacetate salt; |
| 392 | 1-(Azetidin-1-yl)-2-[6-(5-ethyl-2-thienyl)pyrrolo[3,2-b]pyridin-1-yl]ethanone trifluoroacetate salt; |
| 393 | 2-[6-(5-Ethyl-2-thienyl)-3-fluoro-pyrrolo[3,2-b]pyridin-1-yl]-N,N-dimethyl-acetamide; |
| 394 | 1-(Azetidin-1-yl)-2-[6-(4-chloro-2-thienyl)pyrrolo[3,2-b]pyridin-1-yl]ethanone trifluoroacetate salt; |
| 395 | 1-(3-Fluoroazetidin-1-yl)-2-[3-fluoro-6-(2-thienyl)pyrrolo[3,2-b]pyridin-1-yl]ethanone trifluoroacetate salt; |
| 396 | 2-[6-(4-Chloro-2-thienyl)-3-fluoro-pyrrolo[3,2-b]pyridin-1-yl]-N,N-dimethyl-acetamide; |
| 397 | 1-(Azetidin-1-yl)-2-[6-(4-chloro-2-thienyl)-3-fluoro-pyrrolo[3,2-b]pyridin-1-yl]ethanone trifluoroacetate salt; |
| 398 | 2-[6-(5-Ethyl-2-thienyl)-3-fluoro-pyrrolo[3,2-b]pyridin-1-yl]-1-(3-fluoroazetidin-1-yl)ethanone trifluoroacetate salt; |
| 399 | 1-(Azetidin-1-yl)-2-[6-(2-thienyl)pyrrolo[3,2-b]pyridin-1-yl]ethanone; |
| 400 | N,N-Dimethyl-2-[6-(2-thienyl)pyrrolo[3,2-b]pyridin-1-yl]acetamide; |
| 401 | 1-(Azetidin-1-yl)-2-[6-(5-ethyl-2-thienyl)-3-fluoro-pyrrolo[3,2-b]pyridin-1-yl]ethanone; |
| 402 | 1-(3-Fluoroazetidin-1-yl)-2-[3-fluoro-6-(5-methyl-2-thienyl)pyrrolo[3,2-b]pyridin-1-yl]ethanone trifluoroacetate salt; |
| 403 | 1-(Azetidin-1-yl)-2-[6-(3-chloro-2-thienyl)pyrrolo[3,2-b]pyridin-1-yl]ethanone; |
| 404 | 1-(Azetidin-1-yl)-2-[6-(2-methylthiazol-5-yl)pyrrolo[3,2-b]pyridin-1-yl]ethanone; |
| 405 | 1-(Azetidin-1-yl)-2-(6-thiazol-5-ylpyrrolo[3,2-b]pyridin-1-yl)ethanone; |
| 406 | 1-(Azetidin-1-yl)-2-[6-(6-fluoro-3-pyridyl)pyrrolo[3,2-b]pyridin-1-yl]ethanone; |
| 407 | 1-(Azetidin-1-yl)-2-[3-chloro-6-(4-methyl-2-thienyl)pyrrolo[3,2-b]pyridin-1-yl]ethanone; |
| 408 | 1-(Azetidin-1-yl)-2-[3-chloro-6-(5-ethyl-2-thienyl)pyrrolo[3,2-b]pyridin-1-yl]ethanone; |
| 409 | 1-(Azetidin-1-yl)-2-[3-chloro-6-(2-thienyl)pyrrolo[3,2-b]pyridin-1-yl]ethanone; |
| 410 | 1-(Azetidin-1-yl)-2-[3-chloro-6-(5-methyl-2-thienyl)pyrrolo[3,2-b]pyridin-1-yl]ethanone; |
| 411 | 2-[6-(4-Fluorophenyl)pyrrolo[3,2-b]pyridin-1-yl]-N-methyl-N-(2,2,2-trifluoroethyl)acetamide; |
| 412 | 2-[3-Chloro-6-(5-methyl-2-thienyl)pyrrolo[3,2-b]pyridin-1-yl]-1-(3-fluoroazetidin-1-yl)ethanone; |
| 413 | 2-[3-Chloro-6-(5-chloro-2-thienyl)pyrrolo[3,2-b]pyridin-1-yl]-1-(3-fluoroazetidin-1-yl)ethanone; |
| 414 | 2-[3-Chloro-6-(4-chloro-2-thienyl)pyrrolo[3,2-b]pyridin-1-yl]-N,N-dimethyl-acetamide; |
| 415 | 2-[6-(4-Fluoro-3-methyl-phenyl)pyrrolo[3,2-b]pyridin-1-yl]-N-methyl-N-(2,2,2-trifluoroethyl)acetamide; |
| 416 | 2-[3-Chloro-6-(4-methyl-2-thienyl)pyrrolo[3,2-b]pyridin-1-yl]-1-(3-fluoroazetidin-1-yl)ethanone; |
| 417 | 2-[3-Chloro-6-(2-thienyl)pyrrolo[3,2-b]pyridin-1-yl]-1-(3-fluoroazetidin-1-yl)ethanone; |
| 418 | 2-[3-Chloro-6-(4-chloro-2-thienyl)pyrrolo[3,2-b]pyridin-1-yl]-1-(3-fluoroazetidin-1-yl)ethanone; |
| 419 | N-Ethyl-2-[6-(4-fluorophenyl)pyrrolo[3,2-b]pyridin-1-yl]-N-methyl-acetamide; |
| 420 | 2-[3-Chloro-6-(2-thienyl)pyrrolo[3,2-b]pyridin-1-yl]-N,N-dimethyl-acetamide; |
| 421 | 2-[3-Chloro-6-(5-ethyl-2-thienyl)pyrrolo[3,2-b]pyridin-1-yl]-N,N-dimethyl-acetamide; |
| 422 | 1-(Azetidin-1-yl)-2-[3-chloro-6-(4-chloro-2-thienyl)pyrrolo[3,2-b]pyridin-1-yl]ethanone; |
| 423 | 2-[3-Chloro-6-(5-chloro-2-thienyl)pyrrolo[3,2-b]pyridin-1-yl]-N,N-dimethyl-acetamide; |
| 424 | 2-[3-Chloro-6-(5-ethyl-2-thienyl)pyrrolo[3,2-b]pyridin-1-yl]-1-(3-fluoroazetidin-1-yl)ethanone; |
| 425 | 2-[6-[2-Fluoro-3-(trifluoromethyl)phenyl]pyrrolo[3,2-b]pyridin-1-yl]-N,N-dimethyl-acetamide; |
| 426 | 2-[6-(5-Chloro-4-methyl-2-thienyl)pyrrolo[3,2-b]pyridin-1-yl]-N,N-dimethyl-acetamide; |
| 427 | 2-[6-(2,5-Dimethyl-3-thienyl)pyrrolo[3,2-b]pyridin-1-yl]-N,N-dimethyl-acetamide; |
| 428 | N,N-Dimethyl-2-[6-(2,4,5-trimethyl-3-thienyl)pyrrolo[3,2-b]pyridin-1-yl]acetamide; |
| 429 | 2-[6-(3-Chlorophenyl)pyrrolo[3,2-b]pyridin-1-yl]-N,N-dimethyl-acetamide; |
| 430 | 2-[6-(4-Fluorophenyl)pyrrolo[3,2-b]pyridin-1-yl]-N,N-dimethyl-acetamide; |
| 431 | 2-[6-(2-Fluorophenyl)pyrrolo[3,2-b]pyridin-1-yl]-N,N-dimethyl-acetamide; |
| 432 | 2-[6-(2-Fluoro-3-methyl-phenyl)pyrrolo[3,2-b]pyridin-1-yl]-N,N-dimethyl-acetamide; |
| 433 | N,N-Dimethyl-2-(6-phenylpyrrolo[3,2-b]pyridin-1-yl)acetamide; |
| 434 | N,N-Dimethyl-2-[6-(m-tolyl)pyrrolo[3,2-b]pyridin-1-yl]acetamide; |
| 435 | N,N-Dimethyl-2-[6-[3-(trifluoromethyl)phenyl]pyrrolo[3,2-b]pyridin-1-yl]acetamide; |
| 436 | 2-[6-[4-Fluoro-3-(trifluoromethyl)phenyl]pyrrolo[3,2-b]pyridin-1-yl]-N,N-dimethyl-acetamide; |
| 437 | N,N-Dimethyl-2-[6-(2,3,4-trifluorophenyl)pyrrolo[3,2-b]pyridin-1-yl]acetamide; |
| 438 | N,N-Dimethyl-2-[6-[5-(trifluoromethyl)-2-thienyl]pyrrolo[3,2-b]pyridin-1-yl]acetamide; |
| 439 | 2-[6-(5-Chloro-3-thienyl)pyrrolo[3,2-b]pyridin-1-yl]-N,N-dimethyl-acetamide; |
| 440 | 2-[6-(2,5-Dichloro-3-thienyl)pyrrolo[3,2-b]pyridin-1-yl]-N,N-dimethyl-acetamide; |
| 441 | N,N-Dimethyl-2-[6-[6-(trifluoromethyl)-2-pyridyl]pyrrolo[3,2-b]pyridin-1-yl]acetamide; |
| 442 | N,N-Dimethyl-2-[6-[2-(trifluoromethyl)-4-pyridyl]pyrrolo[3,2-b]pyridin-1-yl]acetamide; |
| 443 | N,N-Dimethyl-2-[6-[5-(trifluoromethyl)-3-pyridyl]pyrrolo[3,2-b]pyridin-1-yl]acetamide; |
| 444 | 2-[6-(2,6-Difluoro-3-methyl-phenyl)pyrrolo[3,2-b]pyridin-1-yl]-N,N-dimethyl-acetamide; |
| 445 | 2-[6-(2-Fluoro-5-methyl-phenyl)pyrrolo[3,2-b]pyridin-1-yl]-N,N-dimethyl-acetamide; |
| 446 | 1-(Azetidin-1-yl)-2-[6-[3-(difluoromethyl)phenyl]pyrrolo[3,2-b]pyridin-1-yl]ethanone; |
| 447 | 2-[6-(2,4-Difluoro-3-methyl-phenyl)pyrrolo[3,2-b]pyridin-1-yl]-N,N-dimethyl-acetamide; |
| 448 | 2-[6-(3-Chloro-2-fluoro-phenyl)pyrrolo[3,2-b]pyridin-1-yl]-N,N-dimethyl-acetamide; |
| 449 | 2-[6-(3-Ethylphenyl)pyrrolo[3,2-b]pyridin-1-yl]-N,N-dimethyl-acetamide; |
| 450 | 2-[6-(3-Fluorophenyl)pyrrolo[3,2-b]pyridin-1-yl]-N,N-dimethyl-acetamide; |
| 451 | 1-(Azetidin-1-yl)-2-[6-(2-fluoro-3-methyl-phenyl)pyrrolo[3,2-b]pyridin-1-yl]ethanone; |
| 452 | 1-(Azetidin-1-yl)-2-[6-(2,4-difluoro-3-methyl-phenyl)pyrrolo[3,2-b]pyridin-1-yl]ethanone; |
| 453 | 1-(Azetidin-1-yl)-2-[6-(3-chloro-2-fluoro-phenyl)pyrrolo[3,2-b]pyridin-1-yl]ethanone; |
| 454 | 1-(3-Fluoroazetidin-1-yl)-2-[6-(2-fluoro-3-methyl-phenyl)pyrrolo[3,2-b]pyridin-1-yl]ethanone; |
| 455 | 1-(3-Fluoroazetidin-1-yl)-2-[6-(2,3,4-trifluorophenyl)pyrrolo[3,2-b]pyridin-1-yl]ethanone; |
| 456 | 1-(Azetidin-1-yl)-2-[6-(3-chloro-4-fluoro-phenyl)pyrrolo[3,2-b]pyridin-1-yl]ethanone; |

| Example # | Compound Name |
|---|---|
| 457 | 1-(3-Fluoroazetidin-1-yl)-2-[6-(2-fluorophenyl)pyrrolo[3,2-b]pyridin-1-yl]ethanone; |
| 458 | 2-[6-[3-(Difluoromethyl)phenyl]pyrrolo[3,2-b]pyridin-1-yl]-1-(3-fluoroazetidin-1-yl)ethanone; |
| 459 | N-Ethyl-N-methyl-2-[6-(m-tolyl)pyrrolo[3,2-b]pyridin-1-yl]acetamide; |
| 460 | 2-[6-(2,4-Difluoro-3-methyl-phenyl)pyrrolo[3,2-b]pyridin-1-yl]-1-(3-fluoroazetidin-1-yl)ethanone; |
| 461 | 2-[6-(3,4-Difluorophenyl)pyrrolo[3,2-b]pyridin-1-yl]-N-ethyl-N-methyl-acetamide; |
| 462 | N-Ethyl-N-methyl-2-[6-(3,4,5-trifluorophenyl)pyrrolo[3,2-b]pyridin-1-yl]acetamide; |
| 463 | 1-(Azetidin-1-yl)-2-[6-(3-chlorophenyl)pyrrolo[3,2-b]pyridin-1-yl]ethanone; |
| 464 | N-Ethyl-2-[6-[2-fluoro-3-(trifluoromethyl)phenyl]pyrrolo[3,2-b]pyridin-1-yl]-N-methyl-acetamide; |
| 465 | 2-[6-(3-Chlorophenyl)pyrrolo[3,2-b]pyridin-1-yl]-1-(3-fluoroazetidin-1-yl)ethanone; |
| 466 | 2-[6-(3-Chloro-2-fluoro-phenyl)pyrrolo[3,2-b]pyridin-1-yl]-1-(3-fluoroazetidin-1-yl)ethanone; |
| 467 | 2-[6-(3-Chloro-4-fluoro-phenyl)pyrrolo[3,2-b]pyridin-1-yl]-1-(3-fluoroazetidin-1-yl)ethanone; |
| 468 | 2-[6-(3-Chloro-4-fluoro-phenyl)pyrrolo[3,2-b]pyridin-1-yl]-N,N-dimethyl-acetamide; |
| 469 | 2-[6-(2,4-Difluoro-3-methyl-phenyl)pyrrolo[3,2-b]pyridin-1-yl]-N-ethyl-N-methyl-acetamide; |
| 470 | N-Ethyl-N-methyl-2-[6-[3-(trifluoromethyl)phenyl]pyrrolo[3,2-b]pyridin-1-yl]acetamide; |
| 471 | 1-(Azetidin-1-yl)-2-[3-fluoro-6-(2-fluorophenyl)pyrrolo[3,2-b]pyridin-1-yl]ethanone; |
| 472 | 1-(Azetidin-1-yl)-2-[3-fluoro-6-(2-fluoro-3-methyl-phenyl)pyrrolo[3,2-b]pyridin-1-yl]ethanone; |
| 473 | 1-(Azetidin-1-yl)-2-[3-fluoro-6-(m-tolyl)pyrrolo[3,2-b]pyridin-1-yl]ethanone; |
| 474 | 1-(Azetidin-1-yl)-2-[6-(3,5-difluorophenyl)-3-fluoro-pyrrolo[3,2-b]pyridin-1-yl]ethanone; |
| 475 | 1-(Azetidin-1-yl)-2-[3-fluoro-6-[3-(trifluoromethyl)phenyl]pyrrolo[3,2-b]pyridin-1-yl]ethanone; |
| 476 | 1-(Azetidin-1-yl)-2-[3-fluoro-6-[2-fluoro-3-(trifluoromethyl)phenyl]pyrrolo[3,2-b]pyridin-1-yl]ethanone; |
| 477 | 1-(Azetidin-1-yl)-2-[3-fluoro-6-(2,3,4-trifluorophenyl)pyrrolo[3,2-b]pyridin-1-yl]ethanone; |
| 478 | 1-(Azetidin-1-yl)-2-[6-(3-chlorophenyl)-3-fluoro-pyrrolo[3,2-b]pyridin-1-yl]ethanone; |
| 479 | 1-(Azetidin-1-yl)-2-[6-(3-chloro-2-fluoro-phenyl)-3-fluoro-pyrrolo[3,2-b]pyridin-1-yl]ethanone; |
| 480 | 1-(Azetidin-1-yl)-2-[6-(2,4-difluoro-3-methyl-phenyl)-3-fluoro-pyrrolo[3,2-b]pyridin-1-yl]ethanone; |
| 481 | 1-(Azetidin-1-yl)-2-[6-(3-chloro-4-fluoro-phenyl)-3-fluoro-pyrrolo[3,2-b]pyridin-1-yl]ethanone; |
| 482 | 1-(3-Fluoroazetidin-1-yl)-2-(3-fluoro-6-phenyl-pyrrolo[3,2-b]pyridin-1-yl)ethanone; |
| 483 | 1-(3-Fluoroazetidin-1-yl)-2-[3-fluoro-6-(2-fluoro-3-methyl-phenyl)pyrrolo[3,2-b]pyridin-1-yl]ethanone; |
| 484 | 1-(3-Fluoroazetidin-1-yl)-2-[3-fluoro-6-[3-(trifluoromethyl)phenyl]pyrrolo[3,2-b]pyridin-1-yl]ethanone; |
| 485 | 1-(3-Fluoroazetidin-1-yl)-2-[3-fluoro-6-[2-fluoro-3-(trifluoromethyl)phenyl]pyrrolo[3,2-b]pyridin-1-yl]ethanone; |
| 486 | 1-(3-Fluoroazetidin-1-yl)-2-[3-fluoro-6-(2,3,4-trifluorophenyl)pyrrolo[3,2-b]pyridin-1-yl]ethanone; |
| 487 | 2-[6-(3,5-Difluorophenyl)-3-fluoro-pyrrolo[3,2-b]pyridin-1-yl]-1-(3-fluoroazetidin-1-yl)ethanone; |
| 488 | 2-[6-(2,4-Difluoro-3-methyl-phenyl)-3-fluoro-pyrrolo[3,2-b]pyridin-1-yl]-1-(3-fluoroazetidin-1-yl)ethanone; |
| 489 | 2-[6-(3-Chlorophenyl)-3-fluoro-pyrrolo[3,2-b]pyridin-1-yl]-1-(3-fluoroazetidin-1-yl)ethanone; |
| 490 | 2-[6-(3-Chloro-2-fluoro-phenyl)-3-fluoro-pyrrolo[3,2-b]pyridin-1-yl]-1-(3-fluoroazetidin-1-yl)ethanone; |
| 491 | 2-[6-(3-Ethylphenyl)-3-fluoro-pyrrolo[3,2-b]pyridin-1-yl]-1-(3-fluoroazetidin-1-yl)ethanone; |
| 492 | 1-(3-Fluoroazetidin-1-yl)-2-[3-fluoro-6-(3-fluorophenyl)pyrrolo[3,2-b]pyridin-1-yl]ethanone; |
| 493 | 2-[3-Fluoro-6-(2-fluorophenyl)pyrrolo[3,2-b]pyridin-1-yl]-N,N-dimethyl-acetamide; |
| 494 | 2-[3-Fluoro-6-(2-fluoro-3-methyl-phenyl)pyrrolo[3,2-b]pyridin-1-yl]-N,N-dimethyl-acetamide; |
| 495 | 2-(3-Fluoro-6-phenyl-pyrrolo[3,2-b]pyridin-1-yl)-N,N-dimethyl-acetamide; |
| 496 | 2-[3-Fluoro-6-(m-tolyl)pyrrolo[3,2-b]pyridin-1-yl]-N,N-dimethyl-acetamide; |
| 497 | 1-(Azetidin-1-yl)-2-(3-fluoro-6-phenyl-pyrrolo[3,2-b]pyridin-1-yl)ethanone; |
| 498 | 1-(Azetidin-1-yl)-2-[6-(3-ethylphenyl)-3-fluoro-pyrrolo[3,2-b]pyridin-1-yl]ethanone; |
| 499 | 2-[3-Fluoro-6-[3-(trifluoromethyl)phenyl]pyrrolo[3,2-b]pyridin-1-yl]-N,N-dimethyl-acetamide; |
| 500 | 2-[3-Fluoro-6-[2-fluoro-3-(trifluoromethyl)phenyl]pyrrolo[3,2-b]pyridin-1-yl]-N,N-dimethyl-acetamide; |
| 501 | 2-[3-Fluoro-6-(2,3,4-trifluorophenyl)pyrrolo[3,2-b]pyridin-1-yl]-N,N-dimethyl-acetamide; |
| 502 | 2-[6-(2,4-Difluoro-3-methyl-phenyl)-3-fluoro-pyrrolo[3,2-b]pyridin-1-yl]-N,N-dimethyl-acetamide; |
| 503 | 2-[6-(3-Chlorophenyl)-3-fluoro-pyrrolo[3,2-b]pyridin-1-yl]-N,N-dimethyl-acetamide; |
| 504 | 2-[6-(3-Chloro-4-fluoro-phenyl)-3-fluoro-pyrrolo[3,2-b]pyridin-1-yl]-N,N-dimethyl-acetamide; |
| 505 | 2-[6-(3-Ethylphenyl)-3-fluoro-pyrrolo[3,2-b]pyridin-1-yl]-N,N-dimethyl-acetamide; |
| 506 | 1-(Azetidin-1-yl)-2-[3-fluoro-6-(3-fluorophenyl)pyrrolo[3,2-b]pyridin-1-yl]ethanone; |
| 507 | 1-(3-Fluoroazetidin-1-yl)-2-[3-fluoro-6-(2-fluorophenyl)pyrrolo[3,2-b]pyridin-1-yl]ethanone; |
| 508 | 1-(3-Fluoroazetidin-1-yl)-2-[3-fluoro-6-[4-fluoro-3-(trifluoromethyl)phenyl]pyrrolo[3,2-b]pyridin-1-yl]ethanone; |
| 509 | 2-[6-(3,5-Difluorophenyl)-3-fluoro-pyrrolo[3,2-b]pyridin-1-yl]-N,N-dimethyl-acetamide; |
| 510 | 2-[3-Fluoro-6-(3-fluorophenyl)pyrrolo[3,2-b]pyridin-1-yl]-N,N-dimethyl-acetamide; |
| 46 | 2-[3-Chloro-6-(4-fluorophenyl)pyrrolo[3,2-b]pyridin-1-yl]-N,N-dimethyl-acetamide; |
| 512 | 2-[3-Chloro-6-(2-fluorophenyl)pyrrolo[3,2-b]pyridin-1-yl]-N,N-dimethyl-acetamide; |
| 513 | 2-[3-Chloro-6-(2-fluoro-3-methyl-phenyl)pyrrolo[3,2-b]pyridin-1-yl]-N,N-dimethyl-acetamide; |
| 514 | 2-(3-Chloro-6-phenyl-pyrrolo[3,2-b]pyridin-1-yl)-N,N-dimethyl-acetamide; |
| 515 | 2-[3-Chloro-6-(m-tolyl)pyrrolo[3,2-b]pyridin-1-yl]-N,N-dimethyl-acetamide; |
| 516 | 2-[3-Chloro-6-[4-fluoro-3-(trifluoromethyl)phenyl]pyrrolo[3,2-b]pyridin-1-yl]-N,N-dimethyl-acetamide; |
| 517 | 2-[3-Chloro-6-[2-fluoro-3-(trifluoromethyl)phenyl]pyrrolo[3,2-b]pyridin-1-yl]-N,N-dimethyl-acetamide; |
| 518 | 2-[3-Chloro-6-(2,3,4-trifluorophenyl)pyrrolo[3,2-b]pyridin-1-yl]-N,N-dimethyl-acetamide; |
| 519 | 2-[3-Chloro-6-(2,4-difluoro-3-methyl-phenyl)pyrrolo[3,2-b]pyridin-1-yl]-N,N-dimethyl-acetamide; |
| 520 | 2-[3-Chloro-6-(3-chloro-4-fluoro-phenyl)pyrrolo[3,2-b]pyridin-1-yl]-N,N-dimethyl-acetamide; |
| 521 | 1-(Azetidin-1-yl)-2-[3-chloro-6-(2-fluorophenyl)pyrrolo[3,2-b]pyridin-1-yl]ethanone; |
| 522 | 1-(Azetidin-1-yl)-2-[3-chloro-6-(2-fluoro-3-methyl-phenyl)pyrrolo[3,2-b]pyridin-1-yl]ethanone; |
| 523 | 1-(Azetidin-1-yl)-2-[3-chloro-6-[4-fluoro-3-(trifluoromethyl)phenyl]pyrrolo[3,2-b]pyridin-1-yl]ethanone; |
| 524 | 1-(Azetidin-1-yl)-2-[3-chloro-6-[2-fluoro-3-(trifluoromethyl)phenyl]pyrrolo[3,2-b]pyridin-1-yl]ethanone; |
| 525 | 1-(Azetidin-1-yl)-2-[3-chloro-6-(2,4-difluoro-3-methyl-phenyl)pyrrolo[3,2-b]pyridin-1-yl]ethanone; |
| 526 | 1-(Azetidin-1-yl)-2-[3-chloro-6-(3-chlorophenyl)pyrrolo[3,2-b]pyridin-1-yl]ethanone; |

| Example # | Compound Name |
|---|---|
| 527 | 1-(Azetidin-1-yl)-2-[3-chloro-6-(3-chloro-4-fluoro-phenyl)pyrrolo[3,2-b]pyridin-1-yl]ethanone; |
| 528 | 1-(Azetidin-1-yl)-2-[3-chloro-6-(3-chloro-2-fluoro-phenyl)pyrrolo[3,2-b]pyridin-1-yl]ethanone; |
| 529 | 1-(Azetidin-1-yl)-2-[3-chloro-6-[3-(difluoromethyl)phenyl]pyrrolo[3,2-b]pyridin-1-yl]ethanone; |
| 530 | 1-(Azetidin-1-yl)-2-[3-chloro-6-(3-fluorophenyl)pyrrolo[3,2-b]pyridin-1-yl]ethanone; |
| 531 | 2-[3-Chloro-6-(3-fluorophenyl)pyrrolo[3,2-b]pyridin-1-yl]-N,N-dimethyl-acetamide; |
| 532 | 1-(Azetidin-1-yl)-2-[3-chloro-6-(3,5-difluorophenyl)pyrrolo[3,2-b]pyridin-1-yl]ethanone; |
| 533 | 1-(Azetidin-1-yl)-2-[3-chloro-6-(3-ethylphenyl)pyrrolo[3,2-b]pyridin-1-yl]ethanone; |
| 534 | 2-[3-Chloro-6-(3-chlorophenyl)pyrrolo[3,2-b]pyridin-1-yl]-N,N-dimethyl-acetamide; |
| 535 | 2-[3-Chloro-6-(2-fluorophenyl)pyrrolo[3,2-b]pyridin-1-yl]-1-(3-fluoroazetidin-1-yl)ethanone; |
| 536 | 2-[3-Chloro-6-(2-fluoro-3-methyl-phenyl)pyrrolo[3,2-b]pyridin-1-yl]-1-(3-fluoroazetidin-1-yl)ethanone; |
| 537 | 2-[3-Chloro-6-(3,5-difluorophenyl)pyrrolo[3,2-b]pyridin-1-yl]-1-(3-fluoroazetidin-1-yl)ethanone; |
| 538 | 2-[3-Chloro-6-[2-fluoro-3-(trifluoromethyl)phenyl]pyrrolo[3,2-b]pyridin-1-yl]-1-(3-fluoroazetidin-1-yl)ethanone; |
| 539 | 2-[3-Chloro-6-(2,4-difluoro-3-methyl-phenyl)pyrrolo[3,2-b]pyridin-1-yl]-1-(3-fluoroazetidin-1-yl)ethanone; |
| 540 | 2-[3-Chloro-6-(3-chloro-4-fluoro-phenyl)pyrrolo[3,2-b]pyridin-1-yl]-1-(3-fluoroazetidin-1-yl)ethanone; |
| 541 | 2-[3-Chloro-6-(3-chloro-2-fluoro-phenyl)pyrrolo[3,2-b]pyridin-1-yl]-1-(3-fluoroazetidin-1-yl)ethanone; |
| 542 | 2-[3-Chloro-6-(3-ethylphenyl)pyrrolo[3,2-b]pyridin-1-yl]-1-(3-fluoroazetidin-1-yl)ethanone; |
| 543 | 2-[3-Chloro-6-(3-fluorophenyl)pyrrolo[3,2-b]pyridin-1-yl]-1-(3-fluoroazetidin-1-yl)ethanone; |
| 544 | 2-[3-Chloro-6-(3-chloro-2-fluoro-phenyl)pyrrolo[3,2-b]pyridin-1-yl]-N,N-dimethyl-acetamide; |
| 545 | 2-[3-Chloro-6-(3-chlorophenyl)pyrrolo[3,2-b]pyridin-1-yl]-1-(3-fluoroazetidin-1-yl)ethanone; |
| 546 | 2-[3-Chloro-6-[3-(difluoromethyl)phenyl]pyrrolo[3,2-b]pyridin-1-yl]-1-(3-fluoroazetidin-1-yl)ethanone; |
| 547 | 1-(Azetidin-1-yl)-2-[3-fluoro-2-methyl-6-(m-tolyl)pyrrolo[3,2-b]pyridin-1-yl]ethanone; |
| 548 | 1-(Azetidin-1-yl)-2-[6-(3,4-difluorophenyl)-3-methyl-pyrrolo[3,2-b]pyridin-1-yl]ethanone; |
| 549 | 2-[6-(3,4-Difluorophenyl)-3-methyl-pyrrolo[3,2-b]pyridin-1-yl]-N,N-dimethyl-acetamide; |
| 550 | 1-(3-Fluoroazetidin-1-yl)-2-[3-methyl-6-(m-tolyl)pyrrolo[3,2-b]pyridin-1-yl]ethanone; |
| 551 | 2-[6-(3,4-Difluorophenyl)-3-methyl-pyrrolo[3,2-b]pyridin-1-yl]-1-(3-fluoroazetidin-1-yl)ethanone; |
| 552 | 1-(Azetidin-1-yl)-2-[3-methyl-6-[3-(trifluoromethyl)phenyl]pyrrolo[3,2-b]pyridin-1-yl]ethanone; |
| 553 | N,N-Dimethyl-2-[3-methyl-6-[3-(trifluoromethyl)phenyl]pyrrolo[3,2-b]pyridin-1-yl]acetamide; |
| 554 | 1-(3-Fluoroazetidin-1-yl)-2-[3-methyl-6-[3-(trifluoromethyl)phenyl]pyrrolo[3,2-b]pyridin-1-yl]ethanone; |
| 555 | 2-[6-(3,5-Difluorophenyl)-3-methyl-pyrrolo[3,2-b]pyridin-1-yl]-N,N-dimethyl-acetamide; |
| 556 | 1-(Azetidin-1-yl)-2-[6-(3,5-difluorophenyl)-3-methyl-pyrrolo[3,2-b]pyridin-1-yl]ethanone; |
| 557 | 2-[6-(3,5-Difluorophenyl)-3-methyl-pyrrolo[3,2-b]pyridin-1-yl]-N-ethyl-N-methyl-acetamide; |
| 558 | 2-[6-(4-Fluorophenyl)-3-methyl-pyrrolo[3,2-b]pyridin-1-yl]-N,N-dimethyl-acetamide; |
| 559 | N-Ethyl-2-[6-(4-fluorophenyl)-3-methyl-pyrrolo[3,2-b]pyridin-1-yl]-N-methyl-acetamide; |
| 560 | N-Ethyl-2-[6-(2-fluoro-3-methyl-phenyl)-3-methyl-pyrrolo[3,2-b]pyridin-1-yl]-N-methyl-acetamide; |
| 561 | 1-(Azetidin-1-yl)-2-[6-(2-fluoro-3-methyl-phenyl)-3-methyl-pyrrolo[3,2-b]pyridin-1-yl]ethanone; |
| 562 | 2-[6-(2-Fluoro-3-methyl-phenyl)-3-methyl-pyrrolo[3,2-b]pyridin-1-yl]-N,N-dimethyl-acetamide; |
| 563 | 1-(3-Fluoroazetidin-1-yl)-2-[6-(2-fluoro-3-methyl-phenyl)-3-methyl-pyrrolo[3,2-b]pyridin-1-yl]ethanone; |
| 564 | 1-(3,3-Difluoroazetidin-1-yl)-2-[6-(2-fluoro-3-methyl-phenyl)-3-methyl-pyrrolo[3,2-b]pyridin-1-yl]ethanone; |
| 565 | 2-[6-(2-Fluoro-3-methyl-phenyl)-3-methyl-pyrrolo[3,2-b]pyridin-1-yl]-1-pyrrolidin-1-yl-ethanone; |
| 566 | 2-[6-(4-Fluoro-3-methyl-phenyl)-3-methyl-pyrrolo[3,2-b]pyridin-1-yl]-N,N-dimethyl-acetamide; |
| 567 | 2-[3-Methyl-6-[3-(trifluoromethyl)phenyl]pyrrolo[3,2-b]pyridin-1-yl]-1-pyrrolidin-1-yl-ethanone; |
| 568 | N-Ethyl-N-methyl-2-[3-methyl-6-[3-(trifluoromethyl)phenyl]pyrrolo[3,2-b]pyridin-1-yl]acetamide; |
| 569 | 1-(3,3-Difluoroazetidin-1-yl)-2-[3-methyl-6-[3-(trifluoromethyl)phenyl]pyrrolo[3,2-b]pyridin-1-yl]ethanone; |
| 570 | 1-(Azetidin-1-yl)-2-[3-methyl-6-(3,4,5-trifluorophenyl)pyrrolo[3,2-b]pyridin-1-yl]ethanone; |
| 571 | N,N-Dimethyl-2-[3-methyl-6-(3,4,5-trifluorophenyl)pyrrolo[3,2-b]pyridin-1-yl]acetamide; |
| 572 | N,N-Dimethyl-2-[3-methyl-6-(m-tolyl)pyrrolo[3,2-b]pyridin-1-yl]acetamide; |
| 573 | N,N-Dimethyl-2-[3-methyl-6-(4-methyl-2-thienyl)pyrrolo[3,2-b]pyridin-1-yl]acetamide; |
| 574 | 1-(Azetidin-1-yl)-2-[3-methyl-6-(4-methyl-2-thienyl)pyrrolo[3,2-b]pyridin-1-yl]ethanone; |
| 575 | 1-(3-Fluoroazetidin-1-yl)-2-[3-methyl-6-(4-methyl-2-thienyl)pyrrolo[3,2-b]pyridin-1-yl]ethanone; |
| 576 | N,N-Dimethyl-2-(3-methyl-6-phenyl-pyrrolo[3,2-b]pyridin-1-yl)acetamide; |
| 577 | N-Ethyl-N-methyl-2-(3-methyl-6-phenyl-pyrrolo[3,2-b]pyridin-1-yl)acetamide; |
| 578 | 1-(3-Fluoroazetidin-1-yl)-2-(3-methyl-6-phenyl-pyrrolo[3,2-b]pyridin-1-yl)ethanone; |
| 579 | 1-(3,3-Difluoroazetidin-1-yl)-2-(3-methyl-6-phenyl-pyrrolo[3,2-b]pyridin-1-yl)ethanone; |
| 580 | 1-(3-Fluoroazetidin-1-yl)-2-[6-(4-fluoro-3-methyl-phenyl)-3-methyl-pyrrolo[3,2-b]pyridin-1-yl]ethanone; |
| 581 | 1-(Azetidin-1-yl)-2-[3-methyl-6-(m-tolyl)pyrrolo[3,2-b]pyridin-1-yl]ethanone; |
| 582 | 1-(Azetidin-1-yl)-2-[3-methyl-6-(2,3,4-trifluorophenyl)pyrrolo[3,2-b]pyridin-1-yl]ethanone; |
| 583 | N,N-Dimethyl-2-[3-methyl-6-(2,3,4-trifluorophenyl)pyrrolo[3,2-b]pyridin-1-yl]acetamide; |
| 584 | N-Ethyl-N-methyl-2-[3-methyl-6-(2,3,4-trifluorophenyl)pyrrolo[3,2-b]pyridin-1-yl]acetamide; |
| 585 | 1-(Azetidin-1-yl)-2-[6-[2-fluoro-3-(trifluoromethyl)phenyl]-3-methyl-pyrrolo[3,2-b]pyridin-1-yl]ethanone; |
| 586 | 2-[6-[2-Fluoro-3-(trifluoromethyl)phenyl]-3-methyl-pyrrolo[3,2-b]pyridin-1-yl]-N,N-dimethyl-acetamide; |
| 587 | N-Ethyl-2-[6-[2-fluoro-3-(trifluoromethyl)phenyl]-3-methyl-pyrrolo[3,2-b]pyridin-1-yl]-N-methyl-acetamide; |
| 588 | 1-(3-Fluoroazetidin-1-yl)-2-[3-methyl-6-(2,3,4-trifluorophenyl)pyrrolo[3,2-b]pyridin-1-yl]ethanone; |
| 589 | 1-(3-Fluoroazetidin-1-yl)-2-[6-[2-fluoro-3-(trifluoromethyl)phenyl]-3-methyl-pyrrolo[3,2-b]pyridin-1-yl]ethanone; |
| 590 | 2-[6-[2-Fluoro-3-(trifluoromethyl)phenyl]-3-methyl-pyrrolo[3,2-b]pyridin-1-yl]-1-pyrrolidin-1-yl-ethanone; |
| 591 | 2-[3-Methyl-6-(2,3,4-trifluorophenyl)pyrrolo[3,2-b]pyridin-1-yl]-1-pyrrolidin-1-yl-ethanone; |
| 592 | 1-(Azetidin-1-yl)-2-[6-(2-fluorophenyl)-3-methyl-pyrrolo[3,2-b]pyridin-1-yl]ethanone; |
| 593 | 2-[6-(2-Fluorophenyl)-3-methyl-pyrrolo[3,2-b]pyridin-1-yl]-N,N-dimethyl-acetamide; |
| 594 | N-Ethyl-2-[6-(2-fluorophenyl)-3-methyl-pyrrolo[3,2-b]pyridin-1-yl]-N-methyl-acetamide; |
| 595 | 1-(3,3-Difluoroazetidin-1-yl)-2-[6-[2-fluoro-3-(trifluoromethyl)phenyl]-3-methyl-pyrrolo[3,2-b]pyridin-1-yl]ethanone; |
| 596 | 1-(3,3-Difluoroazetidin-1-yl)-2-[3-methyl-6-(2,3,4-trifluorophenyl)pyrrolo[3,2-b]pyridin-1-yl]ethanone; |

| Example # | Compound Name |
|---|---|
| 597 | 1-(3,3-Difluoroazetidin-1-yl)-2-[6-(2-fluorophenyl)-3-methyl-pyrrolo[3,2-b]pyridin-1-yl]ethanone; |
| 598 | 1-(3-Fluoroazetidin-1-yl)-2-[3-methyl-6-(3,4,5-trifluorophenyl)pyrrolo[3,2-b]pyridin-1-yl]ethanone; |
| 599 | 2-[3-Chloro-6-(2,5-dimethyl-3-thienyl)pyrrolo[3,2-b]pyridin-1-yl]-N,N-dimethyl-acetamide; |
| 600 | 2-[3-Chloro-6-[3-(trifluoromethyl)phenyl]pyrrolo[3,2-b]pyridin-1-yl]-N,N-dimethyl-acetamide; |
| 601 | 2-[3-Chloro-6-[6-(trifluoromethyl)-2-pyridyl]pyrrolo[3,2-b]pyridin-1-yl]-N,N-dimethyl-acetamide; |
| 602 | 2-[3-Chloro-6-(5-chloro-4-methyl-2-thienyl)pyrrolo[3,2-b]pyridin-1-yl]-N,N-dimethyl-acetamide; |
| 603 | 2-[3-Chloro-6-[5-(trifluoromethyl)-2-thienyl]pyrrolo[3,2-b]pyridin-1-yl]-N,N-dimethyl-acetamide; |
| 604 | 2-[6-(Benzothiophen-2-yl)pyrrolo[3,2-b]pyridin-1-yl]-N,N-dimethyl-acetamide; |
| 605 | 2-[3-Fluoro-6-[4-fluoro-3-(trifluoromethyl)phenyl]pyrrolo[3,2-b]pyridin-1-yl]-N,N-dimethyl-acetamide; |
| 606 | 2-[6-(3-Chloro-2-fluoro-phenyl)-3-fluoro-pyrrolo[3,2-b]pyridin-1-yl]-N,N-dimethyl-acetamide; |
| 607 | 1-(3-Fluoroazetidin-1-yl)-2-[3-fluoro-6-(m-tolyl)pyrrolo[3,2-b]pyridin-1-yl]ethanone; |
| 608 | 2-[6-(3-Chloro-4-fluoro-phenyl)-3-fluoro-pyrrolo[3,2-b]pyridin-1-yl]-1-(3-fluoroazetidin-1-yl)ethanone; |
| 609 | 1-(Azetidin-1-yl)-2-(3-[$^3$H]-6-(4-fluoro-3-methylphenyl)-1H-pyrrolo[3,2-b]pyridin-1-yl)ethanone; |
| 610 | 2-[2-Deuterio-6-(4-fluoro-3-methyl-phenyl)pyrrolo[3,2-b]pyridin-1-yl]-N,N-dimethyl-acetamide; |
| 611 | 2-[6-(3,5-Difluorophenyl)-3-(trifluoromethyl)pyrrolo[3,2-b]pyridin-1-yl]-N,N-dimethyl-acetamide; |
| 612 | 3-Chloro-1-(3-pyridylmethyl)-6-[3-(trifluoromethyl)phenyl]pyrrolo[3,2-b]pyridine; |
| 613 | 1-(Pyridazin-3-ylmethyl)-6-[3-(trifluoromethyl)phenyl]pyrrolo[3,2-b]pyridine; |
| 614 | 3-Chloro-6-(4-fluoro-3-methyl-phenyl)-1-(pyridazin-3-ylmethyl)pyrrolo[3,2-b]pyridine; |
| 615 | 3-Chloro-1-(pyridazin-3-ylmethyl)-6-[3-(trifluoromethyl)phenyl]pyrrolo[3,2-b]pyridine; |
| 616 | 2-[6-(4-Fluoro-3-methyl-phenyl)-3-methyl-pyrrolo[3,2-b]pyridin-1-yl]-1-pyrrolidin-1-yl-ethanone; |
| 617 | N-Ethyl-2-[6-(4-fluoro-3-methyl-phenyl)-3-methyl-pyrrolo[3,2-b]pyridin-1-yl]-N-methyl-acetamide; |
| 618 | 1-(3,3-Difluoroazetidin-1-yl)-2-[6-(4-fluoro-3-methyl-phenyl)-3-methyl-pyrrolo[3,2-b]pyridin-1-yl]ethanone; |
| 619 | 2-[6-(3,4-Difluorophenyl)-3-methyl-pyrrolo[3,2-b]pyridin-1-yl]-1-pyrrolidin-1-yl-ethanone; |
| 620 | 2-[6-(3,4-Difluorophenyl)-3-methyl-pyrrolo[3,2-b]pyridin-1-yl]-N-ethyl-N-methyl-acetamide; |
| 621 | 1-(3,3-Difluoroazetidin-1-yl)-2-[6-(3,4-difluorophenyl)-3-methyl-pyrrolo[3,2-b]pyridin-1-yl]ethanone; |
| 622 | 2-[6-(2,4-Difluoro-3-methyl-phenyl)-3-methyl-pyrrolo[3,2-b]pyridin-1-yl]-N,N-dimethyl-acetamide; |
| 623 | 2-[6-(3,5-Difluorophenyl)-3-methyl-pyrrolo[3,2-b]pyridin-1-yl]-1-pyrrolidin-1-yl-ethanone; |
| 624 | 2-[6-(2,4-Difluoro-3-methyl-phenyl)-3-methyl-pyrrolo[3,2-b]pyridin-1-yl]-1-pyrrolidin-1-yl-ethanone; |
| 625 | 2-[6-(2,4-Difluoro-3-methyl-phenyl)-3-methyl-pyrrolo[3,2-b]pyridin-1-yl]-N-ethyl-N-methyl-acetamide; |
| 626 | 1-(3,3-Difluoroazetidin-1-yl)-2-[6-(2,4-difluoro-3-methyl-phenyl)-3-methyl-pyrrolo[3,2-b]pyridin-1-yl]ethanone; |
| 627 | 1-(Azetidin-1-yl)-2-[6-(2,4-difluoro-3-methyl-phenyl)-3-methyl-pyrrolo[3,2-b]pyridin-1-yl]ethanone; |
| 628 | 2-[6-(5-Chloro-2-thienyl)-3-methyl-pyrrolo[3,2-b]pyridin-1-yl]-N,N-dimethyl-acetamide; |
| 629 | 2-[6-(2,4-Difluoro-3-methyl-phenyl)-3-methyl-pyrrolo[3,2-b]pyridin-1-yl]-1-(3-fluoroazetidin-1-yl)ethanone; |
| 630 | N-Ethyl-N-methyl-2-[3-methyl-6-(5-methyl-2-thienyl)pyrrolo[3,2-b]pyridin-1-yl]acetamide; |
| 631 | 2-[3-Methyl-6-(5-methyl-2-thienyl)pyrrolo[3,2-b]pyridin-1-yl]-1-pyrrolidin-1-yl-ethanone; |
| 632 | 1-(3,3-Difluoroazetidin-1-yl)-2-[3-methyl-6-(5-methyl-2-thienyl)pyrrolo[3,2-b]pyridin-1-yl]ethanone; |
| 633 | 1-(Azetidin-1-yl)-2-[3-methyl-6-(5-methyl-2-thienyl)pyrrolo[3,2-b]pyridin-1-yl]ethanone; |
| 634 | 1-(3-Fluoroazetidin-1-yl)-2-[3-methyl-6-(5-methyl-2-thienyl)pyrrolo[3,2-b]pyridin-1-yl]ethanone; |
| 635 | 2-[6-(3,5-Difluorophenyl)-3-methyl-pyrrolo[3,2-b]pyridin-1-yl]-1-(3-fluoroazetidin-1-yl)ethanone; |
| 636 | 2-[6-(5-Chloro-2-thienyl)-3-methyl-pyrrolo[3,2-b]pyridin-1-yl]-1-(3-fluoroazetidin-1-yl)ethanone; |
| 637 | N,N-Dimethyl-2-[3-methyl-6-(5-methyl-2-thienyl)pyrrolo[3,2-b]pyridin-1-yl]acetamide; |
| 638 | 1-(3-Fluoroazetidin-1-yl)-2-[6-(2-fluorophenyl)-3-methyl-pyrrolo[3,2-b]pyridin-1-yl]ethanone; and |
| 639 | 2-[6-[5-(Difluoromethyl)-2-thienyl]pyrrolo[3,2-b]pyridin-1-yl]-N,N-dimethyl-acetamide; | and pharmaceutically acceptable salts, N-oxides, or solvates thereof.

An additional embodiment of the invention is a pharmaceutical composition comprising:

(A) an effective amount of at least one compound selected from compounds of Formula (I):

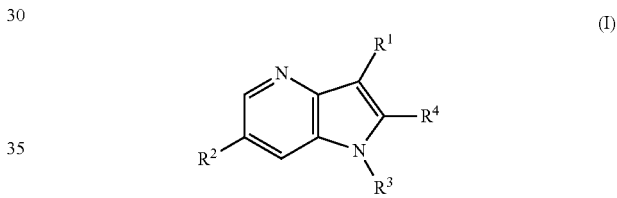

wherein
$R^1$ is selected from the group consisting of: H, $^3$H, halo, $C_{1-3}$alkyl, and $C_{1-3}$haloalkyl;
$R^2$ is selected from the group consisting of: phenyl optionally substituted with one, two, or three members independently selected from: halo, $C_{1-5}$alkyl, and $C_{1-5}$haloalkyl; pyridinyl optionally substituted with halo, $C_{1-5}$alkyl, $C_{1-5}$haloalkyl, and —CN, thiazolyl optionally substituted with $C_{1-5}$alkyl; benzothiophenyl; and thienyl optionally substituted with one, two or three members independently selected from: halo, $C_{1-5}$alkyl; and $C_{1-5}$haloalkyl;
$R^3$ is selected from the brow consisting of:
(a)

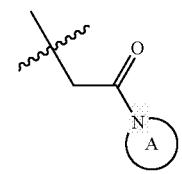

wherein ring A is a 4-7 membered heterocycloalkyl optionally containing an additional oxygen heteroatom selected from the group consisting of: azetidinyl optionally substituted with one or two members independently selected from the group consisting of:

halo, $C_{1-5}$alkyl, $C_{1-5}$haloalkyl, $CH_2OH$, $C_{1-5}$alkoxy, OH, and CN; pyrrolidinyl optionally substituted one or two members independently selected from the group consisting of: halo, $C_{1-5}$alkyl, $C_{1-5}$alkoxy, and OH; morpholino optionally substituted one or two $C_{1-5}$alkyl members; piperidinyl optionally substituted with one or two members independently selected from the group consisting of: halo, $C_{1-5}$alkyl, $C_{1-5}$haloalkyl, $C_{1-5}$alkoxy, and OH; 3-azabicyclo[3.1.0]hexan-3-yl; 5-azaspiro[2.3]hexan-5-yl; and pyrrolidin-3-one; or (b)

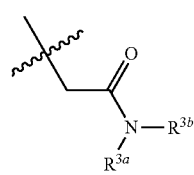

wherein $R^{3a}$ is H, or $C_{1-5}$alkyl;
and $R^{3b}$ is selected from the group consisting of: $C_{1-5}$alkyl optionally substituted with OH, halo, or $OCH_3$; $C_{1-5}$haloalkyl; benzyl; $CH_2$cyclopropyl; cyclopropyl optionally substituted with $C_{1-5}$alkyl; and cyclobutyl; or (c)

wherein $R^{3c}$ is selected from the group consisting of: cyclopropyl; cyclobutyl; pyrimidinyl optionally substituted with halo; pyridinyl; pyridazinyl; furanyl optionally substituted with $C_{1-5}$haloalkyl; oxazolyl; isoxazolyl optionally substituted with $C_{1-5}$alkyl; oxadiazolyl optionally substituted with $C_{1-5}$alkyl; pyrazolyl optionally substituted with $C_{1-5}$alkyl; triazolyl optionally substituted with $C_{1-5}$alkyl; tetrahydrofuranyl; tetrahydropyranyl; oxetanyl; and oxiranyl; or (d)

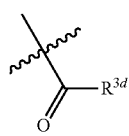

wherein $R^{3d}$ is $CH_2$-cyclopropyl or cyclobutyl; or (e)

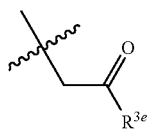

wherein $R^{3e}$ is selected from the group consisting of: OH, $C_{1-5}$alkyl, cyclopropyl, cyclobutyl, and phenyl optionally substituted with one halo substituent; or (f) $C_{1-5}$alkyl optionally substituted with OH or $C_{1-5}$alkoxy; $CH_2S(CH_3)$; $CH_2(S=O)CH_3$; $CH_2(SO_2)CH_3$; and $CH_2CH_2(C=O)CH_3$; or (g)

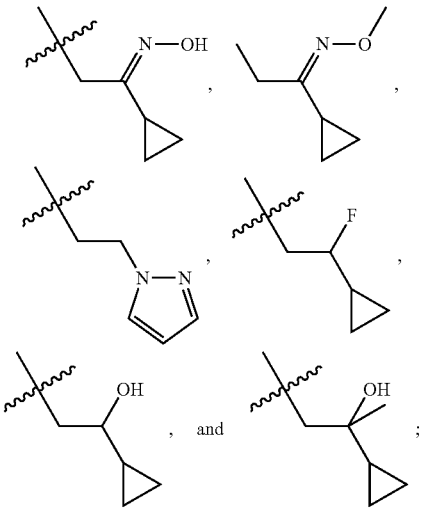

and
$R^4$ is H, $^2H$ or $C_{1-3}$alkyl,
and pharmaceutically acceptable salts, N-oxides or solvates of compounds of Formula (I);
and (B) at least one pharmaceutically acceptable excipient.

An additional embodiment of the invention is a pharmaceutical composition comprising and effective amount of at least one compound of Formula (IIA), as well as pharmaceutically acceptable salts, N-oxides or solvates of compounds of Formula (IIA), pharmaceutically acceptable prodrugs of compounds of Formula (IIA), and pharmaceutically active metabolites of Formula (IIA); and at least one pharmaceutically acceptable excipient.

An additional embodiment of the invention is a pharmaceutical composition comprising and effective amount of at least one compound of Formula (IIB), as well as pharmaceutically acceptable salts, N-oxides or solvates of compounds of Formula (IIB), pharmaceutically acceptable prodrugs of compounds of Formula (IIB), and pharmaceutically active metabolites of Formula (IIB); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

Also within the scope of the invention are enantiomers and diastereomers of the compounds of Formula (I) (as well as Formulas (II), (IIA), (IIB), (III), (IV), (V), and (VI)). Also within the scope of the invention are the pharmaceutically acceptable salts, N-oxides or solvates of the compounds of Formula (I) (as well as Formulas (II), (IIA), (IIB), (III), (IV), (V), and (VI)). Also within the scope of the invention are pharmaceutically acceptable prodrugs of compounds of Formula (I) (as well as Formulas (II), (IIA), (IIB), (III), (IV), (V), and (VI)), and pharmaceutically active metabolites of the compounds of Formula (I) (as well as Formulas (II), (IIA), (IIB), (III), (IV), (V), and (VI)).

Also within the scope of the invention are isotopic variations of compounds of Formula (I) (as well as Formulas (II), (IIA), (IIB), (III), (IV), (V), and (VI)), such as, e.g., deuterated compounds of Formula (I). Also within the scope of the invention are the pharmaceutically acceptable salts, N-oxides or solvates of the isotopic variations of the compounds of Formula (I) (as well as Formulas (II), (IIA), (IIB), (III), (IV), (V), and (VI)). Also within the scope of the invention are the pharmaceutically acceptable prodrugs of the isotopic variations of the compounds of Formula (I) (as well as Formulas (II), (IIA), (IIB), (III), (IV), (V), and (VI)), and pharmaceutically active metabolites of the isotopic variations of the compounds of Formula (I) (as well as Formulas (II), (IIA), (IIB), (III), (IV), (V), and (VI)).

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (I):

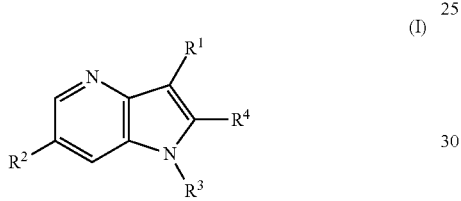

(I)

wherein
- $R^1$ is selected from the group consisting of: H, $^3$H, halo, $C_{1-3}$alkyl, and $C_{1-3}$haloalkyl;
- $R^2$ is selected from the group consisting of: phenyl optionally substituted with one, two, or three members independently selected from: halo, $C_{1-5}$alkyl, and $C_{1-5}$haloalkyl; pyridinyl optionally substituted with halo, $C_{1-5}$alkyl, $C_{1-5}$haloalkyl, and —CN; thiazolyl optionally substituted with $C_{1-5}$alkyl; benzothiophenyl; and thienyl optionally substituted with one, two or three members independently selected from: halo, $C_{1-5}$alkyl, and $C_{1-5}$haloalkyl;
- $R^3$ is selected from the group consisting of:

(a)

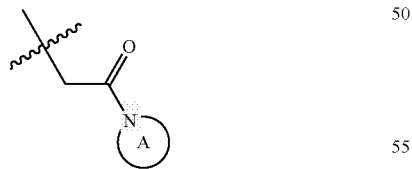

wherein ring A is a 4-7 membered heterocycloalkyl optionally containing an additional oxygen heteroatom selected from the group consisting of: azetidinyl optionally substituted with one or two members independently selected from the group consisting of: halo, $C_{1-5}$alkyl, $C_{1-5}$haloalkyl, $CH_2OH$, $C_{1-5}$alkoxy, OH, and CN; pyrrolidinyl optionally substituted one or two members independently selected from the group consisting of: halo, $C_{1-5}$alkyl, $C_{1-5}$alkoxy, and OH; morpholino optionally substituted one or two $C_{1-5}$alkyl members; piperidinyl optionally substituted with one or two members independently selected from the group consisting of: halo, $C_{1-5}$alkyl, $C_{1-5}$haloalkyl, $C_{1-5}$alkoxy, and OH; 3-azabicyclo[3.1.0]hexan-3-yl; 5-azaspiro[2.3]hexan-5-yl; and pyrrolidin-3-one; or (b)

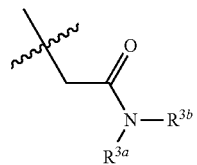

wherein $R^{3a}$ is H, or $C_{1-5}$alkyl;
and $R^{3b}$ is selected from the group consisting of: $C_{1-5}$alkyl optionally substituted with OH, halo, or $OCH_3$; $C_{1-5}$haloalkyl; benzyl; $CH_2$cyclopropyl; cyclopropyl optionally substituted with $C_{1-5}$alkyl; and cyclobutyl; or (c)

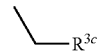

wherein $R^{3c}$ is selected from the group consisting of: cyclopropyl; cyclobutyl; pyrimidinyl optionally substituted with halo; pyridinyl; pyridazinyl; furanyl optionally substituted with $C_{1-5}$haloalkyl; oxazolyl; isoxazolyl optionally substituted with $C_{1-5}$alkyl; oxadiazolyl optionally substituted with $C_{1-5}$alkyl; pyrazolyl optionally substituted with $C_{1-5}$alkyl; triazolyl optionally substituted with $C_{1-5}$alkyl; tetrahydrofuranyl; tetrahydropyranyl; oxetanyl; and oxiranyl; or (d)

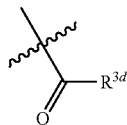

wherein $R^{3d}$ is $CH_2$-cyclopropyl or cyclobutyl; or (e)

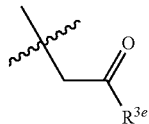

wherein $R^{3e}$ is selected from the group consisting of: OH, $C_{1-5}$alkyl, cyclopropyl, cyclobutyl, and phenyl optionally substituted with one halo substituent; or (f) $C_{1-5}$alkyl optionally substituted with OH or $C_{1-5}$alkoxy; $CH_2S(CH_3)$; $CH_2(S═O)CH_3$; $CH_2(SO_2)CH_3$; and $CH_2CH_2(C═O)CH_3$; or (g)

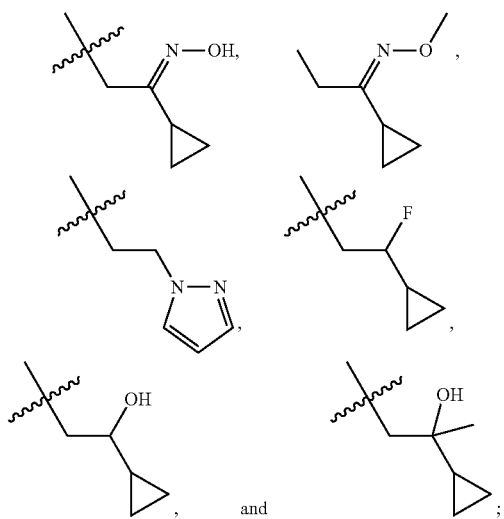

and

R⁴ is H, ²H or $C_{1-3}$alkyl;

and pharmaceutically acceptable salts, N-oxides, or solvates thereof, to a subject in need thereof.

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (I) (as well as Formulas (II), (IIA), (IIB), (III), (IV), (V), and (VI)), enantiomers and diastereomers of the compounds of Formula (I), isotopic variations of the compounds of Formula (I), and pharmaceutically acceptable salts of all of the foregoing.

In preferred embodiments of the inventive method, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequalae of cerebrovascular diseases.

Examples of mood disorders and mood affective disorders that can be treated according to the present invention include, but are not limited to, bipolar disorder I depressed, hypomanic, manic and mixed form; bipolar disorder depressive disorders, such as single depressive episode or recurrent major depressive disorder, minor depressive disorder, treatment-resistant depression, depressive disorder with postpartum onset, depressive disorders with psychotic symptoms; persistent mood disorders, such as cyclothymia, dysthymia, euthymia; and premenstrual dysphoric disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present invention include, but are not limited to mental and behavioural disorders associated with childbirth, including but not limited to postnatal (postpartum) and prenatal depression; eating disorders, including but not limited to anorexia nervosa, bulimia nervosa, pica and binge eating disorder.

Examples of extrapyramidal and movement disorders that can be treated according to the present invention include, but are not limited to Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present invention include, but are not limited to dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord);

Examples for episodic and paroxysmal disorders that can be treated according to the present invention include, but are not limited to epilepsy, including localization-related (focal) (partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, nonpyogenic thrombosis of intracranial venous system, cerebral arteritis, cerebral amyloid angiopathy and sequelae of cerebrovascular diseases.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomotology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-3}$alkyl as used here refers to a straight- or branched-chain alkyl group having from 1 to 3 carbon atoms in the chain. The term $C_{1-5}$alkyl as used here refers to a straight- or branched-chain alkyl group having from 1 to 5 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "aryl" refers to a monocyclic, aromatic carbocycle (ring structure having ring atoms that are all carbon) having 6 atoms per ring. (Carbon atoms in the aryl groups are sp$^2$ hybridized.)

The term "phenyl" represents the following moiety:

The term "thienyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

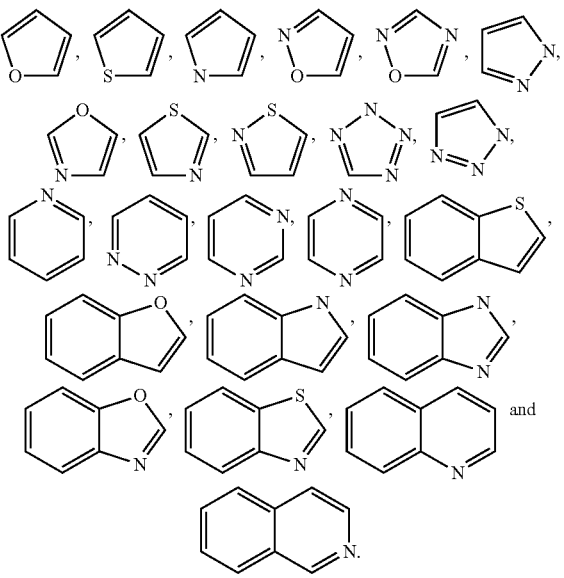

Those skilled in the art will recognize that the species of heteroaryl, cycloalkyl, aryl and heterocycloalkyl groups listed or illustrated above are not exhaustive, and that additional species within the scope of these defined terms may also be selected.

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

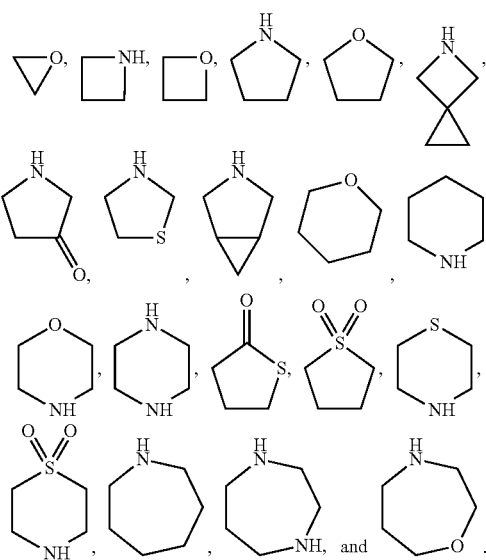

The term "cyano" refers to the group —CN.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

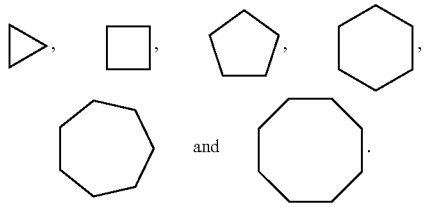

The term "halo" represents chloro, fluoro, bromo or iodo.

The term "perhaloalkyl" or "haloalkyl" refers to a straight- or branched-chain alkyl group having from 1 to 5 carbon atoms in the chain optionally substituting hydrogens with halogens. The term "$C_{1-3}$haloalkyl" as used here refers to a straight- or branched-chain alkyl group having from 1 to 3 carbon atoms in the chain, optionally substituting hydrogens with halogens. The term "$C_{1-5}$haloalkyl" as used here refers to a straight- or branched-chain alkyl group having from 1 to 5 carbon atoms in the chain, optionally substituting hydrogens with halogens. Examples of "perhaloalkyl", "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

The term "perhaloalkoxy" or "haloalkoxy" refers to a straight- or branched-chain alkoxy group having from 1 to 5 carbon atoms in the chain optionally substituting hydrogens with halogens. Examples of perhaloalkoxy groups include trifluoromethoxy ($OCF_3$), difluoromethoxy ($OCF_2H$), monofluoromethoxy ($OCH_2F$), monofluoroethoxy ($OCH_2CH_2F$), pentafluoroethoxy ($OCF_2CF_3$), tetrafluoroethoxy ($OCHFCF_3$), trifluoroethoxy ($OCH_2CF_3$), tetrafluorotrifluoromethylethoxy (—$OCF(CF_3)_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

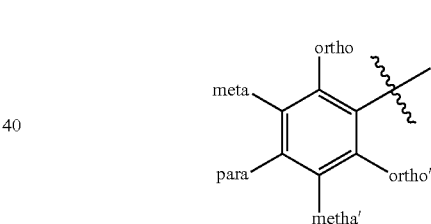

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

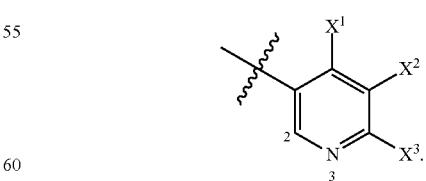

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols  and  are used as meaning the same spatial arrangement in chemical structures shown herein. Analogously, the symbols  and  are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) (as well as Formulas (II), (IIA), (IIB), (III), (IV), (V), and (VI)), or pharmaceutically acceptable salts of compounds of Formula (I) (as well as Formulas (II), (IIA), (IIB), (III), (IV), (V), and (VI)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (II), (IIA), (IIB), (III), (IV), (V), and (VI)) or pharmaceutically acceptable salts of compounds of Formula (I) (as well as Formulas (II), (IIA), (IIB), (III), (IV), (V), and (VI)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(S)}$, R—COOH$_{(sol)}$, and R—COO$^-$$_{(sol)}$. In this example, R—COOH$_{(S)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO⁻ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO⁻$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion ⁺H$_3$NCH$_2$COO⁻. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^{2a}$, $R^{2b}$, $R^{2c}$, $R^{2d}$, $R^{2e}$, $R^{2f}$, $R^3$, $R^{3a}$, $R^{3b}$, $R^{3c}$, $R^{3d}$, $R^{3e}$, $R^{3e1}$, $R^4$, $Het^1$, and $Hal^2$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^{2a}$, $R^{2b}$, $R^{2c}$, $R^{2d}$, $R^{2e}$, $R^{2f}$, $R^3$, $R^{3a}$, $R^{3b}$, $R^{3c}$, $R^{3d}$, $R^{3e}$, $R^{3e1}$, $R^4$, $Het^1$, and $Hal^2$, and any other generic substituent symbol used herein.

The nomenclature "$C_{1-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (II), (IIA), (IIB), (III), (IV), (V), and (VI)), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U.S. Pharmcopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (II), (IIA), (IIB), (III), (IV), (V), and (VI)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", J. Med. Chem., 2007, 50:6665-72, S. M. Berge, et al., "Pharmaceutical Salts", J Pharm Sci., 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (II), (IIA), (IIB), (III), (IV), (V), and (VI)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (II), (IIA), (IIB), (III), (IV), (V), and (VI)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (II), (IIA), (IIB), (III), (IV), (V), and (VI)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) (as well as Formulas (II), (IIA), (IIB), (III), (IV), (V), and (VI)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (II), (IIA), (IIB), (III), (IV), (V), and (VI)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (II), (IIA), (IIB), (III), (IV), (V), and (VI)) as amides or alkyl esters. Examples of amides include those derived from ammonia, primary $C_{1-5}$alkyl amines and secondary di($C_{1-5}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{5-7}$cycloalkyl, phenyl, and phenyl($C_{1-5}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (II), (IIA), (IIB), (III), (IV), (V), and (VI)), which may also be used in the methods of the invention. A "pharmaceutically active metabolite" means a pharmacologically active product of metabolism in the body of a compound of Formula (I) (as well as Formulas (II), (IIA), (IIB), (III), (IV), (V), and (VI) as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (II), (IIA), (IIB), (III), (IV), (V), and (VI)) and their pharmaceutically acceptable salts, pharmaceutically acceptable prodrugs, and pharmaceutically active metabolites of the present invention are useful as modulators of the NR2B receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the NR2B receptor expression or activity, and "activators" are compounds that increase, activate, facilitate, sensitize, or up-regulate NR2B receptor expression or activity.

The term "treat", "treatment" or "treating", as used herein, is intended to refer to administration of an active agent or composition of the invention to a subject for the purpose of affecting a therapeutic or prophylactic benefit through modulation of NR2B receptor activity. Treating includes reversing, ameliorating, alleviating, inhibiting the progress of, lessening the severity of, or preventing a disease, disorder, or condition, or one or more symptoms of such disease, disorder or condition mediated through modulation of NR2B receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by NR2B receptor activity, such as: bipolar disorder I depressed, hypomanic, manic and mixed form; bipolar disorder depressive disorders, such as single depressive episode or recurrent major depressive disorder, minor depressive disorder, treatment-resistant depression, depressive disorder with postpartum onset, disruptive mood dysregulation disorder, depressive disorders with psychotic symptoms; persistent mood disorders, such as cyclothymia, dysthymia, euthymia; and premenstrual dysphoric disorder; anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post traumatic stress disorder (PTSD); other neurotic disorders such as depersonalisation-derealisation syndrome; pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills; postnatal (postpartum) and prenatal depression; eating disorders, including but not limited to anorexia nervosa, bulimia nervosa, pica and binge eating disorder; Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome; dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); epilepsy, including localization-related (focal)(partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures; epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus; persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy; and acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis, and ALS; subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases; glaucoma and other neuopathies; dementias, vascular demensia, Lewy body dementia, frontotemporal dementia, and HIV-dementia; vertigo and nystagmus; tinnitus; neuropsychiatric systemic lupus erythematosus; disruptive mood dysregulation disorder; schizophrenia spectrum disorder; and sleep/wake disorders.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by NR2B activity, such as another NR2B modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 4

| Term | Acronym |
| --- | --- |
| Acetonitrile | ACN |
| Aqueous | aq |
| Atmosphere | atm |
| Gold(III) chloride | Au(III)Cl$_3$ |
| tert-Butylcarbamoyl | Boc |
| Benzotriazol-1-yloxy-tris(dimethylamino)phosphonium hexafluorophosphate | BOP |
| Broad | br |
| Diatomaceous Earth | Celite ® |
| Diethylaminosulfur trifluoride | DAST |
| 1,8-Diazabicyclo[5.4.0]undec-7-ene | DBU |
| N,N'-Dicyclohexylcarbodiimide | DCC |
| Dichloroethane | DCE |
| Dichloromethane | DCM |
| Bis(2-methoxyethyl)aminosulfur trifluoride | Deoxo-Fluor ® |
| Diisopropylethylamine | DIPEA |
| 4-Dimethylaminopyridine | DMAP |
| 1,2-Dimethoxyethane | DME |
| N,N-Dimethylformamide | DMF |
| Dimethylsulfoxide | DMSO |
| 1-Ethyl-3-(3-dimethylaminopropyl)carbodiimide | EDCI, EDAC, or EDC |
| Diethyl ether | Ether, Et$_2$O |
| Ethyl Acetate | EtOAc, or EA |
| Ethanol | EtOH |
| Normal-phase silica gel chromatography | FCC |
| Grams | g |
| Hours | h |
| 1-[Bis(dimethylamino)methylene]-1H-1,2,3-triazolo[4,5-b]pyridinium 3-oxid hexafluorophosphate | HATU |
| N,N,N',N'-Tetramethyl-O-(1H-benzotriazol-1-yl)uronium hexafluorophosphate | HBTU |
| Hydroxybenzotriazole | HOBt |
| High-pressure liquid chromatography | HPLC |
| Hertz | Hz |
| Isopropyl alcohol | iPrOH, IPA |
| Liquid chromatography and mass spectrometry | LCMS |
| Lithium bis(trimethylsilyl)amide | LHMDS |
| Molar | M |
| Mass to charge ratio | m/z |
| meta-Chloroperoxybenzoic acid | mCPBA |
| Methyl Iodide | MeI |
| Methanol | MeOH |
| Milligrams | mg |
| Minute | min |
| Milliliter | mL |
| Microliter | µL |
| Millimoles | mmol |
| Mass spectrometry | MS |
| Normal | N |
| N-Bromosuccinimide | NBS |
| N-Chlorosuccinimide | NCS |
| N-Iodosuccinimide | NIS |
| Nuclear magnetic resonance | NMR |
| CF$_3$SO$_3$— or triflate | OTf |
| Palladium(II)bis(triphenylphosphine) dichloride | Pd(PPh$_3$)$_2$Cl$_2$ |
| Tetrakis(triphenylphosphine)palladium(0) | Pd(PPh$_3$)$_4$ |
| [1,1'-Bis(di-tert-butylphosphino)ferrocene]dichloropalladium(II) | PdCl$_2$(dtbpf) or Pd(dtbpf)$_2$Cl$_2$ |
| Parts per million | ppm |
| Precipitate | ppt |
| Polytetrafluoroethylene | PTFE |
| Bromotripyrrolidinophosphonium hexafluorophosphate | PyBroP ® |
| Retention time | R$_t$ |
| Room temperature | rt |
| Saturated | sat |
| 1-Chloromethyl-4-fluoro-1,4-diazoniabicyclo[2.2.2]octane bis(tetrafluoroborate) | Selectfluor ® |
| [2-(Trimethylsilyl)ethoxy]methyl acetal | SEM |
| Supercritical Fluid Chromatography | SFC |
| Temperature | T |
| Tetra-n-butylammonium fluoride | TBAF |
| Triethylamine | TEA |

TABLE 4-continued

| Term | Acronym |
| --- | --- |
| Trifluoroacetic acid | TFA |
| Tetrahydrofuran | THF |
| Thin layer chromatography | TLC |

PREPARATIVE EXAMPLES

Exemplary compounds useful in methods of the invention will now be described by reference to the illustrative synthetic schemes for their general preparation below and the specific examples to follow.

SCHEME 1

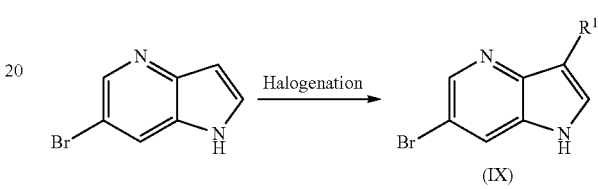

According to SCHEME 1, commercially available or synthetically accessible 6-bromo-1H-pyrrolo[3,2-b]pyridine is halogenated under conditions known to one skilled in the art. For example, 6-bromo-1H-pyrrolo[3,2-b]pyridine is halogenated using a reagent such as NCS, NBS, and like, in a suitable solvent such as DMF, and the like, at a temperature ranging from 0° C. to rt, to provide a compound of formula (IX), where $R^1$ is Cl or Br. A compound of formula (IX), where $R^1$ is F, is prepared under fluorinating conditions known to one skilled in the art, for example, reaction with a fluorinating agent such as Selectfluor®, pyridine, in a suitable solvent such as ACN, and the like, at room temperature.

SCHEME 2

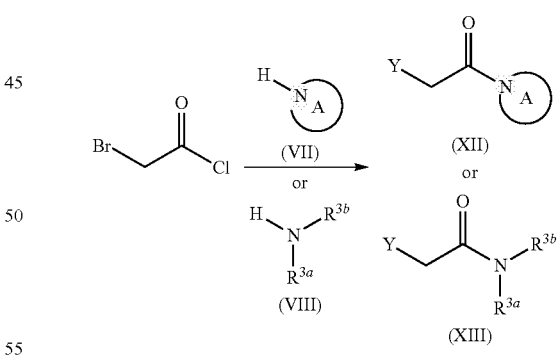

According to SCHEME 2, 2-bromoacetyl chloride is reacted with a commercially available or synthetically accessible suitably substituted heterocycloalkylamine of formula (VII), where A is a fully saturated or partially saturated 3-7 membered ring optionally containing additional S, N, or O atoms, or suitably substituted amine of formula (VIII), where $R^{3a}$ and $R^{3b}$ are as defined in Formula (I), in the presence of a suitable base such as Et$_3$N (TEA), in a solvent such as acetonitrile (ACN), at temperatures ranging from −78° C. to rt, to provide a compound of formula (XII) or (XIII).

SCHEME 3

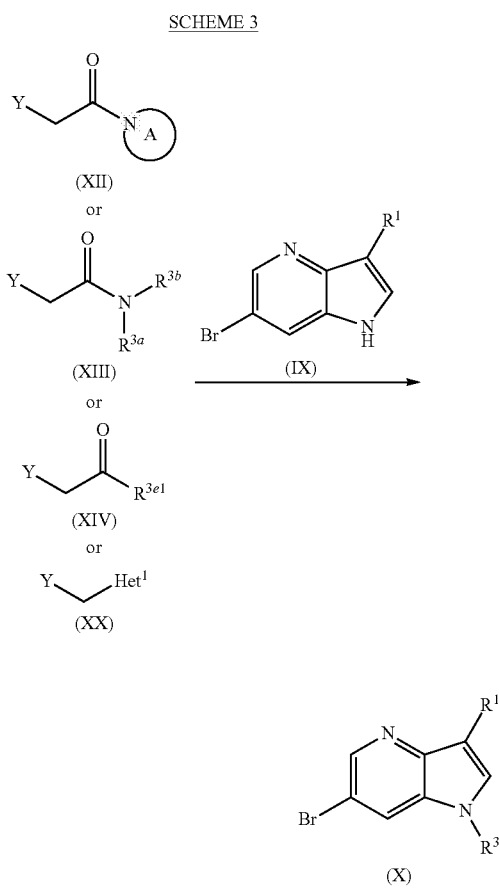

According to SCHEME 3, a compound of formula (IX), where $R^1$ is H, Cl, F, is alkylated with a compound of formula (XII), (XIII), (XIV), or (XX) where Y is Cl, Br or —OSO$_2$Me, employing a base such as NaH, in a suitable solvent such as DMF, at temperatures ranging from 0° C. to rt, to afford a compound of formula (X). When the alkylating agent is a compound of formula (XIV), $R^{3e1}$ is OC$_{1-5}$alkyl, C$_{1-5}$alkyl or cyclopropyl. When the alkylating agent is a compound of formula (XX), Het$^1$ is a suitably substituted heteroaryl such as isoxazole, and Y is Cl.

A compound of formula (X), where $R^1$ is H, is further fluorinated employing conditions previously described, to provide a compound of formula (X), where $R^1$ is F.

SCHEME 4

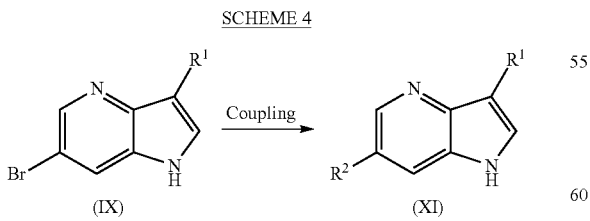

According to SCHEME 4, a compound of formula (IX), where $R^1$ is H, or Cl, is reacted in a metal mediated cross coupling reaction to provide a compound of formula (XI), where $R^2$ is an phenyl, pyridinyl, thienyl, each optionally substituted with of one, two or three members independently selected from halo, —CN, C$_{1-5}$alkyl and C$_{1-5}$haloalkyl. For example, a compound of formula (IX), where $R^1$ is H, or Cl, is reacted with a suitably substituted aryl or heteroaryl boronic acid, boronate ester, and the like, in the presence of a palladium catalyst such as PdCl$_2$(dtbpf), Pd(PPh$_3$)$_4$, and the like, a base such as K$_3$PO$_4$, aq. Na$_2$CO$_3$, Cs$_2$CO$_3$, and the like, in a suitable solvent such as 1,4-dioxane, DMF, water, or a mixture thereof, at a temperature ranging from 60-90° C., for a period of about 16 h, to provide a compound of formula (XI).

A compound of formula (XI), where $R^1$ is H, and $R^2$ is a suitably substituted phenyl, is halogenated, employing conditions known to one skilled in the art, for example, by reaction with NIS, and like, in a suitable solvent such as DMF, and the like, at a temperature ranging from 0° C. to rt, to provide a compound of formula (XI), where $R^1$ is I.

In a further method, a compound of formula (XI), where $R^1$ is Br, the N1 nitrogen is protected with a suitable nitrogen protecting group such as SEM, employing conditions known to one skilled in the art. For example, reaction of bromo-6-(4-fluoro-3-methylphenyl)-1H-pyrrolo[3,2-b]pyridine with 2-chloromethoxyethyl)trimethylsilane, in the presence of a base such as NaH, and the like, in a suitable solvent such as DMF, at temperatures ranging from 0° C. to rt, provides 3-bromo-6-(4-fluoro-3-methylphenyl)-1-((2-(trimethylsilyl)ethoxy)methyl)-1H-pyrrolo[3,2-b]pyridine. Trans-halogenation of a compound where $R^1$ is Br, is achieved under reaction conditions such as tBuLi, and N-fluoro-N-(phenylsulfonyl)benzenesulfonamide, in a solvent such as THF, to provide a compound where $R^1$ is F. Subsequent deprotection of the SEM group, under conditions known to one skilled in the art, such as reaction with TBAF, in a suitable solvent such as THF, at a temperature of about 60° C. provides a compound of formula (XI), where $R^1$ is F.

SCHEME 5

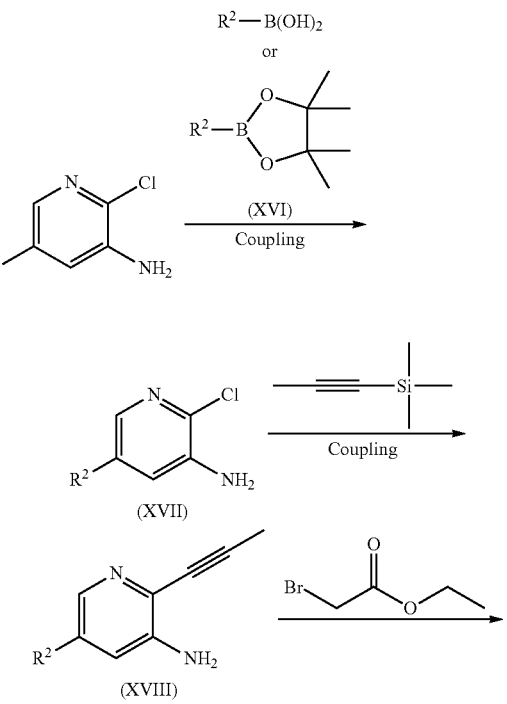

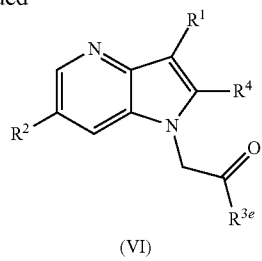

(VI)

According to SCHEME 5, commercially available or synthetically accessible 5-bromo-2-chloropyridin-3-amine is coupled with a boronic acid or boronic ester of formula (XVI), where $R^2$ is a suitably substituted phenyl, in the presence of a palladium catalyst such as $Pd(dtbpf)_2Cl_2$, and the like, a base such as $K_3PO_4$, in a solvent such as dioxane, water, or a mixture thereof, at 80° C. to provide a compound of formula (XVII). A compound of formula (XVII) is reacted in a palladium-catalyzed Sonogashira cross-coupling reaction with a (trimethylsilyl)alkyne, a palladium catalyst such as $Pd(PPh_3)_2Cl_2$, and the like, a ligand such as $PPh_3$, a copper(I) cocatalyst such as CuI, an amine base such as $Et_3N$, DBU, DIPEA, and the like, CsF, in a solvent such as DMF, $Et_2O$, dioxane, THF, and the like, at a temperature of about 90° C., to provide a compound of formula (XVIII). Reaction of a compound of formula (XVIII) with a base such as NaH, ethyl 2-bromoacetate, in a suitable solvent such as DMF, and the like, at a temperature ranging from 0° C. to room temperature, for a period of about 12-24 h, provides a compound of formula (VI), where $R^1$ is H and $R^4$ is $CH_3$.

and $R^2$ is a suitably substituted phenyl or thienyl, is alkylated with electrophile such as ethyl 2-bromoacetate, tert-butyl 2-bromoacetate, and the like, a base such as NaH, and the like, in a suitable solvent such as DMF, a temperatures ranging from 0° C. to it to provide a compound of formula (XXI), where $R^{3e}$ is $C_{1-5}$alkyl. Saponification of an ester compound of formula (XXI) under basic conditions such as LiOH, and the like, in a solvent such as THF and water, at a temperature of about rt, affords a compound of Formula (VI), where $R^4$ is H, and $R^{3e}$ is —OH.

A compound of formula (XXI), is prepared from a compound of formula (IX) in two steps. A compound of formula (IX), in a first step is alkylated employing conditions previously described with an electrophile such as ethyl 2-bromoacetate, tert-butyl 2-bromoacetate, and the like. In a second step, coupling with a suitably substituted phenyl or thienyl boronic acid or ester, employing conditions previously described, provides a compound of formula (XXI).

It will be understood that in certain instances, in situ ester hydrolysis, without the isolation of a discrete ester (XXI) may occur to provide a compound of Formula (VI), where $R^{3e}$ is —OH.

In an alternate method, a compound of formula (VI) where $R^1$ is $C_{1-5}$alkyl, $R^2$ is a suitably substituted phenyl, and $R^4$ is H, is prepared from a compound of formula (XXI), where $R^1$ is H, in 3 steps. In a first step, bromination of a compound of formula (XXI), where $R^1$ is H, employing conditions previously described affords a compound where $R^1$ is Br. In a second step, transition-metal mediated conversion an aryl halide compound where $R^1$ is Br, employing tetramethyltin, a palladium catalyst such as $Pd(PPh_3)_2Cl_2$, and the like, an additive such as LiCl, in a suitable solvent

SCHEME 6

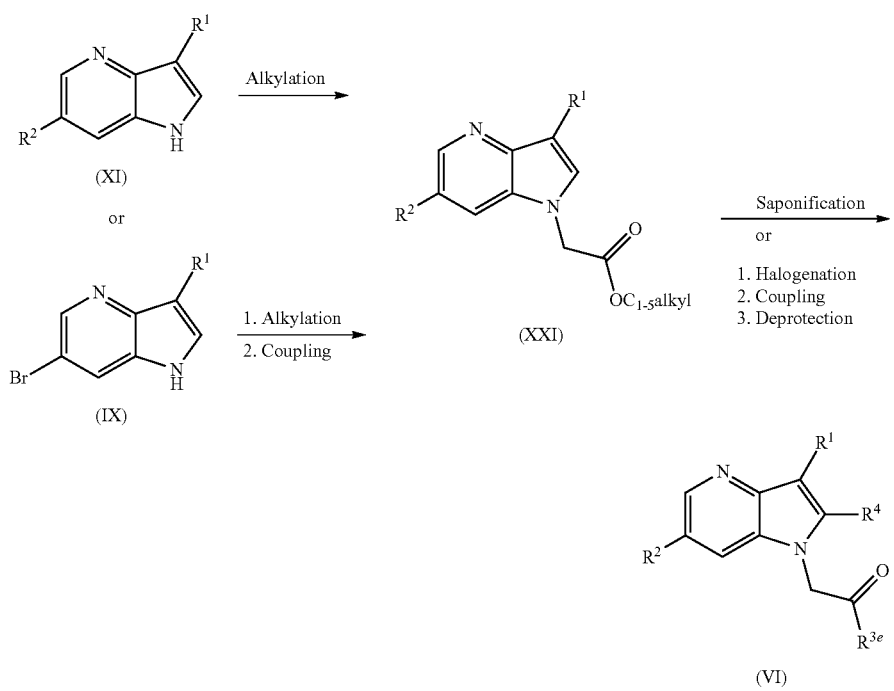

According to SCHEME 6, a compound of formula (VI), is prepared in two steps from a compound of formula (XI). In a first step, a compound of formula (XI) where $R^1$ is H, such as DMF, ACN, dioxane, xylenes, and the like, at temperatures ranging from 80 to 110° C. affords a compound where $R^1$ is $CH_3$. Subsequent deprotection of the ester, employing conditions known to one skilled in the art, for example, reaction with TFA, in a solvent such as DCM, and the like, at temperatures ranging from 0° C. to rt, affords a compound of Formula (VI), where $R^1$ is $CH_3$.

SCHEME 7

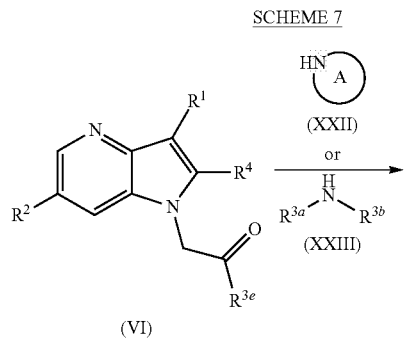

(VI)

According to SCHEME 7, A compound of Formula (I), where $R^1$ and $R^4$ are H or $CH_3$, $R^2$ is a suitably substituted phenyl or thienyl, is prepared by conventional amide bond forming techniques such as coupling reactions which are well known to those skilled in the art. For example, reaction of a suitably substituted heterocycloalkyl amine of formula (XXII) or amine of formula (XXIII) where $R^{3a}$ is H or $C_{1-5}$alkyl and $R^{3b}$ is $C_{1-5}$alkyl, $C_{3-6}$cycloalkyl, with an acid compound of Formula (VI), where $R^{3e}$ is OH, where the acid is activated with an appropriate activating reagent, for example a carbodiimide, such as DCC or EDCI optionally in the presence of HOBt and/or a catalyst such as DMAP; a halotrisaminophosphonium salt such as BOP, or PyBroP; a suitable pyridinium salt such as 2-chloro-1-methyl pyridinium chloride; or another suitable coupling agent such as HBTU, HATU, and the like. Coupling reactions are conducted in a suitable solvent such as DCM, THF, DMF and the like, optionally in the presence of a tertiary amine such as N-methylmorpholine, N-ethyldiisopropylamine, or TEA, at a temperature ranging from about 0° C. to rt, to provide compound a of Formula (I).

SCHEME 8

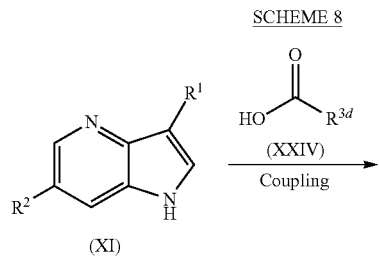

(V)

According to SCHEME 8, a compound of formula (XI), where $R^1$ and $R^4$ are H, is reacted with an acid of formula (XXIV), where $R^{3d}$ is cyclobutyl, or $CH_2$-cyclopropyl, under amide bond forming conditions as previously described, to provide a compound of Formula (V). In a preferred method, HATU is the coupling reagent, DIPEA is the base, DMF is the solvent.

SCHEME 9

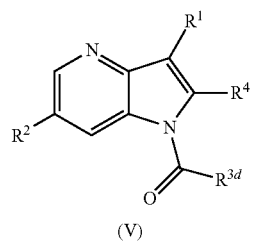

(IV)

According to SCHEME 9, a compound of formula (XI), is reacted with a heteroaryl alkylhalide of formula (XXV), where $Hal^2$ is Cl, employing alkylation conditions previously described to provide a compound of Formula (IV), where $R^1$ is H or halo, $R^2$ is an suitably substituted phenyl or thienyl, $R^{3c}$ is a suitably substituted $C_{3-6}$cycloalkyl, a suitably substituted 3-6-membered heterocycloalkyl, or a suitably substituted 5 or 6 membered heteroaryl ring, and $R^4$ is H. In a preferred method the base is NaH, and the solvent is DMF.

In an alternate method, a compound of formula (IX), where $R^1$ is H, is alkylated with a heteroaryl alkylhalide of formula (XXV), where $Hal^2$ is Cl, then in a second step, reacted in a metal-mediated coupling reaction with a suitably substituted phenyl or thienyl boronic acid or ester, as previously described, to provide a compound of Formula (IV).

SCHEME 10

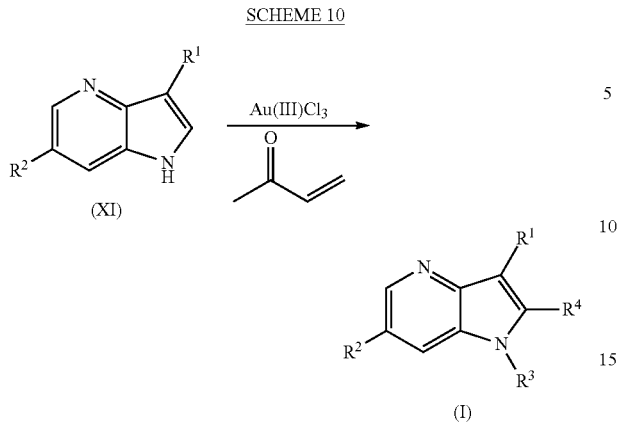

According to SCHEME 10, a compound of formula (XI), where $R^1$ is H, and $R^2$ is a suitably substituted phenyl, is reacted with but-3-en-2-one, Au(III)Cl₃, silver trifluoromethanesulfonate, in a solvent such as DCE, at a temperature of about 100° C., to provide compound of Formula (I), where $R^3$ is $CH_2CH_2(C=O)CH_3$.

SCHEME 11

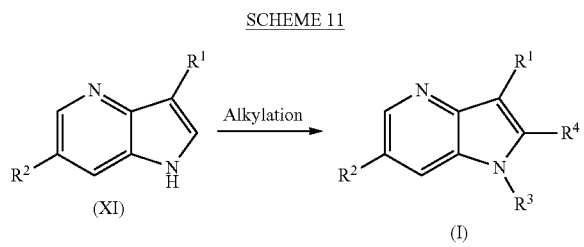

According to SCHEME 10, a compound of formula (XI), is alkylated under conditions previously described, for example, by reaction with (chloromethyl)(methyl)sulfane; optionally substituted $C_{1-5}$haloalkyls such as 1-bromobutane, 1-bromo-3-methylbutane, 1-bromo-2-methoxyethane, and the like; (halomethyl)$C_{3-6}$cycloalkyls such as (bromomethyl)cyclopropane, (bromomethyl)cyclobutane, and the like; (halomethyl)heterocycloalkyls such as 2-(bromomethyl)oxirane, 3-(bromomethyl)tetrahydrofuran, and the like; 2-bromo-1-cyclobutylethanone, 2-bromo-1-cyclopropylethanone, 2-bromo-1-phenylethanone, 1-bromobutan-2-one, (halomethyl)heteroaryls such as 3-(bromomethyl)pyridine, 5-(chloromethyl)-3-methyl-1,2,4-oxadiazole, 4-(chloromethyl)-1-methyl-1H-pyrazole, 4-(chloromethyl)-1-methyl-1H-1,2,3-triazole, and the like; 1-(2-chloroethyl)-1H-pyrazole, (5-fluoropyrimidin-2-yl)methyl methanesulfonate; or pyrimidin-5-ylmethyl methanesulfonate; employing alkylation conditions previously described, provides a compound of Formula (I).

A compound of Formula (I), where $R^3$ is $CH_2(C=O)$ $C_{1-5}$alkyl, is reduced with a reducing agent such as NaBH₄, and the like, in a solvent such as THF, MeOH, or a mixture thereof, at a temperature ranging from ° C. to rt, provides a compound of Formula (I), where $R^3$ is $CH_2CH(OH)$ $C_{1-5}$alkyl.

A compound of Formula (I), where $R^3$ is $CH_2(C=O)$ $C_{3-6}$cycloalkyl, is reacted with a Grignard reagent such as methylmagnesium bromide, and the like, in a suitable solvent such as Et₂O, THF, or a mixture thereof, at a temperature ranging from ° C. to rt, provides a compound of Formula (I), where $R^3$ is $CH_2(CH_3)(OH)$ $C_{3-6}$cycloalkyl.

A compound of Formula (I), where $R^3$ is $CH_2(C=O)$ $C_{3-6}$cycloalkyl, is reacted with O-methylhydroxylamine hydrochloride, a base such as NaHCO₃, and the like, in a suitable solvent such as MeOH, and the like, provides a compound of Formula (I), where $R^3$ is

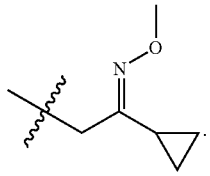

A compound of Formula (I), where $R^3$ is $CH_2CH(OH)$ $C_{3-6}$cycloalkyl is fluorinated under conditions known to one skilled in the art, for example, reaction with a fluorinating agent such as DAST, and the like, in a solvent such as DCM, and the like, at a temperature ranging from ° C. to rt, provides a compound of Formula (I), where $R^3$ is $CH_2CH$ (F)$C_{3-6}$cycloalkyl.

A compound of Formula (I), where $R^3$ is $CH_2SCH_3$, is oxidized under conditions known to one skilled in the art, for example, reaction with an oxidizing agent such as mCPBA, in a solvent such as DCM, and the like, at a temperature ranging from ° C. to rt, provides a compound of Formula (I), where $R^3$ is $CH_2(S=O)CH_3$, and $CH_2(SO_2)CH_3$.

Compounds of Formula (I) may be converted to their corresponding salts using methods known to one of ordinary skill in the art. For example, an amine of Formula (I) is treated with trifluoroacetic acid, HCl, or citric acid in a solvent such as Et₂O, CH₂Cl₂, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16″ PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

Method A.

An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

Method B.

A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

Method C.

A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

Method D.

A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column were heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Intermediate 1:
2-Bromo-1-(3,3-difluoroazetidin-1-yl)ethanone

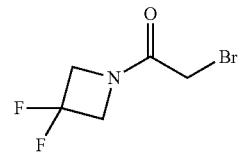

To a solution of 3,3-difluoroazetidine hydrochloride (3 g, 23 mmol) and $Et_3N$ (3.2 mL, 23 mmol) in ACN (29 mL) at −78° C. was added 2-bromoacetyl chloride (1.9 mL, 23 mmol). The reaction mixture was allowed to slowly warm to room temperature. After 30 minutes, water was added and the aqueous phase was extracted with DCM (3×). The combined organic layers were dried ($MgSO_4$), filtered and evaporated to afford the title compound (3.45 g, 70%). $^1H$ NMR (400 MHz, DMSO-$d_6$) δ 4.66 (t, J=12.5 Hz, 2H), 4.36 (t, J=12.6 Hz, 2H), 4.26 (s, 2H).

Intermediate 2:
2-Bromo-1-(3-fluoroazetidin-1-yl)ethanone

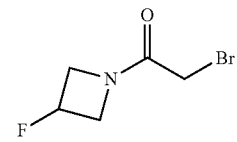

The title compound was prepared in a manner analogous to Intermediate 1. This compound was isolated as a mixture of 2-bromo-1-(3-fluoroazetidin-1-yl)ethanone and 2-chloro-1-(3-fluoroazetidin-1-yl)ethanone and was used in the next step without any further purification.

Intermediate 3: (5-Fluoropyrimidin-2-yl)methyl methanesulfonate

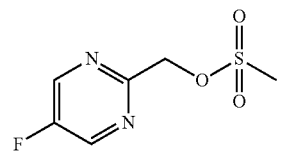

To a solution of (5-fluoropyrimidin-2-yl)methanol (100 mg, 0.78 mmol) in DCM (3 mL) was added Et$_3$N (0.16 mL, 1.2 mmol) followed by methanesulfonyl chloride (79 μL, 1 mmol) at 0° C. After 30 minutes, water (10 mL) and a saturated aqueous solution of NaHCO$_3$ (10 mL) were added. The aqueous phase was extracted with DCM twice and the combined organics layers were dried (MgSO$_4$), filtered and evaporated to afford the title compound (160 mg, quantitative yield). The material was used in the next step without any further purification.

Intermediate 4: Pyrimidin-5-ylmethyl methanesulfonate

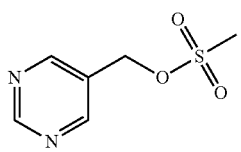

To a solution of 5-pyrimidine methanol (110 mg, 0.999 mmol) in DCM (4 mL) was added Et$_3$N (0.21 mL, 1.5 mmol) followed by methanesulfonyl chloride (0.10 mL, 1.3 mmol) at 0° C. After 30 minutes, water (10 mL) and a saturated aqueous solution of NaHCO$_3$ (10 mL) were added. The aqueous phase was extracted with DCM twice and the combined organics layers were dried (MgSO$_4$), filtered and evaporated to afford the title compound (188 mg, quantitative yield). The material was used in the next step without any further purification.

Intermediate 5: 6-Bromo-3-chloro-1H-pyrrolo[3,2-b]pyridine

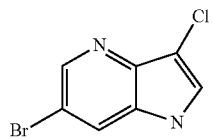 [SMILES: Clc1c[nH]c2cc(Br)cnc12]

To a solution of 6-bromo-1H-pyrrolo[3,2-b]pyridine (3 g, 15 mmol) in DMF (34 mL) cooled at 0° C. was slowly added NCS (2.4 g, 18 mmol). The reaction mixture was allowed to warm to room temperature and stirred for 12 hours. Water was then added and the mixture was stirred for 20 minutes. The title compound was collected via filtration and washed with water (2.6 g, 74%). $^1$H NMR (500 MHz, DMSO-d$_6$) δ 11.74 (s, 1H), 8.45 (d, J=2.0 Hz, 1H), 8.09 (d, J=2.0 Hz, 1H), 7.86 (d, J=3.0 Hz, 1H).

Intermediate 6: 6-Bromo-3-fluoro-1H-pyrrolo[3,2-b]pyridine

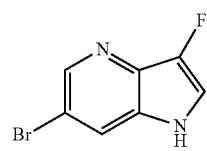

To a solution of 6-bromo-1H-pyrrolo[3,2-b]pyridine (2 g, 10.2 mmol) and Selectfluor® (4.3 g, 12.2 mmol) in ACN (20 mL) was added pyridine (6 mL). After 16 hours at room temperature, solvent was evaporated under reduced pressure. Purification (FCC, SiO$_2$, 50-100% EtOAc in hexanes) gave the title compound (666 mg, 31%). $^1$H NMR (500 MHz, DMSO-d$_6$) δ 11.28 (s, 1H), 8.41 (d, J=2.0 Hz, 1H), 8.04 (t, J=2.2 Hz, 1H), 7.71 (t, J=2.6 Hz, 1H).

Intermediate 7: 6-Phenyl-1H-pyrrolo[3,2-b]pyridine

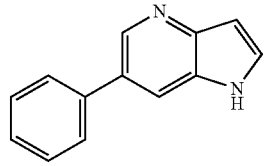 [SMILES: c1ccc(-c2cnc3cc[nH]c3c2)cc1]

To a solution a 6-bromo-1H-pyrrolo[3,2-b]pyridine (400 mg, 2.03 mmol) in dioxane (100 mL) was added phenylboronic acid (297 mg, 2.43 mmol), Pd(dppf)Cl$_2$ (149 mg, 0.203 mmol), Cs$_2$CO$_3$ (1.9 g, 6.09 mmol) and water (10 mL). After 16 hours at 90° C. the reaction mixture cooled and was concentrated under reduced pressure. Purification (FCC, SiO$_2$, 0-100% EtOAc in hexanes) afforded the title compound (257 mg, 65%). MS (ESI): mass calcd. for C$_{13}$H$_{10}$N$_2$, 194.1. m/z found, 195.0 [M+H]$^+$.

Intermediate 8: 3-Bromo-6-phenyl-1H-pyrrolo[3,2-b]pyridine

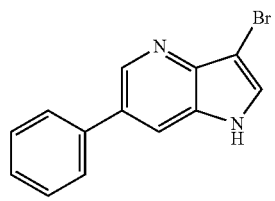 [SMILES: Brc1c[nH]c2cc(-c3ccccc3)cnc12]

To a solution of 6-phenyl-1H-pyrrolo[3,2-b]pyridine (Intermediate 7, 526 mg, 2.708 mmol) in DMF (6 mL) at 0° C. was added N-bromosuccinimide (NBS) (500 mg, 2.809 mmol) in small portions. The reaction mixture was stirred at 0° C. for 15 min. The reaction mixture was poured into water (25 mL). The precipitate was collected and washed with water (2×4 mL) and methanol (2×4 mL) to give the title compound (510 mg, 1.867 mmol, 69%) as a light brown powder. MS (ESI): mass calcd. for C$_{13}$H$_9$BrN$_2$, 272.0. m/z found, 273.0 [M+H]$^+$. $^1$H NMR (300 MHz, DMSO-d$_6$) δ 11.78 (s, 1H), 8.71 (s, 1H), 8.02 (s, 1H), 7.88 (d, J=2.9 Hz, 1H), 7.74 (d, J=7.6 Hz, 2H), 7.51 (t, J=7.5 Hz, 2H), 7.40 (t, J=7.3 Hz, 1H).

Intermediate 9: 6-(3,5-Difluorophenyl)-1H-pyrrolo[3,2-b]pyridine

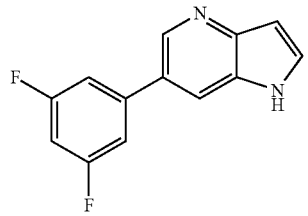 [SMILES: Fc1cc(F)cc(-c2cnc3cc[nH]c3c2)c1]

The title compound was prepared in a manner analogous to Intermediate 7. MS (ESI): mass calcd. for $C_{13}H_6F_2N_2$, 230.07. m/z found, 231=[M+H]$^+$. $^1$H NMR (400 MHz, DMSO-$d_6$) δ 11.61-11.38 (s, 1H), 8.75-8.56 (d, J=2.1 Hz, 1H), 8.16-7.85 (m, 1H), 7.77-7.65 (m, 1H), 7.62-7.39 (m, 2H), 7.29-7.04 (tt, J=9.4, 2.3 Hz, 1H), 6.73-6.47 (d, J=3.1 Hz, 1H).

Intermediate 10: 2-(6-Bromo-1H-pyrrolo[3,2-b]pyridin-1-yl)-1-(pyrrolidin-1-yl)ethanone

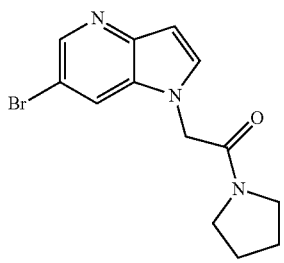 [SMILES: O=C(Cn1ccc2ncc(Br)cc21)N1CCCC1]

To a solution of 6-bromo-1H-pyrrolo[3,2-b]pyridine (1 g, 5.0 mmol) in DMF (20 mL) at 0° C. was added NaH (284 mg, 7.1 mmol, 60% dispersion in oil). The reaction mixture was stirred for 30 minutes and 2-bromo-1-(pyrrolidin-1-yl)ethanone (1.02 g, 5.3 mmol) in DMF (5 mL) was added. The reaction mixture was allowed to warm to room temperature and stirred for 12 hours. Water (1 mL) was added and the reaction mixture was concentrated onto silica gel. Purification (FCC, SiO$_2$, 0-20% MeOH in EtOAc) gave the title compound (quant. yield). $^1$H NMR (400 MHz, DMSO-$d_6$) δ 8.37 (d, J=2.0 Hz, 1H), 8.18 (dd, J=2.1, 0.8 Hz, 1H), 7.58 (d, J=3.3 Hz, 1H), 6.58 (dd, J=3.3, 0.8 Hz, 1H), 5.12 (s, 2H), 3.56 (t, J=6.8 Hz, 2H), 3.37-3.25 (m, 2H), 2.01-1.90 (m, 2H), 1.86-1.75 (m, 2H).

Intermediate 11: 2-(6-Bromo-1H-pyrrolo[3,2-b]pyridin-1-yl)-1-morpholinoethanone

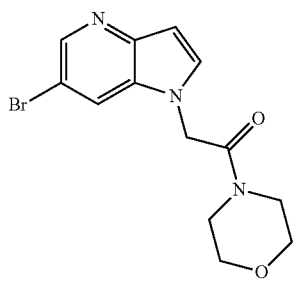 [SMILES: O=C(Cn1ccc2ncc(Br)cc21)N1CCOCC1]

The title compound was prepared in a manner analogous to Intermediate 10, substituting 2-bromo-1-morpholinoethanone for 2-bromo-1-(pyrrolidin-1-yl)ethanone. $^1$H NMR (500 MHz, DMSO-$d_6$) δ 8.37 (d, J=2.0 Hz, 1H), 8.18 (dd, J=2.1, 0.9 Hz, 1H), 7.58 (d, J=3.3 Hz, 1H), 6.59 (dd, J=3.3, 0.9 Hz, 1H), 5.24 (s, 2H), 3.69 (t, J=4.8 Hz, 2H), 3.60 (t, J=4.9 Hz, 2H), 3.54 (t, J=4.8 Hz, 2H), 3.44 (t, J=4.8 Hz, 2H).

Intermediate 12: 2-(6-Bromo-1H-pyrrolo[3,2-b]pyridin-1-yl)-1-(3,3-difluoroazetidin-1-yl)ethanone

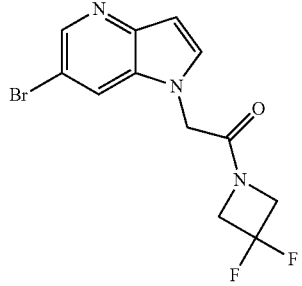 [SMILES: O=C(Cn1ccc2ncc(Br)cc21)N1CC(F)(F)C1]

The title compound was prepared in a manner analogous to Intermediate 10, substituting 2-bromo-1-(3,3-difluoroazetidin-1-yl)ethanone (Intermediate 1) for 2-bromo-1-(pyrrolidin-1-yl)ethanone. MS (ESI): mass calcd. for $C_{12}H_{10}BrF_2N_3O$, 329.0. m/z found, 330.0 [M+H]$^+$.

Intermediate 13: 2-(6-Bromo-1H-pyrrolo[3,2-b]pyridin-1-yl)-1-(3-fluoroazetidin-1-yl)ethanone

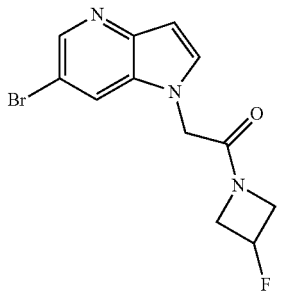 [SMILES: O=C(Cn1ccc2ncc(Br)cc21)N1CC(F)C1]

The title compound was prepared in a manner analogous to Intermediate 10, substituting 2-bromo-1-(3-fluoroazetidin-1-yl)ethanone (Intermediate 2) for 2-bromo-1-(pyrrolidin-1-yl)ethanone. MS (ESI): mass calcd. for $C_{12}H_{11}BrFN_3O$, 311.0. m/z found, 312.0 [M+H]$^+$.

Intermediate 14: 1-(Azetidin-1-yl)-2-(6-bromo-1H-pyrrolo[3,2-b]pyridin-1-yl)ethanone

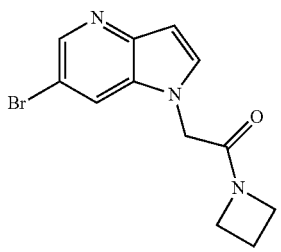 [SMILES: O=C(Cn1ccc2ncc(Br)cc21)N1CCC1]

The title compound was prepared in a manner analogous to Intermediate 10, using 1-(azetidin-1-yl)-2-bromoethanone and 6-bromo-1H-pyrrolo[3,2-b]pyridine. $^1$H NMR (500 MHz, DMSO-$d_6$) δ 8.44-8.31 (d, J=2.0 Hz, 1H), 8.19-8.11 (m, 1H), 7.66-7.43 (d, J=3.3 Hz, 1H), 6.64-6.50 (m, 1H), 5.02-4.85 (s, 2H), 4.29-4.15 (m, 2H), 3.96-3.81 (m, 2H), 2.34-2.20 (m, 2H).

Intermediate 15: 2-(6-bromo-3-fluoro-1H-pyrrolo[3,2-b]pyridin-1-yl)-1-(3,3-difluoroazetidin-1-yl)ethanone

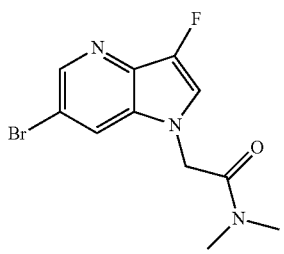 [SMILES: CN(C)C(=O)Cn1cc(F)c2ncc(Br)cc21]

The title compound was prepared in a manner analogous to Intermediate 10, substituting 2-bromo-N,N-dimethylacetamide for 2-bromo-1-(pyrrolidin-1-yl)ethanone and 6-bromo-3-fluoro-1H-pyrrolo[3,2-b]pyridine (Intermediate 6) for 6-bromo-1H-pyrrolo[3,2-b]pyridine. $^1$H NMR (500 MHz, DMSO-$d_6$) δ 8.42 (d, J=1.9 Hz, 1H), 8.29 (t, J=2.1 Hz, 1H), 7.63 (d, J=2.2 Hz, 1H), 5.16 (s, 2H), 3.07 (s, 3H), 2.85 (s, 3H).

Intermediate 16: 2-(6-Bromo-3-fluoro-1H-pyrrolo[3,2-b]pyridin-1-yl)-1-(3,3-difluoroazetidin-1-yl)ethanone

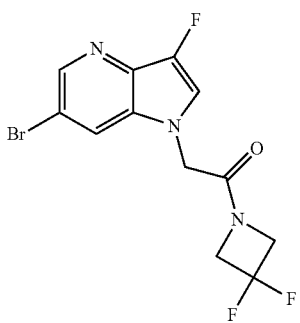 [SMILES: O=C(Cn1cc(F)c2ncc(Br)cc21)N1CC(F)(F)C1]

The title compound was prepared in a manner analogous to Intermediate 10, using 2-bromo-1-(3,3-difluoroazetidin-1-yl)ethanone (Intermediate 1) and 6-bromo-3-fluoro-1H-pyrrolo[3,2-b]pyridine (Intermediate 6). $^1$H NMR (500 MHz, DMSO-$d_6$) δ 8.52-8.39 (d, J=1.9 Hz, 1H), 8.34-8.21 (m, 1H), 7.73-7.53 (d, J=2.2 Hz, 1H), 5.07-4.89 (s, 2H), 4.83-4.56 (m, 2H), 4.46-4.25 (m, 2H).

Intermediate 17: 2-(6-Bromo-3-fluoro-1H-pyrrolo[3,2-b]pyridin-1-yl)-1-(3-fluoroazetidin-1-yl)ethanone

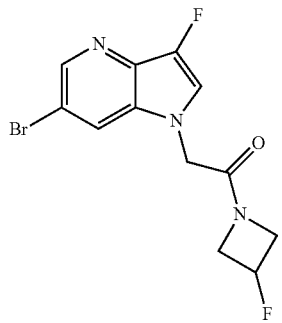 [SMILES: O=C(Cn1cc(F)c2ncc(Br)cc21)N1CC(F)C1]

The title compound was prepared in a manner analogous to Intermediate 10, using 2-bromo-1-(3-fluoroazetidin-1-yl) ethanone (Intermediate 2) and 6-bromo-3-fluoro-1H-pyrrolo[3,2-b]pyridine (Intermediate 6). $^1$H NMR (500 MHz, DMSO-$d_6$) δ 8.51-8.36 (d, J=1.9 Hz, 1H), 8.36-8.17 (t, J=2.1 Hz, 1H), 7.70-7.63 (d, J=2.2 Hz, 1H), 5.60-5.48 (m, 0.5H), 5.48-5.31 (m, 0.5H), 5.07-4.79 (d, J=2.2 Hz, 2H), 4.69-4.47 (m, 1H), 4.40-4.17 (m, 2H), 4.14-3.87 (m, 1H).

Intermediate 18: 2-(6-Bromo-3-fluoro-1H-pyrrolo[3,2-b]pyridin-1-yl)-1-(pyrrolidin-1-yl)ethanone

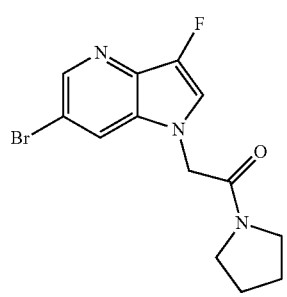 [SMILES: O=C(Cn1cc(F)c2ncc(Br)cc21)N1CCCC1]

The title compound was prepared in a manner analogous to Intermediate 6, using 2-(6-bromo-1H-pyrrolo[3,2-b]pyridin-1-yl)-1-(pyrrolidin-1-yl)ethanone (Intermediate 10). $^1$H NMR (500 MHz, DMSO-$d_6$) δ 8.50-8.36 (d, J=1.9 Hz, 1H), 8.36-8.21 (t, J=2.1 Hz, 1H), 7.76-7.57 (d, J=2.2 Hz, 1H), 5.13-4.86 (s, 2H), 3.62-3.47 (m, 2H), 3.41-3.17 (s, 2H), 2.03-1.86 (m, 2H), 1.86-1.66 (m, 2H).

Intermediate 19: 2-(6-Bromo-3-fluoro-1H-pyrrolo[3,2-b]pyridin-1-yl)-1-morpholinoethanone

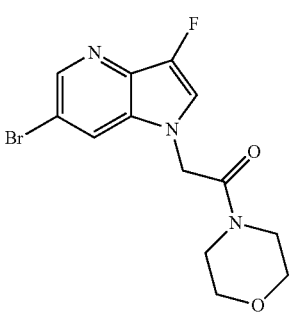 [SMILES: O=C(Cn1cc(F)c2ncc(Br)cc21)N1CCOCC1]

The title compound was prepared in a manner analogous to Intermediate 6, using 2-(6-bromo-1H-pyrrolo[3,2-b]pyridin-1-yl)-1-morpholinoethanone (Intermediate 11). MS (ESI): mass calcd. for $C_{13}H_{13}BrFN_3O_2$, 341.0. m/z found, 342.0 [M+H]$^+$.

Intermediate 20: tert-Butyl 2-(6-(4-fluorophenyl)-1H-pyrrolo[3,2-b]pyridin-1-yl)acetate

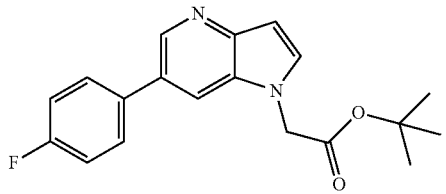 [SMILES: CC(C)(C)OC(=O)Cn1ccc2ncc(-c3ccc(F)cc3)cc21]

Step A: 6-(4-Fluorophenyl)-1H-pyrrolo[3,2-b]pyridine

The title compound was prepared in a manner analogous to Intermediate 7. $^1$H NMR (400 MHz, DMSO-$d_6$) δ 11.39 (s, 1H), 8.60 (d, J=2.1 Hz, 1H), 7.95 (dd, J=2.1, 0.9 Hz, 1H), 7.80-7.73 (m, 2H), 7.70-7.65 (m, 1H), 7.36-7.28 (m, 2H), 6.60-6.56 (m, 1H).

Step B: tert-Butyl 2-(6-(4-fluorophenyl)-1H-pyrrolo[3,2-b]pyridin-1-yl)acetate The title compound was prepared in a manner analogous to Intermediate 10. $^1$H NMR (300 MHz, DMSO-$d_6$) δ 8.65 (s, 1H), 8.16 (s, 1H), 7.79 (dd, J=8.6, 5.5 Hz, 2H), 7.66 (d, J=3.2 Hz, 1H), 7.34 (t, J=8.8 Hz, 2H), 6.61 (d, J=3.0 Hz, 1H), 5.13 (s, 2H), 1.41 (s, 9H).

Example 1

2-(3-Chloro-6-phenyl-pyrrolo[3,2-b]pyridin-1-yl)-N-cyclopropyl-acetamide

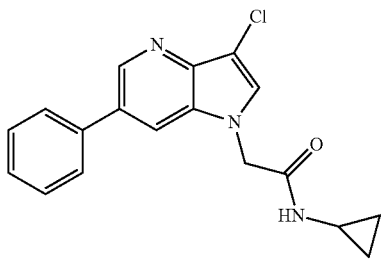

Step A: 6-Phenyl-1H-pyrrolo[3,2-b]pyridine

To a solution of 6-bromo-1H-pyrrolo[3,2-b]pyridine (400 mg, 2.03 mmol) in dioxane (100 mL) was added phenylboronic acid (297 mg, 2.43 mmol), Pd(dppf)Cl$_2$ (149 mg, 0.203 mmol), Cs$_2$CO$_3$ (1.9 g, 6.09 mmol) and water (10 mL). After 16 h at 90° C. the reaction mixture cooled and was concentrated under reduced pressure. Purification (FCC, SiO$_2$, 0-100% EtOAc in hexanes) afforded the title compound (257 mg, 65%). MS (ESI): mass calcd. for C$_{13}$H$_{10}$N$_2$, 194.1. m/z found, 195.0 [M+H]$^+$.

Step B: 3-Chloro-6-phenyl-1H-pyrrolo[3,2-b]pyridine

To a solution of 6-phenyl-1H-pyrrolo[3,2-b]pyridine (600 mg, 3.09 mmol) in N,N-dimethylformamide (6 mL) at 0° C. was added N-chlorosuccinimide (619 mg, 4.64 mmol) in several small portions. The reaction mixture was warmed to room temperature and the stirring was continued for 5 h. The mixture was poured into water (30 mL). The precipitate was collected and washed with warm methanol (5 mL) to afford the title compound (503 mg, 2.20 mmol, 71%) as a pale brown powder. MS (ESI): mass calcd. For C$_{13}$H$_9$ClN$_2$, 229.0. m/z found, 229 [M+H]$^+$. $^1$H NMR (300 MHz, DMSO-$d_6$) δ 11.68 (s, 1H), 8.71 (s, 1H), 8.01 (s, 1H), 7.86 (d, J=2.9 Hz, 1H), 7.74 (d, J=7.5 Hz, 2H), 7.51 (t, J=7.5 Hz, 2H), 7.40 (t, J=7.3 Hz, 1H).

Step C: 2-(3-Chloro-6-phenyl-pyrrolo[3,2-b]pyridin-1-yl)-N-cyclopropyl-acetamide To a solution of 3-chloro-6-phenyl-1H-pyrrolo[3,2-b]pyridine (70 mg, 0.306 mmol) in anhydrous DMF (1.4 mL) was added NaH (60% dispersion, 18 mg, 0.46 mmol) at 0° C. in small portions under argon. The reaction mixture was warmed to room temperature and stirred for 30 min. The reaction mixture was cooled to 0° C. and to the mixture was added 2-bromo-N-cyclopropyl-acetamide (81 mg, 0.46 mmol) in small portions. The reaction mixture was warmed to room temperature and the stirring was continued for 2 h. The reaction mixture was poured into ice water (10 mL). The precipitate was collected and washed with water (2×3 mL). Purification (FCC, SiO$_2$, 100:1 to 95:5 chloroform in MeOH). The product was triturated with warm ethanol (1 mL) to give the title compound (30 mg, 0.09 mmol, 30%) as an off-white powder. MS (ESI): mass calcd. For C$_{16}$H$_{16}$ClN$_3$O, 325.1. m/z found, 326 [M+H]$^+$. $^1$H NMR (300 MHz, DMSO-$d_6$) δ 8.74 (s, 1H), 8.34 (s, 1H), 8.18 (s, 1H), 7.83 (s, 1H), 7.76 (d, J=7.6 Hz, 2H), 7.52 (t, J=7.5 Hz, 2H), 7.41 (t, J=7.4 Hz, 1H), 4.89 (s, 2H), 2.71-2.58 (m, 1H), 0.68-0.57 (m, 2H), 0.51-0.33 (m, 2H).

Example 2

2-[3-Chloro-6-(4-fluorophenyl)pyrrolo[3,2-b]pyridin-1-yl]-N-cyclopropyl-acetamide

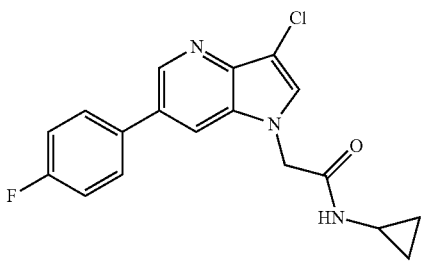 [SMILES: O=C(Cn1cc(Cl)c2ncc(-c3ccc(F)cc3)cc21)NC1CC1]

The title compound was prepared in a manner analogous to Example 1. MS (ESI): mass calcd. for C$_{18}$H$_{15}$ClFN$_3$O, 343.1. m/z found, 344.0 [M+H]$^+$. $^1$H NMR (300 MHz, DMSO-$d_6$) δ 8.71 (s, 1H), 8.31 (d, J=4.2 Hz, 1H), 8.17 (s, 1H), 7.83 (s, 1H), 7.79 (dd, J=8.6, 5.3 Hz, 2H), 7.35 (t, J=8.6 Hz, 2H), 4.88 (s, 2H), 2.71-2.60 (m, 1H), 0.69-0.57 (m, 2H), 0.50-0.39 (m, 2H).

Example 3

1-(Azetidin-1-yl)-2-[3-chloro-6-(4-fluorophenyl)pyrrolo[3,2-b]pyridin-1-yl]ethanone

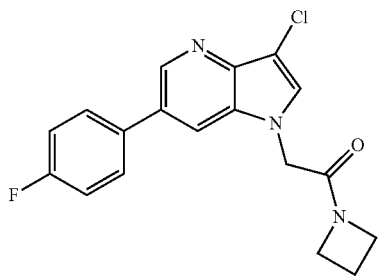 [SMILES: O=C(Cn1cc(Cl)c2ncc(-c3ccc(F)cc3)cc21)N1CCC1]

The title compound was prepared in a manner analogous to Example 1. MS (ESI): mass calcd. for $C_{18}H_{15}ClFN_3O$, 343.1. m/z found, 344.0 [M+H]⁺. ¹H NMR (300 MHz, DMSO-d₆) δ 8.71 (s, 1H), 8.20 (s, 1H), 7.86-7.74 (m, 2H), 7.79 (s, 1H), 7.36 (t, J=8.6 Hz, 2H), 5.01 (s, 2H), 4.24 (t, J=7.6 Hz, 2H), 3.91 (t, J=7.8 Hz, 2H), 2.28 (quint, J=7.8 Hz, 2H).

Example 4

2-(3-Chloro-6-phenyl-pyrrolo[3,2-b]pyridin-1-yl)-1-pyrrolidin-1-yl-ethanone

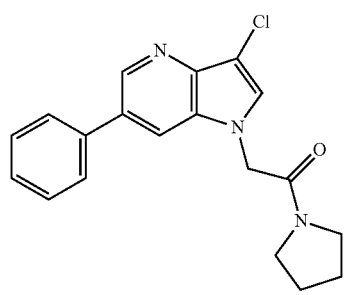

The title compound was prepared in a manner analogous to Example 1. MS (ESI): mass calcd. for $C_{19}H_{18}ClN_3O$, 339.1. m/z found, 340.0 [M+H]⁺. ¹H NMR (300 MHz, DMSO-d₆) δ 8.73 (s, 1H), 8.24 (s, 1H), 7.77 (s, 1H), 7.77 (d, J=7.8 Hz, 2H), 7.52 (t, J=7.5 Hz, 2H), 7.41 (t, J=7.3 Hz, 1H), 5.19 (s, 2H), 3.58 (t, J=6.8 Hz, 2H), 3.37-3.26 (m, 2H), 1.97 (quint, J=6.7 Hz, 2H), 1.81 (quint, J=6.9 Hz, 2H).

Example 5

2-(3-Chloro-6-phenyl-pyrrolo[3,2-b]pyridin-1-yl)-1-morpholinoethanone

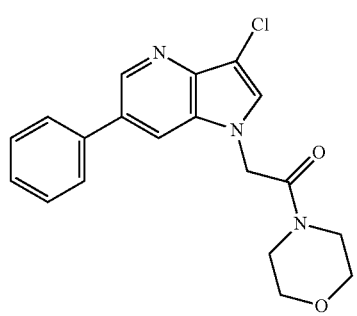 [SMILES: O=C(Cn1cc(Cl)c2ncc(-c3ccccc3)cc21)N1CCOCC1]

The title compound was prepared in a manner analogous to Example 1. MS (ESI): mass calcd. for $C_{19}H_{18}ClN_3O_2$, 355.1. m/z found, 356.0 [M+H]⁺. ¹H NMR (300 MHz, DMSO-d₆) δ 8.73 (s, 1H), 8.22 (s, 1H), 7.77 (s, 1H), 7.76 (d, J=7.0 Hz, 2H), 7.52 (t, J=7.5 Hz, 2H), 7.41 (t, J=7.3 Hz, 1H), 5.31 (s, 2H), 3.90-3.37 (m, 8H).

Example 6

1-(Azetidin-1-yl)-2-(3-chloro-6-phenyl-pyrrolo[3,2-b]pyridin-1-yl)ethanone

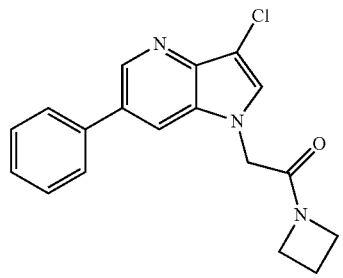 [SMILES: O=C(Cn1cc(Cl)c2ncc(-c3ccccc3)cc21)N1CCC1]

The title compound was prepared in a manner analogous to Example 1. MS (ESI): mass calcd. for $C_{18}H_{16}ClN_3O$, 325.1. m/z found, 326.0 [M+H]⁺. ¹H NMR (300 MHz, DMSO-d₆) δ 8.73 (s, 1H), 8.21 (s, 1H), 7.78 (s, 1H), 7.77 (d, J=7.2 Hz, 2H), 7.53 (t, J=7.5 Hz, 2H), 7.41 (t, J=7.3 Hz, 1H), 5.02 (s, 2H), 4.25 (t, J=7.6 Hz, 2H), 3.91 (t, J=7.7 Hz, 2H), 2.28 (quint, J=7.7 Hz, 2H).

Example 7

2-[3-Chloro-6-(4-fluorophenyl)pyrrolo[3,2-b]pyridin-1-yl]-1-morpholino-ethanone

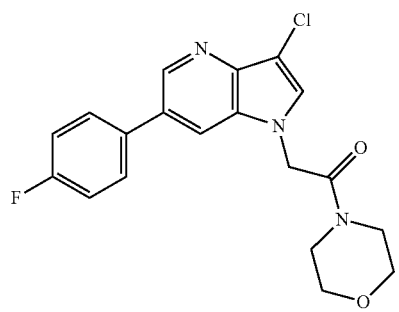

The title compound was prepared in a manner analogous to Example 1. MS (ESI): mass calcd. for $C_{19}H_{17}ClFN_3O_2$, 373.1. m/z found, 374.0 [M+H]⁺. ¹H NMR (300 MHz, DMSO-d₆) δ 8.71 (s, 1H), 8.21 (s, 1H), 7.85-7.72 (m, 2H), 7.78 (s, 1H), 7.36 (t, J=8.7 Hz, 2H), 5.30 (s, 2H), 3.80-3.65 (m, 2H), 3.65-3.50 (m, 4H), 3.50-3.37 (m, 2H).

Example 8

1-(Azetidin-1-yl)-2-[3-chloro-6-(m-tolyl)pyrrolo[3,2-b]pyridin-1-yl]ethanone

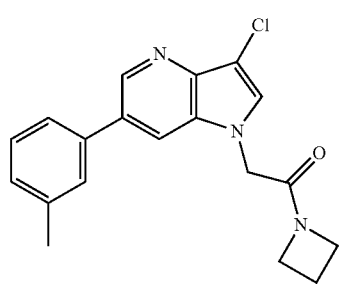 [SMILES: Cc1cccc(-c2cnc3c(Cl)cn(CC(=O)N4CCC4)c3c2)c1]

The title compound was prepared in a manner analogous to Example 1. MS (ESI): mass calcd. for $C_{19}H_{18}ClN_3O$, 339.1. m/z found, 340.0 [M+H]$^+$. $^1$H NMR (300 MHz, DMSO-d$_6$) δ 8.72 (s, 1H), 8.19 (s, 1H), 7.78 (s, 1H), 7.58 (s, 1H), 7.55 (d, J=8.2 Hz, 1H), 7.40 (t, J=7.6 Hz, 1H), 7.23 (d, J=7.5 Hz, 1H), 5.02 (s, 2H), 4.24 (t, J=7.6 Hz, 2H), 3.91 (t, J=7.7 Hz, 2H), 2.42 (s, 3H), 2.28 (quint, J=7.8 Hz, 2H).

Example 9

2-[3-Chloro-6-(4-fluorophenyl)pyrrolo[3,2-b]pyridin-1-yl]-1-pyrrolidin-1-yl-ethanone

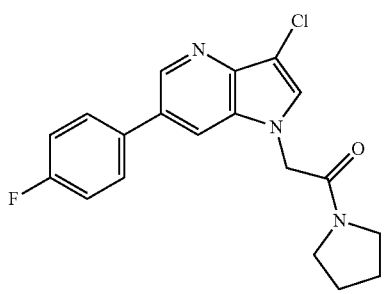 [SMILES: O=C(Cn1cc(Cl)c2ncc(-c3ccc(F)cc3)cc21)N1CCCC1]

The title compound was prepared in a manner analogous to Example 1. MS (ESI): mass calcd. for $C_{19}H_{17}ClFN_3O$, 357.1. m/z found, 358.0 [M+H]$^+$. $^1$H NMR (300 MHz, DMSO-d$_6$) δ 8.71 (s, 1H), 8.22 (s, 1H), 7.80 (dd, J=8.4, 6.1 Hz, 2H), 7.77 (s, 1H), 7.35 (t, J=8.6 Hz, 2H), 5.18 (s, 2H), 3.58 (t, J=6.8 Hz, 2H), 3.36-3.20 (m, 2H), 1.97 (quint, J=6.8 Hz, 2H), 1.81 (quint, J=6.8 Hz, 2H).

Example 10

2-[3-Chloro-6-(m-tolyl)pyrrolo[3,2-b]pyridin-1-yl]-N-cyclopropyl-acetamide

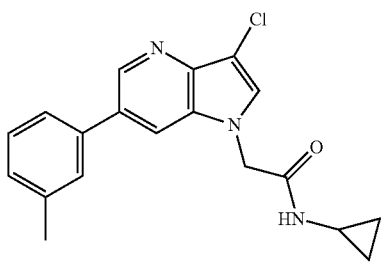 [SMILES: Cc1cccc(-c2cnc3c(Cl)cn(CC(=O)NC4CC4)c3c2)c1]

The title compound was prepared in a manner analogous to Example 1. MS (ESI): mass calcd. for $C_{19}H_{18}ClN_3O$, 339.1. m/z found, 340.0 [M+H]$^+$. $^1$H NMR (300 MHz, DMSO-d$_6$) δ 8.72 (s, 1H), 8.33 (d, J=4.2 Hz, 1H), 8.15 (s, 1H), 7.82 (s, 1H), 7.57 (s, 1H), 7.53 (d, J=7.6 Hz, 1H), 7.40 (t, J=7.6 Hz, 1H), 7.22 (d, J=7.5 Hz, 1H), 4.89 (s, 2H), 2.70-2.58 (m, 1H), 2.41 (s, 3H), 0.70-0.53 (m, 2H), 0.50-0.29 (m, 2H).

Example 11

1-(Azetidin-1-yl)-2-(3-bromo-6-phenyl-pyrrolo[3,2-b]pyridin-1-yl)ethanone

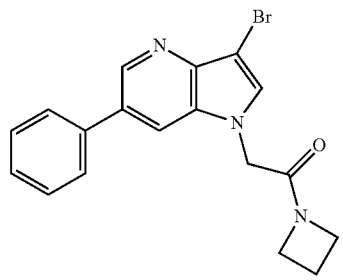 [SMILES: O=C(Cn1cc(Br)c2ncc(-c3ccccc3)cc21)N1CCC1]

The title compound was prepared in a manner analogous to Example 14. MS (ESI): mass calcd. for $C_{18}H_{16}BrN_3O$, 369.0. m/z found, 370.0 [M+H]$^+$. $^1$H NMR (300 MHz, DMSO-d$_6$) δ 8.74 (s, 1H), 8.21 (s, 1H), 7.81 (s, 1H), 7.77 (d, J=7.7 Hz, 2H), 7.53 (t, J=7.5 Hz, 2H), 7.41 (t, J=7.3 Hz, 1H), 5.03 (s, 2H), 4.25 (t, J=7.6 Hz, 2H), 3.91 (t, J=7.8 Hz, 2H), 2.30 (quint, J=7.5 Hz, 2H).

Example 12

2-[3-Chloro-6-(m-tolyl)pyrrolo[3,2-b]pyridin-1-yl]-1-pyrrolidin-1-yl-ethanone

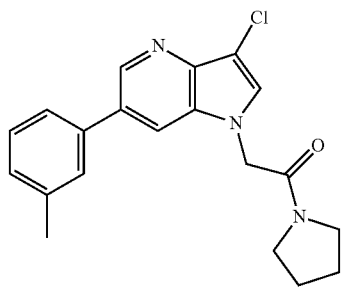

The title compound was prepared in a manner analogous to Example 1. MS (ESI): mass calcd. for $C_{20}H_{20}ClN_3O$, 353.1. m/z found, 354.0 [M+H]$^+$. $^1$H NMR (300 MHz, DMSO-d$_6$) δ 8.71 (s, 1H), 8.21 (s, 1H), 7.76 (s, 1H), 7.57 (s, 1H), 7.54 (d, J=7.8 Hz, 1H), 7.40 (t, J=7.6 Hz, 1H), 7.22 (d, J=7.5 Hz, 1H), 5.19 (s, 2H), 3.59 (t, J=6.8 Hz, 2H), 3.39-3.24 (m, 2H), 2.41 (s, 3H), 1.97 (quint, J=6.8 Hz, 2H), 1.81 (quint, J=6.8 Hz, 2H).

Example 13

2-[3-Chloro-6-(m-tolyl)pyrrolo[3,2-b]pyridin-1-yl]-1-morpholino-ethanone

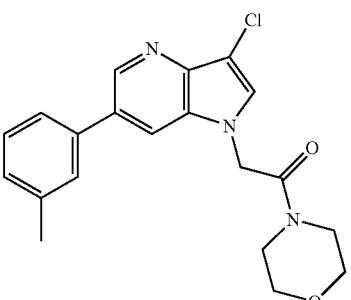

The title compound was prepared in a manner analogous to Example 1. MS (ESI): mass calcd. for $C_{20}H_{20}ClN_3O_2$, 369.1. m/z found, 370.0 [M+H]$^+$. $^1$H NMR (300 MHz, DMSO-d$_6$) δ 8.70 (s, 1H), 8.19 (s, 1H), 7.77 (s, 1H), 7.56 (s, 1H), 7.53 (d, J=7.6 Hz, 1H), 7.40 (t, J=7.6 Hz, 1H), 7.22 (d, J=7.5 Hz, 1H), 5.31 (s, 2H), 3.85-3.65 (m, 2H), 3.65-3.50 (m, 4H), 3.50-3.37 (m, 2H), 2.41 (s, 3H).

Example 14

2-(3-Bromo-6-phenyl-pyrrolo[3,2-b]pyridin-1-yl)-N-cyclopropyl-acetamide

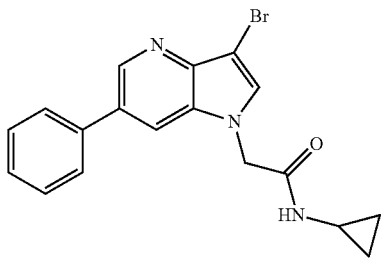 [SMILES: O=C(Cn1cc(Br)c2ncc(-c3ccccc3)cc21)NC1CC1]

Step A: 3-Bromo-6-phenyl-1H-pyrrolo[3,2-b]pyridine

To a solution of 6-phenyl-1H-pyrrolo[3,2-b]pyridine (Intermediate 7, 526 mg, 2.708 mmol) in DMF (6 mL) at 0° C. was added N-bromosuccinimide (NBS) (500 mg, 2.809 mmol) in small portions. The reaction mixture was stirred at 0° C. for 15 min. The reaction mixture was poured into water (25 mL). The precipitate was collected and washed with water (2×4 mL) and methanol (2×4 mL) to give the title compound (510 mg, 1.867 mmol, 69%) as a light brown powder. MS (ESI): mass calcd. for $C_{13}H_9BrN_2$, 272.0. m/z found, 273.0 [M+H]$^+$. $^1$H NMR (300 MHz, DMSO-d$_6$) δ 11.78 (s, 1H), 8.71 (s, 1H), 8.02 (s, 1H), 7.88 (d, J=2.9 Hz, 1H), 7.74 (d, J=7.6 Hz, 2H), 7.51 (t, J=7.5 Hz, 2H), 7.40 (t, J=7.3 Hz, 1H).

Step B: 2-(3-Bromo-6-phenyl-pyrrolo[3,2-b]pyridin-1-yl)-N-cyclopropyl-acetamide

To a solution of 3-bromo-6-phenyl-1H-pyrrolo[3,2-b]pyridine (60 mg, 0.22 mmol) in anhydrous DMF (1.5 mL) was added NaH (60% dispersion, 13 mg, 0.33 mmol) in small portions at 0° C. under argon. The reaction mixture was warmed to room temperature and stirred for 30 min. The reaction mixture was cooled to 0° C. and to the mixture was added 2-bromo-N-cyclopropylacetamide (43 mg, 0.24 mmol) in small portions. The reaction mixture was warmed to room temperature and the stirring was continued for 1 h. The reaction mixture was poured into ice water (6 mL) and the precipitate was collected and washed with water (2×0.5 mL). The crude product was recrystallized from ethanol (1.7 mL) to afford the title compound (49 mg, 0.13 mmol, 60%) as a white powder. MS (ESI): mass calcd. for $C_{18}H_{16}BrN_3O$, 369.0. m/z found, 370 [M+H]$^+$. $^1$H NMR (300 MHz, DMSO-d$_6$) δ 8.74 (s, 1H), 8.35 (d, J=4.1 Hz, 1H), 8.17 (s, 1H), 7.85 (s, 1H), 7.76 (d, J=7.5 Hz, 2H), 7.52 (t, J=7.5 Hz, 2H), 7.41 (t, J=7.3 Hz, 1H), 4.91 (s, 2H), 2.71-2.59 (m, 1H), 0.68-0.55 (m, 2H), 0.49-0.36 (m, 2H).

Example 15

2-(3-Bromo-6-phenyl-pyrrolo[3,2-b]pyridin-1-yl)-1-pyrrolidin-1-yl-ethanone

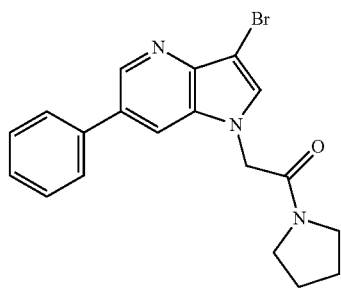 [SMILES: O=C(Cn1cc(Br)c2ncc(-c3ccccc3)cc21)N1CCCC1]

The title compound was prepared in a manner analogous to Example 14. MS (ESI): mass calcd. for $C_{19}H_{18}BrN_3O$, 383.1. m/z found, 384.0 [M+H]$^+$. $^1$H NMR (300 MHz, DMSO-d$_6$) δ 8.73 (s, 1H), 8.23 (s, 1H), 7.79 (s, 1H), 7.76 (d, J=7.8 Hz, 2H), 7.52 (t, J=7.5 Hz, 2H), 7.40 (t, J=7.3 Hz, 1H), 5.20 (s, 2H), 3.59 (t, J=6.8 Hz, 2H), 3.34-3.23 (m, 2H), 1.97 (quint, J=6.8 Hz, 2H), 1.82 (quint, J=6.8 Hz, 2H).

Example 16

2-(3-Bromo-6-phenyl-pyrrolo[3,2-b]pyridin-1-yl)-1-morpholino-ethanone

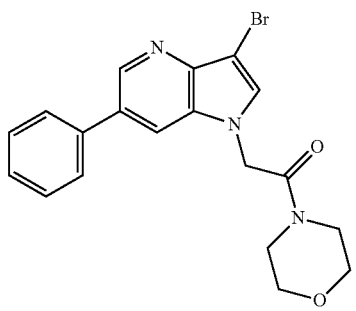

The title compound was prepared in a manner analogous to Example 14. MS (ESI): mass calcd. for $C_{19}H_{18}BrN_3O_2$, 399.1. m/z found, 400.0 [M+H]$^+$. $^1$H NMR (300 MHz, DMSO-d$_6$) δ 8.73 (s, 1H), 8.22 (s, 1H), 7.80 (s, 1H), 7.75 (d, J=7.7 Hz, 2H), 7.52 (t, J=7.5 Hz, 2H), 7.41 (t, J=7.3 Hz, 1H), 5.32 (s, 2H), 3.80-3.65 (m, 2H), 3.65-3.50 (m, 4H), 3.51-3.37 (m, 2H).

Example 17

2-[3-Bromo-6-(4-fluorophenyl)pyrrolo[3,2-b]pyridin-1-yl]-N-cyclopropyl-acetamide

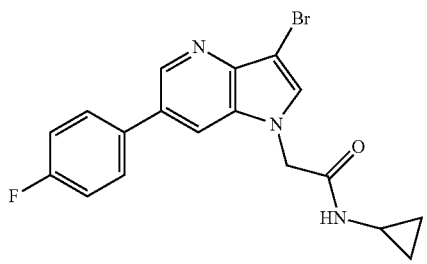 [SMILES: O=C(Cn1cc(Br)c2ncc(-c3ccc(F)cc3)cc21)NC1CC1]

The title compound was prepared in a manner analogous to Example 14. MS (ESI): mass calcd. for $C_{18}H_{15}BrFN_3O$, 387.0. m/z found, 388.0 [M+H]$^+$. $^1$H NMR (300 MHz, DMSO-d$_6$) δ 8.72 (s, 1H), 8.34 (d, J=4.1 Hz, 1H), 8.17 (s, 1H), 7.85 (s, 1H), 7.80 (dd, J=8.5, 5.5 Hz, 2H), 7.36 (t, J=8.7 Hz, 2H), 4.90 (s, 2H), 2.70-2.58 (m, 1H), 0.68-0.57 (m, 2H), 0.50-0.38 (m, 2H).

Example 18

1-(Azetidin-1-yl)-2-[3-bromo-6-(4-fluorophenyl)pyrrolo[3,2-b]pyridin-1-yl]ethanone

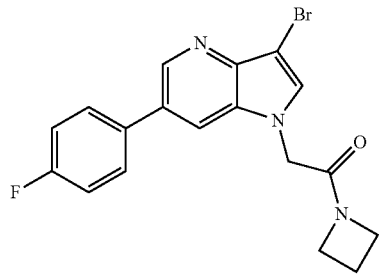

The title compound was prepared in a manner analogous to Example 14. MS (ESI): mass calcd. for $C_{18}H_{15}BrFN_3O$, 387.0. m/z found, 388.0 [M+H]$^+$. $^1$H NMR (300 MHz, DMSO-d$_6$) δ 8.71 (s, 1H), 8.20 (s, 1H), 7.87-7.74 (m, 2H), 7.81 (s, 1H), 7.36 (t, J=8.7 Hz, 2H), 5.02 (s, 2H), 4.25 (t, J=7.6 Hz, 2H), 3.91 (t, J=7.7 Hz, 2H), 2.28 (quint, J=7.7 Hz, 2H).

Example 19

2-[3-Bromo-6-(4-fluorophenyl)pyrrolo[3,2-b]pyridin-1-yl]-1-pyrrolidin-1-yl-ethanone

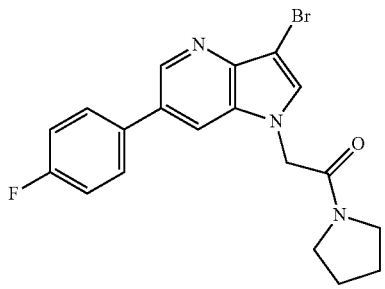 [SMILES: O=C(Cn1cc(Br)c2ncc(-c3ccc(F)cc3)cc21)N1CCCC1]

The title compound was prepared in a manner analogous to Example 14. MS (ESI): mass calcd. for $C_{19}H_{17}BrFN_3O$, 401.1. m/z found, 402.0 [M+H]$^+$. $^1$H NMR (300 MHz, DMSO-d$_6$) δ 8.71 (s, 1H), 8.22 (s, 1H), 7.88-7.70 (m, 2H), 7.79 (s, 1H), 7.35 (t, J=8.7 Hz, 2H), 5.19 (s, 2H), 3.58 (t, J=6.8 Hz, 2H), 3.38-3.25 (m, 2H), 1.97 (quint, J=6.7 Hz, 2H), 1.81 (quint, J=6.8 Hz, 2H).

Example 20

2-[3-Bromo-6-(4-fluorophenyl)pyrrolo[3,2-b]pyridin-1-yl]-1-morpholino-ethanone

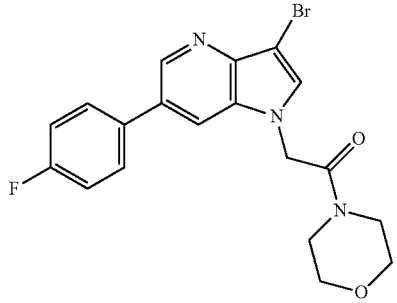 [SMILES: O=C(Cn1cc(Br)c2ncc(-c3ccc(F)cc3)cc21)N1CCOCC1]

The title compound was prepared in a manner analogous to Example 14. MS (ESI): mass calcd. for $C_{19}H_{17}BrFN_3O_2$, 417.0. m/z found, 418.0 [M+H]$^+$. $^1$H NMR (300 MHz, DMSO-d$_6$) δ 8.71 (s, 1H), 8.20 (s, 1H), 7.86-7.74 (m, 2H), 7.80 (s, 1H), 7.36 (t, J=8.6 Hz, 2H), 5.31 (s, 2H), 3.76-3.65 (m, 2H), 3.64-3.51 (m, 4H), 3.51-3.38 (m, 2H).

Example 21

2-[3-Bromo-6-(m-tolyl)pyrrolo[3,2-b]pyridin-1-yl]-N-cyclopropyl-acetamide

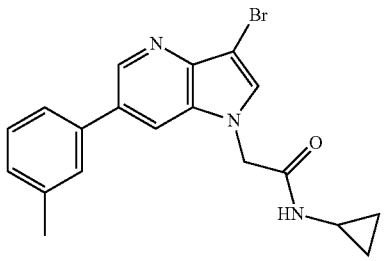 [SMILES: Cc1cccc(-c2cnc3c(Br)cn(CC(=O)NC4CC4)c3c2)c1]

The title compound was prepared in a manner analogous to Example 14. MS (ESI): mass calcd. for $C_{19}H_{16}BrN_3O$, 383.1. m/z found, 384.0 [M+H]$^+$. $^1$H NMR (300 MHz, DMSO-d$_6$) δ 8.72 (s, 1H), 8.35 (d, J=4.1 Hz, 1H), 8.14 (s, 1H), 7.84 (s, 1H), 7.57 (s, 1H), 7.54 (d, J=7.7 Hz, 1H), 7.40 (t, J=7.6 Hz, 1H), 7.22 (d, J=7.5 Hz, 1H), 4.90 (s, 2H), 2.71-2.59 (m, 1H), 2.41 (s, 3H), 0.70-0.57 (m, 2H), 0.50-0.37 (m, 2H).

Example 22

1-(Azetidin-1-yl)-2-[3-bromo-6-(m-tolyl)pyrrolo[3,2-b]pyridin-1-yl]ethanone

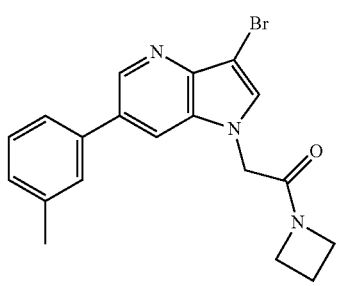

The title compound was prepared in a manner analogous to Example 14. MS (ESI): mass calcd. for $C_{19}H_{18}BrN_3O$, 383.1. m/z found, 384.0 [M+H]$^+$. $^1$H NMR (300 MHz, DMSO-d$_6$) δ 8.72 (s, 1H), 8.19 (s, 1H), 7.80 (s, 1H), 7.58 (s, 1H), 7.53 (d, J=7.7 Hz, 1H), 7.40 (t, J=7.6 Hz, 1H), 7.22 (d, J=7.5 Hz, 1H), 5.03 (s, 2H), 4.25 (t, J=7.8 Hz, 2H), 3.91 (t, J=7.7 Hz, 2H), 2.41 (s, 3H), 2.28 (quint, J=7.8 Hz, 2H).

Example 23

2-[3-Bromo-6-(m-tolyl)pyrrolo[3,2-b]pyridin-1-yl]-1-pyrrolidin-1-yl-ethanone

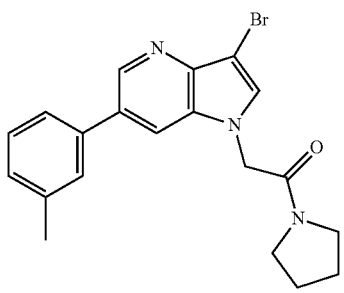

The title compound was prepared in a manner analogous to Example 14. MS (ESI): mass calcd. for $C_{20}H_{20}BrN_3O$, 397.1. m/z found, 398.0 [M+H]$^+$. $^1$H NMR (300 MHz, DMSO-d$_6$) δ 8.71 (s, 1H), 8.20 (s, 1H), 7.78 (s, 1H), 7.57 (s, 1H), 7.54 (d, J=7.5 Hz, 1H), 7.40 (t, J=7.6 Hz, 1H), 7.22 (d, J=7.5 Hz, 1H), 5.20 (s, 2H), 3.59 (t, J=6.8 Hz, 2H), 3.33-3.24 (m, 2H), 2.41 (s, 3H), 1.96 (quint, J=6.7 Hz, 2H), 1.82 (quint, J=6.8 Hz, 2H).

Example 24

2-[3-Bromo-6-(m-tolyl)pyrrolo[3,2-b]pyridin-1-yl]-1-morpholino-ethanone

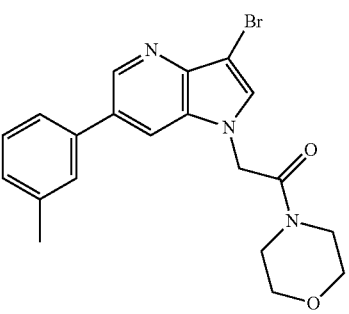

The title compound was prepared in a manner analogous to Example 14. MS (ESI): mass calcd. for $C_{20}H_{20}BrN_3O_2$, 413.1. m/z found, 414.0 [M+H]$^+$. $^1$H NMR (300 MHz, DMSO-d$_6$) δ 8.71 (s, 1H), 8.19 (s, 1H), 7.79 (s, 1H), 7.56 (s, 1H), 7.54 (d, J=7.6 Hz, 1H), 7.40 (t, J=7.6 Hz, 1H), 7.22 (d, J=7.5 Hz, 1H), 5.32 (s, 2H), 3.93-3.66 (m, 2H), 3.66-3.50 (m, 4H), 3.50-3.37 (m, 2H), 2.41 (s, 3H).

Example 25

2-[3-Chloro-6-(4-fluoro-3-methyl-phenyl)pyrrolo[3,2-b]pyridin-1-yl]-1-(3,3-difluoroazetidin-1-yl)ethanone

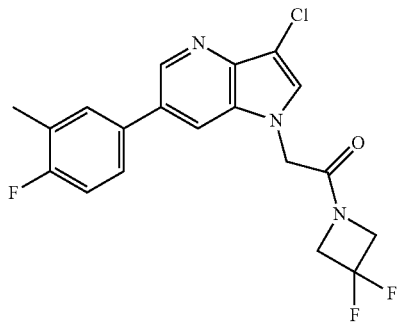 [SMILES: Cc1cc(-c2cnc3c(Cl)cn(CC(=O)N4CC(F)(F)C4)c3c2)ccc1F]

The title compound was prepared in a manner analogous to Example 1. MS (ESI): mass calcd. for $C_{19}H_{15}ClF_3N_3O$, 393.1. m/z found, 394.0 [M+H]$^+$. $^1$H NMR (300 MHz, DMSO-d$_6$) δ 8.71 (s, 1H), 8.20 (s, 1H), 7.78 (s, 1H), 7.68 (d, J=6.8 Hz, 1H), 7.63-7.52 (m, 1H), 7.29 (t, J=9.1 Hz, 1H), 5.14 (s, 2H), 4.76 (t, J=12.5 Hz, 2H), 4.38 (t, J=12.6 Hz, 2H), 2.34 (s, 3H).

Example 26

2-[3-Chloro-6-(4-fluoro-3-methyl-phenyl)pyrrolo[3,2-b]pyridin-1-yl]-1-(3-fluoroazetidin-1-yl)ethanone

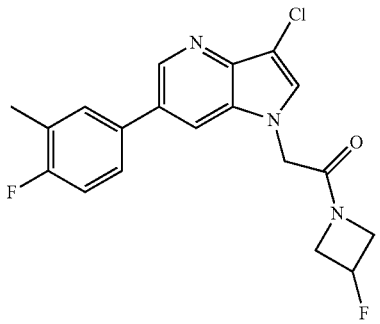 [SMILES: Cc1cc(-c2cnc3c(Cl)cn(CC(=O)N4CC(F)C4)c3c2)ccc1F]

The title compound was prepared in a manner analogous to Example 1. MS (ESI): mass calcd. for $C_{19}H_{16}ClF_2N_3O$, 375.1. m/z found, 376.0 [M+H]$^+$. $^1$H NMR (300 MHz, DMSO-d$_6$) δ 8.70 (s, 1H), 8.19 (s, 1H), 7.78 (s, 1H), 7.68 (d, J=7.5 Hz, 1H), 7.64-7.54 (m, 1H), 7.28 (t, J=9.1 Hz, 1H), 5.62-5.32 (m, 1H), 5.07 (s, 2H), 4.67-4.49 (m, 1H), 4.45-4.13 (m, 2H), 4.08-3.86 (m, 1H), 2.34 (s, 3H).

Example 27

2-[6-(4-Fluorophenyl)-3-methyl-pyrrolo[3,2-b]pyridin-1-yl]-1-pyrrolidin-1-yl-ethanone

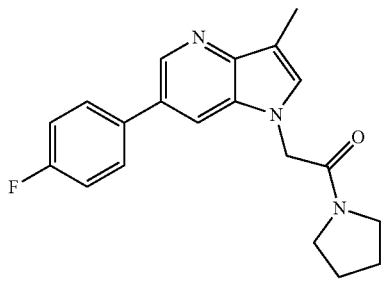 [SMILES: Cc1cn(CC(=O)N2CCCC2)c2cc(-c3ccc(F)cc3)cnc12]

Step A: 6-(4-Fluorophenyl)-1H-pyrrolo[3,2-b]pyridine

The title compound was prepared in a manner analogous to Example 1, Step A. $^1$H NMR (400 MHz, DMSO-d$_6$) δ 11.39 (s, 1H), 8.60 (d, J=2.1 Hz, 1H), 7.95 (dd, J=2.1, 0.9 Hz, 1H), 7.80-7.73 (m, 2H), 7.70-7.65 (m, 1H), 7.36-7.28 (m, 2H), 6.60-6.56 (m, 1H).

Step B: tert-Butyl 2-(6-(4-fluorophenyl)-1H-pyrrolo[3,2-b]pyridin-1-yl)acetate The title compound was prepared in a manner analogous to Example 1, Step C, using tert-butyl 2-bromoacetate and 6-(4-fluorophenyl)-1H-pyrrolo[3,2-b]pyridine. $^1$H NMR (300 MHz, DMSO-d$_6$) δ 8.65 (s, 1H), 8.16 (s, 1H), 7.79 (dd, J=8.6, 5.5 Hz, 2H), 7.66 (d, J=3.2 Hz, 1H), 7.34 (t, J=8.8 Hz, 2H), 6.61 (d, J=3.0 Hz, 1H), 5.13 (s, 2H), 1.41 (s, 9H).

Step C: tert-Butyl 2-(3-bromo-6-(4-fluorophenyl)-1H-pyrrolo[3,2-b]pyridin-1-yl)acetate To a solution of tert-butyl 2-(6-(4-fluorophenyl)-1H-pyrrolo[3,2-b]pyridin-1-yl)acetate (516 mg, 1.58 mmol) in DMF (10 mL) was added N-bromosuccinimide (NBS) (281 mg, 1.58 mmol) in small portions. The reaction mixture was stirred at 50° C. for 2 h. The reaction mixture was poured into water and extracted with EtOAc. The combined organics were dried (MgSO$_4$), filtered, and concentrated. Purification (FCC, SiO$_2$, 0-100% EtOAc/hexanes) afforded the title compound (640 mg, 37%).

Step D: tert-Butyl 2-(6-(4-fluorophenyl)-3-methyl-1H-pyrrolo[3,2-b]pyridin-1-yl)acetate Pd(PPh$_3$)$_2$Cl$_2$ (272 mg, 0.39 mmol) was added to a solution of tert-butyl 2-(3-bromo-6-(4-fluorophenyl)-1H-pyrrolo[3,2-b]pyridin-1-yl)acetate (1.6 g, 3.9 mmol), tetramethylstannane (2.1 mL, 15 mmol) and LiCl (656 mg, 15 mmol) in DMF (5 mL) in a sealed tube. The reaction mixture was heated to 110° C. for 12 hours and water followed by EtOAc was added. The organic layer was separated, dried over MgSO$_4$, filtered and evaporated. Purification (FCC, SiO$_2$, 0-50% EtOAc in heptane) gave the title compound (1.3 g, 22%). MS (ESI): mass calcd. for C$_{20}$H$_{21}$FN$_2$O$_2$, 340.2. m/z found, 341.0 [M+H]$^+$.

Step E: 2-(6-(4-Fluorophenyl)-3-methyl-1H-pyrrolo[3,2-b]pyridin-1-yl)acetic acid To a solution tert-butyl 2-(6-(4-fluorophenyl)-3-methyl-1H-pyrrolo[3,2-b]pyridin-1-yl)acetate (290 mg, 0.85 mmol) in DCM (6 mL) cooled at 0° C. was added TFA (6 mL, 78 mmol) dropwise. The reaction mixture was allowed to warm to room temperature and stirred for 12 hours. The volatiles were evaporated and the crude was used directly in the next step without any further purification.

Step F: 2-[6-(4-Fluorophenyl)-3-methyl-pyrrolo[3,2-b]pyridin-1-yl]-1-pyrrolidin-1-yl-ethanone To a solution of 2-(6-(4-fluorophenyl)-3-methyl-1H-pyrrolo[3,2-b]pyridin-1-yl)acetic acid (80 mg, 0.28 mmol) in DMF (5 mL) was added DIPEA (151 μL, 1.1 mmol) and HBTU (160 mg, 0.42 mmol). After 30 minutes, pyrrolidine (35 μL, 0.42 mmol) in DMF (0.2 mL) was added and the reaction mixture was stirred for another 30 minutes. A saturated aqueous solution of NaHCO$_3$ was added followed by EtOAc. The organic phase was separated, dried over MgSO$_4$, filtered and evaporated. Purification (FCC, SiO$_2$, 0-100% EtOAc in heptane) gave the title compound (31 mg, 32%). MS (ESI): mass calcd. for C$_{20}$H$_{20}$FN$_3$O, 337.2. m/z found, 338.0 [M+H]$^+$. $^1$H NMR (300 MHz, DMSO) δ 8.60 (d, J=1.6 Hz, 1H), 8.05 (d, J=1.4 Hz, 1H), 7.82-7.69 (m, 2H), 7.42-7.25 (m, 3H), 5.09 (s, 2H), 3.57 (t, J=6.7 Hz, 2H), 3.33-3.24 (m, 2H), 2.30 (s, 3H), 2.02-1.88 (m, 2H), 1.87-1.72 (m, 2H).

Example 28

2-[6-(4-Fluorophenyl)-3-methyl-pyrrolo[3,2-b]pyridin-1-yl]-1-morpholino-ethanone

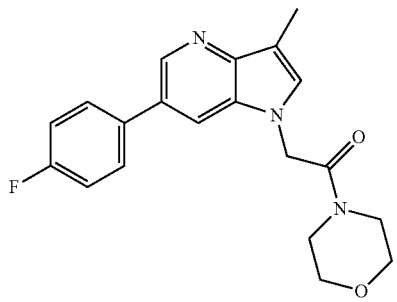 [SMILES: Cc1cn(CC(=O)N2CCOCC2)c2cc(-c3ccc(F)cc3)cnc12]

The title compound was prepared in a manner analogous to Example 27. MS (ESI): mass calcd. for C$_{20}$H$_{20}$FN$_3$O$_2$, 353.2. m/z found, 354.0 [M+H]$^+$. $^1$H NMR (300 MHz, DMSO) δ 8.59 (d, J=1.6 Hz, 1H), 8.02 (d, J=1.7 Hz, 1H), 7.75 (dd, J=8.5, 5.6 Hz, 2H), 7.39-7.25 (m, 3H), 5.21 (s, 2H), 3.75-3.64 (m, 2H), 3.64-3.51 (m, 4H), 3.49-3.39 (m, 2H), 2.30 (s, 3H).

Example 29

1-(Azetidin-1-yl)-2-[3-chloro-6-(3,4-difluorophenyl)pyrrolo[3,2-b]pyridin-1-yl]ethanone

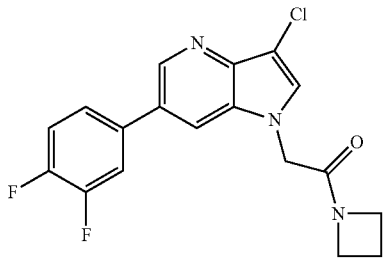 [SMILES: O=C(Cn1cc(Cl)c2ncc(-c3ccc(F)c(F)c3)cc21)N1CCC1]

Step A: 1-(Azetidin-1-yl)-2-(6-bromo-3-chloro-1H-pyrrolo[3,2-b]pyridin-1-yl)ethanone To a solution of 6-bromo-3-chloro-1H-pyrrolo[3,2-b]pyridine (Intermediate 5, 250 mg, 1.08 mmol) in DMF (60 mL) at 0° C. was added NaH (60 mg, 1.51 mmol, 60% dispersion in oil). The reaction mixture was warmed to room temperature and stirred for 30 minutes and then cooled to 0° C. followed by the addition of a solution of 1-(azetidin-1-yl)-2-bromoethanone (1.29 mmol) in DMF. The reaction mixture was warmed to room temperature and stirred for 12 hours. Water was added and the mixture was extracted with EtOAc. The combined organic layers were dried (MgSO$_4$), filtered and evaporated. Purification (FCC, SiO$_2$, 0-100% EtOAc in hexanes) afforded the title compound (247 mg, 70%).

MS (ESI): mass calcd. for C$_{12}$H$_{11}$BrClN$_3$O, 327.0. m/z found, 328.0 [M+H]$^+$.

Step B: 1-(Azetidin-1-yl)-2-[3-chloro-6-(3,4-difluorophenyl)pyrrolo[3,2-b]pyridin-1-yl]ethanone The title compound was prepared in a manner analogous to Example 1, Step A. MS (ESI): mass calcd. for C$_{18}$H$_{14}$ClF$_2$N$_3$O, 361.1. m/z found, 361.9 [M+H]$^+$. $^1$H NMR (400 MHz, DMSO-d$_6$) δ 8.76 (d, J=1.9 Hz, 1H), 8.27 (d, J=1.9 Hz, 1H), 7.90 (ddd, J=12.3, 7.8, 2.2 Hz, 1H), 7.81 (s, 1H), 7.69-7.52 (m, 2H), 5.01 (s, 2H), 4.25 (t, J=7.7 Hz, 2H), 3.91 (t, J=7.7 Hz, 2H), 2.36-2.22 (m, 2H).

Example 30

2-[3-Chloro-6-(3,4-difluorophenyl)pyrrolo[3,2-b]pyridin-1-yl]-1-(3-fluoroazetidin-1-yl)ethanone

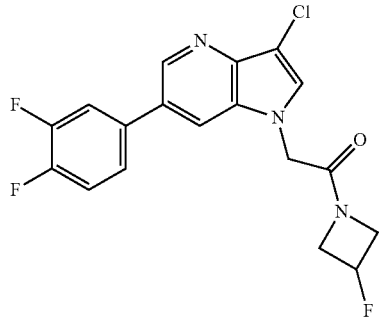 [SMILES: O=C(Cn1cc(Cl)c2ncc(-c3ccc(F)c(F)c3)cc21)N1CC(F)C1]

The title compound was prepared in a manner analogous to Example 1. MS (ESI): mass calcd. for C$_{18}$H$_{13}$ClF$_3$N$_3$O, 379.1. m/z found, 380.0 [M+H]$^+$. $^1$H NMR (300 MHz, DMSO-d$_6$) δ 8.76 (s, 1H), 8.28 (s, 1H), 8.89 (ddd, J=10.4, 7.3, 1.8 Hz, 1H), 7.82 (s, 1H), 7.72-7.49 (m, 2H), 5.48 (d, J=57.3 Hz, 1H), 5.07 (s, 2H), 4.70-4.46 (m, 1H), 4.37 (dd, J=26.4, 15.7 Hz, 1H), 4.29-4.11 (m, 1H), 3.98 (dd, J=25.0, 11.6 Hz, 1H).

Example 31

2-[6-(4-Fluorophenyl)-2-methyl-pyrrolo[3,2-b]pyridin-1-yl]-1-morpholino-ethanone

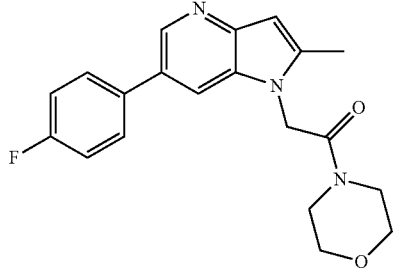 [SMILES: Cc1cc2ncc(-c3ccc(F)cc3)cc2n1CC(=O)N1CCOCC1]

Step A: 2-Chloro-5-(4-fluorophenyl)pyridin-3-amine

To a solution of 5-bromo-2-chloropyridin-3-amine (5 g, 24 mmol) and (4-fluorophenyl)boronic acid (4 g, 29 mmol) in dioxane (100 mL) and water (25 mL) was added K$_3$PO$_4$ (15 g, 72 mmol) followed by PdCl$_2$(dtbpf) (393 mg, 0.60 mmol). The reaction mixture was degassed and then heated to 80° C. for 2 hours. Once cooled to room temperature water and EtOAc were added to the reaction mixture. The aqueous phase was extracted with EtOAc (3×). The combined organic layers were washed with water, dried (Na$_2$SO$_4$), filtered and evaporated to give the title compound (6 g, 76%). The crude was used in the next step without any further purification.

Step B: 5-(4-Fluorophenyl)-2-(prop-1-yn-1-yl)pyridin-3-amine

To a solution of 2-chloro-5-(4-fluorophenyl)pyridin-3-amine (2 g, 6.7 mmol) and trimethyl(prop-1-yn-1-yl)silane (12 mL, 82 mmol) in DMF (100 mL) was added Pd(PPh$_3$)$_2$Cl$_2$ (600 mg, 0.86 mmol), copper(I) iodide (100 mg, 0.53 mmol), CsF (13 g, 86 mmol) and Et$_3$N (22 mL, 158 mmol). The reaction mixture was stirred at 90° C. for 5 hours. The volatiles were evaporated and water was added to the residue and extracted 3 times with EtOAc. The combined organic layers were dried (Na$_2$SO$_4$), filtered and evaporated. Purification (FCC, SiO$_2$, 0-80% EtOAc in petroleum ether) gave the title compound (250 mg, 14%). MS (ESI): mass calcd. for C$_{14}$H$_{11}$FN$_2$, 226.1. m/z found, 227.0 [M+H]$^+$.

Step C: 2-(6-(4-Fluorophenyl)-2-methyl-1H-pyrrolo[3,2-b]pyridin-1-yl)acetic acid To a solution of 5-(4-fluorophenyl)-2-(prop-1-yn-1-yl)pyridin-3-amine (100 mg, 0.44 mmol) in DMF (10 mL), cooled at 0° C., was added NaH (35 mg, 0.88 mmol, 60% dispersion in oil). The reaction mixture was then allowed to warm to room temperature. After 12 hours, the reaction was cooled to 0° C. and NaH (25 mg, 0.63 mmol, 60% dispersion in oil) was added and stirred at this temperature for 30 minutes. Ethyl 2-bromoacetate (60 μL, 0.54 mmol) was added dropwise and the mixture was stirred at room temperature for 5 hours. At 0° C. was added water and the aqueous phase was extracted with MTBE. The aqueous layer was acidified with 1M HCl and the volatiles were evaporated to afford the title compound (100 mg, 55%). The crude was used in the next step without any further purification. MS (ESI): mass calcd. for $C_{16}H_{13}FN_2O_2$, 284.1. m/z found, 285.0 [M+H]$^+$.

Step D: 2-[6-(4-Fluorophenyl)-2-methyl-pyrrolo[3,2-b]pyridin-1-yl]-1-morpholino-ethanone A mixture of intermediate of 2-(6-(4-fluorophenyl)-2-methyl-1H-pyrrolo[3,2-b]pyridin-1-yl)acetic acid (100 mg, 0.24 mmol), morpholine (37 mg, 0.43 mmol), HATU (170 mg, 0.45 mmol) and Et$_3$N (63 μL, 0.45 mmol) in DMF (5 mL) was stirred at room temperature for 1 hour. Water was added and the aqueous phase was extracted 3 times with EtOAc. The combined organic layers were dried (Na$_2$SO$_4$), filtered and evaporated. Purification by via HPLC Method A gave the title compound (30 mg, 33%). MS (ESI): mass calcd. for $C_{20}H_{20}FN_3O_2$, 353.2. m/z found, 354.1 [M+H]$^+$. $^1$H NMR (400 MHz, DMSO-d$_6$) δ 8.53 (d, J=1.5 Hz, 1H), 8.02 (s, 1H), 7.76 (dd, J=5.5, 8.5 Hz, 2H), 7.32 (t, J=8.9 Hz, 2H), 6.38 (s, 1H), 5.25 (s, 2H), 3.72 (br. s., 2H), 3.61 (d, J=14.6 Hz, 4H), 3.44 (br. s., 2H), 2.34 (s, 3H).

Example 32

N-Cyclopropyl-2-[6-(4-fluorophenyl)-3-methyl-pyrrolo[3,2-b]pyridin-1-yl]acetamide

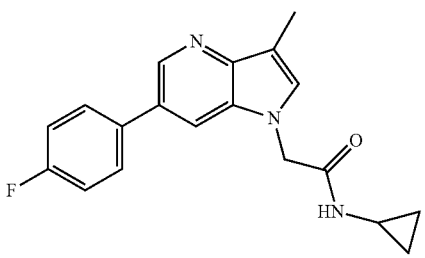 [SMILES: Cc1cn(CC(=O)NC2CC2)c2cc(-c3ccc(F)cc3)cnc12]

The title compound was prepared in a manner analogous to Example 27. MS (ESI): mass calcd. for $C_{19}H_{18}FN_3O$, 323.1. m/z found, 324.0 [M+H]$^+$. $^1$H NMR (300 MHz, CDCl$_3$) δ 8.72 (s, 1H), 7.75-7.48 (m, 3H), 7.36-7.03 (m, 3H), 5.47 (br s, 1H), 4.75 (s, 2H), 2.72-2.60 (m, 1H), 2.45 (s, 3H), 0.91-0.63 (m, 2H), 0.48-0.15 (m, 2H).

Example 33

1-(Azetidin-1-yl)-2-[6-(4-fluorophenyl)-3-methyl-pyrrolo[3,2-b]pyridin-1-yl]ethanone

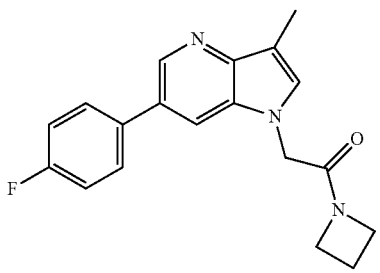 [SMILES: Cc1cn(CC(=O)N2CCC2)c2cc(-c3ccc(F)cc3)cnc12]

The title compound was prepared in a manner analogous to Example 27. MS (ESI): mass calcd. for $C_{19}H_{18}FN_3O$, 323.1. m/z found, 324.0 [M+H]$^+$. $^1$H NMR (300 MHz, DMSO-d$_6$) δ 8.61 (s, 1H), 8.04 (s, 1H), 7.82-7.70 (m, 2H), 7.43-7.25 (m, 3H), 4.93 (s, 2H), 4.19 (t, J=7.4 Hz, 2H), 3.89 (t, J=7.4 Hz, 2H), 2.37-2.15 (m, 5H).

Example 34

2-[3-Chloro-6-(3,4-difluorophenyl)pyrrolo[3,2-b]pyridin-1-yl]-1-(3,3-difluoroazetidin-1-yl)ethanone

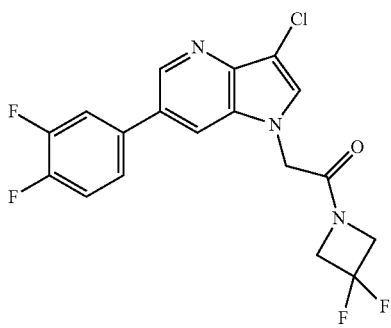 [SMILES: O=C(Cn1cc(Cl)c2ncc(-c3ccc(F)c(F)c3)cc21)N1CC(F)(F)C1]

The title compound was prepared in a manner analogous to Example 1. MS (ESI): mass calcd. for $C_{18}H_{12}ClF_4N_3O$, 397.1. m/z found, 398.0 [M+H]$^+$. $^1$H NMR (300 MHz, DMSO-d$_6$) δ 8.77 (s, 1H), 8.28 (s, 1H), 7.88 (dd, J=12.0, 8.2 Hz, 1H), 7.81 (s, 1H), 7.72-7.52 (m, 2H), 5.14 (s, 2H), 4.76 (t, J=12.4 Hz, 2H), 4.38 (t, J=12.6 Hz, 2H).

Example 35

2-[3-Chloro-6-[4-fluoro-3-(trifluoromethyl)phenyl]pyrrolo[3,2-b]pyridin-1-yl]-1-(3-fluoroazetidin-1-yl)ethanone

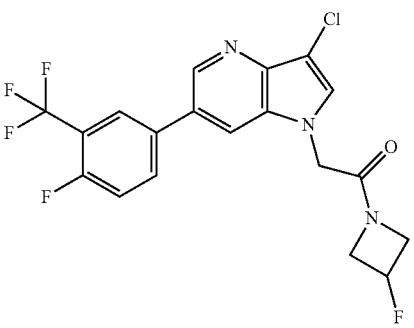 [SMILES: O=C(Cn1cc(Cl)c2ncc(-c3ccc(F)c(C(F)(F)F)c3)cc21)N1CC(F)C1]

The title compound was prepared in a manner analogous to Example 1. MS (ESI): mass calcd. for $C_{19}H_{13}ClF_6N_3O$, 429.1. m/z found, 430.0 [M+H]$^+$. $^1$H NMR (300 MHz, DMSO-d$_6$) δ 8.78 (d, J=1.9 Hz, 1H), 8.32 (d, J=2.0 Hz, 1H), 8.18-8.06 (m, 2H), 7.84 (s, 1H), 7.69 (t, J=9.6 Hz, 1H), 5.62-5.32 (m, 1H), 5.09 (s, 2H), 4.68-4.48 (m, 1H), 4.45-4.15 (m, 2H), 4.07-3.86 (m, 1H).

Example 36

2-[3-Chloro-6-[3-(trifluoromethyl)phenyl]pyrrolo[3,2-b]pyridin-1-yl]-1-(3,3-difluoroazetidin-1-yl)ethanone

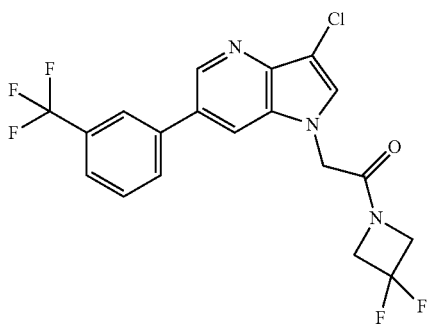 [SMILES: O=C(Cn1cc(Cl)c2ncc(-c3cccc(C(F)(F)F)c3)cc21)N1CC(F)(F)C1]

The title compound was prepared in a manner analogous to Example 1. MS (ESI): mass calcd. for $C_{19}H_{13}ClF_6N_3O$, 429.1. m/z found, 430.0 [M+H]$^+$. $^1$H NMR (300 MHz, DMSO-d$_6$) δ 8.81 (s, 1H), 8.34 (s, 1H), 8.15-7.98 (m, 2H), 7.84 (s, 1H), 7.81-7.70 (m, 2H), 5.17 (s, 2H), 4.76 (t, J=12.5 Hz, 2H), 4.38 (t, J=12.5 Hz, 2H).

Example 37

2-[6-(4-Fluorophenyl)-2-methyl-pyrrolo[3,2-b]pyridin-1-yl]-1-pyrolidin-1-yl-ethanone

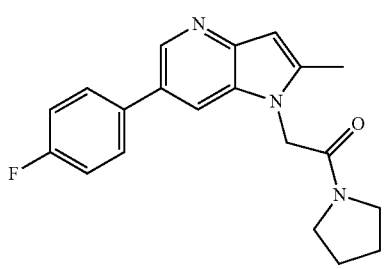 [SMILES: Cc1cc2ncc(-c3ccc(F)cc3)cc2n1CC(=O)N1CCCC1]

The title compound was prepared in a manner analogous to Example 31. MS (ESI): mass calcd. for $C_{20}H_{20}FN_3O$, 337.2. m/z found, 338.1 [M+H]$^+$. $^1$H NMR (400 MHz, CDCl$_3$) δ 8.58 (br. s., 1H), 7.48-7.62 (m, 3H), 7.15 (t, J=8.7 Hz, 2H), 6.55 (s, 1H), 4.82 (s, 2H), 3.54 (t, J=7.0 Hz, 2H), 3.48 (t, J=6.9 Hz, 2H), 2.47 (s, 3H), 2.06 (quin, J=6.8 Hz, 2H), 1.84-1.96 (m, 2H).

Example 38

N-Cyclopropyl-2-[6-(4-fluorophenyl)-2-methyl-pyrrolo[3,2-b]pyridin-1-yl]acetamide

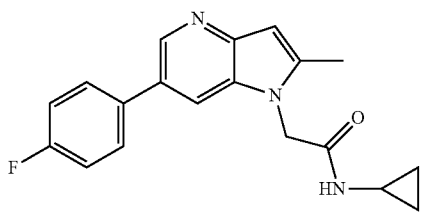 [SMILES: Cc1cc2ncc(-c3ccc(F)cc3)cc2n1CC(=O)NC1CC1]

The title compound was prepared in a manner analogous to Example 31. MS (ESI): mass calcd. for $C_{19}H_{18}FN_3O$, 323.1. m/z found, 324.2 [M+H]$^+$. $^1$H NMR (400 MHz, CDCl$_3$) δ 8.66 (br. s., 1H), 7.50-7.63 (m, 3H), 7.12-7.23 (m, 2H), 6.57 (s, 1H), 5.39 (br. s., 1H), 4.75 (s, 2H), 2.67 (qt, J=3.6, 7.1 Hz, 1H), 2.45 (s, 3H), 0.70-0.80 (m, 2H), 0.30-0.41 (m, 2H).

Example 39

2-[3-Chloro-6-(3,4,5-trifluorophenyl)pyrrolo[3,2-b]pyridin-1-yl]-1-(3-fluoroazetidin-1-yl)ethanone

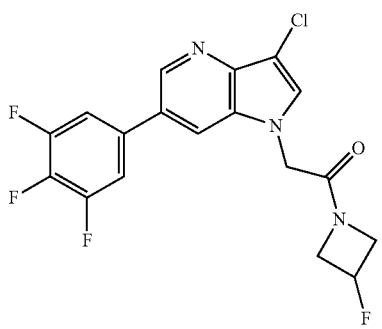 [SMILES: O=C(Cn1cc(Cl)c2ncc(-c3cc(F)c(F)c(F)c3)cc21)N1CC(F)C1]

The title compound was prepared in a manner analogous to Example 1. MS (ESI): mass calcd. for $C_{18}H_{12}ClF_4N_3O$, 397.1. m/z found, 398.0 [M+H]$^+$. $^1$H NMR (300 MHz, DMSO-d$_6$) δ 8.80 (s, 1H), 8.33 (s, 1H), 7.92-7.74 (m, 3H), 5.63-5.34 (m, 1H), 5.07 (s, 2H), 4.68-4.49 (m, 1H), 4.44-4.17 (m, 2H), 4.08-3.87 (m, 1H).

Example 40

2-[3-Chloro-6-[4-fluoro-3-(trifluoromethyl)phenyl]pyrrolo[3,2-b]pyridin-1-yl]-1-(3,3-difluoroazetidin-1-yl)ethanone

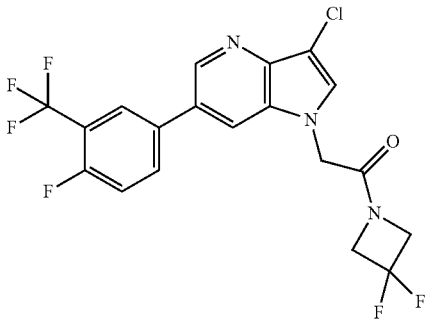 [SMILES: O=C(Cn1cc(Cl)c2ncc(-c3ccc(F)c(C(F)(F)F)c3)cc21)N1CC(F)(F)C1]

The title compound was prepared in a manner analogous to Example 1. MS (ESI): mass calcd. for $C_{19}H_{12}ClF_6N_3O$, 447.1. m/z found, 448.0 [M+H]$^+$. $^1$H NMR (300 MHz, DMSO-d$_6$) δ 8.79 (s, 1H), 8.32 (s, 1H), 8.22-8.02 (m, 2H), 7.83 (s, 1H), 7.69 (t, J=9.7 Hz, 1H), 5.16 (s, 2H), 4.76 (t, J=12.5 Hz, 2H), 4.38 (t, J=12.6 Hz, 2H).

Example 41

1-(Azetidin-1-yl)-2-[2-methyl-6-(m-tolyl)pyrrolo[3,2-b]pyridin-1-yl]ethanone

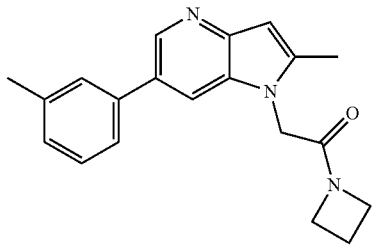 [SMILES: Cc1cccc(-c2cnc3cc(C)n(CC(=O)N4CCC4)c3c2)c1]

The title compound was prepared in a manner analogous to Example 31. MS (ESI): mass calcd. for $C_{20}H_{21}N_3O$, 319.2. m/z found, 320.2 [M+H]$^+$. $^1$H NMR (400 MHz, CDCl$_3$) δ 8.65 (d, J=1.5 Hz, 1H), 7.62 (s, 1H), 7.39-7.47 (m, 2H), 7.31-7.38 (m, 1H), 7.18 (d, J=7.3 Hz, 1H), 6.52 (s, 1H), 4.73 (s, 2H), 4.05 (t, J=7.7 Hz, 2H), 3.59 (t, J=7.7 Hz, 2H), 2.48 (s, 3H), 2.44 (s, 3H), 2.16 (quin, J=7.8 Hz, 2H).

Example 42

2-(2-Methyl-6-phenyl-pyrrolo[3,2-b]pyridin-1-yl)-1-pyrrolidin-1-yl-ethanone

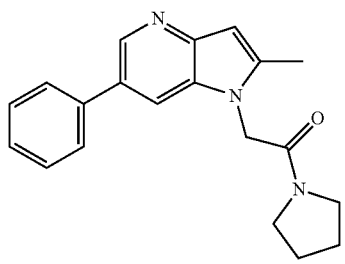 [SMILES: Cc1cc2ncc(-c3ccccc3)cc2n1CC(=O)N1CCCC1]

The title compound was prepared in a manner analogous to Example 31. MS (ESI): mass calcd. for $C_{20}H_{21}N_3O$, 319.2. m/z found, 320.1 [M+H]$^+$. $^1$H NMR (400 MHz, CDCl$_3$) δ 8.60 (br. s., 1H), 7.59 (d, J=7.3 Hz, 3H), 7.44 (t, J=7.6 Hz, 2H), 7.29-7.38 (m, 1H), 6.54 (s, 1H), 4.81 (s, 2H), 3.48 (td, J=6.8, 20.0 Hz, 4H), 2.44 (s, 3H), 2.03 (quin, J=6.7 Hz, 2H), 1.82-1.92 (m, 2H).

Example 43

N-Cyclopropyl-2-(2-methyl-6-phenyl-pyrrolo[3,2-b]pyridin-1-yl)acetamide

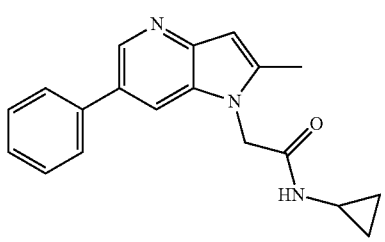 [SMILES: Cc1cc2ncc(-c3ccccc3)cc2n1CC(=O)NC1CC1]

The title compound was prepared in a manner analogous to Example 31. MS (ESI): mass calcd. for $C_{19}H_{19}N_3O$, 305.2. m/z found, 306.2 [M+H]$^+$. $^1$H NMR (400 MHz, CDCl$_3$) δ 8.69 (s, 1H), 7.57-7.67 (m, 3H), 7.49 (t, J=7.6 Hz, 2H), 7.34-7.43 (m, 1H), 6.53 (s, 1H), 5.58 (br. s., 1H), 4.76 (s, 2H), 2.68 (dt, J=3.5, 7.1 Hz, 1H), 2.45 (s, 3H), 0.69-0.80 (m, 2H), 0.31-0.43 (m, 2H).

Example 44

2-[2-Methyl-6-(m-tolyl)pyrrolo[3,2-b]pyridin-1-yl]-1-pyrrolidin-1-yl-ethanone

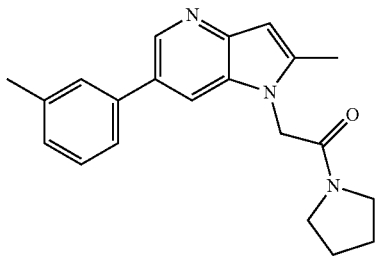 [SMILES: Cc1cccc(-c2cnc3cc(C)n(CC(=O)N4CCCC4)c3c2)c1]

The title compound was prepared in a manner analogous to Example 31. MS (ESI): mass calcd. for $C_{21}H_{23}N_3O$, 333.2. m/z found, 334.1 [M+H]$^+$. $^1$H NMR (400 MHz, CDCl$_3$) δ 8.61 (s, 1H), 7.55 (s, 1H), 7.36-7.44 (m, 2H), 7.29-7.36 (m, 1H), 7.15 (d, J=7.3 Hz, 1H), 6.52 (s, 1H), 4.80 (s, 2H), 3.51 (t, J=6.9 Hz, 2H), 3.43 (t, J=6.7 Hz, 2H), 2.45 (s, 3H), 2.42 (s, 3H), 2.02 (quin, J=6.9 Hz, 2H), 1.87 (quin, J=6.9 Hz, 2H).

Example 45

2-[2-Methyl-6-(m-tolyl)pyrrolo[3,2-b]pyridin-1-yl]-1-morpholino-ethanone

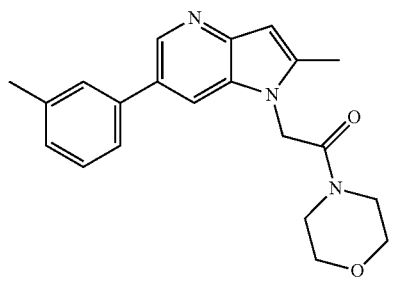 [SMILES: Cc1cccc(-c2cnc3cc(C)n(CC(=O)N4CCOCC4)c3c2)c1]

The title compound was prepared in a manner analogous to Example 31. MS (ESI): mass calcd. for $C_{21}H_{23}N_3O_2$, 349.2. m/z found, 350.1 [M+H]$^+$. $^1$H NMR (400 MHz, CDCl$_3$) δ 8.61 (s, 1H), 7.55 (s, 1H), 7.36-7.44 (m, 2H), 7.29-7.36 (m, 1H), 7.15 (d, J=7.3 Hz, 1H), 6.52 (s, 1H), 4.80 (s, 2H), 3.51 (t, J=6.9 Hz, 2H), 3.43 (t, J=6.7 Hz, 2H), 2.45 (s, 3H), 2.42 (s, 3H), 2.02 (quin, J=6.9 Hz, 2H), 1.87 (quin, J=6.9 Hz, 2H).

Example 46

1-(Azetidin-1-yl)-2-[6-(4-fluorophenyl)-2-methyl-pyrrolo[3,2-b]pyridin-1-yl]ethanone

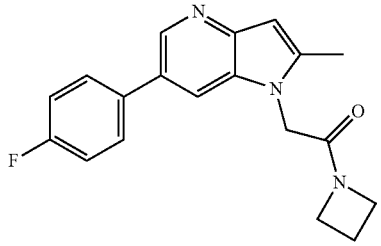 [SMILES: Cc1cc2ncc(-c3ccc(F)cc3)cc2n1CC(=O)N1CCC1]

The title compound was prepared in a manner analogous to Example 31. MS (ESI): mass calcd. for $C_{19}H_{18}FN_3O$, 323.1. m/z found, 324.2 [M+H]$^+$. $^1$H NMR (400 MHz, CDCl$_3$) δ 8.58 (br. s., 1H), 7.66 (s, 1H), 7.57 (dd, J=5.29, 8.4 Hz, 2H), 7.16 (t, J=8.6 Hz, 2H), 6.54 (s, 1H), 4.75 (s, 2H), 4.07 (t, J=7.8 Hz, 2H), 3.76 (t, J=7.6 Hz, 2H), 2.48 (s, 3H), 2.23 (quin, J=7.8 Hz, 2H).

Example 47

1-(Azetidin-1-yl)-2-(2-methyl-6-phenyl-pyrrolo[3,2-b]pyridin-1-yl)ethanone

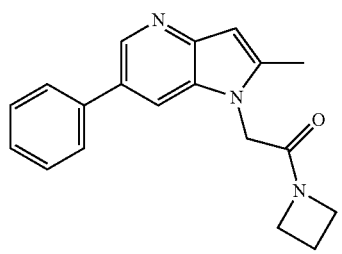 [SMILES: Cc1cc2ncc(-c3ccccc3)cc2n1CC(=O)N1CCC1]

The title compound was prepared in a manner analogous to Example 31. MS (ESI): mass calcd. for $C_{19}H_{19}N_3O$, 305.2. m/z found, 306.2 [M+H]$^+$. $^1$H NMR (400 MHz, CDCl$_3$) δ 8.66 (br. s., 1H), 7.62 (d, J=8.6 Hz, 3H), 7.46 (t, J=7.6 Hz, 2H), 7.32-7.39 (m, 1H), 6.52 (s, 1H), 4.72 (s, 2H), 4.05 (t, J=7.8 Hz, 2H), 3.64 (t, J=7.7 Hz, 2H), 2.47 (s, 3H), 2.17 (quin, J=7.8 Hz, 2H).

Example 48

2-[3-Chloro-6-[3-(trifluoromethyl)phenyl]pyrrolo[3,2-b]pyridin-1-yl]-1-(3-fluoroazetidin-1-yl)ethanone

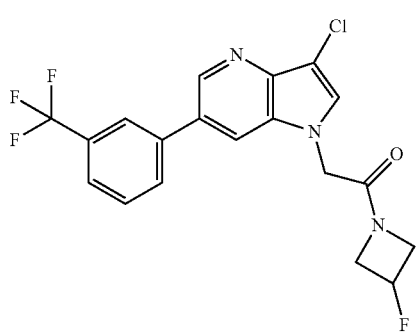 [SMILES: O=C(Cn1cc(Cl)c2ncc(-c3cccc(C(F)(F)F)c3)cc21)N1CC(F)C1]

The title compound was prepared in a manner analogous to Example 1. MS (ESI): mass calcd. for $C_{19}H_{14}ClF_4N_3O$, 411.1. m/z found, 412.0 [M+H]$^+$. $^1$H NMR (300 MHz, DMSO-d$_6$) δ 8.81 (s, 1H), 8.34 (s, 1H), 8.08 (s, 2H), 7.94-7.65 (m, 3H), 5.65-5.32 (m, 1H), 5.11 (s, 2H), 4.70-4.47 (m, 1H), 4.46-4.15 (m, 2H), 4.08-3.84 (m, 1H).

Example 49

2-[3-Chloro-6-(3,4,5-trifluorophenyl)pyrrolo[3,2-b]pyridin-1-yl]-1-(3,3-difluoroazetidin-1-yl)ethanone

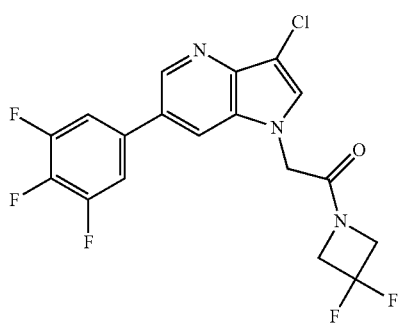 [SMILES: O=C(Cn1cc(Cl)c2ncc(-c3cc(F)c(F)c(F)c3)cc21)N1CC(F)(F)C1]

The title compound was prepared in a manner analogous to Example 1. MS (ESI): mass calcd. for $C_{18}H_{11}ClF_6N_3O$, 415.1. m/z found, 416.0 [M+H]$^+$. $^1$H NMR (300 MHz, DMSO-d$_6$) δ 8.81 (s, 1H), 8.33 (s, 1H), 7.84 (s, 1H), 7.81 (dd, J=9.3, 7.0 Hz, 2H), 5.14 (s, 2H), 4.76 (t, J=12.4 Hz, 2H), 4.38 (t, J=12.6 Hz, 2H).

Example 50

2-[3-Chloro-6-(2,3,4-trifluorophenyl)pyrrolo[3,2-b]pyridin-1-yl]-1-(3,3-difluoroazetidin-1-yl)ethanone

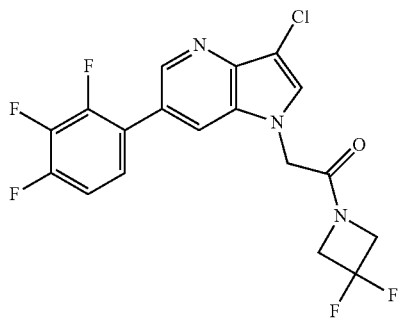 [SMILES: O=C(Cn1cc(Cl)c2ncc(-c3ccc(F)c(F)c3F)cc21)N1CC(F)(F)C1]

The title compound was prepared in a manner analogous to Example 1. MS (ESI): mass calcd. for $C_{18}H_{11}ClF_6N_3O$, 415.1. m/z found, 416.0 [M+H]$^+$. $^1$H NMR (300 MHz, DMSO-d$_6$): 8.58 (s, 1H), 8.18 (s, 1H), 7.86 (s, 1H), 7.57-7.41 (m, 2H), 5.14 (s, 2H), 4.75 (t, J=12.4 Hz, 2H), 4.37 (t, J=12.5 Hz, 2H).

Example 51

N-Cyclopropyl-2-[2-methyl-6-(m-tolyl)pyrrolo[3,2-b]pyridin-1-yl]acetamide

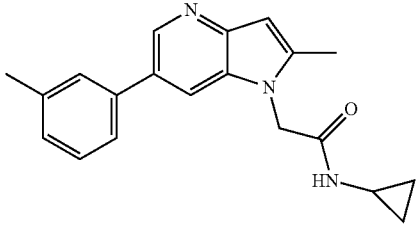 [SMILES: Cc1cccc(-c2cnc3cc(C)n(CC(=O)NC4CC4)c3c2)c1]

The title compound was prepared in a manner analogous to Example 31. MS (ESI): mass calcd. for $C_{20}H_{21}N_3O$, 319.2. m/z found, 320.1 [M+H]+. 1H NMR (400 MHz, CDCl3) δ 8.68 (s, 1H), 7.64 (s, 1H), 7.32-7.47 (m, 3H), 7.21 (d, J=7.1 Hz, 1H), 6.52 (s, 1H), 5.65 (br. s., 1H), 4.76 (s, 2H), 2.68 (dt, J=3.5, 7.1 Hz, 1H), 2.46 (s, 3H), 2.44 (s, 3H), 0.74 (d, J=5.7 Hz, 2H), 0.38 (dd, J=1.0, 3.6 Hz, 2H).

Example 52

2-(2-Methyl-6-phenyl-pyrrolo[3,2-b]pyridin-1-yl)-1-morpholino-ethanone

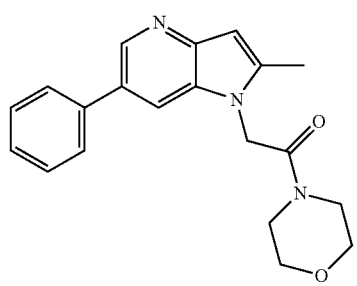 [SMILES: Cc1cc2ncc(-c3ccccc3)cc2n1CC(=O)N1CCOCC1]

The title compound was prepared in a manner analogous to Example 31. MS (ESI): mass calcd. for $C_{20}H_{21}N_3O_2$, 335.2. m/z found, 336.1 [M+H]+. 1H NMR (400 MHz, CDCl3) δ 8.37 (s, 1H), 7.30-7.36 (m, 2H), 7.19 (t, J=7.6 Hz, 2H), 7.05-7.12 (m, 1H), 6.99 (s, 1H), 6.29 (s, 1H), 4.61 (s, 2H), 3.46 (d, J=4.0 Hz, 4H), 3.38 (d, J=4.0 Hz, 2H), 3.30 (d, J=4.4 Hz, 2H), 2.17 (s, 3H).

Example 53

2-[3-Chloro-6-(m-tolyl)pyrrolo[3,2-b]pyridin-1-yl]-1-(3,3-difluoroazetidin-1-yl)ethanone

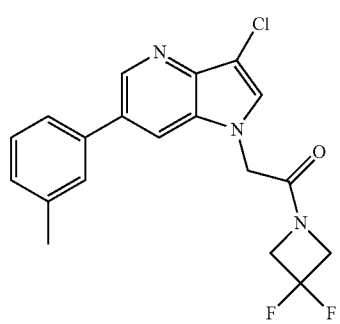 [SMILES: Cc1cccc(-c2cnc3c(Cl)cn(CC(=O)N4CC(F)(F)C4)c3c2)c1]

The title compound was prepared in a manner analogous to Example 1. MS (ESI): mass calcd. for $C_{19}H_{16}ClF_2N_3O$, 375.1. m/z found, 376.1 [M+H]+. 1H NMR (300 MHz, DMSO-d6) δ 8.72 (s, 1H), 8.21 (s, 1H), 7.78 (s, 1H), 7.57 (s, 1H), 7.54 (d, J=8.1 Hz, 1H), 7.41 (t, J=7.6 Hz, 1H), 7.23 (d, J=7.5 Hz, 1H), 5.15 (s, 2H), 4.76 (t, J=12.5 Hz, 2H), 4.38 (t, J=12.5 Hz, 2H), 2.41 (s, 3H).

Example 54

2-[3-Chloro-6-(m-tolyl)pyrrolo[3,2-b]pyridin-1-yl]-1-(3-fluoroazetidin-1-yl)ethanone

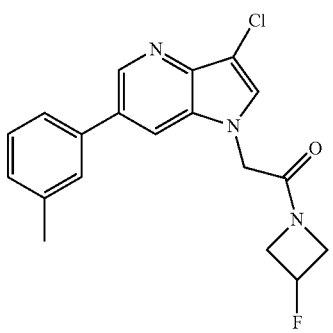

The title compound was prepared in a manner analogous to Example 1. MS (ESI): mass calcd. for $C_{19}H_{17}ClFN_3O$, 357.1. m/z found, 358.1 [M+H]+. 1H NMR (300 MHz, DMSO-d6) δ 8.72 (d, J=2.0 Hz, 1H), 8.20 (d, J=2.0 Hz, 1H), 7.78 (s, 1H), 7.60-7.49 (m, 2H), 7.40 (t, J=7.6 Hz, 1H), 7.23 (d, J=7.6 Hz, 1H), 5.63-5.32 (m, 1H), 5.08 (s, 2H), 4.68-4.48 (m, 1H), 4.44-4.16 (m, 2H), 4.08-3.86 (m, 1H), 2.41 (s, 3H).

Example 55

2-(3-Chloro-6-phenyl-pyrrolo[3,2-b]pyridin-1-yl)-1-(3,3-difluoroazetidin-1-yl)ethanone

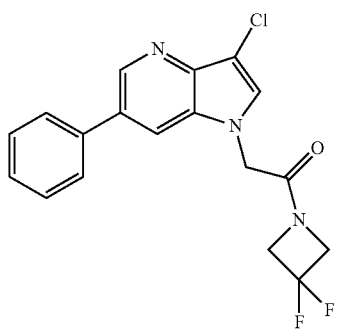 [SMILES: O=C(Cn1cc(Cl)c2ncc(-c3ccccc3)cc21)N1CC(F)(F)C1]

The title compound was prepared in a manner analogous to Example 1. MS (ESI): mass calcd. for $C_{18}H_{14}ClF_2N_3O$, 361.1. m/z found, 362.1 [M+H]+. 1H NMR (300 MHz, DMSO-$d_6$) δ 8.74 (s, 1H), 8.24 (s, 1H), 7.79 (s, 1H), 7.76 (d, J=8.2 Hz, 2H), 7.53 (t, J=7.5 Hz, 2H), 7.42 (t, J=7.4 Hz, 1H), 5.15 (s, 2H), 4.76 (t, J=12.6 Hz, 2H), 4.38 (t, J=12.5 Hz, 2H).

Example 56

2-(3-Chloro-6-phenyl-pyrrolo[3,2-b]pyridin-1-yl)-1-(3-fluoroazetidin-1-yl)ethanone

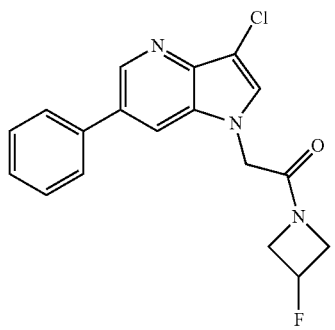

The title compound was prepared in a manner analogous to Example 1. MS (ESI): mass calcd. for $C_{18}H_{15}ClFN_3O$, 343.1. m/z found, 344.1 [M+H]$^+$. $^1$H NMR (500 MHz, DMSO-$d_6$) δ 8.74 (d, J=1.9 Hz, 1H), 8.22 (d, J=2.0 Hz, 1H), 7.81-7.72 (m, 3H), 7.52 (t, J=7.6 Hz, 2H), 7.41 (t, J=7.3 Hz, 1H), 5.56-5.38 (m, 1H), 5.08 (d, J=3.0 Hz, 2H), 4.66-4.51 (m, 1H), 4.42-4.30 (m, 1H), 4.30-4.19 (m, 1H), 4.06-3.88 (m, 1H).

Example 57

2-[3-Chloro-6-(4-fluorophenyl)pyrrolo[3,2-b]pyridin-1-yl]-1-(3,3-difluoroazetidin-1-yl)ethanone

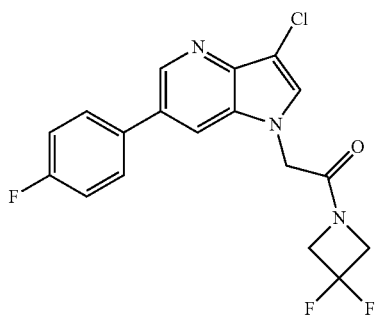 [SMILES: O=C(Cn1cc(Cl)c2ncc(-c3ccc(F)cc3)cc21)N1CC(F)(F)C1]

The title compound was prepared in a manner analogous to Example 1. MS (ESI): mass calcd. for $C_{18}H_{13}ClF_3N_3O$, 379.1. m/z found, 380.1 [M+H]$^+$. $^1$H NMR (300 MHz, DMSO-$d_6$) δ 8.72 (s, 1H), 8.22 (s, 1H), 7.87-7.71 (m, 2H), 7.79 (s, 1H), 7.36 (t, J=8.7 Hz, 2H), 5.14 (s, 2H), 4.76 (t, J=12.4 Hz, 2H), 4.38 (t, J=12.6 Hz, 2H).

Example 58

2-[3-Chloro-6-(4-fluorophenyl)pyrrolo[3,2-b]pyridin-1-yl]-1-(3-fluoroazetidin-1-yl)ethanone

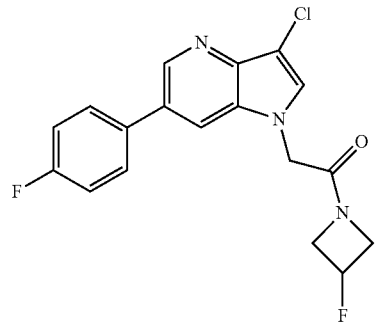 [SMILES: O=C(Cn1cc(Cl)c2ncc(-c3ccc(F)cc3)cc21)N1CC(F)C1]

The title compound was prepared in a manner analogous to Example 1. MS (ESI): mass calcd. for $C_{18}H_{14}ClF_2N_3O$, 361.1. m/z found, 362.1 [M+H]$^+$. $^1$H NMR (300 MHz, DMSO-$d_6$) δ 8.72 (d, J=1.9 Hz, 1H), 8.21 (d, J=1.9 Hz, 1H), 7.88-7.72 (m, 3H), 7.36 (t, J=8.7 Hz, 2H), 5.62-5.32 (m, 1H), 5.07 (s, 2H), 4.66-4.49 (m, 1H), 4.46-4.15 (m, 2H), 4.06-3.89 (m, 1H).

Example 59

3-[[6-(4-Fluoro-2-methyl-phenyl)pyrrolo[3,2-b]pyridin-1-yl]methyl]-5-methyl-isoxazole

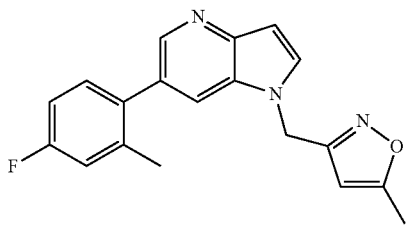 [SMILES: Cc1cc(Cn2ccc3ncc(-c4ccc(F)cc4C)cc32)no1]

Step A: 3-((6-Bromo-1H-pyrrolo[3,2-b]pyridin-1-yl)methyl)-5-methylisoxazole

To a solution of 6-bromo-1H-pyrrolo[3,2-b]pyridine (300 mg, 1.5 mmol) in DMF (2 mL), at 0° C., was added NaH (183 mg, 4.6 mmol, 60% dispersion in oil). The reaction mixture was warmed to room temperature and stirred for 10 minutes and then cooled to 0° C. and 3-(chloromethyl)-5-methylisoxazole (240 mg, 1.8 mmol) was added. The mixture was stirred at 0° C. for 10 minutes then warmed to room temperature and stirred for 4 hours. Water was added and the reaction mixture was extracted with EtOAc. The combined organic layers were dried (MgSO$_4$), filtered and evaporated. Purification (FCC, SiO$_2$, 0-100% EtOAc in hexanes) gave the title compound (407 mg, 92%). $^1$H NMR (400 MHz, DMSO-$d_6$) δ 8.41 (d, J=2.0 Hz, 1H), 8.26 (dd, J=2.0, 0.9 Hz, 1H), 7.78 (d, J=3.4 Hz, 1H), 6.64 (dd, J=3.3, 1.0 Hz, 1H), 6.07 (d, J=1.0 Hz, 1H), 5.52 (s, 2H), 2.33 (d, J=0.9 Hz, 3H).

Step B: 3-[[6-(4-Fluoro-2-methyl-phenyl)pyrrolo[3,2-b]pyridin-1-yl]methyl]-5-methyl-isoxazole In a microwave vial, 3-((6-bromo-1H-pyrrolo[3,2-b]pyridin-1-yl)methyl)-5-methylisoxazole (50 mg, 0.17 mmol) was dissolved in dioxane (3 mL) followed by the addition of (4-fluoro-2-methylphenyl)boronic acid (32 mg, 0.21 mmol), Pd(PPh$_3$)$_4$ (19 mg, 0.02 mmol), Na$_2$CO$_3$ (54 mg, 0.51 mmol) and water (3 mL). The microwave vial was caped and the reaction mixture was heated to 70° C. for 14 hours and then cooled to room temperature. DMSO (1 mL) was added and the reaction mixture was filtered, diluted with MeOH and purified by HPLC Method C to give the title compound (23 mg, 42%). MS (ESI): mass calcd. for C$_{19}$H$_{18}$FN$_3$O, 321.1. m/z found, 322.2 [M+H]$^+$. $^1$H NMR (400 MHz, DMSO-d$_6$) δ 8.66 (d, J=1.6 Hz, 1H), 8.57 (s, 1H), 8.20 (d, J=3.3 Hz, 1H), 7.41 (dd, J=8.5, 6.0 Hz, 1H), 7.27 (dd, J=10.2, 2.7 Hz, 1H), 7.20 (td, J=8.6, 2.8 Hz, 1H), 6.87 (dd, J=3.3, 0.9 Hz, 1H), 6.19 (d, J=0.9 Hz, 1H), 5.72 (s, 2H), 2.34 (s, 3H), 2.28 (s, 3H).

Example 60

5-Methyl-3-[[6-[3-(trifluoromethyl)phenyl]pyrrolo[3,2-b]pyridin-1-yl]methyl]isoxazole

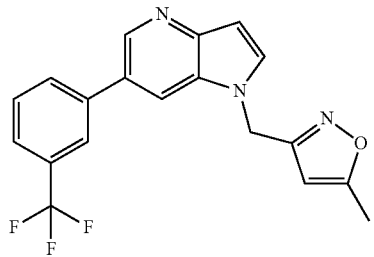 [SMILES: Cc1cc(Cn2ccc3ncc(-c4cccc(C(F)(F)F)c4)cc32)no1]

The title compound was prepared in a manner analogous to Example 59. MS (ESI): mass calcd. for C$_{19}$H$_{14}$F$_3$N$_3$O, 357.1. m/z found, 358.1 [M+H]$^+$. $^1$H NMR (400 MHz, DMSO-d$_6$) δ 9.03 (d, J=1.8 Hz, 1H), 8.93 (s, 1H), 8.20 (s, 1H), 8.19-8.14 (m, 2H), 7.87-7.76 (m, 2H), 6.86 (d, J=3.2 Hz, 1H), 6.18 (s, 1H), 5.77 (s, 2H), 2.33 (s, 3H).

Example 61

5-Methyl-3-[[6-(m-tolyl)pyrrolo[3,2-b]pyridin-1-yl]methyl]isoxazole trifluoroacetate salt

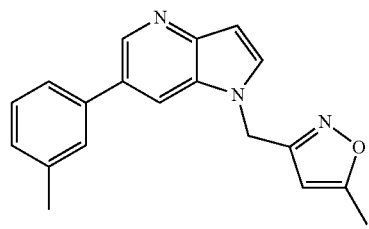 [SMILES: Cc1cccc(-c2cnc3ccn(Cc4cc(C)on4)c3c2)c1]

The title compound was prepared in a manner analogous to Example 59. MS (ESI): mass calcd. for C$_{19}$H$_{17}$N$_3$O, 303.1. m/z found, 304.2 [M+H]$^+$. $^1$H NMR (400 MHz, DMSO-d$_6$) δ 8.99 (d, J=1.7 Hz, 1H), 8.93 (s, 1H), 8.21 (d, J=3.3 Hz, 1H), 7.69 (s, 1H), 7.65 (d, J=7.9 Hz, 1H), 7.46 (t, J=7.6 Hz, 1H), 7.30 (d, J=7.5 Hz, 1H), 6.87 (d, J=3.2 Hz, 1H), 6.20 (d, J=0.8 Hz, 1H), 5.79 (s, 2H), 2.43 (s, 3H), 2.34 (s, 3H).

Example 62

5-Methyl-3-[[6-(o-tolyl)pyrrolo[3,2-b]pyridin-1-yl]methyl]isoxazole trifluoroacetate salt

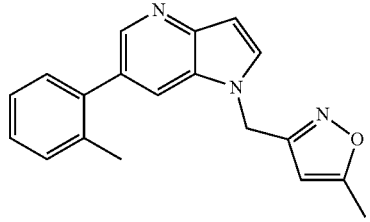 [SMILES: Cc1cc(Cn2ccc3ncc(-c4ccccc4C)cc32)no1]

The title compound was prepared in a manner analogous to Example 59. MS (ESI): mass calcd. for C$_{19}$H$_{17}$N$_3$O, 303.1. m/z found, 304.2 [M+H]$^+$. $^1$H NMR (400 MHz, DMSO-d$_6$) δ 8.69 (d, J=1.6 Hz, 1H), 8.61 (s, 1H), 8.22 (d, J=3.3 Hz, 1H), 7.42-7.34 (m, 4H), 6.88 (dd, J=3.3, 0.9 Hz, 1H), 6.19 (d, J=1.0 Hz, 1H), 5.73 (s, 2H), 2.34 (d, J=0.9 Hz, 3H), 2.27 (s, 3H).

Example 63

3-[[6-(4-Fluoro-3-methyl-phenyl)pyrrolo[3,2-b]pyridin-1-yl]methyl]-5-methyl-isoxazole trifluoroacetate salt

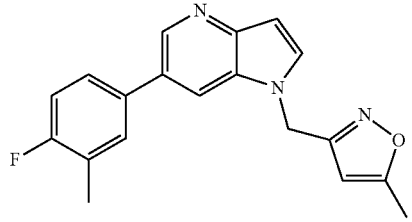 [SMILES: Cc1cc(Cn2ccc3ncc(-c4ccc(F)c(C)c4)cc32)no1]

The title compound was prepared in a manner analogous to Example 59. MS (ESI): mass calcd. for C$_{19}$H$_{18}$FN$_3$O, 321.1. m/z found, 322.2 [M+H]$^+$. $^1$H NMR (400 MHz, DMSO-d$_6$) δ 8.96 (d, J=1.7 Hz, 1H), 8.89 (s, 1H), 8.19 (d, J=3.3 Hz, 1H), 7.80 (dd, J=7.3, 2.4 Hz, 1H), 7.74-7.67 (m, 1H), 7.35 (dd, J=9.6, 8.6 Hz, 1H), 6.86 (d, J=3.3 Hz, 1H), 6.19 (d, J=0.9 Hz, 1H), 5.77 (s, 2H), 2.37-2.32 (m, 6H).

Example 64

3-[[6-(3,5-Difluorophenyl)pyrrolo[3,2-b]pyridin-1-yl]methyl]-5-methyl-isoxazole trifluoroacetate salt

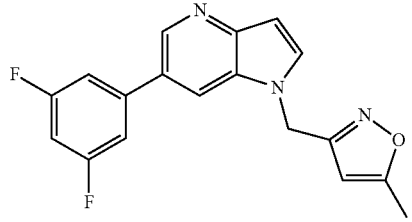 [SMILES: Cc1cc(Cn2ccc3ncc(-c4cc(F)cc(F)c4)cc32)no1]

The title compound was prepared in a manner analogous to Example 59. MS (ESI): mass calcd. for $C_{18}H_{13}F_2N_3O$, 325.1. m/z found, 326.1 [M+H]$^+$. $^1$H NMR (400 MHz, DMSO-$d_6$) δ 9.00 (d, J=1.8 Hz, 1H), 8.89 (s, 1H), 8.14 (d, J=3.3 Hz, 1H), 7.72-7.63 (m, 2H), 7.38-7.28 (m, 1H), 6.83 (dd, J=3.4, 0.8 Hz, 1H), 6.18 (d, J=0.9 Hz, 1H), 5.73 (s, 2H), 2.33 (d, J=0.8 Hz, 3H).

Example 65

3-[[6-(4-Fluorophenyl)pyrrolo[3,2-b]pyridin-1-yl]methyl]-5-methyl-isoxazole trifluoroacetate salt

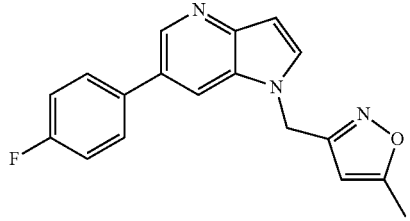

The title compound was prepared in a manner analogous to Example 59. MS (ESI): mass calcd. for $C_{18}H_{14}FN_3O$, 307.1. m/z found, 308.1 [M+H]$^+$. $^1$H NMR (400 MHz, DMSO-$d_6$) δ 8.95 (s, 1H), 8.86 (s, 1H), 8.20-8.15 (m, 1H), 7.93-7.85 (m, 2H), 7.48-7.37 (m, 2H), 6.88-6.83 (m, 1H), 6.19 (s, 1H), 5.76 (s, 2H), 2.33 (d, J=2.1 Hz, 3H).

Example 66

N-Cyclobutyl-2-[6-(4-fluoro-3-methyl-phenyl)pyrrolo[3,2-b]pyridin-1-yl]acetamide trifluoroacetate salt

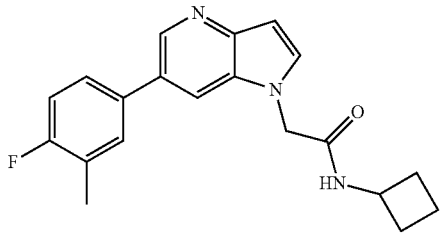 [SMILES: Cc1cc(-c2cnc3ccn(CC(=O)NC4CCC4)c3c2)ccc1F]

Step A: 6-(4-Fluoro-3-methylphenyl)-1H-pyrrolo[3,2-b]pyridine

To a solution a 6-bromo-1H-pyrrolo[3,2-b]pyridine (2 g, 10.2 mmol) in dioxane (50 mL) was added (4-fluoro-3-methylphenyl)boronic acid (1.9 g, 12.2 mmol), Pd(dppf)Cl$_2$ (743 mg, 1.02 mmol), Cs$_2$CO$_3$ (9.9 g, 30.5 mmol) and water (5 mL). After 16 hours at 90° C. the reaction mixture cooled and was concentrated under reduced pressure. Purification (FCC, SiO$_2$, 0-100% EtOAc in hexanes) afforded the title compound (1.95 g, 85%). $^1$H NMR (400 MHz, DMSO-$d_6$) δ 11.37 (s, 1H), 8.59 (d, J=2.0 Hz, 1H), 7.93 (dd, J=2.1, 0.9 Hz, 1H), 7.71-7.62 (m, 2H), 7.59-7.51 (m, 1H), 7.24 (dd, J=9.7, 8.5 Hz, 1H), 6.59-6.55 (m, 1H), 2.33 (d, J=2.0 Hz, 3H).

Step B: Ethyl 2-(6-(4-Fluoro-3-methylphenyl)-1H-pyrrolo[3,2-b]pyridin-1-yl)acetate To a solution of 6-(4-fluoro-3-methylphenyl)-1H-pyrrolo[3,2-b]pyridine (1.5 g, 6.6 mmol) in DMF (60 mL), at 0° C., was added NaH (371 mg, 9.3 mmol, 60% dispersion in oil). The reaction mixture was warmed to room temperature and stirred for 30 minutes. The reaction mixture was cooled to 0° C. and ethyl 2-bromoacetate (0.77 mL, 7 mmol) was added. The reaction mixture was warmed to room temperature and stirred for 12 hours. Water was added and the mixture was extracted with EtOAc. The combined organic layers were dried (MgSO$_4$), filtered and evaporated. Purification (FCC, SiO$_2$, 0-50% EtOAc in hexanes) gave the title compound (1.8 g, 87%). $^1$H NMR (400 MHz, DMSO-$d_6$) δ 8.65 (d, J=2.0 Hz, 1H), 8.18 (dd, J=2.0, 0.9 Hz, 1H), 7.69 (dd, J=7.7, 2.5 Hz, 1H), 7.67 (d, J=3.3 Hz, 1H), 7.63-7.56 (m, 1H), 7.29-7.21 (m, 1H), 6.62 (dd, J=3.2, 0.8 Hz, 1H), 5.24 (s, 2H), 4.16 (q, J=7.1 Hz, 2H), 2.33 (d, J=1.9 Hz, 3H), 1.22 (t, J=7.1 Hz, 3H).

Step C: 2-[6-(4-Fluoro-3-methyl-phenyl)pyrrolo[3,2-b]pyridin-1-yl]acetic acid

To a solution of ethyl 2-(6-(4-Fluoro-3-methylphenyl)-1H-pyrrolo[3,2-b]pyridin-1-yl)acetate (700 mg, 2.2 mmol) in THF (40 mL) was added LiOH (107 mg, 4.5 mmol) in water (10 mL) and the reaction mixture was stirred at room temperature for 30 minutes. The reaction mixture was then acidified with 1N HCl and extracted with EtOAc. The pH of the aqueous layer was adjusted to pH 6 and the product precipitated. The solid was collected via filtration and used crude in the next step (300 mg, 47%). MS (ESI): mass calcd. for $C_{16}H_{13}FN_2O_2$, 284.1. m/z found, 285.1 [M+H]$^+$.

Step D: N-Cyclobutyl-2-[6-(4-fluoro-3-methyl-phenyl)pyrrolo[3,2-b]pyridin-1-yl]acetamide trifluoroacetate salt To a suspension of 2-[6-(4-fluoro-3-methyl-phenyl)pyrrolo[3,2-b]pyridin-1-yl]acetic acid (50 mg, 0.18 mmol) and BOP (78 mg, 0.18 mmol) in DCM (3 mL) was added Et$_3$N (73 μL, 0.53 mmol) followed by cyclobutanamine (30 μL, 0.36 mmol). The crude material was purified by HPLC Method C to give the title compound (9 mg, 11%). MS (ESI): mass calcd. for $C_{20}H_{20}FN_3O$, 337.2. m/z found, 338.2 [M+H]$^+$. $^1$H NMR (600 MHz, DMSO-$d_6$) δ 8.88 (d, J=1.8 Hz, 1H), 8.68 (s, 1H), 8.57 (d, J=7.7 Hz, 1H), 8.00 (d, J=3.3 Hz, 1H), 7.76 (dd, J=7.4, 2.4 Hz, 1H), 7.71-7.65 (m, 1H), 7.33 (t, J=9.1 Hz, 1H), 6.77 (d, J=3.2 Hz, 1H), 5.06 (s, 2H), 4.25-4.13 (m, 1H), 2.35 (d, J=1.8 Hz, 3H), 2.21-2.11 (m, 2H), 1.99-1.89 (m, 2H), 1.71-1.56 (m, 2H).

Example 67

2-[6-(4-Fluoro-3-methyl-phenyl)pyrrolo[3,2-b]pyridin-1-yl]-1-pyrrolidin-1-yl-ethanone trifluoroacetate salt

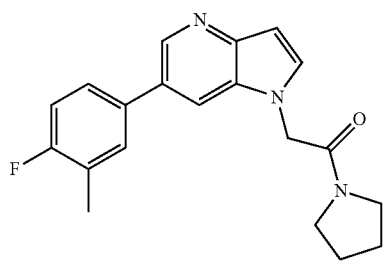

The title compound was prepared in a manner analogous to Example 66. MS (ESI): mass calcd. for $C_{20}H_{20}FN_3O$, 337.2. m/z found, 338.2 [M+H]+. $^1$H NMR (600 MHz, DMSO-d$_6$) δ 8.91 (s, 1H), 8.79 (s, 1H), 8.01 (d, J=3.3 Hz, 1H), 7.80-7.75 (m, 1H), 7.71-7.66 (m, 1H), 7.37-7.31 (m, 1H), 6.81 (d, J=3.4 Hz, 1H), 5.35 (s, 2H), 3.65-3.57 (m, 2H), 3.36-3.30 (m, 2H), 2.35 (s, 3H), 2.03-1.96 (m, 2H), 1.85-1.79 (m, 2H).

Example 68

1-(Azetidin-1-yl)-2-[3-bromo-6-(4-fluoro-3-methyl-phenyl)pyrrolo[3,2-b]pyridin-1-yl]ethanone

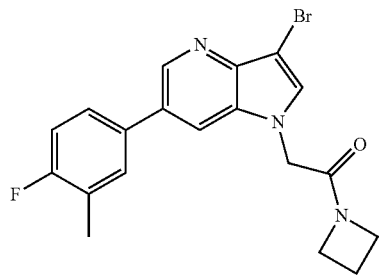 [SMILES: Cc1cc(-c2cnc3c(Br)cn(CC(=O)N4CCC4)c3c2)ccc1F]

Step A: 3-Bromo-6-(4-fluoro-3-methylphenyl)-1H-pyrrolo[3,2-b]pyridine

To a solution of 6-(4-fluoro-3-methylphenyl)-1H-pyrrolo[3,2-b]pyridine (Example 66, Step A, 1 g, 4.4 mmol) in DMF (45 mL) at room temperature was added NBS (944 mg, 5.3 mmol). After 1 hour, water was added and the reaction mixture was extracted with 60% EtOAc in hexanes. The combined organic layers were washed with water, dried over MgSO$_4$, filtered and evaporated. Purification (FCC, SiO$_2$, 0-100% EtOAc in hexanes) gave the title compound (1.2 g, 89%). $^1$H NMR (400 MHz, DMSO-d$_6$) δ 11.78 (s, 1H), 8.67 (d, J=2.0 Hz, 1H), 7.98 (d, J=1.9 Hz, 1H), 7.88 (d, J=2.9 Hz, 1H), 7.72-7.63 (m, 1H), 7.62-7.53 (m, 1H), 7.25 (dd, J=9.7, 8.5 Hz, 1H), 2.33 (d, J=1.9 Hz, 3H).

Step B: 1-(Azetidin-1-yl)-2-[3-bromo-6-(4-fluoro-3-methyl-phenyl)pyrrolo[3,2-b]pyridin-1-yl]ethanone To a solution of 3-bromo-6-(4-fluoro-3-methylphenyl)-1H-pyrrolo[3,2-b]pyridine (200 mg, 0.66 mmol) in DMF (7 mL) at 0° C. was added NaH (37 mg, 0.92 mmol, 60% dispersion in oil). The reaction mixture was warmed to room temperature and stirred for 30 minutes and then cooled to 0° C. followed by the addition of 1-(azetidin-1-yl)-2-bromoethanone (140 mg, 0.78 mmol) in DMF (3 mL). The reaction mixture was warmed to room temperature and stirred for 12 hours. Water was added and the mixture was extracted with EtOAc. The combined organic layers were dried (MgSO$_4$), filtered and evaporated. Purification (FCC, SiO$_2$, 0-100% EtOAc in hexanes) gave the title compound (178 mg, 68%). MS (ESI): mass calcd. for C$_{19}$H$_{17}$BrFN$_3$O, 401.1. m/z found, 402.1 [M+H]+. $^1$H NMR (400 MHz, DMSO-d$_6$) δ 8.70 (d, J=1.8 Hz, 1H), 8.18 (d, J=1.9 Hz, 1H), 7.80 (s, 1H), 7.71-7.67 (m, 1H), 7.64-7.56 (m, 1H), 7.28 (dd, J=9.7, 8.5 Hz, 1H), 5.02 (s, 2H), 4.24 (t, J=7.7 Hz, 2H), 3.91 (t, J=7.7 Hz, 2H), 2.34 (d, J=1.9 Hz, 3H), 2.33-2.23 (m, 2H).

Example 69

1-(Azetidin-1-yl)-2-[3-fluoro-6-(4-fluoro-3-methyl-phenyl)pyrrolo[3,2-b]pyridin-1-yl]ethanone

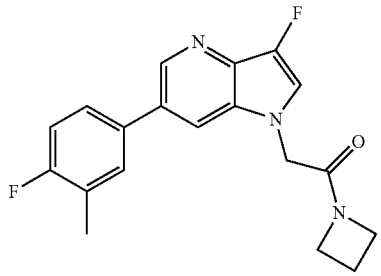 [SMILES: Cc1cc(-c2cnc3c(F)cn(CC(=O)N4CCC4)c3c2)ccc1F]

Step A: 3-Bromo-6-(4-fluoro-3-methylphenyl)-1-((2-(trimethylsilyl)ethoxy)methyl)-1H-pyrrolo[3,2-b]pyridine To a solution of 3-bromo-6-(4-fluoro-3-methylphenyl)-1H-pyrrolo[3,2-b]pyridine (Example 68, Step A, 200 mg, 0.66 mmol) in DMF (5 mL) at 0° C. was added NaH (34 mg, 0.85 mmol, 60% dispersion in oil). The reaction mixture was warmed to room temperature and stirred for 30 minutes and then cooled to 0° C. followed by the addition of a solution of (2-(chloromethoxy)ethyl)trimethylsilane (120 mg, 0.72 mmol) in DMF (3 mL). The reaction mixture was warmed to room temperature and stirred for 12 hours. Water was added and the mixture was extracted with EtOAc. The combined organic layers were dried (MgSO$_4$), filtered and evaporated. Purification (FCC, SiO$_2$, 0-100% EtOAc in hexanes) gave the title compound (166 mg, 58%). $^1$H NMR (500 MHz, DMSO-d$_6$) δ 8.75 (d, J=1.9 Hz, 1H), 8.32 (d, J=1.9 Hz, 1H), 8.07 (s, 1H), 7.73-7.69 (m, 1H), 7.64-7.59 (m, 1H), 7.32-7.25 (m, 1H), 5.65 (s, 2H), 3.52-3.44 (m, 2H), 2.34 (d, J=1.8 Hz, 3H), 0.84-0.76 (m, 2H), −0.11 (s, 9H).

Step B: 3-Fluoro-6-(4-fluoro-3-methylphenyl)-1-((2-(trimethylsilyl)ethoxy)methyl)-1H-pyrrolo[3,2-b]pyridine To a solution of 3-bromo-6-(4-fluoro-3-methylphenyl)-1-((2-(trimethylsilyl)ethoxy)methyl)-1H-pyrrolo[3,2-b]pyridine (160 mg, 0.34 mmol) in THF (10 ml) at −78° C. was added tBuLi (0.65 mL, 1.1 mmol, 1.7M in pentane) and the reaction mixture was stirred at −78° C. for 1 hour. N-fluoro-N-(phenylsulfonyl)benzenesulfonamide (348 mg, 1.10 mmol) in THF (2 mL) was added dropwise and the reaction mixture was stirred at −78° C. for 30 minutes, warmed to 0° C. and stirred for 30 minutes. The reaction mixture was poured into water and extracted with EtOAc. The combined organic layers were dried (MgSO$_4$), filtered and evaporated. Purification (FCC, SiO$_2$, 0-100% EtOAc in hexanes) gave the title compound (77 mg, 56%). MS (ESI): mass calcd. for C$_{20}$H$_{24}$F$_2$N$_2$OSi, 374.2. m/z found, 375.2 [M+H]+.

Step C: 3-Fluoro-6-(4-fluoro-3-methylphenyl)-1H-pyrrolo[3,2-b]pyridine

To a solution of 3-fluoro-6-(4-fluoro-3-methylphenyl)-1-((2-(trimethylsilyl)ethoxy)methyl)-1H-pyrrolo[3,2-b]pyridine (75 mg, 0.2 mmol) in THF (3 mL) was added TBAF (0.8 mL, 0.8 mmol, 1M in THF) and the reaction mixture was heated to 60° C. for 12 hours. Water was added and the reaction mixture was extracted with EtOAc. The combined organic layers were dried (MgSO$_4$), filtered and evaporated. Purification (FCC, SiO$_2$, 0-100% EtOAc in hexanes) gave the title compound (29 mg, 59%). MS (ESI): mass calcd. for C$_{14}$H$_{10}$F$_2$N$_2$, 244.1. m/z found, 245.1 [M+H]+.

Step D: 1-(Azetidin-1-yl)-2-[3-fluoro-6-(4-fluoro-3-methyl-phenyl)pyrrolo[3,2-b]pyridin-1-yl]ethanone The title compound was prepared in a manner analogous to Example 68 Step B. MS (ESI): mass calcd. for $C_{19}H_{17}F_2N_3O$, 341.1. m/z found, 342.2 [M+H]$^+$. $^1$H NMR (600 MHz, CDCl$_3$) δ 8.69 (s, 1H), 7.68 (s, 1H), 7.44-7.40 (m, 1H), 7.40-7.36 (m, 1H), 7.18 (dd, J=2.6, 1.1 Hz, 1H), 7.11 (t, J=8.9 Hz, 1H), 4.68 (s, 2H), 4.09 (t, J=7.8 Hz, 2H), 3.92 (t, J=7.7 Hz, 2H), 2.37 (s, 3H), 2.31-2.24 (m, 2H).

Example 70

2-[6-(4-Fluoro-3-methyl-phenyl)pyrrolo[3,2-b]pyridin-1-yl]acetic acid

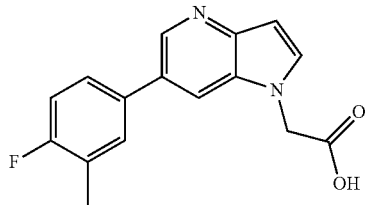 [SMILES: Cc1cc(-c2cnc3ccn(CC(=O)O)c3c2)ccc1F]

The title compound was prepared in a manner analogous to Example 66 Step A through Step C. MS (ESI): mass calcd. for $C_{16}H_{13}FN_2O_2$, 284.1. m/z found, 285.1 [M+H]$^+$. $^1$H NMR (400 MHz, DMSO-d$_6$) δ 13.32 (s, 1H), 9.06 (s, 1H), 9.00 (d, J=1.7 Hz, 1H), 8.19 (d, J=3.3 Hz, 1H), 7.85 (dd, J=7.3, 2.4 Hz, 1H), 7.79-7.71 (m, 1H), 7.36 (dd, J=9.6, 8.6 Hz, 1H), 6.89 (d, J=3.3 Hz, 1H), 5.35 (s, 2H), 2.35 (d, J=1.9 Hz, 3H).

Example 71

1-(azetidin-1-yl)-2-[6-(2-fluorophenyl)pyrrolo[3,2-b]pyridin-1-yl]ethanone

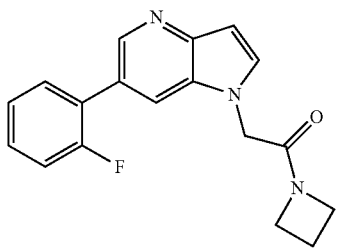 [SMILES: O=C(Cn1ccc2ncc(-c3ccccc3F)cc21)N1CCC1]

Step A: 1-(Azetidin-1-yl)-2-(6-bromo-1H-pyrrolo[3,2-b]pyridin-1-yl)ethanone

To a solution of 6-bromo-1H-pyrrolo[3,2-b]pyridine (1.5 g, 7.6 mmol) at 0° C. was added NaH (913 mg, 22.8 mmol, 60% dispersion in oil). The reaction mixture was stirred for 30 minutes at rt, then cooled to 0° C. and 1-(azetidin-1-yl)-2-bromoethanone (1.6 g, 9.1 mmol) in DMF (10 mL) was added. The reaction mixture was allowed to warm to room temperature and stirred for 12 hours. Water was added and the reaction mixture was extracted with EtOAc. The organics were combined, dried, and concentrated under reduced pressure. Purification (FCC, 0-30% MeOH in DCM) afforded the title compound 1.39 g, 62%). $^1$H NMR (400 MHz, DMSO-d$_6$) δ 8.38 (d, J=2.0 Hz, 1H), 8.16 (dd, J=2.0, 1.0 Hz, 1H), 7.59 (d, J=3.3 Hz, 1H), 6.59 (dd, J=3.3, 0.9 Hz, 1H), 4.95 (s, 2H), 4.22 (t, J=7.6 Hz, 2H), 3.91 (t, J=7.7 Hz, 2H), 2.33-2.22 (m, 2H).

Step B: 1-(Azetidin-1-yl)-2-[6-(2-fluorophenyl)pyrrolo[3,2-b]pyridin-1-yl]ethanone The title compound was prepared in a manner analogous to Example 59, Step B using 1-(azetidin-1-yl)-2-(6-bromo-1H-pyrrolo[3,2-b]pyridin-1-yl)ethanone and (2-fluorophenyl)boronic acid. MS (ESI): mass calcd. for $C_{18}H_{16}FN_3O$, 309.1. m/z found, 310.2 [M+H]$^+$. $^1$H NMR (500 MHz, DMSO-d$_6$) δ 8.52-8.49 (m, 1H), 8.01 (s, 1H), 7.64 (d, J=3.3 Hz, 1H), 7.60 (td, J=7.8, 1.7 Hz, 1H), 7.48-7.42 (m, 1H), 7.39-7.32 (m, 2H), 6.62 (dd, J=3.2, 0.9 Hz, 1H), 4.99 (s, 2H), 4.20 (t, J=7.7 Hz, 2H), 3.90 (t, J=7.7 Hz, 2H), 2.30-2.21 (m, 2H).

Example 72

1-(Azetidin-1-yl)-2-[6-(3-fluorophenyl)pyrrolo[3,2-b]pyridin-1-yl]ethanone

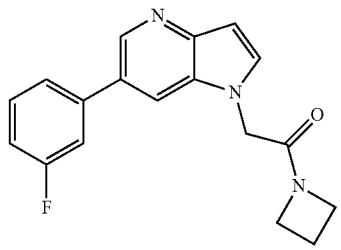

The title compound was prepared in a manner analogous to Example 71 using 1-(azetidin-1-yl)-2-(6-bromo-1H-pyrrolo[3,2-b]pyridin-1-yl)ethanone and (3-fluorophenyl)boronic acid. MS (ESI): mass calcd. for $C_{16}H_{16}FN_3O$, 309.1; m/z found, 310.2 [M+H]$^+$. $^1$H NMR (500 MHz, DMSO-d$_6$) δ 8.70 (d, J=2.0 Hz, 1H), 8.18 (dd, J=2.1, 0.9 Hz, 1H), 7.65-7.60 (m, 3H), 7.58-7.51 (m, 1H), 7.24-7.18 (m, 1H), 6.61 (dd, J=3.2, 0.9 Hz, 1H), 5.02 (s, 2H), 4.21 (t, J=7.7 Hz, 2H), 3.91 (t, J=7.7 Hz, 2H), 2.32-2.22 (m, 2H).

Example 73

1-(Azetidin-1-yl)-2-[6-(p-tolyl)pyrrolo[3,2-b]pyridin-1-yl]ethanone

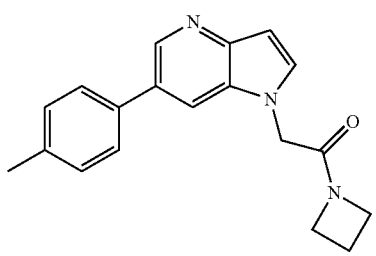

The title compound was prepared in a manner analogous to Example 71 using 1-(azetidin-1-yl)-2-(6-bromo-1H-pyrrolo[3,2-b]pyridin-1-yl)ethanone and p-tolylboronic acid. MS (ESI): mass calcd. for C$_{19}$H$_{19}$N$_3$O, 305.2. m/z found, 306.2 [M+H]$^+$. $^1$H NMR (500 MHz, DMSO-d$_6$) δ 8.65-8.60 (m, 1H), 8.06 (s, 1H), 7.67-7.61 (m, 2H), 7.59-7.55 (m, 1H), 7.34-7.28 (m, 2H), 6.60-6.56 (m, 1H), 5.00 (s, 2H), 4.20 (t, J=7.7 Hz, 2H), 3.90 (t, J=7.8 Hz, 2H), 2.36 (s, 3H), 2.30-2.21 (m, 2H).

Example 74

1-(Azetidin-1-yl)-2-[6-(3-ethylphenyl)pyrrolo[3,2-b]pyridin-1-yl]ethanone

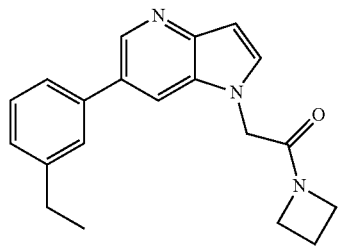 [SMILES: CCc1cccc(-c2cnc3ccn(CC(=O)N4CCC4)c3c2)c1]

The title compound was prepared in a manner analogous to Example 71 using 1-(azetidin-1-yl)-2-(6-bromo-1H-pyrrolo[3,2-b]pyridin-1-yl)ethanone and (3-ethylphenyl)boronic acid. MS (ESI): mass calcd. for C$_{20}$H$_{21}$N$_3$O, 319.2. m/z found, 320.2 [M+H]$^+$. $^1$H NMR (500 MHz, DMSO-d$_6$) δ 8.65 (d, J=2.0 Hz, 1H), 8.08 (dd, J=2.0, 0.9 Hz, 1H), 7.61-7.52 (m, 3H), 7.41 (t, J=7.6 Hz, 1H), 7.23 (d, J=7.7 Hz, 1H), 6.60 (dd, J=3.3, 0.9 Hz, 1H), 5.01 (s, 2H), 4.20 (t, J=7.7 Hz, 2H), 3.90 (t, J=7.7 Hz, 2H), 2.70 (q, J=7.6 Hz, 2H), 2.31-2.21 (m, 2H), 1.25 (t, J=7.6 Hz, 3H).

Example 75

N-Cyclopropyl-2-[6-(2-fluorophenyl)pyrrolo[3,2-b]pyridin-1-yl]acetamide

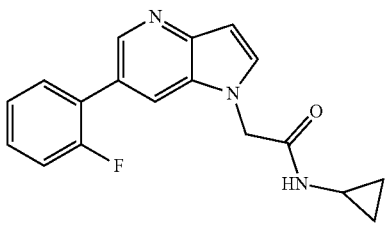 [SMILES: O=C(Cn1ccc2ncc(-c3ccccc3F)cc21)NC1CC1]

Step A: 2-(6-Bromo-1H-pyrrolo[3,2-b]pyridin-1-yl)-N-cyclopropylacetamide

To a solution of 6-bromo-1H-pyrrolo[3,2-b]pyridine (1 g, 5.0 mmol) in DMF (20 mL) at 0° C. was added NaH (284 mg, 7.1 mmol, 60% dispersion in oil). The reaction mixture was stirred for 30 minutes and 2-bromo-N-cyclopropylacetamide (1.08 g, 6.1 mmol) in DMF (5 mL) was added. The reaction mixture was allowed to warm to room temperature and stirred for 12 hours. Water was then added and the reaction mixture was extracted with 60% EtOAc in hexanes. The combined organic layers were dried (MgSO$_4$), filtered and evaporated. Purification (FCC, SiO$_2$, 0-100% EtOAc in hexanes) gave the title compound (1.21 g, 81%). $^1$H NMR (400 MHz, DMSO-d$_6$) δ 8.38 (d, J=2.1 Hz, 1H), 8.31 (d, J=4.3 Hz, 1H), 8.12 (dd, J=2.0, 0.9 Hz, 1H), 7.62 (d, J=3.3 Hz, 1H), 6.59 (dd, J=3.3, 0.9 Hz, 1H), 4.81 (s, 2H), 2.69-2.60 (m, 1H), 0.67-0.60 (m, 2H), 0.47-0.41 (m, 2H).

Step B: N-Cyclopropyl-2-[6-(2-fluorophenyl)pyrrolo[3,2-b]pyridin-1-yl]acetamide

The title compound was prepared in a manner analogous to Example 59, Step B. MS (ESI): mass calcd. for C$_{18}$H$_{16}$FN$_3$O, 309.1. m/z found, 310.2 [M+H]$^+$. $^1$H NMR (400 MHz, DMSO-d$_6$) δ 8.50 (t, J=2.0 Hz, 1H), 8.34 (d, J=4.3 Hz, 1H), 7.96 (s, 1H), 7.66 (d, J=3.2 Hz, 1H), 7.60 (td, J=7.8, 1.7 Hz, 1H), 7.48-7.41 (m, 1H), 7.39-7.31 (m, 2H), 6.61 (dd, J=3.3, 0.9 Hz, 1H), 4.85 (s, 2H), 2.68-2.59 (m, 1H), 0.66-0.58 (m, 2H), 0.46-0.39 (m, 2H).

Example 76

N-Cyclopropyl-2-[6-(3-fluorophenyl)pyrrolo[3,2-b]pyridin-1-yl]acetamide

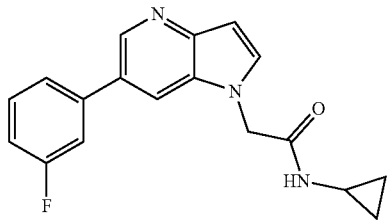 [SMILES: O=C(Cn1ccc2ncc(-c3cccc(F)c3)cc21)NC1CC1]

The title compound was prepared in a manner analogous to Example 75. MS (ESI): mass calcd. for C$_{18}$H$_{16}$FN$_3$O, 309.1. m/z found, 310.2 [M+H]$^+$. $^1$H NMR (400 MHz, DMSO-d$_6$) δ 8.70 (d, J=2.0 Hz, 1H), 8.34 (d, J=4.2 Hz, 1H), 8.17-8.14 (m, 1H), 7.66 (d, J=3.3 Hz, 1H), 7.64-7.58 (m, 2H), 7.58-7.50 (m, 1H), 7.24-7.17 (m, 1H), 6.60 (d, J=3.3 Hz, 1H), 4.88 (s, 2H), 2.69-2.60 (m, 1H), 0.67-0.60 (m, 2H), 0.47-0.41 (m, 2H).

Example 77

N-Cyclopropyl-2-[6-(p-tolyl)pyrrolo[3,2-b]pyridin-1-yl]acetamide

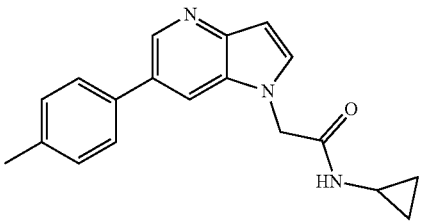 [SMILES: Cc1ccc(-c2cnc3ccn(CC(=O)NC4CC4)c3c2)cc1]

The title compound was prepared in a manner analogous to Example 75. MS (ESI): mass calcd. for C$_{19}$H$_{19}$N$_3$O, 305.2. m/z found, 306.2 [M+H]$^+$. $^1$H NMR (400 MHz, DMSO-d$_6$) δ 8.63 (d, J=2.0 Hz, 1H), 8.34 (d, J=4.2 Hz, 1H), 8.03 (dd, J=2.0, 0.9 Hz, 1H), 7.66-7.58 (m, 3H), 7.34-7.28

(m, 2H), 6.57 (dd, J=3.2, 0.8 Hz, 1H), 4.86 (s, 2H), 2.70-2.59 (m, 1H), 2.36 (s, 3H), 0.67-0.59 (m, 2H), 0.47-0.40 (m, 2H).

Example 78

2-(6-Phenylpyrrolo[3,2-b]pyridin-1-yl)-1-pyrrolidin-1-yl-ethanone

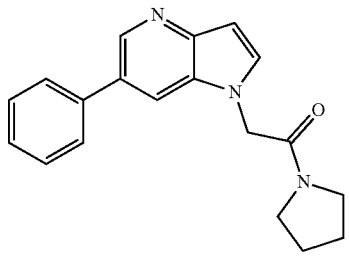 [SMILES: O=C(Cn1ccc2ncc(-c3ccccc3)cc21)N1CCCC1]

Step A: 2-(6-Bromo-1H-pyrrolo[3,2-b]pyridin-1-yl)-1-(pyrrolidin-1-yl)ethanone

To a solution of 6-bromo-1H-pyrrolo[3,2-b]pyridine (1 g, 5.0 mmol) in DMF (20 mL) at 0° C. was added NaH (284 mg, 7.1 mmol, 60% dispersion in oil). The reaction mixture was stirred for 30 minutes and 2-bromo-1-(pyrrolidin-1-yl)ethanone (1.02 g, 5.3 mmol) in DMF (5 mL) was added. The reaction mixture was allowed to warm to room temperature and stirred for 12 hours. Water (1 mL) was added and the reaction mixture was concentrated onto silica gel. Purification (FCC, SiO$_2$, 0-20% MeOH in EtOAc) gave the title compound (quant. yield). $^1$H NMR (400 MHz, DMSO-d$_6$) δ 8.37 (d, J=2.0 Hz, 1H), 8.18 (dd, J=2.1, 0.8 Hz, 1H), 7.58 (d, J=3.3 Hz, 1H), 6.58 (dd, J=3.3, 0.8 Hz, 1H), 5.12 (s, 2H), 3.56 (t, J=6.8 Hz, 2H), 3.37-3.25 (m, 2H), 2.01-1.90 (m, 2H), 1.86-1.75 (m, 2H).

Step B: 2-(6-Phenylpyrrolo[3,2-b]pyridin-1-yl)-1-pyrrolidin-1-yl-ethanone

The title compound was prepared in a manner analogous to Example 59, Step B. MS (ESI): mass calcd. for C$_{19}$H$_{19}$N$_3$O, 305.2. m/z found, 306.2 [M+H]$^+$. $^1$H NMR (600 MHz, DMSO-d$_6$) δ 8.66-8.62 (m, 1H), 8.12-8.10 (m, 1H), 7.77-7.71 (m, 2H), 7.61-7.56 (m, 1H), 7.53-7.46 (m, 2H), 7.40-7.34 (m, 1H), 6.60-6.57 (m, 1H), 5.17 (s, 2H), 3.62-3.56 (m, 2H), 3.35-3.30 (m, 2H), 2.01-1.92 (m, 2H), 1.85-1.76 (m, 2H).

Example 79

2-[6-(2-Fluorophenyl)pyrrolo[3,2-b]pyridin-1-yl]-1-pyrrolidin-1-yl-ethanone

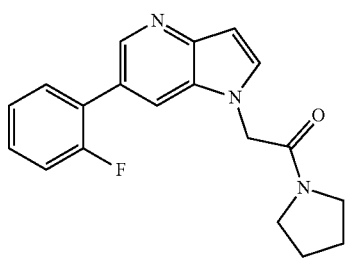 [SMILES: O=C(Cn1ccc2ncc(-c3ccccc3F)cc21)N1CCCC1]

The title compound was prepared in a manner analogous to Example 78. MS (ESI): mass calcd. for C$_{19}$H$_{18}$FN$_3$O, 323.1. m/z found, 324.2 [M+H]$^+$. $^1$H NMR (600 MHz, DMSO-d$_6$) δ 8.49 (s, 1H), 8.01 (s, 1H), 7.63 (d, J=3.4 Hz, 1H), 7.61-7.56 (m, 1H), 7.48-7.41 (m, 1H), 7.38-7.30 (m, 2H), 6.63-6.60 (m, 1H), 5.16 (s, 2H), 3.61-3.53 (m, 2H), 3.34-3.30 (m, 2H), 1.98-1.92 (m, 2H), 1.83-1.76 (m, 2H).

Example 80

2-[6-(4-Fluorophenyl)pyrrolo[3,2-b]pyridin-1-yl]-1-pyrrolidin-1-yl-ethanone

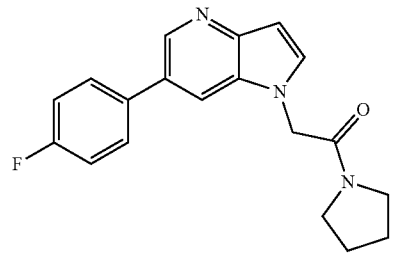 [SMILES: O=C(Cn1ccc2ncc(-c3ccc(F)cc3)cc21)N1CCCC1]

The title compound was prepared in a manner analogous to Example 78. MS (ESI): mass calcd. for C$_{19}$H$_{18}$FN$_3$O, 323.1. m/z found, 324.2 [M+H]$^+$. $^1$H NMR (600 MHz, DMSO-d$_6$) δ 8.63-8.61 (m, 1H), 8.10 (s, 1H), 7.80-7.73 (m, 2H), 7.60-7.57 (m, 1H), 7.36-7.29 (m, 2H), 6.60-6.57 (m, 1H), 5.17 (s, 2H), 3.59 (t, J=6.9 Hz, 2H), 3.32 (t, J=7.0 Hz, 2H), 1.99-1.93 (m, 2H), 1.84-1.77 (m, 2H).

Example 81

2-[6-(m-Tolyl)pyrrolo[3,2-b]pyridin-1-yl]-1-pyrrolidin-1-yl-ethanone

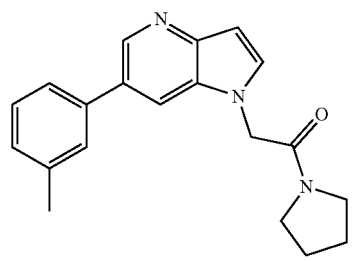

The title compound was prepared in a manner analogous to Example 78. MS (ESI): mass calcd. for C$_{20}$H$_{21}$N$_3$O, 319.2. m/z found, 320.2 [M+H]$^+$. $^1$H NMR (600 MHz, DMSO-d$_6$) δ 8.63 (dd, J=2.0, 0.9 Hz, 1H), 8.10-8.07 (m, 1H), 7.58 (dd, J=3.2, 0.9 Hz, 1H), 7.55 (s, 1H), 7.52 (d, J=7.9 Hz, 1H), 7.38 (t, J=7.6 Hz, 1H), 7.19 (d, J=7.5 Hz, 1H), 6.58 (d, J=3.2 Hz, 1H), 5.17 (s, 2H), 3.59 (t, J=6.9 Hz, 2H), 3.33 (t, J=6.9 Hz, 2H), 2.40 (s, 3H), 1.99-1.94 (m, 2H), 1.84-1.77 (m, 2H).

Example 82

2-[6-(p-Tolyl)pyrrolo[3,2-b]pyridin-1-yl]-1-pyrrolidin-1-yl-ethanone

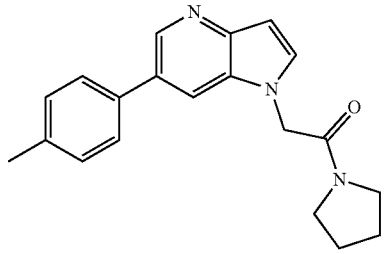 [SMILES: Cc1ccc(-c2cnc3ccn(CC(=O)N4CCCC4)c3c2)cc1]

The title compound was prepared in a manner analogous to Example 78. MS (ESI): mass calcd. for $C_{20}H_{21}N_3O$, 319.2. m/z found, 320.2 [M+H]+. $^1$H NMR (600 MHz, DMSO-$d_6$) δ 8.64-8.60 (m, 1H), 8.07 (s, 1H), 7.65-7.61 (m, 2H), 7.56 (dd, J=3.2, 1.0 Hz, 1H), 7.30 (d, J=8.3 Hz, 2H), 6.58-6.55 (m, 1H), 5.16 (s, 2H), 3.59 (t, J=6.9 Hz, 2H), 3.32 (t, J=7.0 Hz, 2H), 2.36 (s, 3H), 2.00-1.92 (m, 2H), 1.84-1.76 (m, 2H).

Example 83

2-[6-(3-Ethylphenyl)pyrrolo[3,2-b]pyridin-1-yl]-1-pyrrolidin-1-yl-ethanone

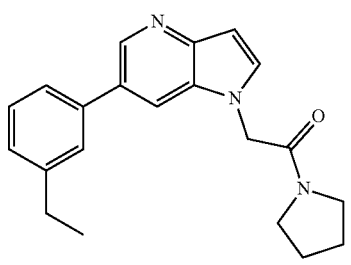 [SMILES: CCc1cccc(-c2cnc3ccn(CC(=O)N4CCCC4)c3c2)c1]

The title compound was prepared in a manner analogous to Example 78. MS (ESI): mass calcd. for $C_{21}H_{23}N_3O$, 333.2. m/z found, 334.2 [M+H]+. $^1$H NMR (600 MHz, DMSO-$d_6$) δ 8.64-8.62 (m, 1H), 8.09-8.07 (m, 1H), 7.59-7.51 (m, 3H), 7.42-7.38 (m, 1H), 7.22 (d, J=7.1 Hz, 1H), 6.59-6.57 (m, 1H), 5.17 (s, 2H), 3.59 (t, J=6.9 Hz, 2H), 3.32 (t, J=7.0 Hz, 2H), 2.70 (q, J=7.6 Hz, 2H), 2.00-1.94 (m, 2H), 1.84-1.77 (m, 2H), 1.27-1.22 (m, 3H).

Example 84

2-[6-(3-Fluorophenyl)pyrrolo[3,2-b]pyridin-1-yl]-1-pyrrolidin-1-yl-ethanone

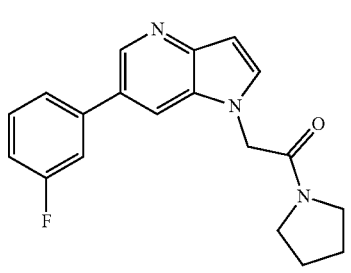 [SMILES: O=C(Cn1ccc2ncc(-c3cccc(F)c3)cc21)N1CCCC1]

The title compound was prepared in a manner analogous to Example 78. MS (ESI): mass calcd. for $C_{19}H_{18}FN_3O$, 323.1. m/z found, 324.2 [M+H]+. $^1$H NMR (600 MHz, DMSO-$d_6$) δ 8.70-8.68 (m, 1H), 8.20-8.17 (m, 1H), 7.64-7.58 (m, 3H), 7.56-7.50 (m, 1H), 7.23-7.17 (m, 1H), 6.62-6.58 (m, 1H), 5.18 (s, 2H), 3.59 (t, J=6.8 Hz, 2H), 3.33 (t, J=6.9 Hz, 2H), 2.00-1.94 (m, 2H), 1.85-1.77 (m, 2H).

Example 85

1-Morpholino-2-(6-phenylpyrrolo[3,2-b]pyridin-1-yl)ethanone

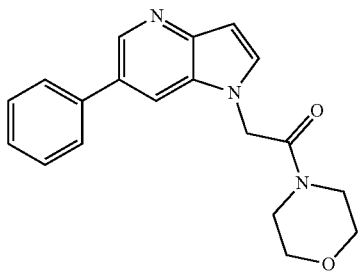 [SMILES: O=C(Cn1ccc2ncc(-c3ccccc3)cc21)N1CCOCC1]

Step A: 2-(6-Bromo-1H-pyrrolo[3,2-b]pyridin-1-yl)-1-morpholinoethanone

The title compound was prepared in a manner analogous to Example 78, Step A substituting 2-bromo-1-morpholinoethanone for 2-bromo-1-(pyrrolidin-1-yl)ethanone. $^1$H NMR (500 MHz, DMSO-$d_6$) δ 8.37 (d, J=2.0 Hz, 1H), 8.18 (dd, J=2.1, 0.9 Hz, 1H), 7.58 (d, J=3.3 Hz, 1H), 6.59 (dd, J=3.3, 0.9 Hz, 1H), 5.24 (s, 2H), 3.69 (t, J=4.8 Hz, 2H), 3.60 (t, J=4.9 Hz, 2H), 3.54 (t, J=4.8 Hz, 2H), 3.44 (t, J=4.8 Hz, 2H).

Step B: 1-Morpholino-2-(6-phenylpyrrolo[3,2-b]pyridin-1-yl)ethanone

The title compound was prepared in a manner analogous to Example 78, Step B. MS (ESI): mass calcd. for $C_{19}H_{19}N_3O_2$, 321.1. m/z found, 322.2 [M+H]+. $^1$H NMR (600 MHz, DMSO-$d_6$) δ 8.65 (s, 1H), 8.11 (s, 1H), 7.76-7.70 (m, 2H), 7.61-7.56 (m, 1H), 7.54-7.47 (m, 2H), 7.41-7.35 (m, 1H), 6.59 (s, 1H), 5.31 (s, 2H), 3.70 (s, 2H), 3.59 (s, 4H), 3.44 (s, 2H).

Example 86

2-[6-(2-Fluorophenyl)pyrrolo[3,2-b]pyridin-1-yl]-1-morpholino-ethanone

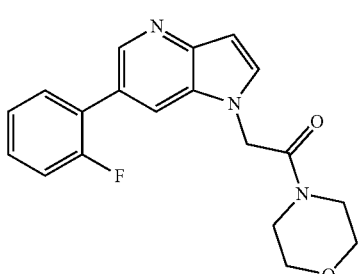

The title compound was prepared in a manner analogous to Example 85. MS (ESI): mass calcd. for $C_{19}H_{18}FN_3O_2$, 339.1. m/z found, 340.2 [M+H]+. 1H NMR (600 MHz, DMSO-d6) δ 8.50-8.48 (m, 1H), 8.02-8.00 (m, 1H), 7.62 (d, J=3.3 Hz, 1H), 7.59 (td, J=7.8, 1.7 Hz, 1H), 7.48-7.42 (m, 1H), 7.38-7.32 (m, 2H), 6.62 (dd, J=3.2, 0.8 Hz, 1H), 5.29 (s, 2H), 3.70-3.65 (m, 2H), 3.60-3.55 (m, 4H), 3.43 (t, J=5.0 Hz, 2H).

Example 87

2-[6-(3-Fluorophenyl)pyrrolo[3,2-b]pyridin-1-yl]-1-morpholino-ethanone

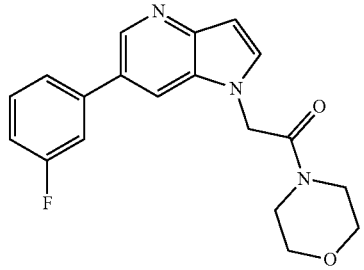 [SMILES: O=C(Cn1ccc2ncc(-c3cccc(F)c3)cc21)N1CCOCC1]

The title compound was prepared in a manner analogous to Example 85. MS (ESI): mass calcd. for $C_{19}H_{18}FN_3O_2$, 339.1. m/z found, 340.2 [M+H]+. 1H NMR (600 MHz, DMSO-d6) δ 8.69 (d, J=2.0 Hz, 1H), 8.18 (s, 1H), 7.65-7.58 (m, 3H), 7.57-7.50 (m, 1H), 7.24-7.17 (m, 1H), 6.60 (dd, J=3.3, 0.8 Hz, 1H), 5.30 (s, 2H), 3.75-3.68 (m, 2H), 3.62-3.56 (m, 4H), 3.47-3.41 (m, 2H).

Example 88

2-[6-(4-Fluorophenyl)pyrrolo[3,2-b]pyridin-1-yl]-1-morpholino-ethanone

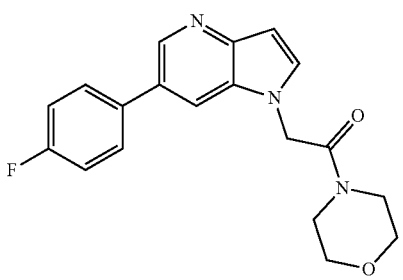 [SMILES: O=C(Cn1ccc2ncc(-c3ccc(F)cc3)cc21)N1CCOCC1]

The title compound was prepared in a manner analogous to Example 85. MS (ESI): mass calcd. for $C_{19}H_{18}FN_3O_2$, 339.1. m/z found, 340.2 [M+H]+. 1H NMR (600 MHz, DMSO-d6) δ 8.64-8.60 (m, 1H), 8.10 (s, 1H), 7.80-7.74 (m, 2H), 7.60-7.57 (m, 1H), 7.37-7.30 (m, 2H), 6.61-6.58 (m, 1H), 5.30 (s, 2H), 3.72-3.68 (m, 2H), 3.61-3.55 (m, 4H), 3.47-3.41 (m, 2H).

Example 89

1-Morpholino-2-[6-(m-tolyl)pyrrolo[3,2-b]pyridin-1-yl]ethanone

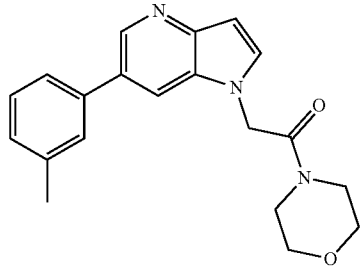 [SMILES: Cc1cccc(-c2cnc3ccn(CC(=O)N4CCOCC4)c3c2)c1]

The title compound was prepared in a manner analogous to Example 85. MS (ESI): mass calcd. for $C_{20}H_{21}N_3O_2$, 335.2. m/z found, 336.2 [M+H]+. 1H NMR (600 MHz, DMSO-d6) δ 8.63 (s, 1H), 8.08 (s, 1H), 7.58 (dd, J=3.3, 0.9 Hz, 1H), 7.55 (s, 1H), 7.52 (d, J=7.7 Hz, 1H), 7.38 (t, J=7.5 Hz, 1H), 7.19 (d, J=7.5 Hz, 1H), 6.59 (d, J=3.2 Hz, 1H), 5.30 (s, 2H), 3.73-3.67 (m, 2H), 3.62-3.56 (m, 4H), 3.47-3.42 (m, 2H), 2.40 (s, 3H).

Example 90

1-Morpholino-2-[6-(p-tolyl)pyrrolo[3,2-b]pyridin-1-yl]ethanone

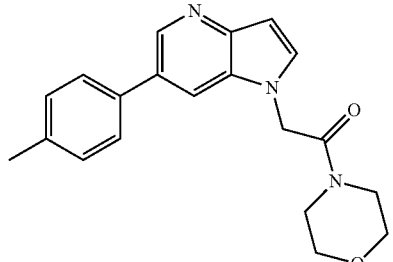

The title compound was prepared in a manner analogous to Example 85. MS (ESI): mass calcd. for $C_{20}H_{21}N_3O_2$, 335.2. m/z found, 336.2 [M+H]+. 1H NMR (600 MHz, DMSO-d6) δ 8.64-8.60 (m, 1H), 8.07 (s, 1H), 7.65-7.61 (m, 2H), 7.58-7.55 (m, 1H), 7.33-7.28 (m, 2H), 6.58 (d, J=3.1 Hz, 1H), 5.29 (s, 2H), 3.72-3.66 (m, 2H), 3.62-3.55 (m, 4H), 3.46-3.41 (m, 2H), 2.36 (s, 3H).

Example 91

2-[6-(3-ethylphenyl)pyrrolo[3,2-b]pyridin-1-yl]-1-morpholino-ethanone

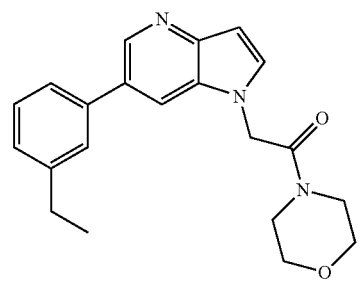 [SMILES: CCc1cccc(-c2cnc3ccn(CC(=O)N4CCOCC4)c3c2)c1]

The title compound was prepared in a manner analogous to Example 85. MS (ESI): mass calcd. for $C_{21}H_{23}N_3O_2$, 349.2. m/z found, 350.2 [M+H]$^+$. $^1$H NMR (600 MHz, DMSO-d$_6$) δ 8.66-8.59 (m, 1H), 8.07 (s, 1H), 7.60-7.51 (m, 3H), 7.41 (t, J=7.6 Hz, 1H), 7.23 (d, J=7.6 Hz, 1H), 6.59 (d, J=3.3 Hz, 1H), 5.31 (s, 2H), 3.72-3.67 (m, 2H), 3.62-3.56 (m, 4H), 3.46-3.42 (m, 2H), 2.74-2.66 (m, 2H), 1.25 (t, J=7.6 Hz, 3H).

Example 92

2-[3-Fluoro-6-(4-fluoro-3-methyl-phenyl)pyrrolo[3,2-b]pyridin-1-yl]-N,N-dimethyl-acetamide

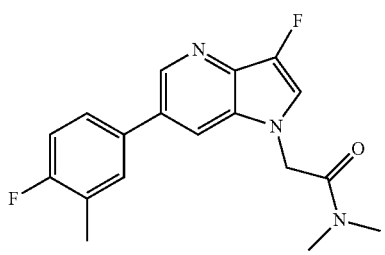

To a solution of 2-(6-bromo-3-fluoro-1H-pyrrolo[3,2-b]pyridin-1-yl)-N,N-dimethylacetamide (Intermediate 15, 68 mg, 0.22 mmol) in dioxane (1 mL) was added (4-fluoro-3-methylphenyl)boronic acid (419 mg, 0.27 mmol), Pd(dppf)Cl$_2$ (16.6 mg, 0.203 mmol), Cs$_2$CO$_3$ (221 mg, 0.68 mmol). After 16 hours at 90° C. the reaction mixture cooled and was concentrated under reduced pressure. Purification (FCC, SiO$_2$, 0-20% MeOH in EtOAc) afforded the title compound (37 mg, 50%). MS (ESI): mass calcd. for $C_{16}H_{17}F_2N_3O$, 329.1. m/z found, 330.1 [M+H]$^+$. $^1$H NMR (400 MHz, DMSO-d$_6$) δ 8.66 (d, J=1.8 Hz, 1H), 8.17-8.12 (m, 1H), 7.68 (dd, J=7.6, 2.4 Hz, 1H), 7.62-7.55 (m, 2H), 7.27 (dd, J=9.6, 8.5 Hz, 1H), 5.20 (s, 2H), 3.10 (s, 3H), 2.85 (s, 3H), 2.33 (d, J=1.9 Hz, 3H).

Example 93

2-[6-(3,4-Difluorophenyl)-3-fluoro-pyrrolo[3,2-b]pyridin-1-yl]-N,N-dimethyl-acetamide

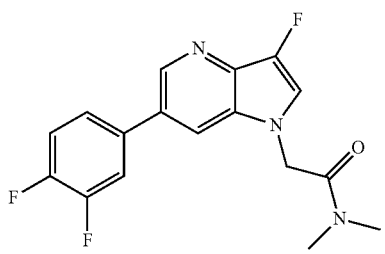

The title compound was prepared in a manner analogous to Example 92 using 2-(6-bromo-3-fluoro-1H-pyrrolo[3,2-b]pyridin-1-yl)-N,N-dimethylacetamide (Intermediate 15) and (3,4-difluorophenyl)boronic acid. MS (ESI): mass calcd. for $C_{17}H_{14}F_3N_3O$, 333.1. m/z found, 334.0 [M+H]$^+$. $^1$H NMR (400 MHz, DMSO-d$_6$) δ 8.74-8.70 (m, 1H), 8.27-8.22 (m, 1H), 7.88 (ddd, J=12.3, 7.8, 2.3 Hz, 1H), 7.68-7.52 (m, 3H), 5.20 (s, 2H), 3.10 (s, 3H), 2.85 (s, 3H).

Example 94

2-[3-Fluoro-6-(3,4,5-trifluorophenyl)pyrrolo[3,2-b]pyridin-1-yl]-N,N-dimethyl-acetamide

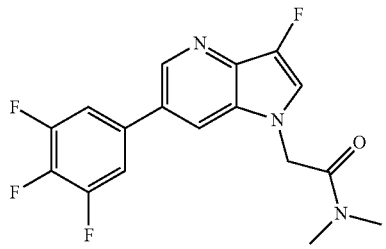

The title compound was prepared in a manner analogous to Example 92 using 2-(6-bromo-3-fluoro-1H-pyrrolo[3,2-b]pyridin-1-yl)-N,N-dimethylacetamide (Intermediate 15) and (2,3,4-trifluorophenyl)boronic acid. MS (ESI): mass calcd. for $C_{17}H_{13}F_4N_3O$, 351.1. m/z found, 352.0 [M+H]$^+$. $^1$H NMR (400 MHz, DMSO-d$_6$) δ 8.77 (d, J=1.9 Hz, 1H), 8.30 (t, J=2.2 Hz, 1H), 7.85-7.79 (m, 2H), 7.67 (d, J=2.2 Hz, 1H), 5.21 (s, 2H), 3.12 (s, 3H), 2.86 (s, 3H).

Example 95

2-[6-[3-(Difluoromethyl)phenyl]-3-fluoro-pyrrolo[3,2-b]pyridin-1-yl]-N,N-dimethyl-acetamide

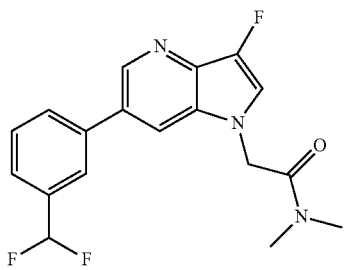 [SMILES: CN(C)C(=O)Cn1cc(F)c2ncc(-c3cccc(C(F)F)c3)cc21]

The title compound was prepared in a manner analogous to Example 92 using 2-(6-bromo-3-fluoro-1H-pyrrolo[3,2-b]pyridin-1-yl)-N,N-dimethylacetamide (Intermediate 15) and (3-(difluoromethyl)phenyl)boronic acid. MS (ESI): mass calcd. for $C_{18}H_{16}F_3N_3O$, 347.1. m/z found, 348.0 [M+H]$^+$. $^1$H NMR (400 MHz, DMSO-d$_6$) δ 8.72 (d, J=1.9 Hz, 1H), 8.27-8.23 (m, 1H), 7.94 (s, 2H), 7.71-7.58 (m, 3H), 7.12 (t, J=55.8 Hz, 1H), 5.24 (s, 2H), 3.10 (s, 3H), 2.85 (s, 3H).

Example 96

2-[3-Fluoro-6-(4-methyl-2-thienyl)pyrrolo[3,2-b]pyridin-1-yl]-N,N-dimethyl-acetamide

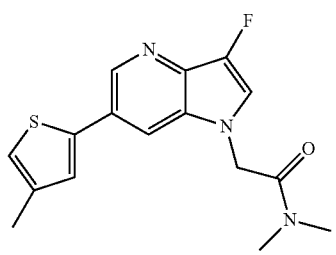 [SMILES: Cc1csc(-c2cnc3c(F)cn(CC(=O)N(C)C)c3c2)c1]

The title compound was prepared in a manner analogous to Example 92, using 2-(6-bromo-3-fluoro-1H-pyrrolo[3,2-b]pyridin-1-yl)-N,N-dimethylacetamide (Intermediate 15) and 4,4,5,5-tetramethyl-2-(4-methylthiophen-2-yl)-1,3,2-dioxaborolane. MS (ESI): mass calcd. for $C_{16}H_{16}FN_3OS$, 317.1. m/z found, 318.0 [M+H]+. 1H NMR (400 MHz, DMSO-d6) δ 8.64 (d, J=1.9 Hz, 1H), 8.13-8.09 (m, 1H), 7.59 (d, J=2.2 Hz, 1H), 7.42 (d, J=1.4 Hz, 1H), 7.18-7.14 (m, 1H), 5.19 (s, 2H), 3.10 (s, 3H), 2.86 (s, 3H), 2.26 (s, 3H).

Example 97

2-[6-(5-Chloro-2-thienyl)-3-fluoro-pyrrolo[3,2-b]pyridin-1-yl]-N,N-dimethyl-acetamide

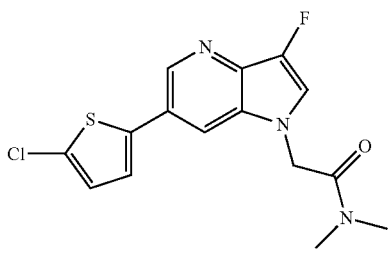 [SMILES: CN(C)C(=O)Cn1cc(F)c2ncc(-c3ccc(Cl)s3)cc21]

The title compound was prepared in a manner analogous to Example 92, using 2-(6-bromo-3-fluoro-1H-pyrrolo[3,2-b]pyridin-1-yl)-N,N-dimethylacetamide (Intermediate 15) and (5-chlorothiophen-2-yl)boronic acid. MS (ESI): mass calcd. for $C_{15}H_{13}ClFN_3OS$, 337.0. m/z found, 338.0 [M+H]+. 1H NMR (400 MHz, DMSO-d6) δ 8.65 (d, J=1.9 Hz, 1H), 8.14 (t, J=2.2 Hz, 1H), 7.64 (d, J=2.3 Hz, 1H), 7.47 (d, J=3.9 Hz, 1H), 7.22 (d, J=4.0 Hz, 1H), 5.20 (s, 2H), 3.10 (s, 3H), 2.86 (s, 3H).

Example 98

2-[3-Fluoro-6-(4-fluorophenyl)pyrrolo[3,2-b]pyridin-1-yl]-N,N-dimethyl-acetamide

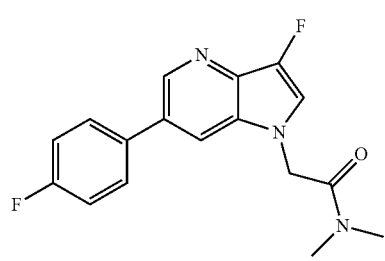 [SMILES: CN(C)C(=O)Cn1cc(F)c2ncc(-c3ccc(F)cc3)cc21]

The title compound was prepared in a manner analogous to Example 92, using 2-(6-bromo-3-fluoro-1H-pyrrolo[3,2-b]pyridin-1-yl)-N,N-dimethylacetamide (Intermediate 15) and (4-fluorophenyl)boronic acid. MS (ESI): mass calcd. for $C_{17}H_{16}F_2N_3O$, 315.1. m/z found, 316.0 [M+H]+. 1H NMR (400 MHz, DMSO-d6) δ 8.69-8.65 (m, 1H), 8.20-8.16 (m, 1H), 7.83-7.76 (m, 2H), 7.64-7.60 (m, 1H), 7.40-7.30 (m, 2H), 5.21 (s, 2H), 3.10 (s, 3H), 2.85 (s, 3H).

Example 99

N-Cyclopropyl-2-[6-[5-(trifluoromethyl)-3-pyridyl]pyrrolo[3,2-b]pyridin-1-yl]acetamide

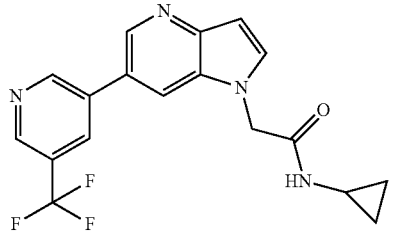 [SMILES: O=C(Cn1ccc2ncc(-c3cncc(C(F)(F)F)c3)cc21)NC1CC1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (5-(trifluoromethyl)pyridin-3-yl)boronic acid. MS (ESI): mass calcd. for $C_{18}H_{15}F_3N_4O$, 360.1. m/z found, 361.2 [M+H]+. 1H NMR (500 MHz, CD3OD) δ 9.16 (d, J=2.1 Hz, 1H), 8.88 (s, 1H), 8.68 (d, J=1.9 Hz, 1H), 8.47 (s, 1H), 8.24-8.22 (m, 1H), 7.64 (d, J=3.3 Hz, 1H), 6.70 (d, J=3.2 Hz, 1H), 4.95 (s, 2H), 2.73-2.66 (m, 1H), 0.76-0.69 (m, 2H), 0.56-0.50 (m, 2H).

Example 100

N-Cyclopropyl-2-[6-(3,4-difluorophenyl)pyrrolo[3,2-b]pyridin-1-yl]acetamide

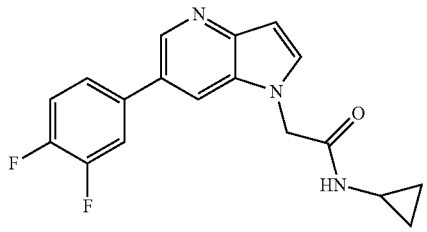

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (3,4-difluorophenyl)boronic acid. MS (ESI): mass calcd. for $C_{18}H_{15}F_2N_3O$, 327.1. m/z found, 328.2 [M+H]+. 1H NMR (500 MHz, CD3OD) δ 8.55 (d, J=1.9 Hz, 1H), 8.03-8.01 (m, 1H), 7.64-7.58 (m, 1H), 7.57 (d, J=3.3 Hz, 1H), 7.50-7.45 (m, 1H), 7.40-7.33 (m, 1H), 6.67-6.65 (m, 1H), 4.90 (s, 2H), 2.72-2.66 (m, 1H), 0.75-0.69 (m, 2H), 0.54-0.49 (m, 2H).

Example 101

N-Cyclopropyl-2-[6-[4-fluoro-3-(trifluoromethyl)phenyl]pyrrolo[3,2-b]pyridin-1-yl]acetamide

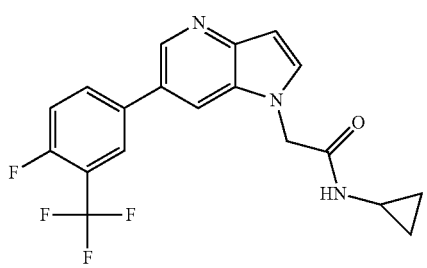 [SMILES: O=C(Cn1ccc2ncc(-c3ccc(F)c(C(F)(F)F)c3)cc21)NC1CC1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (4-fluoro-3-(trifluoromethyl)phenyl)boronic acid. MS (ESI): mass calcd. for $C_{19}H_{15}F_4N_3O$, 377.1. m/z found, 378.2 [M+H]$^+$. $^1$H NMR (500 MHz, CD$_3$OD) δ 8.58 (d, J=1.9 Hz, 1H), 8.07 (s, 1H), 8.00-7.94 (m, 2H), 7.59 (d, J=3.3 Hz, 1H), 7.45 (t, J=9.6 Hz, 1H), 6.67 (d, J=3.3 Hz, 1H), 4.92 (s, 2H), 2.73-2.66 (m, 1H), 0.77-0.69 (m, 2H), 0.55-0.49 (m, 2H).

Example 102

1-(Azetidin-1-yl)-2-[6-[5-(trifluoromethyl)-3-pyridyl]pyrrolo[3,2-b]pyridin-1-yl]ethanone

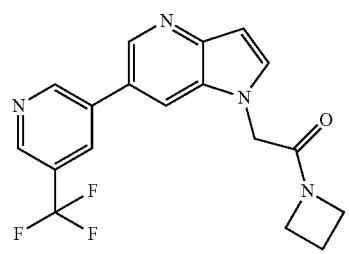 [SMILES: O=C(Cn1ccc2ncc(-c3cncc(C(F)(F)F)c3)cc21)N1CCC1]

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and (5-(trifluoromethyl)pyridin-3-yl)boronic acid. MS (ESI): mass calcd. for $C_{18}H_{15}F_3N_4O$, 360.1. m/z found, 361.2 [M+H]$^+$. $^1$H NMR (500 MHz, CD$_3$OD) δ 9.16 (d, J=2.1 Hz, 1H), 8.87 (s, 1H), 8.67 (d, J=1.9 Hz, 1H), 8.47 (s, 1H), 8.24 (s, 1H), 7.62 (d, J=3.3 Hz, 1H), 6.69 (d, J=3.3 Hz, 1H), 5.03 (s, 2H), 4.30 (t, J=7.8 Hz, 2H), 4.06 (t, J=7.8 Hz, 2H), 3.33-3.29 (m, 2H).

Example 103

1-(Azetidin-1-yl)-2-[6-(3,4-difluorophenyl)pyrrolo[3,2-b]pyridin-1-yl]ethanone

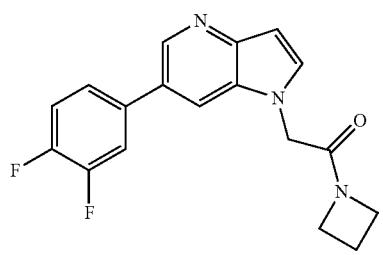 [SMILES: O=C(Cn1ccc2ncc(-c3ccc(F)c(F)c3)cc21)N1CCC1]

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and (3,4-difluorophenyl)boronic acid. MS (ESI): mass calcd. for $C_{18}H_{15}F_2N_3O$, 327.1. m/z found, 328.2 [M+H]$^+$. $^1$H NMR (500 MHz, CD$_3$OD) δ 8.55 (d, J=1.9 Hz, 1H), 8.05-8.03 (m, 1H), 7.66-7.59 (m, 1H), 7.56 (d, J=3.3 Hz, 1H), 7.51-7.46 (m, 1H), 7.39-7.32 (m, 1H), 6.66 (dd, J=3.3, 0.9 Hz, 1H), 4.98 (s, 2H), 4.26 (t, J=7.7 Hz, 2H), 4.05 (t, J=7.8 Hz, 2H), 2.40-2.31 (m, 2H).

Example 104

1-(Azetidin-1-yl)-2-[6-[4-fluoro-3-(trifluoromethyl)phenyl]pyrrolo[3,2-b]pyridin-1-yl]ethanone

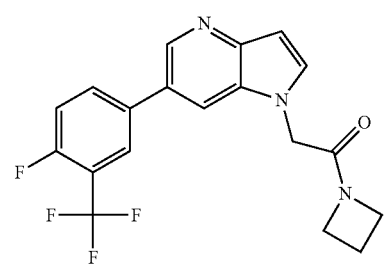 [SMILES: O=C(Cn1ccc2ncc(-c3ccc(F)c(C(F)(F)F)c3)cc21)N1CCC1]

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and 4-fluoro-3-(trifluoromethyl)phenyl)boronic acid. MS (ESI): mass calcd. for $C_{19}H_{15}F_4N_3O$, 377.1. m/z found, 378.2 [M+H]$^+$. $^1$H NMR (500 MHz, CD$_3$OD) δ 8.56 (d, J=1.9 Hz, 1H), 8.09-8.07 (m, 1H), 7.98-7.90 (m, 2H), 7.56 (d, J=3.3 Hz, 1H), 7.45-7.39 (m, 1H), 6.66 (dd, J=3.3, 0.9 Hz, 1H), 4.98 (s, 2H), 4.26 (t, J=7.7 Hz, 2H), 4.05 (t, J=7.8 Hz, 2H), 2.40-2.30 (m, 2H).

Example 105

2-[6-[4-Fluoro-3-(trifluoromethyl)phenyl]pyrrolo[3,2-b]pyridin-1-yl]-1-pyrrolidin-1-yl-ethanone

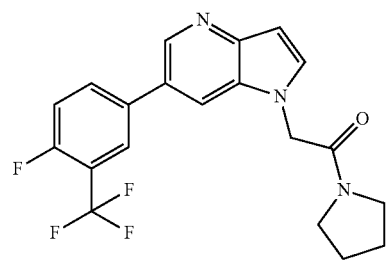 [SMILES: O=C(Cn1ccc2ncc(-c3ccc(F)c(C(F)(F)F)c3)cc21)N1CCCC1]

The title compound was prepared in a manner analogous to Example 1, Step A, using 2-(6-bromo-1H-pyrrolo[3,2-b]pyridin-1-yl)-1-(pyrrolidin-1-yl)ethanone (Intermediate 10) and (4-fluoro-3-(trifluoromethyl)phenyl)boronic acid. Purification by HPLC Method A gave the title compound (35 mg, 27%). MS (ESI): mass calcd. for $C_{20}H_{17}F_4N_3O$, 391.1. m/z found, 392.2 [M+H]$^+$. $^1$H NMR (400 MHz, CD$_3$OD) δ 8.57 (d, J=1.9 Hz, 1H), 8.13-8.11 (m, 1H), 8.01-7.94 (m, 2H), 7.58 (d, J=3.3 Hz, 1H), 7.48-7.40 (m, 1H), 6.68 (dd, J=3.3, 0.9 Hz, 1H), 5.19 (s, 2H), 3.65 (t, J=6.8 Hz, 2H), 3.46 (t, J=6.9 Hz, 2H), 2.12-2.02 (m, 2H), 1.97-1.87 (m, 2H).

Example 106

1-(3,3-Difluoroazetidin-1-yl)-2-[6-[4-fluoro-3-(trifluoromethyl)phenyl]pyrrolo[3,2-b]pyridin-1-yl]ethanone

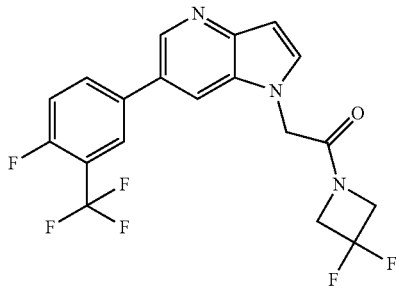 [SMILES: O=C(Cn1ccc2ncc(-c3ccc(F)c(C(F)(F)F)c3)cc21)N1CC(F)(F)C1]

The title compound was prepared in a manner analogous to Example 1, Step A, using 2-(6-bromo-1H-pyrrolo[3,2-b]pyridin-1-yl)-1-(3,3-difluoroazetidin-1-yl)ethanone (Intermediate 12) and (4-fluoro-3-(trifluoromethyl)phenyl)boronic acid. MS (ESI): mass calcd. for $C_{19}H_{13}F_6N_3O$, 413.1. m/z found, 414.2 [M+H]$^+$. $^1$H NMR (400 MHz, CD$_3$OD) δ 8.62-8.59 (m, 1H), 8.16-8.13 (m, 1H), 8.03-7.96 (m, 2H), 7.61-7.58 (m, 1H), 7.50-7.42 (m, 1H), 6.71-6.68 (m, 1H), 5.14 (s, 2H), 4.67 (t, J=12.0 Hz, 2H), 4.41 (t, J=12.2 Hz, 2H).

Example 107

2-[6-(3,4-Difluorophenyl)pyrrolo[3,2-b]pyridin-1-yl]-1-morpholino-ethanone

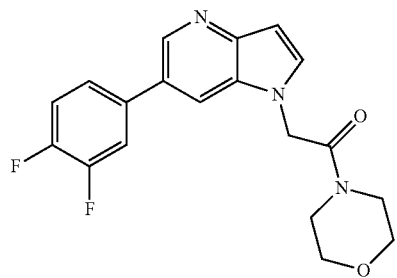 [SMILES: O=C(Cn1ccc2ncc(-c3ccc(F)c(F)c3)cc21)N1CCOCC1]

The title compound was prepared in a manner analogous to Example 1, Step A, using 2-(6-bromo-1H-pyrrolo[3,2-b]pyridin-1-yl)-1-morpholinoethanone (Intermediate 11) and (3,4-difluorophenyl)boronic acid. Purification by HPLC Method A gave the title compound (21 mg, 38%). MS (ESI): mass calcd. for $C_{19}H_{17}F_2N_3O_2$, 357.1. m/z found, 358.2 [M+H]$^+$. $^1$H NMR (400 MHz, CD$_3$OD) δ 8.56 (d, J=1.9 Hz, 1H), 8.07-8.05 (m, 1H), 7.63 (ddd, J=12.0, 7.6, 2.3 Hz, 1H), 7.55 (d, J=3.3 Hz, 1H), 7.52-7.47 (m, 1H), 7.41-7.32 (m, 1H), 6.67 (dd, J=3.3, 0.8 Hz, 1H), 5.28 (s, 2H), 3.80-3.74 (m, 2H), 3.72-3.63 (m, 4H), 3.61-3.55 (m, 2H).

Example 108

2-[6-[4-Fluoro-3-(trifluoromethyl)phenyl]pyrrolo[3,2-b]pyridin-1-yl]-1-morpholino-ethanone

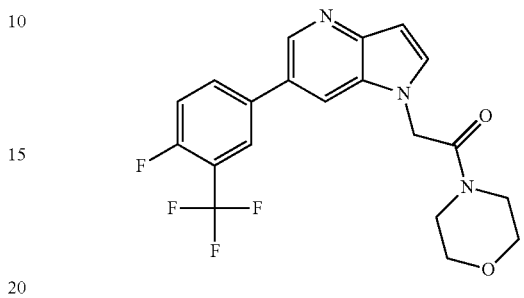

The title compound was prepared in a manner analogous to Example 1, Step A, using 2-(6-bromo-1H-pyrrolo[3,2-b]pyridin-1-yl)-1-morpholinoethanone (Intermediate 11) and (4-fluoro-3-(trifluoromethyl)phenyl)boronic acid. MS (ESI): mass calcd. for $C_{20}H_{17}F_4N_3O_2$, 407.1. m/z found, 408.2 [M+H]$^+$. $^1$H NMR (400 MHz, CD$_3$OD) δ 8.58 (d, J=2.0 Hz, 1H), 8.13-8.10 (m, 1H), 8.01-7.95 (m, 2H), 7.57 (d, J=3.3 Hz, 1H), 7.49-7.41 (m, 1H), 6.69 (dd, J=3.3, 0.8 Hz, 1H), 5.31 (s, 2H), 3.81-3.75 (m, 2H), 3.72-3.64 (m, 4H), 3.61-3.55 (m, 2H).

Example 109

1-(Azetidin-1-yl)-2-[6-[2-(trifluoromethyl)-4-pyridyl]pyrrolo[3,2-b]pyridin-1-yl]ethanone

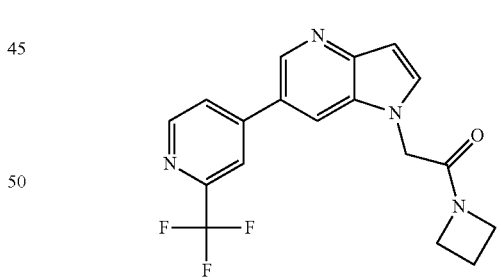

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and (2-(trifluoromethyl)pyridin-4-yl)boronic acid. MS (ESI): mass calcd. for $C_{18}H_{15}F_3N_4O$, 360.1. m/z found, 361.2 [M+H]$^+$. $^1$H NMR (400 MHz, CD$_3$OD) δ 8.79-8.73 (m, 2H), 8.35-8.32 (m, 1H), 8.21 (d, J=2.0 Hz, 1H), 8.03 (dd, J=5.2, 1.7 Hz, 1H), 7.66 (d, J=3.3 Hz, 1H), 6.71 (dd, J=3.3, 0.9 Hz, 1H), 5.06 (s, 2H), 4.32 (t, J=7.7 Hz, 2H), 4.07 (t, J=7.8 Hz, 2H), 2.44-2.34 (m, 2H).

Example 110

N-Cyclopropyl-2-[6-[2-(trifluoromethyl)-4-pyridyl]pyrrolo[3,2-b]pyridin-1-yl]acetamide

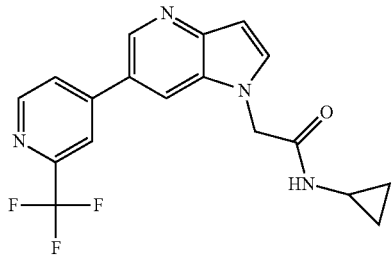 [SMILES: O=C(Cn1ccc2ncc(-c3ccnc(C(F)(F)F)c3)cc21)NC1CC1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (2-(trifluoromethyl)pyridin-4-yl)boronic acid. MS (ESI): mass calcd. for $C_{18}H_{15}F_3N_4O$, 360.1. m/z found, 361.2 [M+H]$^+$. $^1$H NMR (400 MHz, CD$_3$OD) δ 8.80-8.74 (m, 2H), 8.33-8.30 (m, 1H), 8.21-8.19 (m, 1H), 8.03 (dd, J=5.1, 1.7 Hz, 1H), 7.67 (d, J=3.3 Hz, 1H), 6.72 (dd, J=3.3, 0.9 Hz, 1H), 4.97 (s, 2H), 2.74-2.67 (m, 1H), 0.77-0.70 (m, 2H), 0.56-0.50 (m, 2H).

Example 111

N-Cyclopropyl-2-[6-[6-(trifluoromethyl)-2-pyridyl]pyrrolo[3,2-b]pyridin-1-yl]acetamide

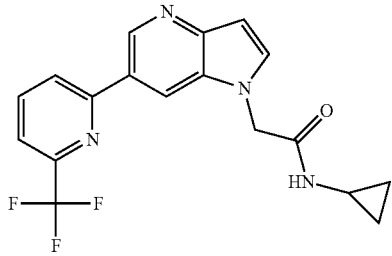 [SMILES: O=C(Cn1ccc2ncc(-c3cccc(C(F)(F)F)n3)cc21)NC1CC1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (5-(trifluoromethyl)pyridin-3-yl)boronic acid. MS (ESI): mass calcd. for $C_{18}H_{15}F_3N_4O$, 360.1. m/z found, 361.2 [M+H]$^+$. $^1$H NMR (500 MHz, CD$_3$OD) δ 9.06 (d, J=1.9 Hz, 1H), 8.53-8.50 (m, 1H), 8.21 (d, J=8.1 Hz, 1H), 8.07 (t, J=7.9 Hz, 1H), 7.74-7.69 (m, 1H), 7.64 (d, J=3.3 Hz, 1H), 6.68 (dd, J=3.3, 0.9 Hz, 1H), 4.93 (s, 2H), 2.74-2.67 (m, 1H), 0.76-0.70 (m, 2H), 0.58-0.53 (m, 2H).

Example 112

1-(Azetidin-1-yl)-2-[6-(6-methyl-3-pyridyl)pyrrolo[3,2-b]pyridin-1-yl]ethanone

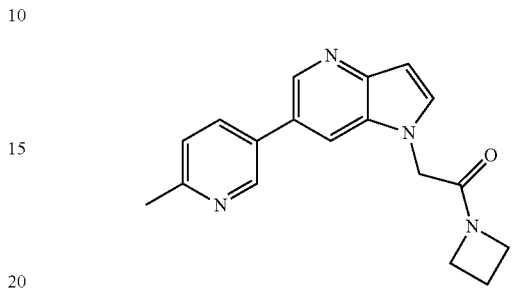

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and (6-methylpyridin-3-yl)boronic acid. MS (ESI): mass calcd. for $C_{18}H_{18}N_4O$, 306.1. m/z found, 307.2 [M+H]$^+$. $^1$H NMR (400 MHz, CD$_3$OD) δ 8.75 (d, J=2.4 Hz, 1H), 8.60 (d, J=1.8 Hz, 1H), 8.14-8.12 (m, 1H), 8.08 (dd, J=8.1, 2.5 Hz, 1H), 7.59 (d, J=3.5 Hz, 1H), 7.43 (d, J=8.1 Hz, 1H), 6.69 (dd, J=3.3, 0.8 Hz, 1H), 5.03 (s, 2H), 4.28 (t, J=7.7 Hz, 2H), 4.07 (t, J=7.8 Hz, 2H), 2.60 (s, 3H), 2.42-2.32 (m, 2H).

Example 113

5-[1-[2-(Azetidin-1-yl)-2-oxo-ethyl]pyrrolo[3,2-b]pyridin-6-yl]pyridine-2-carbonitrile

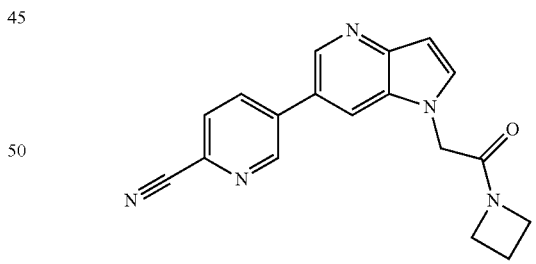

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and 5-(4,4,5,5-tetramethyl-1,3,2-dioxaborolan-2-yl)picolinonitrile. MS (ESI): mass calcd. for $C_{18}H_{15}N_5O$, 317.1. m/z found, 318.1 [M+H]$^+$. $^1$H NMR (400 MHz, CD$_3$OD) δ 9.10-9.07 (m, 1H), 8.69 (d, J=1.9 Hz, 1H), 8.36-8.30 (m, 1H), 8.26-8.21 (m, 1H), 7.99-7.93 (m, 1H), 7.67-7.63 (m, 1H), 6.72-6.69 (m, 1H), 5.04 (s, 2H), 4.31 (t, J=7.8 Hz, 2H), 4.07 (t, J=7.9 Hz, 2H), 2.44-2.32 (m, 2H).

Example 114

6-(3,4-Difluorophenyl)-1-(pyrimidin-5-ylmethyl)pyrrolo[3,2-b]pyridine

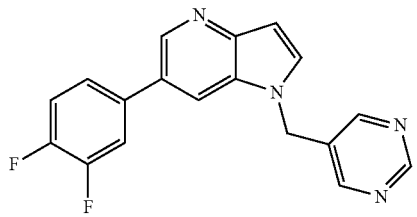 [SMILES: Fc1ccc(-c2cnc3ccn(Cc4cncnc4)c3c2)cc1F]

The title compound was prepared in a manner analogous to Example 115 substituting pyrimidin-5-ylmethyl methanesulfonate for (5-fluoropyrimidin-2-yl)methyl methanesulfonate (Intermediate 3). MS (ESI): mass calcd. for $C_{18}H_{12}F_2N_4$, 322.1. m/z found, 323.1 [M+H]$^+$. $^1$H NMR (500 MHz, CD$_3$OD) δ 9.07 (s, 1H), 8.66 (s, 2H), 8.61 (d, J=1.9 Hz, 1H), 8.20-8.18 (m, 1H), 7.77 (d, J=3.3 Hz, 1H), 7.66-7.60 (m, 1H), 7.50-7.46 (m, 1H), 7.39-7.33 (m, 1H), 6.74 (dd, J=3.3, 0.9 Hz, 1H), 5.62 (s, 2H).

Example 115

6-(3,4-Difluorophenyl)-1-[(5-fluoropyrimidin-2-Vl)methyl]pyrrolo[3,2-b]pyridine

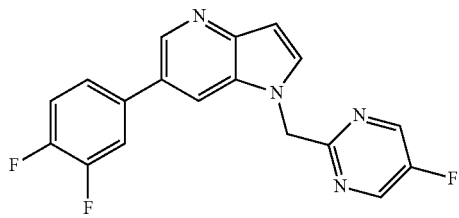 [SMILES: Fc1cnc(Cn2ccc3ncc(-c4ccc(F)c(F)c4)cc32)nc1]

Step A: 6-(3,4-Difluorophenyl)-1H-pyrrolo[3,2-b]pyridine

The title compound was prepared in a manner analogous to Example 106, Step B, substituting (3,4-difluorophenyl)boronic acid for (4-fluoro-3-(trifluoromethyl)phenyl)boronic acid. MS (ESI): mass calcd. for $C_{13}H_8F_2N_2$, 230.1. m/z found, 231.1 [M+H]$^+$.

Step B: 6-(3,4-Difluorophenyl)-1-[(5-fluoropyrimidin-2-yl)methyl]pyrrolo[3,2-b]pyridine The title compound was prepared in a manner analogous to Example 106 Step A substituting (5-fluoropyrimidin-2-yl)methyl methanesulfonate (Intermediate 3) for 2-bromo-1-(3,3-difluoroazetidin-1-yl)ethanone. MS (ESI): mass calcd. for $C_{18}H_{11}F_3N_4$, 340.1. m/z found, 341.1 [M+H]$^+$. $^1$H NMR (500 MHz, CD$_3$OD) δ 8.66 (d, J=0.8 Hz, 2H), 8.55 (d, J=1.9 Hz, 1H), 8.13-8.11 (m, 1H), 7.72 (d, J=3.3 Hz, 1H), 7.62-7.56 (m, 1H), 7.49-7.43 (m, 1H), 7.39-7.31 (m, 1H), 6.66 (dd, J=3.3, 0.9 Hz, 1H), 5.70 (s, 2H).

Example 116

Cyclobutyl-[6-(3,4-difluorophenyl)pyrrolo[3,2-b]pyridin-1-yl]methanone

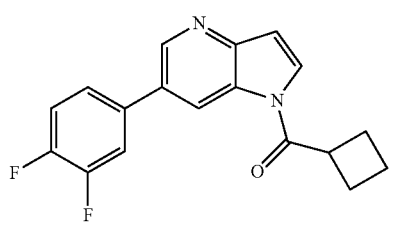 [SMILES: O=C(C1CCC1)n1ccc2ncc(-c3ccc(F)c(F)c3)cc21]

To a solution of 6-(3,4-difluorophenyl)-1H-pyrrolo[3,2-b]pyridine (50 mg, 0.22 mmol) in DMF (1 mL) was added cyclobutanecarboxylic acid (25 µL, 0.26 mmol), DIPEA (0.11 mL, 0.65 mmol) and HATU (91 mg, 0.24 mmol). The reaction mixture was stirred at room temperature for 1 hour and water was added. The aqueous phase was extracted 3 times with DCM and the combined organic layers were dried (MgSO$_4$), filtered and evaporated. Purification by HPLC Method A afforded the title compound (28 mg, 41%). MS (ESI): mass calcd. for $C_{18}H_{14}F_2N_2O$, 312.1. m/z found, 313.1 [M+H]$^+$. $^1$H NMR (500 MHz, CD$_3$OD) δ 8.93-8.90 (m, 1H), 8.68 (d, J=2.1 Hz, 1H), 7.97 (d, J=3.8 Hz, 1H), 7.65-7.59 (m, 1H), 7.51-7.46 (m, 1H), 7.43-7.36 (m, 1H), 6.79 (d, J=3.9 Hz, 1H), 4.10-4.01 (m, 1H), 2.57-2.39 (m, 4H), 2.24-2.12 (m, 1H), 2.04-1.94 (m, 1H).

Example 117

1-(3,3-Difluoroazetidin-1-yl)-2-[6-[6-(trifluoromethyl)-2-pyridyl]pyrrolo[3,2-b]pyridin-1-yl]ethanone

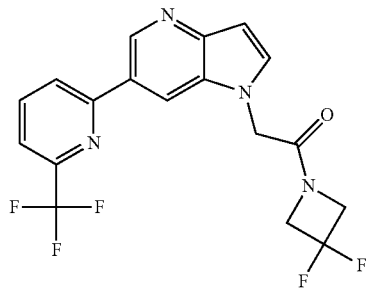 [SMILES: O=C(Cn1ccc2ncc(-c3cccc(C(F)(F)F)n3)cc21)N1CC(F)(F)C1]

The title compound was prepared in a manner analogous to Example 106 substituting 2-(4,4,5,5-tetramethyl-1,3,2-dioxaborolan-2-yl)-6-(trifluoromethyl)pyridine for (4-fluoro-3-(trifluoromethyl)phenyl)boronic acid. MS (ESI): mass calcd. for $C_{18}H_{13}F_5N_4O$, 396.1. m/z found, 397.2 [M+H]$^+$. $^1$H NMR (500 MHz, CD$_3$OD) δ 9.10 (d, J=1.9 Hz, 1H), 8.58-8.56 (m, 1H), 8.23 (d, J=8.0 Hz, 1H), 8.12-8.07 (m, 1H), 7.73 (dd, J=7.7, 0.8 Hz, 1H), 7.64 (d, J=3.3 Hz, 1H), 6.72 (dd, J=3.3, 0.9 Hz, 1H), 5.17 (s, 2H), 4.69 (t, J=11.9 Hz, 2H), 4.42 (t, J=12.1 Hz, 2H).

Example 118

1-(Azetidin-1-yl)-2-[6-(2,3,4-trifluorophenyl)pyrrolo[3,2-b]pyridin-1-yl]ethanone

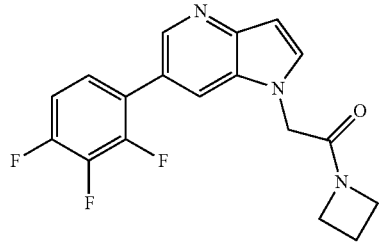 [SMILES: O=C(Cn1ccc2ncc(-c3ccc(F)c(F)c3F)cc21)N1CCC1]

The title compound was prepared in a manner analogous to Example 102. MS (ESI): mass calcd. for $C_{18}H_{14}F_3N_3O$, 345.1. m/z found, 346.2 [M+H]$^+$. $^1$H NMR (500 MHz, CD$_3$OD) δ 8.49-8.46 (m, 1H), 8.01 (s, 1H), 7.62 (dd, J=3.4, 1.0 Hz, 1H), 7.42-7.35 (m, 1H), 7.29-7.21 (m, 1H), 6.71-6.68 (m, 1H), 5.00 (s, 2H), 4.27 (t, J=7.7 Hz, 2H), 4.06 (t, J=7.8 Hz, 2H), 2.41-2.31 (m, 2H).

Example 119

2-Cyclopropyl-1-[6-(3,4-difluorophenyl)pyrrolo[3,2-b]pyridin-1-yl]ethanone

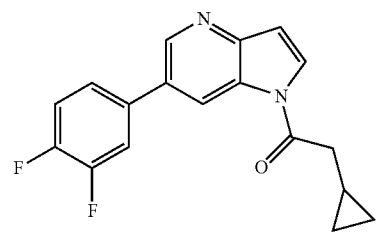 [SMILES: O=C(CC1CC1)n1ccc2ncc(-c3ccc(F)c(F)c3)cc21]

The title compound was prepared in a manner analogous to Example 116. MS (ESI): mass calcd. for $C_{18}H_{14}F_2N_2O$, 312.1. m/z found, 313.2 [M+H]$^+$. $^1$H NMR (400 MHz, CD$_3$OD) δ 8.88 (d, J=2.5 Hz, 1H), 8.67 (d, J=2.0 Hz, 1H), 8.09 (d, J=3.9 Hz, 1H), 7.64-7.55 (m, 1H), 7.50-7.43 (m, 1H), 7.42-7.30 (m, 1H), 6.79 (dd, J=3.8, 0.7 Hz, 1H), 2.97 (d, J=6.8 Hz, 2H), 1.28-1.17 (m, 1H), 0.68-0.61 (m, 2H), 0.35-0.29 (m, 2H).

Example 120

1-Pyrrolidin-1-yl-2-[6-(2,3,4-trifluorophenyl)pyrrolo[3,2-b]pyridin-1-yl]ethanone

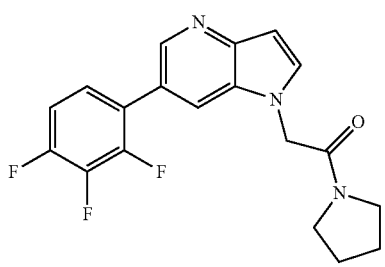 [SMILES: O=C(Cn1ccc2ncc(-c3ccc(F)c(F)c3F)cc21)N1CCCC1]

The title compound was prepared in a manner analogous to Example 1, Step A, using 2-(6-bromo-1H-pyrrolo[3,2-b]pyridin-1-yl)-1-(pyrrolidin-1-yl)ethanone (Intermediate 10) and (2,3,4-trifluorophenyl)boronic acid. MS (ESI): mass calcd. for $C_{19}H_{16}F_3N_3O$, 359.1. m/z found, 360.2 [M+H]$^+$. $^1$H NMR (400 MHz, CD$_3$OD) δ 8.47-8.43 (m, 1H), 8.00 (s, 1H), 7.60 (d, J=3.3 Hz, 1H), 7.40-7.31 (m, 1H), 7.26-7.18 (m, 1H), 6.68 (dd, J=3.3, 1.0 Hz, 1H), 5.15 (s, 2H), 3.62 (t, J=6.9 Hz, 2H), 3.44 (t, J=7.0 Hz, 2H), 2.09-2.00 (m, 2H), 1.95-1.85 (m, 2H).

Example 121

1-(3,3-difluoroazetidin-1-yl)-2-[6-(3,5-difluorophenyl)pyrrolo[3,2-b]pyridin-1-yl]ethanone

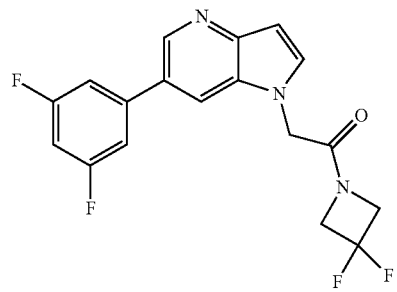 [SMILES: O=C(Cn1ccc2ncc(-c3cc(F)cc(F)c3)cc21)N1CC(F)(F)C1]

The title compound was prepared in a manner analogous to Example 1, Step A, using 2-(6-bromo-1H-pyrrolo[3,2-b]pyridin-1-yl)-1-(3,3-difluoroazetidin-1-yl)ethanone (Intermediate 12) and (3,5-difluorophenyl)boronic acid. MS (ESI): mass calcd. for $C_{18}H_{13}F_4N_3O$, 363.1. m/z found, 364.2 [M+H]$^+$. $^1$H NMR (400 MHz, CD$_3$OD) δ 8.60 (d, J=1.9 Hz, 1H), 8.15-8.12 (m, 1H), 7.58 (d, J=3.4 Hz, 1H), 7.37-7.29 (m, 2H), 6.98-6.91 (m, 1H), 6.68 (dd, J=3.4, 0.9 Hz, 1H), 5.10 (s, 2H), 4.66 (t, J=12.0 Hz, 2H), 4.41 (t, J=12.2 Hz, 2H).

Example 122

2-[6-(3,5-Difluorophenyl)pyrrolo[3,2-b]pyridin-1-yl]-1-pyrrolidin-1-yl-ethanone

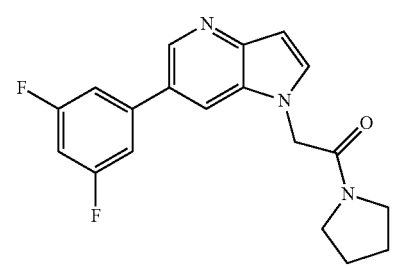 [SMILES: O=C(Cn1ccc2ncc(-c3cc(F)cc(F)c3)cc21)N1CCCC1]

The title compound was prepared in a manner analogous to Example 1, Step A, using 2-(6-bromo-1H-pyrrolo[3,2-b]pyridin-1-yl)-1-(pyrrolidin-1-yl)ethanone (Intermediate 10) and (3,5-difluorophenyl)boronic acid. MS (ESI): mass calcd.

for C₁₉H₁₇F₂N₃O, 341.1. m/z found, 342.2 [M+H]⁺. ¹H NMR (500 MHz, CD₃OD) δ 8.58 (d, J=2.1 Hz, 1H), 8.12-8.10 (m, 1H), 7.58 (d, J=3.4 Hz, 1H), 7.37-7.29 (m, 2H), 6.96-6.91 (m, 1H), 6.67 (dd, J=3.3, 0.9 Hz, 1H), 5.16 (s, 2H), 3.64 (t, J=6.8 Hz, 2H), 3.46 (t, J=7.0 Hz, 2H), 2.10-2.02 (m, 2H), 1.95-1.87 (m, 2H).

Example 123

1-Pyrrolidin-1-yl-2-[6-(3,4,5-trifluorophenyl)pyrrolo[3,2-b]pyridin-1-yl]ethanone

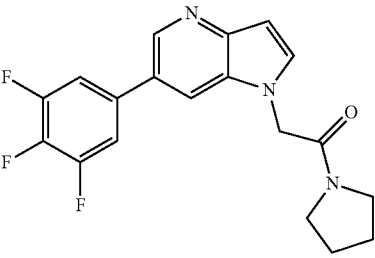 [SMILES: O=C(Cn1ccc2ncc(-c3cc(F)c(F)c(F)c3)cc21)N1CCCC1]

The title compound was prepared in a manner analogous to Example 1, Step A, using 2-(6-bromo-1H-pyrrolo[3,2-b]pyridin-1-yl)-1-(pyrrolidin-1-yl)ethanone (Intermediate 10) and (3,4,5-trifluorophenyl)boronic acid. MS (ESI): mass calcd. for C₁₉H₁₆F₃N₃O, 359.1. m/z found, 360.2 [M+H]⁺. ¹H NMR (400 MHz, CD₃OD) δ 8.55 (d, J=1.9 Hz, 1H), 8.09-8.06 (m, 1H), 7.57 (d, J=3.3 Hz, 1H), 7.53-7.44 (m, 2H), 6.65 (dd, J=3.4, 0.9 Hz, 1H), 5.14 (s, 2H), 3.64 (t, J=6.8 Hz, 2H), 3.45 (t, J=6.9 Hz, 2H), 2.11-2.02 (m, 2H), 1.96-1.87 (m, 2H).

Example 124

1-(3,3-Difluoroazetidin-1-yl)-2-[6-(3,4,5-trifluorophenyl)pyrrolo[3,2-b]pyridin-1-yl]ethanone

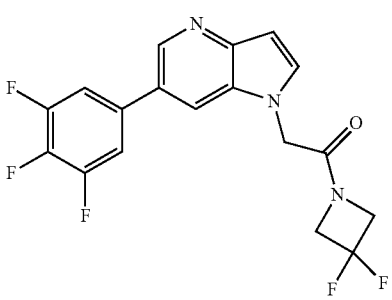 [SMILES: O=C(Cn1ccc2ncc(-c3cc(F)c(F)c(F)c3)cc21)N1CC(F)(F)C1]

The title compound was prepared in a manner analogous to Example 1, Step A, using 2-(6-bromo-1H-pyrrolo[3,2-b]pyridin-1-yl)-1-(3,3-difluoroazetidin-1-yl)ethanone (Intermediate 12) and (3,4,5-trifluorophenyl)boronic acid. MS (ESI): mass calcd. for C₁₈H₁₂F₅N₃O, 381.1. m/z found, 382.1 [M+H]⁺. ¹H NMR (400 MHz, CD₃OD) δ 8.60 (d, J=2.0 Hz, 1H), 8.15-8.13 (m, 1H), 7.60 (d, J=3.3 Hz, 1H), 7.58-7.49 (m, 2H), 6.69 (dd, J=3.3, 0.9 Hz, 1H), 5.13 (s, 2H), 4.68 (t, J=11.9 Hz, 2H), 4.41 (t, J=12.2 Hz, 2H).

Example 125

2-[6-(3,5-Difluorophenyl)pyrrolo[3,2-b]pyridin-1-yl]-1-morpholino-ethanone

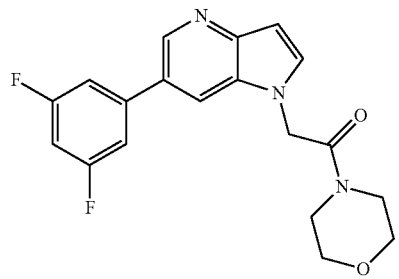 [SMILES: O=C(Cn1ccc2ncc(-c3cc(F)cc(F)c3)cc21)N1CCOCC1]

The title compound was prepared in a manner analogous to Example 1, Step A, using 2-(6-bromo-1H-pyrrolo[3,2-b]pyridin-1-yl)-1-morpholinoethanone (Intermediate 11) and (3,5-difluorophenyl)boronic acid. MS (ESI): mass calcd. for C₁₉H₁₇F₂N₃O₂, 357.1. m/z found, 358.2 [M+H]⁺. ¹H NMR (400 MHz, CD₃OD) δ 8.54 (d, J=1.9 Hz, 1H), 8.06-8.02 (m, 1H), 7.53 (d, J=3.3 Hz, 1H), 7.31-7.23 (m, 2H), 6.96-6.88 (m, 1H), 6.65 (d, J=3.2 Hz, 1H), 5.20 (s, 2H), 3.77-3.73 (m, 2H), 3.69-3.64 (m, 2H), 3.63-3.53 (m, 4H).

Example 126

1-Morpholino-2-[6-(2,3,4-trifluorophenyl)pyrrolo[3,2-b]pyridin-1-yl]ethanone

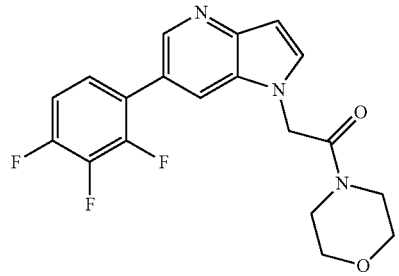 [SMILES: O=C(Cn1ccc2ncc(-c3ccc(F)c(F)c3F)cc21)N1CCOCC1]

The title compound was prepared in a manner analogous to Example 1, Step A, using 2-(6-bromo-1H-pyrrolo[3,2-b]pyridin-1-yl)-1-morpholinoethanone (Intermediate 11) and (2,3,4-trifluorophenyl)boronic acid. MS (ESI): mass calcd. for C₁₉H₁₆F₃N₃O₂, 375.1. m/z found, 376.2 [M+H]⁺. ¹H NMR (400 MHz, CD₃OD) δ 8.47 (t, J=1.8 Hz, 1H), 8.04-7.99 (m, 1H), 7.60 (d, J=3.4 Hz, 1H), 7.43-7.35 (m, 1H), 7.30-7.20 (m, 1H), 6.70 (dd, J=3.3, 0.9 Hz, 1H), 5.30 (s, 2H), 3.79-3.73 (m, 2H), 3.72-3.62 (m, 4H), 3.61-3.55 (m, 2H).

Example 127

1-Morpholino-2-[6-(3,4,5-trifluorophenyl)pyrrolo[3,2-b]pyridin-1-yl]ethanone

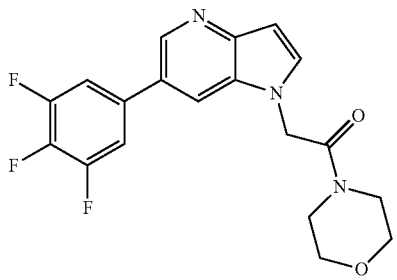 [SMILES: O=C(Cn1ccc2ncc(-c3cc(F)c(F)c(F)c3)cc21)N1CCOCC1]

The title compound was prepared in a manner analogous to Example 1, Step A, using 2-(6-bromo-1H-pyrrolo[3,2-b]pyridin-1-yl)-1-morpholinoethanone (Intermediate 11) and (3,4,5-trifluorophenyl)boronic acid. MS (ESI): mass calcd. for $C_{19}H_{16}F_3N_3O_2$, 375.1. m/z found, 376.2 [M+H]$^+$. $^1$H NMR (400 MHz, CD$_3$OD) δ 8.54 (d, J=2.0 Hz, 1H), 8.07-8.04 (m, 1H), 7.55 (d, J=3.3 Hz, 1H), 7.52-7.41 (m, 2H), 6.66 (d, J=3.3 Hz, 1H), 5.24 (s, 2H), 3.80-3.74 (m, 2H), 3.71-3.66 (m, 2H), 3.66-3.60 (m, 2H), 3.60-3.53 (m, 2H).

Example 128

2-[6-(3,4-Difluorophenyl)pyrrolo[3,2-b]pyridin-1-yl]-1-(3-fluoroazetidin-1-yl)ethanone

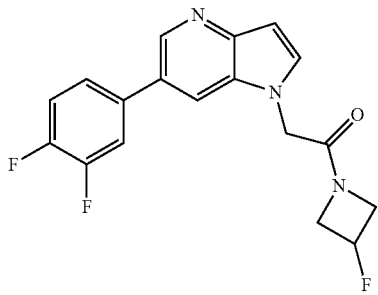 [SMILES: O=C(Cn1ccc2ncc(-c3ccc(F)c(F)c3)cc21)N1CC(F)C1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (3,4-difluorophenyl)boronic acid. MS (ESI): mass calcd. for $C_{18}H_{14}F_3N_3O$, 345.1. m/z found, 346.2 [M+H]$^+$. $^1$H NMR (500 MHz, CD$_3$OD) δ 8.57 (d, J=1.9 Hz, 1H), 8.08-8.06 (m, 1H), 7.67-7.60 (m, 1H), 7.57 (d, J=3.3 Hz, 1H), 7.52-7.48 (m, 1H), 7.40-7.33 (m, 1H), 6.67 (dd, J=3.4, 0.9 Hz, 1H), 5.47-5.30 (m, 1H), 5.05 (d, J=3.4 Hz, 2H), 4.58-4.48 (m, 1H), 4.40-4.27 (m, 2H), 4.16-4.03 (m, 1H).

Example 129

2-[6-(3,5-Difluorophenyl)pyrrolo[3,2-b]pyridin-1-yl]-1-(3-fluoroazetidin-1-yl)ethanone

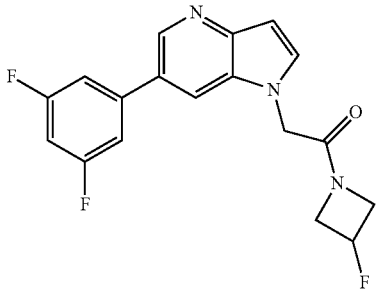 [SMILES: O=C(Cn1ccc2ncc(-c3cc(F)cc(F)c3)cc21)N1CC(F)C1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (3,5-difluorophenyl)boronic acid. MS (ESI): mass calcd. for $C_{18}H_{14}F_3N_3O$, 345.1. m/z found, 346.2 [M+H]$^+$. $^1$H NMR (500 MHz, CD$_3$OD) δ 8.61 (d, J=2.0 Hz, 1H), 8.13 (dd, J=1.9, 0.9 Hz, 1H), 7.60 (d, J=3.3 Hz, 1H), 7.39-7.32 (m, 2H), 7.00-6.92 (m, 1H), 6.69 (dd, J=3.3, 0.9 Hz, 1H), 5.48-5.31 (m, 1H), 5.07 (d, J=3.2 Hz, 2H), 4.60-4.50 (m, 1H), 4.40-4.30 (m, 2H), 4.15-4.05 (m, 1H).

Example 130

6-(4-Methyl-2-thienyl)-1-(pyridazin-3-ylmethyl)pyrrolo[3,2-b]pyridine

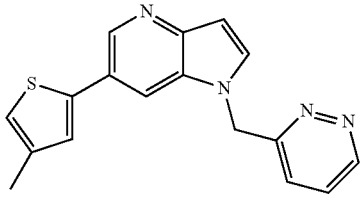 [SMILES: Cc1csc(-c2cnc3ccn(Cc4cccnn4)c3c2)c1]

Step A: 6-(4-Methylthiophen-2-yl)-1H-pyrrolo[3,2-b]pyridine

The title compound was prepared in a manner analogous to Example 115, Step A substituting 4,4,5,5-tetramethyl-2-(4-methylthiophen-2-yl)-1,3,2-dioxaborolane for (3,4-difluorophenyl)boronic acid. MS (ESI): mass calcd. for $C_{12}H_{10}N_2S$, 214.1. m/z found, 215.1 [M+H]$^+$.

Step B: 6-(4-Methyl-2-thienyl)-1-(pyridazin-3-ylmethyl)pyrrolo[3,2-b]pyridine The title compound was prepared in a manner analogous to Example 115, Step B, using 6-(4-methylthiophen-2-yl)-1H-pyrrolo[3,2-b]pyridine and 3-(chloromethyl)pyridazine hydrochloride. MS (ESI): mass calcd. for $C_{17}H_{14}N_4S$, 306.1. m/z found, 307.1 [M+H]⁺. ¹H NMR (500 MHz, CD₃OD) δ 9.10 (dd, J=5.0, 1.6 Hz, 1H), 8.58 (d, J=1.9 Hz, 1H), 8.08 (dd, J=1.9, 0.9 Hz, 1H), 7.74 (d, J=3.3 Hz, 1H), 7.65 (dd, J=8.6, 4.9 Hz, 1H), 7.45 (dd, J=8.5, 1.6 Hz, 1H), 7.25 (d, J=1.4 Hz, 1H), 6.96 (s, 1H), 6.69 (dd, J=3.4, 1.0 Hz, 1H), 5.80 (s, 2H), 2.27 (s, 3H).

Example 131

6-(3,4-Difluorophenyl)-1-(pyridazin-3-ylmethyl)pyrrolo[3,2-b]pyridine

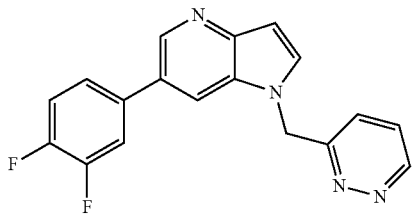 [SMILES: Fc1ccc(-c2cnc3ccn(Cc4cccnn4)c3c2)cc1F]

The title compound was prepared in a manner analogous to Example 115 substituting 3-(chloromethyl)pyridazine hydrochloride for (5-fluoropyrimidin-2-yl)methyl methanesulfonate (Intermediate 2). MS (ESI): mass calcd. for $C_{18}H_{12}F_2N_4$, 322.1. m/z found, 323.1 [M+H]⁺. ¹H NMR (500 MHz, CD₃OD) δ 9.10 (dd, J=4.9, 1.6 Hz, 1H), 8.58 (d, J=2.0 Hz, 1H), 8.17 (dd, J=2.0, 0.9 Hz, 1H), 7.79 (d, J=3.3 Hz, 1H), 7.65 (dd, J=8.5, 5.0 Hz, 1H), 7.63-7.57 (m, 1H), 7.51-7.43 (m, 2H), 7.38-7.31 (m, 1H), 6.72 (dd, J=3.3, 0.9 Hz, 1H), 5.83 (s, 2H).

Example 132

2-[6-(4-Methyl-2-thienyl)pyrrolo[3,2-b]pyridin-1-yl]-1-morpholino-ethanone

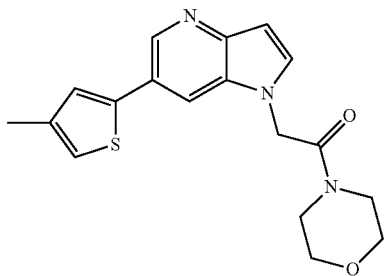 [SMILES: Cc1csc(-c2cnc3ccn(CC(=O)N4CCOCC4)c3c2)c1]

The title compound was prepared in a manner analogous to Example 85 substituting 4,4,5,5-tetramethyl-2-(4-methylthiophen-2-yl)-1,3,2-dioxaborolane for phenylboronic acid. MS (ESI): mass calcd. for $C_{18}H_{19}N_3O_2S$, 341.1. m/z found, 342.2 [M+H]⁺. ¹H NMR (500 MHz, CD₃OD) δ 8.56 (d, J=1.9 Hz, 1H), 8.00-7.97 (m, 1H), 7.49 (d, J=3.3 Hz, 1H), 7.26 (d, J=1.4 Hz, 1H), 6.98-6.96 (m, 1H), 6.62 (dd, J=3.3, 0.9 Hz, 1H), 5.22 (s, 2H), 3.78-3.73 (m, 2H), 3.70-3.66 (m, 2H), 3.65-3.61 (m, 2H), 3.59-3.55 (m, 2H), 2.29 (d, J=1.1 Hz, 3H).

Example 133

1-(Azetidin-1-yl)-2-[6-(2,4-difluorophenyl)pyrrolo[3,2-b]pyridin-1-yl]ethanone

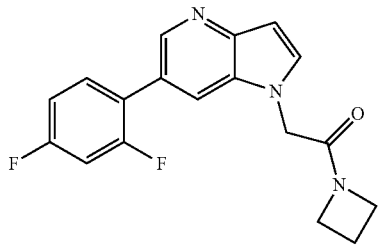 [SMILES: O=C(Cn1ccc2ncc(-c3ccc(F)cc3F)cc21)N1CCC1]

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and (2,4-difluorophenyl)boronic acid. MS (ESI): mass calcd. for $C_{18}H_{15}F_2N_3O$, 327.1. m/z found, 328.2 [M+H]⁺. ¹H NMR (500 MHz, CD₃OD) δ 8.46 (s, 1H), 7.98 (s, 1H), 7.63-7.55 (m, 2H), 7.14-7.07 (m, 2H), 6.68 (d, J=3.2 Hz, 1H), 4.98 (s, 2H), 4.24 (t, J=7.7 Hz, 2H), 4.05 (t, J=7.8 Hz, 2H), 2.39-2.30 (m, 2H).

Example 134

1-(Azetidin-1-yl)-2-[6-(2,3-difluorophenyl)pyrrolo[3,2-b]pyridin-1-yl]ethanone

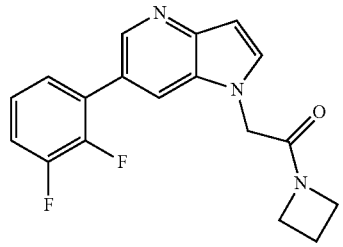 [SMILES: O=C(Cn1ccc2ncc(-c3cccc(F)c3F)cc21)N1CCC1]

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and (2,3-difluorophenyl)boronic acid. MS (ESI): mass calcd. for $C_{18}H_{15}F_2N_3O$, 327.1. m/z found, 328.2 [M+H]⁺. ¹H NMR (500 MHz, CD₃OD) δ 8.52-8.49 (m, 1H), 8.04 (s, 1H), 7.61 (d, J=3.3 Hz, 1H), 7.40-7.35 (m, 1H), 7.34-7.25 (m, 2H), 6.70 (dd, J=3.4, 1.0 Hz, 1H), 5.00 (s, 2H), 4.26 (t, J=7.7 Hz, 2H), 4.06 (t, J=7.8 Hz, 2H), 2.40-2.31 (m, 2H).

Example 135

1-(Azetidin-1-yl)-2-[6-(2,5-difluorophenyl)pyrrolo[3,2-b]pyridin-1-yl]ethanone

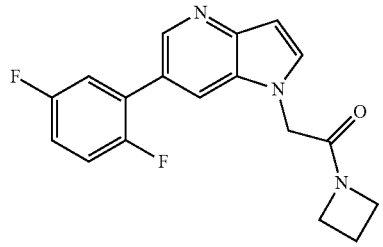 [SMILES: O=C(Cn1ccc2ncc(-c3cc(F)ccc3F)cc21)N1CCC1]

The title compound was prepared in a manner analogous to Example 1, Step A, using 1-(azetidin-1-yl)-2-(6-bromo-1H-pyrrolo[3,2-b]pyridin-1-yl)ethanone (Intermediate 14) and (2,5-difluorophenyl)boronic acid. MS (ESI): mass calcd. for $C_{18}H_{15}F_2N_3O$, 327.1. m/z found, 328.2 [M+H]$^+$. $^1$H NMR (500 MHz, CD$_3$OD) δ 8.53-8.51 (m, 1H), 8.03 (s, 1H), 7.61 (d, J=3.3 Hz, 1H), 7.41-7.34 (m, 1H), 7.30-7.23 (m, 1H), 7.18-7.12 (m, 1H), 6.69 (d, J=3.3 Hz, 1H), 5.00 (s, 2H), 4.26 (t, J=7.7 Hz, 2H), 4.06 (t, J=7.8 Hz, 2H), 2.40-2.32 (m, 2H).

Example 136

1-Cyclopropyl-2-[6-(3,4-difluorophenyl)-3-fluoro-pyrrolo[3,2-b]pyridin-1-yl]ethanone

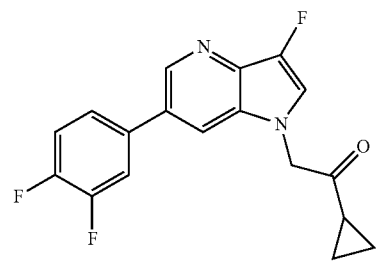 [SMILES: O=C(Cn1cc(F)c2ncc(-c3ccc(F)c(F)c3)cc21)C1CC1]

Step A: 2-(6-Bromo-3-fluoro-1H-pyrrolo[3,2-b]pyridin-1-yl)-1-cyclopropylethanone The title compound was prepared in a manner analogous to Intermediate 15, using 2-bromo-1-cyclopropylethanone and 6-bromo-3-fluoro-1H-pyrrolo[3,2-b]pyridine (Intermediate 6). MS (ESI): mass calcd. for $C_{12}H_{10}BrFN_2O$, 296.0. m/z found, 297.0 [M+H]$^+$.

Step B: 1-Cyclopropyl-2-[6-(3,4-difluorophenyl)-3-fluoro-pyrrolo[3,2-b]pyridin-1-yl]ethanone The title compound was prepared in a manner analogous to Example 1, Step A, using 2-(6-bromo-3-fluoro-1H-pyrrolo[3,2-b]pyridin-1-yl)-1-cyclopropylethanone and (3,4-difluorophenyl)boronic acid. MS (ESI): mass calcd. for $C_{18}H_{13}F_3N_2O$, 330.1. m/z found, 331.0 [M+H]$^+$. $^1$H NMR (400 MHz, DMSO-d$_6$) δ 8.72 (d, J=1.9 Hz, 1H), 8.28-8.24 (m, 1H), 7.88 (ddd, J=12.3, 7.7, 2.2 Hz, 1H), 7.69 (d, J=2.2 Hz, 1H), 7.67-7.52 (m, 2H), 5.42 (s, 2H), 2.16-2.07 (m, 1H), 1.05-0.91 (m, 4H).

Example 137

6-(4-Methyl-2-thienyl)-1-[[5-(trifluoromethyl)-2-furyl]methyl]pyrrolo[3,2-b]pyridine

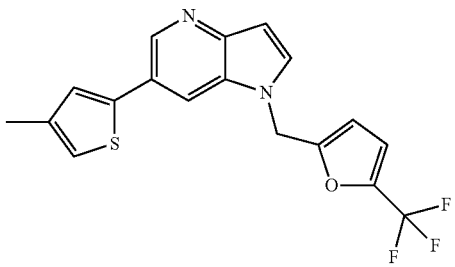 [SMILES: Cc1csc(-c2cnc3ccn(Cc4ccc(C(F)(F)F)o4)c3c2)c1]

The title compound was prepared in a manner analogous to Example 130. MS (ESI): mass calcd. for $C_{18}H_{13}F_3N_2OS$, 362.1. m/z found, 363.0 [M+H]$^+$. $^1$H NMR (400 MHz, CD$_3$OD) δ 8.60 (s, 1H), 8.15 (s, 1H), 7.65 (d, J=3.3 Hz, 1H), 7.29 (s, 1H), 7.00 (s, 1H), 6.93-6.90 (m, 1H), 6.65 (d, J=3.4 Hz, 1H), 6.52 (d, J=3.4 Hz, 1H), 5.55 (s, 2H), 2.30 (s, 3H).

Example 138

6-(3,4-Difluorophenyl)-1-[[5-(trifluoromethyl)-2-furyl]methyl]pyrrolo[3,2-b]pyridine

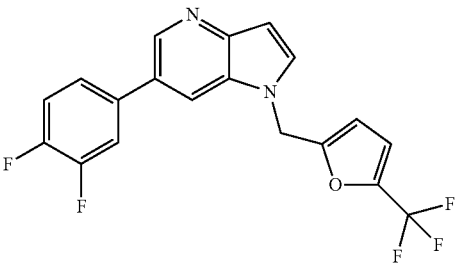 [SMILES: Fc1ccc(-c2cnc3ccn(Cc4ccc(C(F)(F)F)o4)c3c2)cc1F]

The title compound was prepared in a manner analogous to Example 115 substituting 2-(bromomethyl)-5-(trifluoromethyl)furan for (5-fluoropyrimidin-2-yl)methyl methanesulfonate (Intermediate 2). MS (ESI): mass calcd. for $C_{19}H_{11}F_5N_2O$, 378.1. m/z found, 379.0 [M+H]$^+$. $^1$H NMR (400 MHz, CD$_3$OD) δ 8.58 (d, J=1.9 Hz, 1H), 8.23-8.20 (m, 1H), 7.69 (d, J=3.4 Hz, 1H), 7.66-7.59 (m, 1H), 7.52-7.46 (m, 1H), 7.41-7.33 (m, 1H), 6.92-6.89 (m, 1H), 6.68 (d, J=3.3 Hz, 1H), 6.53 (d, J=3.4 Hz, 1H), 5.57 (s, 2H).

Example 139

N,N-Dimethyl-2-[6-(4-methyl-2-thienyl)pyrrolo[3,2-b]pyridin-1-yl]acetamide

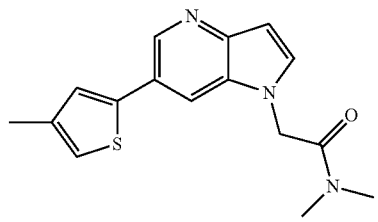

The title compound was prepared in a manner analogous to Example 1, Step A, using 2-(6-bromo-1H-pyrrolo[3,2-b]pyridin-1-yl)-N,N-dimethylacetamide (Example 375, Intermediate from Step A) and 4,4,5,5-tetramethyl-2-(4-methylthiophen-2-yl)-1,3,2-dioxaborolane. MS (ESI): mass calcd. for $C_{16}H_{17}N_3OS$, 299.1. m/z found, 300.1 [M+H]$^+$. $^1$H NMR (500 MHz, CD$_3$OD) δ 8.55 (d, J=1.9 Hz, 1H), 7.97-7.94 (m, 1H), 7.47 (d, J=3.3 Hz, 1H), 7.25 (d, J=1.4 Hz, 1H), 6.96 (s, 1H), 6.61 (dd, J=3.3, 0.9 Hz, 1H), 5.19 (s, 2H), 3.17 (s, 3H), 2.97 (s, 3H), 2.28 (s, 3H).

Example 140

1-[6-(3,4-Difluorophenyl)pyrrolo[3,2-b]pyridin-1-yl]-3,3-dimethyl-butan-2-one

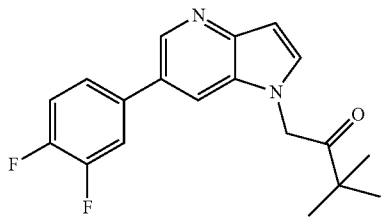 [SMILES: CC(C)(C)C(=O)Cn1ccc2ncc(-c3ccc(F)c(F)c3)cc21]

Step A: 1-(6-Bromo-1H-pyrrolo[3,2-b]pyridin-1-yl)-3,3-dimethylbutan-2-one

The title compound was prepared in a manner analogous to Intermediate 10, using 1-bromo-3,3-dimethylbutan-2-one and 6-bromo-1H-pyrrolo[3,2-b]pyridine. MS (ESI): mass calcd. for $C_{13}H_{15}BrN_2O$, 294.0. m/z found, 295.0 [M+H]$^+$.

Step B: 1-[6-(3,4-Difluorophenyl)pyrrolo[3,2-b]pyridin-1-yl]-3,3-dimethyl-butan-2-one The title compound was prepared in a manner analogous to Example 1, Step A, using 1-(6-bromo-1H-pyrrolo[3,2-b]pyridin-1-yl)-3,3-dimethylbutan-2-one and (3,4-difluorophenyl)boronic acid. MS (ESI): mass calcd. for $C_{19}H_{18}F_2N_2O$, 328.1. m/z found, 329.1 [M+H]$^+$. $^1$H NMR (500 MHz, CD$_3$OD) δ 8.54 (s, 1H), 7.89 (s, 1H), 7.63-7.56 (m, 1H), 7.50-7.43 (m, 2H), 7.39-7.32 (m, 1H), 6.66 (d, J=3.3 Hz, 1H), 5.44 (s, 2H), 1.32 (s, 9H).

Example 141

1-[6-(4-Fluoro-3-methyl-phenyl)pyrrolo[3,2-b]pyridin-1-yl]-3,3-dimethyl-butan-2-one

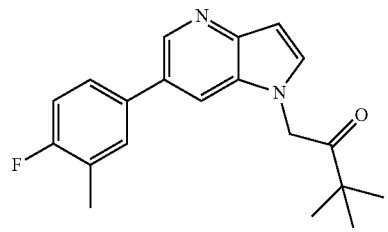 [SMILES: Cc1cc(-c2cnc3ccn(CC(=O)C(C)(C)C)c3c2)ccc1F]

The title compound was prepared in a manner analogous to Example 140. MS (ESI): mass calcd. for $C_{20}H_{21}FN_2O$, 324.2. m/z found, 325.1 [M+H]$^+$. $^1$H NMR (500 MHz, CD$_3$OD) δ 8.51 (d, J=1.9 Hz, 1H), 7.82 (s, 1H), 7.52-7.49 (m, 1H), 7.47-7.42 (m, 2H), 7.14-7.09 (m, 1H), 6.64 (dd, J=3.3, 0.9 Hz, 1H), 5.41 (s, 2H), 2.34 (d, J=1.9 Hz, 3H), 1.31 (s, 9H).

Example 142

1-[6-(3,5-Difluorophenyl)pyrrolo[3,2-b]pyridin-1-yl]-3,3-dimethyl-butan-2-one

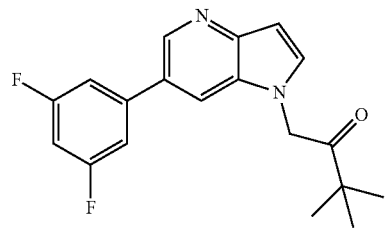 [SMILES: CC(C)(C)C(=O)Cn1ccc2ncc(-c3cc(F)cc(F)c3)cc21]

The title compound was prepared in a manner analogous to Example 140. MS (ESI): mass calcd. for $C_{19}H_{18}F_2N_2O$, 328.1. m/z found, 329.1 [M+H]$^+$. $^1$H NMR (500 MHz, CD$_3$OD) δ 8.58 (d, J=1.9 Hz, 1H), 7.96-7.94 (m, 1H), 7.50 (d, J=3.3 Hz, 1H), 7.34-7.28 (m, 2H), 6.98-6.91 (m, 1H), 6.67 (dd, J=3.4, 0.9 Hz, 1H), 5.45 (s, 2H), 1.32 (s, 9H).

Example 143

3,3-Dimethyl-1-[6-(4-methyl-2-thienyl)pyrrolo[3,2-b]pyridin-1-yl]butan-2-one

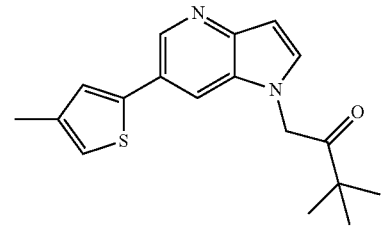 [SMILES: Cc1csc(-c2cnc3ccn(CC(=O)C(C)(C)C)c3c2)c1]

The title compound was prepared in a manner analogous to Example 140 substituting 4,4,5,5-tetramethyl-2-(4-methylthiophen-2-yl)-1,3,2-dioxaborolane for (3,4-difluorophenyl)boronic acid. MS (ESI): mass calcd. for $C_{18}H_{20}N_2OS$, 312.1. m/z found, 313.1 [M+H]$^+$. $^1$H NMR (500 MHz, CD$_3$OD) δ 8.56 (d, J=1.9 Hz, 1H), 7.82-7.79 (m, 1H), 7.43 (d, J=3.3 Hz, 1H), 7.24 (d, J=1.4 Hz, 1H), 6.98-6.95 (m, 1H), 6.61 (dd, J=3.3, 0.9 Hz, 1H), 5.39 (s, 2H), 2.28 (d, J=1.1 Hz, 3H), 1.32 (s, 9H).

Example 144

1-[6-[3-(Difluoromethyl)phenyl]pyrrolo[3,2-b]pyridin-1-yl]-3,3-dimethyl-butan-2-one

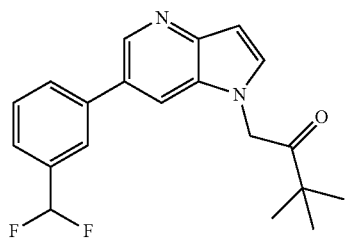 [SMILES: CC(C)(C)C(=O)Cn1ccc2ncc(-c3cccc(C(F)F)c3)cc21]

The title compound was prepared in a manner analogous to Example 140. MS (ESI): mass calcd. for $C_{20}H_{20}F_2N_2O$, 342.2. m/z found, 343.1 [M+H]$^+$. $^1$H NMR (500 MHz, CD$_3$OD) δ 8.58 (s, 1H), 7.92 (s, 1H), 7.83-7.77 (m, 2H), 7.62-7.53 (m, 2H), 7.48 (d, J=3.3 Hz, 1H), 6.84 (t, J=56.2 Hz, 1H), 6.66 (dd, J=3.3, 0.9 Hz, 1H), 5.43 (s, 2H), 1.31 (s, 9H).

Example 145

1-[6-(3-Ethylphenyl)pyrrolo[3,2-b]pyridin-1-yl]-3,3-dimethyl-butan-2-one

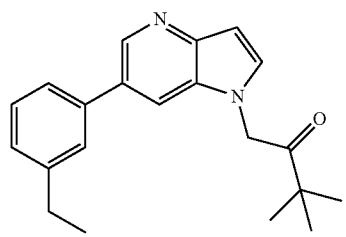 [SMILES: CCc1cccc(-c2cnc3ccn(CC(=O)C(C)(C)C)c3c2)c1]

The title compound was prepared in a manner analogous to Example 140. MS (ESI): mass calcd. for $C_{21}H_{24}N_2O$, 320.2. m/z found, 321.1 [M+H]$^+$. $^1$H NMR (500 MHz, CD$_3$OD) δ 8.54 (d, J=1.9 Hz, 1H), 7.84 (dd, J=1.9, 0.9 Hz, 1H), 7.49-7.41 (m, 3H), 7.37 (t, J=7.6 Hz, 1H), 7.21 (d, J=7.6 Hz, 1H), 6.64 (dd, J=3.3, 0.9 Hz, 1H), 5.42 (s, 2H), 2.72 (q, J=7.6 Hz, 2H), 1.31 (s, 9H), 1.28 (t, J=7.6 Hz, 3H).

Example 146

2-[3-Chloro-6-(4-fluoro-3-methyl-phenyl)pyrrolo[3,2-b]pyridin-1-yl]-N,N-dimethyl-acetamide

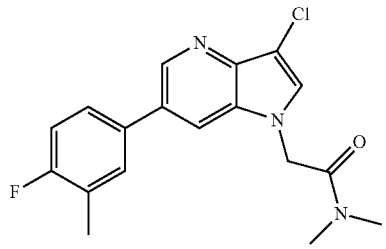 [SMILES: Cc1cc(-c2cnc3c(Cl)cn(CC(=O)N(C)C)c3c2)ccc1F]

Step A: 2-(6-Bromo-3-chloro-1H-pyrrolo[3,2-b]pyridin-1-yl)-N,N-dimethylacetamide To a solution of 6-bromo-3-chloro-1H-pyrrolo[3,2-b]pyridine (Intermediate 5, 500 mg, 2.16 mmol) in DMF (60 mL) at 0° C. was added NaH (121 mg, 3.02 mmol, 60% dispersion in oil). The reaction mixture was stirred for 30 minutes at rt, then cooled to 0° C. and 2-bromo-N,N-dimethylacetamide (430 mg, 2.59 mmol) was added. The reaction mixture was allowed to warm to room temperature and stirred for 12 hours. The reaction mixture was concentrated onto silica gel. Purification (FCC, SiO$_2$, 0-30% MeOH in DCM) gave the title compound (282 mg, 41%). MS (ESI): mass calcd. for $C_{11}H_{11}BrClN_3O$, 315.0. m/z found, 316.0 [M+H]$^+$.

Step B: 2-[3-Chloro-6-(4-fluoro-3-methyl-phenyl)pyrrolo[3,2-b]pyridin-1-yl]-N,N-dimethyl-acetamide To a solution 2-(6-bromo-3-chloro-1H-pyrrolo[3,2-b]pyridin-1-yl)-N,N-dimethylacetamide (100 mg, 0.31 mmol) in dioxane (2.9 mL) was added (4-fluoro-3-methylphenyl)boronic acid (73 mg, 0.47 mmol), Pd(dppf)Cl$_2$ (16 mg, 0.02 mmol), Cs$_2$CO$_3$ (205 mg, 0.63 mmol) and water (0.6 mL). After 3 hours at 90° C. the reaction mixture cooled and NaHCO$_3$ (aq) was added. The reaction mixture was extracted with EtOAc (3×60 mL). The combined organics were dried (MgSO4), filtered, and concentrated under reduced pressure. Purification (basic HPLC 5-95% ACN) afforded the title compound (36 mg, 33%). MS (ESI): mass calcd. for $C_{18}H_{17}ClFN_3O$, 345.1; m/z found, 346.1 [M+H]$^+$. $^1$H NMR (500 MHz, CDCl$_3$) δ 8.69 (d, J=1.9 Hz, 1H), 7.62 (d, J=1.9 Hz, 1H), 7.41-7.33 (m, 2H), 7.31 (s, 1H), 7.09 (t, J=8.9 Hz, 1H), 4.90 (s, 2H), 3.12 (s, 3H), 3.00 (s, 3H), 2.35 (d, J=2.0 Hz, 3H).

Example 147

2-[3-Chloro-6-(3,4-difluorophenyl)pyrrolo[3,2-b]pyridin-1-yl]-N,N-dimethyl-acetamide

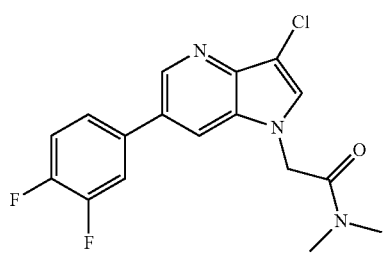

The title compound was prepared in a manner analogous to Example 146. MS (ESI): mass calcd. for C$_{17}$H$_{14}$ClF$_2$N$_3$O, 349.1. m/z found, 350.0 [M+H]$^+$. $^1$H NMR (500 MHz, CDCl$_3$) δ 8.71 (d, J=1.9 Hz, 1H), 7.64 (d, J=1.8 Hz, 1H), 7.43-7.38 (m, 1H), 7.36 (s, 1H), 7.35-7.30 (m, 1H), 7.29-7.23 (m, 1H), 4.93 (s, 2H), 3.15 (s, 3H), 3.02 (s, 3H).

Example 148

2-[3-Chloro-6-(3,5-difluorophenyl)pyrrolo[3,2-b]pyridin-1-yl]-N,N-dimethyl-acetamide

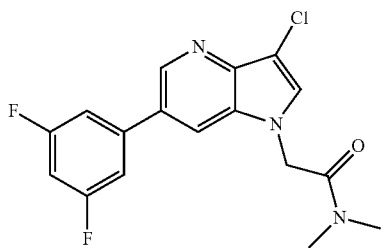 [SMILES: CN(C)C(=O)Cn1cc(Cl)c2ncc(-c3cc(F)cc(F)c3)cc21]

The title compound was prepared in a manner analogous to Example 146. MS (ESI): mass calcd. for C$_{17}$H$_{14}$ClF$_2$N$_3$O, 349.1. m/z found, 350.0 [M+H]$^+$. $^1$H NMR (500 MHz, CDCl$_3$) δ 8.73 (d, J=1.9 Hz, 1H), 7.67 (d, J=1.9 Hz, 1H), 7.38 (s, 1H), 7.17-7.11 (m, 2H), 6.86-6.79 (m, 1H), 4.94 (s, 2H), 3.15 (s, 3H), 3.03 (s, 3H).

Example 149

2-[3-Chloro-6-(4-methyl-2-thienyl)pyrrolo[3,2-b]pyridin-1-yl]-N,N-dimethyl-acetamide

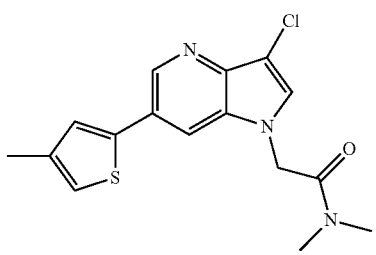

The title compound was prepared in a manner analogous to Example 146 substituting 4,4,5,5-tetramethyl-2-(4-methylthiophen-2-yl)-1,3,2-dioxaborolane for (4-fluoro-3-methylphenyl)boronic acid. MS (ESI): mass calcd. for C$_{16}$H$_{16}$ClN$_3$OS, 333.1. m/z found, 334.0 [M+H]$^+$. $^1$H NMR (500 MHz, CDCl$_3$) δ 8.78 (d, J=1.8 Hz, 1H), 7.63 (d, J=1.8 Hz, 1H), 7.30 (s, 1H), 7.15 (d, J=1.4 Hz, 1H), 6.90 (s, 1H), 4.88 (s, 2H), 3.12 (s, 3H), 3.01 (s, 3H), 2.30 (d, J=1.1 Hz, 3H).

Example 150

2-[3-Chloro-6-[3-(difluoromethyl)phenyl]pyrrolo[3,2-b]pyridin-1-yl]-N,N-dimethyl-acetamide

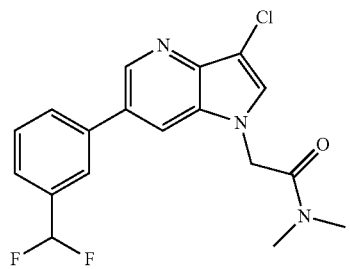

The title compound was prepared in a manner analogous to Example 146. MS (ESI): mass calcd. for C$_{18}$H$_{16}$ClF$_2$N$_3$O, 363.1. m/z found, 364.0 [M+H]$^+$. $^1$H NMR (500 MHz, CDCl$_3$) δ 8.76 (d, J=1.9 Hz, 1H), 7.76-7.67 (m, 3H), 7.60-7.49 (m, 2H), 7.35 (s, 1H), 6.73 (t, J=56.4 Hz, 1H), 4.93 (s, 2H), 3.14 (s, 3H), 3.01 (s, 3H).

Example 151

2-[3-Chloro-6-(3-ethylphenyl)pyrrolo[3,2-b]pyridin-1-yl]-N,N-dimethyl-acetamide

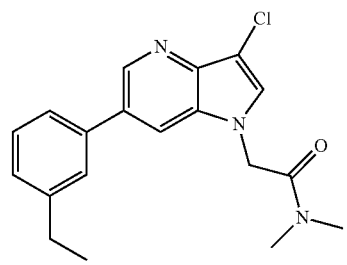

The title compound was prepared in a manner analogous to Example 146. MS (ESI): mass calcd. for C$_{19}$H$_{20}$ClN$_3$O, 341.1. m/z found, 342.1 [M+H]$^+$. $^1$H NMR (500 MHz, CD$_3$OD) δ 8.63 (s, 1H), 8.10 (s, 1H), 7.61-7.47 (m, 3H), 7.40 (t, J=7.3 Hz, 1H), 7.25 (d, J=7.6 Hz, 1H), 5.29 (s, 2H), 3.20 (s, 3H), 2.98 (s, 3H), 2.74 (q, J=7.5 Hz, 2H), 1.30 (t, J=7.6 Hz, 3H).

Example 152

2-[3-Chloro-6-(3,4,5-trifluorophenyl)pyrrolo[3,2-b]pyridin-1-yl]-N,N-dimethyl-acetamide

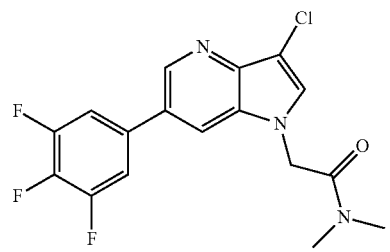 [SMILES: CN(C)C(=O)Cn1cc(Cl)c2ncc(-c3cc(F)c(F)c(F)c3)cc21]

The title compound was prepared in a manner analogous to Example 146. MS (ESI): mass calcd. for $C_{17}H_{13}ClF_3N_3O$, 367.1. m/z found, 368.0 [M+H]$^+$. $^1$H NMR (500 MHz, CDCl$_3$) δ 8.68 (d, J=1.9 Hz, 1H), 7.63 (d, J=1.9 Hz, 1H), 7.38 (s, 1H), 7.25-7.20 (m, 2H), 4.94 (s, 2H), 3.16 (s, 3H), 3.03 (s, 3H).

Example 153

N-Cyclopropyl-2-[6-(4-methyl-2-thienyl)pyrrolo[3,2-b]pyridin-1-yl]acetamide trifluoroacetate salt

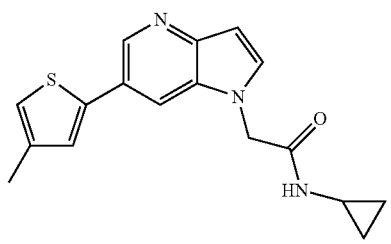 [SMILES: Cc1csc(-c2cnc3ccn(CC(=O)NC4CC4)c3c2)c1]

The title compound was prepared in a manner analogous to Example 75. MS (ESI): mass calcd. for $C_{17}H_{17}N_3OS$, 311.1. m/z found, 312.1 [M+H]$^+$. $^1$H NMR (500 MHz, DMSO-d$_6$) δ 8.88 (s, 1H), 8.60 (s, 1H), 8.41 (d, J=4.3 Hz, 1H), 8.00 (s, 1H), 7.55 (s, 1H), 7.27 (s, 1H), 6.79-6.75 (m, 1H), 5.04 (s, 2H), 2.69-2.62 (m, 1H), 2.29 (t, J=1.3 Hz, 3H), 0.68-0.62 (m, 2H), 0.49-0.44 (m, 2H).

Example 154

N-Cyclopropyl-2-[6-(2,3-dimethylphenyl)pyrrolo[3,2-b]pyridin-1-yl]acetamide trifluoroacetate salt

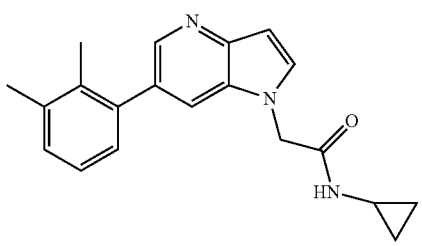 [SMILES: Cc1cccc(-c2cnc3ccn(CC(=O)NC4CC4)c3c2)c1C]

The title compound was prepared in a manner analogous to Example 75. MS (ESI): mass calcd. for $C_{20}H_{21}N_3O$, 319.2. m/z found, 320.2 [M+H]$^+$. $^1$H NMR (500 MHz, DMSO-d$_6$) δ 8.67 (d, J=1.5 Hz, 1H), 8.56 (s, 1H), 8.38 (d, J=4.1 Hz, 1H), 8.14 (d, J=3.2 Hz, 1H), 7.33-7.29 (m, 1H), 7.25 (t, J=7.5 Hz, 1H), 7.21-7.18 (m, 1H), 6.86 (dd, J=3.3, 0.9 Hz, 1H), 5.06 (s, 2H), 2.66-2.59 (m, 1H), 2.35 (s, 3H), 2.16 (s, 3H), 0.66-0.60 (m, 2H), 0.45-0.40 (m, 2H).

Example 155

N-Cyclopropyl-2-[6-(m-tolyl)pyrrolo[3,2-b]pyridin-1-yl]acetamide trifluoroacetate salt

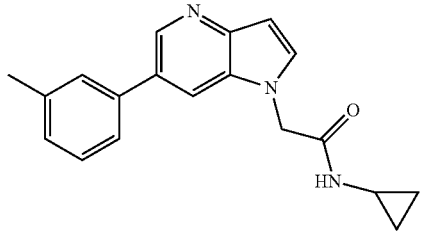 [SMILES: Cc1cccc(-c2cnc3ccn(CC(=O)NC4CC4)c3c2)c1]

The title compound was prepared in a manner analogous to Example 75. MS (ESI): mass calcd. for $C_{19}H_{19}N_3O$, 305.2. m/z found, 306.2 [M+H]$^+$. $^1$H NMR (500 MHz, DMSO-d$_6$) δ 9.00 (s, 1H), 8.92 (s, 1H), 8.43 (d, J=4.1 Hz, 1H), 8.16-8.12 (m, 1H), 7.69 (s, 1H), 7.66 (d, J=7.9 Hz, 1H), 7.49-7.44 (m, 1H), 7.31 (d, J=7.5 Hz, 1H), 6.87-6.83 (m, 1H), 5.13 (s, 2H), 2.69-2.62 (m, 1H), 2.43 (d, J=1.7 Hz, 3H), 0.68-0.61 (m, 2H), 0.49-0.43 (m, 2H).

Example 156

N-Cyclopropyl-2-[6-(3,4-dichlorophenyl)pyrrolo[3,2-b]pyridin-1-yl]acetamide trifluoroacetate salt

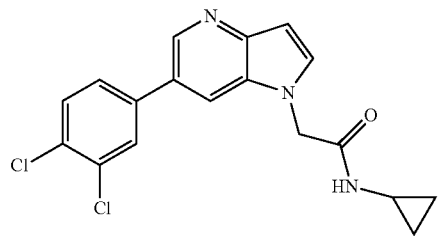 [SMILES: O=C(Cn1ccc2ncc(-c3ccc(Cl)c(Cl)c3)cc21)NC1CC1]

The title compound was prepared in a manner analogous to Example 75. MS (ESI): mass calcd. for $C_{18}H_{15}Cl_2N_3O$, 359.1. m/z found, 360.1 [M+H]$^+$. $^1$H NMR (500 MHz, DMSO-d$_6$) δ 8.99 (d, J=1.8 Hz, 1H), 8.80 (s, 1H), 8.40 (d, J=4.1 Hz, 1H), 8.17 (d, J=2.1 Hz, 1H), 8.05 (d, J=3.3 Hz, 1H), 7.89-7.82 (m, 2H), 6.81 (dd, J=3.3, 0.9 Hz, 1H), 5.06 (s, 2H), 2.69-2.62 (m, 1H), 0.67-0.62 (m, 2H), 0.48-0.44 (m, 2H).

Example 157

N-Cyclopropyl-2-[6-[2-methyl-3-(trifluoromethyl)phenyl]pyrrolo[3,2-b]pyridin-1-yl]acetamide trifluoroacetate salt

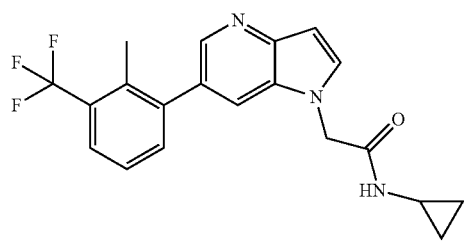 [SMILES: Cc1c(-c2cnc3ccn(CC(=O)NC4CC4)c3c2)cccc1C(F)(F)F]

The title compound was prepared in a manner analogous to Example 75. MS (ESI): mass calcd. for $C_{20}H_{18}F_3N_3O$, 373.1. m/z found, 374.1 [M+H]$^+$. $^1$H NMR (500 MHz, DMSO-d$_6$) δ 8.67-8.64 (m, 1H), 8.50 (s, 1H), 8.37-8.33 (m, 1H), 8.08-8.04 (m, 1H), 7.85-7.81 (m, 1H), 7.66 (d, J=7.7 Hz, 1H), 7.56 (t, J=7.9 Hz, 1H), 6.84-6.81 (m, 1H), 5.01 (s, 2H), 2.66-2.59 (m, 1H), 2.34 (s, 3H), 0.65-0.59 (m, 2H), 0.45-0.39 (m, 2H).

Example 158

N-Cyclopropyl-2-(6-phenylpyrrolo[3,2-b]pyridin-1-yl)acetamide trifluoroacetate salt

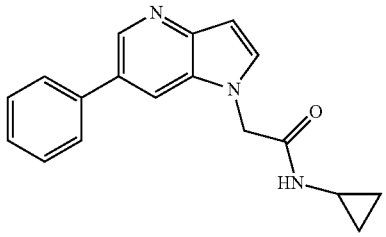 [SMILES: O=C(Cn1ccc2ncc(-c3ccccc3)cc21)NC1CC1]

The title compound was prepared in a manner analogous to Example 75. MS (ESI): mass calcd. for $C_{18}H_{17}N_3O$, 291.1. m/z found, 292.1 [M+H]$^+$. $^1$H NMR (500 MHz, DMSO-d$_6$) δ 9.03 (d, J=1.6 Hz, 1H), 8.97 (s, 1H), 8.42 (d, J=4.1 Hz, 1H), 8.16 (d, J=3.3 Hz, 1H), 7.90-7.85 (m, 2H), 7.62-7.57 (m, 2H), 7.53-7.48 (m, 1H), 6.87 (dd, J=3.3, 0.8 Hz, 1H), 5.13 (s, 2H), 2.68-2.62 (m, 1H), 0.67-0.61 (m, 2H), 0.48-0.43 (m, 2H).

Example 159

N-Cyclopropyl-2-[6-(4-fluoro-2,3-dimethyl-phenyl)pyrrolo[3,2-b]pyridin-1-yl]acetamide trifluoroacetate salt

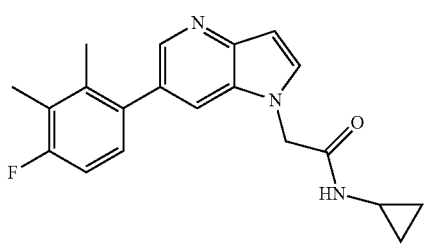 [SMILES: Cc1c(F)ccc(-c2cnc3ccn(CC(=O)NC4CC4)c3c2)c1C]

The title compound was prepared in a manner analogous to Example 75. MS (ESI): mass calcd. for $C_{20}H_{20}FN_3O$, 337.2. m/z found, 338.2 [M+H]$^+$. $^1$H NMR (400 MHz, DMSO-d$_6$) δ 8.63 (d, J=1.5 Hz, 1H), 8.50 (s, 1H), 8.37 (d, J=4.1 Hz, 1H), 8.11 (d, J=3.3 Hz, 1H), 7.27-7.15 (m, 2H), 6.84 (d, J=3.3 Hz, 1H), 5.04 (s, 2H), 2.65-2.59 (m, 1H), 2.25 (d, J=2.1 Hz, 3H), 2.19 (s, 3H), 0.66-0.60 (m, 2H), 0.45-0.40 (m, 2H).

Example 160

N-Cyclopropyl-2-[6-(o-tolyl)pyrrolo[3,2-b]pyridin-1-yl]acetamide

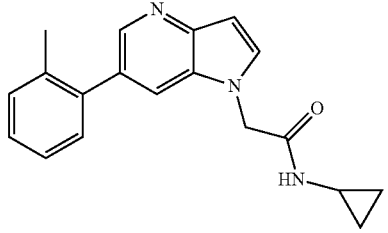 [SMILES: Cc1ccccc1-c1cnc2ccn(CC(=O)NC3CC3)c2c1]

The title compound was prepared in a manner analogous to Example 75. MS (ESI): mass calcd. for $C_{19}H_{19}N_3O$, 305.2. m/z found, 306.2 [M+H]$^+$. $^1$H NMR (500 MHz, DMSO-d$_6$) δ 8.35-8.27 (m, 2H), 7.78 (s, 1H), 7.67-7.58 (m, 1H), 7.39-7.24 (m, 4H), 6.60 (d, J=3.4 Hz, 1H), 4.82 (s, 2H), 2.66-2.60 (m, 1H), 2.27 (s, 3H), 0.66-0.58 (m, 2H), 0.45-0.37 (m, 2H).

Example 161

N-Cyclopropyl-2-[6-(4-fluoro-2-methyl-phenyl)pyrrolo[3,2-b]pyridin-1-yl]acetamide trifluoroacetate salt

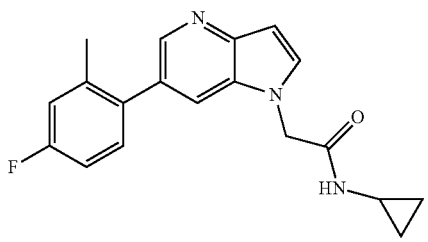 [SMILES: Cc1cc(F)ccc1-c1cnc2ccn(CC(=O)NC3CC3)c2c1]

The title compound was prepared in a manner analogous to Example 75. MS (ESI): mass calcd. for $C_{19}H_{18}FN_3O$, 323.1. m/z found, 324.2 [M+H]$^+$. $^1$H NMR (500 MHz, DMSO-d$_6$) δ 8.72 (s, 1H), 8.64 (s, 1H), 8.38 (d, J=4.4 Hz, 1H), 8.16 (d, J=3.2 Hz, 1H), 7.42 (dd, J=8.4, 5.9 Hz, 1H), 7.30 (dd, J=10.2, 3.0 Hz, 1H), 7.27-7.18 (m, 1H), 6.87 (d, J=3.3 Hz, 1H), 5.07 (s, 2H), 2.67-2.61 (m, 1H), 2.30 (d, J=2.2 Hz, 3H), 0.69-0.60 (m, 2H), 0.47-0.39 (m, 2H).

Example 162

1-(Azetidin-1-yl)-2-[6-(o-tolyl)pyrrolo[3,2-b]pyridin-1-yl]ethanone trifluoroacetate salt

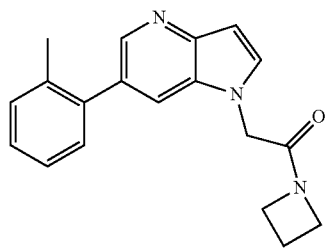 [SMILES: Cc1ccccc1-c1cnc2ccn(CC(=O)N3CCC3)c2c1]

The title compound was prepared in a manner analogous to Example 71 using 1-(azetidin-1-yl)-2-(6-bromo-1H-pyrrolo[3,2-b]pyridin-1-yl)ethanone and o-tolylboronic acid. MS (ESI): mass calcd. for $C_{19}H_{19}N_3O$, 305.2. m/z found, 306.2 [M+H]$^+$. $^1$H NMR (500 MHz, DMSO-d$_6$) δ 8.72 (s, 1H), 8.66 (s, 1H), 8.11-8.07 (m, 1H), 7.43-7.34 (m, 4H), 6.88-6.84 (m, 1H), 5.18 (s, 2H), 4.30-4.22 (m, 2H), 3.94-3.86 (m, 2H), 2.32-2.24 (m, 5H).

Example 163

1-(Azetidin-1-yl)-2-[6-(4-fluoro-2-methyl-phenyl)pyrrolo[3,2-b]pyridin-1-yl]ethanone trifluoroacetate salt

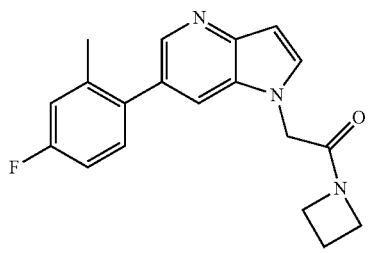 [SMILES: Cc1cc(F)ccc1-c1cnc2ccn(CC(=O)N3CCC3)c2c1]

The title compound was prepared in a manner analogous to Example 71. MS (ESI): mass calcd. for $C_{19}H_{18}FN_3O$, 323.1. m/z found, 324.1 [M+H]$^+$. $^1$H NMR (400 MHz, DMSO-d$_6$) δ 8.67 (d, J=1.6 Hz, 1H), 8.59 (s, 1H), 8.06 (d, J=3.2 Hz, 1H), 7.41 (dd, J=8.5, 6.0 Hz, 1H), 7.29 (dd, J=10.1, 2.8 Hz, 1H), 7.21 (td, J=8.5, 2.9 Hz, 1H), 6.85 (dd, J=3.3, 0.7 Hz, 1H), 5.16 (s, 2H), 4.26 (t, J=7.7 Hz, 2H), 3.90 (t, J=7.7 Hz, 2H), 2.34-2.24 (m, 5H).

Example 164

1-(Azetidin-1-yl)-2-[6-(4-fluoro-2,3-dimethyl-phenyl)pyrrolo[3,2-b]pyridin-1-yl]ethanone trifluoroacetate salt

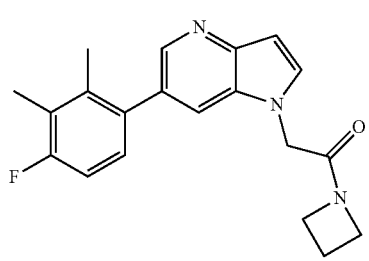 [SMILES: Cc1c(F)ccc(-c2cnc3ccn(CC(=O)N4CCC4)c3c2)c1C]

The title compound was prepared in a manner analogous to Example 71. MS (ESI): mass calcd. for $C_{20}H_{20}FN_3O$, 337.2. m/z found, 338.2 [M+H]$^+$. $^1$H NMR (400 MHz, DMSO-d$_6$) δ 8.57 (s, 1H), 8.42 (s, 1H), 7.99 (d, J=3.4 Hz, 1H), 7.25-7.13 (m, 2H), 6.81 (d, J=3.3 Hz, 1H), 5.12 (s, 2H), 4.24 (t, J=7.7 Hz, 2H), 3.90 (t, J=7.7 Hz, 2H), 2.31-2.22 (m, 5H), 2.17 (s, 3H).

Example 165

1-(Azetidin-1-yl)-2-[6-(2,3-dimethylphenyl)pyrrolo[3,2-b]pyridin-1-yl]ethanone trifluoroacetate salt

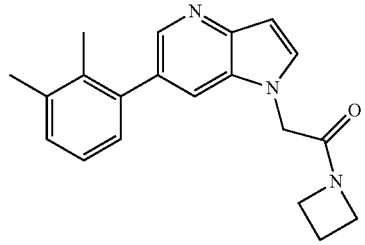 [SMILES: Cc1cccc(-c2cnc3ccn(CC(=O)N4CCC4)c3c2)c1C]

The title compound was prepared in a manner analogous to Example 71. MS (ESI): mass calcd. for $C_{20}H_{21}N_3O$, 319.2. m/z found, 320.2 [M+H]$^+$. $^1$H NMR (400 MHz, DMSO-d$_6$) δ 8.66 (d, J=1.6 Hz, 1H), 8.59 (s, 1H), 8.07 (d, J=3.3 Hz, 1H), 7.31 (dd, J=7.6, 1.5 Hz, 1H), 7.25 (t, J=7.5 Hz, 1H), 7.19 (dd, J=7.7, 1.6 Hz, 1H), 6.86 (d, J=3.1 Hz, 1H), 5.17 (s, 2H), 4.26 (t, J=7.6 Hz, 2H), 3.90 (t, J=7.7 Hz, 2H), 2.35 (s, 3H), 2.33-2.24 (m, 2H), 2.15 (s, 3H).

Example 166

1-(Azetidin-1-yl)-2-[6-[3-(trifluoromethyl)phenyl]pyrrolo[3,2-b]pyridin-1-yl]ethanone trifluoroacetate salt

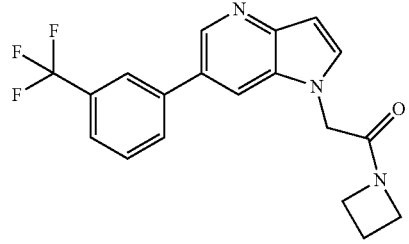 [SMILES: O=C(Cn1ccc2ncc(-c3cccc(C(F)(F)F)c3)cc21)N1CCC1]

The title compound was prepared in a manner analogous to Example 71. MS (ESI): mass calcd. for $C_{19}H_{18}F_3N_3O$, 359.1. m/z found, 360.1 [M+H]$^+$. $^1$H NMR (400 MHz, DMSO-d$_6$) δ 9.05 (s, 1H), 8.90 (s, 1H), 8.19 (s, 1H), 8.18-8.14 (m, 1H), 8.05 (d, J=3.3 Hz, 1H), 7.88-7.79 (m, 2H), 6.85 (d, J=3.3 Hz, 1H), 5.21 (s, 2H), 4.28 (t, J=7.7 Hz, 2H), 3.92 (t, J=7.7 Hz, 2H), 2.36-2.25 (m, 2H).

Example 167

1-(Azetidin-1-yl)-2-[6-[2-methyl-3-(trifluoromethyl)phenyl]pyrrolo[3,2-b]pyridin-1-yl]ethanone trifluoroacetate salt

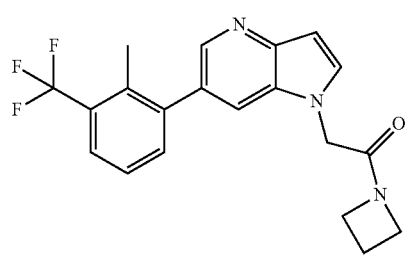 [SMILES: Cc1c(-c2cnc3ccn(CC(=O)N4CCC4)c3c2)cccc1C(F)(F)F]

The title compound was prepared in a manner analogous to Example 71. MS (ESI): mass calcd. for C$_{20}$H$_{18}$F$_3$N$_3$O, 373.1. m/z found, 374.2 [M+H]$^+$. $^1$H NMR (400 MHz, DMSO-d$_6$) δ 8.71 (d, J=1.5 Hz, 1H), 8.61 (s, 1H), 8.07 (d, J=3.3 Hz, 1H), 7.85 (dd, J=8.0, 1.3 Hz, 1H), 7.67 (d, J=7.2 Hz, 1H), 7.58 (t, J=7.7 Hz, 1H), 6.87 (d, J=3.2 Hz, 1H), 5.16 (s, 2H), 4.25 (t, J=7.7 Hz, 2H), 3.90 (t, J=7.7 Hz, 2H), 2.34 (d, J=1.9 Hz, 3H), 2.33-2.24 (m, 2H).

Example 168

N-Cyclopropyl-2-[6-(4-fluorophenyl)pyrrolo[3,2-b]pyridin-1-yl]acetamide

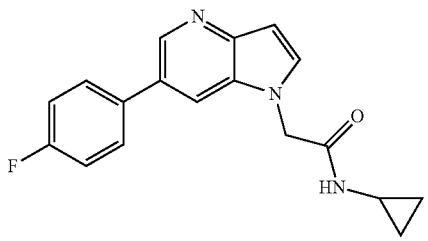 [SMILES: O=C(Cn1ccc2ncc(-c3ccc(F)cc3)cc21)NC1CC1]

The title compound was prepared in a manner analogous to Example 75. MS (ESI): mass calcd. for C$_{18}$H$_{16}$FN$_3$O, 309.1. m/z found, 310.2 [M+H]$^+$. $^1$H NMR (400 MHz, DMSO-d$_6$) δ 8.63 (d, J=2.0 Hz, 1H), 8.35-8.32 (m, 1H), 8.07-8.05 (m, 1H), 7.80-7.74 (m, 2H), 7.63 (d, J=3.3 Hz, 1H), 7.37-7.31 (m, 2H), 6.60-6.57 (m, 1H), 4.86 (s, 2H), 2.68-2.65 (m, 1H), 0.65-0.60 (m, 2H), 0.46-0.41 (m, 2H).

Example 169

1-(Azetidin-1-yl)-2-[6-(4-fluoro-3-methyl-phenyl)-3-methyl-pyrrolo[3,2-b]pyridin-1-yl]ethanone trifluoroacetate salt

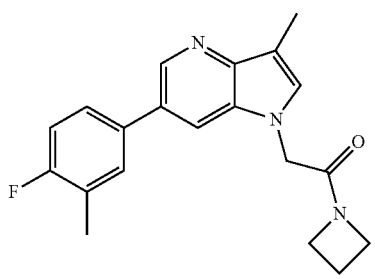 [SMILES: Cc1cc(-c2cnc3c(C)cn(CC(=O)N4CCC4)c3c2)ccc1F]

The title compound was prepared in a manner analogous to Example 27. MS (ESI): mass calcd. for C$_{20}$H$_{20}$FN$_3$O, 337.2. m/z found, 338.2 [M+H]$^+$. $^1$H NMR (300 MHz, DMSO) δ 8.59 (s, 1H), 8.01 (s, 1H), 7.65 (d, J=7.2 Hz, 1H), 7.61-7.51 (m, 1H), 7.36 (s, 1H), 7.32-7.19 (m, 1H), 4.92 (s, 2H), 4.18 (t, J=7.6 Hz, 2H), 3.89 (t, J=7.6 Hz, 2H), 2.33 (s, 3H), 2.31-2.18 (m, 5H).

Example 170

1-Butyl-6-(4-fluoro-3-methyl-phenyl)pyrrolo[3,2-b]pyridine trifluoroacetate salt

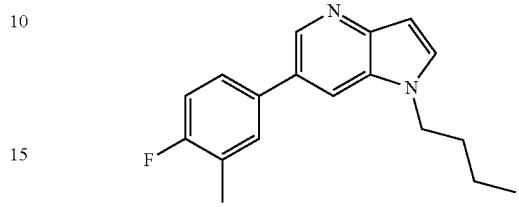

To a solution of 6-(4-fluoro-3-methylphenyl)-1H-pyrrolo[3,2-b]pyridine (60 mg, 0.26 mmol) in DMF (1.5 mL) at 0° C. was added NaH (14.8 mg, 0.37 mmol, 60% dispersion in oil). The reaction mixture was stirred for 30 minutes, then cooled to 0° C. and 1-bromobutane (0.22 mL, 0.278 mmol) was added. The reaction mixture was allowed to warm to room temperature and stirred for 12 hours. The reaction was diluted with methanol to 3 mL, filtered, and purified via HPLC Method C. MS (ESI): mass calcd. for C$_{16}$H$_{19}$FN$_2$, 282.2. m/z found, 283.2 [M+H]$^+$. $^1$H NMR (400 MHz, DMSO-d$_6$) δ 8.95-8.88 (m, 2H), 8.19 (d, J=3.2 Hz, 1H), 7.83 (dd, J=7.6, 2.5 Hz, 1H), 7.77-7.71 (m, 1H), 7.35 (dd, J=9.6, 8.5 Hz, 1H), 6.80 (dd, J=3.2, 0.9 Hz, 1H), 4.43 (t, J=7.1 Hz, 2H), 2.36 (d, J=1.9 Hz, 3H), 1.86-1.75 (m, 2H), 1.33-1.20 (m, 2H), 0.89 (t, J=7.3 Hz, 3H).

Example 171

6-(4-Fluoro-3-methyl-phenyl)-1-isopentyl-pyrrolo[3,2-b]pyridine trifluoroacetate salt

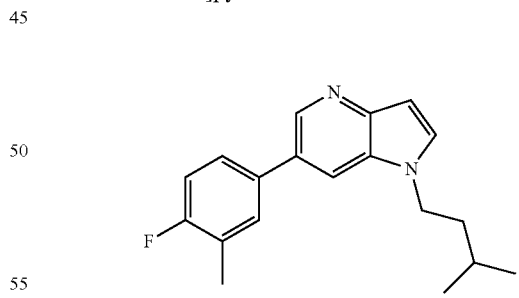

The title compound was prepared in a manner analogous to Example 170 using 1-bromo-3-methylbutane and 6-(4-fluoro-3-methylphenyl)-1H-pyrrolo[3,2-b]pyridine. MS (ESI): mass calcd. for C$_{19}$H$_{21}$FN$_2$, 296.2. m/z found, 297.2 [M+H]$^+$. $^1$H NMR (400 MHz, DMSO-d$_6$) δ 8.94 (d, J=1.6 Hz, 1H), 8.92 (s, 1H), 8.22 (d, J=3.3 Hz, 1H), 7.86-7.81 (m, 1H), 7.78-7.72 (m, 1H), 7.36 (dd, J=9.6, 8.6 Hz, 1H), 6.82 (dd, J=3.3, 0.8 Hz, 1H), 4.50-4.41 (m, 2H), 2.36 (d, J=1.9 Hz, 3H), 1.78-1.70 (m, 2H), 1.58-1.48 (m, 1H), 0.94 (d, J=6.6 Hz, 6H).

Example 172

6-(4-Fluoro-3-methyl-phenyl)-1-(3-pyridylmethyl) pyrrolo[3,2-b]pyridine trifluoroacetate salt

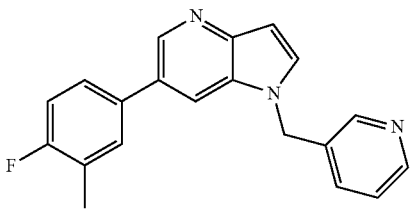 [SMILES: Cc1cc(-c2cnc3ccn(Cc4cccnc4)c3c2)ccc1F]

The title compound was prepared in a manner analogous to Example 170 using 6-(4-fluoro-3-methylphenyl)-1H-pyrrolo[3,2-b]pyridine and 3-(bromomethyl)pyridine. MS (ESI): mass calcd. for $C_{20}H_{16}FN_3$, 317.1. m/z found, 318.2 [M+H]$^+$. $^1$H NMR (500 MHz, DMSO-$d_6$) δ 9.03 (s, 1H), 8.99-8.96 (m, 1H), 8.72-8.69 (m, 1H), 8.58-8.53 (m, 1H), 8.32 (d, J=3.4 Hz, 1H), 7.86-7.79 (m, 2H), 7.75-7.69 (m, 1H), 7.49-7.45 (m, 1H), 7.38-7.32 (m, 1H), 6.89 (d, J=3.3 Hz, 1H), 5.77 (s, 2H), 2.35 (s, 3H).

Example 173

1-(Cyclobutylmethyl)-6-(4-fluoro-3-methyl-phenyl) pyrrolo[3,2-b]pyridine trifluoroacetate salt

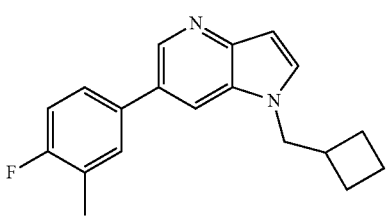 [SMILES: Cc1cc(-c2cnc3ccn(CC4CCC4)c3c2)ccc1F]

The title compound was prepared in a manner analogous to Example 170 using 6-(4-fluoro-3-methylphenyl)-1H-pyrrolo[3,2-b]pyridine and (bromomethyl)cyclobutane. MS (ESI): mass calcd. for $C_{19}H_{19}FN_2$, 294.2. m/z found, 295.2 [M+H]$^+$. $^1$H NMR (400 MHz, DMSO-$d_6$) δ 8.98 (s, 1H), 8.95 (d, J=1.6 Hz, 1H), 8.20 (d, J=3.3 Hz, 1H), 7.84 (dd, J=7.3, 2.5 Hz, 1H), 7.78-7.72 (m, 1H), 7.39-7.32 (m, 1H), 6.81 (d, J=3.2 Hz, 1H), 4.47 (d, J=7.5 Hz, 2H), 2.91-2.81 (m, 1H), 2.36 (d, J=1.9 Hz, 3H), 1.99-1.77 (m, 6H).

Example 174

1-(Cyclopropylmethyl)-6-(4-fluoro-3-methyl-phenyl)pyrrolo[3,2-b]pyridine trifluoroacetate salt

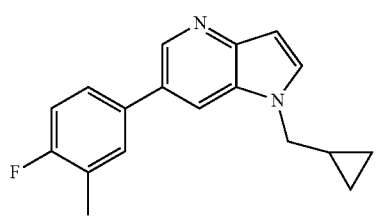 [SMILES: Cc1cc(-c2cnc3ccn(CC4CC4)c3c2)ccc1F]

The title compound was prepared in a manner analogous to Example 170 using 6-(4-fluoro-3-methylphenyl)-1H-pyrrolo[3,2-b]pyridine and (bromomethyl)cyclopropane. MS (ESI): mass calcd. for $C_{16}H_{17}FN_2$, 280.1. m/z found, 281.2 [M+H]$^+$. $^1$H NMR (500 MHz, DMSO-$d_6$) δ 8.95-8.90 (m, 2H), 8.22 (d, J=3.2 Hz, 1H), 7.84 (dd, J=7.7, 2.5 Hz, 1H), 7.77-7.71 (m, 1H), 7.35 (dd, J=9.6, 8.5 Hz, 1H), 6.81 (d, J=3.2 Hz, 1H), 4.30 (d, J=7.3 Hz, 2H), 2.36 (d, J=1.8 Hz, 3H), 1.41-1.33 (m, 1H), 0.58-0.52 (m, 2H), 0.49-0.44 (m, 2H).

Example 175

2-[6-(4-Fluoro-3-methyl-phenyl)pyrrolo[3,2-b]pyridin-1-yl]-N,N-dimethyl-acetamide trifluoroacetate salt

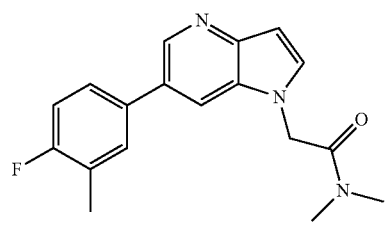 [SMILES: Cc1cc(-c2cnc3ccn(CC(=O)N(C)C)c3c2)ccc1F]

The title compound was prepared in a manner analogous to Example 375. MS (ESI): mass calcd. for $C_{18}H_{18}FN_3O$, 311.1. m/z found, 312.2 [M+H]$^+$. $^1$H NMR (500 MHz, DMSO-$d_6$) δ 8.99 (s, 1H), 8.93 (s, 1H), 8.09 (d, J=3.3 Hz, 1H), 7.82-7.78 (m, 1H), 7.74-7.68 (m, 1H), 7.37 (t, J=9.0 Hz, 1H), 6.86 (d, J=3.2 Hz, 1H), 5.48 (s, 2H), 3.13 (s, 3H), 2.87 (s, 3H), 2.36 (s, 3H).

Example 176

2-[3-Chloro-6-(4-fluoro-3-methyl-phenyl)pyrrolo[3,2-b]pyridin-1-yl]-N-cyclopropyl-acetamide trifluoroacetate salt

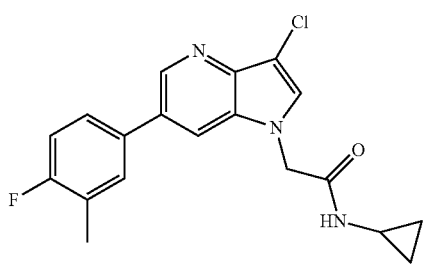 [SMILES: Cc1cc(-c2cnc3c(Cl)cn(CC(=O)NC4CC4)c3c2)ccc1F]

Step A: 3-Chloro-6-(4-fluoro-3-methylphenyl)-1H-pyrrolo[3,2-b]pyridine

To a solution of 6-(4-fluoro-3-methylphenyl)-1H-pyrrolo[3,2-b]pyridine (Example 66, intermediate of Step A, 500 mg, 2.2 mmol) in DMF (5 mL) cooled at 0° C. was slowly added NCS (384 mg, 2.9 mmol). The reaction mixture was allowed to warm to room temperature and stirred at room temperature for 12 hours. Water was added and it was allowed to stir for 20 minutes. The title compound was collected via filtration and washed with water (472 mg, 82%). The crude was used without any further purification in the next step. $^1$H NMR (500 MHz, DMSO-$d_6$) δ 11.68 (s, 1H), 8.67 (s, 1H), 7.98 (s, 1H), 7.88-7.81 (m, 1H), 7.67 (d, J=7.0 Hz, 1H), 7.61-7.52 (m, 1H), 7.26 (t, J=9.2 Hz, 1H), 2.33 (s, 3H).

Step B: 2-[3-Chloro-6-(4-fluoro-3-methyl-phenyl)pyrrolo[3,2-b]pyridin-1-yl]-N-cyclopropyl-acetamide trifluoroacetate salt The title compound was prepared in a manner analogous to Example 136, Step A substituting 2-bromo-N-cyclopropylacetamide for 2-bromo-1-cyclopropylethanone. MS (ESI): mass calcd. for $C_{19}H_{17}ClFN_3O$, 357.1. m/z found, 358.1 [M+H]$^+$. $^1$H NMR (500 MHz, DMSO-$d_6$) δ 8.74-8.71 (m, 1H), 8.35-8.32 (m, 1H), 8.22-8.20 (m, 1H), 7.86 (d, J=1.6 Hz, 1H), 7.70 (d, J=7.6 Hz, 1H), 7.63-7.57 (m, 1H), 7.32-7.25 (m, 1H), 4.90 (s, 2H), 2.68-2.62 (m, 1H), 2.34 (s, 3H), 0.66-0.60 (m, 2H), 0.47-0.41 (m, 2H).

Example 177

6-(4-Fluoro-3-methyl-phenyl)-1-(2-pyridylmethyl)pyrrolo[3,2-b]pyridine trifluoroacetate salt

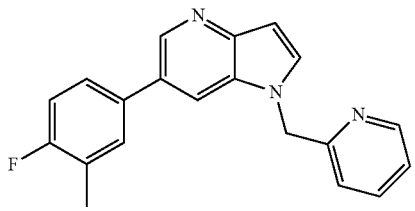 [SMILES: Cc1cc(-c2cnc3ccn(Cc4ccccn4)c3c2)ccc1F]

The title compound was prepared in a manner analogous to Example 170 using 6-(4-fluoro-3-methylphenyl)-1H-pyrrolo[3,2-b]pyridine and 2-(bromomethyl)pyridine. MS (ESI): mass calcd. for $C_{20}H_{16}FN_3$, 317.1. m/z found, 318.1 [M+H]$^+$. $^1$H NMR (500 MHz, DMSO-$d_6$) δ 8.92 (s, 1H), 8.89-8.85 (m, 1H), 8.50-8.47 (m, 1H), 8.21 (d, J=2.4 Hz, 1H), 7.81-7.75 (m, 2H), 7.70-7.65 (m, 1H), 7.36-7.26 (m, 3H), 6.84 (d, J=3.3 Hz, 1H), 5.79 (s, 2H), 2.33 (d, J=1.8 Hz, 3H).

Example 178

(R/S)-6-(4-Fluoro-3-methyl-phenyl)-1-(tetrahydrofuran-3-ylmethyl)pyrrolo[3,2-b]pyridine trifluoroacetate salt

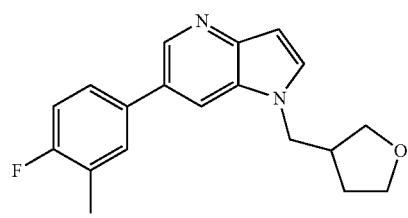 [SMILES: Cc1cc(-c2cnc3ccn(CC4CCOC4)c3c2)ccc1F]

The title compound was prepared in a manner analogous to Example 170 using 6-(4-fluoro-3-methylphenyl)-1H-pyrrolo[3,2-b]pyridine and 3-(bromomethyl)tetrahydrofuran. MS (ESI): mass calcd. for $C_{19}H_{19}FN_2O$, 310.1; m/z found, 311.2 [M+H]$^+$. $^1$H NMR (400 MHz, DMSO-$d_6$) δ 8.97-8.92 (m, 2H), 8.22 (d, J=3.3 Hz, 1H), 7.83 (dd, J=7.4, 2.5 Hz, 1H), 7.78-7.72 (m, 1H), 7.39-7.31 (m, 1H), 6.83 (d, J=3.2 Hz, 1H), 4.50-4.37 (m, 2H), 3.88-3.80 (m, 1H), 3.70-3.60 (m, 2H), 3.51-3.43 (m, 1H), 2.92-2.81 (m, 1H), 2.36 (d, J=1.8 Hz, 3H), 1.94-1.83 (m, 1H), 1.69-1.56 (m, 1H).

Example 179

6-(4-Fluoro-3-methyl-phenyl)-1-(4-pyridylmethyl)pyrrolo[3,2-b]pyridine trifluoroacetate salt

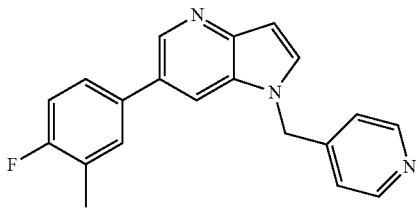 [SMILES: Cc1cc(-c2cnc3ccn(Cc4ccncc4)c3c2)ccc1F]

The title compound was prepared in a manner analogous to Example 170 using 2-(chloromethyl)pyridine and 6-(4-fluoro-3-methylphenyl)-1H-pyrrolo[3,2-b]pyridine. MS (ESI): mass calcd. for $C_{20}H_{16}FN_3$, 317.1. m/z found, 318.2 [M+H]$^+$. $^1$H NMR (500 MHz, DMSO-$d_6$) δ 8.96 (d, J=1.7 Hz, 1H), 8.85 (s, 1H), 8.63-8.58 (m, 2H), 8.24 (d, J=3.3 Hz, 1H), 7.77 (dd, J=7.5, 2.4 Hz, 1H), 7.70-7.65 (m, 1H), 7.36-7.29 (m, 3H), 6.91 (dd, J=3.3, 0.9 Hz, 1H), 5.84 (s, 2H), 2.33 (d, J=1.9 Hz, 3H).

Example 180

(R/S)-6-(4-Fluoro-3-methyl-phenyl)-1-(oxiran-2-ylmethyl)pyrrolo[3,2-b]pyridine trifluoroacetate salt

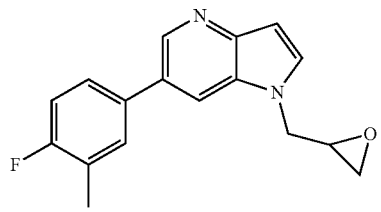 [SMILES: Cc1cc(-c2cnc3ccn(CC4CO4)c3c2)ccc1F]

The title compound was prepared in a manner analogous to Example 170. MS (ESI): mass calcd. for $C_{17}H_{15}FN_2O$, 282.1. m/z found, 283.1 [M+H]$^+$. $^1$H NMR (500 MHz, DMSO-$d_6$) δ 8.93 (d, J=1.7 Hz, 1H), 8.84 (s, 1H), 8.10 (d, J=3.2 Hz, 1H), 7.83-7.79 (m, 1H), 7.74-7.69 (m, 1H), 7.35 (t, J=9.1 Hz, 1H), 6.83-6.79 (m, 1H), 4.54 (dd, J=14.5, 3.5 Hz, 1H), 4.42-4.36 (m, 1H), 3.88-3.82 (m, 1H), 3.41 (dd, J=10.9, 5.2 Hz, 1H), 3.27 (dd, J=10.9, 6.4 Hz, 1H), 2.36 (s, 3H).

Example 181

6-(4-Fluoro-3-methyl-phenyl)-1-(2-pyrazol-1-yl-ethyl)pyrrolo[3,2-b]pyridine trifluoroacetate salt

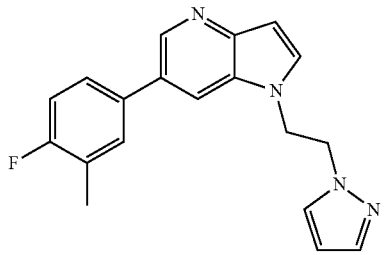 [SMILES: Cc1cc(-c2cnc3ccn(CCn4cccn4)c3c2)ccc1F]

The title compound was prepared in a manner analogous to Example 170 using 1-(2-chloroethyl)-1H-pyrazole and 6-(4-fluoro-3-methylphenyl)-1H-pyrrolo[3,2-b]pyridine. MS (ESI): mass calcd. for $C_{19}H_{17}FN_4$, 320.1. m/z found, 321.2 [M+H]$^+$. $^1$H NMR (500 MHz, DMSO-$d_6$) δ 8.87 (d, J=1.7 Hz, 1H), 8.50 (s, 1H), 7.81-7.72 (m, 2H), 7.70-7.63 (m, 1H), 7.42 (d, J=2.3 Hz, 1H), 7.39-7.32 (m, 2H), 6.73 (d, J=3.2 Hz, 1H), 6.08 (t, J=2.1 Hz, 1H), 4.85 (t, J=5.6 Hz, 2H), 4.59 (dd, J=6.5, 4.5 Hz, 2H), 2.36 (d, J=1.9 Hz, 3H).

Example 182

1-(Azetidin-1-yl)-2-[6-(5-chloro-2-thienyl)-3-fluoro-pyrrolo[3,2-b]pyridin-1-yl]ethanone

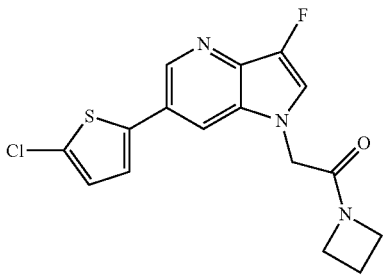 [SMILES: O=C(Cn1cc(F)c2ncc(-c3ccc(Cl)s3)cc21)N1CCC1]

Step A: 1-(Azetidin-1-yl)-2-(6-bromo-3-fluoro-1H-pyrrolo[3,2-b]pyridin-1-yl)ethanone The title compound was prepared in a manner analogous to Example 29, Step A. $^1$H NMR (400 MHz, DMSO-$d_6$) δ 8.43 (d, J=2.0 Hz, 1H), 8.28 (t, J=2.1 Hz, 1H), 7.66 (d, J=2.2 Hz, 1H), 4.90 (s, 2H), 4.22 (t, J=7.6 Hz, 2H), 3.90 (t, J=7.7 Hz, 2H), 2.33-2.23 (m, 2H).

Step B: 1-(Azetidin-1-yl)-2-[6-(5-chloro-2-thienyl)-3-fluoro-pyrrolo[3,2-b]pyridin-1-yl]ethanone The title compound was prepared in a manner analogous to Example 29, Step B, substituting (5-chlorothiophen-2-yl)boronic acid for (3,4-difluorophenyl)boronic acid. MS (ESI): mass calcd. for $C_{16}H_{13}ClFN_3OS$, 349.0. m/z found, 349.9 [M+H]$^+$. $^1$H NMR (400 MHz, CD$_3$OD) δ 8.59 (d, J=1.8 Hz, 1H), 8.05 (s, 1H), 7.49 (d, J=2.3 Hz, 1H), 7.33 (d, J=3.9 Hz, 1H), 7.04 (d, J=3.9 Hz, 1H), 4.94 (s, 2H), 4.36-4.28 (m, 2H), 4.07 (t, J=7.8 Hz, 2H), 2.44-2.34 (m, 2H).

Example 183

6-(4-Fluoro-3-methyl-phenyl)-1-(pyrimidin-2-ylmethyl)pyrrolo[3,2-b]pyridine trifluoroacetate salt

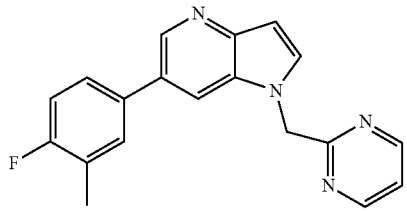 [SMILES: Cc1cc(-c2cnc3ccn(Cc4ncccn4)c3c2)ccc1F]

The title compound was prepared in a manner analogous to Example 170 using 6-(4-fluoro-3-methylphenyl)-1H-pyrrolo[3,2-b]pyridine and 2-(chloromethyl)pyrimidine. MS (ESI): mass calcd. for $C_{19}H_{15}FN_4$, 318.1. m/z found, 319.2 [M+H]$^+$. $^1$H NMR (500 MHz, CD$_3$OD) δ 8.86-8.82 (m, 2H), 8.73 (d, J=5.0 Hz, 2H), 8.19 (d, J=3.3 Hz, 1H), 7.67 (dd, J=7.2, 2.5 Hz, 1H), 7.62-7.57 (m, 1H), 7.39 (t, J=4.9 Hz, 1H), 7.21 (t, J=9.0 Hz, 1H), 6.92 (dd, J=3.3, 0.9 Hz, 1H), 5.93 (s, 2H), 2.37 (d, J=2.0 Hz, 3H).

Example 184

(R/S)-6-(4-Fluoro-3-methyl-phenyl)-1-(oxetan-2-yl)methyl)pyrrolo[3,2-b]pyridine trifluoroacetate salt

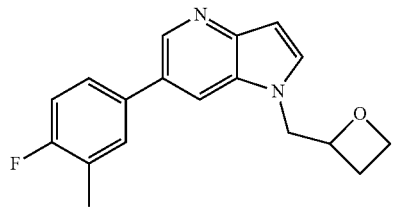 [SMILES: Cc1cc(-c2cnc3ccn(CC4CCO4)c3c2)ccc1F]

The title compound was prepared in a manner analogous to Example 170. MS (ESI): mass calcd. for $C_{18}H_{17}FN_2O$, 296.1. m/z found, 297.2 [M+H]$^+$.

Example 185

1-(3,3-Difluoroazetidin-1-yl)-2-[3-fluoro-6-(4-fluoro-3-methyl-phenyl)pyrrolo[3,2-b]pyridin-1-yl]ethanone

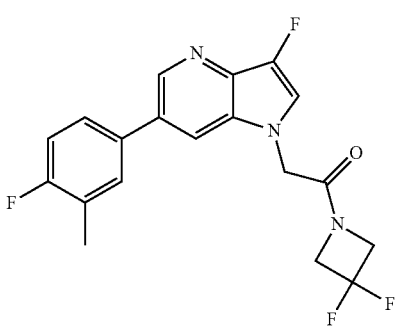 [SMILES: Cc1cc(-c2cnc3c(F)cn(CC(=O)N4CC(F)(F)C4)c3c2)ccc1F]

The title compound was prepared in a manner analogous to Example 92, using 2-(6-bromo-3-fluoro-1H-pyrrolo[3,2-b]pyridin-1-yl)-1-(3,3-difluoroazetidin-1-yl)ethanone (Intermediate 16) and (4-fluoro-3-methylphenyl)boronic acid. MS (ESI): mass calcd. for $C_{19}H_{18}F_4N_3O$, 377.1; m/z found, 378.0 [M+H]$^+$. $^1$H NMR (500 MHz, DMSO-d$_6$) δ 8.67 (d, J=1.8 Hz, 1H), 8.16 (t, J=2.2 Hz, 1H), 7.70-7.65 (m, 1H), 7.63 (d, J=2.1 Hz, 1H), 7.62-7.56 (m, 1H), 7.32-7.21 (m, 1H), 5.08 (s, 2H), 4.73 (t, J=12.3 Hz, 2H), 4.37 (t, J=12.6 Hz, 2H), 2.33 (d, J=1.9 Hz, 3H).

Example 186

1-Cyclopropyl-2-[6-(4-fluoro-3-methyl-phenyl)pyrrolo[3,2-b]pyridin-1-yl]ethanone trifluoroacetate salt

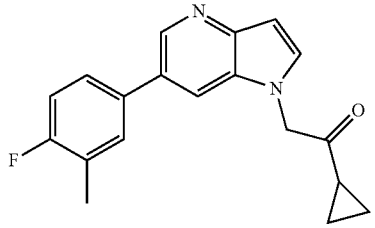 [SMILES: Cc1cc(-c2cnc3ccn(CC(=O)C4CC4)c3c2)ccc1F]

The title compound was prepared in a manner analogous to Example 170 using 6-(4-fluoro-3-methylphenyl)-1H-pyrrolo[3,2-b]pyridine and 2-bromo-1-cyclopropylethanone. MS (ESI): mass calcd. for $C_{19}H_{17}FN_2O$, 308.1. m/z found, 309.2 [M+H]$^+$. $^1$H NMR (500 MHz, DMSO-d$_6$) δ 13.05 (s, 1H), 9.05 (s, 1H), 8.85 (s, 1H), 8.33-8.28 (m, 1H), 7.81-7.76 (m, 1H), 7.72-7.66 (m, 1H), 7.38 (t, J=9.1 Hz, 1H), 7.02 (s, 1H), 6.12 (s, 2H), 2.41-2.31 (m, 4H), 1.18-1.11 (m, 2H), 1.08-1.00 (m, 2H).

Example 187

1-[6-(4-Fluoro-3-methyl-phenyl)pyrrolo[3,2-b]pyridin-1-yl]-3-methyl-butan-2-one trifluoroacetate salt

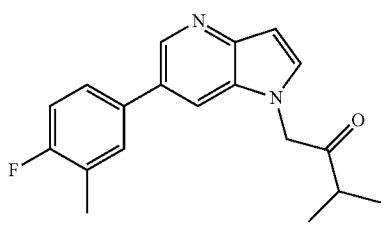 [SMILES: Cc1cc(-c2cnc3ccn(CC(=O)C(C)C)c3c2)ccc1F]

The title compound was prepared in a manner analogous to Example 170 using 6-(4-fluoro-3-methylphenyl)-1H-pyrrolo[3,2-b]pyridine and 1-bromo-3-methylbutan-2-one. MS (ESI): mass calcd. for $C_{19}H_{19}FN_2O$, 310.1. m/z found, 311.2 [M+H]$^+$. $^1$H NMR (400 MHz, DMSO-d$_6$) δ 13.03 (s, 1H), 9.01 (d, J=1.5 Hz, 1H), 8.87-8.84 (m, 1H), 8.32 (t, J=3.1 Hz, 1H), 7.78 (dd, J=7.6, 2.4 Hz, 1H), 7.73-7.66 (m, 1H), 7.43-7.36 (m, 1H), 7.00-6.96 (m, 1H), 6.05 (s, 2H), 3.05-2.97 (m, 1H), 2.36 (d, J=1.9 Hz, 3H), 1.21 (d, J=6.9 Hz, 6H).

Example 188

2-[6-(4-Fluoro-3-methyl-phenyl)pyrrolo[3,2-b]pyridin-1-yl]-1-(4-hydroxy-1-piperidyl)ethanone trifluoroacetate salt

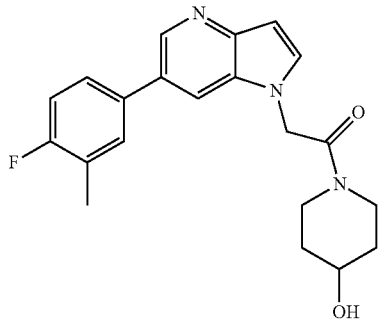

The title compound was prepared in a manner analogous to Example 66. MS (ESI): mass calcd. for $C_{21}H_{22}FN_3O_2$, 367.2. m/z found, 368.2 [M+H]$^+$. $^1$H NMR (500 MHz, DMSO-d$_6$) δ 8.97 (d, J=1.5 Hz, 1H), 8.91 (s, 1H), 8.11 (d, J=3.3 Hz, 1H), 7.79 (dd, J=7.4, 2.5 Hz, 1H), 7.73-7.68 (m, 1H), 7.37 (t, J=9.1 Hz, 1H), 6.86 (d, J=3.3 Hz, 1H), 5.51 (s, 2H), 3.87-3.74 (m, 4H), 3.12-3.04 (m, 2H), 2.35 (d, J=1.8 Hz, 3H), 1.92-1.85 (m, 1H), 1.76-1.68 (m, 1H), 1.58-1.50 (m, 1H), 1.35-1.26 (m, 1H).

Example 189

(R/S)-1-(3-Azabicyclo[3.1.0]hexan-3-yl)-2-[6-(4-fluoro-3-methyl-phenyl)pyrrolo[3,2-b]pyridin-1-yl]ethanone trifluoroacetate salt

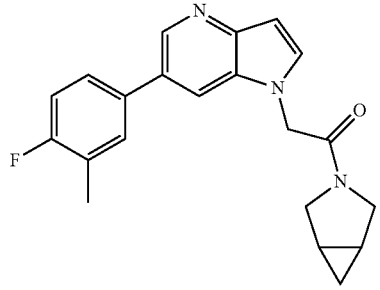 [SMILES: Cc1cc(-c2cnc3ccn(CC(=O)N4CC5CC5C4)c3c2)ccc1F]

The title compound was prepared in a manner analogous to Example 66. MS (ESI): mass calcd. for $C_{21}H_{20}FN_3O$, 349.2. m/z found, 350.2 [M+H]$^+$. $^1$H NMR (500 MHz, DMSO-d$_6$) δ 8.92 (s, 1H), 8.79 (s, 1H), 8.01 (d, J=3.4 Hz, 1H), 7.76 (dd, J=7.2, 2.4 Hz, 1H), 7.71-7.65 (m, 1H), 7.35 (t, J=9.1 Hz, 1H), 6.81 (d, J=3.2 Hz, 1H), 5.37 (d, J=17.3 Hz, 1H), 5.24 (d, J=17.2 Hz, 1H), 3.77-3.68 (m, 2H), 3.57 (d, J=11.6 Hz, 2H), 2.35 (s, 3H), 1.77-1.70 (m, 1H), 1.62-1.55 (m, 1H), 0.81-0.73 (m, 1H), 0.24-0.19 (m, 1H).

Example 190

2-[6-(4-Fluoro-3-methyl-phenyl)pyrrolo[3,2-b]pyridin-1-yl]-1-(4-methoxy-1-piperidyl)ethanone trifluoroacetate salt

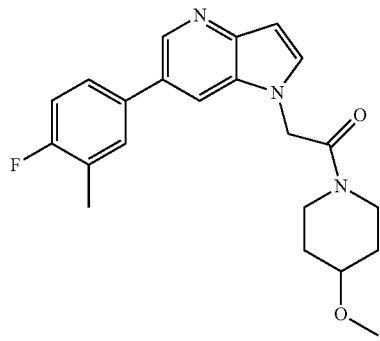 [SMILES: COC1CCN(C(=O)Cn2ccc3ncc(-c4ccc(F)c(C)c4)cc32)CC1]

The title compound was prepared in a manner analogous to Example 66. MS (ESI): mass calcd. for $C_{22}H_{24}FN_3O_2$, 381.2. m/z found, 382.2 [M+H]$^+$. $^1$H NMR (500 MHz, CDCl$_3$) δ 8.61 (d, J=1.7 Hz, 1H), 8.19 (s, 1H), 7.54 (d, J=3.3 Hz, 1H), 7.38-7.35 (m, 1H), 7.34-7.29 (m, 1H), 7.10 (t, J=8.8 Hz, 1H), 6.86 (dd, J=3.3, 0.9 Hz, 1H), 5.22 (d, J=16.9 Hz, 1H), 5.14 (d, J=16.9 Hz, 1H), 3.80-3.72 (m, 2H), 3.56-3.49 (m, 2H), 3.48-3.41 (m, 1H), 3.38 (s, 3H), 2.34 (d, J=1.9 Hz, 3H), 1.99-1.90 (m, 1H), 1.88-1.80 (m, 1H), 1.80-1.72 (m, 1H), 1.70-1.62 (m, 1H).

Example 191

2-[6-(4-Fluoro-3-methyl-phenyl)pyrrolo[3,2-b]pyridin-1-yl]-1-(4-fluoro-1-piperidyl)ethanone trifluoroacetate salt

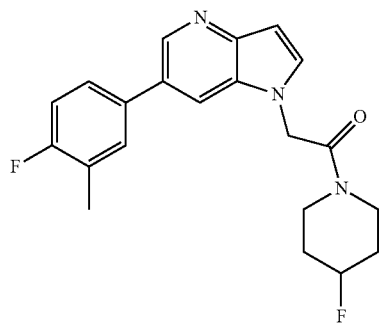 [SMILES: Cc1cc(-c2cnc3ccn(CC(=O)N4CCC(F)CC4)c3c2)ccc1F]

The title compound was prepared in a manner analogous to Example 66. MS (ESI): mass calcd. for $C_{21}H_{21}F_2N_3O$, 369.2. m/z found, 370.2 [M+H]$^+$. $^1$H NMR (500 MHz, CDCl$_3$) δ 8.66 (d, J=1.6 Hz, 1H), 8.20 (s, 1H), 7.56 (d, J=3.4 Hz, 1H), 7.38 (dd, J=7.0, 2.4 Hz, 1H), 7.36-7.31 (m, 1H), 7.12 (t, J=8.7 Hz, 1H), 6.94-6.91 (m, 1H), 5.23 (d, J=16.8 Hz, 1H), 5.16 (d, J=16.8 Hz, 1H), 5.04-4.87 (m, 1H), 4.04-3.96 (m, 1H), 3.77-3.68 (m, 1H), 3.67-3.59 (m, 1H), 3.50-3.40 (m, 1H), 2.35 (d, J=1.9 Hz, 3H), 2.11-2.02 (m, 1H), 2.01-1.87 (m, 2H), 1.86-1.78 (m, 1H).

Example 192

2-[6-(4-Fluoro-3-methyl-phenyl)pyrrolo[3,2-b]pyridin-1-yl]-1-[4-(fluoromethyl)-1-piperidyl]ethanone trifluoroacetate salt

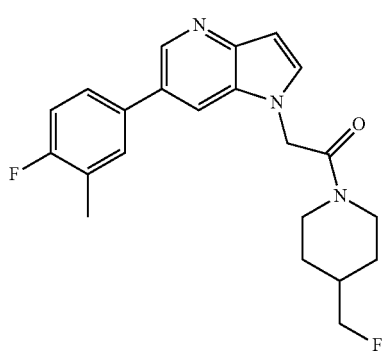 [SMILES: Cc1cc(-c2cnc3ccn(CC(=O)N4CCC(CF)CC4)c3c2)ccc1F]

The title compound was prepared in a manner analogous to Example 66. MS (ESI): mass calcd. for $C_{22}H_{23}F_2N_3O$, 383.2. m/z found, 384.2 [M+H]$^+$. $^1$H NMR (500 MHz, CDCl$_3$) δ 8.57 (s, 1H), 8.25 (s, 1H), 7.57 (d, J=3.2 Hz, 1H), 7.37-7.34 (m, 1H), 7.34-7.29 (m, 1H), 7.10 (t, J=8.7 Hz, 1H), 6.82 (d, J=3.2 Hz, 1H), 5.24 (d, J=17.0 Hz, 1H), 5.19 (d, J=17.0 Hz, 1H), 4.58 (d, J=13.5 Hz, 1H), 4.43-4.34 (m, 1H), 4.33-4.24 (m, 1H), 3.97 (d, J=13.8 Hz, 1H), 3.33-3.23 (m, 1H), 2.77-2.67 (m, 1H), 2.33 (d, J=1.9 Hz, 3H), 2.09-1.91 (m, 2H), 1.80 (d, J=13.5 Hz, 1H), 1.49-1.38 (m, 1H), 1.37-1.26 (m, 1H).

Example 193

2-[6-(4-Fluoro-3-methyl-phenyl)pyrrolo[3,2-b]pyridin-1-yl]-1-(1-piperidyl)ethanone trifluoroacetate salt

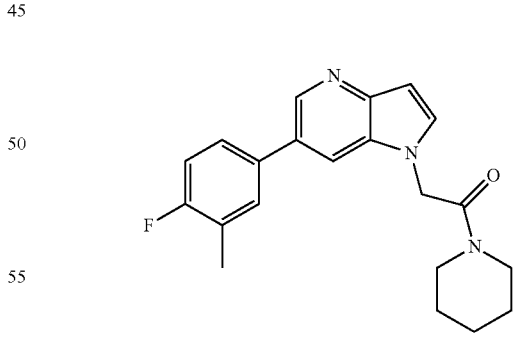

The title compound was prepared in a manner analogous to Example 66. MS (ESI): mass calcd. for $C_{21}H_{22}FN_3O$, 351.2. m/z found, 352.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=0.95 min at 254 nm.

Example 194

(R/S)-2-[6-(4-Fluoro-3-methyl-phenyl)pyrrolo[3,2-b]pyridin-1-yl]-1-(2-methylmorpholin-4-yl)ethanone trifluoroacetate salt

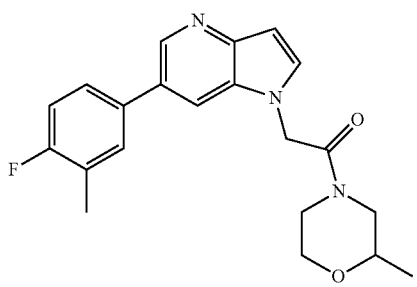 [SMILES: Cc1cc(-c2cnc3ccn(CC(=O)N4CCOC(C)C4)c3c2)ccc1F]

The title compound was prepared in a manner analogous to Example 66. MS (ESI): mass calcd. for $C_{21}H_{22}FN_3O_2$, 367.2. m/z found, 368.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.89 min. at 254 nm.

Example 195

(R/S)-2-[6-(4-Fluoro-3-methyl-phenyl)pyrrolo[3,2-b]pyridin-1-yl]-1-[3-(trifluoromethyl)-1-piperidyl]ethanone trifluoroacetate salt

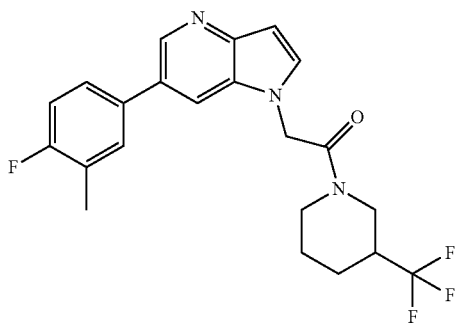 [SMILES: Cc1cc(-c2cnc3ccn(CC(=O)N4CCCC(C(F)(F)F)C4)c3c2)ccc1F]

The title compound was prepared in a manner analogous to Example 66. MS (ESI): mass calcd. for $C_{22}H_{21}F_4N_3O$, 419.2. m/z found, 420.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.03 min at 254 nm.

Example 196

(R/S)-1-(2-Ethylpyrrolidin-1-yl)-2-[6-(4-fluoro-3-methyl-phenyl)pyrrolo[3,2-b]pyridin-1-yl]ethanone trifluoroacetate salt

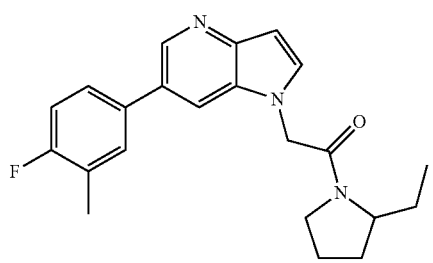 [SMILES: CCC1CCCN1C(=O)Cn1ccc2ncc(-c3ccc(F)c(C)c3)cc21]

The title compound was prepared in a manner analogous to Example 66. MS (ESI): mass calcd. for $C_{22}H_{24}FN_3O$, 365.2. m/z found, 366.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.99 min at 254 nm.

Example 197

1-(2,2-Dimethylmorpholin-4-yl)-2-[6-(4-fluoro-3-methyl-phenyl)pyrrolo[3,2-b]pyridin-1-yl]ethanone trifluoroacetate salt

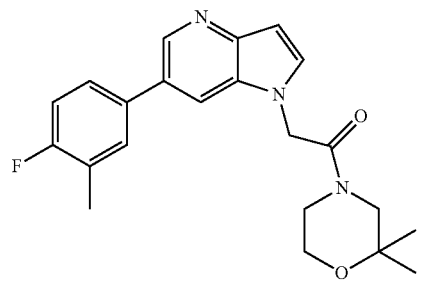 [SMILES: Cc1cc(-c2cnc3ccn(CC(=O)N4CCOC(C)(C)C4)c3c2)ccc1F]

The title compound was prepared in a manner analogous to Example 66. MS (ESI): mass calcd. for $C_{22}H_{24}FN_3O_2$, 381.2. m/z found, 382.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.91 min at 254 nm.

Example 198

(R/S)-2-[6-(4-Fluoro-3-methyl-phenyl)pyrrolo[3,2-b]pyridin-1-yl]-1-(3-methoxypyrrolidin-1-yl)ethanone trifluoroacetate salt

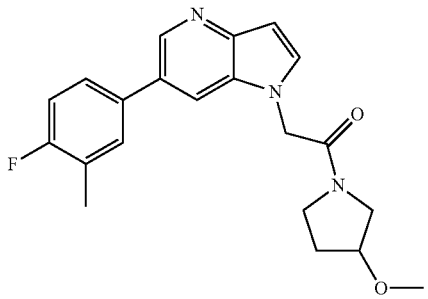 [SMILES: COC1CCN(C(=O)Cn2ccc3ncc(-c4ccc(F)c(C)c4)cc32)C1]

The title compound was prepared in a manner analogous to Example 66. MS (ESI): mass calcd. for $C_{21}H_{22}FN_3O_2$, 367.2. m/z found, 368.2 $[M+H]^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.88 min at 254 nm.

Example 199

(R/S)-2-[6-(4-Fluoro-3-methyl-phenyl)pyrrolo[3,2-b]pyridin-1-yl]-1-(3-fluoro-1-piperidyl)ethanone trifluoroacetate salt

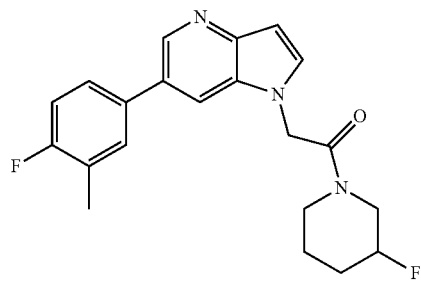 [SMILES: Cc1cc(-c2cnc3ccn(CC(=O)N4CCCC(F)C4)c3c2)ccc1F]

The title compound was prepared in a manner analogous to Example 66. MS (ESI): mass calcd. for $C_{21}H_{21}F_2N_3O$, 369.2. m/z found, 370.2 $[M+H]^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.92 min at 254 nm.

Example 200

1-(2,2-Dimethylpyrrolidin-1-yl)-2-[6-(4-fluoro-3-methyl-phenyl)pyrrolo[3,2-b]pyridin-1-yl]ethanone trifluoroacetate salt

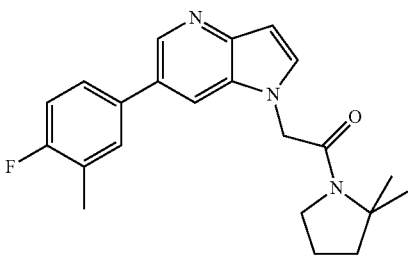 [SMILES: Cc1cc(-c2cnc3ccn(CC(=O)N4CCCC4(C)C)c3c2)ccc1F]

The title compound was prepared in a manner analogous to Example 66. MS (ESI): mass calcd. for $C_{22}H_{24}FN_3O$, 365.2. m/z found, 366.2 $[M+H]^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.00 min at 254 nm.

Example 201

2-[6-(4-Fluoro-3-methyl-phenyl)pyrrolo[3,2-b]pyridin-1-yl]-1-[(3R)-3-fluoropyrrolidin-1-yl]ethanone trifluoroacetate salt

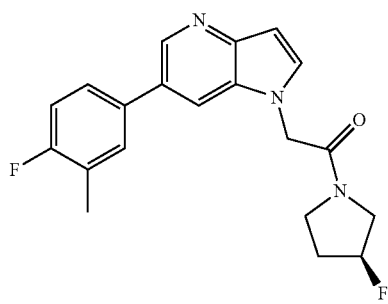 [SMILES: Cc1cc(-c2cnc3ccn(CC(=O)N4CC[C@H](F)C4)c3c2)ccc1F]

The title compound was prepared in a manner analogous to Example 66. MS (ESI): mass calcd. for $C_{20}H_{19}F_2N_3O$, 355.1. m/z found, 356.2 $[M+H]^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.31 min at 254 nm.

Example 202

2-[6-(4-Fluorophenyl)pyrrolo[3,2-b]pyridin-1-yl]-1-(3-hydroxy-3-methyl-azetidin-1-yl)ethanone

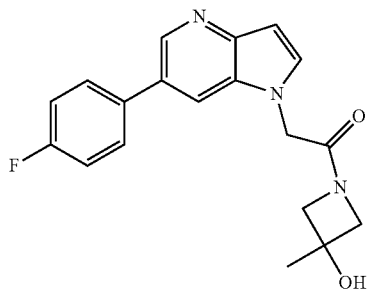 [SMILES: CC1(O)CN(C(=O)Cn2ccc3ncc(-c4ccc(F)cc4)cc32)C1]

The title compound was prepared in a manner analogous to Example 66. MS (ESI): mass calcd. for $C_{19}H_{18}FN_3O_2$, 339.1. m/z found, 340.2 [M+H]$^+$. $^1$H NMR (400 MHz, DMSO-d$_6$) δ 8.64 (d, J=2.0 Hz, 1H), 8.11-8.08 (m, 1H), 7.82-7.75 (m, 2H), 7.61 (d, J=3.3 Hz, 1H), 7.39-7.30 (m, 2H), 6.61 (dd, J=3.2, 1.0 Hz, 1H), 5.69 (s, 1H), 5.04 (s, 2H), 4.07-3.99 (m, 2H), 3.80-3.69 (m, 2H), 1.40 (s, 3H).

Example 203

2-[6-(4-Fluorophenyl)pyrrolo[3,2-b]pyridin-1-yl]-1-[3-hydroxy-3-(trifluoromethyl)azetidin-1-yl]ethanone

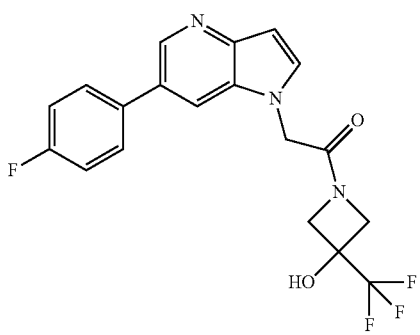 [SMILES: O=C(Cn1ccc2ncc(-c3ccc(F)cc3)cc21)N1CC(O)(C(F)(F)F)C1]

The title compound was prepared in a manner analogous to Example 66. MS (ESI): mass calcd. for $C_{19}H_{15}F_4N_3O_2$, 393.1. m/z found, 394.1 [M+H]$^+$. $^1$H NMR (400 MHz, DMSO-d$_6$) δ 8.64 (d, J=2.0 Hz, 1H), 8.11-8.08 (m, 1H), 7.80-7.74 (m, 2H), 7.63 (d, J=3.3 Hz, 1H), 7.51 (s, 1H), 7.38-7.30 (m, 2H), 6.62 (dd, J=3.3, 0.9 Hz, 1H), 5.12 (s, 2H), 4.47 (d, J=10.0 Hz, 1H), 4.24 (d, J=9.9 Hz, 1H), 4.14 (d, J=10.8 Hz, 1H), 3.91 (d, J=10.8 Hz, 1H).

Example 204

1-(3-Fluoroazetidin-1-yl)-2-[6-(4-fluorophenyl)pyrrolo[3,2-b]pyridin-1-yl]ethanone

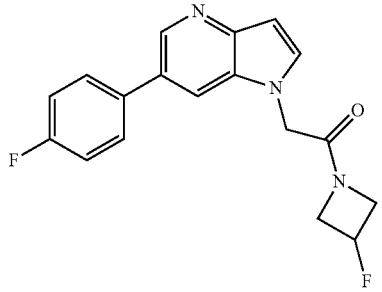 [SMILES: O=C(Cn1ccc2ncc(-c3ccc(F)cc3)cc21)N1CC(F)C1]

The title compound was prepared in a manner analogous to Example 66. MS (ESI): mass calcd. for $C_{18}H_{15}F_2N_3O$, 327.1. m/z found, 328.1 [M+H]$^+$. $^1$H NMR (400 MHz, DMSO-d$_6$) δ 8.64 (d, J=1.9 Hz, 1H), 8.12-8.08 (m, 1H), 7.81-7.74 (m, 2H), 7.60 (d, J=3.3 Hz, 1H), 7.38-7.30 (m, 2H), 6.61 (dd, J=3.2, 0.9 Hz, 1H), 5.55-5.35 (m, 1H), 5.07 (d, J=2.3 Hz, 2H), 4.61-4.45 (m, 1H), 4.38-4.17 (m, 2H), 4.04-3.88 (m, 1H).

Example 205

N-Cyclopropyl-2-[6-(4-fluorophenyl)pyrrolo[3,2-b]pyridin-1-yl]-N-methyl-acetamide

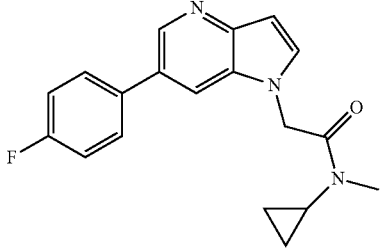 [SMILES: CN(C(=O)Cn1ccc2ncc(-c3ccc(F)cc3)cc21)C1CC1]

The title compound was prepared in a manner analogous to Example 66. MS (ESI): mass calcd. for $C_{19}H_{18}FN_3O$, 323.1. m/z found, 324.2 [M+H]$^+$. $^1$H NMR (500 MHz, DMSO-d$_6$) δ 8.62 (d, J=2.0 Hz, 1H), 8.09 (s, 1H), 7.82-7.74 (m, 2H), 7.62 (d, J=3.2 Hz, 1H), 7.37-7.29 (m, 2H), 6.58 (d, J=3.3 Hz, 1H), 5.35 (s, 2H), 3.00-2.95 (m, 1H), 2.83 (s, 3H), 1.02-0.95 (m, 2H), 0.93 (dd, J=7.0, 4.6 Hz, 2H).

Example 206

2-[6-(4-Fluorophenyl)pyrrolo[3,2-b]pyridin-1-yl]-1-[3-(hydroxymethyl)azetidin-1-yl]ethanone

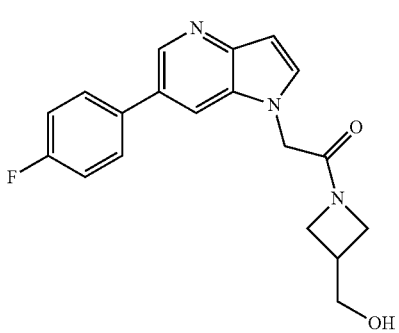 [SMILES: O=C(Cn1ccc2ncc(-c3ccc(F)cc3)cc21)N1CC(CO)C1]

The title compound was prepared in a manner analogous to Example 66. MS (ESI): mass calcd. for $C_{19}H_{18}FN_3O_2$, 339.1. m/z found, 340.2 [M+H]$^+$. $^1$H NMR (500 MHz, DMSO-d$_6$) δ 8.65-8.61 (m, 1H), 8.10-8.06 (m, 1H), 7.81-7.75 (m, 2H), 7.61-7.58 (m, 1H), 7.37-7.30 (m, 2H), 6.59 (d, J=3.3 Hz, 1H), 5.01 (s, 2H), 4.83 (t, J=5.1 Hz, 1H), 4.20 (t, J=8.3 Hz, 1H), 3.96-3.86 (m, 2H), 3.65-3.60 (m, 1H), 3.57-3.51 (m, 2H), 2.77-2.67 (m, 1H).

Example 207

2-[6-(4-Fluorophenyl)pyrrolo[3,2-b]pyridin-1-yl]-1-(3-methoxyazetidin-1-yl)ethanone

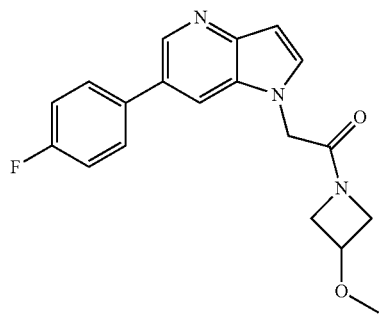 [SMILES: COC1CN(C(=O)Cn2ccc3ncc(-c4ccc(F)cc4)cc32)C1]

The title compound was prepared in a manner analogous to Example 66. MS (ESI): mass calcd. for $C_{19}H_{18}FN_3O_2$, 339.1. m/z found, 340.2 [M+H]$^+$. $^1$H NMR (500 MHz, DMSO-d$_6$) δ 8.65-8.61 (m, 1H), 8.11-8.06 (m, 1H), 7.82-7.74 (m, 2H), 7.62-7.57 (m, 1H), 7.37-7.30 (m, 2H), 6.61-6.58 (m, 1H), 5.04 (s, 2H), 4.41-4.34 (m, 1H), 4.29-4.22 (m, 1H), 4.11-4.02 (m, 2H), 3.75-3.68 (m, 1H), 3.23 (s, 3H).

Example 208

1-(5-Azaspiro[2.3]hexan-5-yl)-2-[6-(4-fluoro-3-methyl-phenyl)pyrrolo[3,2-b]pyridin-1-yl]ethanone trifluoroacetate salt

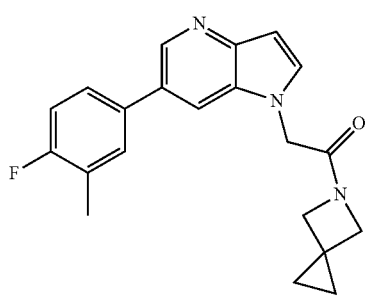 [SMILES: Cc1cc(-c2cnc3ccn(CC(=O)N4CC5(CC5)C4)c3c2)ccc1F]

The title compound was prepared in a manner analogous to Example 66. MS (ESI): mass calcd. for $C_{21}H_{20}FN_3O$, 349.2. m/z found, 350.2 [M+H]$^+$. $^1$H NMR (500 MHz, DMSO-d$_6$) δ 9.00 (s, 1H), 8.96 (s, 1H), 8.11 (d, J=3.2 Hz, 1H), 7.83-7.79 (m, 1H), 7.75-7.69 (m, 1H), 7.38 (t, J=9.1 Hz, 1H), 6.87 (d, J=3.3 Hz, 1H), 5.29 (s, 2H), 4.35 (s, 2H), 3.99 (s, 2H), 2.36 (s, 3H), 0.74-0.65 (m, 4H).

Example 209

2-[6-(4-Fluoro-3-methyl-phenyl)pyrrolo[3,2-b]pyridin-1-yl]-1-(4-hydroxy-4-methyl-1-piperidyl)ethanone trifluoroacetate salt

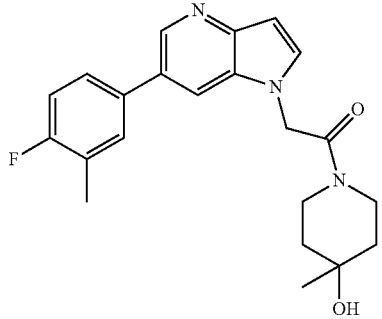 [SMILES: Cc1cc(-c2cnc3ccn(CC(=O)N4CCC(C)(O)CC4)c3c2)ccc1F]

The title compound was prepared in a manner analogous to Example 66. MS (ESI): mass calcd. for $C_{22}H_{24}FN_3O_2$, 381.2. m/z found, 382.2 [M+H]$^+$.

Example 210

(R/S)-2-[6-(4-Fluoro-3-methyl-phenyl)pyrrolo[3,2-b]pyridin-1-yl]-1-(3-methylmorpholin-4-yl)ethanone trifluoroacetate salt

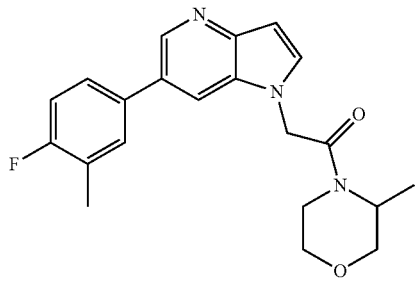 [SMILES: Cc1cc(-c2cnc3ccn(CC(=O)N4CCOCC4C)c3c2)ccc1F]

The title compound was prepared in a manner analogous to Example 66. MS (ESI): mass calcd. for $C_{21}H_{22}FN_3O_2$, 367.2. m/z found, 368.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=0.88 min at 254 nm.

Example 211

2-[6-(4-Fluorophenyl)pyrrolo[3,2-b]pyridin-1-yl]-1-(3-hydroxyazetidin-1-yl)ethanone

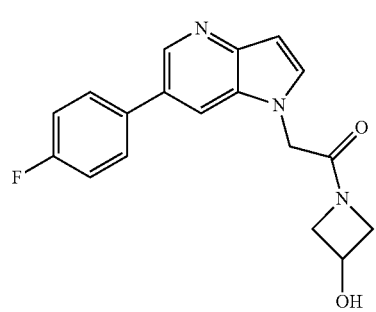 [SMILES: O=C(Cn1ccc2ncc(-c3ccc(F)cc3)cc21)N1CC(O)C1]

The title compound was prepared in a manner analogous to Example 66. MS (ESI): mass calcd. for $C_{18}H_{16}FN_3O_2$, 325.1. m/z found, 326.2 [M+H]$^+$. $^1$H NMR (500 MHz, DMSO-d$_6$) δ 8.63 (d, J=2.0 Hz, 1H), 8.10-8.08 (m, 1H), 7.80-7.76 (m, 2H), 7.60 (d, J=3.3 Hz, 1H), 7.36-7.31 (m, 2H), 6.61-6.59 (m, 1H), 5.78 (d, J=5.7 Hz, 1H), 5.03 (d, J=2.8 Hz, 2H), 4.55-4.47 (m, 1H), 4.38-4.33 (m, 1H), 4.12-4.07 (m, 1H), 3.96-3.91 (m, 1H), 3.65-3.61 (m, 1H).

Example 212

1-[2-[6-(4-Fluorophenyl)pyrrolo[3,2-b]pyridin-1-yl]acetyl]azetidine-3-carbonitrile

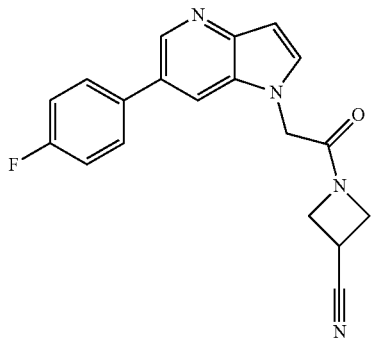 [SMILES: N#CC1CN(C(=O)Cn2ccc3ncc(-c4ccc(F)cc4)cc32)C1]

The title compound was prepared in a manner analogous to Example 66. MS (ESI): mass calcd. for $C_{19}H_{15}FN_4O$, 334.1. m/z found, 335.1 [M+H]$^+$. $^1$H NMR (400 MHz, DMSO-d$_6$) δ 8.64 (d, J=2.0 Hz, 1H), 8.11-8.08 (m, 1H), 7.81-7.75 (m, 2H), 7.59 (d, J=3.3 Hz, 1H), 7.37-7.31 (m, 2H), 6.61 (dd, J=3.3, 0.9 Hz, 1H), 5.05 (s, 2H), 4.52-4.36 (m, 1H), 4.23-4.16 (m, 1H), 4.12-4.01 (m, 2H), 3.91-3.81 (m, 1H).

Example 213

1-(3,3-Difluoroazetidin-1-yl)-2-[6-(4-fluorophenyl)pyrrolo[3,2-b]pyridin-1-yl]ethanone

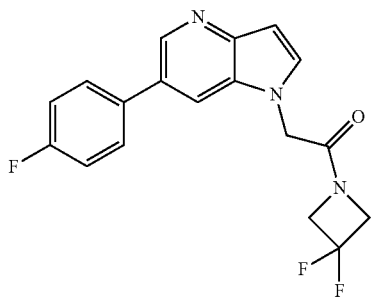 [SMILES: O=C(Cn1ccc2ncc(-c3ccc(F)cc3)cc21)N1CC(F)(F)C1]

The title compound was prepared in a manner analogous to Example 66. MS (ESI): mass calcd. for $C_{18}H_{14}F_3N_3O$, 345.1. m/z found, 346.2 [M+H]$^+$. $^1$H NMR (500 MHz, DMSO-d$_6$) δ 8.64 (d, J=2.0 Hz, 1H), 8.12-8.10 (m, 1H), 7.80-7.75 (m, 2H), 7.59 (d, J=3.3 Hz, 1H), 7.37-7.31 (m, 2H), 6.62 (dd, J=3.3, 0.9 Hz, 1H), 5.14 (s, 2H), 4.75-4.68 (m, 2H), 4.41-4.33 (m, 2H).

Example 214

2-[6-(4-Fluorophenyl)pyrrolo[3,2-b]pyridin-1-yl]-1-(3-methylazetidin-1-yl)ethanone

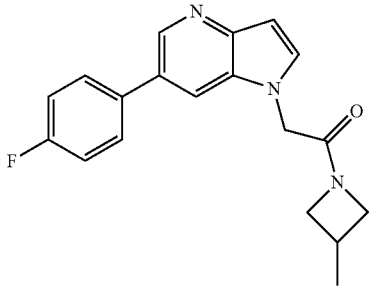 [SMILES: CC1CN(C(=O)Cn2ccc3ncc(-c4ccc(F)cc4)cc32)C1]

The title compound was prepared in a manner analogous to Example 66. MS (ESI): mass calcd. for $C_{19}H_{18}FN_3O$, 323.1. m/z found, 324.2 [M+H]$^+$. $^1$H NMR (500 MHz, DMSO-d$_6$) δ 8.63 (d, J=2.0 Hz, 1H), 8.10-8.08 (m, 1H), 7.80-7.76 (m, 2H), 7.60 (d, J=3.3 Hz, 1H), 7.37-7.31 (m, 2H), 6.60 (dd, J=3.3, 0.9 Hz, 1H), 5.00 (s, 2H), 4.30 (t, J=8.4 Hz, 1H), 4.01 (t, J=8.9 Hz, 1H), 3.76 (dd, J=8.4, 5.6 Hz, 1H), 3.46 (dd, J=9.5, 5.6 Hz, 1H), 2.77-2.68 (m, 1H), 1.21 (d, J=6.9 Hz, 3H).

Example 215

1-(3,3-Dimethylazetidin-1-yl)-2-[6-(4-fluorophenyl)pyrrolo[3,2-b]pyridin-1-yl]ethanone

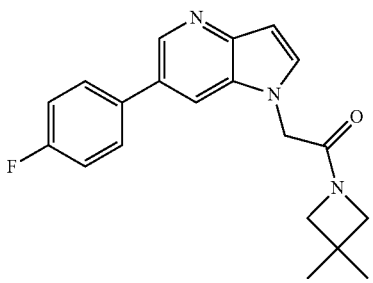 [SMILES: CC1(C)CN(C(=O)Cn2ccc3ncc(-c4ccc(F)cc4)cc32)C1]

The title compound was prepared in a manner analogous to Example 66. MS (ESI): mass calcd. for $C_{20}H_{20}FN_3O$, 337.2. m/z found, 338.2 [M+H]$^+$. $^1$H NMR (500 MHz, DMSO-d$_6$) δ 8.64 (d, J=2.0 Hz, 1H), 8.12 (s, 1H), 7.81-7.75 (m, 2H), 7.62 (d, J=3.3 Hz, 1H), 7.37-7.30 (m, 2H), 6.60 (d, J=3.3 Hz, 1H), 5.02 (s, 2H), 3.88 (s, 2H), 3.59 (s, 2H), 1.25 (s, 6H).

Example 216

1-[2-[6-(4-Fluorophenyl)pyrrolo[3,2-b]pyridin-1-yl]acetyl]pyrrolidin-3-one trifluoroacetate salt

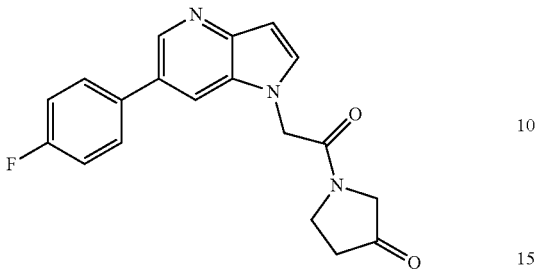

The title compound was prepared in a manner analogous to Example 66. MS (ESI): mass calcd. for $C_{19}H_{18}FN_3O_2$, 337.1. m/z found, 338.1 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.75 min at 254 nm.

Example 217

1-(3,3-Difluoropyrrolidin-1-yl)-2-[6-(4-fluorophenyl)pyrrolo[3,2-b]pyridin-1-yl]ethanone

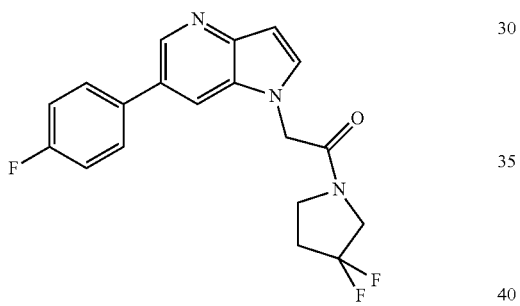

The title compound was prepared in a manner analogous to Example 66. MS (ESI): mass calcd. for $C_{19}H_{18}F_3N_3O$, 359.1. m/z found, 360.1 [M+H]$^+$. $^1$H NMR (500 MHz, DMSO-d$_6$) δ 8.63 (s, 1H), 8.11 (s, 1H), 7.80-7.73 (m, 2H), 7.60-7.56 (m, 1H), 7.37-7.30 (m, 2H), 6.62-6.58 (m, 1H), 5.26 (s, 1H), 5.19 (s, 1H), 4.13 (t, J=13.2 Hz, 1H), 3.90 (t, J=7.4 Hz, 1H), 3.74 (t, J=13.2 Hz, 1H), 3.57 (t, J=7.4 Hz, 1H), 2.64-2.53 (m, 1H), 2.46-2.38 (m, 1H).

Example 218

(R/S)-2-[6-(4-Fluorophenyl)pyrrolo[3,2-b]pyridin-1-yl]-1-(3-hydroxypyrrolidin-1-yl)ethanone

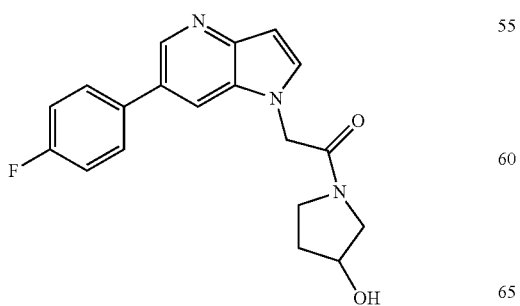

The title compound was prepared in a manner analogous to Example 66. MS (ESI): mass calcd. for $C_{19}H_{18}FN_3O_2$, 339.1. m/z found, 340.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.72 min at 254 nm.

Example 219

1-Cyclopropyl-2-[6-(m-tolyl)pyrrolo[3,2-b]pyridin-1-yl]ethanone

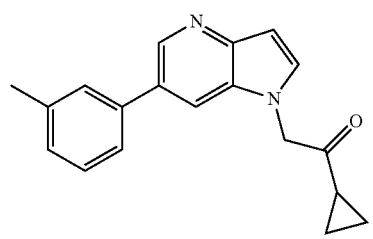 [SMILES: Cc1cccc(-c2cnc3ccn(CC(=O)C4CC4)c3c2)c1]

The title compound was prepared in a manner analogous to Example 75. MS (ESI): mass calcd. for $C_{19}H_{18}N_2O$, 290.1. m/z found, 291.2 [M+H]$^+$. $^1$H NMR (400 MHz, DMSO-d$_6$) δ 8.64 (d, J=1.9 Hz, 1H), 8.08-8.05 (m, 1H), 7.60 (d, J=3.3 Hz, 1H), 7.55 (s, 1H), 7.52 (d, J=7.6 Hz, 1H), 7.37 (t, J=7.6 Hz, 1H), 7.19 (d, J=7.7 Hz, 1H), 6.60 (dd, J=3.2, 0.9 Hz, 1H), 5.48 (s, 2H), 2.40 (s, 3H), 2.13-2.06 (m, 1H), 1.01-0.91 (m, 4H).

Example 220

1-Cyclopropyl-2-(6-phenylpyrrolo[3,2-b]pyridin-1-yl)ethanone

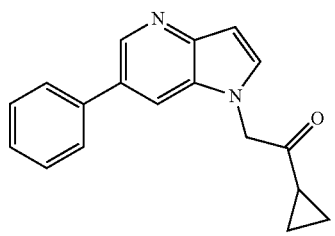 [SMILES: O=C(Cn1ccc2ncc(-c3ccccc3)cc21)C1CC1]

The title compound was prepared in a manner analogous to Example 75. MS (ESI): mass calcd. for $C_{18}H_{16}N_2O$, 276.1. m/z found, 277.1 [M+H]$^+$. $^1$H NMR (400 MHz, DMSO-d$_6$) δ 8.66 (d, J=2.0 Hz, 1H), 8.10-8.08 (m, 1H), 7.77-7.71 (m, 2H), 7.61 (d, J=3.3 Hz, 1H), 7.53-7.47 (m, 2H), 7.41-7.35 (m, 1H), 6.61 (dd, J=3.3, 0.9 Hz, 1H), 5.48 (s, 2H), 2.14-2.06 (m, 1H), 1.02-0.91 (m, 4H).

Example 221

1-Cyclopropyl-2-[6-(3-fluorophenyl)pyrrolo[3,2-b]pyridin-1-yl]ethanone

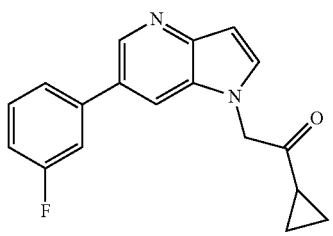 [SMILES: O=C(Cn1ccc2ncc(-c3cccc(F)c3)cc21)C1CC1]

The title compound was prepared in a manner analogous to Example 75. MS (ESI): mass calcd. for $C_{18}H_{16}FN_2O$, 294.1. m/z found, 295.1 [M+H]$^+$. $^1$H NMR (500 MHz, DMSO-d$_6$) δ 8.70 (d, J=2.0 Hz, 1H), 8.19-8.17 (m, 1H), 7.65-7.59 (m, 3H), 7.56-7.50 (m, 1H), 7.23-7.17 (m, 1H), 6.62 (dd, J=3.2, 0.9 Hz, 1H), 5.48 (s, 2H), 2.14-2.07 (m, 1H), 1.02-0.96 (m, 2H), 0.96-0.91 (m, 2H).

Example 222

1-Cyclopropyl-2-[6-(4-fluorophenyl)pyrrolo[3,2-b]pyridin-1-yl]ethanone

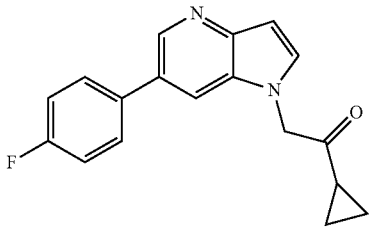 [SMILES: O=C(Cn1ccc2ncc(-c3ccc(F)cc3)cc21)C1CC1]

The title compound was prepared in a manner analogous to Example 75. MS (ESI): mass calcd. for $C_{18}H_{16}FN_2O$, 294.1. m/z found, 295.1 [M+H]$^+$. $^1$H NMR (500 MHz, DMSO-d$_6$) δ 8.63 (d, J=2.0 Hz, 1H), 8.10-8.07 (m, 1H), 7.80-7.74 (m, 2H), 7.61 (d, J=3.3 Hz, 1H), 7.35-7.30 (m, 2H), 6.61 (dd, J=3.3, 0.9 Hz, 1H), 5.47 (s, 2H), 2.13-2.06 (m, 1H), 1.01-0.96 (m, 2H), 0.96-0.92 (m, 2H).

Example 223

1-[6-(4-Fluoro-2,3-dimethyl-phenyl)pyrrolo[3,2-b]pyridin-1-yl]-3-methyl-butan-2-one

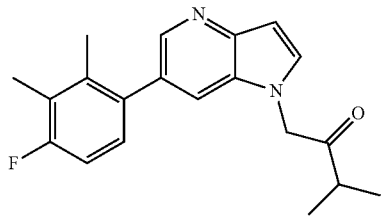 [SMILES: Cc1c(F)ccc(-c2cnc3ccn(CC(=O)C(C)C)c3c2)c1C]

The title compound was prepared in a manner analogous to Example 75. MS (ESI): mass calcd. for $C_{20}H_{21}FN_2O$, 324.2. m/z found, 325.2 [M+H]$^+$. $^1$H NMR (400 MHz, DMSO-d$_6$) δ 8.24 (d, J=1.9 Hz, 1H), 7.70-7.67 (m, 1H), 7.57 (d, J=3.3 Hz, 1H), 7.15-7.05 (m, 2H), 6.62 (dd, J=3.3, 0.9 Hz, 1H), 5.36 (s, 2H), 2.84-2.75 (m, 1H), 2.22 (d, J=2.1 Hz, 3H), 2.15 (s, 3H), 1.10 (d, J=7.0 Hz, 6H).

Example 224

1-[6-(3-Ethylphenyl)pyrrolo[3,2-b]pyridin-1-yl]-3-methyl-butan-2-one

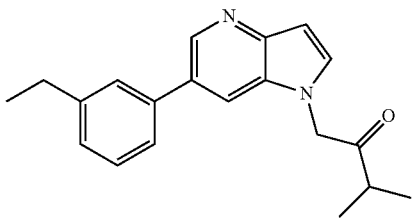 [SMILES: CCc1cccc(-c2cnc3ccn(CC(=O)C(C)C)c3c2)c1]

The title compound was prepared in a manner analogous to Example 75. MS (ESI): mass calcd. for $C_{20}H_{22}N_2O$, 306.2. m/z found, 307.2 [M+H]$^+$. $^1$H NMR (400 MHz, DMSO-d$_6$) δ 8.64 (d, J=2.0 Hz, 1H), 8.02-8.00 (m, 1H), 7.57 (d, J=3.3 Hz, 1H), 7.56-7.54 (m, 1H), 7.54-7.50 (m, 1H), 7.40 (t, J=7.6 Hz, 1H), 7.24-7.20 (m, 1H), 6.61 (dd, J=3.3, 0.9 Hz, 1H), 5.42 (s, 2H), 2.88-2.79 (m, 1H), 2.69 (q, J=7.6 Hz, 2H), 1.24 (t, J=7.6 Hz, 3H), 1.13 (d, J=6.9 Hz, 6H).

Example 225

1-[6-(2,3-Dimethylphenyl)pyrrolo[3,2-b]pyridin-1-yl]-3-methyl-butan-2-one

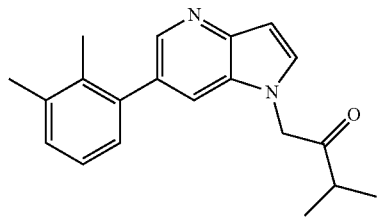 [SMILES: Cc1cccc(-c2cnc3ccn(CC(=O)C(C)C)c3c2)c1C]

The title compound was prepared in a manner analogous to Example 75. MS (ESI): mass calcd. for $C_{20}H_{22}N_2O$, 306.2. m/z found, 307.2 [M+H]$^+$. $^1$H NMR (400 MHz, DMSO-d$_6$) δ 8.28 (d, J=1.8 Hz, 1H), 7.75 (s, 1H), 7.60 (d, J=3.3 Hz, 1H), 7.23-7.14 (m, 2H), 7.09 (dd, J=7.3, 1.8 Hz, 1H), 6.64-6.62 (m, 1H), 5.38 (s, 2H), 2.84-2.75 (m, 1H), 2.31 (s, 3H), 2.12 (s, 3H), 1.10 (d, J=6.9 Hz, 6H).

Example 226

2-[6-(4-Fluorophenyl)pyrrolo[3,2-b]pyridin-1-yl]-1-phenylethanone

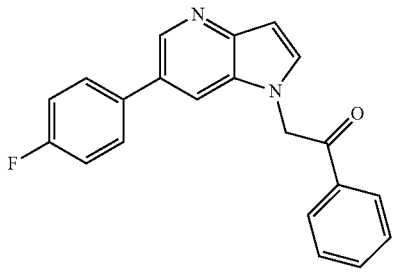 [SMILES: O=C(Cn1ccc2ncc(-c3ccc(F)cc3)cc21)c1ccccc1]

Step A: 6-(4-Fluorophenyl)-1H-pyrrolo[3,2-b]pyridine

To a solution a 6-bromo-1H-pyrrolo[3,2-b]pyridine (5 g, 25 mmol) in dioxane (100 mL) was added 4-fluorophenylboronic acid (4.26 g, 30.5 mmol), Pd(dppf)Cl$_2$ (1.86 g, 2.54 mmol), Cs$_2$CO$_3$ (24.8 g, 76.1 mmol) and water (10 mL). After 16 hours at 90° C. the reaction mixture cooled and was concentrated under reduced pressure. Purification (FCC, SiO$_2$, 0-100% EtOAc in hexanes) afforded the title compound (5.3 g, 98%). MS (ESI): mass calcd. for C$_{13}$H$_9$FN$_2$, 212.1. m/z found, 213.1 [M+H]$^+$.

Step B: 2-[6-(4-Fluorophenyl)pyrrolo[3,2-b]pyridin-1-yl]-1-phenyl-ethanone

To a solution of 6-(4-fluorophenyl)-1H-pyrrolo[3,2-b]pyridine (100 mg, 0.471 mmol) in anhydrous DMF (5 mL) was added NaH (60% dispersion, 26 mg, 0.66 mmol) at 0° C. in small portions under argon. The reaction mixture was warmed to room temperature and stirred for 30 min. The reaction mixture was cooled to 0° C. and to the mixture was added 2-bromoacetophenone (98 mg, 0.495 mmol) in small portions. The reaction mixture was warmed to room temperature and the stirring was continued for 12 h. Water was added to the reaction mixture and the reaction extracted with EtOAc. The organic layers were combined, dried, filtered, and concentrated. Purification by HPLC Method C provided the title compound. MS (ESI): mass calcd. for C$_{21}$H$_{15}$FN$_2$O, 330.1. m/z found, 331.2 [M+H]$^+$. $^1$H NMR (500 MHz, DMSO-d$_6$) δ 8.70-8.60 (s, 1H), 8.28-8.18 (s, 1H), 8.14-7.98 (m, 2H), 7.83-7.70 (m, 3H), 7.70-7.57 (m, 3H), 7.36-7.19 (m, 2H), 6.72-6.57 (d, J=3.4 Hz, 1H), 6.11-5.94 (s, 1H).

Example 227

1-(4-Fluorophenyl)-2-[6-(4-fluorophenyl)pyrrolo[3,2-b]pyridin-1-yl]ethanone

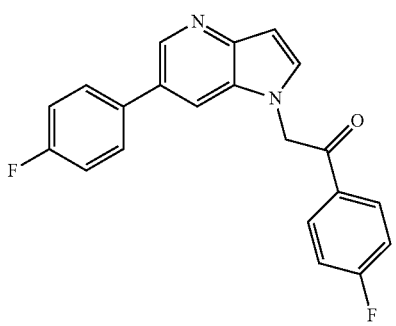 [SMILES: O=C(Cn1ccc2ncc(-c3ccc(F)cc3)cc21)c1ccc(F)cc1]

The title compound was prepared in a manner analogous to Example 226. MS (ESI): mass calcd. for C$_{21}$H$_{14}$F$_2$N$_2$O, 348.1. m/z found, 349.1 [M+H]$^+$. $^1$H NMR (500 MHz, DMSO-d$_6$) δ 8.66 (d, J=2.0 Hz, 1H), 8.22-8.20 (m, 1H), 8.20-8.17 (m, 2H), 7.79-7.75 (m, 2H), 7.65 (d, J=3.3 Hz, 1H), 7.49-7.44 (m, 2H), 7.32-7.27 (m, 2H), 6.65 (dd, J=3.2, 0.9 Hz, 1H), 6.02 (s, 2H).

Example 228

(R/S)-6-(4-Fluorophenyl)-1-(tetrahydropyran-2-ylmethyl)pyrrolo[3,2-b]pyridine trifluoroacetate salt

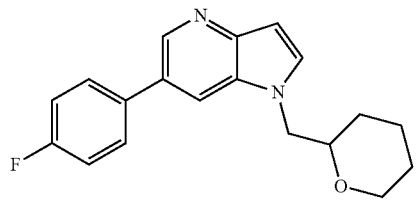 [SMILES: Fc1ccc(-c2cnc3ccn(CC4CCCCO4)c3c2)cc1]

The title compound was prepared in a manner analogous to Example 226. MS (ESI): mass calcd. for C$_{19}$H$_{19}$FN$_2$O, 310.1. m/z found, 311.2 [M+H]$^+$. $^1$H NMR (500 MHz, DMSO-d$_6$) δ 9.01 (br. s, 1H), 8.86 (s, 1H), 8.06 (s, 1H), 7.95-7.89 (m, 2H), 7.47-7.39 (m, 2H), 6.80 (s, 1H), 4.50 (dd, J=14.6, 3.5 Hz, 1H), 4.41 (dd, J=14.6, 7.8 Hz, 1H), 3.84-3.79 (m, 1H), 3.70-3.63 (m, 1H), 3.30-3.22 (m, 1H), 1.78 (d, J=12.2 Hz, 1H), 1.70-1.64 (m, 1H), 1.52-1.36 (m, 3H), 1.25-1.13 (m, 1H).

Example 229

2-[6-(4-Fluorophenyl)pyrrolo[3,2-b]pyridin-1-yl]-N-isopropyl-acetamide

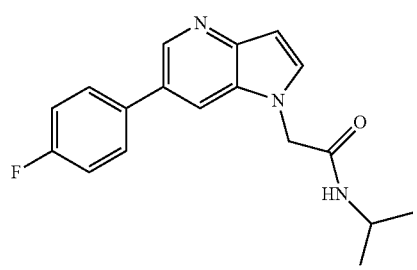 [SMILES: CC(C)NC(=O)Cn1ccc2ncc(-c3ccc(F)cc3)cc21]

The title compound was prepared in a manner analogous to Example 66. MS (ESI): mass calcd. for C$_{18}$H$_{18}$FN$_3$O, 311.1. m/z found, 312.2 [M+H]$^+$. $^1$H NMR (500 MHz, DMSO-d$_6$) δ 8.63 (s, 1H), 8.16 (d, J=7.8 Hz, 1H), 8.07 (s, 1H), 7.81-7.72 (m, 2H), 7.63 (s, 1H), 7.34 (t, J=8.4 Hz, 2H), 6.59 (s, 1H), 4.87 (s, 2H), 3.88-3.79 (m, 1H), 1.08 (d, J=6.6 Hz, 6H).

Example 230

2-[6-(4-Fluorophenyl)pyrrolo[3,2-b]pyridin-1-yl]-N-propyl-acetamide

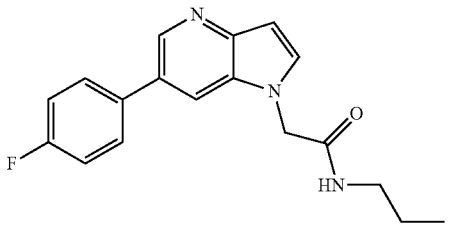 [SMILES: CCCNC(=O)Cn1ccc2ncc(-c3ccc(F)cc3)cc21]

The title compound was prepared in a manner analogous to Example 66. MS (ESI): mass calcd. for $C_{18}H_{18}FN_3O$, 311.1. m/z found, 312.2 [M+H]$^+$. $^1$H NMR (500 MHz, DMSO-d$_6$) δ 8.64 (d, J=2.0 Hz, 1H), 8.18 (t, J=5.6 Hz, 1H), 8.08-8.06 (m, 1H), 7.80-7.73 (m, 2H), 7.64 (d, J=3.3 Hz, 1H), 7.37-7.31 (m, 2H), 6.59 (d, J=3.2, 0.9 Hz, 1H), 4.91 (s, 2H), 3.05 (q, J=6.6 Hz, 2H), 1.47-1.38 (m, 2H), 0.83 (t, J=7.4 Hz, 3H).

Example 231

(R/S)-2-[6-(4-Fluorophenyl)pyrrolo[3,2-b]pyridin-1-yl]-N-(2,2,2-trifluoro-1-methyl-ethyl)acetamide

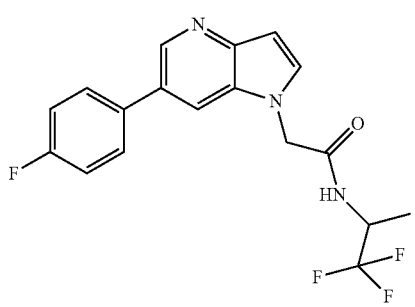 [SMILES: CC(NC(=O)Cn1ccc2ncc(-c3ccc(F)cc3)cc21)C(F)(F)F]

The title compound was prepared in a manner analogous to Example 66. MS (ESI): mass calcd. for $C_{18}H_{15}F_4N_3O$, 365.1. m/z found, 366.1 [M+H]$^+$. $^1$H NMR (400 MHz, DMSO-d$_6$) δ 8.91 (d, J=8.8 Hz, 1H), 8.64 (d, J=2.0 Hz, 1H), 8.05-8.03 (m, 1H), 7.79-7.73 (m, 2H), 7.65 (d, J=3.3 Hz, 1H), 7.38-7.30 (m, 2H), 6.60 (dd, J=3.3, 0.8 Hz, 1H), 5.02 (s, 2H), 4.65-4.53 (m, 1H), 1.28 (d, J=7.0 Hz, 3H).

Example 232

2-[6-(4-Fluorophenyl)pyrrolo[3,2-b]pyridin-1-yl]-N-(1-methylcyclopropyl)acetamide

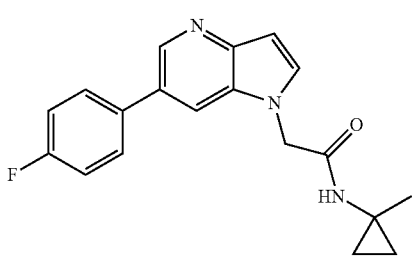 [SMILES: CC1(NC(=O)Cn2ccc3ncc(-c4ccc(F)cc4)cc32)CC1]

The title compound was prepared in a manner analogous to Example 66. MS (ESI): mass calcd. for $C_{19}H_{18}FN_3O$, 323.1. m/z found, 324.2 [M+H]$^+$. $^1$H NMR (500 MHz, DMSO-d$_6$) δ 8.63 (d, J=2.0 Hz, 1H), 8.50 (s, 1H), 8.05-8.02 (m, 1H), 7.79-7.73 (m, 2H), 7.62 (d, J=3.2 Hz, 1H), 7.38-7.31 (m, 2H), 6.59 (dd, J=3.3, 0.9 Hz, 1H), 4.82 (s, 2H), 1.26 (s, 3H), 0.65-0.60 (m, 2H), 0.55-0.51 (m, 2H).

Example 233

N-(2-Fluoroethyl)-2-[6-(4-fluorophenyl)pyrrolo[3,2-b]pyridin-1-yl]acetamide

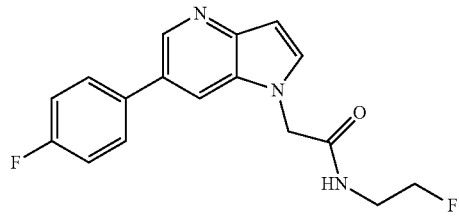 [SMILES: O=C(Cn1ccc2ncc(-c3ccc(F)cc3)cc21)NCCF]

The title compound was prepared in a manner analogous to Example 66. MS (ESI): mass calcd. for $C_{17}H_{15}F_2N_3O$, 315.1. m/z found, 316.1 [M+H]$^+$. $^1$H NMR (400 MHz, DMSO-d$_6$) δ 8.64 (s, 1H), 8.50 (t, J=5.7 Hz, 1H), 8.10-8.06 (m, 1H), 7.81-7.74 (m, 2H), 7.65 (d, J=3.3 Hz, 1H), 7.37-7.30 (m, 2H), 6.62-6.59 (m, 1H), 4.97 (s, 2H), 4.50 (t, J=5.0 Hz, 1H), 4.39 (t, J=4.9 Hz, 1H), 3.47-3.41 (m, 2H).

Example 234

2-[6-(4-Fluorophenyl)pyrrolo[3,2-b]pyridin-1-yl]-N-isobutyl-acetamide

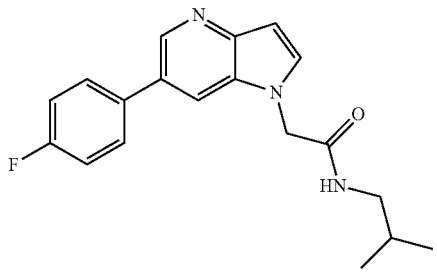 [SMILES: CC(C)CNC(=O)Cn1ccc2ncc(-c3ccc(F)cc3)cc21]

The title compound was prepared in a manner analogous to Example 66. MS (ESI): mass calcd. for $C_{19}H_{20}FN_3O$, 325.2. m/z found, 326.2 [M+H]$^+$. $^1$H NMR (400 MHz, DMSO-d$_6$) δ 8.63 (d, J=2.0 Hz, 1H), 8.19 (t, J=5.8 Hz, 1H), 8.07 (dd, J=1.9, 0.8 Hz, 1H), 7.80-7.73 (m, 2H), 7.65 (d, J=3.3 Hz, 1H), 7.38-7.30 (m, 2H), 6.59 (dd, J=3.2, 0.9 Hz, 1H), 4.93 (s, 2H), 2.92 (t, J=6.3 Hz, 2H), 1.75-1.63 (m, 1H), 0.83 (d, J=6.7 Hz, 6H).

Example 235

5-[[6-(4-Fluoro-3-methyl-phenyl)pyrrolo[3,2-b]pyridin-1-yl]methyl]-3-methyl-1,2,4-oxadiazole

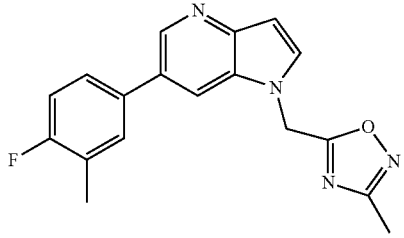 [SMILES: Cc1noc(Cn2ccc3ncc(-c4ccc(F)c(C)c4)cc32)n1]

The title compound was prepared in a manner analogous to Example 170 using 6-(4-fluoro-3-methylphenyl)-1H-pyrrolo[3,2-b]pyridine and 5-(chloromethyl)-3-methyl-1,2,4-oxadiazole. MS (ESI): mass calcd. for $C_{18}H_{15}FN_4O$, 322.1. m/z found, 323.1 [M+H]$^+$. $^1$H NMR (400 MHz, DMSO-d$_6$) δ 8.68 (d, J=2.0 Hz, 1H), 8.29-8.25 (m, 1H), 7.79 (d, J=3.5 Hz, 1H), 7.71-7.66 (m, 1H), 7.62-7.55 (m, 1H), 7.26 (dd, J=9.7, 8.5 Hz, 1H), 6.68 (dd, J=3.3, 0.9 Hz, 1H), 5.96 (s, 2H), 2.32 (d, J=1.9 Hz, 3H), 2.27 (s, 3H).

Example 236

6-(4-Fluoro-3-methyl-phenyl)-1-[(1-methylpyrazol-4-yl)methyl]pyrrolo[3,2-b]pyridine

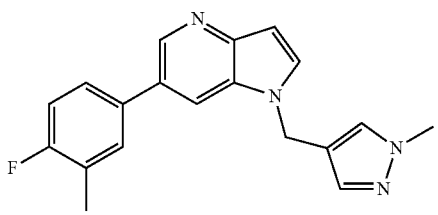 [SMILES: Cc1cc(-c2cnc3ccn(Cc4cnn(C)c4)c3c2)ccc1F]

The title compound was prepared in a manner analogous to Example 170 using 6-(4-fluoro-3-methylphenyl)-1H-pyrrolo[3,2-b]pyridine and 4-(chloromethyl)-1-methyl-1H-pyrazole. MS (ESI): mass calcd. for $C_{19}H_{17}FN_4$, 320.1. m/z found, 321.2 [M+H]$^+$. $^1$H NMR (400 MHz, DMSO-d$_6$) δ 8.61 (d, J=2.0 Hz, 1H), 8.22-8.19 (m, 1H), 7.72 (d, J=3.2 Hz, 1H), 7.70-7.66 (m, 1H), 7.61-7.55 (m, 2H), 7.26 (dd, J=9.7, 8.5 Hz, 1H), 6.57 (dd, J=3.3, 0.9 Hz, 1H), 6.14 (d, J=2.1 Hz, 1H), 5.41 (s, 2H), 3.77 (s, 3H), 2.33 (d, J=2.0 Hz, 3H).

Example 237

N-(Cyclopropylmethyl)-2-[6-(4-fluorophenyl)pyrrolo[3,2-b]pyridin-1-yl]acetamide

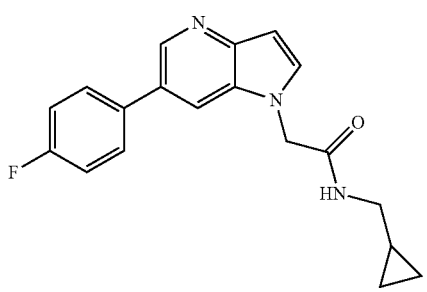 [SMILES: O=C(Cn1ccc2ncc(-c3ccc(F)cc3)cc21)NCC1CC1]

The title compound was prepared in a manner analogous to Example 66. MS (ESI): mass calcd. for $C_{19}H_{18}FN_3O$, 323.1. m/z found, 324.2 [M+H]$^+$. $^1$H NMR (500 MHz, DMSO-d$_6$) δ 8.65-8.62 (m, 1H), 8.31 (t, J=5.8 Hz, 1H), 8.08 (s, 1H), 7.81-7.74 (m, 2H), 7.66-7.63 (m, 1H), 7.37-7.30 (m, 2H), 6.61-6.58 (m, 1H), 4.93 (s, 2H), 3.00-2.95 (m, 2H), 0.95-0.86 (m, 1H), 0.42-0.36 (m, 2H), 0.17-0.12 (m, 2H).

Example 238

6-(4-Fluoro-3-methyl-phenyl)-1-[(1-methyltriazol-4-yl)methyl]pyrrolo[3,2-b]pyridine

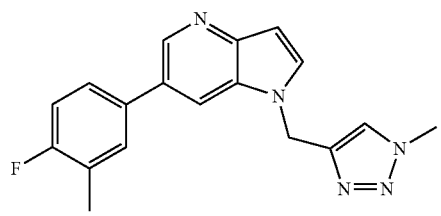 [SMILES: Cc1cc(-c2cnc3ccn(Cc4cn(C)nn4)c3c2)ccc1F]

The title compound was prepared in a manner analogous to Example 170 using 6-(4-fluoro-3-methylphenyl)-1H-pyrrolo[3,2-b]pyridine and 4-(chloromethyl)-1-methyl-1H-1,2,3-triazole. MS (ESI): mass calcd. for $C_{18}H_{16}FN_5$, 321.1. m/z found, 322.2 [M+H]$^+$. $^1$H NMR (400 MHz, DMSO-d$_6$) δ 8.62 (d, J=2.0 Hz, 1H), 8.29-8.26 (m, 1H), 8.01 (s, 1H), 7.75 (d, J=3.3 Hz, 1H), 7.72-7.67 (m, 1H), 7.63-7.57 (m, 1H), 7.27 (dd, J=9.7, 8.5 Hz, 1H), 6.59 (dd, J=3.2, 0.9 Hz, 1H), 5.56 (s, 2H), 3.97 (s, 3H), 2.34 (d, J=1.9 Hz, 3H).

Example 239

5-[[3-Chloro-6-(4-fluoro-3-methyl-phenyl)pyrrolo[3,2-b]pyridin-1-yl]methyl]-3-methyl-1,2,4-oxadiazole

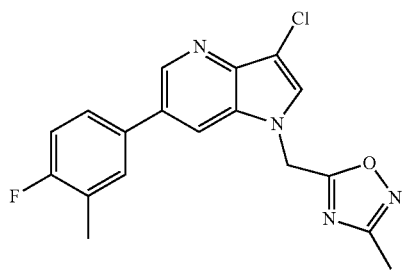 [SMILES: Cc1noc(Cn2cc(Cl)c3ncc(-c4ccc(F)c(C)c4)cc32)n1]

The title compound was prepared in a manner analogous to Example 176. MS (ESI): mass calcd. for $C_{18}H_{14}ClFN_4O$, 356.1. m/z found, 357.1 [M+H]$^+$. $^1$H NMR (400 MHz, DMSO-d$_6$) δ 8.77 (d, J=1.8 Hz, 1H), 8.39 (d, J=2.0 Hz, 1H), 8.00 (s, 1H), 7.73-7.69 (m, 1H), 7.64-7.57 (m, 1H), 7.28 (dd, J=9.7, 8.5 Hz, 1H), 5.96 (s, 2H), 2.33 (d, J=1.9 Hz, 3H), 2.26 (s, 3H).

Example 240

3-Chloro-6-(4-fluoro-3-methyl-phenyl)-1-[(1-methylpyrazol-4-yl)methyl]pyrrolo[3,2-b]pyridine

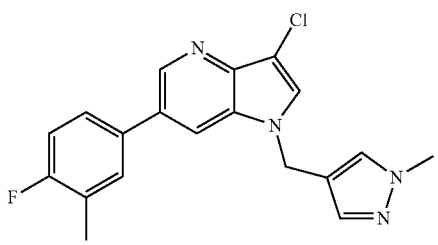 [SMILES: Cc1cc(-c2cnc3c(Cl)cn(Cc4cnn(C)c4)c3c2)ccc1F]

The title compound was prepared in a manner analogous to Example 176. MS (ESI): mass calcd. for $C_{19}H_{16}ClFN_4$, 354.1. m/z found, 355.1 [M+H]$^+$. $^1$H NMR (400 MHz, DMSO-d$_6$) δ 8.69 (d, J=1.9 Hz, 1H), 8.31 (d, J=2.0 Hz, 1H), 7.91 (s, 1H), 7.72-7.68 (m, 1H), 7.63-7.57 (m, 2H), 7.28 (t, J=9.7, 8.5 Hz, 1H), 6.19 (d, J=2.2 Hz, 1H), 5.41 (s, 2H), 3.77 (s, 3H), 2.34 (d, J=2.0 Hz, 3H).

Example 241

2-[3-Chloro-6-(4-fluoro-3-methyl-phenyl)pyrrolo[3,2-b]pyridin-1-yl]-1-cyclobutyl-ethanone

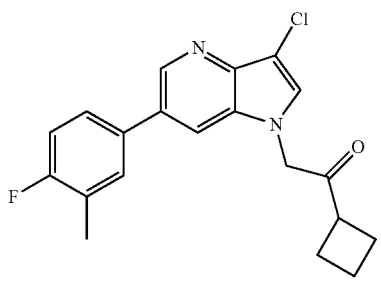 [SMILES: Cc1cc(-c2cnc3c(Cl)cn(CC(=O)C4CCC4)c3c2)ccc1F]

The title compound was prepared in a manner analogous to Example 176. MS (ESI): mass calcd. for $C_{20}H_{18}ClFN_2O$, 356.1. m/z found, 357.1 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.28 min at 254 nm.

Example 242

1-Cyclobutyl-2-[6-(4-fluoro-3-methyl-phenyl)pyrrolo[3,2-b]pyridin-1-yl]ethanone

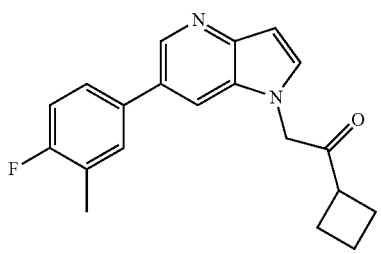

The title compound was prepared in a manner analogous to Example 170 using 6-(4-fluoro-3-methylphenyl)-1H-pyrrolo[3,2-b]pyridine and 2-bromo-1-cyclobutylethanone. MS (ESI): mass calcd. for $C_{20}H_{19}FN_2O$, 322.1. m/z found, 323.2 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.99 min at 254 nm.

Example 243

1-(Azetidin-1-yl)-2-[3-chloro-6-[5-(trifluoromethyl)-3-pyridyl]pyrrolo[3,2-b]pyridin-1-yl]ethanone trifluoroacetate salt

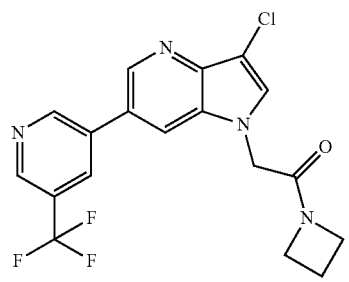 [SMILES: O=C(Cn1cc(Cl)c2ncc(-c3cncc(C(F)(F)F)c3)cc21)N1CCC1]

Step A: 3-Chloro-6-(5-(trifluoromethyl)pyridin-3-yl)-1H-pyrrolo[3,2-b]pyridine

The title compound was prepared in a manner analogous to Example 27, Step A, substituting (5-(trifluoromethyl)pyridin-3-yl)boronic acid for (4-fluorophenyl)boronic acid. $^1$H NMR (400 MHz, DMSO-d$_6$) δ 11.87 (s, 1H), 9.29 (d, J=2.2 Hz, 1H), 9.01-8.97 (m, 1H), 8.84 (d, J=2.0 Hz, 1H), 8.60-8.56 (m, 1H), 8.26 (d, J=2.0 Hz, 1H), 7.95 (s, 1H).

Step B: 1-(Azetidin-1-yl)-2-[3-chloro-6-[5-(trifluoromethyl)-3-pyridyl]pyrrolo[3,2-b]pyridin-1-yl]ethanone trifluoroacetate salt The title compound was prepared in a manner analogous to Example 68, step B. MS (ESI): mass calcd. for $C_{18}H_{14}ClF_3N_4O$, 394.1. m/z found, 395.1 [M+H]$^+$. $^1$H NMR (400 MHz, DMSO-d$_6$) δ 9.33 (s, 1H), 9.01 (s, 1H), 8.90 (d, J=1.9 Hz, 1H), 8.59 (t, J=2.2 Hz, 1H), 8.48 (d, J=1.9 Hz, 1H), 7.88 (s, 1H), 5.04 (s, 2H), 4.25 (t, J=7.7 Hz, 2H), 3.91 (t, J=7.7 Hz, 2H), 2.34-2.25 (m, 2H).

Example 244

2-[3-Chloro-6-[5-(trifluoromethyl)-3-pyridyl]pyrrolo[3,2-b]pyridin-1-yl]-N-cyclopropyl-acetamide trifluoroacetate salt

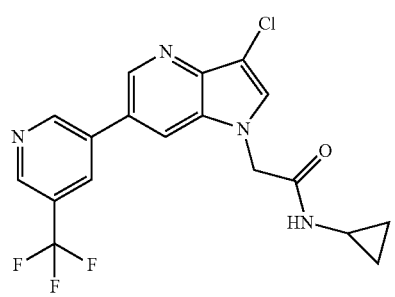

The title compound was prepared in a manner analogous to Example 243. MS (ESI): mass calcd. for C$_{18}$H$_{14}$ClF$_3$N$_4$O, 394.1. m/z found, 395.1 [M+H]$^+$. $^1$H NMR (400 MHz, DMSO-d$_6$) δ 9.33 (s, 1H), 9.01 (s, 1H), 8.92 (d, J=1.9 Hz, 1H), 8.61-8.57 (m, 1H), 8.49 (d, J=1.9 Hz, 1H), 8.34 (d, J=4.2 Hz, 1H), 7.94 (s, 1H), 4.93 (s, 2H), 2.69-2.61 (m, 1H), 0.67-0.60 (m, 2H), 0.49-0.41 (m, 2H).

Example 245

1-(Azetidin-1-yl)-2-[3-chloro-6-[6-(trifluoromethyl)-2-pyridyl]pyrrolo[3,2-b]pyridin-1-yl]ethanone

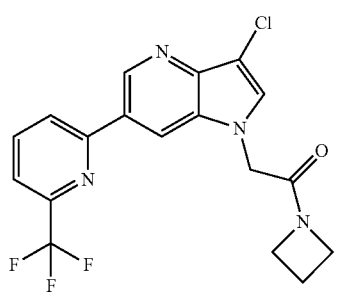 [SMILES: O=C(Cn1cc(Cl)c2ncc(-c3cccc(C(F)(F)F)n3)cc21)N1CCC1]

The title compound was prepared in a manner analogous to Example 243, substituting 2-(4,4,5,5-tetramethyl-1,3,2-dioxaborolan-2-yl)-6-(trifluoromethyl)pyridine for (5-(trifluoromethyl)pyridin-3-yl)boronic acid. MS (ESI): mass calcd. for C$_{18}$H$_{14}$ClF$_3$N$_4$O, 394.1. m/z found, 395.1 [M+H]$^+$. $^1$H NMR (400 MHz, DMSO-d$_6$) δ 9.17 (d, J=1.8 Hz, 1H), 8.59 (d, J=1.8 Hz, 1H), 8.40 (d, J=8.1 Hz, 1H), 8.24 (t, J=7.9 Hz, 1H), 7.90 (s, 2H), 5.07 (s, 2H), 4.28 (t, J=7.7 Hz, 2H), 3.92 (t, J=7.7 Hz, 2H), 2.35-2.25 (m, 2H).

Example 246

2-[3-Chloro-6-[6-(trifluoromethyl)-2-pyridyl]pyrrolo[3,2-b]pyridin-1-yl]-N-cyclopropyl-acetamide

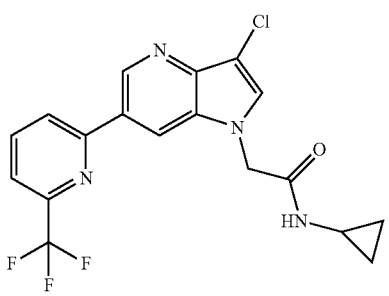 [SMILES: O=C(Cn1cc(Cl)c2ncc(-c3cccc(C(F)(F)F)n3)cc21)NC1CC1]

The title compound was prepared in a manner analogous to Example 243 substituting 2-(4,4,5,5-tetramethyl-1,3,2-dioxaborolan-2-yl)-6-(trifluoromethyl)pyridine for (5-(trifluoromethyl)pyridin-3-yl)boronic acid. MS (ESI): mass calcd. for C$_{18}$H$_{14}$ClF$_3$N$_4$O, 394.1. m/z found, 395.1 [M+H]$^+$. $^1$H NMR (400 MHz, DMSO-d$_6$) δ 9.18 (d, J=1.8 Hz, 1H), 8.55 (d, J=1.9 Hz, 1H), 8.44-8.39 (m, 2H), 8.23 (t, J=7.9 Hz, 1H), 7.95 (s, 1H), 7.89 (d, J=7.5 Hz, 1H), 4.93 (s, 2H), 2.69-2.61 (m, 1H), 0.67-0.60 (m, 2H), 0.49-0.43 (m, 2H).

Example 247

2-[3-Chloro-6-[6-(trifluoromethyl)-2-pyridyl]pyrrolo[3,2-b]pyridin-1-yl]-1-(3-fluoroazetidin-1-yl)ethanone

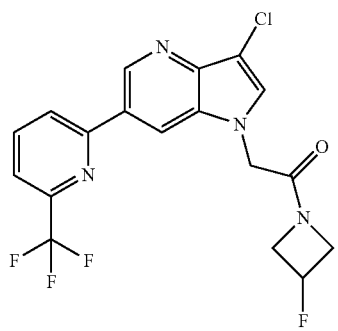 [SMILES: O=C(Cn1cc(Cl)c2ncc(-c3cccc(C(F)(F)F)n3)cc21)N1CC(F)C1]

The title compound was prepared in a manner analogous to Example 243 substituting 2-(4,4,5,5-tetramethyl-1,3,2-dioxaborolan-2-yl)-6-(trifluoromethyl)pyridine for (5-(trifluoromethyl)pyridin-3-yl)boronic acid. MS (ESI): mass calcd. for C$_{18}$H$_{13}$ClF$_4$N$_4$O, 412.1. m/z found, 413.1 [M+H]$^+$. $^1$H NMR (400 MHz, CD$_3$OD) δ 9.16 (d, J=1.8 Hz, 1H), 8.60 (d, J=1.8 Hz, 1H), 8.25 (d, J=8.0 Hz, 1H), 8.12 (t, J=7.9 Hz, 1H), 7.76 (d, J=7.7 Hz, 1H), 7.71 (s, 1H), 5.54-5.32 (m, 1H), 5.11 (s, 2H), 4.70-4.56 (m, 1H), 4.51-4.27 (m, 2H), 4.19-4.04 (m, 1H).

Example 248

N-Cyclopropyl-2-[6-(3,4,5-trifluorophenyl)pyrrolo[3,2-b]pyridin-1-yl]acetamide

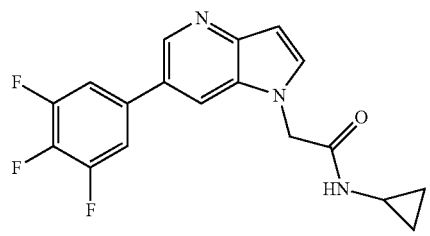 [SMILES: O=C(Cn1ccc2ncc(-c3cc(F)c(F)c(F)c3)cc21)NC1CC1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (3,4,5-trifluorophenyl)boronic acid. MS (ESI): mass calcd. for C$_{18}$H$_{14}$F$_3$N$_3$O, 345.1. m/z found, 346.1 [M+H]$^+$. $^1$H NMR (400 MHz, DMSO-d$_6$) δ 8.73 (d, J=2.0 Hz, 1H), 8.32 (d, J=4.3 Hz, 1H), 8.23-8.20 (m, 1H), 7.84-7.76 (m, 2H), 7.68 (d, J=3.3 Hz, 1H), 6.61 (dd, J=3.2, 0.9 Hz, 1H), 4.88 (s, 2H), 2.69-2.61 (m, 1H), 0.67-0.60 (m, 2H), 0.47-0.41 (m, 2H).

Example 249

N-Cyclopropyl-2-[6-(2,3,4-trifluorophenyl)pyrrolo[3,2-b]pyridin-1-yl]acetamide

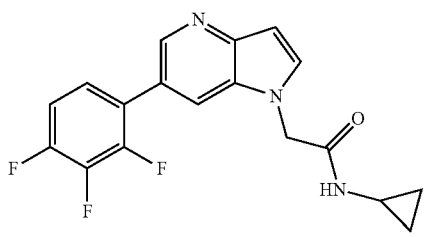 [SMILES: O=C(Cn1ccc2ncc(-c3ccc(F)c(F)c3F)cc21)NC1CC1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (2,3,4-trifluorophenyl)boronic acid. MS (ESI): mass calcd. for $C_{18}H_{14}F_3N_3O$, 345.1. m/z found, 346.1 [M+H]$^+$. $^1$H NMR (400 MHz, DMSO-d$_6$) δ 8.50 (t, J=2.0 Hz, 1H), 8.34 (d, J=4.1 Hz, 1H), 8.01-7.98 (m, 1H), 7.70 (d, J=3.3 Hz, 1H), 7.51-7.45 (m, 2H), 6.63 (dd, J=3.2, 0.9 Hz, 1H), 4.86 (s, 2H), 2.67-2.60 (m, 1H), 0.63 (td, J=7.0, 4.7 Hz, 2H), 0.46-0.40 (m, 2H).

Example 250

N-Cyclopropyl-2-[6-[3-(difluoromethyl)phenyl]pyrrolo[3,2-b]pyridin-1-yl]acetamide

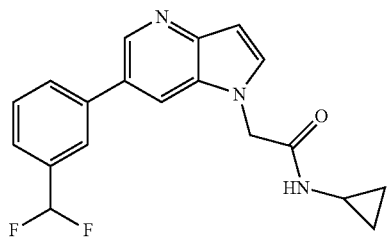 [SMILES: O=C(Cn1ccc2ncc(-c3cccc(C(F)F)c3)cc21)NC1CC1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (3-(difluoromethyl)phenyl)boronic acid. MS (ESI): mass calcd. for $C_{19}H_{17}F_2N_3O$, 341.1. m/z found, 342.1 [M+H]$^+$. $^1$H NMR (400 MHz, DMSO-d$_6$) δ 8.69 (d, J=2.0 Hz, 1H), 8.35 (d, J=4.2 Hz, 1H), 8.15-8.13 (m, 1H), 7.95-7.90 (m, 2H), 7.69-7.63 (m, 2H), 7.61-7.56 (m, 1H), 7.12 (t, J=55.8 Hz, 1H), 6.61 (dd, J=3.3, 0.8 Hz, 1H), 4.89 (s, 2H), 2.70-2.61 (m, 1H), 0.66-0.60 (m, 2H), 0.47-0.42 (m, 2H).

Example 251

N-Benzyl-2-[6-(4-fluorophenyl)pyrrolo[3,2-b]pyridin-1-yl]acetamide

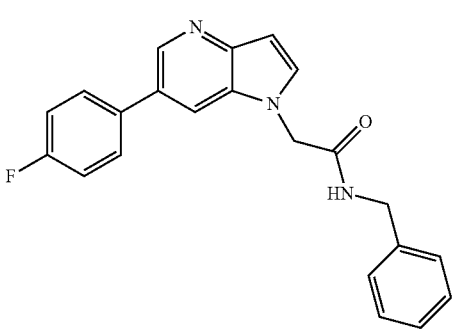 [SMILES: O=C(Cn1ccc2ncc(-c3ccc(F)cc3)cc21)NCc1ccccc1]

The title compound was prepared in a manner analogous to Example 66. MS (ESI): mass calcd. for $C_{22}H_{16}FN_3O$, 359.1. m/z found, 360.2 [M+H]$^+$. $^1$H NMR (400 MHz, DMSO-d$_6$) δ 8.70 (t, J=5.9 Hz, 1H), 8.64 (d, J=2.0 Hz, 1H), 8.07 (dd, J=2.0, 0.9 Hz, 1H), 7.77-7.71 (m, 2H), 7.68 (d, J=3.2 Hz, 1H), 7.37-7.30 (m, 2H), 7.28-7.19 (m, 5H), 6.60 (dd, J=3.2, 0.9 Hz, 1H), 5.01 (s, 2H), 4.31 (d, J=5.9 Hz, 2H).

Example 252

2-[[6-(4-Fluoro-3-methyl-phenyl)pyrrolo[3,2-b]pyridin-1-yl]methyl]oxazole

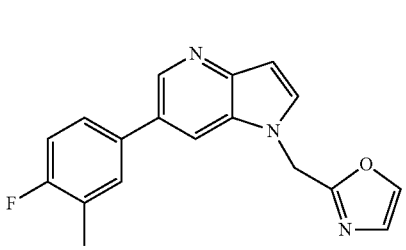 [SMILES: Cc1cc(-c2cnc3ccn(Cc4ncco4)c3c2)ccc1F]

The title compound was prepared in a manner analogous to Example 170 using 6-(4-fluoro-3-methylphenyl)-1H-pyrrolo[3,2-b]pyridine and 2-(chloromethyl)oxazole. MS (ESI): mass calcd. for $C_{18}H_{14}FN_3O$, 307.1. m/z found, 308.2 [M+H]$^+$. $^1$H NMR (400 MHz, DMSO-d$_6$) δ 8.65 (d, J=2.0 Hz, 1H), 8.21 (dd, J=2.1, 0.9 Hz, 1H), 8.06 (d, J=1.0 Hz, 1H), 7.77 (d, J=3.3 Hz, 1H), 7.69-7.65 (m, 1H), 7.60-7.54 (m, 1H), 7.26 (dd, J=9.7, 8.5 Hz, 1H), 7.17 (d, J=0.9 Hz, 1H), 6.64 (dd, J=3.3, 0.9 Hz, 1H), 5.74 (s, 2H), 2.33 (d, J=1.9 Hz, 3H).

Example 253

2-[6-(4-Fluorophenyl)pyrrolo[3,2-b]pyridin-1-yl]-N-(2-hydroxyethyl)acetamide

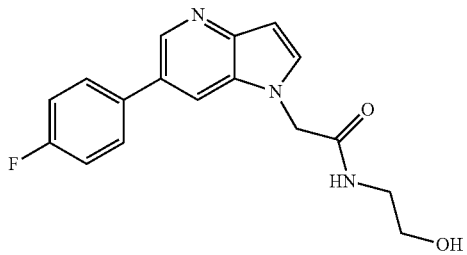 [SMILES: O=C(Cn1ccc2ncc(-c3ccc(F)cc3)cc21)NCCO]

The title compound was prepared in a manner analogous to Example 66. MS (ESI): mass calcd. for $C_{17}H_{16}FN_3O_2$, 313.1. m/z found, 314.1 [M+H]$^+$. $^1$H NMR (400 MHz, DMSO-d$_6$) δ 8.64 (d, J=2.0 Hz, 1H), 8.25-8.20 (m, 1H), 8.12-8.09 (m, 1H), 7.81-7.76 (m, 2H), 7.66 (d, J=3.3 Hz, 1H), 7.37-7.30 (m, 2H), 6.60 (dd, J=3.2, 0.9 Hz, 1H), 4.94 (s, 2H), 4.74-4.70 (m, 1H), 3.46-3.40 (m, 2H), 3.19-3.13 (m, 2H).

Example 254

2-[6-(4-Fluorophenyl)pyrrolo[3,2-b]pyridin-1-yl]-N-(2-methoxyethyl)acetamide

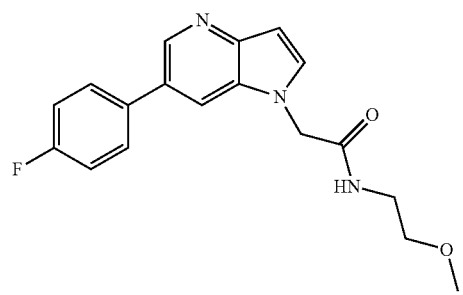 [SMILES: COCCNC(=O)Cn1ccc2ncc(-c3ccc(F)cc3)cc21]

The title compound was prepared in a manner analogous to Example 66. MS (ESI): mass calcd. for $C_{18}H_{18}FN_3O_2$, 327.1. m/z found, 328.2 [M+H]$^+$. $^1$H NMR (400 MHz, DMSO-d$_6$) δ 8.64 (d, J=2.0 Hz, 1H), 8.32 (t, J=5.5 Hz, 1H), 8.09-8.07 (m, 1H), 7.81-7.74 (m, 2H), 7.65 (d, J=3.3 Hz, 1H), 7.37-7.30 (m, 2H), 6.59 (dd, J=3.4, 0.8 Hz, 1H), 4.94 (s, 2H), 3.38-3.31 (m, 2H), 3.28-3.23 (m, 2H), 3.21 (s, 3H).

Example 255

1-(3,3-Difluoroazetidin-1-yl)-2-[6-[2-fluoro-3-(trifluoromethyl)phenyl]pyrrolo[3,2-b]pyridin-1-yl]ethanone trifluoroacetate salt

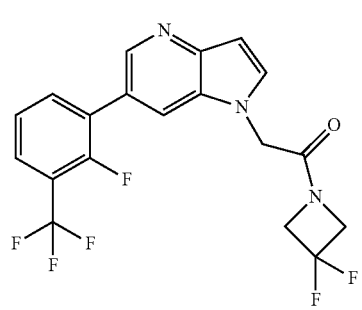

The title compound was prepared in a manner analogous to Example 106. MS (ESI): mass calcd. for $C_{19}H_{13}F_6N_3O$, 413.1. m/z found, 414.1 [M+H]$^+$. $^1$H NMR (400 MHz, DMSO-d$_6$) δ 8.82 (s, 1H), 8.63 (s, 1H), 8.04-7.98 (m, 2H), 7.92 (t, J=6.8 Hz, 1H), 7.62 (t, J=7.8 Hz, 1H), 6.85 (d, J=3.4 Hz, 1H), 5.29 (s, 2H), 4.76 (t, J=12.3 Hz, 2H), 4.38 (t, J=12.5 Hz, 2H).

Example 256

1-(3,3-Difluoroazetidin-1-yl)-2-[6-(3-fluorophenyl)pyrrolo[3,2-b]pyridin-1-yl]ethanone trifluoroacetate salt

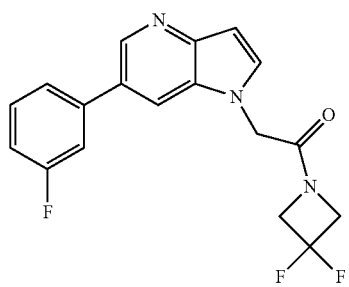 [SMILES: O=C(Cn1ccc2ncc(-c3cccc(F)c3)cc21)N1CC(F)(F)C1]

The title compound was prepared in a manner analogous to Example 106. MS (ESI): mass calcd. for $C_{18}H_{14}F_3N_3O$, 345.1. m/z found, 346.1 [M+H]$^+$. $^1$H NMR (400 MHz, CD$_3$OD) δ 9.01-8.93 (m, 2H), 8.09 (d, J=3.3 Hz, 1H), 7.68-7.57 (m, 3H), 7.30-7.23 (m, 1H), 6.94 (dd, J=3.3, 1.0 Hz, 1H), 5.38 (s, 2H), 4.84-4.77 (m, 2H), 4.50-4.39 (m, 2H).

Example 257

1-(3,3-Difluoroazetidin-1-yl)-2-(6-phenylpyrrolo[3,2-b]pyridin-1-yl)ethanone trifluoroacetate salt

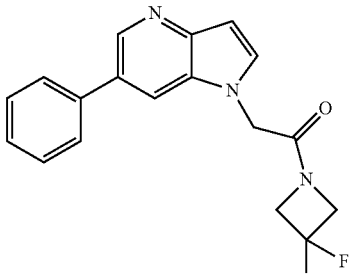

The title compound was prepared in a manner analogous to Example 106. MS (ESI): mass calcd. for $C_{18}H_{15}F_2N_3O$, 327.1. m/z found, 328.1 [M+H]$^+$. $^1$H NMR (400 MHz, CD$_3$OD) δ 8.97 (s, 1H), 8.91 (s, 1H), 8.07 (d, J=3.3 Hz, 1H), 7.85-7.79 (m, 2H), 7.62-7.55 (m, 2H), 7.54-7.49 (m, 1H), 6.94 (d, J=3.3 Hz, 1H), 5.38 (s, 2H), 4.81 (t, J=11.9 Hz, 2H), 4.45 (t, J=12.1 Hz, 2H).

Example 258

1-(3,3-Difluoroazetidin-1-yl)-2-[6-(3-ethylphenyl)pyrrolo[3,2-b]pyridin-1-yl]ethanone trifluoroacetate salt

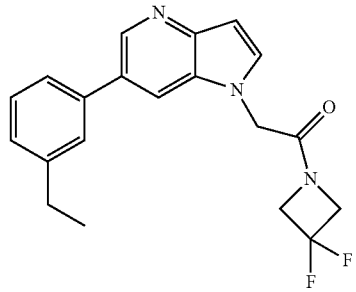 [SMILES: CCc1cccc(-c2cnc3ccn(CC(=O)N4CC(F)(F)C4)c3c2)c1]

The title compound was prepared in a manner analogous to Example 106. MS (ESI): mass calcd. for $C_{20}H_{19}F_2N_3O$, 355.1. m/z found, 356.2 [M+H]$^+$. $^1$H NMR (400 MHz, CD$_3$OD) δ 8.96-8.94 (m, 1H), 8.90 (d, J=1.5 Hz, 1H), 8.06 (d, J=3.4 Hz, 1H), 7.67-7.65 (m, 1H), 7.63-7.58 (m, 1H), 7.49 (t, J=7.7 Hz, 1H), 7.39-7.35 (m, 1H), 6.93 (dd, J=3.3, 0.8 Hz, 1H), 5.39 (s, 2H), 4.81 (t, J=12.0 Hz, 2H), 4.45 (t, J=12.1 Hz, 2H), 2.78 (q, J=7.6 Hz, 2H), 1.32 (t, J=7.6 Hz, 3H).

Example 259

1-(3,3-Difluoroazetidin-1-yl)-2-[6-(4-fluoro-3-methyl-phenyl)pyrrolo[3,2-b]pyridin-1-yl]ethanone trifluoroacetate salt

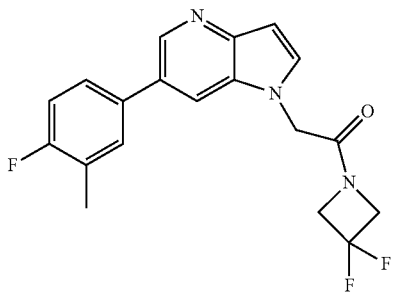 [SMILES: Cc1cc(-c2cnc3ccn(CC(=O)N4CC(F)(F)C4)c3c2)ccc1F]

The title compound was prepared in a manner analogous to Example 106. MS (ESI): mass calcd. for $C_{19}H_{16}F_3N_3O$, 359.1. m/z found, 360.1 [M+H]$^+$. $^1$H NMR (400 MHz, DMSO-d$_6$) δ 8.99 (s, 1H), 8.87 (s, 1H), 8.06 (d, J=3.2 Hz, 1H), 7.79 (dd, J=7.3, 2.4 Hz, 1H), 7.73-7.67 (m, 1H), 7.41-7.34 (m, 1H), 6.87 (d, J=3.3 Hz, 1H), 5.35 (s, 2H), 4.79 (t, J=12.4 Hz, 2H), 4.39 (t, J=12.5 Hz, 2H), 2.36 (d, J=1.9 Hz, 3H).

Example 260

1-(3,3-Difluoroazetidin-1-yl)-2-[6-[3-(trifluoromethyl)phenyl]pyrrolo[3,2-b]pyridin-1-yl]ethanone trifluoroacetate salt

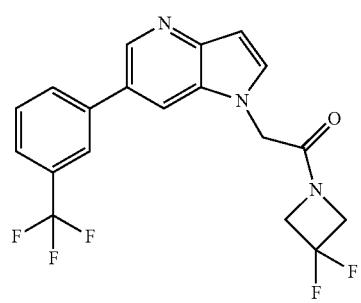 [SMILES: O=C(Cn1ccc2ncc(-c3cccc(C(F)(F)F)c3)cc21)N1CC(F)(F)C1]

The title compound was prepared in a manner analogous to Example 106. MS (ESI): mass calcd. for $C_{19}H_{14}F_5N_3O$, 395.1. m/z found, 396.1 [M+H]$^+$. $^1$H NMR (400 MHz, CD$_3$OD) δ 8.97 (s, 2H), 8.15 (s, 1H), 8.10-8.09 (m, 1H), 8.08 (d, J=3.4 Hz, 1H), 7.85-7.76 (m, 2H), 6.94 (d, J=3.3 Hz, 1H), 5.38 (s, 2H), 4.80 (t, J=11.8 Hz, 2H), 4.45 (t, J=12.1 Hz, 2H).

Example 261

1-(3,3-Difluoroazetidin-1-yl)-2-[6-(4-fluoro-2-methyl-phenyl)pyrrolo[3,2-b]pyridin-1-yl]ethanone trifluoroacetate salt

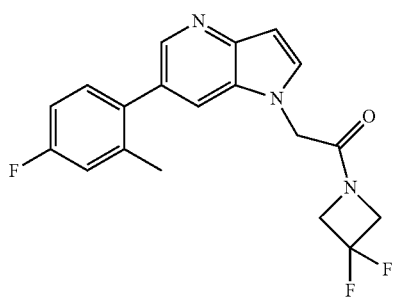 [SMILES: Cc1cc(F)ccc1-c1cnc2ccn(CC(=O)N3CC(F)(F)C3)c2c1]

The title compound was prepared in a manner analogous to Example 106. MS (ESI): mass calcd. for $C_{19}H_{16}F_3N_3O$, 359.1. m/z found, 360.2 [M+H]$^+$. $^1$H NMR (500 MHz, CD$_3$OD) δ 8.68-8.65 (m, 1H), 8.63-8.60 (m, 1H), 8.09 (d, J=3.4 Hz, 1H), 7.39 (dd, J=8.5, 5.8 Hz, 1H), 7.17 (dd, J=9.8, 2.7 Hz, 1H), 7.13-7.07 (m, 1H), 6.96 (dd, J=3.4, 1.0 Hz, 1H), 5.33 (s, 2H), 4.77 (t, J=11.9 Hz, 2H), 4.42 (t, J=12.1 Hz, 2H), 2.31 (s, 3H).

Example 262

1-(3-Fluoroazetidin-1-yl)-2-[6-[4-fluoro-3-(trifluoromethyl)phenyl]pyrrolo[3,2-b]pyridin-1-yl]ethanone trifluoroacetate salt

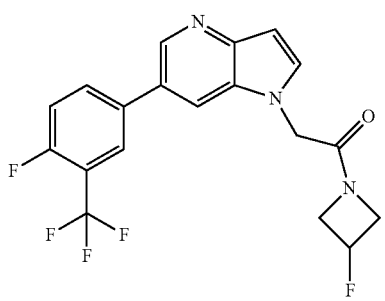 [SMILES: O=C(Cn1ccc2ncc(-c3ccc(F)c(C(F)(F)F)c3)cc21)N1CC(F)C1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (4-fluoro-3-(trifluoromethyl)phenyl)boronic acid. MS (ESI): mass calcd. for $C_{19}H_{14}F_5N_3O$, 395.1. m/z found, 396.0 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.93 min at 254 nm.

Example 263

1-(3-Fluoroazetidin-1-yl)-2-[6-(3-fluorophenyl)pyrrolo[3,2-b]pyridin-1-yl]ethanone trifluoroacetate salt

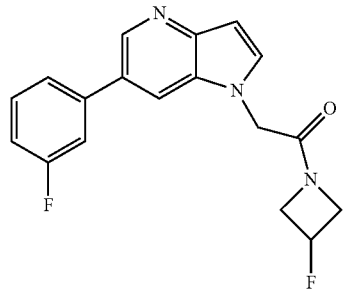 [SMILES: O=C(Cn1ccc2ncc(-c3cccc(F)c3)cc21)N1CC(F)C1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (4-fluorophenyl)boronic acid. MS (ESI): mass calcd. for $C_{18}H_{15}F_2N_3O$, 327.1. m/z found, 328.0 [M+H]$^+$. $^1$H NMR (400 MHz, CD$_3$OD) δ 8.96-8.91 (m, 2H), 8.08 (d, J=3.4 Hz, 1H), 7.69-7.56 (m, 3H), 7.29-7.21 (m, 1H), 6.93 (dd, J=3.4, 0.9 Hz, 1H), 5.57-5.37 (m, 1H), 5.32 (d, J=3.5 Hz, 2H), 4.78-4.64 (m, 1H), 4.56-4.44 (m, 1H), 4.44-4.32 (m, 1H), 4.20-4.07 (m, 1H).

Example 264

1-(3-Fluoroazetidin-1-yl)-2-[6-(4-fluoro-2-methylphenyl)pyrrolo[3,2-b]pyridin-1-yl]ethanone trifluoroacetate salt

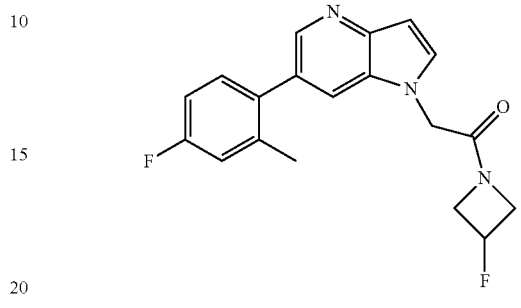

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (4-fluoro-2-methylphenyl)boronic acid. MS (ESI): mass calcd. for $C_{19}H_{17}F_2N_3O$, 341.1. m/z found, 342.1 [M+H]$^+$. $^1$H NMR (400 MHz, CD$_3$OD) δ 8.65 (t, J=1.2 Hz, 1H), 8.61 (d, J=1.5 Hz, 1H), 8.09 (d, J=3.3 Hz, 1H), 7.39 (dd, J=8.5, 5.7 Hz, 1H), 7.17 (dd, J=9.8, 2.7 Hz, 1H), 7.13-7.06 (m, 1H), 6.95 (dd, J=3.4, 0.9 Hz, 1H), 5.54-5.34 (m, 1H), 5.28 (d, J=4.2 Hz, 2H), 4.74-4.62 (m, 1H), 4.53-4.41 (m, 1H), 4.41-4.30 (m, 1H), 4.17-4.05 (m, 1H), 2.32 (s, 3H).

Example 265

1-(3-Fluoroazetidin-1-yl)-2-[6-[3-(trifluoromethyl)phenyl]pyrrolo[3,2-b]pyridin-1-yl]ethanone trifluoroacetate salt

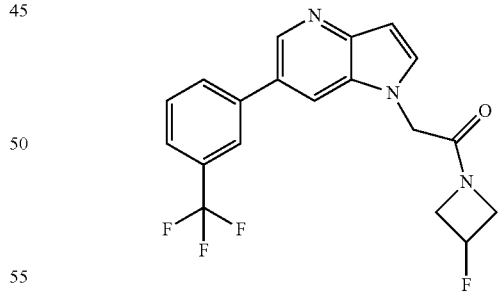

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (3-(trifluoromethyl)phenyl)boronic acid. MS (ESI): mass calcd. for $C_{19}H_{18}F_4N_3O$, 377.1. m/z found, 378.0 [M+H]$^+$. $^1$H NMR (500 MHz, DMSO-d$_6$) δ 9.04 (s, 1H), 8.85 (s, 1H), 8.21-8.12 (m, 2H), 8.03 (d, J=3.4 Hz, 1H), 7.88-7.79 (m, 2H), 6.85 (d, J=3.3 Hz, 1H), 5.58-5.41 (m, 1H), 5.27 (s, 2H), 4.67-4.56 (m, 1H), 4.43-4.32 (m, 1H), 4.31-4.21 (m, 1H), 4.04-3.93 (m, 1H).

Example 266

1-(3-Fluoroazetidin-1-yl)-2-[6-(m-tolyl)pyrrolo[3,2-b]pyridin-1-yl]ethanone trifluoroacetate salt

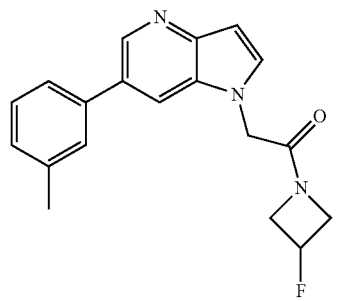 [SMILES: Cc1cccc(-c2cnc3ccn(CC(=O)N4CC(F)C4)c3c2)c1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and m-tolylboronic acid. MS (ESI): mass calcd. for $C_{19}H_{18}FN_3O$, 323.1. m/z found, 324.1 $[M+H]^+$. $^1$H NMR (400 MHz, DMSO-$d_6$) δ 9.00 (d, J=1.6 Hz, 1H), 8.93-8.91 (m, 1H), 8.08 (d, J=3.3 Hz, 1H), 7.68 (s, 1H), 7.67-7.63 (m, 1H), 7.51-7.44 (m, 1H), 7.35-7.28 (m, 1H), 6.89-6.86 (m, 1H), 5.61-5.40 (m, 1H), 5.30 (s, 2H), 4.70-4.56 (m, 1H), 4.46-4.33 (m, 1H), 4.32-4.20 (m, 1H), 4.07-3.92 (m, 1H), 2.44 (s, 3H).

Example 267

1-(3-Fluoroazetidin-1-yl)-2-[6-[2-fluoro-3-(trifluoromethyl)phenyl]pyrrolo[3,2-b]pyridin-1-yl]ethanone trifluoroacetate salt

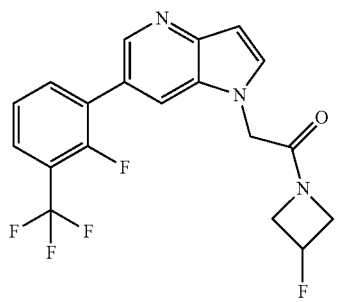 [SMILES: O=C(Cn1ccc2ncc(-c3cccc(C(F)(F)F)c3F)cc21)N1CC(F)C1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (2-fluoro-3-(trifluoromethyl)phenyl)boronic acid. MS (ESI): mass calcd. for $C_{19}H_{14}F_5N_3O$, 395.1. m/z found, 396.2 $[M+H]^+$. $^1$H NMR (400 MHz, DMSO-$d_6$) δ 8.77 (s, 1H), 8.54 (s, 1H), 8.04-7.97 (m, 1H), 7.95 (d, J=3.2 Hz, 1H), 7.93-7.87 (m, 1H), 7.61 (t, J=7.8 Hz, 1H), 6.81 (d, J=3.3 Hz, 1H), 5.59-5.37 (m, 1H), 5.20 (d, J=2.6 Hz, 2H), 4.66-4.52 (m, 1H), 4.42-4.30 (m, 1H), 4.30-4.18 (m, 1H), 4.03-3.91 (m, 1H).

Example 268

2-[6-(3-Ethylphenyl)pyrrolo[3,2-b]pyridin-1-yl]-1-(3-fluoroazetidin-1-yl)ethanone trifluoroacetate salt

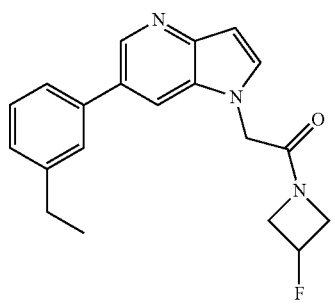 [SMILES: CCc1cccc(-c2cnc3ccn(CC(=O)N4CC(F)C4)c3c2)c1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and (3-ethylphenyl)boronic acid. MS (ESI): mass calcd. for $C_{20}H_{20}FN_3O$, 337.2. m/z found, 338.1 $[M+H]^+$. $^1$H NMR (400 MHz, DMSO-$d_6$) δ 8.96 (d, J=1.7 Hz, 1H), 8.80 (s, 1H), 8.02 (d, J=3.3 Hz, 1H), 7.72-7.61 (m, 2H), 7.49 (t, J=7.6 Hz, 1H), 7.34 (d, J=7.7 Hz, 1H), 6.84 (d, J=3.2 Hz, 1H), 5.61-5.39 (m, 1H), 5.27 (d, J=1.9 Hz, 2H), 4.68-4.54 (m, 1H), 4.47-4.32 (m, 1H), 4.33-4.20 (m, 1H), 4.04-3.91 (m, 1H), 2.73 (q, J=7.6 Hz, 2H), 1.27 (t, J=7.6 Hz, 3H).

Example 269

1-(3,3-Difluoroazetidin-1-yl)-2-[6-(m-tolyl)pyrrolo[3,2-b]pyridin-1-yl]ethanone

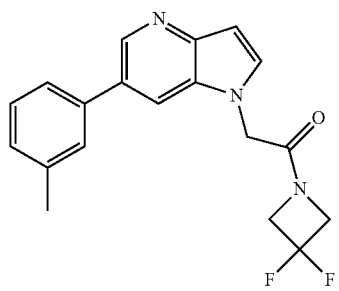 [SMILES: Cc1cccc(-c2cnc3ccn(CC(=O)N4CC(F)(F)C4)c3c2)c1]

The title compound was prepared in a manner analogous to Example 1, Step A, using 2-(6-bromo-1H-pyrrolo[3,2-b]pyridin-1-yl)-1-(3,3-difluoroazetidin-1-yl)ethanone (Intermediate 12) and m-tolylboronic acid. MS (ESI): mass calcd. for $C_{19}H_{17}F_2N_3O$, 341.1. m/z found, 342.1 $[M+H]^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.88 min at 254 nm.

Example 270

1-(3-Fluoroazetidin-1-yl)-2-(6-phenylpyrrolo[3,2-b]pyridin-1-yl)ethanone

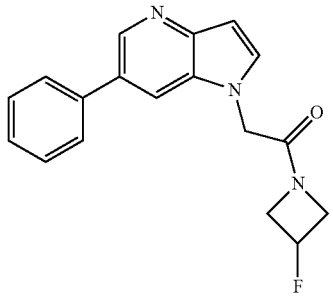 [SMILES: O=C(Cn1ccc2ncc(-c3ccccc3)cc21)N1CC(F)C1]

The title compound was prepared in a manner analogous to Example 1, Step A, using 2-(6-bromo-1H-pyrrolo[3,2-b]pyridin-1-yl)-1-(3-fluoroazetidin-1-yl)ethanone (Intermediate 13) and phenyl boronic acid. MS (ESI): mass calcd. for $C_{18}H_{16}FN_3O$, 309.1. m/z found, 310.1 [M+H]$^+$.

Example 271

1-(3,3-Difluoroazetidin-1-yl)-2-[6-(2,4-difluoro-3-methyl-phenyl)-3-fluoro-pyrrolo[3,2-b]pyridin-1-yl]ethanone

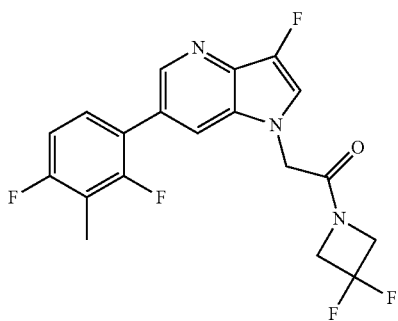

The title compound was prepared in a manner analogous to Example 92, using 2-(6-bromo-3-fluoro-1H-pyrrolo[3,2-b]pyridin-1-yl)-1-(3,3-difluoroazetidin-1-yl)ethanone (Intermediate 16) and (2,4-difluoro-3-methylphenyl)boronic acid. MS (ESI): mass calcd. for $C_{19}H_{14}F_6N_3O$, 395.1; m/z found, 396.0 [M+H]$^+$. $^1$H NMR (500 MHz, DMSO-d$_6$) δ 8.52-8.47 (m, 1H), 8.08 (s, 1H), 7.68 (d, J=2.1 Hz, 1H), 7.50-7.42 (m, 1H), 7.27-7.18 (m, 1H), 5.07 (s, 2H), 4.72 (t, J=12.3 Hz, 2H), 4.42-4.30 (m, 2H), 2.25 (s, 3H).

Example 272

(R/S)-1-[6-(3,5-Difluorophenyl)pyrrolo[3,2-b]pyridin-1-yl]-3-methyl-butan-2-ol

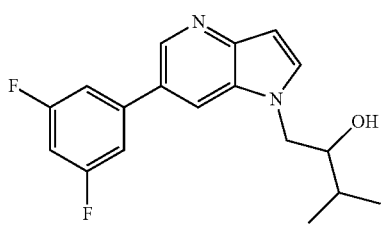 [SMILES: CC(C)C(O)Cn1ccc2ncc(-c3cc(F)cc(F)c3)cc21]

To a solution of compound of 1-[6-(3,5-difluorophenyl)pyrrolo[3,2-b]pyridin-1-yl]-3-methyl-butan-2-one (Example 364, 60 mg, 0.19 mmol) in a mixture of THF (2.5 mL) and MeOH (2.5 mL) cooled at 0° C. was added NaBH$_4$ (14 mg, 0.38 mmol). The reaction mixture was stirred at 0° C. for 30 minutes. The volatiles were evaporated and the residue was taken up in EtOAc and water. The aqueous phase was extracted 2 times with EtOAc. The combined organic layers were washed with water, dried (MgSO$_4$), filtered and evaporated to afford the title compound (39 mg, 64%). MS (ESI): mass calcd. for $C_{18}H_{18}F_2N_2O$, 316.1. m/z found, 317.1 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=0.93 min at 254 nm.

Example 273

2-[6-(4-Fluoro-3-methyl-phenyl)pyrrolo[3,2-b]pyridin-1-yl]-1-(3-hydroxyazetidin-1-yl)ethanone

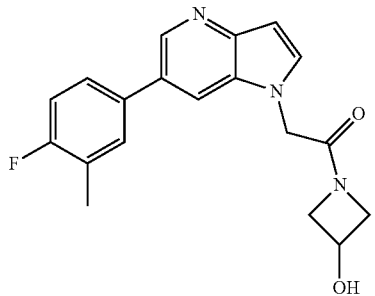 [SMILES: Cc1cc(-c2cnc3ccn(CC(=O)N4CC(O)C4)c3c2)ccc1F]

The title compound was prepared in a manner analogous to Example 66. MS (ESI): mass calcd. for $C_{19}H_{18}FN_3O_2$, 339.1. m/z found, 340.1 [M+H]$^+$. $^1$H NMR (500 MHz, CDCl$_3$) δ 8.61 (d, J=1.9 Hz, 1H), 7.70 (dd, J=1.9, 0.9 Hz, 1H), 7.42-7.38 (m, 1H), 7.39-7.34 (m, 1H), 7.28 (d, J=3.3 Hz, 1H), 7.08 (t, J=8.9 Hz, 1H), 6.70 (dd, J=3.3, 0.9 Hz, 1H), 4.76 (s, 2H), 4.59-4.53 (m, 1H), 4.28-4.20 (m, 1H), 3.94-3.85 (m, 2H), 3.69-3.64 (m, 1H), 2.35 (d, J=1.9 Hz, 3H), 2.16 (br. s, 1H).

Example 274

(R/S)-1-Cyclopropyl-2-[6-(4-fluoro-3-methyl-phenyl)pyrrolo[3,2-b]pyridin-1-yl]ethanol

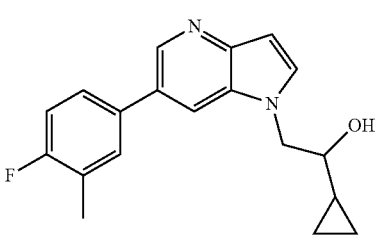 [SMILES: Cc1cc(-c2cnc3ccn(CC(O)C4CC4)c3c2)ccc1F]

The title compound was prepared in a manner analogous to Example 272. MS (ESI): mass calcd. for $C_{19}H_{19}FN_2O$, 310.1. m/z found, 311.1 [M+H]$^+$. $^1$H NMR (500 MHz, DMSO-d$_6$) δ 8.59 (d, J=2.0 Hz, 1H), 8.13 (dd, J=2.1, 0.9 Hz, 1H), 7.71-7.65 (m, 2H), 7.62-7.55 (m, 1H), 7.29-7.22 (m, 1H), 6.55 (dd, J=3.2, 0.9 Hz, 1H), 4.92 (d, J=5.0 Hz, 1H), 4.33 (dd, J=14.2, 4.3 Hz, 1H), 4.24 (dd, J=14.3, 7.1 Hz, 1H), 3.29-3.24 (m, 1H), 2.33 (d, J=1.9 Hz, 3H), 0.84-0.75 (m, 1H), 0.37-0.22 (m, 3H), 0.18-0.11 (m, 1H).

Example 275

(R/S)-2-Cyclopropyl-1-[6-(4-fluoro-3-methyl-phenyl)pyrrolo[3,2-b]pyridin-1-yl]propan-2-ol trifluoroacetate salt

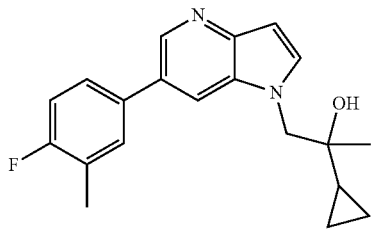 [SMILES: Cc1cc(-c2cnc3ccn(CC(C)(O)C4CC4)c3c2)ccc1F]

To a solution of compound of 1-cyclopropyl-2-[6-(4-fluoro-3-methyl-phenyl)pyrrolo[3,2-b]pyridin-1-yl]ethanone (Example 186, 35 mg, 0.11 mmol) in THF (4 mL) cooled at 0° C. was slowly added a solution of 3M CH$_3$MgBr in Et$_2$O (114 µL, 0.34 mmol). The reaction mixture was stirred at 0° C. for 3 hours and water was added. The aqueous phase was extracted 2 times with EtOAc. The combined organic layers were dried (MgSO$_4$), filtered and evaporated. Purification by HPLC Method C gave the title compound (4 mg, 8%). MS (ESI): mass calcd. for C$_{20}$H$_{21}$FN$_2$O, 324.2. m/z found, 325.1 [M+H]$^+$. $^1$H NMR (400 MHz, DMSO-d$_6$) ⌊ 8.90 (s, 2H), 8.08-8.02 (m, 1H), 7.81-7.75 (m, 1H), 7.73-7.66 (m, 1H), 7.35 (t, J=9.1 Hz, 1H), 6.79 (d, J=3.3 Hz, 1H), 4.44 (s, 2H), 2.35 (s, 3H), 1.09 (s, 3H), 0.94-0.84 (m, 1H), 0.29-0.14 (m, 2H), 0.06--0.09 (m, 2H).

Example 276

1-Cyclopropyl-2-[6-(4-fluoro-3-methyl-phenyl)pyrrolo[3,2-b]pyridin-1-yl]-N-methoxy-ethanimine

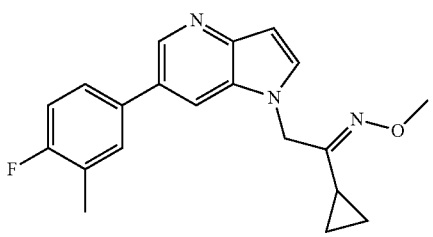 [SMILES: CO/N=C(/Cn1ccc2ncc(-c3ccc(F)c(C)c3)cc21)C1CC1]

To a solution of compound of 1-cyclopropyl-2-[6-(4-fluoro-3-methyl-phenyl)pyrrolo[3,2-b]pyridin-1-yl]ethanone (Example 186, 35 mg, 0.11 mmol) in EtOH (5.7 mL) was added O-methylhydroxylamine hydrochloride (19 mg, 0.23 mmol). The reaction mixture was stirred at room temperature for 10 minutes and NaHCO$_3$ (19 mg, 0.23 mmol) was added. After 2 hours, water was added and the aqueous phase was extracted with EtOAc. The organic phase was then dried over MgSO$_4$, filtered and evaporated. Purification (FCC, SiO$_2$, 0-100% EtOAc in hexanes) gave the title compound (6 mg, 15%). MS (ESI): mass calcd. for C$_{20}$H$_{20}$FN$_3$O, 337.2. m/z found, 338.1 [M+H]$^+$. $^1$H NMR (500 MHz, DMSO-d$_6$) δ 8.66 (d, J=2.0 Hz, 1H), 8.15-8.11 (m, 1H), 7.73 (d, J=3.3 Hz, 1H), 7.71-7.68 (m, 1H), 7.63-7.58 (m, 1H), 7.30-7.22 (m, 1H), 6.65 (dd, J=3.3, 0.9 Hz, 1H), 5.24 (s, 2H), 3.84 (s, 3H), 2.33 (d, J=1.9 Hz, 3H), 0.88-0.83 (m, 1H), 0.56-0.50 (m, 2H), 0.40-0.34 (m, 2H).

Example 277

1-(3-Fluoroazetidin-1-yl)-2-[6-(2-thienyl)pyrrolo[3,2-b]pyridin-1-yl]ethanone

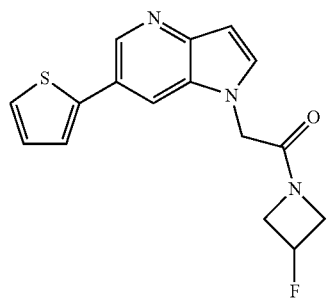 [SMILES: O=C(Cn1ccc2ncc(-c3cccs3)cc21)N1CC(F)C1]

The title compound was prepared in a manner analogous to Example 128. MS (ESI): mass calcd. for C$_{16}$H$_{14}$FN$_3$OS, 315.1. m/z found, 316.0 [M+H]$^+$. $^1$H NMR (400 MHz, DMSO-d$_6$) δ 8.67 (d, J=1.9 Hz, 1H), 8.07 (dd, J=2.1, 0.9 Hz, 1H), 7.59 (d, J=3.3 Hz, 1H), 7.58-7.53 (m, 2H), 7.18 (dd, J=5.1, 3.7 Hz, 1H), 6.60 (dd, J=3.2, 1.0 Hz, 1H), 5.57-5.36 (m, 1H), 5.06 (d, J=2.5 Hz, 2H), 4.61-4.49 (m, 1H), 4.37-4.20 (m, 2H), 4.04-3.91 (m, 1H).

Example 278

1-Pyrrolidin-1-yl-2-[6-(2-thienyl)pyrrolo[3,2-b]pyridin-1-yl]ethanone

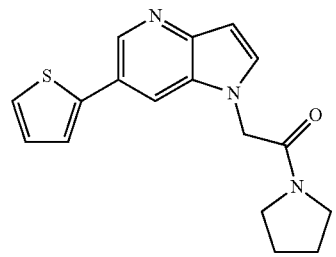 [SMILES: O=C(Cn1ccc2ncc(-c3cccs3)cc21)N1CCCC1]

The title compound was prepared in a manner analogous to Example 105. MS (ESI): mass calcd. for C$_{17}$H$_{17}$N$_3$OS, 311.1. m/z found, 312.0 [M+H]$^+$. $^1$H NMR (400 MHz, CD$_3$OD) δ 8.61 (d, J=1.9 Hz, 1H), 8.08-8.06 (m, 1H), 7.54

(d, J=3.3 Hz, 1H), 7.47 (dd, J=3.6, 1.2 Hz, 1H), 7.42 (dd, J=5.1, 1.2 Hz, 1H), 7.13 (dd, J=5.1, 3.6 Hz, 1H), 6.64 (dd, J=3.4, 0.9 Hz, 1H), 5.18 (s, 2H), 3.66 (t, J=6.8 Hz, 2H), 3.47 (t, J=6.9 Hz, 2H), 2.13-2.04 (m, 2H), 1.98-1.89 (m, 2H).

Example 279

1-(3,3-Difluoroazetidin-1-yl)-2-[6-(5-methyl-2-thienyl)pyrrolo[3,2-b]pyridin-1-yl]ethanone

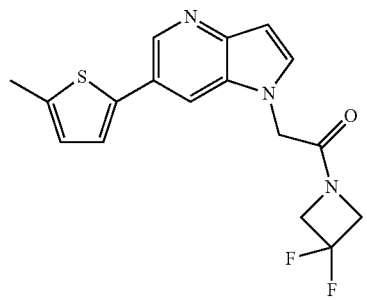 [SMILES: Cc1ccc(-c2cnc3ccn(CC(=O)N4CC(F)(F)C4)c3c2)s1]

The title compound was prepared in a manner analogous to Example 106 substituting 4,4,5,5-tetramethyl-2-(5-methylthiophen-2-yl)-1,3,2-dioxaborolane for (4-fluoro-3-(trifluoromethyl)phenyl)boronic acid. MS (ESI): mass calcd. for $C_{17}H_{16}F_2N_3OS$, 347.1. m/z found, 348.0 [M+H]+. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=0.87 min at 254 nm.

Example 280

1-(3-Fluoroazetidin-1-yl)-2-[6-(5-methyl-2-thienyl)pyrrolo[3,2-b]pyridin-1-yl]ethanone

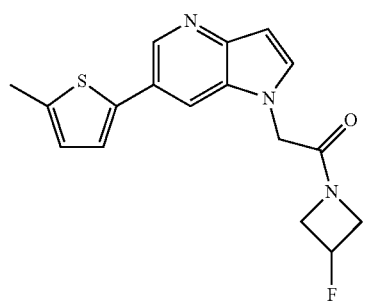 [SMILES: Cc1ccc(-c2cnc3ccn(CC(=O)N4CC(F)C4)c3c2)s1]

The title compound was prepared in a manner analogous to Example 128 substituting 4,4,5,5-tetramethyl-2-(5-methylthiophen-2-yl)-1,3,2-dioxaborolane for (3,4-difluorophenyl)boronic acid. MS (ESI): mass calcd. for $C_{17}H_{16}FN_3OS$, 329.1. m/z found, 330.0 [M+H]+. 1H NMR (400 MHz, CD3OD) δ 8.56 (d, J=1.9 Hz, 1H), 8.01-7.97 (m, 1H), 7.52 (d, J=3.3 Hz, 1H), 7.25 (d, J=3.5 Hz, 1H), 6.82-6.77 (m, 1H), 6.64 (dd, J=3.3, 0.9 Hz, 1H), 5.49-5.28 (m, 1H), 5.04 (d, J=2.0 Hz, 2H), 4.58-4.46 (m, 1H), 4.42-4.26 (m, 2H), 4.17-4.03 (m, 1H), 2.52 (d, J=1.1 Hz, 3H).

Example 281

2-[6-(5-Ethyl-2-thienyl)pyrrolo[3,2-b]pyridin-1-yl]-1-(3-fluoroazetidin-1-yl)ethanone

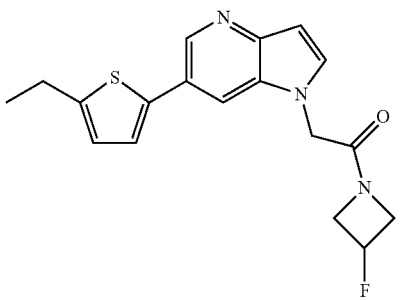 [SMILES: CCc1ccc(-c2cnc3ccn(CC(=O)N4CC(F)C4)c3c2)s1]

The title compound was prepared in a manner analogous to Example 128 substituting 5-ethylthiophene-2-boronic acid for (4-fluoro-3-(trifluoromethyl)phenyl)boronic acid. MS (ESI): mass calcd. for $C_{18}H_{18}FN_3OS$, 343.1. m/z found, 344.0 [M+H]+. 1H NMR (400 MHz, CD3OD) δ 8.58 (d, J=1.8 Hz, 1H), 8.01-7.99 (m, 1H), 7.52 (d, J=3.3 Hz, 1H), 7.27 (d, J=3.7 Hz, 1H), 6.83 (dd, J=3.7, 1.0 Hz, 1H), 6.66-6.62 (m, 1H), 5.48-5.28 (m, 1H), 5.04 (d, J=1.8 Hz, 2H), 4.59-4.45 (m, 1H), 4.41-4.26 (m, 2H), 4.11 (dd, J=24.7, 11.6 Hz, 1H), 2.89 (q, J=7.5 Hz, 2H), 1.38-1.31 (m, 3H).

Example 282

2-[6-(5-Ethyl-2-thienyl)pyrrolo[3,2-b]pyridin-1-yl]-1-pyrrolidin-1-yl-ethanone

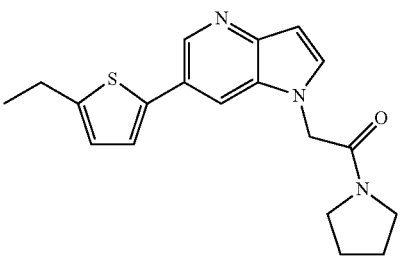 [SMILES: CCc1ccc(-c2cnc3ccn(CC(=O)N4CCCC4)c3c2)s1]

The title compound was prepared in a manner analogous to Example 105 substituting 5-ethylthiophene-2-boronic acid for (3,4-difluorophenyl)boronic acid. MS (ESI): mass calcd. for $C_{19}H_{21}N_3OS$, 339.1. m/z found, 340.1 [M+H]+. 1H NMR (400 MHz, CD3OD) δ 8.56 (d, J=1.9 Hz, 1H), 8.01-7.99 (m, 1H), 7.52 (d, J=3.4 Hz, 1H), 7.26 (d, J=3.6 Hz, 1H), 6.85-6.81 (m, 1H), 6.63 (dd, J=3.3, 0.9 Hz, 1H), 5.16 (s, 2H), 3.66 (t, J=6.9 Hz, 2H), 3.47 (t, J=6.9 Hz, 2H), 2.93-2.84 (m, 2H), 2.13-2.03 (m, 2H), 1.97-1.89 (m, 2H), 1.34 (t, J=7.5 Hz, 3H).

Example 283

2-[6-(5-Methyl-2-thienyl)pyrrolo[3,2-b]pyridin-1-yl]-1-pyrrolidin-1-yl-ethanone

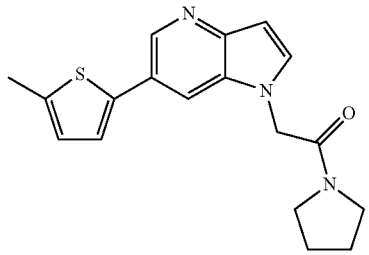 [SMILES: Cc1ccc(-c2cnc3ccn(CC(=O)N4CCCC4)c3c2)s1]

The title compound was prepared in a manner analogous to Example 105 substituting 4,4,5,5-tetramethyl-2-(5-methylthiophen-2-yl)-1,3,2-dioxaborolane for (4-fluoro-3-(trifluoromethyl)phenyl)boronic acid. $^1$H NMR (400 MHz, CD$_3$OD) δ 8.54 (d, J=1.9 Hz, 1H), 8.00-7.97 (m, 1H), 7.51 (d, J=3.4 Hz, 1H), 7.24 (d, J=3.5 Hz, 1H), 6.81-6.77 (m, 1H), 6.62 (dd, J=3.3, 0.9 Hz, 1H), 5.15 (s, 2H), 3.66 (t, J=6.8 Hz, 2H), 3.47 (t, J=6.9 Hz, 2H), 2.51 (s, 3H), 2.12-2.03 (m, 2H), 1.99-1.89 (m, 2H).

Example 284

1-(3,3-Difluoroazetidin-1-yl)-2-[6-(5-ethyl-2-thienyl)pyrrolo[3,2-b]pyridin-1-yl]ethanone

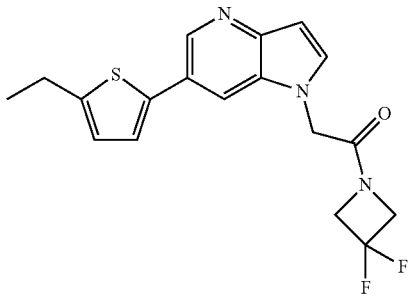 [SMILES: CCc1ccc(-c2cnc3ccn(CC(=O)N4CC(F)(F)C4)c3c2)s1]

The title compound was prepared in a manner analogous to Example 106. MS (ESI): mass calcd. for C$_{18}$H$_{17}$F$_2$N$_3$OS, 361.1. m/z found, 362.0 [M+H]$^+$. $^1$H NMR (500 MHz, DMSO-d$_6$) δ 8.62 (d, J=2.0 Hz, 1H), 8.02-7.99 (m, 1H), 7.56 (d, J=3.3 Hz, 1H), 7.35 (d, J=3.5 Hz, 1H), 6.89 (d, J=3.5 Hz, 1H), 6.59 (dd, J=3.3, 0.9 Hz, 1H), 5.12 (s, 2H), 4.72 (t, J=11.5 Hz, 2H), 4.42-4.34 (m, 2H), 2.89-2.81 (m, 2H), 1.28 (t, J=7.5 Hz, 3H).

Example 285

2-[6-(4-Chloro-2-thienyl)pyrrolo[3,2-b]pyridin-1-yl]-1-(3-fluoroazetidin-1-yl)ethanone

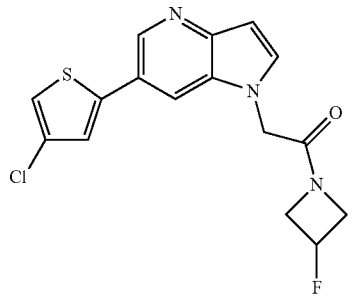 [SMILES: O=C(Cn1ccc2ncc(-c3cc(Cl)cs3)cc21)N1CC(F)C1]

The title compound was prepared in a manner analogous to Example 128 substituting 2-(4-chlorothiophen-2-yl)-4,4,5,5-tetramethyl-1,3,2-dioxaborolane for (3,4-difluorophenyl)boronic acid. MS (ESI): mass calcd. for C$_{16}$H$_{13}$ClFN$_3$OS, 349.0. m/z found, 350.0 [M+H]$^+$. $^1$H NMR (500 MHz, CD$_3$OD) δ 8.61 (d, J=1.9 Hz, 1H), 8.12-8.10 (m, 1H), 7.58 (d, J=3.4 Hz, 1H), 7.42 (d, J=1.5 Hz, 1H), 7.31 (d, J=1.5 Hz, 1H), 6.67 (dd, J=3.3, 0.9 Hz, 1H), 5.49-5.32 (m, 1H), 5.07 (d, J=3.2 Hz, 2H), 4.62-4.52 (m, 1H), 4.41-4.31 (m, 2H), 4.16-4.05 (m, 1H).

Example 286

1-Cyclopropyl-2-[6-(4-fluoro-3-methyl-phenyl)pyrrolo[3,2-b]pyridin-1-yl]ethanone oxime trifluoroacetate salt

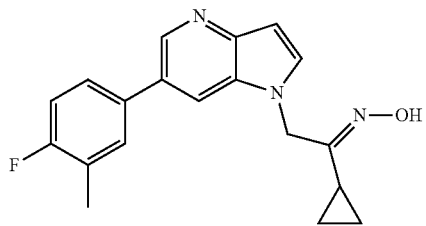 [SMILES: Cc1cc(-c2cnc3ccn(C/C(=N/O)C4CC4)c3c2)ccc1F]

The title compound was prepared in a manner analogous to Example 276 substituting hydroxylamine hydrochloride for O-methylhydroxylamine hydrochloride. MS (ESI): mass calcd. for C$_{19}$H$_{18}$FN$_3$O, 323.1. m/z found, 324.1 [M+H]$^+$. $^1$H NMR (400 MHz, CD$_3$OD) δ 8.89-8.85 (m, 2H), 8.17 (d, J=3.3 Hz, 1H), 7.71-7.67 (m, 1H), 7.65-7.58 (m, 1H), 7.29-7.18 (m, 1H), 6.91 (dd, J=3.3, 0.9 Hz, 1H), 5.43 (s, 2H), 2.39 (d, J=2.1 Hz, 3H), 1.23-1.14 (m, 1H), 0.60-0.47 (m, 4H).

Example 287

2-[6-(5-Chloro-2-thienyl)pyrrolo[3,2-b]pyridin-1-yl]-1-pyrrolidin-1-yl-ethanone

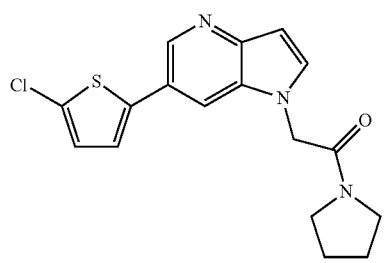 [SMILES: O=C(Cn1ccc2ncc(-c3ccc(Cl)s3)cc21)N1CCCC1]

The title compound was prepared in a manner analogous to Example 105 substituting 5-chlorothiophene-2-boronic acid for (4-fluoro-3-(trifluoromethyl)phenyl)boronic acid. MS (ESI): mass calcd. for C$_{17}$H$_{16}$ClN$_3$OS, 345.1. m/z found, 346.0 [M+H]$^+$. $^1$H NMR (400 MHz, CD$_3$OD) δ 8.54 (d, J=1.9 Hz, 1H), 8.04-8.00 (m, 1H), 7.56 (d, J=3.3 Hz, 1H), 7.28 (d, J=3.9 Hz, 1H), 7.01 (d, J=3.9 Hz, 1H), 6.65 (dd, J=3.3, 0.9 Hz, 1H), 5.17 (s, 2H), 3.66 (t, J=6.8 Hz, 2H), 3.47 (t, J=6.9 Hz, 2H), 2.13-2.03 (m, 2H), 1.98-1.88 (m, 2H).

Example 288

2-[6-(4-Chloro-2-thienyl)pyrrolo[3,2-b]pyridin-1-yl]-1-pyrrolidin-1-yl-ethanone

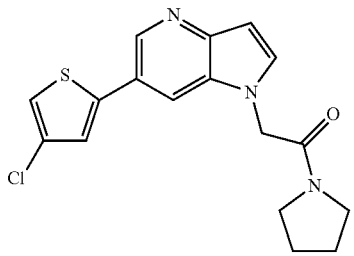 [SMILES: O=C(Cn1ccc2ncc(-c3cc(Cl)cs3)cc21)N1CCCC1]

The title compound was prepared in a manner analogous to Example 105 substituting 2-(4-chlorothiophen-2-yl)-4,4,5,5-tetramethyl-1,3,2-dioxaborolane for (4-fluoro-3-(trifluoromethyl)phenyl)boronic acid. MS (ESI): mass calcd. for $C_{17}H_{16}ClN_3OS$, 345.1. m/z found, 346.0 [M+H]$^+$. $^1$H NMR (400 MHz, CD$_3$OD) δ 8.59 (d, J=1.9 Hz, 1H), 8.10 (s, 1H), 7.58 (d, J=3.4 Hz, 1H), 7.40 (s, 1H), 7.30 (s, 1H), 6.66 (d, J=3.4 Hz, 1H), 5.18 (s, 2H), 3.67 (t, J=6.8 Hz, 2H), 3.47 (t, J=6.9 Hz, 2H), 2.13-2.04 (m, 2H), 1.98-1.89 (m, 2H).

Example 289

(R/S)-1-(2-Cyclopropyl-2-fluoro-ethyl)-6-(4-fluoro-3-methyl-phenyl)pyrrolo[3,2-b]pyridine

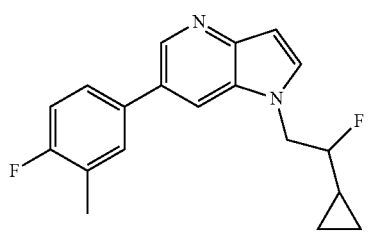 [SMILES: Cc1cc(-c2cnc3ccn(CC(F)C4CC4)c3c2)ccc1F]

To a solution of compound of (R/S)-1-cyclopropyl-2-[6-(4-fluoro-3-methyl-phenyl)pyrrolo[3,2-b]pyridin-1-yl]ethanol (Example 274, 14 mg, 0.05 mmol) in DCM (1 mL) cooled at 0° C. was added DAST (29 μL, 0.22 mmol). The reaction mixture was warmed to room temperature and after 30 minutes a saturated aqueous solution of NaHCO$_3$ was added. The organic phase was separated, dried over MgSO$_4$, filtered and evaporated to afford the title compound (6.5 mg, 47%). MS (ESI): mass calcd. for $C_{19}H_{18}F_2N_2$, 312.1. m/z found, 313.1 [M+H]$^+$. $^1$H NMR (500 MHz, DMSO-d$_6$) δ 8.62 (d, J=2.0 Hz, 1H), 8.19-8.15 (m, 1H), 7.72-7.66 (m, 2H), 7.62-7.56 (m, 1H), 7.26 (dd, J=9.7, 8.5 Hz, 1H), 6.61 (dd, J=3.2, 0.8 Hz, 1H), 4.66-4.56 (m, 2H), 4.32-4.15 (m, 1H), 2.33 (d, J=1.9 Hz, 3H), 1.05-0.96 (m, 1H), 0.57-0.48 (m, 2H), 0.45-0.34 (m, 2H).

Example 290

2-[6-(4-Fluoro-3-methyl-phenyl)pyrrolo[3,2-b]pyridin-1-yl]-1-(3-methoxyazetidin-1-yl)ethanone

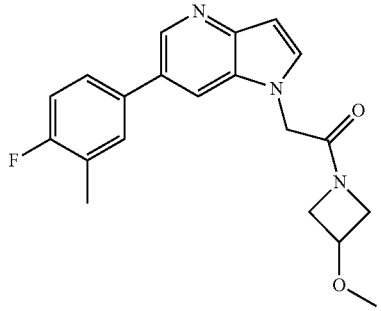

The title compound was prepared in a manner analogous to Example 66. MS (ESI): mass calcd. for $C_{20}H_{20}FN_3O_2$, 353.2. m/z found, 354.1 [M+H]$^+$. $^1$H NMR (400 MHz, DMSO-d$_6$) δ 8.64-8.60 (m, 1H), 8.07 (s, 1H), 7.66 (dd, J=7.7, 2.4 Hz, 1H), 7.61-7.54 (m, 2H), 7.26 (t, J=9.1 Hz, 1H), 6.59 (d, J=3.3 Hz, 1H), 5.04 (s, 2H), 4.41-4.35 (m, 1H), 4.31-4.22 (m, 1H), 4.13-4.00 (m, 2H), 3.75-3.68 (m, 1H), 3.23 (s, 3H), 2.33 (s, 3H).

Example 291

6-(4-Fluoro-3-methyl-phenyl)-1-(2-methoxyethyl)pyrrolo[3,2-b]pyridine trifluoroacetate salt

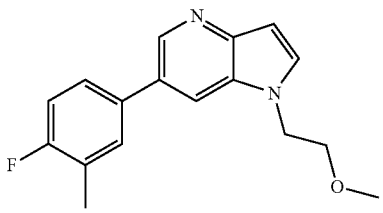

The title compound was prepared in a manner analogous to Example 170 using 6-(4-fluoro-3-methylphenyl)-1H-pyrrolo[3,2-b]pyridine and 1-bromo-2-methoxyethane. MS (ESI): mass calcd. for $C_{17}H_{17}FN_2O$, 284.1. m/z found, 285.1 [M+H]$^+$. $^1$H NMR (400 MHz, DMSO-d$_6$) δ 8.88 (s, 1H), 8.76 (s, 1H), 8.04 (d, J=3.3 Hz, 1H), 7.81 (dd, J=7.6, 2.4 Hz, 1H), 7.74-7.68 (m, 1H), 7.38-7.30 (m, 1H), 6.76 (d, J=3.3 Hz, 1H), 4.58 (t, J=5.1 Hz, 2H), 3.71 (t, J=5.1 Hz, 2H), 3.22 (s, 3H), 2.35 (d, J=1.9 Hz, 3H).

Example 292

1-Cyclobutyl-2-[6-(3-fluorophenyl)pyrrolo[3,2-b]pyridin-1-yl]ethanone

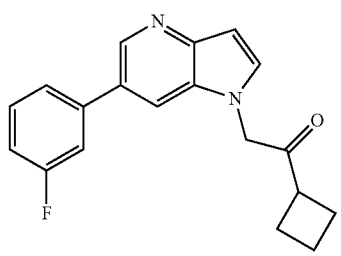 [SMILES: O=C(Cn1ccc2ncc(-c3cccc(F)c3)cc21)C1CCC1]

The title compound was prepared in a manner analogous to Example 170 using 6-(3-fluoro-phenyl)-1H-pyrrolo[3,2-b]pyridine and 2-bromo-1-cyclobutylethanone. MS (ESI): mass calcd. for $C_{19}H_{17}FN_2O$, 308.1. m/z found, 309.1 [M+H]$^+$. $^1$H NMR (400 MHz, CD$_3$OD) δ 8.61 (d, J=1.9 Hz, 1H), 8.01 (s, 1H), 7.58-7.42 (m, 4H), 7.15-7.08 (m, 1H), 6.69 (d, J=3.3 Hz, 1H), 5.21 (s, 2H), 3.58-3.45 (m, 1H), 2.38-2.25 (m, 2H), 2.24-2.13 (m, 2H), 2.10-1.97 (m, 1H), 1.92-1.80 (m, 1H).

Example 293

2-[6-(4-Fluorophenyl)pyrrolo[3,2-b]pyridin-1-yl]-1-[(3R)-3-fluoropyrrolidin-1-yl]ethanone trifluoroacetate salt

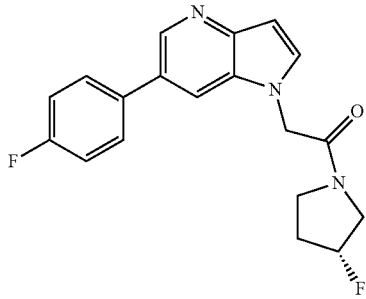 [SMILES: O=C(Cn1ccc2ncc(-c3ccc(F)cc3)cc21)N1CC[C@@H](F)C1]

The title compound was prepared in a manner analogous to Example 66. MS (ESI): mass calcd. for $C_{19}H_{17}F_2N_3O$, 341.1. m/z found, 342.1 [M+H]$^+$. Analytical HPLC was obtained on a Agilent 1100 Series using a XBridge C18 column (4.6×100 mm, 5 μm), mobile phase of 10-100% ACN in 20 mM NH$_4$OH over 8 min and then hold at 100% ACN for 3 min, at a flow rate of 1 mL/min (Temperature=45° C.). R$_t$=5.62 min at 254 nm.

Example 294

2-[6-(4-Fluorophenyl)pyrrolo[3,2-b]pyridin-1-yl]-1-[(3S)-3-fluoropyrrolidin-1-yl]ethanone trifluoroacetate salt

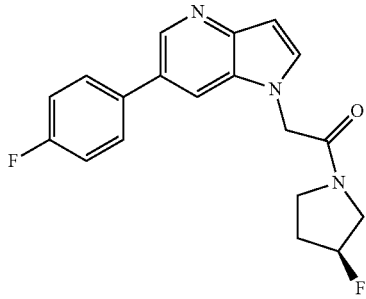 [SMILES: O=C(Cn1ccc2ncc(-c3ccc(F)cc3)cc21)N1CC[C@H](F)C1]

The title compound was prepared in a manner analogous to Example 66. MS (ESI): mass calcd. for $C_{19}H_{17}F_2N_3O$, 341.1. m/z found, 342.1 [M+H]$^+$.]$^+$. Analytical HPLC was obtained on a Agilent 1100 Series using a XBridge C18 column (4.6×100 mm, 5 μm), mobile phase of 10-100% ACN in 20 mM NH$_4$OH over 8 min and then hold at 100% ACN for 3 min, at a flow rate of 1 mL/min (Temperature=45° C.). R$_t$=5.63 min at 254 nm.

Example 295

1-[6-(4-Fluoro-3-methyl-phenyl)pyrrolo[3,2-b]pyridin-1-yl]butan-2-one trifluoroacetate salt

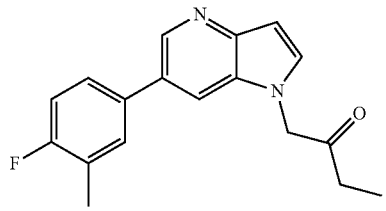 [SMILES: CCC(=O)Cn1ccc2ncc(-c3ccc(F)c(C)c3)cc21]

The title compound was prepared in a manner analogous to Example 170 using 6-(4-fluoro-3-methylphenyl)-1H-pyrrolo[3,2-b]pyridine and 1-bromobutan-2-one. MS (ESI): mass calcd. for $C_{18}H_{17}FN_2O$, 296.1. m/z found, 297.1 [M+H]$^+$. $^1$H NMR (500 MHz, CD$_3$OD) δ 8.86 (d, J=1.7 Hz, 1H), 8.81 (s, 1H), 8.00 (d, J=3.3 Hz, 1H), 7.72-7.67 (m, 1H), 7.65-7.59 (m, 1H), 7.26-7.20 (m, 1H), 6.91 (dd, J=3.3, 0.9 Hz, 1H), 5.49 (s, 2H), 2.72 (q, J=7.3 Hz, 2H), 2.39 (d, J=2.1 Hz, 3H), 1.13 (t, J=7.3 Hz, 3H).

Example 296

N-Ethyl-2-[6-(4-fluoro-3-methyl-phenyl)pyrrolo[3,2-b]pyridin-1-yl]-N-methyl-acetamide

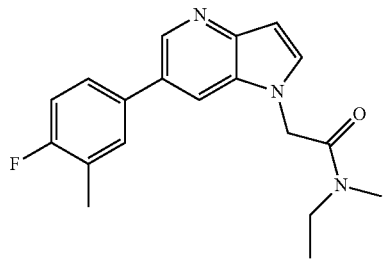 [SMILES: CCN(C)C(=O)Cn1ccc2ncc(-c3ccc(F)c(C)c3)cc21]

The title compound was prepared in a manner analogous to Example 66. MS (ESI): mass calcd. for $C_{19}H_{20}FN_3O$, 325.2. m/z found, 326.1 [M+H]$^+$. Analytical HPLC was obtained on a Agilent 1100 Series using a XBridge C18 column (4.6×100 mm, 5 μm), mobile phase of 10-100% ACN in 20 mM NH$_4$OH over 8 min and then hold at 100% ACN for 3 min, at a flow rate of 1 mL/min (Temperature=45° C.). R$_t$=6.12 min at 254 nm.

Example 297

N,N-Diethyl-2-[6-(4-fluoro-3-methyl-phenyl)pyrrolo[3,2-b]pyridin-1-yl]acetamide

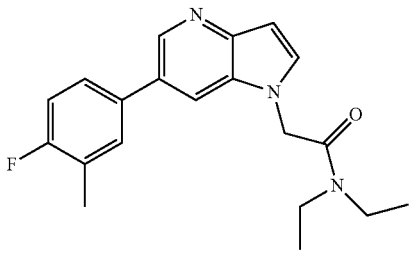 [SMILES: CCN(CC)C(=O)Cn1ccc2ncc(-c3ccc(F)c(C)c3)cc21]

The title compound was prepared in a manner analogous to Example 66. MS (ESI): mass calcd. for $C_{20}H_{22}FN_3O$, 339.2. m/z found, 340.1 [M+H]$^+$. $^1$H NMR (500 MHz, DMSO-d$_6$) δ 8.60 (d, J=2.0 Hz, 1H), 8.02-8.00 (m, 1H), 7.65 (dd, J=7.6, 2.4 Hz, 1H), 7.60 (d, J=3.2 Hz, 1H), 7.58-7.53 (m, 1H), 7.28-7.23 (m, 1H), 6.57 (dd, J=3.2, 0.9 Hz, 1H), 5.25 (s, 2H), 3.47 (q, J=7.1 Hz, 2H), 3.30-3.26 (m, 2H), 2.33 (d, J=1.9 Hz, 3H), 1.24 (t, J=7.1 Hz, 3H), 1.03 (t, J=7.1 Hz, 3H).

Example 298

1-(Azetidin-1-yl)-2-[3-chloro-6-[3-(trifluoromethyl)phenyl]pyrrolo[3,2-b]pyridin-1-yl]ethanone

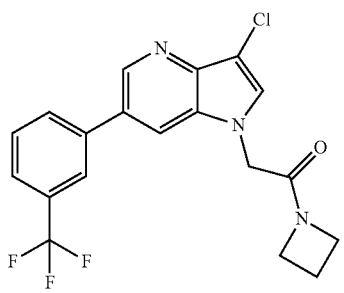 [SMILES: O=C(Cn1cc(Cl)c2ncc(-c3cccc(C(F)(F)F)c3)cc21)N1CCC1]

The title compound was prepared in a manner analogous to Example 29. MS (ESI): mass calcd. for $C_{19}H_{15}ClF_3N_3O$, 393.1. m/z found, 394.0 [M+H]$^+$. $^1$H NMR (400 MHz, DMSO-d$_6$) δ 8.80 (d, J=2.0 Hz, 1H), 8.34 (d, J=2.0 Hz, 1H), 8.12-8.06 (m, 2H), 7.83 (s, 1H), 7.79-7.75 (m, 2H), 5.04 (s, 2H), 4.25 (t, J=7.7 Hz, 2H), 3.91 (t, J=7.7 Hz, 2H), 2.34-2.24 (m, 2H).

Example 299

2-[3-Chloro-6-(m-tolyl)pyrrolo[3,2-b]pyridin-1-yl]-1-cyclopropylethanone

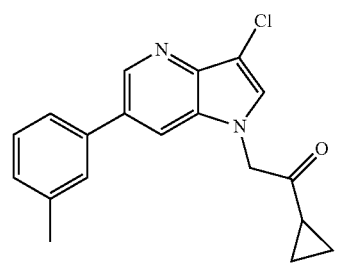 [SMILES: Cc1cccc(-c2cnc3c(Cl)cn(CC(=O)C4CC4)c3c2)c1]

The title compound was prepared in a manner analogous to Example 1. MS (ESI): mass calcd. for $C_{19}H_{17}ClN_2O$, 324.1. m/z found, 325.0 [M+H]$^+$. $^1$H NMR (400 MHz, DMSO-d$_6$) δ 8.72 (d, J=1.9 Hz, 1H), 8.19 (d, J=1.9 Hz, 1H), 7.79 (s, 1H), 7.57 (s, 1H), 7.54 (d, J=7.8 Hz, 1H), 7.39 (t, J=7.6 Hz, 1H), 7.22 (d, J=7.5 Hz, 1H), 5.50 (s, 2H), 2.41 (s, 3H), 2.16-2.09 (m, 1H), 1.04-0.98 (m, 2H), 0.97-0.92 (m, 2H).

Example 300

2-(3-Chloro-6-phenyl-pyrrolo[3,2-b]pyridin-1-yl)-1-cyclopropylethanone

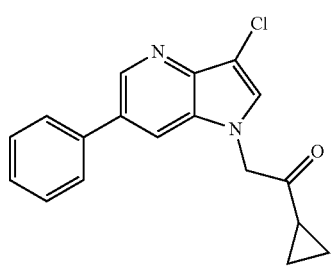 [SMILES: O=C(Cn1cc(Cl)c2ncc(-c3ccccc3)cc21)C1CC1]

The title compound was prepared in a manner analogous to Example 1. MS (ESI): mass calcd. for $C_{18}H_{15}ClN_2O$, 310.1. m/z found, 311.0 [M+H]$^+$. $^1$H NMR (400 MHz, DMSO-d$_6$) δ 8.74 (d, J=1.8 Hz, 1H), 8.22 (d, J=1.9 Hz, 1H), 7.80 (s, 1H), 7.78-7.73 (m, 2H), 7.55-7.47 (m, 2H), 7.45-7.37 (m, 1H), 5.50 (s, 2H), 2.18-2.09 (m, 1H), 1.04-0.97 (m, 2H), 0.97-0.92 (m, 2H).

Example 301

1-(Azetidin-1-yl)-2-[3-chloro-6-(3,4,5-trifluorophenyl)pyrrolo[3,2-b]pyridin-1-yl]ethanone

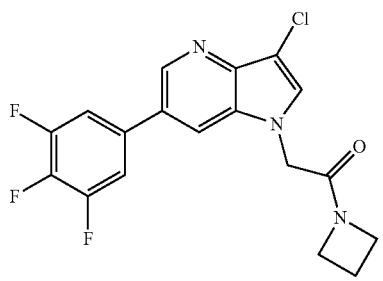

The title compound was prepared in a manner analogous to Example 29. MS (ESI): mass calcd. for $C_{18}H_{13}ClF_3N_3O$, 379.1. m/z found, 380.0 [M+H]$^+$. $^1$H NMR (400 MHz, DMSO-d$_6$) δ 8.80 (d, J=2.0 Hz, 1H), 8.33 (d, J=1.9 Hz, 1H), 7.87-7.79 (m, 3H), 5.01 (s, 2H), 4.25 (t, J=7.7 Hz, 2H), 3.91 (t, J=7.6 Hz, 2H), 2.33-2.24 (m, 2H).

Example 302

1-(Azetidin-1-yl)-2-[3-fluoro-6-(4-fluorophenyl) pyrrolo[3,2-b]pyridin-1-yl]ethanone

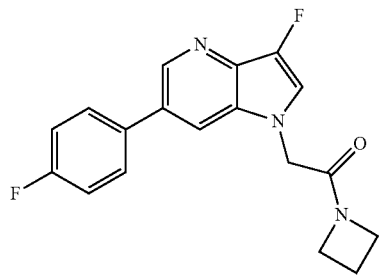 [SMILES: O=C(Cn1cc(F)c2ncc(-c3ccc(F)cc3)cc21)N1CCC1]

The title compound was prepared in a manner analogous to Example 182. MS (ESI): mass calcd. for $C_{18}H_{15}F_2N_3O$, 327.1. m/z found, 328.0 [M+H]$^+$. $^1$H NMR (400 MHz, DMSO-d$_6$) δ 8.68 (d, J=1.9 Hz, 1H), 8.18-8.16 (m, 1H), 7.83-7.77 (m, 2H), 7.65 (d, J=2.2 Hz, 1H), 7.39-7.33 (m, 2H), 4.95 (s, 2H), 4.22 (t, J=7.7 Hz, 2H), 3.90 (t, J=7.7 Hz, 2H), 2.32-2.23 (m, 2H).

Example 303

1-(Azetidin-1-yl)-2-[3-chloro-6-(3,5-dimethylphenyl)pyrrolo[3,2-b]pyridin-1-yl]ethanone

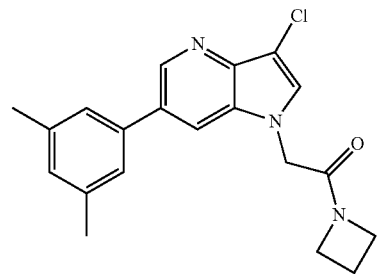 [SMILES: Cc1cc(C)cc(-c2cnc3c(Cl)cn(CC(=O)N4CCC4)c3c2)c1]

The title compound was prepared in a manner analogous to Example 29. MS (ESI): mass calcd. for $C_{20}H_{20}ClN_3O$, 353.1. m/z found, 354.1 [M+H]$^+$. $^1$H NMR (400 MHz, CD$_3$OD) δ 8.61 (d, J=1.8 Hz, 1H), 8.05 (d, J=1.8 Hz, 1H), 7.59 (s, 1H), 7.29 (s, 2H), 7.04 (s, 1H), 4.98 (s, 2H), 4.30 (t, J=7.8 Hz, 2H), 4.09-4.01 (m, 2H), 2.44-2.31 (m, 8H).

Example 304

2-[3-Fluoro-6-(4-fluoro-3-methyl-phenyl)pyrrolo[3,2-b]pyridin-1-yl]-1-morpholino-ethanone

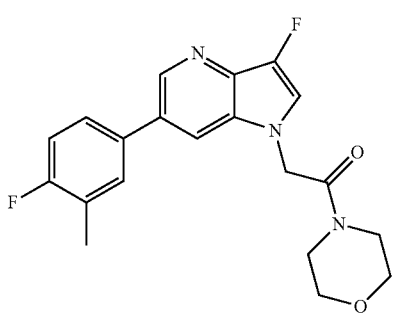

The title compound was prepared in a manner analogous to Example 1, Step A, using 2-(6-bromo-3-fluoro-1H-pyrrolo[3,2-b]pyridin-1-yl)-1-morpholinoethanone (Intermediate 19) and (4-fluoro-3-methylphenyl)boronic acid. MS (ESI): mass calcd. for $C_{20}H_{19}F_2N_3O_2$, 371.1. m/z found, 372.1 [M+H]$^+$. $^1$H NMR (500 MHz, DMSO-d$_6$) δ 8.65 (d, J=1.9 Hz, 1H), 8.15 (s, 1H), 7.69-7.66 (m, 1H), 7.63 (d, J=2.1 Hz, 1H), 7.61-7.55 (m, 1H), 7.31-7.24 (m, 1H), 5.24 (s, 2H), 3.72-3.67 (m, 2H), 3.62-3.53 (m, 4H), 3.45-3.40 (m, 2H), 2.33 (s, 3H).

Example 305

2-[3-Fluoro-6-(4-fluorophenyl)pyrrolo[3,2-b]pyridin-1-yl]-1-morpholino-ethanone

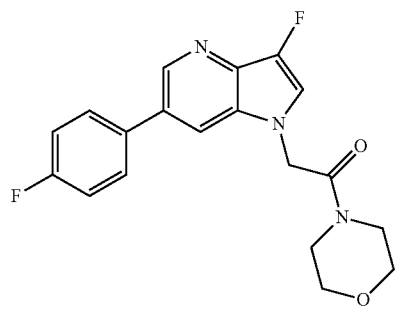 [SMILES: O=C(Cn1cc(F)c2ncc(-c3ccc(F)cc3)cc21)N1CCOCC1]

The title compound was prepared in a manner analogous to Example 1, Step A, using 2-(6-bromo-3-fluoro-1H-pyrrolo[3,2-b]pyridin-1-yl)-1-morpholinoethanone (Intermediate 19) and (4-fluorophenyl)boronic acid. MS (ESI): mass calcd. for $C_{19}H_{17}F_2N_3O_2$, 357.1. m/z found, 358.1 [M+H]$^+$. $^1$H NMR (500 MHz, DMSO-d$_6$) δ 8.67 (d, J=1.9 Hz, 1H), 8.19-8.16 (m, 1H), 7.81-7.76 (m, 2H), 7.63 (d, J=2.1 Hz, 1H), 7.38-7.32 (m, 2H), 5.24 (s, 2H), 3.72-3.67 (m, 2H), 3.61-3.53 (m, 4H), 3.45-3.41 (m, 2H).

Example 306

1-(3-Fluoroazetidin-1-yl)-2-[3-fluoro-6-(3,4,5-trifluorophenyl)pyrrolo[3,2-b]pyridin-1-yl]ethanone

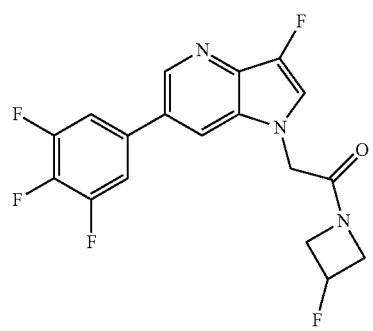 [SMILES: O=C(Cn1cc(F)c2ncc(-c3cc(F)c(F)c(F)c3)cc21)N1CC(F)C1]

The title compound was prepared in a manner analogous to Example 92, using 2-(6-bromo-3-fluoro-1H-pyrrolo[3,2-b]pyridin-1-yl)-1-(3-fluoroazetidin-1-yl)ethanone (Intermediate 17) and (3,4,5-trifluorophenyl)boronic acid. MS (ESI): mass calcd. for $C_{18}H_{12}F_6N_3O$, 381.1. m/z found, 382.0 [M+H]$^+$. $^1$H NMR (500 MHz, CDCl$_3$) δ 8.66 (d, J=1.9 Hz, 1H), 7.64 (t, J=2.0 Hz, 1H), 7.25-7.20 (m, 3H), 5.40-5.19 (m, 1H), 4.73 (s, 2H), 4.42-4.29 (m, 1H), 4.27-4.03 (m, 3H).

Example 307

1-(3-Fluoroazetidin-1-yl)-2-[3-fluoro-6-(4-fluoro-3-methyl-phenyl)pyrrolo[3,2-b]pyridin-1-yl]ethanone

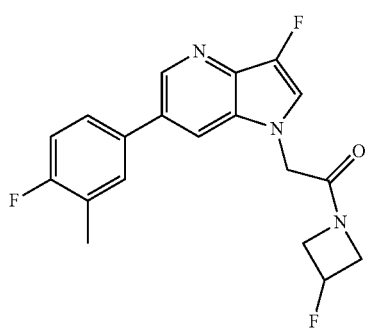 [SMILES: Cc1cc(-c2cnc3c(F)cn(CC(=O)N4CC(F)C4)c3c2)ccc1F]

The title compound was prepared in a manner analogous to Example 92, using 2-(6-bromo-3-fluoro-1H-pyrrolo[3,2-b]pyridin-1-yl)-1-(3-fluoroazetidin-1-yl)ethanone (Intermediate 17) and (4-fluoro-3-methylphenyl)boronic acid. MS (ESI): mass calcd. for $C_{19}H_{18}F_3N_3O$, 359.1. m/z found, 360.0 [M+H]$^+$. $^1$H NMR (500 MHz, DMSO-d$_6$) δ 8.67 (d, J=1.9 Hz, 1H), 8.15 (t, J=2.1 Hz, 1H), 7.68 (dd, J=7.5, 2.4 Hz, 1H), 7.64 (d, J=2.1 Hz, 1H), 7.62-7.56 (m, 1H), 7.31-7.25 (m, 1H), 5.55-5.38 (m, 1H), 5.01 (d, J=3.4 Hz, 2H), 4.60-4.49 (m, 1H), 4.38-4.18 (m, 2H), 4.03-3.91 (m, 1H), 2.33 (d, J=1.9 Hz, 3H).

Example 308

1-(3-Fluoroazetidin-1-yl)-2-[3-fluoro-6-(4-fluorophenyl)pyrrolo[3,2-b]pyridin-1-yl]ethanone

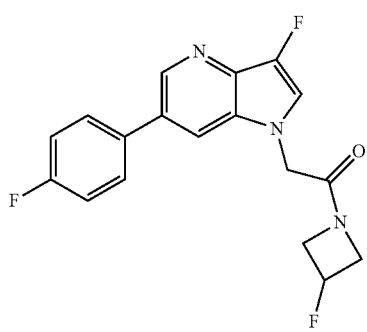 [SMILES: O=C(Cn1cc(F)c2ncc(-c3ccc(F)cc3)cc21)N1CC(F)C1]

The title compound was prepared in a manner analogous to Example 92, using 2-(6-bromo-3-fluoro-1H-pyrrolo[3,2-b]pyridin-1-yl)-1-(3-fluoroazetidin-1-yl)ethanone (Intermediate 17) and (4-fluorophenyl)boronic acid. MS (ESI): mass calcd. for $C_{18}H_{14}F_3N_3O$, 345.1. m/z found, 346.0 [M+H]$^+$. $^1$H NMR (500 MHz, DMSO-d$_6$) δ 8.68 (d, J=1.9 Hz, 1H), 8.17 (t, J=2.2 Hz, 1H), 7.82-7.77 (m, 2H), 7.65 (d, J=2.2 Hz, 1H), 7.38-7.32 (m, 2H), 5.54-5.38 (m, 1H), 5.01 (d, J=3.1 Hz, 2H), 4.60-4.50 (m, 1H), 4.37-4.19 (m, 2H), 4.02-3.91 (m, 1H).

Example 309

1-(3-Fluoroazetidin-1-yl)-2-[3-fluoro-6-(4-methyl-2-thienyl)pyrrolo[3,2-b]pyridin-1-yl]ethanone

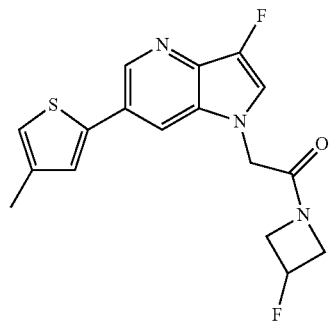 [SMILES: Cc1csc(-c2cnc3c(F)cn(CC(=O)N4CC(F)C4)c3c2)c1]

The title compound was prepared in a manner analogous to Example 92, using 2-(6-bromo-3-fluoro-1H-pyrrolo[3,2-b]pyridin-1-yl)-1-(3-fluoroazetidin-1-yl)ethanone (Intermediate 17) and 4,4,5,5-tetramethyl-2-(4-methylthiophen-2-yl)-1,3,2-dioxaborolane. MS (ESI): mass calcd. for $C_{17}H_{15}F_2N_3OS$, 347.1. m/z found, 348.0 [M+H]$^+$. $^1$H NMR (400 MHz, DMSO-d$_6$) δ 8.66 (s, 1H), 8.11 (s, 1H), 7.63 (s, 1H), 7.42 (s, 1H), 7.17 (s, 1H), 5.58-5.37 (m, 1H), 5.00 (s, 2H), 4.63-4.50 (m, 1H), 4.40-4.18 (m, 2H), 4.04-3.90 (m, 1H), 2.26 (s, 3H).

Example 310

2-[6-[3-(Difluoromethyl)phenyl]-3-fluoro-pyrrolo[3,2-b]pyridin-1-yl]-1-(3-fluoroazetidin-1-yl)ethanone

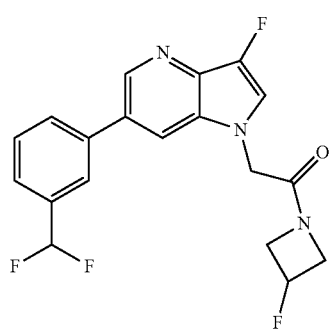 [SMILES: O=C(Cn1cc(F)c2ncc(-c3cccc(C(F)F)c3)cc21)N1CC(F)C1]

The title compound was prepared in a manner analogous to Example 92, using 2-(6-bromo-3-fluoro-1H-pyrrolo[3,2-b]pyridin-1-yl)-1-(3-fluoroazetidin-1-yl)ethanone (Intermediate 17) and (3-(difluoromethyl)phenyl)boronic acid. MS (ESI): mass calcd. for $C_{19}H_{15}F_4N_3O$, 377.1. m/z found, 378.0 [M+H]$^+$. $^1$H NMR (400 MHz, DMSO-d$_6$) δ 8.73 (d, J=1.8 Hz, 1H), 8.25 (t, J=2.2 Hz, 1H), 7.96-7.91 (m, 2H), 7.72-7.57 (m, 3H), 7.12 (t, J=55.8 Hz, 1H), 5.58-5.36 (m, 1H), 5.04 (s, 2H), 4.62-4.49 (m, 1H), 4.39-4.18 (m, 2H), 4.04-3.87 (m, 1H).

Example 311

2-[6-(3,4-Difluorophenyl)-3-fluoro-pyrrolo[3,2-b]pyridin-1-yl]-1-(3-fluoroazetidin-1-yl)ethanone

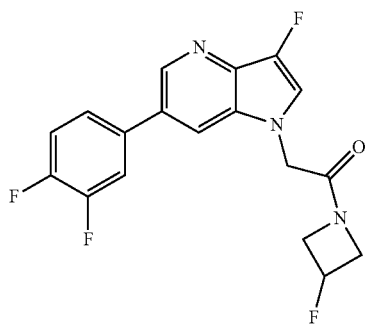

The title compound was prepared in a manner analogous to Example 92, using 2-(6-bromo-3-fluoro-1H-pyrrolo[3,2-b]pyridin-1-yl)-1-(3-fluoroazetidin-1-yl)ethanone (Intermediate 17) and (3,4-difluorophenyl)boronic acid. MS (ESI): mass calcd. for $C_{18}H_{13}F_4N_3O$, 363.1. m/z found, 364.0 [M+H]$^+$. $^1$H NMR (400 MHz, DMSO-d$_6$) δ 8.72 (d, J=1.9 Hz, 1H), 8.24 (t, J=2.2 Hz, 1H), 7.92-7.85 (m, 1H), 7.68 (d, J=2.2 Hz, 1H), 7.65-7.54 (m, 2H), 5.57-5.36 (m, 1H), 5.02 (s, 2H), 4.62-4.48 (m, 1H), 4.39-4.19 (m, 2H), 4.03-3.90 (m, 1H).

Example 312

1-(Azetidin-1-yl)-2-[3-chloro-6-(2,3,4-trifluorophenyl)pyrrolo[3,2-b]pyridin-1-yl]ethanone

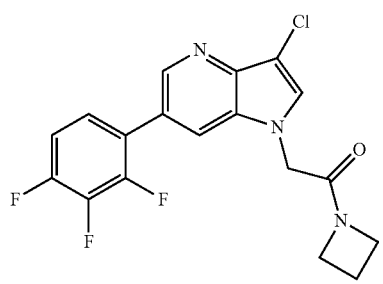 [SMILES: O=C(Cn1cc(Cl)c2ncc(-c3ccc(F)c(F)c3F)cc21)N1CCC1]

The title compound was prepared in a manner analogous to Example 29. MS (ESI): mass calcd. for $C_{18}H_{13}ClF_3N_3O$, 379.1. m/z found, 379.9 [M+H]$^+$. $^1$H NMR (400 MHz, CD$_3$OD) δ 8.55 (s, 1H), 8.08 (s, 1H), 7.69 (s, 1H), 7.46-7.35 (m, 1H), 7.33-7.22 (m, 1H), 5.01 (s, 2H), 4.33 (t, J=7.8 Hz, 2H), 4.06 (t, J=7.8 Hz, 2H), 2.47-2.31 (m, 2H).

Example 313

2-[3-Fluoro-6-(4-fluoro-3-methyl-phenyl)pyrrolo[3,2-b]pyridin-1-yl]-1-pyrrolidin-1-yl-ethanone

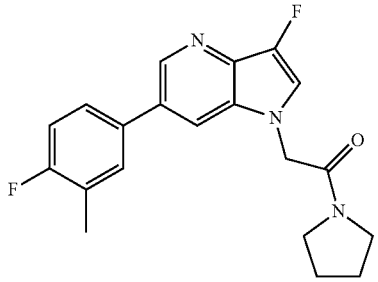 [SMILES: Cc1cc(-c2cnc3c(F)cn(CC(=O)N4CCCC4)c3c2)ccc1F]

The title compound was prepared in a manner analogous to Example 1, Step A, using 2-(6-bromo-3-fluoro-1H-pyrrolo[3,2-b]pyridin-1-yl)-1-(pyrrolidin-1-yl)ethanone (Intermediate 18) and (4-fluoro-3-methylphenyl)boronic acid. MS (ESI): mass calcd. for $C_{20}H_{19}F_2N_3O$, 355.1. m/z found, 356.1 [M+H]$^+$. $^1$H NMR (400 MHz, CD$_3$OD) δ 8.57 (d, J=1.9 Hz, 1H), 8.09-8.04 (m, 1H), 7.61-7.56 (m, 1H), 7.54-7.48 (m, 1H), 7.46 (d, J=2.4 Hz, 1H), 7.14 (t, J=9.0 Hz, 1H), 5.13 (s, 2H), 3.65 (t, J=6.7 Hz, 2H), 3.51-3.42 (m, 2H), 2.35 (s, 3H), 2.13-2.02 (m, 2H), 1.98-1.87 (m, 2H).

Example 314

2-[3-Fluoro-6-(4-fluorophenyl)pyrrolo[3,2-b]pyridin-1-yl]-1-pyrrolidin-1-yl-ethanone

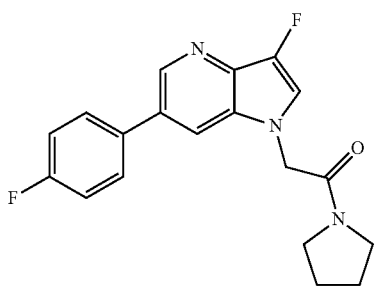 [SMILES: O=C(Cn1cc(F)c2ncc(-c3ccc(F)cc3)cc21)N1CCCC1]

The title compound was prepared in a manner analogous to Example 1, Step A, using 2-(6-bromo-3-fluoro-1H-pyrrolo[3,2-b]pyridin-1-yl)-1-(pyrrolidin-1-yl)ethanone (Intermediate 18) and (4-fluorophenyl)boronic acid. MS (ESI): mass calcd. for $C_{19}H_{17}F_2N_3O$, 341.1. m/z found, 342.1 [M+H]$^+$. Analytical HPLC was obtained on a Agilent 1100 Series using a XBridge C18 column (4.6×100 mm, 5 μm), mobile phase of 10-100% ACN in 20 mM NH$_4$OH over 8 min and then hold at 100% ACN for 3 min, at a flow rate of 1 mL/min (Temperature=45° C.). R$_t$=5.92 min at 254 nm.

Example 315

2-[3-Fluoro-6-(3,4,5-trifluorophenyl)pyrrolo[3,2-b]pyridin-1-yl]-1-Pyrrolidin-1-yl-ethanone

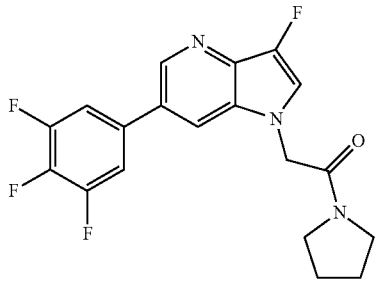 [SMILES: O=C(Cn1cc(F)c2ncc(-c3cc(F)c(F)c(F)c3)cc21)N1CCCC1]

The title compound was prepared in a manner analogous to Example 1, Step A, using 2-(6-bromo-3-fluoro-1H-pyrrolo[3,2-b]pyridin-1-yl)-1-(pyrrolidin-1-yl)ethanone (Intermediate 18) and (3,4,5-trifluorophenyl)boronic acid. MS (ESI): mass calcd. for $C_{19}H_{15}F_4N_3O$, 377.1. m/z found, 378.0 [M+H]$^+$. $^1$H NMR (400 MHz, DMSO-d$_6$) δ 8.61 (d, J=1.8 Hz, 1H), 8.15 (s, 1H), 7.59-7.49 (m, 3H), 5.14 (s, 2H), 3.65 (t, J=6.8 Hz, 2H), 3.45 (t, J=6.9 Hz, 2H), 2.13-2.02 (m, 2H), 1.92 (p, J=6.9 Hz, 2H).

Example 316

1-Cyclopropyl-2-[3-fluoro-6-(4-fluoro-3-methylphenyl)pyrrolo[3,2-b]pyridin-1-yl]ethanone

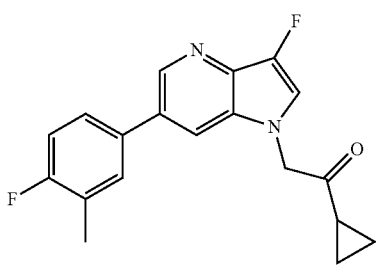 [SMILES: Cc1cc(-c2cnc3c(F)cn(CC(=O)C4CC4)c3c2)ccc1F]

The title compound was prepared in a manner analogous to Example 136. MS (ESI): mass calcd. for $C_{19}H_{16}F_2N_2O$, 326.1. m/z found, 327.0 [M+H]$^+$. $^1$H NMR (600 MHz, DMSO-d$_6$) δ 8.67 (d, J=1.9 Hz, 1H), 8.14 (t, J=2.2 Hz, 1H), 7.69-7.66 (m, 1H), 7.65 (d, J=2.1 Hz, 1H), 7.60-7.56 (m, 1H), 7.26 (dd, J=9.7, 8.5 Hz, 1H), 5.41 (s, 2H), 2.33 (d, J=1.9 Hz, 3H), 2.12-2.07 (m, 1H), 1.01-0.97 (m, 2H), 0.95-0.91 (m, 2H).

Example 317

1-Cyclopropyl-2-[3-fluoro-6-(4-methyl-2-thienyl)pyrrolo[3,2-b]pyridin-1-yl]ethanone

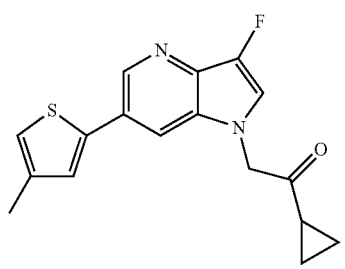 [SMILES: Cc1csc(-c2cnc3c(F)cn(CC(=O)C4CC4)c3c2)c1]

The title compound was prepared in a manner analogous to Example 136 substituting 4,4,5,5-tetramethyl-2-(4-methylthiophen-2-yl)-1,3,2-dioxaborolane for (3,4-difluorophenyl)boronic acid. MS (ESI): mass calcd. for $C_{17}H_{15}FN_2OS$, 314.1. m/z found, 315.0 [M+H]$^+$. $^1$H NMR (400 MHz, DMSO-d$_6$) δ 8.65 (d, J=1.9 Hz, 1H), 8.11 (s, 1H), 7.64 (s, 1H), 7.42 (s, 1H), 7.16 (s, 1H), 5.41 (s, 2H), 2.26 (s, 3H), 2.16-2.06 (m, 1H), 1.09-0.90 (m, 4H).

Example 318

2-[6-(5-Chloro-2-thienyl)-3-fluoro-pyrrolo[3,2-b]pyridin-1-yl]-1-cyclopropyl-ethanone

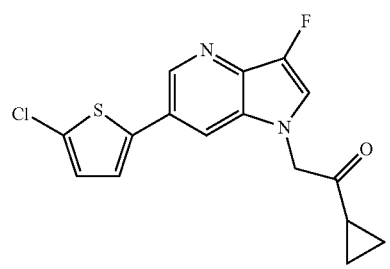 [SMILES: O=C(Cn1cc(F)c2ncc(-c3ccc(Cl)s3)cc21)C1CC1]

The title compound was prepared in a manner analogous to Example 136. MS (ESI): mass calcd. for $C_{16}H_{12}ClFN_2OS$, 334.0. m/z found, 335.0 [M+H]$^+$. $^1$H NMR (400 MHz, DMSO-d$_6$) δ 8.65 (d, J=1.9 Hz, 1H), 8.14 (t, J=2.2 Hz, 1H), 7.68 (d, J=2.2 Hz, 1H), 7.47 (d, J=3.9 Hz, 1H), 7.21 (d, J=3.9 Hz, 1H), 5.41 (s, 2H), 2.15-2.06 (m, 1H), 1.04-0.97 (m, 2H), 0.97-0.90 (m, 2H).

Example 319

1-Cyclopropyl-2-[3-fluoro-6-(4-fluorophenyl)pyrrolo[3,2-b]pyridin-1-yl]ethanone

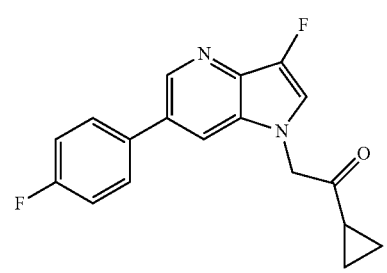 [SMILES: O=C(Cn1cc(F)c2ncc(-c3ccc(F)cc3)cc21)C1CC1]

The title compound was prepared in a manner analogous to Example 136. MS (ESI): mass calcd. for $C_{18}H_{14}F_2N_2O$, 312.1. m/z found, 313.0 [M+H]$^+$. $^1$H NMR (400 MHz, CD$_3$OD) δ 8.59 (d, J=1.8 Hz, 1H), 7.99 (t, J=2.1 Hz, 1H), 7.73-7.67 (m, 2H), 7.46 (d, J=2.3 Hz, 1H), 7.27-7.19 (m, 2H), 5.35 (s, 2H), 2.16-2.08 (m, 1H), 1.08-1.02 (m, 4H).

Example 320

1-Cyclopropyl-2-[3-fluoro-6-(3,4,5-trifluorophenyl)pyrrolo[3,2-b]pyridin-1-yl]ethanone

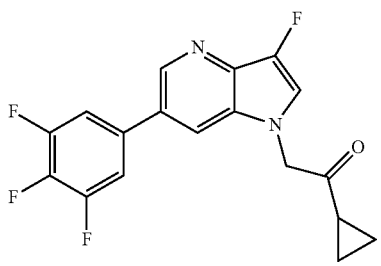 [SMILES: O=C(Cn1cc(F)c2ncc(-c3cc(F)c(F)c(F)c3)cc21)C1CC1]

The title compound was prepared in a manner analogous to Example 136. MS (ESI): mass calcd. for $C_{18}H_{12}F_4N_2O$, 348.1. m/z found, 349.0 [M+H]$^+$.

Example 321

1-Cyclopropyl-2-[6-[3-(difluoromethyl)phenyl]-3-fluoro-pyrrolo[3,2-b]pyridin-1-yl]ethanone

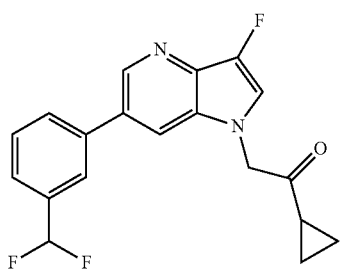 [SMILES: O=C(Cn1cc(F)c2ncc(-c3cccc(C(F)F)c3)cc21)C1CC1]

The title compound was prepared in a manner analogous to Example 136. MS (ESI): mass calcd. for $C_{19}H_{15}F_3N_2O$, 344.1. m/z found, 345.0 [M+H]$^+$. $^1$H NMR (500 MHz, CD$_3$OD) δ 8.65 (d, J=1.8 Hz, 1H), 8.08 (t, J=2.1 Hz, 1H), 7.87-7.83 (m, 2H), 7.65-7.56 (m, 2H), 7.49 (d, J=2.3 Hz, 1H), 6.86 (t, J=56.2 Hz, 1H), 5.38 (s, 2H), 2.16-2.10 (m, 1H), 1.08-1.02 (m, 4H).

Example 322

1-(Azetidin-1-yl)-2-[3-fluoro-6-(4-methyl-2-thienyl)pyrrolo[3,2-b]pyridin-1-yl]ethanone

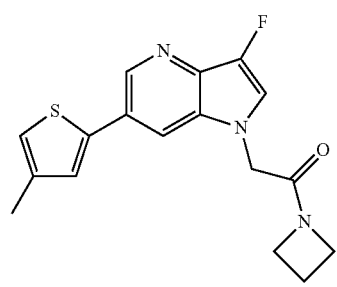 [SMILES: Cc1csc(-c2cnc3c(F)cn(CC(=O)N4CCC4)c3c2)c1]

The title compound was prepared in a manner analogous to Example 182 substituting 4,4,5,5-tetramethyl-2-(4-methylthiophen-2-yl)-1,3,2-dioxaborolane for (5-chlorothiophen-2-yl)boronic acid. MS (ESI): mass calcd. for $C_{17}H_{16}FN_3OS$, 329.1. m/z found, 330.0 [M+H]$^+$. $^1$H NMR (500 MHz, CD$_3$OD) δ 8.61 (d, J=1.8 Hz, 1H), 8.03 (t, J=2.1 Hz, 1H), 7.44 (d, J=2.3 Hz, 1H), 7.32 (d, J=1.3 Hz, 1H), 7.02 (t, J=1.2 Hz, 1H), 4.92 (s, 2H), 4.32-4.28 (m, 2H), 4.07 (t, J=7.8 Hz, 2H), 2.42-2.34 (m, 2H), 2.30 (d, J=1.1 Hz, 3H).

Example 323

1-(Azetidin-1-yl)-2-[6-[3-(difluoromethyl)phenyl]-3-fluoro-pyrrolo[3,2-b]pyridin-1-yl]ethanone

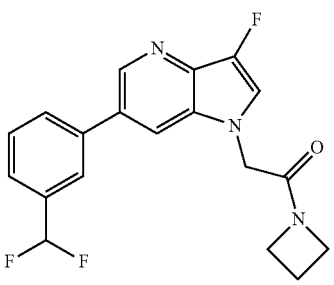 [SMILES: O=C(Cn1cc(F)c2ncc(-c3cccc(C(F)F)c3)cc21)N1CCC1]

The title compound was prepared in a manner analogous to Example 182. MS (ESI): mass calcd. for $C_{19}H_{16}F_3N_3O$, 359.1. m/z found, 360.1 [M+H]$^+$. $^1$H NMR (500 MHz, CD$_3$OD) δ 8.65 (d, J=1.8 Hz, 1H), 8.15 (t, J=2.1 Hz, 1H), 7.90-7.85 (m, 2H), 7.66-7.57 (m, 2H), 7.51 (d, J=2.3 Hz, 1H), 6.87 (t, J=56.2 Hz, 1H), 4.97 (s, 2H), 4.31 (t, J=7.8 Hz, 2H), 4.07 (t, J=7.8 Hz, 2H), 2.43-2.34 (m, 2H).

Example 324

1-[3-Fluoro-6-(4-fluoro-3-methyl-phenyl)pyrrolo[3,2-b]pyridin-1-yl]-3-methyl-butan-2-one

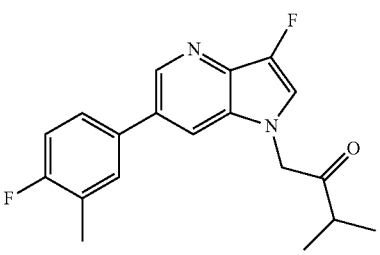

Step A: 1-(6-Bromo-3-fluoro-1H-pyrrolo[3,2-b]pyridin-1-yl)-3-methylbutan-2-one

The title compound was prepared in a manner analogous to Intermediate 15, using 6-bromo-3-fluoro-1H-pyrrolo[3,2-b]pyridine (Intermediate 6) and 1-bromo-3-methylbutan-2-one.

Step B: 1-[3-Fluoro-6-(4-fluoro-3-methyl-phenyl)pyrrolo[3,2-b]pyridin-1-yl]-3-methyl-butan-2-one The title compound was prepared in a manner analogous to Example 92, using 1-(6-bromo-3-fluoro-1H-pyrrolo[3,2- b]pyridin-1-yl)-3-methylbutan-2-one and (4-fluoro-3-methylphenyl)boronic acid. MS (ESI): mass calcd. for $C_{19}H_{18}F_2N_2O$, 328.1. m/z found, 329.0 [M+H]$^+$. $^1$H NMR (400 MHz, CD$_3$OD) δ 8.57 (d, J=1.8 Hz, 1H), 7.92 (t, J=2.1 Hz, 1H), 7.57-7.52 (m, 1H), 7.50-7.45 (m, 1H), 7.41 (d, J=2.3 Hz, 1H), 7.14 (dd, J=9.6, 8.4 Hz, 1H), 5.27 (s, 2H), 2.90-2.82 (m, 1H), 2.35 (d, J=2.0 Hz, 3H), 1.20 (d, J=6.9 Hz, 6H).

Example 325

1-[6-(3-Ethylphenyl)-3-fluoro-pyrrolo[3,2-b]pyridin-1-yl]-3-methyl-butan-2-one

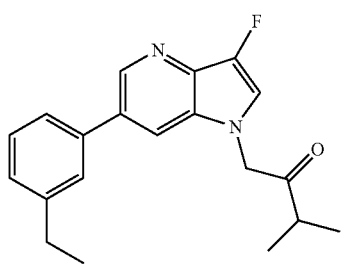 [SMILES: CCc1cccc(-c2cnc3c(F)cn(CC(=O)C(C)C)c3c2)c1]

The title compound was prepared in a manner analogous to Example 324. MS (ESI): mass calcd. for $C_{20}H_{21}FN_2O$, 324.2. m/z found, 325.1 [M+H]$^+$. $^1$H NMR (400 MHz, CD$_3$OD) δ 8.59 (d, J=1.8 Hz, 1H), 7.96-7.92 (m, 1H), 7.51-7.48 (m, 1H), 7.48-7.44 (m, 1H), 7.41 (d, J=2.4 Hz, 1H), 7.39-7.35 (m, 1H), 7.26-7.22 (m, 1H), 5.28 (s, 2H), 2.92-2.81 (m, 1H), 2.73 (q, J=7.6 Hz, 2H), 1.29 (t, J=7.5 Hz, 3H), 1.20 (d, J=7.2 Hz, 6H).

Example 326

1-[6-(3,4-Difluorophenyl)-3-fluoro-pyrrolo[3,2-b]pyridin-1-yl]-3-methyl-butan-2-one

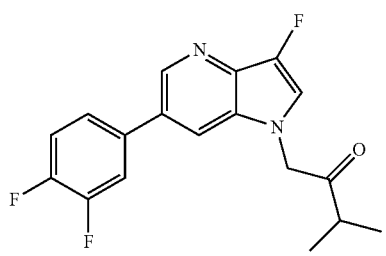 [SMILES: CC(C)C(=O)Cn1cc(F)c2ncc(-c3ccc(F)c(F)c3)cc21]

The title compound was prepared in a manner analogous to Example 324. MS (ESI): mass calcd. for $C_{18}H_{15}F_3N_2O$, 332.1. m/z found, 333.0 [M+H]$^+$. $^1$H NMR (400 MHz, CD$_3$OD) δ 8.60 (d, J=1.8 Hz, 1H), 7.99 (t, J=2.1 Hz, 1H), 7.67-7.59 (m, 1H), 7.52-7.47 (m, 1H), 7.45 (d, J=2.3 Hz, 1H), 7.43-7.33 (m, 1H), 5.29 (s, 2H), 2.92-2.83 (m, 1H), 1.21 (d, J=6.9 Hz, 6H).

Example 327

1-[3-Fluoro-6-(3-fluorophenyl)pyrrolo[3,2-b]pyridin-1-yl]-3-methyl-butan-2-one

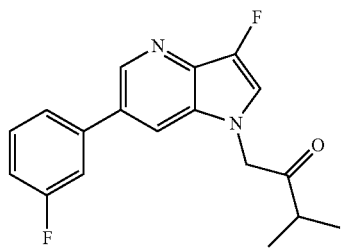

The title compound was prepared in a manner analogous to Example 324. MS (ESI): mass calcd. for $C_{18}H_{16}F_2N_2O$, 314.1. m/z found, 315.1 [M+H]$^+$. $^1$H NMR (400 MHz, CD$_3$OD) δ 8.62 (d, J=1.8 Hz, 1H), 8.00 (s, 1H), 7.54-7.47 (m, 2H), 7.48-7.40 (m, 2H), 7.18-7.08 (m, 1H), 5.29 (s, 2H), 2.93-2.81 (m, 1H), 1.21 (d, J=7.0 Hz, 6H).

Example 328

1-[3-Fluoro-6-[3-(trifluoromethyl)phenyl]pyrrolo[3,2-b]pyridin-1-yl]-3-methyl-butan-2-one

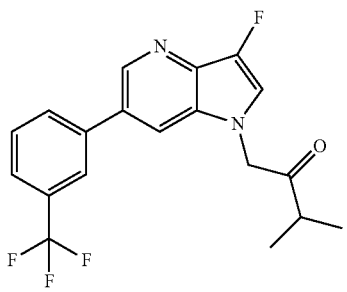 [SMILES: CC(C)C(=O)Cn1cc(F)c2ncc(-c3cccc(C(F)(F)F)c3)cc21]

The title compound was prepared in a manner analogous to Example 324. MS (ESI): mass calcd. for $C_{19}H_{16}F_4N_2O$, 364.1. m/z found, 365.0 [M+H]$^+$. $^1$H NMR (400 MHz, CD$_3$OD) δ 8.65 (d, J=1.8 Hz, 1H), 8.09-8.05 (m, 1H), 8.01-7.93 (m, 2H), 7.73-7.68 (m, 2H), 7.47 (d, J=2.4 Hz, 1H), 5.32 (s, 2H), 2.93-2.82 (m, 1H), 1.21 (d, J=6.8 Hz, 6H).

Example 329

1-[3-Fluoro-6-(m-tolyl)pyrrolo[3,2-b]pyridin-1-yl]-3-methyl-butan-2-one

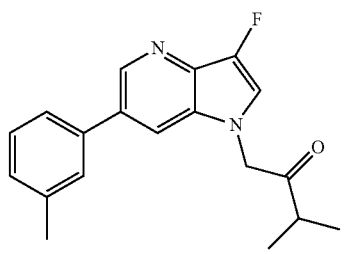

The title compound was prepared in a manner analogous to Example 324. MS (ESI): mass calcd. for $C_{19}H_{19}FN_2O$, 310.1. m/z found, 311.1 $[M+H]^+$. $^1H$ NMR (400 MHz, $CD_3OD$) δ 8.59 (d, J=1.8 Hz, 1H), 7.94 (t, J=2.1 Hz, 1H), 7.50-7.48 (m, 1H), 7.47-7.43 (m, 1H), 7.42 (d, J=2.3 Hz, 1H), 7.36 (t, J=7.6 Hz, 1H), 7.21 (d, J=7.6 Hz, 1H), 5.28 (s, 2H), 2.92-2.81 (m, 1H), 2.43 (s, 3H), 1.20 (d, J=7.0 Hz, 6H).

Example 330

6-(4-Fluoro-3-methyl-phenyl)-1-(methylsulfanylmethyl)pyrrolo[3,2-b]pyridine

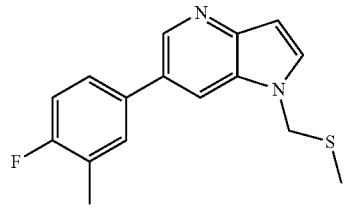 [SMILES: CSCn1ccc2ncc(-c3ccc(F)c(C)c3)cc21]

The title compound was prepared in a manner analogous to Example 170 using 6-(4-fluoro-3-methylphenyl)-1H-pyrrolo[3,2-b]pyridine and chloromethyl methyl sulfide. MS (ESI): mass calcd. for $C_{16}H_{15}FN_2S$, 286.1. m/z found, 287.1 $[M+H]^+$. $^1H$ NMR (500 MHz, DMSO-$d_6$) δ 8.66 (d, J=2.0 Hz, 1H), 8.30 (dd, J=2.1, 0.9 Hz, 1H), 7.78 (d, J=3.3 Hz, 1H), 7.71-7.68 (m, 1H), 7.63-7.58 (m, 1H), 7.26 (dd, J=9.7, 8.5 Hz, 1H), 6.61 (dd, J=3.3, 0.9 Hz, 1H), 5.49 (s, 2H), 3.17 (s, 3H), 2.33 (d, J=1.9 Hz, 3H).

Example 331

(R/S)-6-(4-Fluoro-3-methyl-phenyl)-1-(methylsulfinylmethyl)pyrrolo[3,2-b]pyridine

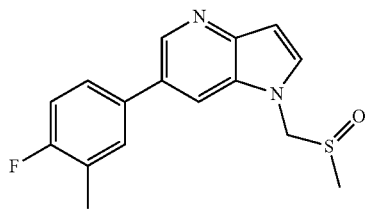 [SMILES: Cc1cc(-c2cnc3ccn(CS(C)=O)c3c2)ccc1F]

To a solution of compound of 6-(4-fluoro-3-methyl-phenyl)-1-(methylsulfanylmethyl)pyrrolo[3,2-b]pyridine (Example 330, 155 mg, 0.54 mmol) in DCM (3 mL) cooled at 0° C. was added HCl 4M (0.16 mL, 0.65 mmol). After 5 minutes, MCPBA (140 mg, 0.81 mmol) was added and the reaction mixture was stirred at 0° C. for 10 minutes. Aqueous saturated solution of $NaHCO_3$ was added to the mixture and the aqueous phase was extracted 2 times with DCM. The combined organic layers were dried ($MgSO_4$), filtered and evaporated. Purification by HPLC Method A gave the title compound (24 mg, 14%) along with the compound of 6-(4-fluoro-3-methyl-phenyl)-1-(methylsulfonylmethyl)pyrrolo[3,2-b]pyridine (Example 332) (14 mg, 8%). MS (ESI): mass calcd. for $C_{16}H_{15}FN_2OS$, 302.1. m/z found, 303.0 $[M+H]^+$. $^1H$ NMR (500 MHz, DMSO-$d_6$) δ 8.68 (d, J=2.0 Hz, 1H), 8.34 (dd, J=2.0, 0.9 Hz, 1H), 7.71 (d, J=3.3 Hz, 1H), 7.69-7.66 (m, 1H), 7.61-7.56 (m, 1H), 7.27 (dd, J=9.7, 8.5 Hz, 1H), 6.70 (dd, J=3.3, 0.9 Hz, 1H), 5.69 (d, J=13.5 Hz, 1H), 5.45 (d, J=13.5 Hz, 1H), 2.57 (s, 3H), 2.33 (d, J=1.8 Hz, 3H).

Example 332

6-(4-Fluoro-3-methyl-phenyl)-1-(methylsulfonylmethyl)pyrrolo[3,2-b]pyridine

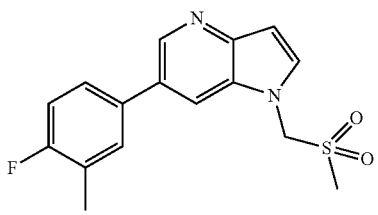 [SMILES: Cc1cc(-c2cnc3ccn(CS(C)(=O)=O)c3c2)ccc1F]

The title compound was prepared as described in Example 331. MS (ESI): mass calcd. for $C_{16}H_{15}FN_2O_2S$, 318.1. m/z found, 319.0 $[M+H]^+$. $^1H$ NMR (500 MHz, DMSO-$d_6$) δ 8.70 (d, J=2.0 Hz, 1H), 8.39 (dd, J=2.1, 0.9 Hz, 1H), 7.75 (d, J=3.4 Hz, 1H), 7.69 (dd, J=7.6, 2.4 Hz, 1H), 7.62-7.57 (m, 1H), 7.31-7.25 (m, 1H), 6.75 (dd, J=3.4, 0.9 Hz, 1H), 5.91 (s, 2H), 2.95 (s, 3H), 2.33 (d, J=1.8 Hz, 3H).

Example 333

1-[3-Fluoro-6-(4-fluorophenyl)pyrrolo[3,2-b]pyridin-1-yl]butan-2-one

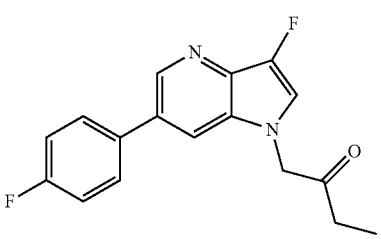 [SMILES: CCC(=O)Cn1cc(F)c2ncc(-c3ccc(F)cc3)cc21]

Step A: 1-(6-bromo-3-fluoro-1H-pyrrolo[3,2-b]pyridin-1-yl)butan-2-one

The title compound was prepared in a manner analogous to Intermediate 15, using 6-bromo-3-fluoro-1H-pyrrolo[3,2-b]pyridine (Intermediate 6) and 1-bromobutan-2-one.

229

Step B: 1-[3-Fluoro-6-(4-fluorophenyl)pyrrolo[3,2-b]pyridin-1-yl]butan-2-one

The title compound was prepared in a manner analogous to Example 1, Step A, using 1-(6-bromo-3-fluoro-1H-pyrrolo[3,2-b]pyridin-1-yl)butan-2-one and (4-fluorophenyl)boronic acid. MS (ESI): mass calcd. for $C_{17}H_{14}F_2N_2O$, 300.1. m/z found, 301.0 [M+H]$^+$. $^1$H NMR (400 MHz, DMSO-d$_6$) δ 8.68 (d, J=1.9 Hz, 1H), 8.16 (t, J=2.2 Hz, 1H), 7.81-7.75 (m, 2H), 7.61 (d, J=2.2 Hz, 1H), 7.38-7.30 (m, 2H), 5.22 (s, 2H), 2.60-2.53 (m, 2H), 0.98 (t, J=7.3 Hz, 3H).

Example 334

1-[3-Fluoro-6-(3,4,5-trifluorophenyl)pyrrolo[3,2-b]pyridin-1-yl]butan-2-one

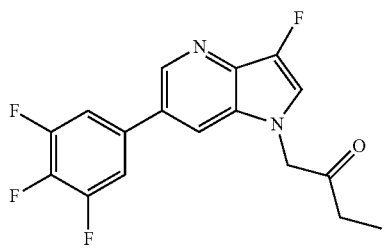 [SMILES: CCC(=O)Cn1cc(F)c2ncc(-c3cc(F)c(F)c(F)c3)cc21]

The title compound was prepared in a manner analogous to Example 333. MS (ESI): mass calcd. for $C_{17}H_{12}F_4N_2O$, 336.1. m/z found, 337.0 [M+H]$^+$. $^1$H NMR (500 MHz, DMSO-d$_6$) δ 8.77 (d, J=1.9 Hz, 1H), 8.28 (t, J=2.2 Hz, 1H), 7.84-7.77 (m, 2H), 7.68 (d, J=2.2 Hz, 1H), 5.22 (s, 2H), 2.56 (q, J=7.3 Hz, 2H), 0.99 (t, J=7.3 Hz, 3H).

Example 335

1-[3-Fluoro-6-(4-fluoro-3-methyl-phenyl)pyrrolo[3,2-b]pyridin-1-yl]butan-2-one

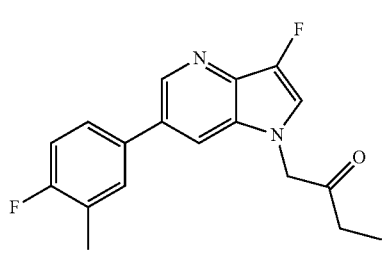 [SMILES: CCC(=O)Cn1cc(F)c2ncc(-c3ccc(F)c(C)c3)cc21]

The title compound was prepared in a manner analogous to Example 333. MS (ESI): mass calcd. for $C_{18}H_{16}F_2N_2O$, 314.1. m/z found, 315.1 [M+H]$^+$. $^1$H NMR (400 MHz, DMSO-d$_6$) δ 8.67 (d, J=1.8 Hz, 1H), 8.16-8.13 (m, 1H), 7.67 (dd, J=7.8, 2.1 Hz, 1H), 7.63-7.54 (m, 2H), 7.27 (t, J=9.1 Hz, 1H), 5.22 (s, 2H), 2.55 (q, J=7.3 Hz, 2H), 2.33 (s, 3H), 0.98 (t, J=7.3 Hz, 3H).

230

Example 336

1-[6-(3,4-Difluorophenyl)-3-fluoro-pyrrolo[3,2-b]pyridin-1-yl]butan-2-one

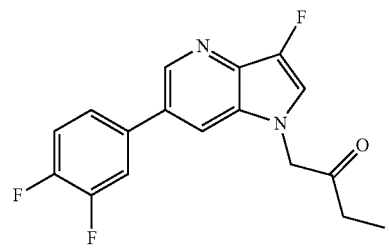 [SMILES: CCC(=O)Cn1cc(F)c2ncc(-c3ccc(F)c(F)c3)cc21]

The title compound was prepared in a manner analogous to Example 333. MS (ESI): mass calcd. for $C_{17}H_{13}F_3N_2O$, 318.1. m/z found, 319.0 [M+H]$^+$. $^1$H NMR (500 MHz, DMSO-d$_6$) δ 8.72 (d, J=1.9 Hz, 1H), 8.22 (t, J=2.2 Hz, 1H), 7.90-7.84 (m, 1H), 7.64 (d, J=2.1 Hz, 1H), 7.63-7.60 (m, 1H), 7.60-7.53 (m, 1H), 5.22 (s, 2H), 2.56 (q, J=7.3 Hz, 2H), 0.98 (t, J=7.3 Hz, 3H).

Example 337

1-[6-[3-(Difluoromethyl)phenyl]-3-fluoro-pyrrolo[3,2-b]pyridin-1-yl]butan-2-one

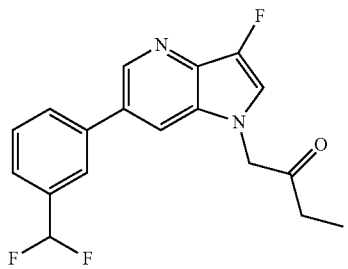 [SMILES: CCC(=O)Cn1cc(F)c2ncc(-c3cccc(C(F)F)c3)cc21]

The title compound was prepared in a manner analogous to Example 333. MS (ESI): mass calcd. for $C_{18}H_{15}F_3N_2O$, 332.1. m/z found, 333.1 [M+H]$^+$. $^1$H NMR (500 MHz, CD$_3$OD) δ 8.65 (d, J=1.8 Hz, 1H), 8.09 (t, J=2.1 Hz, 1H), 7.88-7.82 (m, 2H), 7.65-7.55 (m, 2H), 7.46 (d, J=2.3 Hz, 1H), 6.85 (t, J=56.2 Hz, 1H), 5.19 (s, 2H), 2.62 (q, J=7.3 Hz, 2H), 1.09 (t, J=7.3 Hz, 3H).

Example 338

1-[6-(5-Chloro-2-thienyl)-3-fluoro-pyrrolo[3,2-b]pyridin-1-yl]butan-2-one

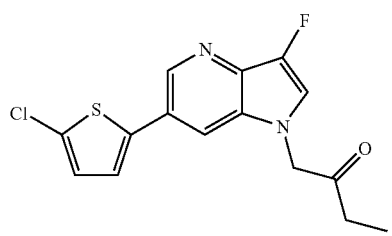 [SMILES: CCC(=O)Cn1cc(F)c2ncc(-c3ccc(Cl)s3)cc21]

The title compound was prepared in a manner analogous to Example 333. MS (ESI): mass calcd. for C$_{15}$H$_{12}$ClFN$_2$OS, 322.0. m/z found, 323.0 [M+H]$^+$. $^1$H NMR (500 MHz, CD$_3$OD) δ 8.57 (d, J=1.8 Hz, 1H), 7.98 (t, J=2.1 Hz, 1H), 7.43 (d, J=2.3 Hz, 1H), 7.30 (d, J=3.9 Hz, 1H), 7.02 (d, J=3.9 Hz, 1H), 5.16 (s, 2H), 2.61 (q, J=7.3 Hz, 2H), 1.10 (t, J=7.3 Hz, 3H).

Example 339

1-[3-Fluoro-6-(4-methyl-2-thienyl)pyrrolo[3,2-b]pyridin-1-yl]butan-2-one

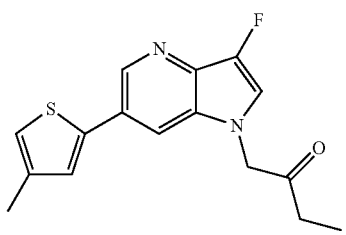 [SMILES: CCC(=O)Cn1cc(F)c2ncc(-c3cc(C)cs3)cc21]

The title compound was prepared in a manner analogous to Example 333. MS (ESI): mass calcd. for C$_{16}$H$_{15}$FN$_2$OS, 302.1. m/z found, 303.0 [M+H]$^+$. $^1$H NMR (500 MHz, CD$_3$OD) δ 8.61 (d, J=1.8 Hz, 1H), 7.97 (t, J=2.1 Hz, 1H), 7.40 (d, J=2.3 Hz, 1H), 7.31 (d, J=1.4 Hz, 1H), 7.03-6.99 (m, 1H), 5.15 (s, 2H), 2.61 (q, J=7.3 Hz, 2H), 2.29 (d, J=1.1 Hz, 3H), 1.09 (t, J=7.3 Hz, 3H).

Example 340

4-[6-(4-Fluorophenyl)pyrrolo[3,2-b]pyridin-1-yl]butan-2-one

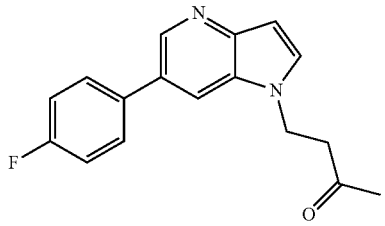 [SMILES: CC(=O)CCn1ccc2ncc(-c3ccc(F)cc3)cc21]

To a solution of compound of 6-(4-fluorophenyl)-1H-pyrrolo[3,2-b]pyridine (Example 27, step a, 30 mg, 0.14 mmol), gold (III) chloride (2 mg, 0.007 mmol) and silver trifluoromethanesulfonate (4 mg, 0.014 mmol) in DCE (1.5 mL) was added methyl vinyl ketone (35 μL, 0.42 mmol). The reaction mixture was heated to 100° C. After 1 hour the reaction mixture was cooled to room temperature and solids were filtered. Solvent was then evaporated and the crude was purified by HPLC Method A to afford the title compound (1 mg, 2%). MS (ESI): mass calcd. for C$_{17}$H$_{15}$FN$_2$O, 282.1. m/z found, 283.1 [M+H]$^+$. $^1$H NMR (500 MHz, CD$_3$OD) δ 8.54 (d, J=1.9 Hz, 1H), 8.16-8.14 (m, 1H), 7.76-7.72 (m, 2H), 7.61 (d, J=3.3 Hz, 1H), 7.26-7.21 (m, 2H), 6.60 (d, J=3.2 Hz, 1H), 4.52 (t, J=6.5 Hz, 2H), 3.09 (t, J=6.4 Hz, 2H), 2.12 (s, 3H).

Example 341

1-[3-Fluoro-6-(4-fluorophenyl)pyrrolo[3,2-b]pyridin-1-yl]-3-methyl-butan-2-one

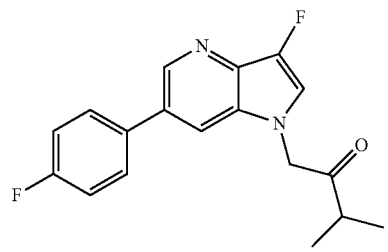 [SMILES: CC(C)C(=O)Cn1cc(F)c2ncc(-c3ccc(F)cc3)cc21]

The title compound was prepared in a manner analogous to Example 324. MS (ESI): mass calcd. for C$_{18}$H$_{16}$F$_2$N$_2$O, 314.1. m/z found, 315.0 [M+H]$^+$. $^1$H NMR (400 MHz, DMSO-d$_6$) δ 8.68 (d, J=1.9 Hz, 1H), 8.12 (t, J=2.2 Hz, 1H), 7.81-7.75 (m, 2H), 7.63 (d, J=2.2 Hz, 1H), 7.38-7.32 (m, 2H), 5.36 (s, 2H), 2.86-2.78 (m, 1H), 1.12 (d, J=6.9 Hz, 6H).

Example 342

1-[6-[3-(Difluoromethyl)phenyl]-3-fluoro-pyrrolo[3,2-b]pyridin-1-yl]-3-methyl-butan-2-one

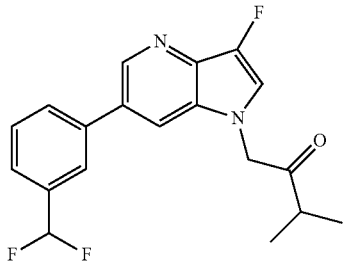

The title compound was prepared in a manner analogous to Example 324. MS (ESI): mass calcd. for C$_{19}$H$_{17}$F$_3$N$_2$O, 346.1. m/z found, 347.1 [M+H]$^+$. $^1$H NMR (400 MHz, DMSO-d$_6$) δ 8.72 (d, J=1.9 Hz, 1H), 8.19 (t, J=2.2 Hz, 1H), 7.94-7.89 (m, 2H), 7.69-7.63 (m, 2H), 7.62-7.58 (m, 1H), 7.11 (t, J=55.8 Hz, 1H), 5.38 (s, 2H), 2.87-2.77 (m, 1H), 1.12 (d, J=6.9 Hz, 6H).

Example 343

1-[3-Fluoro-6-(4-methyl-2-thienyl)pyrrolo[3,2-b]pyridin-1-yl]-3-methyl-butan-2-one

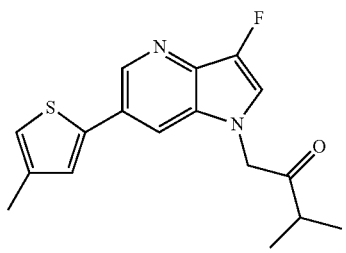 [SMILES: Cc1csc(-c2cnc3c(F)cn(CC(=O)C(C)C)c3c2)c1]

The title compound was prepared in a manner analogous to Example 324. MS (ESI): mass calcd. for C$_{17}$H$_{17}$FN$_2$OS, 316.1. m/z found, 317.0 [M+H]$^+$. $^1$H NMR (400 MHz, DMSO-d$_6$) δ 8.65 (d, J=1.8 Hz, 1H), 8.04 (s, 1H), 7.61 (d, J=2.2 Hz, 1H), 7.40 (s, 1H), 7.16 (s, 1H), 5.35 (s, 2H), 2.87-2.78 (m, 1H), 2.26 (s, 3H), 1.13 (d, J=6.9 Hz, 6H).

Example 344

1-[3-Fluoro-6-(3,4,5-trifluorophenyl)pyrrolo[3,2-b]pyridin-1-yl]-3-methyl-butan-2-one

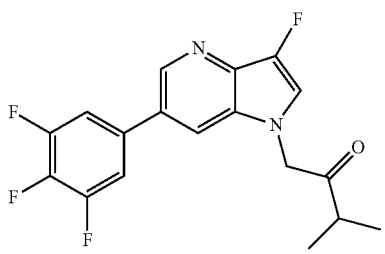

The title compound was prepared in a manner analogous to Example 324. MS (ESI): mass calcd. for C$_{18}$H$_{14}$F$_4$N$_2$O, 350.1. m/z found, 351.0 [M+H]$^+$. $^1$H NMR (400 MHz, DMSO-d$_6$) δ 8.77 (d, J=1.9 Hz, 1H), 8.25 (t, J=2.2 Hz, 1H), 7.84-7.76 (m, 2H), 7.69 (d, J=2.2 Hz, 1H), 5.35 (s, 2H), 2.87-2.79 (m, 1H), 1.13 (d, J=6.9 Hz, 6H).

Example 345

1-[6-(5-Chloro-2-thienyl)-3-fluoro-pyrrolo[3,2-b]pyridin-1-yl]-3-methyl-butan-2-one

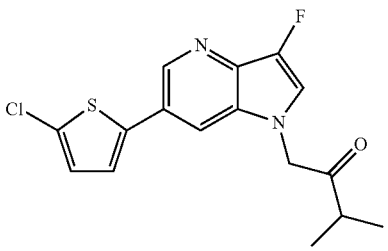 [SMILES: CC(C)C(=O)Cn1cc(F)c2ncc(-c3ccc(Cl)s3)cc21]

The title compound was prepared in a manner analogous to Example 324. MS (ESI): mass calcd. for C$_{16}$H$_{14}$ClFN$_2$OS, 336.0. m/z found, 337.0 [M+H]$^+$. $^1$H NMR (400 MHz, CD$_3$OD) δ 8.58 (d, J=1.8 Hz, 1H), 7.92 (t, J=2.1 Hz, 1H), 7.44 (d, J=2.3 Hz, 1H), 7.30 (d, J=3.9 Hz, 1H), 7.02 (d, J=3.8 Hz, 1H), 5.27 (s, 2H), 2.93-2.82 (m, 1H), 1.21 (d, J=7.0 Hz, 6H).

Example 346

2-[6-(4-Fluoro-3-methyl-phenyl)pyrrolo[3,2-b]pyridin-1-yl]-1-morpholino-ethanone

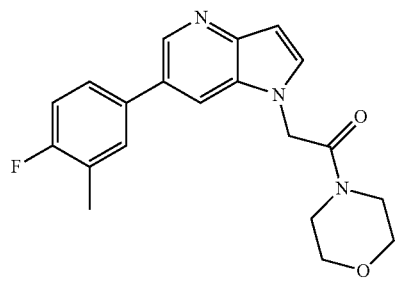 [SMILES: Cc1cc(-c2cnc3ccn(CC(=O)N4CCOCC4)c3c2)ccc1F]

The title compound was prepared in a manner analogous to Example 66. MS (ESI): mass calcd. for C$_{20}$H$_{20}$FN$_3$O$_2$, 353.2. m/z found, 354.2 [M+H]$^+$. $^1$H NMR (400 MHz, DMSO-d$_6$) δ 8.61 (d, J=2.0 Hz, 1H), 8.07 (dd, J=2.1, 0.9 Hz, 1H), 7.69-7.62 (m, 1H), 7.61-7.52 (m, 2H), 7.26 (dd, J=9.7, 8.5 Hz, 1H), 6.59 (dd, J=3.3, 0.8 Hz, 1H), 5.29 (s, 2H), 3.74-3.66 (m, 2H), 3.63-3.56 (m, 4H), 3.48-3.42 (m, 2H), 2.33 (d, J=1.9 Hz, 3H).

Example 347

1-(3-Fluoroazetidin-1-yl)-2-[6-(4-fluoro-3-methyl-phenyl)pyrrolo[3,2-b]pyridin-1-yl]ethanone

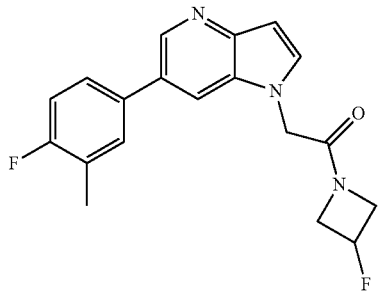

The title compound was prepared in a manner analogous to Example 66. MS (ESI): mass calcd. for C$_{19}$H$_{18}$F$_2$N$_3$O, 341.1. m/z found, 342.1 [M+H]$^+$. $^1$H NMR (600 MHz, DMSO-d$_6$) δ 8.62 (d, J=2.0 Hz, 1H), 8.07 (d, J=2.0 Hz, 1H), 7.69-7.64 (m, 1H), 7.62-7.54 (m, 2H), 7.30-7.22 (m, 1H), 6.60 (d, J=3.3 Hz, 1H), 5.54-5.38 (m, 1H), 5.06 (d, J=5.3 Hz, 2H), 4.59-4.47 (m, 1H), 4.36-4.19 (m, 2H), 4.03-3.91 (m, 1H), 2.33 (s, 3H).

Example 348

N-Cyclopropyl-2-[6-(4-fluoro-3-methyl-phenyl)pyrrolo[3,2-b]pyridin-1-yl]acetamide

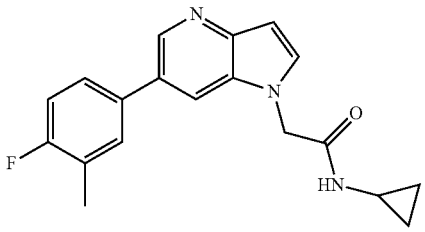 [SMILES: Cc1cc(-c2cnc3ccn(CC(=O)NC4CC4)c3c2)ccc1F]

The title compound was prepared in a manner analogous to Example 66. MS (ESI): mass calcd. for $C_{19}H_{18}FN_3O$, 323.1. m/z found, 324.2 [M+H]$^+$. $^1$H NMR (600 MHz, DMSO-d$_6$) δ 8.62 (d, J=2.0 Hz, 1H), 8.32 (d, J=4.2 Hz, 1H), 8.06-8.01 (m, 1H), 7.66 (dd, J=7.5, 2.5 Hz, 1H), 7.62 (d, J=3.3 Hz, 1H), 7.59-7.54 (m, 1H), 7.29-7.23 (m, 1H), 6.58 (d, J=3.2 Hz, 1H), 4.86 (s, 2H), 2.69-2.62 (m, 1H), 2.33 (s, 3H), 0.67-0.60 (m, 2H), 0.47-0.42 (m, 2H).

Example 349

1-(Azetidin-1-yl)-2-[6-(4-fluoro-3-methyl-phenyl)pyrrolo[3,2-b]pyridin-1-yl]ethanone

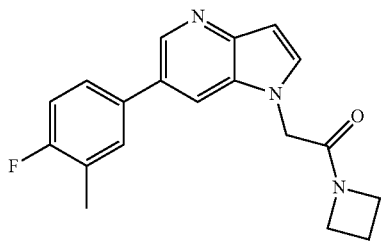 [SMILES: Cc1cc(-c2cnc3ccn(CC(=O)N4CCC4)c3c2)ccc1F]

The title compound was prepared in a manner analogous to Example 66. MS (ESI): mass calcd. for $C_{19}H_{18}FN_3O$, 323.1. m/z found, 324.2 [M+H]$^+$. $^1$H NMR (400 MHz, DMSO-d$_6$) δ 8.62 (d, J=2.0 Hz, 1H), 8.07 (dd, J=2.0, 0.9 Hz, 1H), 7.68 (dd, J=7.6, 2.3 Hz, 1H), 7.62-7.55 (m, 2H), 7.27 (dd, J=9.7, 8.5 Hz, 1H), 6.59 (dd, J=3.3, 0.9 Hz, 1H), 5.00 (s, 2H), 4.20 (t, J=7.7 Hz, 2H), 3.91 (t, J=7.8 Hz, 2H), 2.34 (d, J=1.9 Hz, 3H), 2.31-2.21 (m, 2H).
The compound of Example 349 can also be prepared from the compound of Example 68 in the presence of 10 wt. % Pd/C in methanol at room temperature under H$_2$ atmosphere.

Example 350

N-Cyclopropyl-2-[6-(3,5-difluorophenyl)pyrrolo[3,2-b]pyridin-1-yl]acetamide trifluoroacetate salt

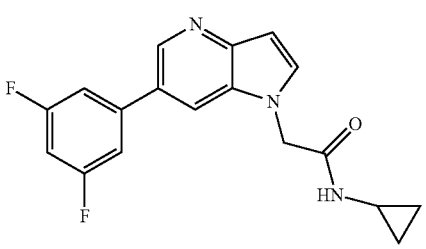 [SMILES: O=C(Cn1ccc2ncc(-c3cc(F)cc(F)c3)cc21)NC1CC1]

The title compound was prepared in a manner analogous to Example 75. MS (ESI): mass calcd. for $C_{18}H_{15}F_2N_3O$, 327.1. m/z found, 328.1 [M+H]$^+$. $^1$H NMR (500 MHz, DMSO-d$_6$) δ 9.03 (s, 1H), 8.89 (s, 1H), 8.43-8.36 (m, 1H), 8.11-8.06 (m, 1H), 7.72-7.65 (m, 2H), 7.40-7.32 (m, 1H), 6.87-6.78 (m, 1H), 5.08 (s, 2H), 2.70-2.59 (m, 1H), 0.67-0.59 (m, 2H), 0.49-0.42 (m, 2H).

Example 351

N-Cyclopropyl-2-[6-[3-(trifluoromethyl)phenyl]pyrrolo[3,2-b]pyridin-1-yl]acetamide trifluoroacetate salt

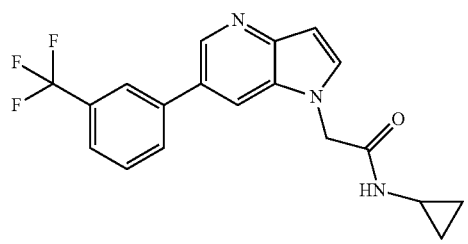 [SMILES: O=C(Cn1ccc2ncc(-c3cccc(C(F)(F)F)c3)cc21)NC1CC1]

The title compound was prepared in a manner analogous to Example 75. MS (ESI): mass calcd. for $C_{19}H_{18}F_3N_3O$, 359.1. m/z found, 360.1 [M+H]$^+$. $^1$H NMR (500 MHz, DMSO-d$_6$) δ 9.05-9.01 (m, 1H), 8.85 (s, 1H), 8.42 (d, J=4.2 Hz, 1H), 8.21-8.14 (m, 2H), 8.07 (d, J=3.2 Hz, 1H), 7.87-7.79 (m, 2H), 6.83 (d, J=3.3 Hz, 1H), 5.09 (s, 2H), 2.70-2.62 (m, 1H), 0.68-0.61 (m, 2H), 0.49-0.43 (m, 2H).

Example 352

N-Cyclopropyl-2-[6-[2-fluoro-3-(trifluoromethyl)phenyl]pyrrolo[3,2-b]pyridin-1-yl]acetamide trifluoroacetate salt

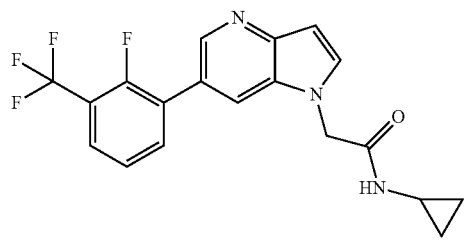

The title compound was prepared in a manner analogous to Example 75. MS (ESI): mass calcd. for $C_{19}H_{15}F_4N_3O$, 377.1. m/z found, 378.1 [M+H]$^+$. $^1$H NMR (500 MHz, DMSO-d$_6$) δ 8.79 (s, 1H), 8.56 (s, 1H), 8.39 (d, J=4.2 Hz, 1H), 8.06-7.98 (m, 2H), 7.90 (t, J=6.8 Hz, 1H), 7.61 (t, J=7.8 Hz, 1H), 6.81 (d, J=3.2 Hz, 1H), 5.02 (s, 2H), 2.68-2.60 (m, 1H), 0.67-0.60 (m, 2H), 0.47-0.41 (m, 2H).

Example 353

1-(Azetidin-1-yl)-2-[6-(4-fluorophenyl)pyrrolo[3,2-b]pyridin-1-yl]ethanone

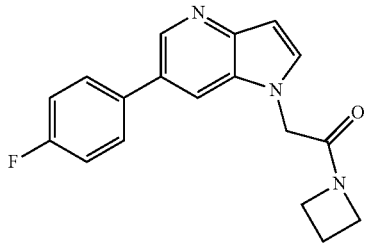 [SMILES: O=C(Cn1ccc2ncc(-c3ccc(F)cc3)cc21)N1CCC1]

The title compound was prepared in a manner analogous to Example 71. MS (ESI): mass calcd. for $C_{18}H_{16}FN_3O$, 309.1. m/z found, 310.1 [M+H]$^+$. $^1$H NMR (500 MHz, DMSO-d$_6$) δ 8.63 (d, J=1.9 Hz, 1H), 8.09 (d, J=1.7 Hz, 1H), 7.83-7.75 (m, 2H), 7.60 (d, J=3.2 Hz, 1H), 7.39-7.31 (m, 2H), 6.60 (dd, J=3.3, 0.9 Hz, 1H), 5.00 (s, 2H), 4.25-4.17 (m, 2H), 3.94-3.88 (m, 2H), 2.32-2.23 (m, 2H).

Example 354

1-(Azetidin-1-yl)-2-(6-phenylpyrrolo[3,2-b]pyridin-1-yl)ethanone

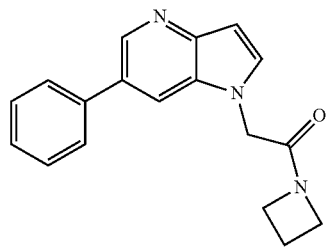 [SMILES: O=C(Cn1ccc2ncc(-c3ccccc3)cc21)N1CCC1]

The title compound was prepared in a manner analogous to Example 71. MS (ESI): mass calcd. for $C_{18}H_{17}N_3O$, 291.1. m/z found, 292.2 [M+H]$^+$. $^1$H NMR (400 MHz, DMSO-d$_6$) δ 8.66 (d, J=2.0 Hz, 1H), 8.11 (dd, J=2.1, 0.9 Hz, 1H), 7.77-7.73 (m, 2H), 7.60 (d, J=3.3 Hz, 1H), 7.54-7.48 (m, 2H), 7.42-7.36 (m, 1H), 6.60 (dd, J=3.2, 0.9 Hz, 1H), 5.01 (s, 2H), 4.21 (t, J=7.7 Hz, 2H), 3.91 (t, J=7.8 Hz, 2H), 2.32-2.20 (m, 2H).

Example 355

1-(Azetidin-1-yl)-2-[6-(3,5-difluorophenyl)pyrrolo[3,2-b]pyridin-1-yl]ethanone

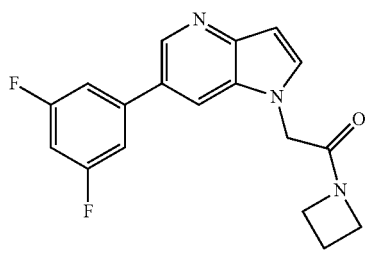 [SMILES: O=C(Cn1ccc2ncc(-c3cc(F)cc(F)c3)cc21)N1CCC1]

The title compound was prepared in a manner analogous to Example 71. MS (ESI): mass calcd. for $C_{18}H_{15}F_2N_3O$, 327.1. m/z found, 328.1 [M+H]$^+$. $^1$H NMR (400 MHz, DMSO-d$_6$) δ 8.74 (d, J=2.0 Hz, 1H), 8.25 (dd, J=2.0, 0.9 Hz, 1H), 7.65 (d, J=3.3 Hz, 1H), 7.60-7.52 (m, 2H), 7.28-7.19 (m, 1H), 6.62 (dd, J=3.3, 0.8 Hz, 1H), 5.02 (s, 2H), 4.22 (t, J=7.7 Hz, 2H), 3.91 (t, J=7.7 Hz, 2H), 2.33-2.22 (m, 2H).

Example 356

1-(Azetidin-1-yl)-2-[6-(m-tolyl)pyrrolo[3,2-b]pyridin-1-yl]ethanone trifluoroacetate salt

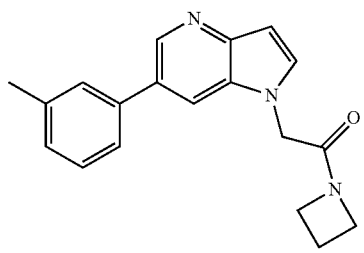 [SMILES: Cc1cccc(-c2cnc3ccn(CC(=O)N4CCC4)c3c2)c1]

The title compound was prepared in a manner analogous to Example 71. MS (ESI): mass calcd. for $C_{19}H_{19}N_3O$, 305.2. m/z found, 306.2 [M+H]$^+$. $^1$H NMR (400 MHz, DMSO-d$_6$) δ 8.97 (d, J=1.6 Hz, 1H), 8.87 (s, 1H), 8.06 (d, J=3.3 Hz, 1H), 7.69-7.61 (m, 2H), 7.47 (t, J=7.6 Hz, 1H), 7.31 (d, J=7.6 Hz, 1H), 6.85 (d, J=3.4 Hz, 1H), 5.23 (s, 2H), 4.29 (t, J=7.6 Hz, 2H), 3.93 (t, J=7.7 Hz, 2H), 2.44 (s, 3H), 2.37-2.25 (m, 2H).

Example 357

1-(Azetidin-1-yl)-2-[6-(3,4-dichlorophenyl)pyrrolo[3,2-b]pyridin-1-yl]ethanone trifluoroacetate salt

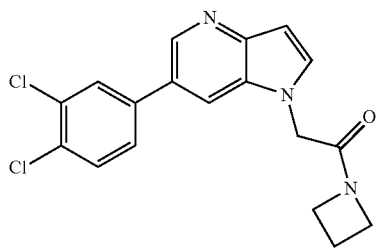 [SMILES: O=C(Cn1ccc2ncc(-c3ccc(Cl)c(Cl)c3)cc21)N1CCC1]

The title compound was prepared in a manner analogous to Example 71. MS (ESI): mass calcd. for $C_{18}H_{15}Cl_2N_3O$, 359.1. m/z found, 360.1 [M+H]$^+$. $^1$H NMR (400 MHz, DMSO-d$_6$) δ 9.00 (d, J=1.8 Hz, 1H), 8.84 (s, 1H), 8.17 (d, J=1.9 Hz, 1H), 8.02 (d, J=3.3 Hz, 1H), 7.91-7.81 (m, 2H), 6.83 (d, J=3.2 Hz, 1H), 5.19 (s, 2H), 4.28 (t, J=7.7 Hz, 2H), 3.93 (t, J=7.7 Hz, 2H), 2.37-2.25 (m, 2H).

Example 358

1-(Azetidin-1-yl)-2-[6-[2-fluoro-3-(trifluoromethyl)phenyl]pyrrolo[3,2-b]pyridin-1-yl]ethanone trifluoroacetate salt

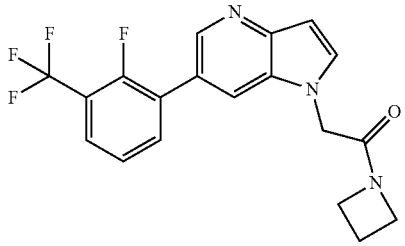

The title compound was prepared in a manner analogous to Example 71. MS (ESI): mass calcd. for $C_{19}H_{15}F_4N_3O$, 377.1. m/z found, 378.1 [M+H]$^+$. $^1$H NMR (400 MHz, DMSO-d$_6$) δ 8.84 (s, 1H), 8.67 (s, 1H), 8.07-7.99 (m, 2H), 7.92 (t, J=7.2 Hz, 1H), 7.62 (t, J=7.8 Hz, 1H), 6.85 (d, J=3.3 Hz, 1H), 5.17 (s, 2H), 4.27 (t, J=7.7 Hz, 2H), 3.92 (t, J=7.7 Hz, 2H), 2.36-2.24 (m, 2H).

Example 359

1-(Azetidin-1-yl)-2-[6-(4-methyl-2-thienyl)pyrrolo[3,2-b]pyridin-1-yl]ethanone trifluoroacetate salt

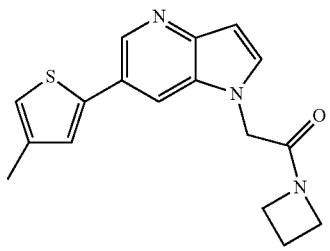 [SMILES: Cc1csc(-c2cnc3ccn(CC(=O)N4CCC4)c3c2)c1]

The title compound was prepared in a manner analogous to Example 71 substituting 4,4,5,5-tetramethyl-2-(4-methylthiophen-2-yl)-1,3,2-dioxaborolane for (2-fluorophenyl)boronic acid. MS (ESI): mass calcd. for $C_{17}H_{17}N_3OS$, 311.1. m/z found, 312.1 [M+H]$^+$. $^1$H NMR (400 MHz, DMSO-d$_6$) δ 8.86 (s, 1H), 8.58 (s, 1H), 7.93 (s, 1H), 7.56-7.50 (m, 1H), 7.29-7.23 (m, 1H), 6.76 (s, 1H), 5.15 (s, 2H), 4.28 (t, J=7.7 Hz, 2H), 3.93 (t, J=7.7 Hz, 2H), 2.37-2.25 (m, 5H).

Example 360

1-(Azetidin-1-yl)-2-[3-chloro-6-(4-fluoro-3-methylphenyl)pyrrolo[3,2-b]pyridin-1-yl]ethanone

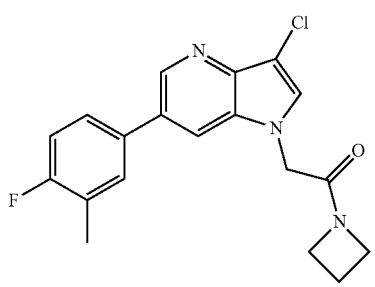 [SMILES: Cc1cc(-c2cnc3c(Cl)cn(CC(=O)N4CCC4)c3c2)ccc1F]

The title compound was prepared in a manner analogous to Example 176. MS (ESI): mass calcd. for $C_{19}H_{17}ClFN_3O$, 357.1. m/z found, 358.1 [M+H]$^+$. $^1$H NMR (500 MHz, DMSO-d$_6$) δ 8.70 (d, J=1.9 Hz, 1H), 8.19 (d, J=1.9 Hz, 1H), 7.78 (s, 1H), 7.72-7.66 (m, 1H), 7.64-7.56 (m, 1H), 7.28 (dd, J=9.7, 8.5 Hz, 1H), 5.01 (s, 2H), 4.24 (t, J=7.7 Hz, 2H), 3.91 (t, J=7.7 Hz, 2H), 2.34 (d, J=1.9 Hz, 3H), 2.32-2.24 (m, 2H).

Example 361

1-(3,3-Difluoroazetidin-1-yl)-2-[6-(3,4-difluorophenyl)pyrrolo[3,2-b]pyridin-1-yl]ethanone

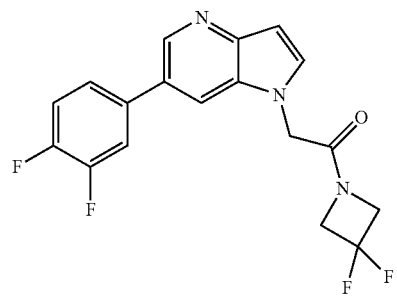 [SMILES: O=C(Cn1ccc2ncc(-c3ccc(F)c(F)c3)cc21)N1CC(F)(F)C1]

The title compound was prepared in a manner analogous to Example 106. MS (ESI): mass calcd. for $C_{18}H_{13}F_4N_3O$, 363.1. m/z found, 364.2 [M+H]$^+$. $^1$H NMR (500 MHz, CD$_3$OD) δ 8.60-8.57 (m, 1H), 8.10 (dd, J=1.9, 1.0 Hz, 1H), 7.68-7.61 (m, 1H), 7.58 (dd, J=3.4, 0.9 Hz, 1H), 7.54-7.48 (m, 1H), 7.42-7.33 (m, 1H), 6.70-6.66 (m, 1H), 5.12 (s, 2H), 4.66 (t, J=11.9 Hz, 2H), 4.41 (t, J=12.2 Hz, 2H).

Example 362

1-(Azetidin-1-yl)-2-[6-[6-(trifluoromethyl)-2-pyridyl]pyrrolo[3,2-b]pyridin-1-yl]ethanone

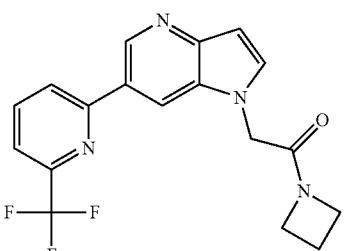

The title compound was prepared in a manner analogous to Example 102 substituting 2-(4,4,5,5-tetramethyl-1,3,2-dioxaborolan-2-yl)-6-(trifluoromethyl)pyridine for (5-(trifluoromethyl)pyridin-3-yl)boronic acid. MS (ESI): mass calcd. for $C_{18}H_{15}F_3N_4O$, 360.1. m/z found, 361.2 [M+H]$^+$. $^1$H NMR (500 MHz, CD$_3$OD) δ 9.08 (dd, J=1.9, 0.9 Hz, 1H), 8.53 (s, 1H), 8.22 (d, J=8.1 Hz, 1H), 8.08 (t, J=7.9 Hz, 1H), 7.72 (d, J=7.7 Hz, 1H), 7.63 (dd, J=3.3, 0.8 Hz, 1H), 6.69 (dd, J=3.2, 1.0 Hz, 1H), 5.02 (s, 2H), 4.30 (t, J=7.7 Hz, 2H), 4.07 (t, J=7.8 Hz, 2H), 2.43-2.30 (m, 2H).

Example 363

1-(Azetidin-1-yl)-2-[6-(3,4,5-trifluorophenyl)pyrrolo[3,2-b]pyridin-1-yl]ethanone

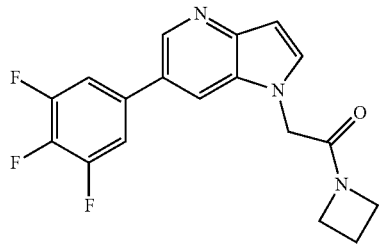 [SMILES: O=C(Cn1ccc2ncc(-c3cc(F)c(F)c(F)c3)cc21)N1CCC1]

The title compound was prepared in a manner analogous to Example 102. MS (ESI): mass calcd. for $C_{18}H_{14}F_3N_3O$, 345.1. m/z found, 346.1 [M+H]⁺. ¹H NMR (400 MHz, CD₃OD) δ 8.57 (d, J=1.9 Hz, 1H), 8.10-8.06 (m, 1H), 7.58 (d, J=3.3 Hz, 1H), 7.56-7.46 (m, 2H), 6.67 (d, J=3.3 Hz, 1H), 5.00 (s, 2H), 4.28 (t, J=7.7 Hz, 2H), 4.06 (t, J=7.8 Hz, 2H), 2.42-2.31 (m, 2H).

Example 364

1-[6-(3,5-Difluorophenyl)pyrrolo[3,2-b]pyridin-1-yl]-3-methyl-butan-2-one

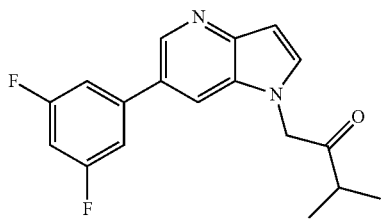 [SMILES: CC(C)C(=O)Cn1ccc2ncc(-c3cc(F)cc(F)c3)cc21]

The title compound was prepared in a manner analogous to Example 75. MS (ESI): mass calcd. for $C_{18}H_{16}F_2N_2O$, 314.1. m/z found, 315.1 [M+H]⁺. ¹H NMR (400 MHz, DMSO-d₆) δ 8.75 (d, J=2.0 Hz, 1H), 8.20 (dd, J=2.2, 0.9 Hz, 1H), 7.63 (d, J=3.3 Hz, 1H), 7.60-7.51 (m, 2H), 7.28-7.19 (m, 1H), 6.64 (dd, J=3.3, 0.9 Hz, 1H), 5.42 (s, 2H), 2.91-2.78 (m, 1H), 1.14 (d, J=6.9 Hz, 6H).

Example 365

1-Cyclobutyl-2-[6-(4-fluorophenyl)pyrrolo[3,2-b]pyridin-1-yl]ethanone

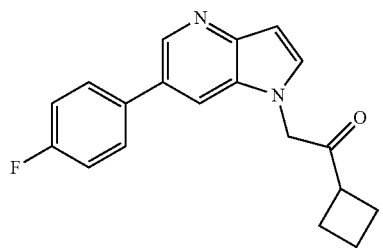

The title compound was prepared in a manner analogous to Example 170 using 6-(4-fluoro-phenyl)-1H-pyrrolo[3,2-b]pyridine and 2-bromo-1-cyclobutylethanone. MS (ESI): mass calcd. for $C_{19}H_{17}FN_2O$, 308.1. m/z found, 309.2 [M+H]⁺. ¹H NMR (400 MHz, CD₃OD) δ 8.56 (d, J=1.9 Hz, 1H), 7.94-7.89 (m, 1H), 7.72-7.64 (m, 2H), 7.51 (d, J=3.3 Hz, 1H), 7.25-7.16 (m, 2H), 6.67 (dd, J=3.4, 1.0 Hz, 1H), 5.21-5.13 (m, 2H), 3.55-3.43 (m, 1H), 2.37-2.23 (m, 2H), 2.22-2.11 (m, 2H), 2.09-1.95 (m, 1H), 1.91-1.79 (m, 1H).

Example 366

N-Cyclopropyl-2-[6-(3-ethylphenyl)pyrrolo[3,2-b]pyridin-1-yl]acetamide

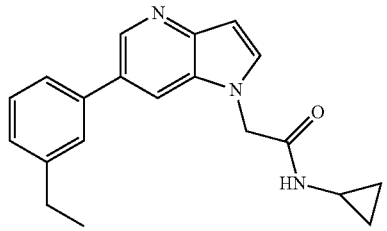 [SMILES: CCc1cccc(-c2cnc3ccn(CC(=O)NC4CC4)c3c2)c1]

The title compound was prepared in a manner analogous to Example 1, Step A, using 2-(6-bromo-1H-pyrrolo[3,2-b]pyridin-1-yl)-N-cyclopropylacetamide (intermediate of Step A, Example 75) and (3-ethylphenyl)boronic acid. MS (ESI): mass calcd. for $C_{20}H_{21}N_3O$, 319.2. m/z found, 320.2 [M+H]⁺. ¹H NMR (400 MHz, DMSO-d₆) δ 8.65 (d, J=1.9 Hz, 1H), 8.37 (d, J=4.2 Hz, 1H), 8.04 (dd, J=2.0, 0.9 Hz, 1H), 7.63 (d, J=3.2 Hz, 1H), 7.59-7.51 (m, 2H), 7.41 (t, J=7.6 Hz, 1H), 7.23 (d, J=7.6 Hz, 1H), 6.59 (d, J=3.6 Hz, 1H), 4.87 (s, 2H), 2.75-2.61 (m, 3H), 1.26 (t, J=7.6 Hz, 3H), 0.67-0.59 (m, 2H), 0.48-0.41 (m, 2H).

Example 367

2-[6-(3,4-Difluorophenyl)pyrrolo[3,2-b]pyridin-1-yl]-1-pyrrolidin-1-yl-ethanone

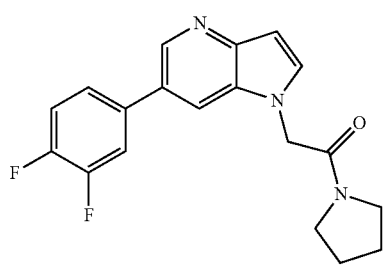 [SMILES: O=C(Cn1ccc2ncc(-c3ccc(F)c(F)c3)cc21)N1CCCC1]

The title compound was prepared in a manner analogous to Example 105. MS (ESI): mass calcd. for $C_{19}H_{17}F_2N_3O$, 341.1. m/z found, 342.2 [M+H]⁺. ¹H NMR (400 MHz, CD₃OD) δ 8.53 (d, J=1.9 Hz, 1H), 8.03 (dd, J=1.9, 0.9 Hz, 1H), 7.60 (ddd, J=12.0, 7.6, 2.3 Hz, 1H), 7.54 (d, J=3.3 Hz, 1H), 7.49-7.43 (m, 1H), 7.37-7.29 (m, 1H), 6.65 (dd, J=3.3, 0.9 Hz, 1H), 5.13 (s, 2H), 3.62 (t, J=6.8 Hz, 2H), 3.44 (t, J=6.9 Hz, 2H), 2.10-2.00 (m, 2H), 1.95-1.85 (m, 2H).

Example 368

1-(3,3-Difluoroazetidin-1-yl)-2-[6-(4-methyl-2-thienyl)pyrrolo[3,2-b]pyridin-1-yl]ethanone

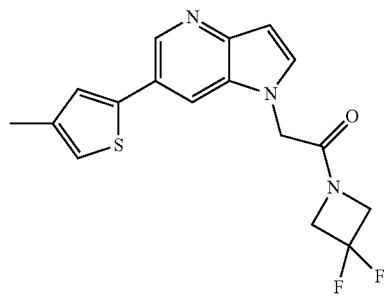 [SMILES: Cc1csc(-c2cnc3ccn(CC(=O)N4CC(F)(F)C4)c3c2)c1]

Step A: Ethyl 2-(6-bromo-1H-pyrrolo[3,2-b]pyridin-1-yl)acetate

The title compound was prepared in a manner analogous to Example 66 Step B. MS (ESI): mass calcd. for $C_{11}H_{11}BrN_2O_2$, 282.0. m/z found, 283.0 [M+H]$^+$.

Step B: 2-(6-(4-Methylthiophen-2-yl)-1H-pyrrolo[3,2-b]pyridin-1-yl)acetic acid The title compound was prepared in a manner analogous to Example 66 Step A. MS (ESI): mass calcd. for $C_{14}H_{12}N_2O_2S$, 272.1. m/z found, 273.1 [M+H]$^+$.

Step C: 1-(3,3-Difluoroazetidin-1-yl)-2-[6-(4-methyl-2-thienyl)pyrrolo[3,2-b]pyridin-1-yl]ethanone The title compound was prepared in a manner analogous to Example 31 Step D. MS (ESI): mass calcd. for $C_{17}H_{15}F_2N_3OS$, 347.1. m/z found, 348.1 [M+H]$^+$. $^1$H NMR (400 MHz, CD$_3$OD) δ 8.58 (d, J=1.9 Hz, 1H), 8.03 (dd, J=2.0, 0.9 Hz, 1H), 7.52 (d, J=3.3 Hz, 1H), 7.28 (d, J=1.4 Hz, 1H), 6.99-6.97 (m, 1H), 6.64 (dd, J=3.3, 0.9 Hz, 1H), 5.08 (s, 2H), 4.64 (t, J=11.9 Hz, 2H), 4.40 (t, J=12.2 Hz, 2H), 2.29 (s, 3H).

Example 369

2-[6-(4-Methyl-2-thienyl)pyrrolo[3,2-b]pyridin-1-yl]-1-pyrrolidin-1-yl-ethanone

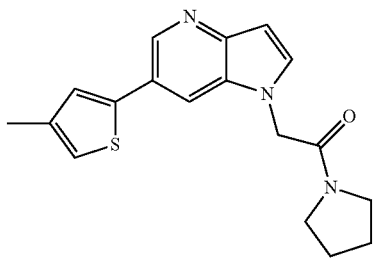 [SMILES: Cc1csc(-c2cnc3ccn(CC(=O)N4CCCC4)c3c2)c1]

The title compound was prepared in a manner analogous to Example 368. MS (ESI): mass calcd. for $C_{18}H_{19}N_3OS$, 325.1. m/z found, 326.2 [M+H]$^+$. $^1$H NMR (400 MHz, CD$_3$OD) δ 8.56 (d, J=1.9 Hz, 1H), 8.00 (dd, J=1.9, 0.9 Hz, 1H), 7.51 (d, J=3.3 Hz, 1H), 7.27 (d, J=1.3 Hz, 1H), 6.97 (s, 1H), 6.62 (dd, J=3.3, 0.9 Hz, 1H), 5.13 (s, 2H), 3.63 (t, J=6.8 Hz, 2H), 3.46 (t, J=6.9 Hz, 2H), 2.28 (s, 3H), 2.13-2.00 (m, 2H), 1.97-1.86 (m, 2H).

Example 370

1-(3-Fluoroazetidin-1-yl)-2-[6-(4-methyl-2-thienyl)pyrrolo[3,2-b]pyridin-1-yl]ethanone

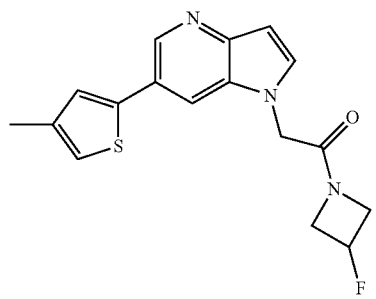 [SMILES: Cc1csc(-c2cnc3ccn(CC(=O)N4CC(F)C4)c3c2)c1]

The title compound was prepared in a manner analogous to Example 368. MS (ESI): mass calcd. for $C_{17}H_{16}FN_3OS$, 329.1. m/z found, 330.2 [M+H]$^+$. $^1$H NMR (400 MHz, CD$_3$OD) δ 8.58 (d, J=1.9 Hz, 1H), 8.01 (dd, J=1.9, 0.9 Hz, 1H), 7.52 (d, J=3.3 Hz, 1H), 7.28 (d, J=1.4 Hz, 1H), 6.98 (s, 1H), 6.64 (dd, J=3.4, 0.9 Hz, 1H), 5.51-5.26 (m, 1H), 5.02 (s, 2H), 4.60-4.42 (m, 1H), 4.41-4.22 (m, 2H), 4.18-4.00 (m, 1H), 2.29 (s, 3H).

Example 371

1-(3-Fluoroazetidin-1-yl)-2-[6-(3,4,5-trifluorophenyl)pyrrolo[3,2-b]pyridin-1-yl]ethanone

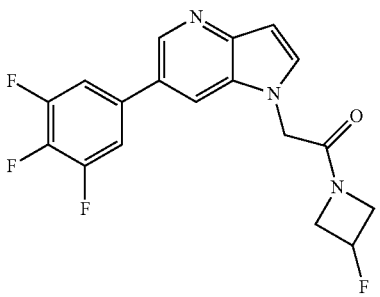 [SMILES: O=C(Cn1ccc2ncc(-c3cc(F)c(F)c(F)c3)cc21)N1CC(F)C1]

The title compound was prepared in a manner analogous to Example 128. MS (ESI): mass calcd. for $C_{18}H_{13}F_4N_3O$, 363.1. m/z found, 364.2 [M+H]$^+$. $^1$H NMR (500 MHz, CD$_3$OD) δ 8.59 (d, J=2.0 Hz, 1H), 8.11 (s, 1H), 7.60 (d, J=3.3 Hz, 1H), 7.56-7.48 (m, 2H), 6.68 (dd, J=3.3, 0.9 Hz, 1H), 5.51-5.29 (m, 1H), 5.07 (d, J=3.5 Hz, 2H), 4.64-4.48 (m, 1H), 4.42-4.27 (m, 2H), 4.16-4.02 (m, 1H).

Example 372

2-[6-(5-Chloro-2-thienyl)pyrrolo[3,2-b]pyridin-1-yl]-1-(3-fluoroazetidin-1-yl)ethanone

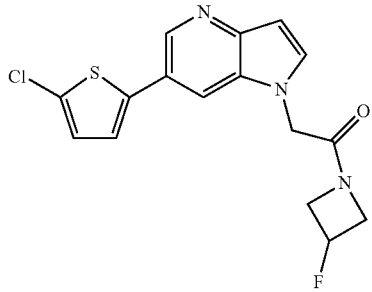 [SMILES: O=C(Cn1ccc2ncc(-c3ccc(Cl)s3)cc21)N1CC(F)C1]

The title compound was prepared in a manner analogous to Example 130. MS (ESI): mass calcd. for $C_{16}H_{13}ClFN_3OS$, 349.0. m/z found, 350.0 $[M+H]^+$. $^1H$ NMR (400 MHz, DMSO-$d_6$) δ 8.62 (d, J=2.0 Hz, 1H), 8.06 (dd, J=2.1, 0.9 Hz, 1H), 7.62 (d, J=3.3 Hz, 1H), 7.43 (d, J=3.9 Hz, 1H), 7.20 (d, J=3.9 Hz, 1H), 6.61 (dd, J=3.4, 0.8 Hz, 1H), 5.59-5.35 (m, 1H), 5.06 (s, 2H), 4.65-4.47 (m, 1H), 4.40-4.16 (m, 2H), 4.07-3.88 (m, 1H).

Example 373

1-(Azetidin-1-yl)-2-[6-(5-chloro-2-thienyl)pyrrolo[3,2-b]pyridin-1-yl]ethanone

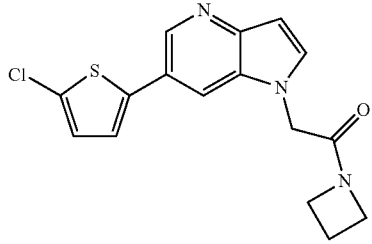 [SMILES: O=C(Cn1ccc2ncc(-c3ccc(Cl)s3)cc21)N1CCC1]

The title compound was prepared in a manner analogous to Example 102. MS (ESI): mass calcd. for $C_{16}H_{14}ClN_3OS$, 331.1. m/z found, 332.0 $[M+H]^+$. $^1H$ NMR (400 MHz, DMSO-$d_6$) δ 8.61 (d, J=2.0 Hz, 1H), 8.06 (dd, J=2.1, 0.8 Hz, 1H), 7.62 (d, J=3.3 Hz, 1H), 7.44 (d, J=3.9 Hz, 1H), 7.20 (d, J=3.9 Hz, 1H), 6.60 (dd, J=3.3, 0.8 Hz, 1H), 4.99 (s, 2H), 4.23 (t, J=7.7 Hz, 2H), 3.92 (t, J=7.7 Hz, 2H), 2.34-2.22 (m, 2H).

Example 374

2-[3-Chloro-6-(2,3,4-trifluorophenyl)pyrrolo[3,2-b]pyridin-1-yl]-1-(3-fluoroazetidin-1-yl)ethanone

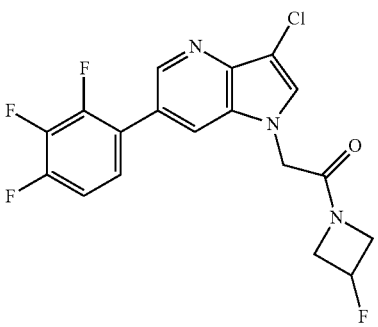 [SMILES: O=C(Cn1cc(Cl)c2ncc(-c3ccc(F)c(F)c3F)cc21)N1CC(F)C1]

The title compound was prepared in a manner analogous to Example 1. MS (ESI): mass calcd. for $C_{18}H_{12}ClF_4N_3O$, 397.1. m/z found, 398.0 $[M+H]^+$. $^1H$ NMR (300 MHz, DMSO-$d_6$) δ 8.58 (s, 1H), 8.17 (s, 1H), 7.86 (s, 1H), 7.58-7.43 (m, 2H), 5.62-5.31 (m, 1H), 5.07 (s, 2H), 4.68-4.47 (m, 1H), 4.46-4.14 (m, 2H), 4.07-3.88 (m, 1H).

Example 375

N,N-Dimethyl-2-[6-(3,4,5-trifluorophenyl)pyrrolo[3,2-b]pyridin-1-yl]acetamide

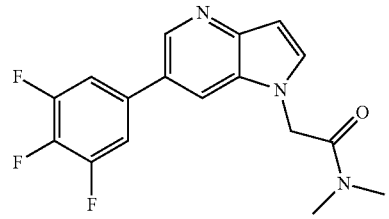 [SMILES: CN(C)C(=O)Cn1ccc2ncc(-c3cc(F)c(F)c(F)c3)cc21]

Step A: 2-(6-Bromo-1H-pyrrolo[3,2-b]pyridin-1-yl)-N,N-dimethylacetamide

The title compound was prepared in a manner analogous to Intermediate 10, using 6-bromo-1H-pyrrolo[3,2-b]pyridine and 2-bromo-N,N-dimethylacetamide. MS (ESI): mass calcd. for $C_{11}H_{12}BrN_3O$, 281.1. m/z found, 282.0 $[M+H]^+$.

Step B: N,N-dimethyl-2-[6-(3,4,5-trifluorophenyl)pyrrolo[3,2-b]pyridin-1-yl]acetamide The title compound was prepared in a manner analogous to Example 1, Step A, using 2-(6-bromo-1H-pyrrolo[3,2-b]pyridin-1-yl)-N,N-dimethylacetamide and (3,4,5-trifluorophenyl)boronic acid. MS (ESI): mass calcd. for $C_{17}H_{14}F_3N_3O$, 333.1. m/z found, 334.1 $[M+H]^+$. $^1H$ NMR (500 MHz, CD$_3$OD) δ 8.55 (d, J=2.0 Hz, 1H), 8.07 (dd, J=2.0, 0.9 Hz, 1H), 7.55 (d, J=3.3 Hz, 1H), 7.53-7.46 (m, 2H), 6.66 (dd, J=3.3, 0.9 Hz, 1H), 5.25 (s, 2H), 3.20 (s, 3H), 2.98 (s, 3H).

Example 376

2-[6-(3,5-Difluorophenyl)pyrrolo[3,2-b]pyridin-1-yl]-N,N-dimethyl-acetamide

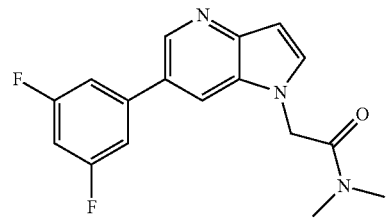 [SMILES: CN(C)C(=O)Cn1ccc2ncc(-c3cc(F)cc(F)c3)cc21]

The title compound was prepared in a manner analogous to Example 375. MS (ESI): mass calcd. for $C_{17}H_{15}F_2N_3O$, 315.1. m/z found, 316.1 $[M+H]^+$. $^1H$ NMR (500 MHz, CD$_3$OD) δ 8.58 (d, J=1.9 Hz, 1H), 8.09 (dd, J=1.9, 0.9 Hz, 1H), 7.56 (d, J=3.3 Hz, 1H), 7.37-7.29 (m, 2H), 6.97-6.90 (m, 1H), 6.66 (dd, J=3.4, 0.9 Hz, 1H), 5.26 (s, 2H), 3.19 (s, 3H), 2.98 (s, 3H).

Example 377

2-[6-[3-(Difluoromethyl)phenyl]pyrrolo[3,2-b]pyridin-1-yl]-N,N-dimethyl-acetamide

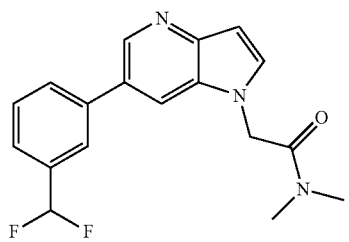 [SMILES: CN(C)C(=O)Cn1ccc2ncc(-c3cccc(C(F)F)c3)cc21]

The title compound was prepared in a manner analogous to Example 375. MS (ESI): mass calcd. for $C_{18}H_{17}F_2N_3O$, 329.1. m/z found, 330.1 [M+H]$^+$. $^1$H NMR (500 MHz, CD$_3$OD) δ 8.58 (d, J=1.9 Hz, 1H), 8.06 (dd, J=2.0, 0.9 Hz, 1H), 7.87-7.77 (m, 2H), 7.61-7.50 (m, 3H), 6.84 (t, J=56.2 Hz, 1H), 6.66 (dd, J=3.3, 0.9 Hz, 1H), 5.24 (s, 2H), 3.17 (s, 3H), 2.96 (s, 3H).

Example 378

2-[6-(5-Chloro-2-thienyl)pyrrolo[3,2-b]pyridin-1-yl]-N,N-dimethyl-acetamide

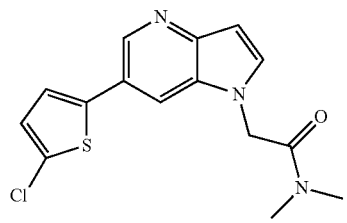 [SMILES: CN(C)C(=O)Cn1ccc2ncc(-c3ccc(Cl)s3)cc21]

The title compound was prepared in a manner analogous to Example 375. MS (ESI): mass calcd. for $C_{15}H_{14}ClN_3OS$, 319.1. m/z found, 320.0 [M+H]$^+$. $^1$H NMR (500 MHz, CD$_3$OD) δ 8.52 (d, J=1.9 Hz, 1H), 7.99 (dd, J=1.9, 0.9 Hz, 1H), 7.53 (d, J=3.3 Hz, 1H), 7.27 (d, J=3.9 Hz, 1H), 7.00 (d, J=3.9 Hz, 1H), 6.64 (dd, J=3.4, 0.9 Hz, 1H), 5.25 (s, 2H), 3.20 (s, 3H), 2.98 (s, 3H).

Example 379

2-[6-(3,4-Difluorophenyl)pyrrolo[3,2-b]pyridin-1-yl]-N,N-dimethyl-acetamide

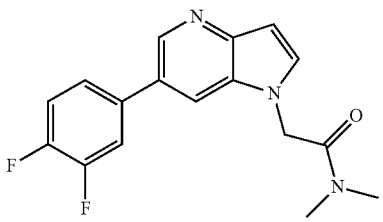

The title compound was prepared in a manner analogous to Example 375. MS (ESI): mass calcd. for $C_{17}H_{15}F_2N_3O$, 315.1. m/z found, 316.1 [M+H]$^+$. $^1$H NMR (500 MHz, CD$_3$OD) δ 8.56 (d, J=1.9 Hz, 1H), 8.05 (dd, J=2.0, 0.9 Hz, 1H), 7.64 (ddd, J=11.9, 7.7, 2.3 Hz, 1H), 7.54 (d, J=3.3 Hz, 1H), 7.53-7.47 (m, 1H), 7.40-7.32 (m, 1H), 6.66 (dd, J=3.3, 0.9 Hz, 1H), 5.27 (s, 2H), 3.20 (s, 3H), 2.98 (s, 3H).

Example 380

1-(Azetidin-1-yl)-2-[6-(5-methyl-2-thienyl)pyrrolo[3,2-b]pyridin-1-yl]ethanone

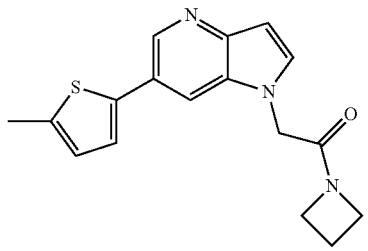 [SMILES: Cc1ccc(-c2cnc3ccn(CC(=O)N4CCC4)c3c2)s1]

The title compound was prepared in a manner analogous to Example 130. MS (ESI): mass calcd. for $C_{17}H_{17}N_3OS$, 311.1. m/z found, 312.0 [M+H]$^+$. $^1$H NMR (400 MHz, DMSO-d$_6$) δ 8.59 (d, J=2.0 Hz, 1H), 7.98 (d, J=1.7 Hz, 1H), 7.57 (d, J=3.3 Hz, 1H), 7.34 (d, J=3.5 Hz, 1H), 6.86 (dd, J=3.5, 1.3 Hz, 1H), 6.57 (d, J=2.9 Hz, 1H), 4.98 (s, 2H), 4.21 (t, J=7.7 Hz, 2H), 3.91 (t, J=7.8 Hz, 2H), 2.49 (s, 3H), 2.39-2.17 (m, 2H).

Example 381

1-(Azetidin-1-yl)-2-[3-chloro-6-(5-chloro-2-thienyl)pyrrolo[3,2-b]pyridin-1-yl]ethanone

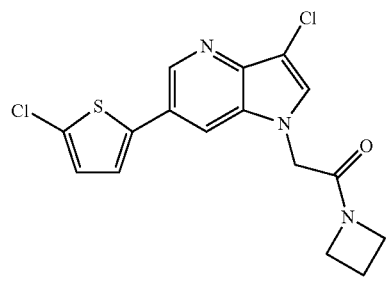 [SMILES: O=C(Cn1cc(Cl)c2ncc(-c3ccc(Cl)s3)cc21)N1CCC1]

The title compound was prepared in a manner analogous to Example 29. MS (ESI): mass calcd. for $C_{16}H_{13}Cl_2N_3OS$, 365.0. m/z found, 365.8 [M+H]$^+$. $^1$H NMR (400 MHz, DMSO-d$_6$) δ 8.69 (d, J=1.9 Hz, 1H), 8.16 (d, J=2.0 Hz, 1H), 7.80 (s, 1H), 7.49 (d, J=4.0 Hz, 1H), 7.22 (d, J=3.9 Hz, 1H), 4.99 (s, 2H), 4.25 (t, J=7.6 Hz, 2H), 3.92 (t, J=7.7 Hz, 2H), 2.34-2.25 (m, 2H).

Example 382

1-(Azetidin-1-yl)-2-[6-(3,4-difluorophenyl)-3-fluoro-pyrrolo[3,2-b]pyridin-1-yl]ethanone

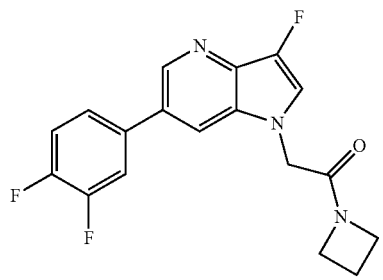 [SMILES: O=C(Cn1cc(F)c2ncc(-c3ccc(F)c(F)c3)cc21)N1CCC1]

The title compound was prepared in a manner analogous to Example 182. MS (ESI): mass calcd. for $C_{18}H_{14}F_3N_3O$, 345.1. m/z found, 346.0 [M+H]$^+$. $^1$H NMR (400 MHz, DMSO-d$_6$) δ 8.72 (d, J=1.9 Hz, 1H), 8.26-8.22 (m, 1H), 7.89 (ddd, J=12.4, 7.8, 2.2 Hz, 1H), 7.71-7.53 (m, 3H), 4.95 (s, 2H), 4.22 (t, J=7.7 Hz, 2H), 3.90 (t, J=7.7 Hz, 2H), 2.32-2.21 (m, 2H).

Example 383

1-(Azetidin-1-yl)-2-[3-fluoro-6-(3,4,5-trifluorophenyl)pyrrolo[3,2-b]pyridin-1-yl]ethanone

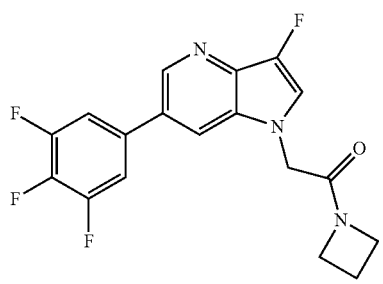 [SMILES: O=C(Cn1cc(F)c2ncc(-c3cc(F)c(F)c(F)c3)cc21)N1CCC1]

The title compound was prepared in a manner analogous to Example 182. MS (ESI): mass calcd. for $C_{18}H_{13}F_4N_3O$, 363.1. m/z found, 364.0 [M+H]$^+$. $^1$H NMR (400 MHz, DMSO-d$_6$) δ 8.77 (d, J=1.9 Hz, 1H), 8.33-8.27 (m, 1H), 7.86-7.79 (m, 2H), 7.70 (d, J=2.2 Hz, 1H), 4.95 (s, 2H), 4.22 (t, J=7.7 Hz, 2H), 3.91 (t, J=7.7 Hz, 2H), 2.34-2.23 (m, 2H).

Example 384

2-[3-Chloro-6-(4-fluorophenyl)pyrrolo[3,2-b]pyridin-1-yl]-1-cyclopropyl-ethanone

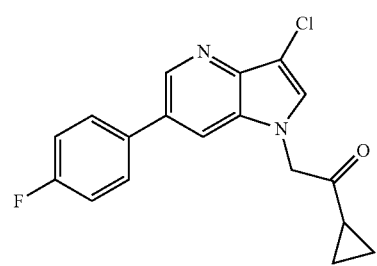 [SMILES: O=C(Cn1cc(Cl)c2ncc(-c3ccc(F)cc3)cc21)C1CC1]

The title compound was prepared in a manner analogous to Example 1. MS (ESI): mass calcd. for $C_{18}H_{14}ClFN_2O$, 328.1. m/z found, 328.9 [M+H]$^+$. $^1$H NMR (400 MHz, DMSO-d$_6$) δ 8.72 (d, J=1.9 Hz, 1H), 8.22 (d, J=2.0 Hz, 1H), 7.87-7.74 (m, 3H), 7.35 (t, J=8.9 Hz, 2H), 5.49 (s, 2H), 2.19-2.08 (m, 1H), 1.07-0.89 (m, 4H).

Example 385

1-(Azetidin-1-yl)-2-[6-(3-thienyl)pyrrolo[3,2-b]pyridin-1-yl]ethanone trifluoroacetate salt

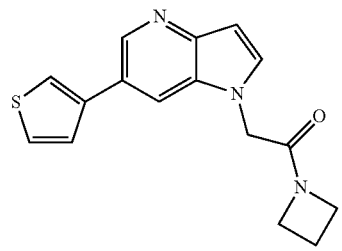 [SMILES: O=C(Cn1ccc2ncc(-c3ccsc3)cc21)N1CCC1]

The title compound was prepared in a manner analogous to Example 102. MS (ESI): mass calcd. for $C_{16}H_{15}N_3OS$, 297.1. m/z found, 298.0 [M+H]$^+$. $^1$H NMR (500 MHz, DMSO-d$_6$) δ 9.04 (d, J=1.7 Hz, 1H), 8.88 (s, 1H), 8.17-8.11 (m, 1H), 8.03 (d, J=3.3 Hz, 1H), 7.80 (dd, J=5.0, 2.9 Hz, 1H), 7.76 (dd, J=5.0, 1.4 Hz, 1H), 6.82 (dd, J=3.2, 0.9 Hz, 1H), 5.18 (s, 2H), 4.29 (t, J=7.7 Hz, 2H), 3.94 (t, J=7.7 Hz, 2H), 2.37-2.28 (m, 2H).

Example 386

N,N-Dimethyl-2-[6-(5-methyl-2-thienyl)pyrrolo[3,2-b]pyridin-1-yl]acetamide trifluoroacetate salt

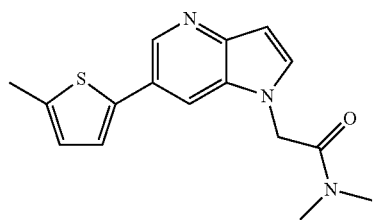

The title compound was prepared in a manner analogous to Example 375 substituting 4,4,5,5-tetramethyl-2-(5-methylthiophen-2-yl)-1,3,2-dioxaborolane for (3,4,5-trifluorophenyl)boronic acid. MS (ESI): mass calcd. for $C_{16}H_{17}N_3OS$, 299.1. m/z found, 300.0 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=0.79 min at 254 nm.

Example 387

2-[3-Fluoro-6-(2-thienyl)pyrrolo[3,2-b]pyridin-1-yl]-N,N-dimethyl-acetamide

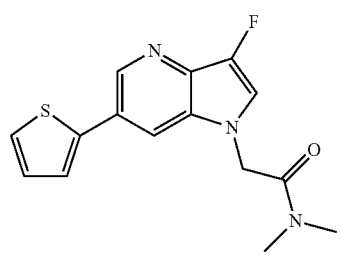 [SMILES: CN(C)C(=O)Cn1cc(F)c2ncc(-c3cccs3)cc21]

The title compound was prepared in a manner analogous to Example 92. MS (ESI): mass calcd. for $C_{15}H_{14}FN_3OS$, 303.1. m/z found, 304.0 [M+H]$^+$. $^1$H NMR (400 MHz, DMSO) δ 8.69 (d, J=1.8 Hz, 1H), 8.14 (t, 1H), 7.61-7.57 (m, 3H), 7.21-7.16 (m, 1H), 5.20 (s, 2H), 3.10 (s, 3H), 2.86 (s, 3H).

Example 388

2-[6-(5-Ethyl-2-thienyl)pyrrolo[3,2-b]pyridin-1-yl]-N,N-dimethyl-acetamide trifluoroacetate salt

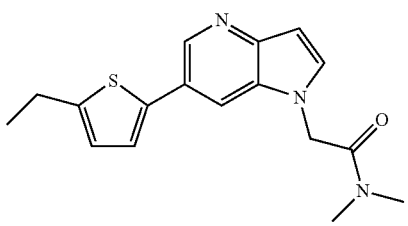 [SMILES: CCc1ccc(-c2cnc3ccn(CC(=O)N(C)C)c3c2)s1]

The title compound was prepared in a manner analogous to Example 375. MS (ESI): mass calcd. for $C_{17}H_{19}N_3OS$, 313.1. m/z found, 314.1 [M+H]$^+$. $^1$H NMR (500 MHz, DMSO-$d_6$) δ 8.76 (s, 1H), 8.37 (br. s, 1H), 7.81-7.76 (m, 1H), 7.45 (d, J=3.6 Hz, 1H), 6.93 (d, J=3.7 Hz, 1H), 6.71-6.65 (m, 1H), 5.34 (s, 2H), 3.12 (s, 3H), 2.87 (d, J=6.1 Hz, 5H), 1.29 (t, J=7.5 Hz, 3H).

Example 389

1-(Azetidin-1-yl)-2-[3-fluoro-6-(2-thienyl)pyrrolo[3,2-b]pyridin-1-yl]ethanone trifluoroacetate salt

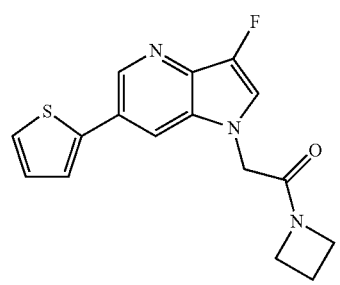 [SMILES: O=C(Cn1cc(F)c2ncc(-c3cccs3)cc21)N1CCC1]

The title compound was prepared in a manner analogous to Example 182. MS (ESI): mass calcd. for $C_{16}H_{14}FN_3OS$, 315.1. m/z found, 316.0 [M+H]$^+$. $^1$H NMR (400 MHz, DMSO-$d_6$) δ 8.71 (d, J=1.9 Hz, 1H), 8.15 (t, J=2.2 Hz, 1H), 7.65 (d, J=2.2 Hz, 1H), 7.63-7.59 (m, 2H), 7.22-7.15 (m, 1H), 4.95 (s, 2H), 4.23 (t, J=7.7 Hz, 2H), 3.91 (t, J=7.7 Hz, 2H), 2.35-2.22 (m, 2H).

Example 390

2-[3-Fluoro-6-(5-methyl-2-thienyl)pyrrolo[3,2-b]pyridin-1-yl]-N,N-dimethyl-acetamide

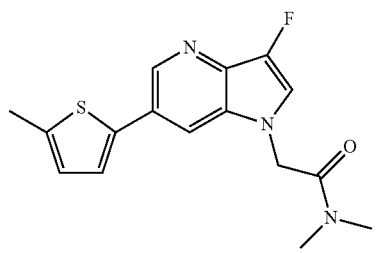

The title compound was prepared in a manner analogous to Example 92 substituting 4,4,5,5-tetramethyl-2-(5-methylthiophen-2-yl)-1,3,2-dioxaborolane for (4-fluoro-3-methylphenyl)boronic acid. MS (ESI): mass calcd. for $C_{18}H_{16}FN_3OS$, 317.1. m/z found, 318.0 [M+H]$^+$. $^1$H NMR (500 MHz, DMSO-$d_6$) δ 8.69 (d, J=1.9 Hz, 1H), 8.21 (t, J=2.2 Hz, 1H), 7.65 (d, J=2.2 Hz, 1H), 7.64-7.60 (m, 2H), 5.20 (s, 2H), 3.10 (s, 3H), 2.86 (s, 3H), 2.07 (s, 3H).

Example 391

2-[6-(4-Chloro-2-thienyl)pyrrolo[3,2-b]pyridin-1-yl]-N,N-dimethyl-acetamide trifluoroacetate salt

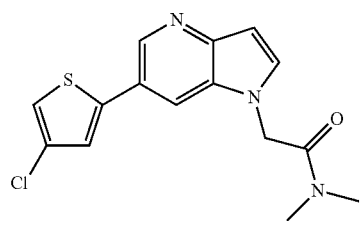 [SMILES: CN(C)C(=O)Cn1ccc2ncc(-c3cc(Cl)cs3)cc21]

The title compound was prepared in a manner analogous to Example 375 substituting 2-(4-chlorothiophen-2-yl)-4,4,5,5-tetramethyl-1,3,2-dioxaborolane for (3,4,5-trifluorophenyl)boronic acid. MS (ESI): mass calcd. for $C_{15}H_{14}ClN_3OS$, 319.1. m/z found, 320.0 [M+H]$^+$. $^1$H NMR (500 MHz, DMSO-$d_6$) δ 8.84 (s, 1H), 8.52 (s, 1H), 7.85 (d, J=3.3 Hz, 1H), 7.68 (s, 2H), 6.73 (d, J=3.3 Hz, 1H), 5.36 (s, 2H), 3.13 (s, 3H), 2.88 (s, 3H).

Example 392

1-(Azetidin-1-yl)-2-[6-(5-ethyl-2-thienyl)pyrrolo[3,2-b]pyridin-1-yl]ethanone trifluoroacetate salt

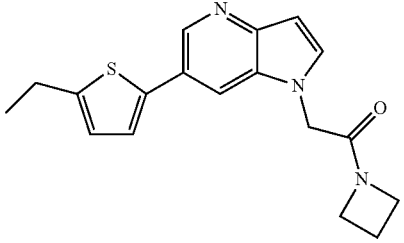 [SMILES: CCc1ccc(-c2cnc3ccn(CC(=O)N4CCC4)c3c2)s1]

The title compound was prepared in a manner analogous to Example 102. MS (ESI): mass calcd. for C₁8H19N3OS, 325.1. m/z found, 326.0 [M+H]⁺. ¹H NMR (400 MHz, DMSO-d₆) δ 8.79 (s, 1H), 8.40 (s, 1H), 7.82 (s, 1H), 7.47 (d, J=3.6 Hz, 1H), 6.94 (d, J=3.6 Hz, 1H), 6.71 (d, J=3.1 Hz, 1H), 5.10 (s, 2H), 4.26 (t, J=7.7 Hz, 2H), 3.93 (t, J=7.6 Hz, 2H), 2.88 (q, J=7.6 Hz, 2H), 2.36-2.24 (m, 2H), 1.30 (t, J=7.5 Hz, 3H).

Example 393

2-[6-(5-Ethyl-2-thienyl)-3-fluoro-pyrrolo[3,2-b]pyridin-1-yl]-N,N-dimethyl-acetamide

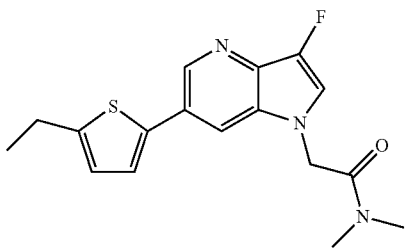 [SMILES: CCc1ccc(-c2cnc3c(F)cn(CC(=O)N(C)C)c3c2)s1]

The title compound was prepared in a manner analogous to Example 92. MS (ESI): mass calcd. for $C_{17}H_{18}FN_3OS$, 331.1. m/z found, 332.1 [M+H]⁺. ¹H NMR (400 MHz, DMSO-d₆) δ 8.64 (d, J=1.8 Hz, 1H), 8.06 (s, 1H), 7.58 (d, J=2.2 Hz, 1H), 7.39 (d, J=3.6 Hz, 1H), 6.90 (d, J=3.5 Hz, 1H), 5.18 (s, 2H), 3.10 (s, 3H), 2.91-2.80 (m, 5H), 1.28 (t, J=7.5 Hz, 3H).

Example 394

1-(Azetidin-1-yl)-2-[6-(4-chloro-2-thienyl)pyrrolo[3,2-b]pyridin-1-yl]ethanone trifluoroacetate salt

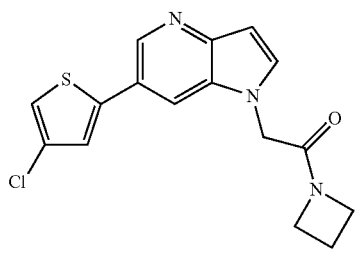 [SMILES: O=C(Cn1ccc2ncc(-c3cc(Cl)cs3)cc21)N1CCC1]

The title compound was prepared in a manner analogous to Example 102 substituting 2-(4-chlorothiophen-2-yl)-4,4,5,5-tetramethyl-1,3,2-dioxaborolane for (5-(trifluoromethyl)pyridin-3-yl)boronic acid. MS (ESI): mass calcd. for $C_{16}H_{14}ClN_3OS$, 331.1. m/z found, 332.0 [M+H]⁺. ¹H NMR (500 MHz, DMSO-d₆) δ 8.08 (d, J=1.7 Hz, 1H), 8.00-7.98 (m, 1H), 7.22 (d, J=3.3 Hz, 1H), 6.80 (d, J=1.5 Hz, 1H), 6.68 (d, J=1.5 Hz, 1H), 6.08 (dd, J=3.5, 1.0 Hz, 1H), 4.42 (s, 2H), 3.61 (t, J=7.7 Hz, 2H), 3.29 (t, J=7.8 Hz, 2H), 1.69-1.59 (m, 2H).

Example 395

1-(3-Fluoroazetidin-1-yl)-2-[3-fluoro-6-(2-thienyl)pyrrolo[3,2-b]pyridin-1-yl]ethanone trifluoroacetate salt

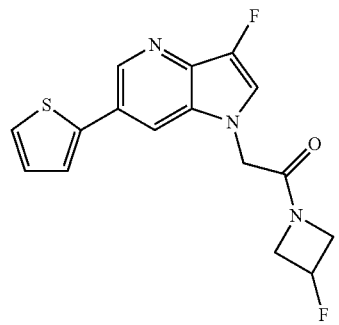 [SMILES: O=C(Cn1cc(F)c2ncc(-c3cccs3)cc21)N1CC(F)C1]

The title compound was prepared in a manner analogous to Example 182. MS (ESI): mass calcd. for $C_{16}H_{13}F_2N_3OS$, 333.1. m/z found, 334.0 [M+H]⁺. ¹H NMR (500 MHz, DMSO-d₆) δ 8.72 (d, J=1.9 Hz, 1H), 8.17 (t, J=2.1 Hz, 1H), 7.66 (d, J=2.2 Hz, 1H), 7.64-7.57 (m, 2H), 7.19 (dd, J=5.1, 3.6 Hz, 1H), 5.56-5.38 (m, 1H), 5.02 (d, J=2.8 Hz, 2H), 4.65-4.50 (m, 1H), 4.41-4.18 (m, 2H), 4.05-3.92 (m, 1H).

Example 396

2-[6-(4-Chloro-2-thienyl)-3-fluoro-pyrrolo[3,2-b]pyridin-1-yl]-N,N-dimethyl-acetamide

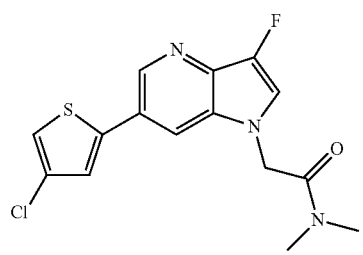 [SMILES: CN(C)C(=O)Cn1cc(F)c2ncc(-c3cc(Cl)cs3)cc21]

The title compound was prepared in a manner analogous to Example 182 substituting 2-(4-chlorothiophen-2-yl)-4,4,5,5-tetramethyl-1,3,2-dioxaborolane for (5-chlorothiophen-2-yl)boronic acid. MS (ESI): mass calcd. for $C_{15}H_{13}ClFN_3OS$, 337.0. m/z found, 338.0 [M+H]⁺. ¹H NMR (500 MHz, DMSO-d₆) δ 8.62 (d, J=1.9 Hz, 1H), 8.05 (t, J=2.2 Hz, 1H), 7.58 (d, J=2.2 Hz, 1H), 7.37 (d, J=3.5 Hz, 1H), 6.86 (dd, J=3.6, 1.2 Hz, 1H), 5.18 (s, 2H), 3.10 (s, 3H), 2.86 (s, 3H).

Example 397

1-(Azetidin-1-yl)-2-[6-(4-chloro-2-thienyl)-3-fluoro-pyrrolo[3,2-b]pyridin-1-yl]ethanone trifluoroacetate salt

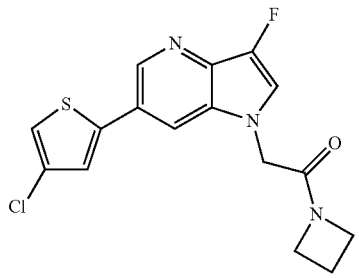

The title compound was prepared in a manner analogous to Example 182 substituting 2-(4-chlorothiophen-2-yl)-4,4,5,5-tetramethyl-1,3,2-dioxaborolane for (5-chlorothiophen-2-yl)boronic acid. MS (ESI): mass calcd. for $C_{16}H_{13}ClFN_3OS$, 349.0. m/z found, 350.0 [M+H]$^+$. $^1$H NMR (500 MHz, DMSO-$d_6$) δ 8.71 (d, J=1.8 Hz, 1H), 8.21 (t, J=2.1 Hz, 1H), 7.68 (d, J=2.2 Hz, 1H), 7.64 (s, 2H), 4.95 (s, 2H), 4.23 (t, J=7.7 Hz, 2H), 3.91 (t, J=7.7 Hz, 2H), 2.33-2.24 (m, 2H).

Example 398

2-[6-(5-Ethyl-2-thienyl)-3-fluoro-pyrrolo[3,2-b]pyridin-1-yl]-1-(3-fluoroazetidin-1-yl)ethanone trifluoroacetate salt

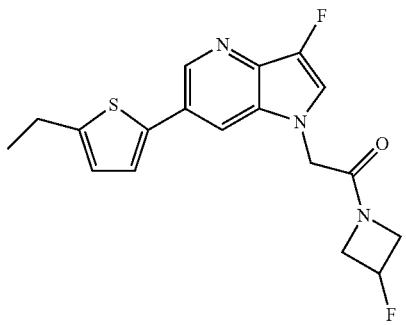 [SMILES: CCc1ccc(-c2cnc3c(F)cn(CC(=O)N4CC(F)C4)c3c2)s1]

The title compound was prepared in a manner analogous to Example 182. MS (ESI): mass calcd. for $C_{16}H_{17}F_2N_3OS$, 361.1. m/z found, 362.0 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=1.14 min at 254 nm.

Example 399

1-(Azetidin-1-yl)-2-[6-(2-thienyl)pyrrolo[3,2-b]pyridin-1-yl]ethanone

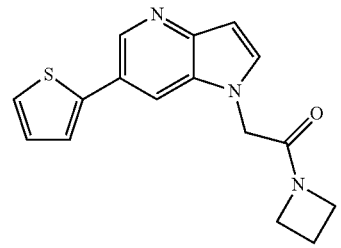

The title compound was prepared in a manner analogous to Example 102. MS (ESI): mass calcd. for $C_{16}H_{15}N_3OS$, 297.1. m/z found, 298.0 [M+H]$^+$. $^1$H NMR (400 MHz, CD$_3$OD) δ 8.63 (d, J=1.9 Hz, 1H), 8.08-8.05 (m, 1H), 7.55 (d, J=3.3 Hz, 1H), 7.48 (dd, J=3.6, 1.2 Hz, 1H), 7.43 (dd, J=5.1, 1.2 Hz, 1H), 7.14 (dd, J=5.2, 3.6 Hz, 1H), 6.68-6.62 (m, 1H), 5.00 (s, 2H), 4.27 (t, J=7.7 Hz, 2H), 4.07 (t, J=7.7 Hz, 2H), 2.43-2.31 (m, 2H).

Example 400

N,N-Dimethyl-2-[6-(2-thienyl)pyrrolo[3,2-b]pyridin-1-yl]acetamide

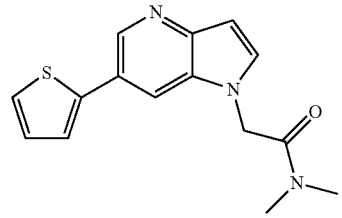 [SMILES: CN(C)C(=O)Cn1ccc2ncc(-c3cccs3)cc21]

The title compound was prepared in a manner analogous to Example 375. MS (ESI): mass calcd. for $C_{15}H_{15}N_3OS$, 285.1. m/z found, 286.0 [M+H]$^+$. $^1$H NMR (500 MHz, CD$_3$OD) δ 8.61 (d, J=1.9 Hz, 1H), 8.08-8.02 (m, 1H), 7.51 (d, J=3.3 Hz, 1H), 7.46 (dd, J=3.6, 1.1 Hz, 1H), 7.42 (dd, J=5.1, 1.1 Hz, 1H), 7.13 (dd, J=5.1, 3.6 Hz, 1H), 6.64 (dd, J=3.3, 0.9 Hz, 1H), 5.26 (s, 2H), 3.21 (s, 3H), 2.99 (s, 3H).

Example 401

1-(Azetidin-1-yl)-2-[6-(5-ethyl-2-thienyl)-3-fluoro-pyrrolo[3,2-b]pyridin-1-yl]ethanone

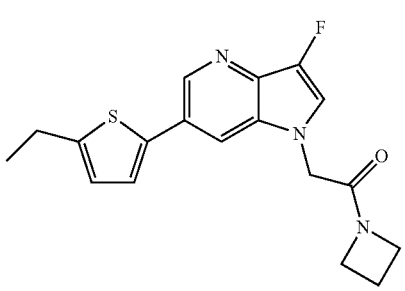 [SMILES: CCc1ccc(-c2cnc3c(F)cn(CC(=O)N4CCC4)c3c2)s1]

The title compound was prepared in a manner analogous to Example 182. MS (ESI): mass calcd. for $C_{18}H_{18}FN_3OS$, 343.1. m/z found, 344.0 [M+H]$^+$. $^1$H NMR (400 MHz, CD$_3$OD) δ 8.60 (d, J=1.8 Hz, 1H), 8.01 (t, J=2.1 Hz, 1H), 7.44 (d, J=2.4 Hz, 1H), 7.30 (d, J=3.6 Hz, 1H), 6.87-6.83 (m, 1H), 4.92 (s, 2H), 4.34-4.26 (m, 2H), 4.07 (t, J=7.8 Hz, 2H), 2.94-2.84 (m, 2H), 2.44-2.33 (m, 2H), 1.35 (t, J=7.5 Hz, 3H).

Example 402

1-(3-Fluoroazetidin-1-yl)-2-[3-fluoro-6-(5-methyl-2-thienyl)pyrrolo[3,2-b]pyridin-1-yl]ethanone trifluoroacetate salt

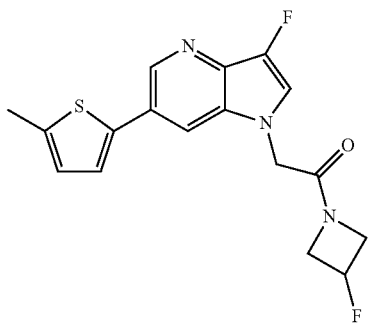 [SMILES: Cc1ccc(-c2cnc3c(F)cn(CC(=O)N4CC(F)C4)c3c2)s1]

The title compound was prepared in a manner analogous to Example 182 substituting 4,4,5,5-tetramethyl-2-(5-methylthiophen-2-yl)-1,3,2-dioxaborolane for (5-chlorothiophen-2-yl)boronic acid. MS (ESI): mass calcd. for C$_{17}$H$_{15}$F$_2$N$_3$OS, 347.1. m/z found, 348.0 [M+H]$^+$. $^1$H NMR (400 MHz, CD$_3$OD) δ 8.71 (s, 1H), 8.34 (s, 1H), 7.67 (d, J=2.2 Hz, 1H), 7.36 (d, J=3.6 Hz, 1H), 6.85 (d, J=3.6 Hz, 1H), 5.54-5.31 (m, 1H), 5.08 (d, J=3.1 Hz, 2H), 4.71-4.55 (m, 1H), 4.49-4.28 (m, 2H), 4.19-4.02 (m, 1H), 2.54 (s, 3H).

Example 403

1-(Azetidin-1-yl)-2-[6-(3-chloro-2-thienyl)pyrrolo[3,2-b]pyridin-1-yl]ethanone

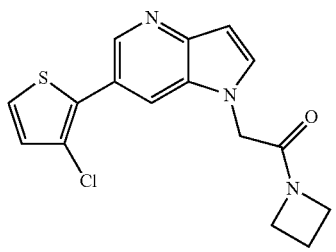 [SMILES: O=C(Cn1ccc2ncc(-c3sccc3Cl)cc21)N1CCC1]

The title compound was prepared in a manner analogous to Example 102. MS (ESI): mass calcd. for C$_{16}$H$_{14}$ClN$_3$OS, 331.1. m/z found, 332.0 [M+H]$^+$. $^1$H NMR (500 MHz, CD$_3$OD) δ 8.56 (d, J=1.8 Hz, 1H), 8.08 (dd, J=1.9, 0.9 Hz, 1H), 7.62 (d, J=3.3 Hz, 1H), 7.55 (d, J=5.4 Hz, 1H), 7.11 (d, J=5.4 Hz, 1H), 6.69 (dd, J=3.3, 0.9 Hz, 1H), 5.00 (s, 2H), 4.31-4.24 (m, 2H), 4.07 (t, J=7.8 Hz, 2H), 2.41-2.31 (m, 2H).

Example 404

1-(Azetidin-1-yl)-2-[6-(2-methylthiazol-5-yl)pyrrolo[3,2-b]pyridin-1-yl]ethanone

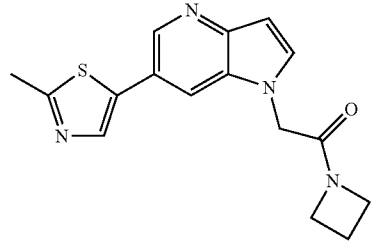 [SMILES: Cc1ncc(-c2cnc3ccn(CC(=O)N4CCC4)c3c2)s1]

The title compound was prepared in a manner analogous to Example 102 substituting 2-methyl-5-(4,4,5,5-tetramethyl-1,3,2-dioxaborolan-2-yl)thiazole for (5-(trifluoromethyl)pyridin-3-yl)boronic acid. MS (ESI): mass calcd. for C$_{16}$H$_{16}$N$_4$OS, 312.1. m/z found, 313.0 [M+H]$^+$. $^1$H NMR (500 MHz, CD$_3$OD) δ 8.56 (d, J=1.9 Hz, 1H), 8.08 (dd, J=1.9, 0.9 Hz, 1H), 7.97 (s, 1H), 7.58 (d, J=3.3 Hz, 1H), 6.67 (dd, J=3.3, 0.9 Hz, 1H), 5.01 (s, 2H), 4.32-4.25 (m, 2H), 4.07 (t, J=7.8 Hz, 2H), 2.75 (s, 3H), 2.43-2.34 (m, 2H).

Example 405

1-(Azetidin-1-yl)-2-(6-thiazol-5-ylpyrrolo[3,2-b]pyridin-1-yl)ethanone

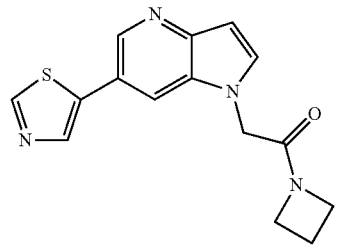 [SMILES: O=C(Cn1ccc2ncc(-c3cncs3)cc21)N1CCC1]

The title compound was prepared in a manner analogous to Example 102 substituting 5-(4,4,5,5-tetramethyl-1,3,2-dioxaborolan-2-yl)thiazole for (5-(trifluoromethyl)pyridin-3-yl)boronic acid. MS (ESI): mass calcd. for C$_{15}$H$_{14}$N$_4$OS, 298.1. m/z found, 299.0 [M+H]$^+$.

Example 406

1-(Azetidin-1-yl)-2-[6-(6-fluoro-3-pyridyl)pyrrolo[3,2-b]pyridin-1-yl]ethanone

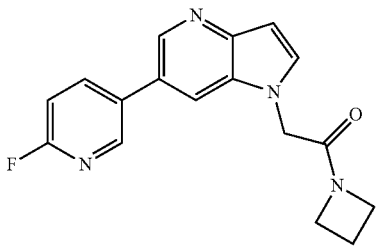 [SMILES: O=C(Cn1ccc2ncc(-c3ccc(F)nc3)cc21)N1CCC1]

The title compound was prepared in a manner analogous to Example 102. MS (ESI): mass calcd. for $C_{17}H_{15}FN_4O$, 310.1. m/z found, 311.1 [M+H]$^+$. $^1$H NMR (500 MHz, CD$_3$OD) δ 8.61 (d, J=1.9 Hz, 1H), 8.56-8.53 (m, 1H), 8.32-8.27 (m, 1H), 8.14 (dd, J=2.0, 0.9 Hz, 1H), 7.61 (d, J=3.3 Hz, 1H), 7.23-7.18 (m, 1H), 6.70 (dd, J=3.4, 0.9 Hz, 1H), 5.03 (s, 2H), 4.32-4.25 (m, 2H), 4.07 (t, J=7.8 Hz, 2H), 2.42-2.33 (m, 2H).

Example 407

1-(Azetidin-1-yl)-2-[3-chloro-6-(4-methyl-2-thienyl)pyrrolo[3,2-b]pyridin-1-yl]ethanone

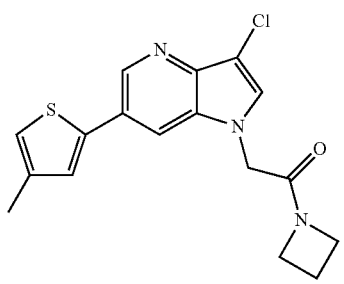 [SMILES: Cc1csc(-c2cnc3c(Cl)cn(CC(=O)N4CCC4)c3c2)c1]

The title compound was prepared in a manner analogous to Example 29. MS (ESI): mass calcd. for $C_{17}H_{16}ClN_3OS$, 345.1. m/z found, 346.0 [M+H]$^+$. $^1$H NMR (500 MHz, DMSO-d$_6$) δ 8.69 (d, J=1.9 Hz, 1H), 8.14 (d, J=1.9 Hz, 1H), 7.76 (s, 1H), 7.44 (d, J=1.4 Hz, 1H), 7.18 (t, J=1.3 Hz, 1H), 5.00 (s, 2H), 4.25 (t, J=7.7 Hz, 2H), 3.95-3.89 (m, 2H), 2.33-2.25 (m, 5H).

Example 408

1-(Azetidin-1-yl)-2-[3-chloro-6-(5-ethyl-2-thienyl)pyrrolo[3,2-b]pyridin-1-yl]ethanone

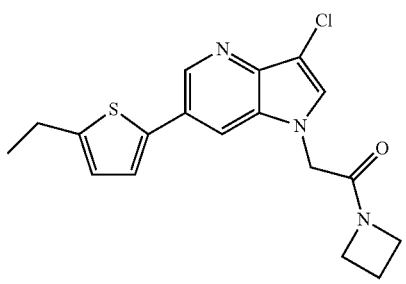 [SMILES: CCc1ccc(-c2cnc3c(Cl)cn(CC(=O)N4CCC4)c3c2)s1]

The title compound was prepared in a manner analogous to Example 29. MS (ESI): mass calcd. for $C_{18}H_{18}ClN_3OS$, 359.1. m/z found, 360.0 [M+H]$^+$. $^1$H NMR (500 MHz, CD$_3$OD) δ 8.64 (d, J=1.8 Hz, 1H), 8.05 (d, J=1.9 Hz, 1H), 7.59 (s, 1H), 7.31 (d, J=3.6 Hz, 1H), 6.87-6.84 (m, 1H), 4.99 (s, 2H), 4.36-4.29 (m, 2H), 4.08 (t, J=7.8 Hz, 2H), 2.94-2.86 (m, 2H), 2.45-2.35 (m, 2H), 1.35 (t, J=7.5 Hz, 3H).

Example 409

1-(Azetidin-1-yl)-2-[3-chloro-6-(2-thienyl)pyrrolo[3,2-b]pyridin-1-yl]ethanone

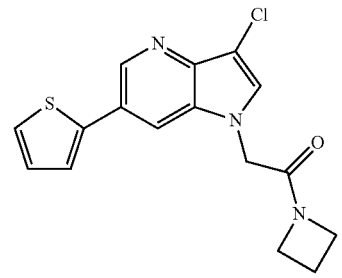 [SMILES: O=C(Cn1cc(Cl)c2ncc(-c3cccs3)cc21)N1CCC1]

The title compound was prepared in a manner analogous to Example 29. MS (ESI): mass calcd. for $C_{16}H_{14}ClN_3OS$, 331.1. m/z found, 332.0 [M+H]$^+$. $^1$H NMR (500 MHz, DMSO-d$_6$) δ 8.74 (d, J=1.9 Hz, 1H), 8.17 (d, J=1.9 Hz, 1H), 7.78 (s, 1H), 7.64-7.58 (m, 2H), 7.20 (dd, J=5.0, 3.6 Hz, 1H), 5.01 (s, 2H), 4.25 (t, J=7.7 Hz, 2H), 3.92 (t, J=7.7 Hz, 2H), 2.34-2.25 (m, 2H).

Example 410

1-(Azetidin-1-yl)-2-[3-chloro-6-(5-methyl-2-thienyl)pyrrolo[3,2-b]pyridin-1-yl]ethanone The title compound was prepared in a manner analogous to Example 29 substituting 4,4,5,5-tetramethyl-2-(5-methylthiophen-2-yl)-1,3,2-dioxaborolane for (3,4-difluorophenyl)boronic acid. MS (ESI): mass calcd. for $C_{17}H_{16}ClN_3OS$, 345.1. m/z found, 346.0 [M+H]$^+$. $^1$H NMR (500 MHz, CD$_3$OD) δ 8.62 (d, J=1.8 Hz, 1H), 8.03 (d, J=1.8 Hz, 1H), 7.59 (s, 1H), 7.29 (d, J=3.5 Hz, 1H), 6.84-6.79 (m, 1H), 4.98 (s, 2H), 4.37-4.28 (m, 2H), 4.07 (t, J=7.8 Hz, 2H), 2.53 (d, J=1.1 Hz, 3H), 2.44-2.34 (m, 2H).

Example 411

2-[6-(4-Fluorophenyl)pyrrolo[3,2-b]pyridin-1-yl]-N-methyl-N-(2,2,2-trifluoroethyl)acetamide

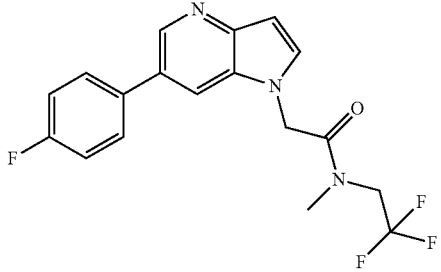 [SMILES: CN(CC(F)(F)F)C(=O)Cn1ccc2ncc(-c3ccc(F)cc3)cc21]

The title compound was prepared in a manner analogous to Example 66. MS (ESI): mass calcd. for $C_{18}H_{15}F_4N_3O$, 365.1. m/z found, 366.0 [M+H]$^+$. $^1$H NMR (500 MHz, CD$_3$OD) δ 8.55 (d, J=1.9 Hz, 1H), 8.01-7.99 (m, 1H), 7.71-7.66 (m, 2H), 7.54 (d, J=3.4 Hz, 1H), 7.24-7.18 (m, 2H), 6.67 (dd, J=3.3, 0.9 Hz, 1H), 5.37 (s, 2H), 4.16 (q, J=9.3 Hz, 2H), 3.33 (s, 3H).

Example 412

2-[3-Chloro-6-(5-methyl-2-thienyl)pyrrolo[3,2-b]pyridin-1-yl]-1-(3-fluoroazetidin-1-yl)ethanone

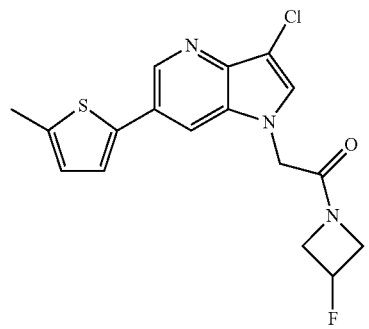 [SMILES: Cc1ccc(-c2cnc3c(Cl)cn(CC(=O)N4CC(F)C4)c3c2)s1]

The title compound was prepared in a manner analogous to Example 146 substituting 2-bromo-1-(3-fluoroazetidin-1-yl)ethanone (Intermediate 2) for 2-bromo-N,N-dimethylacetamide and 4,4,5,5-tetramethyl-2-(5-methylthiophen-2-yl)-1,3,2-dioxaborolane for (4-fluoro-3-methylphenyl)boronic acid. MS (ESI): mass calcd. for $C_{17}H_{15}ClFN_3OS$, 363.1. m/z found, 364.0 [M+H]$^+$. $^1$H NMR (500 MHz, CD$_3$OD) δ 8.63 (d, J=1.9 Hz, 1H), 8.05 (d, J=1.8 Hz, 1H), 7.59 (s, 1H), 7.29 (d, J=3.5 Hz, 1H), 6.83-6.80 (m, 1H), 5.50-5.33 (m, 1H), 5.04 (d, J=3.5 Hz, 2H), 4.64-4.54 (m, 1H), 4.45-4.30 (m, 2H), 4.16-4.06 (m, 1H), 2.52 (d, J=1.1 Hz, 3H).

Example 413

2-[3-Chloro-6-(5-chloro-2-thienyl)pyrrolo[3,2-b]pyridin-1-yl]-1-(3-fluoroazetidin-1-yl)ethanone

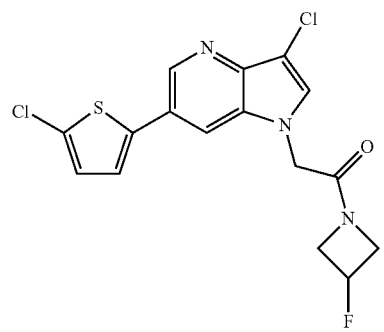 [SMILES: O=C(Cn1cc(Cl)c2ncc(-c3ccc(Cl)s3)cc21)N1CC(F)C1]

The title compound was prepared in a manner analogous to Example 146. MS (ESI): mass calcd. for $C_{16}H_{12}Cl_2FN_3OS$, 383.0. m/z found, 384.0 [M+H]$^+$. $^1$H NMR (500 MHz, CD$_3$OD) δ 8.62 (d, J=1.8 Hz, 1H), 8.09 (d, J=1.9 Hz, 1H), 7.63 (s, 1H), 7.33 (d, J=3.9 Hz, 1H), 7.04 (d, J=3.9 Hz, 1H), 5.51-5.34 (m, 1H), 5.05 (d, J=4.0 Hz, 2H), 4.66-4.57 (m, 1H), 4.46-4.31 (m, 2H), 4.16-4.06 (m, 1H).

Example 414

2-[3-Chloro-6-(4-chloro-2-thienyl)pyrrolo[3,2-b]pyridin-1-yl]-N,N-dimethyl-acetamide

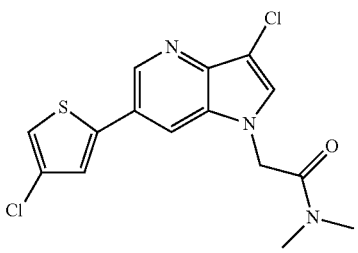 [SMILES: CN(C)C(=O)Cn1cc(Cl)c2ncc(-c3cc(Cl)cs3)cc21]

The title compound was prepared in a manner analogous to Example 146 substituting 2-(4-chlorothiophen-2-yl)-4,4,5,5-tetramethyl-1,3,2-dioxaborolane for (4-fluoro-3-methylphenyl)boronic acid. MS (ESI): mass calcd. for $C_{15}H_{13}Cl_2N_3OS$, 353.0. m/z found, 354.0 [M+H]$^+$. $^1$H NMR (500 MHz, CD$_3$OD) δ 7.84 (d, J=1.9 Hz, 1H), 7.33 (d, J=1.9 Hz, 1H), 6.80 (s, 1H), 6.62 (d, J=1.5 Hz, 1H), 6.52 (d, J=1.5 Hz, 1H), 4.46 (s, 2H), 2.39 (s, 3H), 2.17 (s, 3H).

Example 415

2-[6-(4-Fluoro-3-methyl-phenyl)pyrrolo[3,2-b]pyridin-1-yl]-N-methyl-N-(2,2,2-trifluoroethyl)acetamide

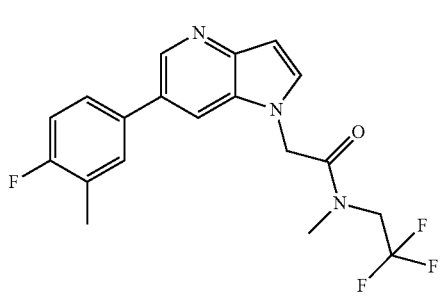 [SMILES: Cc1cc(-c2cnc3ccn(CC(=O)N(C)CC(F)(F)F)c3c2)ccc1F]

The title compound was prepared in a manner analogous to Example 66. MS (ESI): mass calcd. for $C_{19}H_{17}F_4N_3O$, 379.1. m/z found, 380.0 [M+H]$^+$. $^1$H NMR (500 MHz, DMSO-d$_6$) δ 8.61 (d, J=2.0 Hz, 1H), 8.05 (dd, J=2.0, 0.9 Hz, 1H), 7.63 (dd, J=7.6, 2.4 Hz, 1H), 7.57 (d, J=3.3 Hz, 1H), 7.57-7.53 (m, 1H), 7.26 (dd, J=9.7, 8.5 Hz, 1H), 6.59 (dd, J=3.3, 0.9 Hz, 1H), 5.39 (s, 2H), 4.19 (q, J=9.6 Hz, 2H), 3.26 (s, 3H), 2.33 (d, J=1.8 Hz, 3H).

Example 416

2-[3-Chloro-6-(4-methyl-2-thienyl)pyrrolo[3,2-b]pyridin-1-yl]-1-(3-fluoroazetidin-1-yl)ethanone

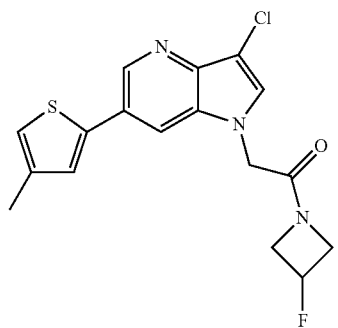 [SMILES: Cc1csc(-c2cnc3c(Cl)cn(CC(=O)N4CC(F)C4)c3c2)c1]

The title compound was prepared in a manner analogous to Example 146 substituting 2-bromo-1-(3-fluoroazetidin-1-yl)ethanone (Intermediate 2) for 2-bromo-N,N-dimethylacetamide and 4,4,5,5-tetramethyl-2-(4-methylthiophen-2-yl)-1,3,2-dioxaborolane for (4-fluoro-3-methylphenyl)boronic acid. MS (ESI): mass calcd. for $C_{17}H_{15}ClFN_3OS$, 363.1. m/z found, 364.0 [M+H]$^+$. $^1$H NMR (500 MHz, DMSO-d$_6$) δ 8.70 (d, J=1.9 Hz, 1H), 8.15 (d, J=1.9 Hz, 1H), 7.77 (s, 1H), 7.43 (d, J=1.4 Hz, 1H), 7.18 (t, J=1.2 Hz, 1H), 5.56-5.40 (m, 1H), 5.06 (d, J=3.2 Hz, 2H), 4.63-4.54 (m, 1H), 4.40-4.31 (m, 1H), 4.31-4.21 (m, 1H), 4.04-3.93 (m, 1H), 2.27 (d, J=1.1 Hz, 3H).

Example 417

2-[3-Chloro-6-(2-thienyl)pyrrolo[3,2-b]pyridin-1-yl]-1-(3-fluoroazetidin-1-yl)ethanone

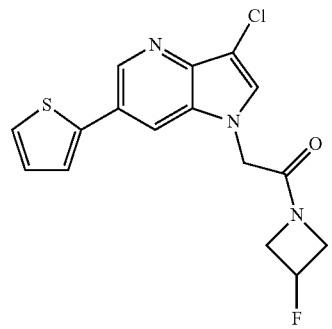 [SMILES: O=C(Cn1cc(Cl)c2ncc(-c3cccs3)cc21)N1CC(F)C1]

The title compound was prepared in a manner analogous to Example 146. MS (ESI): mass calcd. for $C_{16}H_{13}ClFN_3OS$, 349.0. m/z found, 350.0 [M+H]$^+$. $^1$H NMR (500 MHz, DMSO-d$_6$) δ 9.58 (d, J=1.9 Hz, 1H), 9.01 (d, J=1.9 Hz, 1H), 8.61 (s, 1H), 8.47-8.39 (m, 2H), 8.03 (dd, J=5.1, 3.6 Hz, 1H), 6.40-6.21 (m, 1H), 5.90 (d, J=2.9 Hz, 2H), 5.48-5.35 (m, 1H), 5.28-5.14 (m, 1H), 5.14-5.03 (m, 1H), 4.88-4.75 (m, 1H).

Example 418

2-[3-Chloro-6-(4-chloro-2-thienyl)pyrrolo[3,2-b]pyridin-1-yl]-1-(3-fluoroazetidin-1-yl)ethanone

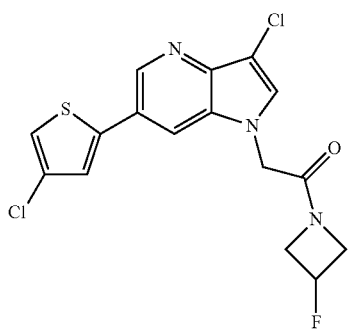 [SMILES: O=C(Cn1cc(Cl)c2ncc(-c3cc(Cl)cs3)cc21)N1CC(F)C1]

The title compound was prepared in a manner analogous to Example 146 substituting 2-bromo-1-(3-fluoroazetidin-1-yl)ethanone (Intermediate 2) for 2-bromo-N,N-dimethylacetamide and 2-(4-chlorothiophen-2-yl)-4,4,5,5-tetramethyl-1,3,2-dioxaborolane for (4-fluoro-3-methylphenyl)boronic acid. MS (ESI): mass calcd. for $C_{16}H_{12}Cl_2FN_3OS$, 383.0. m/z found, 384.0 [M+H]$^+$. $^1$H NMR (500 MHz, DMSO-d$_6$) δ 8.75 (d, J=1.8 Hz, 1H), 8.24 (d, J=1.9 Hz, 1H), 7.82 (s, 1H), 7.67-7.61 (m, 2H), 5.59-5.39 (m, 1H), 5.07 (s, 2H), 4.65-4.53 (m, 1H), 4.41-4.31 (m, 1H), 4.31-4.20 (m, 1H), 4.04-3.92 (m, 1H).

Example 419

N-Ethyl-2-[6-(4-fluorophenyl)pyrrolo[3,2-b]pyridin-1-yl]-N-methyl-acetamide

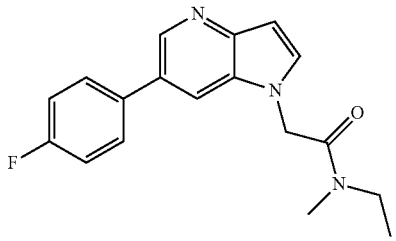 [SMILES: CCN(C)C(=O)Cn1ccc2ncc(-c3ccc(F)cc3)cc21]

The title compound was prepared in a manner analogous to Example 66. MS (ESI): mass calcd. for $C_{18}H_{18}FN_3O$, 311.1. m/z found, 312.1 [M+H]$^+$. Analytical HPLC was obtained on a Agilent 1100 Series using an Inertsil ODS-3 column (3 um, 50×3 mm), mobile phase of 5-99% ACN in 0.05% TFA over 1.6 min and then hold at 99% ACN for 0.4 min, at a flow rate of 2.2 mL/min (Temperature=50° C.). R$_t$=0.82 min at 254 nm.

Example 420

2-[3-Chloro-6-(2-thienyl)pyrrolo[3,2-b]pyridin-1-yl]-N,N-dimethyl-acetamide

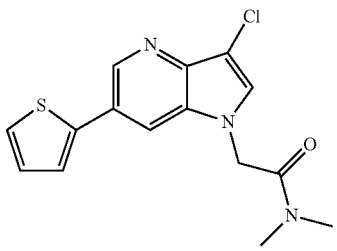

The title compound was prepared in a manner analogous to Example 146. MS (ESI): mass calcd. for $C_{15}H_{14}ClN_3OS$, 319.1. m/z found, 320.0 [M+H]$^+$. $^1$H NMR (500 MHz, CD$_3$OD) δ 8.68 (d, J=1.9 Hz, 1H), 8.11 (d, J=1.8 Hz, 1H), 7.58 (s, 1H), 7.50 (dd, J=3.6, 1.2 Hz, 1H), 7.45 (dd, J=5.2, 1.2 Hz, 1H), 7.15 (dd, J=5.2, 3.6 Hz, 1H), 5.27 (s, 2H), 3.20 (s, 3H), 2.98 (s, 3H).

Example 421

2-[3-Chloro-6-(5-ethyl-2-thienyl)pyrrolo[3,2-b]pyridin-1-yl]-N,N-dimethyl-acetamide

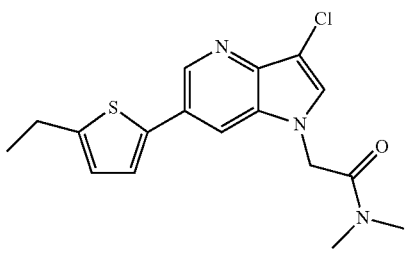

The title compound was prepared in a manner analogous to Example 146. MS (ESI): mass calcd. for $C_{17}H_{18}ClN_3OS$, 347.1. m/z found, 348.0 [M+H]$^+$. $^1$H NMR (500 MHz, CD$_3$OD) δ 8.62 (d, J=1.8 Hz, 1H), 8.03 (d, J=1.9 Hz, 1H), 7.55 (s, 1H), 7.29 (d, J=3.6 Hz, 1H), 6.88-6.81 (m, 1H), 5.25 (s, 2H), 3.20 (s, 3H), 2.98 (s, 3H), 2.93-2.85 (m, 2H), 1.35 (t, J=7.5 Hz, 3H).

Example 422

1-(Azetidin-1-yl)-2-[3-chloro-6-(4-chloro-2-thienyl)pyrrolo[3,2-b]pyridin-1-yl]ethanone

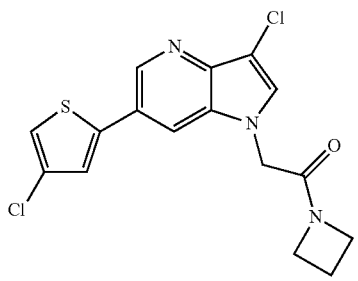

The title compound was prepared in a manner analogous to Example 29 substituting 2-(4-chlorothiophen-2-yl)-4,4,5,5-tetramethyl-1,3,2-dioxaborolane for (3,4-difluorophenyl) boronic acid. MS (ESI): mass calcd. for $C_{16}H_{13}Cl_2N_3OS$, 365.0. m/z found, 366.0 [M+H]$^+$. $^1$H NMR (500 MHz, CD$_3$OD) δ 8.66 (d, J=1.8 Hz, 1H), 8.15 (d, J=1.9 Hz, 1H), 7.65 (s, 1H), 7.45 (d, J=1.5 Hz, 1H), 7.34 (d, J=1.5 Hz, 1H), 5.00 (s, 2H), 4.34 (t, J=7.7 Hz, 2H), 4.08 (t, J=7.8 Hz, 2H), 2.44-2.35 (m, 2H).

Example 423

2-[3-Chloro-6-(5-chloro-2-thienyl)pyrrolo[3,2-b]pyridin-1-yl]-N,N-dimethyl-acetamide

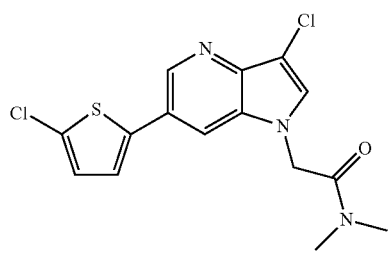

The title compound was prepared in a manner analogous to Example 146. MS (ESI): mass calcd. for $C_{15}H_{13}Cl_2N_3OS$, 353.0. m/z found, 354.0 [M+H]$^+$. $^1$H NMR (500 MHz, CD$_3$OD) δ 8.61 (d, J=1.8 Hz, 1H), 8.07 (d, J=1.9 Hz, 1H), 7.60 (s, 1H), 7.32 (d, J=3.9 Hz, 1H), 7.03 (d, J=4.0 Hz, 1H), 5.27 (s, 2H), 3.20 (s, 3H), 2.98 (s, 3H).

Example 424

2-[3-Chloro-6-(5-ethyl-2-thienyl)pyrrolo[3,2-b]pyridin-1-yl]-1-(3-fluoroazetidin-1-yl)ethanone

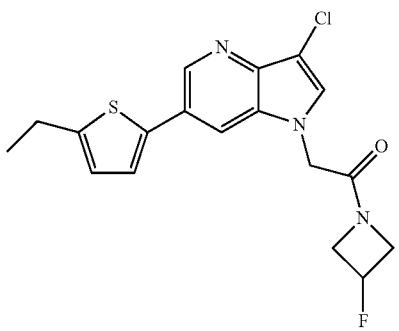 [SMILES: CCc1ccc(-c2cnc3c(Cl)cn(CC(=O)N4CC(F)C4)c3c2)s1]

The title compound was prepared in a manner analogous to Example 146. MS (ESI): mass calcd. for $C_{18}H_{17}ClFN_3OS$, 377.1. m/z found, 378.0 [M+H]$^+$. $^1$H NMR (500 MHz, CD$_3$OD) δ 8.64 (d, J=1.8 Hz, 1H), 8.06 (d, J=1.8 Hz, 1H), 7.58 (s, 1H), 7.30 (d, J=3.6 Hz, 1H), 6.86-6.83 (m, 1H), 5.50-5.33 (m, 1H), 5.04 (d, J=3.5 Hz, 2H), 4.65-4.55 (m, 1H), 4.45-4.29 (m, 2H), 4.18-4.05 (m, 1H), 2.94-2.85 (m, 2H), 1.35 (t, J=7.5 Hz, 3H).

Example 425

2-[6-[2-Fluoro-3-(trifluoromethyl)phenyl]pyrrolo[3,2-b]pyridin-1-yl]-N,N-dimethyl-acetamide

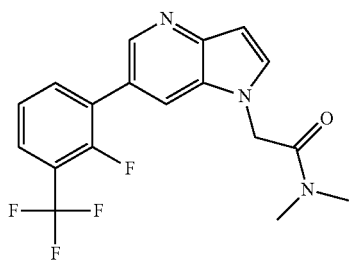 [SMILES: CN(C)C(=O)Cn1ccc2ncc(-c3cccc(C(F)(F)F)c3F)cc21]

The title compound was prepared in a manner analogous to Example 375. MS (ESI): mass calcd. for $C_{18}H_{15}F_4N_3O$, 365.1. m/z found, 366.0 [M+H]$^+$. $^1$H NMR (500 MHz, CDCl$_3$) δ 8.61-8.59 (m, 1H), 7.78-7.74 (m, 1H), 7.73-7.68 (m, 1H), 7.64-7.58 (m, 1H), 7.39 (d, J=3.4 Hz, 1H), 7.34 (t, J=7.7 Hz, 1H), 6.81 (dd, J=3.3, 0.9 Hz, 1H), 4.96 (s, 2H), 3.11 (s, 3H), 3.00 (s, 3H).

Example 426

2-[6-(5-Chloro-4-methyl-2-thienyl)pyrrolo[3,2-b]pyridin-1-yl]-N,N-dimethyl-acetamide

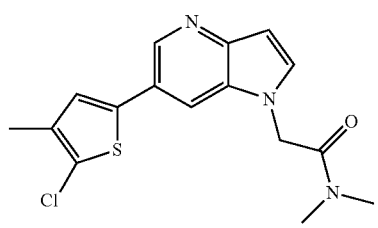

The title compound was prepared in a manner analogous to Example 375 substituting 2-(5-chloro-4-methylthiophen-2-yl)-4,4,5,5-tetramethyl-1,3,2-dioxaborolane for (3,4,5-trifluorophenyl)boronic acid. MS (ESI): mass calcd. for $C_{16}H_{16}ClN_3OS$, 333.1. m/z found, 334.0 [M+H]$^+$. $^1$H NMR (500 MHz, CDCl$_3$) δ 8.64 (d, J=2.0 Hz, 1H), 7.58 (s, 1H), 7.32 (d, J=3.4 Hz, 1H), 7.01 (s, 1H), 6.76 (d, J=3.3 Hz, 1H), 4.92 (s, 2H), 3.11 (s, 3H), 3.01 (s, 3H), 2.22 (s, 3H).

Example 427

2-[6-(2,5-Dimethyl-3-thienyl)pyrrolo[3,2-b]pyridin-1-yl]-N,N-dimethyl-acetamide

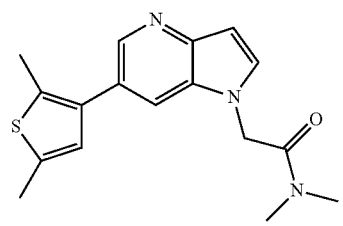 [SMILES: Cc1cc(-c2cnc3ccn(CC(=O)N(C)C)c3c2)c(C)s1]

The title compound was prepared in a manner analogous to Example 375. MS (ESI): mass calcd. for $C_{17}H_{19}N_3OS$, 313.1. m/z found, 314.1 [M+H]$^+$. $^1$H NMR (500 MHz, CDCl$_3$) δ 8.49 (d, J=1.8 Hz, 1H), 7.51 (s, 1H), 7.32 (d, J=3.4 Hz, 1H), 6.76 (dd, J=3.3, 0.9 Hz, 1H), 6.73 (s, 1H), 4.91 (s, 2H), 3.07 (s, 3H), 2.99 (s, 3H), 2.46 (s, 3H), 2.44 (s, 3H).

Example 428

N,N-Dimethyl-2-[6-(2,4,5-trimethyl-3-thienyl)pyrrolo[3,2-b]pyridin-1-yl]acetamide

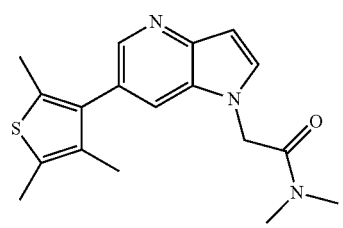 [SMILES: Cc1sc(C)c(-c2cnc3ccn(CC(=O)N(C)C)c3c2)c1C]

The title compound was prepared in a manner analogous to Example 375 substituting 4,4,5,5-tetramethyl-2-(2,4,5-trimethylthiophen-3-yl)-1,3,2-dioxaborolane for (3,4,5-trifluorophenyl)boronic acid. MS (ESI): mass calcd. for $C_{18}H_{21}N_3OS$, 327.1. m/z found, 328.1 [M+H]$^+$. $^1$H NMR (500 MHz, CDCl$_3$) δ 8.32 (d, J=1.7 Hz, 1H), 7.41-7.38 (m, 1H), 7.35 (d, J=3.3 Hz, 1H), 6.78 (dd, J=3.3, 0.9 Hz, 1H), 4.90 (s, 2H), 3.06 (s, 3H), 2.98 (s, 3H), 2.35 (s, 3H), 2.26 (s, 3H), 1.92 (s, 3H).

Example 429

2-[6-(3-Chlorophenyl)pyrrolo[3,2-b]pyridin-1-yl]-N,N-dimethyl-acetamide

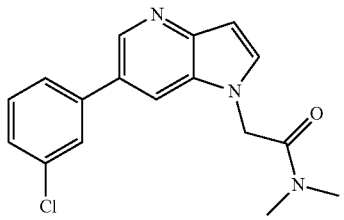 [SMILES: CN(C)C(=O)Cn1ccc2ncc(-c3cccc(Cl)c3)cc21]

The title compound was prepared in a manner analogous to Example 375. MS (ESI): mass calcd. for $C_{17}H_{16}ClN_3O$, 313.1. m/z found, 314.1 [M+H]$^+$. $^1$H NMR (500 MHz, CDCl$_3$) δ 8.67 (s, 1H), 7.66 (dd, J=2.0, 0.9 Hz, 1H), 7.59 (t, J=1.9 Hz, 1H), 7.52-7.46 (m, 1H), 7.38 (t, J=7.8 Hz, 1H), 7.35-7.31 (m, 2H), 6.78 (dd, J=3.4, 0.9 Hz, 1H), 4.94 (s, 2H), 3.10 (s, 3H), 3.00 (s, 3H).

Example 430

2-[6-(4-Fluorophenyl)pyrrolo[3,2-b]pyridin-1-yl]-N,N-dimethyl-acetamide

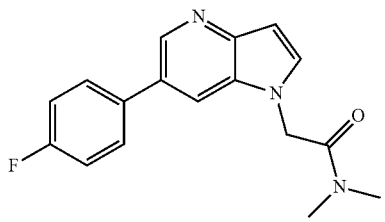

The title compound was prepared in a manner analogous to Example 375. MS (ESI): mass calcd. for $C_{17}H_{16}FN_3O$, 297.1. m/z found, 298.0 [M+H]$^+$. $^1$H NMR (500 MHz, DMSO-d$_6$) δ 8.62 (d, J=2.0 Hz, 1H), 8.10-8.08 (m, 1H), 7.80-7.74 (m, 2H), 7.57 (d, J=3.3 Hz, 1H), 7.36-7.30 (m, 2H), 6.58 (dd, J=3.3, 0.8 Hz, 1H), 5.25 (s, 2H), 3.12 (s, 3H), 2.86 (s, 3H).

Example 431

2-[6-(2-Fluorophenyl)pyrrolo[3,2-b]pyridin-1-yl]-N,N-dimethyl-acetamide

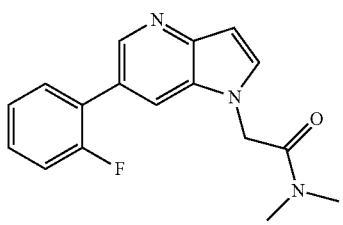 [SMILES: CN(C)C(=O)Cn1ccc2ncc(-c3ccccc3F)cc21]

The title compound was prepared in a manner analogous to Example 375. MS (ESI): mass calcd. for $C_{17}H_{16}FN_3O$, 297.1. m/z found, 298.0 [M+H]$^+$. $^1$H NMR (500 MHz, DMSO-d$_6$) δ 8.49 (t, J=2.0 Hz, 1H), 8.00 (s, 1H), 7.60 (d, J=3.3 Hz, 1H), 7.58 (dd, J=8.1, 1.8 Hz, 1H), 7.47-7.41 (m, 1H), 7.38-7.31 (m, 2H), 6.61 (dd, J=3.3, 0.9 Hz, 1H), 5.25 (s, 2H), 3.10 (s, 3H), 2.85 (s, 3H).

Example 432

2-[6-(2-Fluoro-3-methyl-phenyl)pyrrolo[3,2-b]pyridin-1-yl]-N,N-dimethyl-acetamide

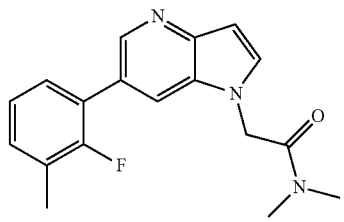 [SMILES: Cc1cccc(-c2cnc3ccn(CC(=O)N(C)C)c3c2)c1F]

The title compound was prepared in a manner analogous to Example 375. MS (ESI): mass calcd. for $C_{18}H_{18}FN_3O$, 311.1. m/z found, 312.1 [M+H]$^+$. $^1$H NMR (500 MHz, DMSO-d$_6$) δ 8.46 (t, J=1.9 Hz, 1H), 7.97 (s, 1H), 7.59 (d, J=3.3 Hz, 1H), 7.40-7.34 (m, 1H), 7.34-7.29 (m, 1H), 7.21 (t, J=7.5 Hz, 1H), 6.60 (dd, J=3.3, 0.9 Hz, 1H), 5.24 (s, 2H), 3.10 (s, 3H), 2.85 (s, 3H), 2.32 (d, J=2.1 Hz, 3H).

Example 433

N,N-Dimethyl-2-(6-phenylpyrrolo[3,2-b]pyridin-1-yl)acetamide

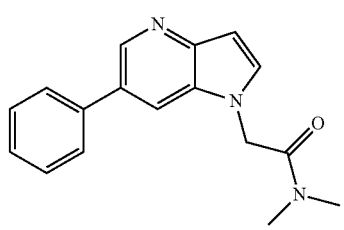 [SMILES: CN(C)C(=O)Cn1ccc2ncc(-c3ccccc3)cc21]

The title compound was prepared in a manner analogous to Example 375. MS (ESI): mass calcd. for $C_{17}H_{17}N_3O$, 279.1. m/z found, 280.1 [M+H]$^+$. $^1$H NMR (500 MHz, DMSO-d$_6$) δ 8.64 (d, J=2.0 Hz, 1H), 8.11-8.09 (m, 1H), 7.76-7.72 (m, 2H), 7.56 (d, J=3.2 Hz, 1H), 7.50 (t, J=7.7 Hz, 2H), 7.40-7.35 (m, 1H), 6.58 (dd, J=3.2, 0.9 Hz, 1H), 5.26 (s, 2H), 3.12 (s, 3H), 2.86 (s, 3H).

Example 434

N,N-Dimethyl-2-[6-(m-tolyl)pyrrolo[3,2-b]pyridin-1-yl]acetamide

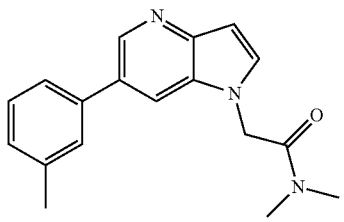 [SMILES: Cc1cccc(-c2cnc3ccn(CC(=O)N(C)C)c3c2)c1]

The title compound was prepared in a manner analogous to Example 375. MS (ESI): mass calcd. for $C_{18}H_{19}N_3O$, 293.2. m/z found, 294.1 [M+H]$^+$. $^1$H NMR (500 MHz, DMSO-d$_6$) δ 8.62 (d, J=2.0 Hz, 1H), 8.07 (dd, J=2.0, 0.9 Hz, 1H), 7.57-7.54 (m, 2H), 7.54-7.50 (m, 1H), 7.38 (t, J=7.6 Hz, 1H), 7.21-7.16 (m, 1H), 6.57 (dd, J=3.3, 0.9 Hz, 1H), 5.26 (s, 2H), 3.12 (s, 3H), 2.86 (s, 3H), 2.40 (s, 3H).

Example 435

N,N-Dimethyl-2-[6-[3-(trifluoromethyl)phenyl]pyrrolo[3,2-b]pyridin-1-yl]acetamide

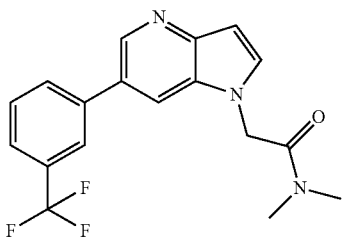 [SMILES: CN(C)C(=O)Cn1ccc2ncc(-c3cccc(C(F)(F)F)c3)cc21]

The title compound was prepared in a manner analogous to Example 375. MS (ESI): mass calcd. for $C_{18}H_{16}F_3N_3O$, 347.1. m/z found, 348.0 [M+H]$^+$. $^1$H NMR (500 MHz, DMSO-d$_6$) δ 8.71 (d, J=2.0 Hz, 1H), 8.22 (dd, J=2.1, 0.9 Hz, 1H), 8.09-8.05 (m, 1H), 8.05 (s, 1H), 7.75-7.71 (m, 2H), 7.61 (d, J=3.2 Hz, 1H), 6.61 (dd, J=3.3, 0.8 Hz, 1H), 5.29 (s, 2H), 3.13 (s, 3H), 2.86 (s, 3H).

Example 436

2-[6-[4-Fluoro-3-(trifluoromethyl)phenyl]pyrrolo[3,2-b]pyridin-1-yl]-N,N-dimethyl-acetamide

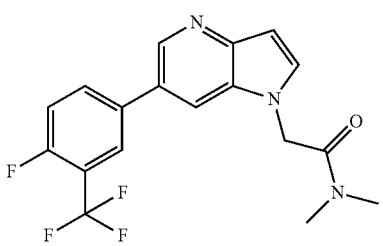 [SMILES: CN(C)C(=O)Cn1ccc2ncc(-c3ccc(F)c(C(F)(F)F)c3)cc21]

The title compound was prepared in a manner analogous to Example 375. MS (ESI): mass calcd. for $C_{18}H_{15}F_4N_3O$, 365.1. m/z found, 366.0 [M+H]$^+$. $^1$H NMR (500 MHz, DMSO-d$_6$) δ 8.68 (d, J=2.0 Hz, 1H), 8.20 (dd, J=2.0, 0.9 Hz, 1H), 8.14-8.08 (m, 1H), 8.06 (dd, J=6.8, 2.4 Hz, 1H), 7.68-7.63 (m, 1H), 7.61 (d, J=3.3 Hz, 1H), 6.61 (dd, J=3.3, 0.8 Hz, 1H), 5.27 (s, 2H), 3.12 (s, 3H), 2.86 (s, 3H).

Example 437

N,N-Dimethyl-2-[6-(2,3,4-trifluorophenyl)pyrrolo[3,2-b]pyridin-1-yl]acetamide

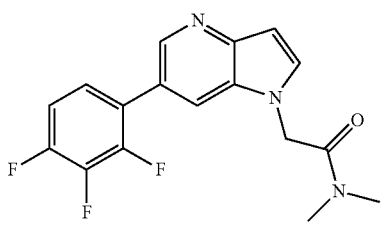

The title compound was prepared in a manner analogous to Example 375. MS (ESI): mass calcd. for $C_{17}H_{14}F_3N_3O$, 333.1. m/z found, 334.0 [M+H]$^+$. $^1$H NMR (500 MHz, DMSO-d$_6$) δ 8.48 (t, J=2.0 Hz, 1H), 8.03 (s, 1H), 7.64 (d, J=3.2 Hz, 1H), 7.49-7.42 (m, 2H), 6.62 (dd, J=3.3, 0.8 Hz, 1H), 5.25 (s, 2H), 3.10 (s, 3H), 2.85 (s, 3H).

Example 438

N,N-Dimethyl-2-[6-[5-(trifluoromethyl)-2-thienyl]pyrrolo[3,2-b]pyridin-1-yl]acetamide

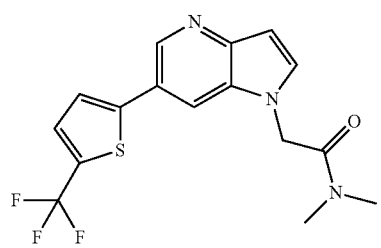 [SMILES: CN(C)C(=O)Cn1ccc2ncc(-c3ccc(C(F)(F)F)s3)cc21]

The title compound was prepared in a manner analogous to Example 375 substituting 4,4,5,5-tetramethyl-2-(5-(trifluoromethyl)thiophen-2-yl)-1,3,2-dioxaborolane for (3,4,5-trifluorophenyl)boronic acid. MS (ESI): mass calcd. for $C_{16}H_{14}F_3N_3OS$, 353.1. m/z found, 354.0 [M+H]$^+$. $^1$H NMR (500 MHz, CD$_3$OD) δ 8.69 (d, J=1.9 Hz, 1H), 8.25 (dd, J=1.9, 0.9 Hz, 1H), 7.65 (d, J=3.3 Hz, 1H), 7.59-7.56 (m, 1H), 7.54-7.51 (m, 1H), 6.71 (dd, J=3.3, 0.9 Hz, 1H), 5.32 (s, 2H), 3.22 (s, 3H), 2.99 (s, 3H).

Example 439

2-[6-(5-Chloro-3-thienyl)pyrrolo[3,2-b]pyridin-1-yl]-N,N-dimethyl-acetamide

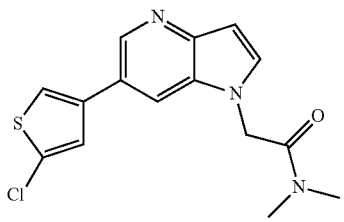 [SMILES: CN(C)C(=O)Cn1ccc2ncc(-c3csc(Cl)c3)cc21]

The title compound was prepared in a manner analogous to Example 375. MS (ESI): mass calcd. for C₁₅H₁₄ClN₃OS, 319.1. m/z found, 320.0 [M+H]⁺. ¹H NMR (500 MHz, CD₃OD) δ 8.60 (d, J=1.7 Hz, 1H), 8.24 (dd, J=1.8, 0.9 Hz, 1H), 7.72 (d, J=3.4 Hz, 1H), 7.43 (d, J=5.8 Hz, 1H), 7.24 (d, J=5.8 Hz, 1H), 6.74 (dd, J=3.3, 0.9 Hz, 1H), 5.33 (s, 2H), 3.19 (s, 3H), 2.97 (s, 3H).

Example 440

2-[6-(2,5-Dichloro-3-thienyl)pyrrolo[3,2-b]pyridin-1-yl]-N,N-dimethyl-acetamide

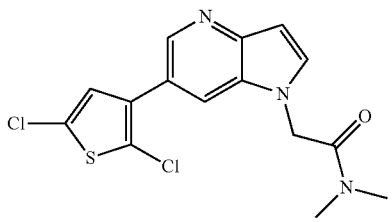 [SMILES: CN(C)C(=O)Cn1ccc2ncc(-c3cc(Cl)sc3Cl)cc21]

The title compound was prepared in a manner analogous to Example 375. MS (ESI): mass calcd. for C₁₅H₁₃Cl₂N₃OS, 353.0. m/z found, 354.0 [M+H]⁺. ¹H NMR (500 MHz, CD₃OD) δ 8.51 (d, J=1.8 Hz, 1H), 7.99-7.96 (m, 1H), 7.58 (d, J=3.3 Hz, 1H), 7.19 (s, 1H), 6.67 (dd, J=3.3, 0.9 Hz, 1H), 5.25 (s, 2H), 3.19 (s, 3H), 2.97 (s, 3H).

Example 441

N,N-Dimethyl-2-[6-[6-(trifluoromethyl)-2-pyridyl]pyrrolo[3,2-b]pyridin-1-yl]acetamide

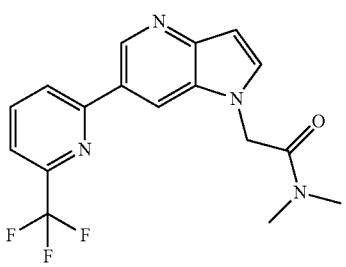 [SMILES: CN(C)C(=O)Cn1ccc2ncc(-c3cccc(C(F)(F)F)n3)cc21]

The title compound was prepared in a manner analogous to Example 375. MS (ESI): mass calcd. for C₁₇H₁₅F₃N₄O, 348.1. m/z found, 349.0 [M+H]⁺. ¹H NMR (500 MHz, CD₃OD) δ 9.08 (d, J=1.9 Hz, 1H), 8.50 (s, 1H), 8.21 (d, J=8.0 Hz, 1H), 8.08 (t, J=7.9 Hz, 1H), 7.72 (d, J=7.7 Hz, 1H), 7.60 (d, J=3.3 Hz, 1H), 6.69 (dd, J=3.3, 0.9 Hz, 1H), 5.30 (s, 2H), 3.22 (s, 3H), 2.99 (s, 3H).

Example 442

N,N-Dimethyl-2-[6-[2-(trifluoromethyl)-4-pyridyl]pyrrolo[3,2-b]pyridin-1-yl]acetamide

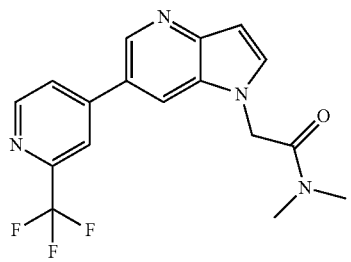 [SMILES: CN(C)C(=O)Cn1ccc2ncc(-c3ccnc(C(F)(F)F)c3)cc21]

The title compound was prepared in a manner analogous to Example 375. MS (ESI): mass calcd. for C₁₇H₁₅F₃N₄O, 348.1. m/z found, 349.1 [M+H]⁺. ¹H NMR (500 MHz, CD₃OD) δ 8.79-8.72 (m, 2H), 8.34 (s, 1H), 8.21 (s, 1H), 8.06-8.00 (m, 1H), 7.66-7.60 (m, 1H), 6.73-6.68 (m, 1H), 5.32 (s, 2H), 3.22 (s, 3H), 2.99 (s, 3H).

Example 443

N,N-Dimethyl-2-[6-[5-(trifluoromethyl)-3-pyridyl]pyrrolo[3,2-b]pyridin-1-yl]acetamide

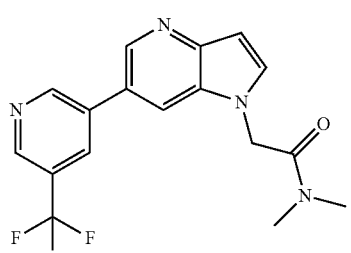

The title compound was prepared in a manner analogous to Example 375. MS (ESI): mass calcd. for C₁₇H₁₅F₃N₄O, 348.1. m/z found, 349.1 [M+H]⁺. ¹H NMR (500 MHz, CD₃OD) δ 9.16 (d, J=2.2 Hz, 1H), 8.90-8.84 (m, 1H), 8.67 (d, J=1.9 Hz, 1H), 8.49-8.46 (m, 1H), 8.25-8.22 (m, 1H), 7.60 (d, J=3.3 Hz, 1H), 6.70 (dd, J=3.3, 0.9 Hz, 1H), 5.30 (s, 2H), 3.21 (s, 3H), 2.98 (s, 3H).

Example 444

2-[6-(2,6-Difluoro-3-methyl-phenyl)pyrrolo[3,2-b]pyridin-1-yl]-N,N-dimethyl-acetamide

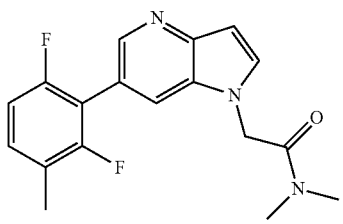 [SMILES: Cc1ccc(F)c(-c2cnc3ccn(CC(=O)N(C)C)c3c2)c1F]

The title compound was prepared in a manner analogous to Example 375. MS (ESI): mass calcd. for $C_{18}H_{17}F_2N_3O$, 329.1. m/z found, 330.0 [M+H]$^+$. $^1$H NMR (500 MHz, CD$_3$OD) δ 8.35-8.33 (m, 1H), 7.93-7.91 (m, 1H), 7.58 (d, J=3.3 Hz, 1H), 7.32-7.25 (m, 1H), 7.03-6.98 (m, 1H), 6.69 (dd, J=3.4, 0.9 Hz, 1H), 5.25 (s, 2H), 3.17 (s, 3H), 2.97 (s, 3H), 2.32-2.29 (m, 3H).

Example 445

2-[6-(2-Fluoro-5-methyl-phenyl)pyrrolo[3,2-b]pyridin-1-yl]-N,N-dimethyl-acetamide

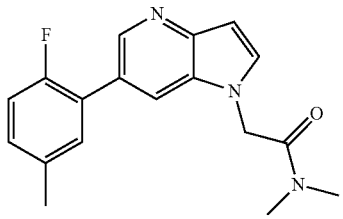 [SMILES: Cc1ccc(F)c(-c2cnc3ccn(CC(=O)N(C)C)c3c2)c1]

The title compound was prepared in a manner analogous to Example 375. MS (ESI): mass calcd. for $C_{18}H_{18}FN_3O$, 311.1. m/z found, 312.1 [M+H]$^+$. $^1$H NMR (500 MHz, DMSO-d$_6$) δ 8.47 (t, J=2.1 Hz, 1H), 7.97 (s, 1H), 7.59 (d, J=3.3 Hz, 1H), 7.40-7.35 (m, 1H), 7.25-7.19 (m, 2H), 6.60 (dd, J=3.2, 0.9 Hz, 1H), 5.25 (s, 2H), 3.10 (s, 3H), 2.85 (s, 3H), 2.36 (s, 3H).

Example 446

1-(Azetidin-1-yl)-2-[6-[3-(difluoromethyl)phenyl]pyrrolo[3,2-b]pyridin-1-yl]ethanone

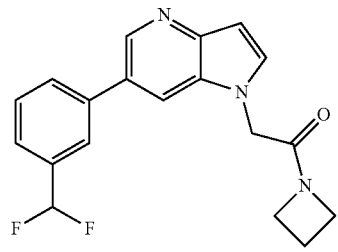 [SMILES: O=C(Cn1ccc2ncc(-c3cccc(C(F)F)c3)cc21)N1CCC1]

The title compound was prepared in a manner analogous to Example 102. MS (ESI): mass calcd. for $C_{19}H_{17}F_2N_3O$, 341.1. m/z found, 342.0 [M+H]$^+$. $^1$H NMR (500 MHz, DMSO-d$_6$) δ 8.69 (d, J=2.0 Hz, 1H), 8.17 (dd, J=2.1, 0.9 Hz, 1H), 7.96-7.91 (m, 2H), 7.69-7.56 (m, 3H), 7.12 (t, J=55.8 Hz, 1H), 6.62 (dd, J=3.3, 0.9 Hz, 1H), 5.03 (s, 2H), 4.21 (t, J=7.6 Hz, 2H), 3.91 (t, J=7.7 Hz, 2H), 2.30-2.22 (m, 2H).

Example 447

2-[6-(2,4-Difluoro-3-methyl-phenyl)pyrrolo[3,2-b]pyridin-1-yl]-N,N-dimethyl-acetamide

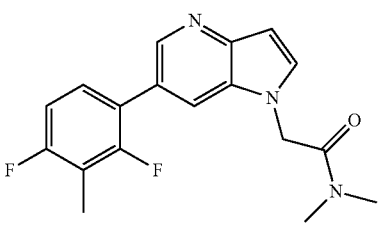 [SMILES: Cc1c(F)ccc(-c2cnc3ccn(CC(=O)N(C)C)c3c2)c1F]

The title compound was prepared in a manner analogous to Example 375. MS (ESI): mass calcd. for $C_{18}H_{17}F_2N_3O$, 329.1. m/z found, 330.0 [M+H]$^+$. $^1$H NMR (400 MHz, DMSO-d$_6$) δ 8.44 (t, J=1.9 Hz, 1H), 7.96 (s, 1H), 7.60 (d, J=3.3 Hz, 1H), 7.48-7.39 (m, 1H), 7.23-7.16 (m, 1H), 6.60 (dd, J=3.3, 0.8 Hz, 1H), 5.24 (s, 2H), 3.10 (s, 3H), 2.85 (s, 3H), 2.26-2.23 (m, 3H).

Example 448

2-[6-(3-Chloro-2-fluoro-phenyl)pyrrolo[3,2-b]pyridin-1-yl]-N,N-dimethyl-acetamide

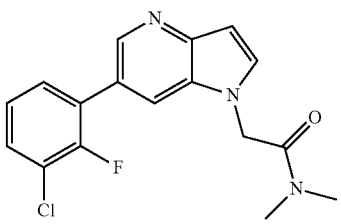

The title compound was prepared in a manner analogous to Example 375. MS (ESI): mass calcd. for $C_{17}H_{15}ClFN_3O$, 331.1. m/z found, 332.0 [M+H]$^+$. $^1$H NMR (400 MHz, DMSO-d$_6$) δ 8.49 (d, J=2.0 Hz, 1H), 8.05 (s, 1H), 7.66-7.59 (m, 2H), 7.60-7.53 (m, 1H), 7.36 (t, J=7.8 Hz, 1H), 6.62 (d, J=2.7 Hz, 1H), 5.26 (s, 2H), 3.10 (s, 3H), 2.85 (s, 3H).

Example 449

2-[6-(3-Ethylphenyl)pyrrolo[3,2-b]pyridin-1-yl]-N,N-dimethyl-acetamide

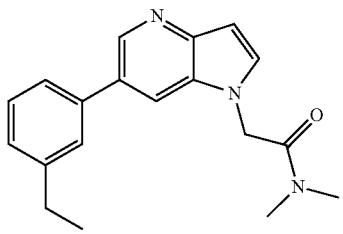 [SMILES: CCc1cccc(-c2cnc3ccn(CC(=O)N(C)C)c3c2)c1]

The title compound was prepared in a manner analogous to Example 375. MS (ESI): mass calcd. for $C_{19}H_{21}N_3O$, 307.2. m/z found, 308.1 [M+H]$^+$. $^1$H NMR (400 MHz, DMSO-d$_6$) δ 8.63 (d, J=2.0 Hz, 1H), 8.09-8.04 (m, 1H), 7.59-7.49 (m, 3H), 7.40 (t, J=7.6 Hz, 1H), 7.22 (d, J=7.5 Hz, 1H), 6.58 (d, J=3.3 Hz, 1H), 5.26 (s, 2H), 3.12 (s, 3H), 2.86 (s, 3H), 2.70 (q, J=7.6 Hz, 2H), 1.25 (t, J=7.6 Hz, 3H).

Example 450

2-[6-(3-Fluorophenyl)pyrrolo[3,2-b]pyridin-1-yl]-N,N-dimethyl-acetamide

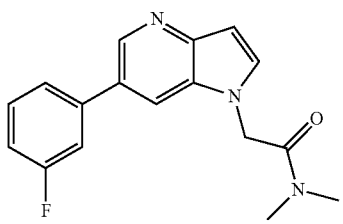

The title compound was prepared in a manner analogous to Example 375. MS (ESI): mass calcd. for $C_{17}H_{16}FN_3O$, 297.1. m/z found, 298.0 [M+H]$^+$. $^1$H NMR (400 MHz, DMSO-d$_6$) δ 8.69 (d, J=2.0 Hz, 1H), 8.18 (dd, J=2.1, 0.9 Hz, 1H), 7.64-7.58 (m, 3H), 7.57-7.50 (m, 1H), 7.23-7.16 (m, 1H), 6.59 (dd, J=3.3, 0.9 Hz, 1H), 5.27 (s, 2H), 3.12 (s, 3H), 2.86 (s, 3H).

Example 451

1-(Azetidin-1-yl)-2-[6-(2-fluoro-3-methyl-phenyl)pyrrolo[3,2-b]pyridin-1-yl]ethanone

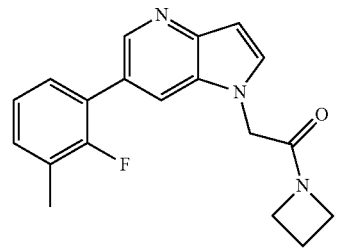 [SMILES: Cc1cccc(-c2cnc3ccn(CC(=O)N4CCC4)c3c2)c1F]

The title compound was prepared in a manner analogous to Example 102. MS (ESI): mass calcd. for $C_{19}H_{18}FN_3O$, 323.1. m/z found, 324.0 [M+H]$^+$. $^1$H NMR (500 MHz, DMSO-d$_6$) δ 8.48 (t, J=1.9 Hz, 1H), 7.98 (s, 1H), 7.62 (d, J=3.2 Hz, 1H), 7.41-7.37 (m, 1H), 7.35-7.29 (m, 1H), 7.22 (t, J=7.5 Hz, 1H), 6.61 (dd, J=3.3, 0.9 Hz, 1H), 4.99 (s, 2H), 4.20 (t, J=7.7 Hz, 2H), 3.90 (t, J=7.7 Hz, 2H), 2.33 (d, J=2.1 Hz, 3H), 2.30-2.21 (m, 2H).

Example 452

1-(Azetidin-1-yl)-2-[6-(2,4-difluoro-3-methyl-phenyl)pyrrolo[3,2-b]pyridin-1-yl]ethanone

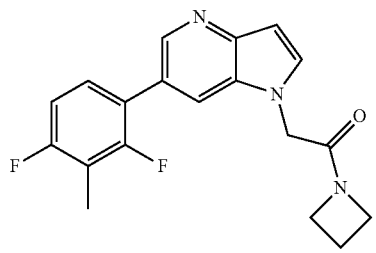 [SMILES: Cc1c(F)ccc(-c2cnc3ccn(CC(=O)N4CCC4)c3c2)c1F]

The title compound was prepared in a manner analogous to Example 102. MS (ESI): mass calcd. for $C_{19}H_{17}F_2N_3O$, 341.1. m/z found, 342.1 [M+H]$^+$. $^1$H NMR (500 MHz, DMSO-d$_6$) δ 8.45 (t, J=2.0 Hz, 1H), 7.96 (s, 1H), 7.63 (d, J=3.3 Hz, 1H), 7.50-7.41 (m, 1H), 7.24-7.17 (m, 1H), 6.62 (dd, J=3.3, 0.9 Hz, 1H), 4.98 (s, 2H), 4.20 (t, J=7.7 Hz, 2H), 3.90 (t, J=7.7 Hz, 2H), 2.31-2.21 (m, 5H).

Example 453

1-(Azetidin-1-yl)-2-[6-(3-chloro-2-fluoro-phenyl)pyrrolo[3,2-b]pyridin-1-yl]ethanone

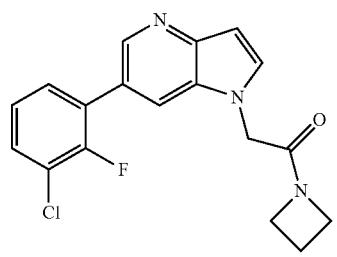 [SMILES: O=C(Cn1ccc2ncc(-c3cccc(Cl)c3F)cc21)N1CCC1]

The title compound was prepared in a manner analogous to Example 102. MS (ESI): mass calcd. for $C_{18}H_{15}ClFN_3O$, 343.1. m/z found, 344.0 [M+H]$^+$. $^1$H NMR (500 MHz, DMSO-d$_6$) δ 8.50 (t, J=1.9 Hz, 1H), 8.06-8.04 (m, 1H), 7.66 (d, J=3.3 Hz, 1H), 7.65-7.61 (m, 1H), 7.60-7.55 (m, 1H), 7.40-7.34 (m, 1H), 6.64 (dd, J=3.3, 0.9 Hz, 1H), 5.00 (s, 2H), 4.21 (t, J=7.6 Hz, 2H), 3.90 (t, J=7.7 Hz, 2H), 2.30-2.22 (m, 2H).

Example 454

1-(3-Fluoroazetidin-1-yl)-2-[6-(2-fluoro-3-methyl-phenyl)pyrrolo[3,2-b]pyridin-1-yl]ethanone

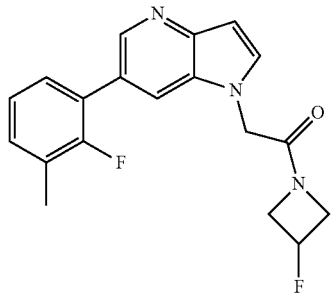 [SMILES: Cc1cccc(-c2cnc3ccn(CC(=O)N4CC(F)C4)c3c2)c1F]

The title compound was prepared in a manner analogous to Example 128. MS (ESI): mass calcd. for $C_{19}H_{17}F_2N_3O$, 341.1. m/z found, 342.1 [M+H]$^+$. $^1$H NMR (500 MHz, DMSO-d$_6$) δ 8.49 (t, J=1.9 Hz, 1H), 8.02 (s, 1H), 7.64 (d, J=3.3 Hz, 1H), 7.42-7.36 (m, 1H), 7.36-7.29 (m, 1H), 7.23 (t, J=7.6 Hz, 1H), 6.63 (dd, J=3.2, 0.9 Hz, 1H), 5.54-5.36 (m, 1H), 5.07 (d, J=4.7 Hz, 2H), 4.59-4.48 (m, 1H), 4.36-4.18 (m, 2H), 4.02-3.90 (m, 1H), 2.33 (d, J=2.2 Hz, 3H).

Example 455

1-(3-Fluoroazetidin-1-yl)-2-[6-(2,3,4-trifluorophenyl)pyrrolo[3,2-b]pyridin-1-yl]ethanone

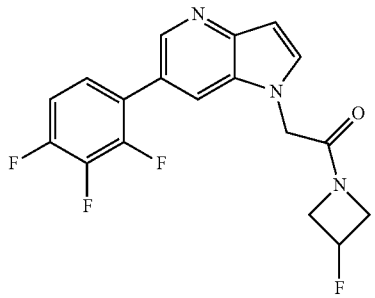

The title compound was prepared in a manner analogous to Example 128. MS (ESI): mass calcd. for $C_{18}H_{13}F_4N_3O$, 363.1. m/z found, 364.0 [M+H]$^+$. $^1$H NMR (500 MHz, DMSO-d$_6$) δ 8.50 (t, J=1.9 Hz, 1H), 8.05 (s, 1H), 7.67 (d, J=3.3 Hz, 1H), 7.51-7.45 (m, 2H), 6.65 (dd, J=3.3, 0.9 Hz, 1H), 5.54-5.36 (m, 1H), 5.07 (d, J=4.6 Hz, 2H), 4.59-4.49 (m, 1H), 4.37-4.18 (m, 2H), 4.02-3.90 (m, 1H).

Example 456

1-(Azetidin-1-yl)-2-[6-(3-chloro-4-fluoro-phenyl)pyrrolo[3,2-b]pyridin-1-yl]ethanone

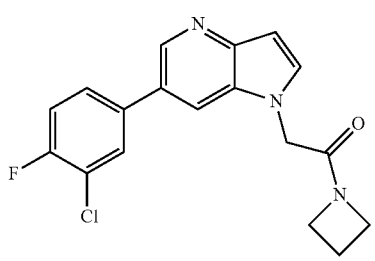 [SMILES: O=C(Cn1ccc2ncc(-c3ccc(F)c(Cl)c3)cc21)N1CCC1]

The title compound was prepared in a manner analogous to Example 102. MS (ESI): mass calcd. for $C_{18}H_{15}ClFN_3O$, 343.1. m/z found, 344.0 [M+H]$^+$. $^1$H NMR (400 MHz, DMSO-d$_6$) δ 8.67 (d, J=1.9 Hz, 1H), 8.18-8.15 (m, 1H), 7.98 (dd, J=7.2, 2.2 Hz, 1H), 7.81-7.76 (m, 1H), 7.62 (d, J=3.4 Hz, 1H), 7.55 (t, J=9.0 Hz, 1H), 6.61 (d, J=3.3 Hz, 1H), 5.01 (s, 2H), 4.21 (t, J=7.6 Hz, 2H), 3.91 (t, J=7.7 Hz, 2H), 2.32-2.21 (m, 2H).

Example 457

1-(3-Fluoroazetidin-1-yl)-2-[6-(2-fluorophenyl)pyrrolo[3,2-b]pyridin-1-yl]ethanone

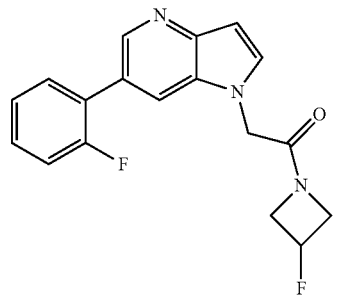 [SMILES: O=C(Cn1ccc2ncc(-c3ccccc3F)cc21)N1CC(F)C1]

The title compound was prepared in a manner analogous to Example 128. MS (ESI): mass calcd. for $C_{18}H_{15}F_2N_3O$, 327.1. m/z found, 328.0 [M+H]$^+$. $^1$H NMR (400 MHz, DMSO-d$_6$) δ 8.52 (t, J=2.0 Hz, 1H), 8.05 (s, 1H), 7.65 (d, J=3.3 Hz, 1H), 7.64-7.56 (m, 1H), 7.49-7.42 (m, 1H), 7.40-7.32 (m, 2H), 6.64 (d, J=3.4 Hz, 1H), 5.55-5.34 (m, 1H), 5.07 (d, J=3.0 Hz, 2H), 4.61-4.46 (m, 1H), 4.37-4.17 (m, 2H), 4.03-3.88 (m, 1H).

Example 458

2-[6-[3-(Difluoromethyl)phenyl]pyrrolo[3,2-b]pyridin-1-yl]-1-(3-fluoroazetidin-1-yl)ethanone

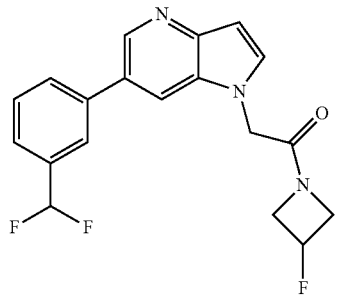 [SMILES: O=C(Cn1ccc2ncc(-c3cccc(C(F)F)c3)cc21)N1CC(F)C1]

The title compound was prepared in a manner analogous to Example 128. MS (ESI): mass calcd. for $C_{19}H_{16}F_3N_3O$, 359.1. m/z found, 360.0 [M+H]$^+$. $^1$H NMR (400 MHz, DMSO-d$_6$) δ 8.69 (d, J=2.0 Hz, 1H), 8.18 (dd, J=1.9, 0.9 Hz, 1H), 7.95-7.91 (m, 2H), 7.69-7.62 (m, 2H), 7.62-7.57 (m, 1H), 7.12 (t, J=55.8 Hz, 1H), 6.63 (dd, J=3.3, 0.8 Hz, 1H), 5.56-5.36 (m, 1H), 5.10 (d, J=2.3 Hz, 2H), 4.60-4.47 (m, 1H), 4.37-4.18 (m, 2H), 4.04-3.91 (m, 1H).

Example 459

N-Ethyl-N-methyl-2-[6-(m-tolyl)pyrrolo[3,2-b]pyridin-1-yl]acetamide

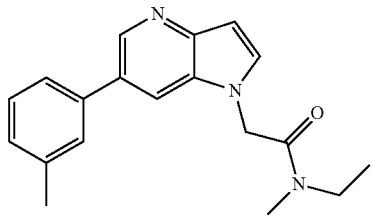 [SMILES: CCN(C)C(=O)Cn1ccc2ncc(-c3cccc(C)c3)cc21]

The title compound was prepared in a manner analogous to Example 66. MS (ESI): mass calcd. for $C_{19}H_{21}N_3O$, 307.2. m/z found, 308.1 $[M+H]^+$.

Example 460

2-[6-(2,4-Difluoro-3-methyl-phenyl)pyrrolo[3,2-b]pyridin-1-yl]-1-(3-fluoroazetidin-1-yl)ethanone

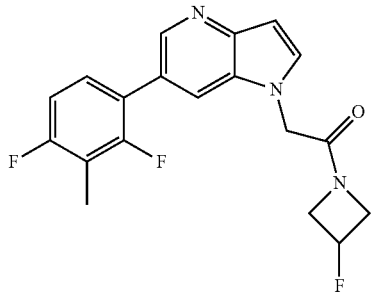 [SMILES: Cc1c(F)ccc(-c2cnc3ccn(CC(=O)N4CC(F)C4)c3c2)c1F]

The title compound was prepared in a manner analogous to Example 128. MS (ESI): mass calcd. for $C_{19}H_{16}F_3N_3O$, 359.1. m/z found, 360.0 $[M+H]^+$. $^1$H NMR (500 MHz, DMSO-$d_6$) δ 8.46 (t, J=1.9 Hz, 1H), 7.99 (s, 1H), 7.64 (d, J=3.3 Hz, 1H), 7.48-7.41 (m, 1H), 7.24-7.18 (m, 1H), 6.63 (dd, J=3.2, 0.9 Hz, 1H), 5.53-5.36 (m, 1H), 5.06 (d, J=4.8 Hz, 2H), 4.58-4.48 (m, 1H), 4.36-4.19 (m, 2H), 4.01-3.91 (m, 1H), 2.25 (s, 3H).

Example 461

2-[6-(3,4-Difluorophenyl)pyrrolo[3,2-b]pyridin-1-yl]-N-ethyl-N-methyl-acetamide

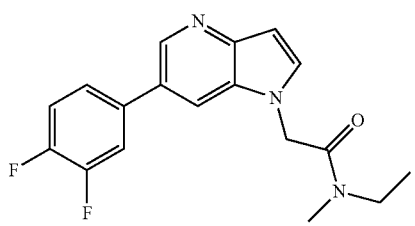 [SMILES: CCN(C)C(=O)Cn1ccc2ncc(-c3ccc(F)c(F)c3)cc21]

The title compound was prepared in a manner analogous to Example 66. MS (ESI): mass calcd. for $C_{18}H_{17}F_2N_3O$, 329.1. m/z found, 330.1 $[M+H]^+$.

Example 462

N-Ethyl-N-methyl-2-[6-(3,4,5-trifluorophenyl)pyrrolo[3,2-b]pyridin-1-yl]acetamide

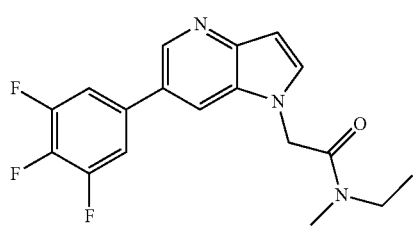 [SMILES: CCN(C)C(=O)Cn1ccc2ncc(-c3cc(F)c(F)c(F)c3)cc21]

The title compound was prepared in a manner analogous to Example 66. MS (ESI): mass calcd. for $C_{18}H_{16}F_3N_3O$, 347.1. m/z found, 348.0 $[M+H]^+$.

Example 463

1-(Azetidin-1-yl)-2-[6-(3-chlorophenyl)pyrrolo[3,2-b]pyridin-1-yl]ethanone

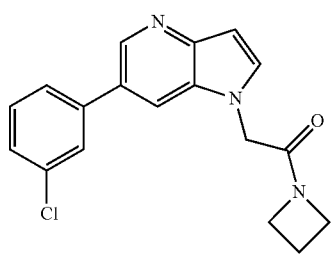 [SMILES: O=C(Cn1ccc2ncc(-c3cccc(Cl)c3)cc21)N1CCC1]

The title compound was prepared in a manner analogous to Example 102. MS (ESI): mass calcd. for $C_{18}H_{16}ClN_3O$, 325.1. m/z found, 326.0 $[M+H]^+$. $^1$H NMR (400 MHz, DMSO-$d_6$) δ 8.68 (d, J=2.0 Hz, 1H), 8.18 (dd, J=2.0, 0.9 Hz, 1H), 7.83 (t, J=1.9 Hz, 1H), 7.77-7.72 (m, 1H), 7.62 (d, J=3.3 Hz, 1H), 7.53 (t, J=7.9 Hz, 1H), 7.47-7.41 (m, 1H), 6.61 (dd, J=3.3, 0.9 Hz, 1H), 5.02 (s, 2H), 4.21 (t, J=7.6 Hz, 2H), 3.91 (t, J=7.7 Hz, 2H), 2.32-2.21 (m, 2H).

Example 464

N-Ethyl-2-[6-[2-fluoro-3-(trifluoromethyl)phenyl]pyrrolo[3,2-b]pyridin-1-yl]-N-methyl-acetamide

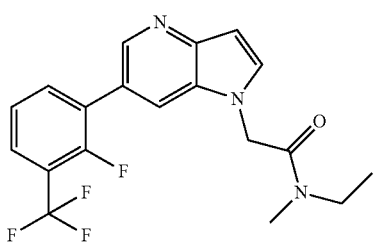 [SMILES: CCN(C)C(=O)Cn1ccc2ncc(-c3cccc(C(F)(F)F)c3F)cc21]

The title compound was prepared in a manner analogous to Example 66. MS (ESI): mass calcd. for $C_{19}H_{17}F_4N_3O$, 379.1. m/z found, 380.0 [M+H]$^+$.

Example 465

2-[6-(3-Chlorophenyl)pyrrolo[3,2-b]pyridin-1-yl]-1-(3-fluoroazetidin-1-yl)ethanone

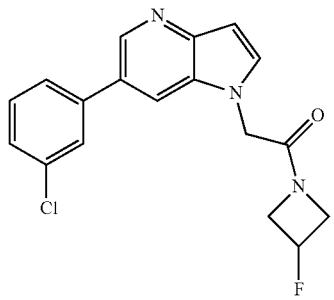

The title compound was prepared in a manner analogous to Example 128. MS (ESI): mass calcd. for $C_{18}H_{15}ClFN_3O$, 343.1. m/z found, 344.0 [M+H]$^+$. $^1$H NMR (500 MHz, DMSO-d$_6$) δ 8.69 (t, J=1.8 Hz, 1H), 8.19 (s, 1H), 7.82 (d, J=1.9 Hz, 1H), 7.74 (d, J=7.4 Hz, 1H), 7.65-7.61 (m, 1H), 7.56-7.50 (m, 1H), 7.46-7.41 (m, 1H), 6.62 (d, J=3.0 Hz, 1H), 5.55-5.37 (m, 1H), 5.09 (s, 2H), 4.60-4.49 (m, 1H), 4.36-4.19 (m, 2H), 4.00-3.91 (m, 1H).

Example 466

2-[6-(3-Chloro-2-fluoro-phenyl)pyrrolo[3,2-b]pyridin-1-yl]-1-(3-fluoroazetidin-1-yl)ethanone

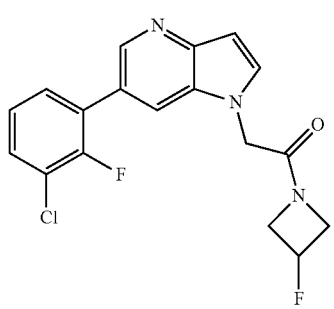 [SMILES: O=C(Cn1ccc2ncc(-c3cccc(Cl)c3F)cc21)N1CC(F)C1]

The title compound was prepared in a manner analogous to Example 128. MS (ESI): mass calcd. for $C_{18}H_{14}ClF_2N_3O$, 361.1. m/z found, 362.0 [M+H]$^+$. $^1$H NMR (500 MHz, DMSO-d$_6$) δ 8.69 (d, J=2.0 Hz, 1H), 8.20 (s, 1H), 7.98 (dd, J=7.1, 2.3 Hz, 1H), 7.81-7.75 (m, 1H), 7.64 (d, J=3.3 Hz, 1H), 7.55 (t, J=8.9 Hz, 1H), 6.63 (dd, J=3.2, 0.9 Hz, 1H), 5.55-5.38 (m, 1H), 5.08 (d, J=2.9 Hz, 2H), 4.60-4.48 (m, 1H), 4.37-4.19 (m, 2H), 4.02-3.90 (m, 1H).

Example 467

2-[6-(3-Chloro-4-fluoro-phenyl)pyrrolo[3,2-b]pyridin-1-yl]-1-(3-fluoroazetidin-1-yl)ethanone

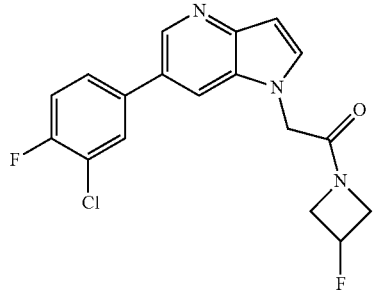 [SMILES: O=C(Cn1ccc2ncc(-c3ccc(F)c(Cl)c3)cc21)N1CC(F)C1]

The title compound was prepared in a manner analogous to Example 128. MS (ESI): mass calcd. for $C_{18}H_{14}ClF_2N_3O$, 361.1. m/z found, 362.0 [M+H]$^+$. $^1$H NMR (500 MHz, DMSO-d$_6$) δ 8.67 (d, J=2.0 Hz, 1H), 8.18 (dd, J=2.2, 0.9 Hz, 1H), 7.98 (dd, J=7.1, 2.3 Hz, 1H), 7.80-7.75 (m, 1H), 7.63 (d, J=3.3 Hz, 1H), 7.55 (t, J=9.0 Hz, 1H), 6.62 (dd, J=3.3, 0.8 Hz, 1H), 5.54-5.37 (m, 1H), 5.08 (d, J=2.8 Hz, 2H), 4.59-4.48 (m, 1H), 4.36-4.19 (m, 2H), 4.01-3.90 (m, 1H).

Example 468

2-[6-(3-Chloro-4-fluoro-phenyl)pyrrolo[3,2-b]pyridin-1-yl]-N,N-dimethyl-acetamide

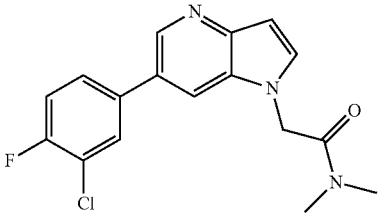

The title compound was prepared in a manner analogous to Example 375. MS (ESI): mass calcd. for $C_{17}H_{15}ClFN_3O$, 331.1. m/z found, 332.0 [M+H]$^+$. $^1$H NMR (500 MHz, CD$_3$OD) δ 8.55 (d, J=1.9 Hz, 1H), 8.06 (dd, J=2.0, 0.9 Hz, 1H), 7.83 (dd, J=7.0, 2.3 Hz, 1H), 7.69-7.62 (m, 1H), 7.55 (d, J=3.3 Hz, 1H), 7.35 (t, J=8.9 Hz, 1H), 6.67 (dd, J=3.3, 0.9 Hz, 1H), 5.28 (s, 2H), 3.21 (s, 3H), 2.98 (s, 3H).

Example 469

2-[6-(2,4-Difluoro-3-methyl-phenyl)pyrrolo[3,2-b]pyridin-1-yl]-N-ethyl-N-methyl-acetamide

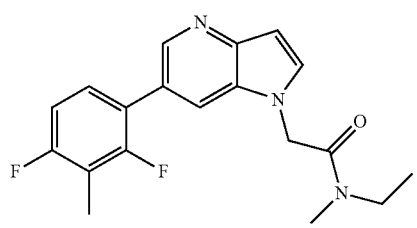 [SMILES: CCN(C)C(=O)Cn1ccc2ncc(-c3ccc(F)c(C)c3F)cc21]

The title compound was prepared in a manner analogous to Example 66. MS (ESI): mass calcd. for $C_{19}H_{19}F_2N_3O$, 343.1. m/z found, 344.1 [M+H]+. 1H NMR (500 MHz, CD3OD) δ 8.37-8.33 (m, 1H), 7.93-7.87 (m, 1H), 7.59 (dd, J=8.5, 3.3 Hz, 1H), 7.33-7.24 (m, 1H), 7.04-6.96 (m, 1H), 6.73-6.66 (m, 1H), 5.26 (s, 0.8H), 5.22 (s, 1.2H), 3.54 (q, J=7.1 Hz, 0.8H), 3.42 (q, J=7.1 Hz, 1.2H), 3.15 (s, 1.8H), 2.93 (s, 1.2H), 2.33-2.27 (m, 3H), 1.26 (t, J=7.2 Hz, 1.2H), 1.11 (t, J=7.2 Hz, 1.8H).

Example 470

N-Ethyl-N-methyl-2-[6-[3-(trifluoromethyl)phenyl]pyrrolo[3,2-b]pyridin-1-yl]acetamide

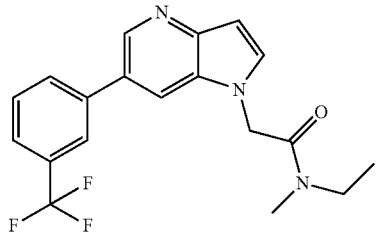 [SMILES: CCN(C)C(=O)Cn1ccc2ncc(-c3cccc(C(F)(F)F)c3)cc21]

The title compound was prepared in a manner analogous to Example 66. MS (ESI): mass calcd. for $C_{19}H_{18}F_3N_3O$, 361.1. m/z found, 362.1 [M+H]+. 1H NMR (500 MHz, CD3OD) δ 8.59-8.57 (m, 1H), 8.11-8.06 (m, 1H), 7.95 (s, 1H), 7.94-7.90 (m, 1H), 7.68-7.63 (m, 2H), 7.56 (dd, J=7.3, 3.3 Hz, 1H), 6.67 (dd, J=3.3, 0.9 Hz, 1H), 5.26 (s, 0.8H), 5.23 (s, 1.2H), 3.54 (q, J=7.1 Hz, 0.8H), 3.43 (q, J=7.1 Hz, 1.2H), 3.16 (s, 1.8H), 2.94 (s, 1.2H), 1.29 (t, J=7.2 Hz, 1.2H), 1.12 (t, J=7.2 Hz, 1.8H).

Example 471

1-(Azetidin-1-yl)-2-[3-fluoro-6-(2-fluorophenyl)pyrrolo[3,2-b]pyridin-1-yl]ethanone

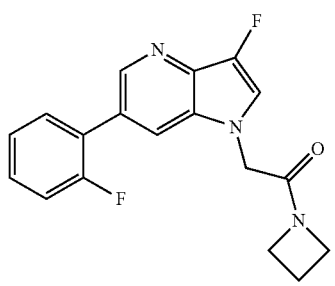 [SMILES: O=C(Cn1cc(F)c2ncc(-c3ccccc3F)cc21)N1CCC1]

The title compound was prepared in a manner analogous to Example 182. MS (ESI): mass calcd. for $C_{18}H_{15}F_2N_3O$, 327.1. m/z found, 328.0 [M+H]+. 1H NMR (400 MHz, DMSO-d6) δ 8.54 (t, J=1.9 Hz, 1H), 8.09 (s, 1H), 7.69 (d, J=2.2 Hz, 1H), 7.64-7.57 (m, 1H), 7.52-7.44 (m, 1H), 7.41-7.33 (m, 2H), 4.94 (s, 2H), 4.22 (t, J=7.6 Hz, 2H), 3.89 (t, J=7.8 Hz, 2H), 2.32-2.21 (m, 2H).

Example 472

1-(Azetidin-1-yl)-2-[3-fluoro-6-(2-fluoro-3-methylphenyl)pyrrolo[3,2-b]pyridin-1-yl]ethanone

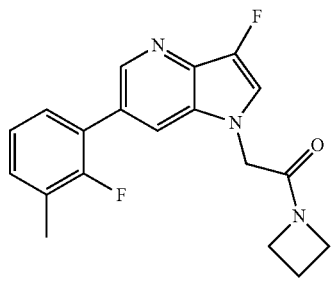 [SMILES: Cc1cccc(-c2cnc3c(F)cn(CC(=O)N4CCC4)c3c2)c1F]

The title compound was prepared in a manner analogous to Example 182. MS (ESI): mass calcd. for $C_{19}H_{17}F_2N_3O$, 341.1. m/z found, 342.0 [M+H]+. 1H NMR (400 MHz, DMSO-d6) δ 8.51 (t, J=1.9 Hz, 1H), 8.06 (s, 1H), 7.68 (d, J=2.2 Hz, 1H), 7.44-7.31 (m, 2H), 7.23 (t, J=7.6 Hz, 1H), 4.94 (s, 2H), 4.21 (t, J=7.7 Hz, 2H), 3.89 (t, J=7.7 Hz, 2H), 2.33 (d, J=2.2 Hz, 3H), 2.30-2.21 (m, 2H).

Example 473

1-(Azetidin-1-yl)-2-[3-fluoro-6-(m-tolyl)pyrrolo[3,2-b]pyridin-1-yl]ethanone

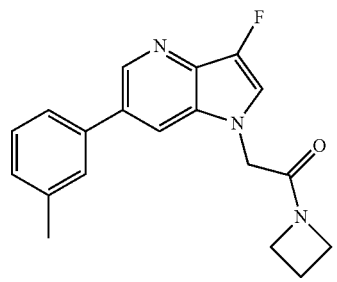

The title compound was prepared in a manner analogous to Example 182. MS (ESI): mass calcd. for $C_{19}H_{18}FN_3O$, 323.1. m/z found, 324.1 [M+H]+. 1H NMR (400 MHz, DMSO-d6) δ 8.68 (d, J=1.8 Hz, 1H), 8.16 (t, J=2.2 Hz, 1H), 7.63 (d, J=2.2 Hz, 1H), 7.60-7.51 (m, 2H), 7.40 (t, J=7.6 Hz, 1H), 7.22 (d, J=7.9 Hz, 1H), 4.96 (s, 2H), 4.22 (t, J=7.7 Hz, 2H), 3.90 (t, J=7.7 Hz, 2H), 2.41 (s, 3H), 2.31-2.22 (m, 2H).

Example 474

1-(Azetidin-1-yl)-2-[6-(3,5-difluorophenyl)-3-fluoro-pyrrolo[3,2-b]pyridin-1-yl]ethanone

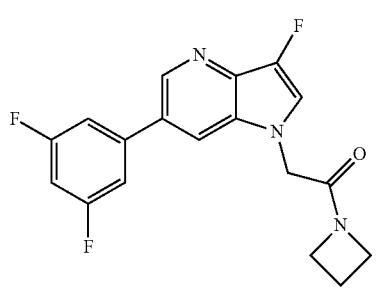 [SMILES: O=C(Cn1cc(F)c2ncc(-c3cc(F)cc(F)c3)cc21)N1CCC1]

The title compound was prepared in a manner analogous to Example 182. MS (ESI): mass calcd. for $C_{18}H_{14}F_3N_3O$, 345.1. m/z found, 346.0 [M+H]⁺. ¹H NMR (400 MHz, DMSO-d₆) δ 8.79 (d, J=2.0 Hz, 1H), 8.32 (t, J=2.3 Hz, 1H), 7.70 (d, J=2.3 Hz, 1H), 7.62-7.56 (m, 2H), 7.30-7.23 (m, 1H), 4.97 (s, 2H), 4.26-4.19 (m, 2H), 3.94-3.87 (m, 2H), 2.35-2.24 (m, 2H).

Example 475

1-(Azetidin-1-yl)-2-[3-fluoro-6-[3-(trifluoromethyl)phenyl]pyrrolo[3,2-b]pyridin-1-yl]ethanone

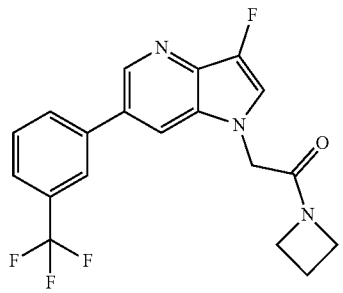 [SMILES: O=C(Cn1cc(F)c2ncc(-c3cccc(C(F)(F)F)c3)cc21)N1CCC1]

The title compound was prepared in a manner analogous to Example 182. MS (ESI): mass calcd. for $C_{19}H_{15}F_4N_3O$, 377.1. m/z found, 378.0 [M+H]⁺. ¹H NMR (400 MHz, DMSO-d₆) δ 8.77 (d, J=1.9 Hz, 1H), 8.31 (t, J=2.2 Hz, 1H), 8.12-8.06 (m, 2H), 7.80-7.74 (m, 2H), 7.70 (d, J=2.2 Hz, 1H), 4.99 (s, 2H), 4.22 (t, J=7.6 Hz, 2H), 3.91 (t, J=7.7 Hz, 2H), 2.33-2.21 (m, 2H).

Example 476

1-(Azetidin-1-yl)-2-[3-fluoro-6-[2-fluoro-3-(trifluoromethyl)phenyl]pyrrolo[3,2-b]pyridin-1-yl]ethanone

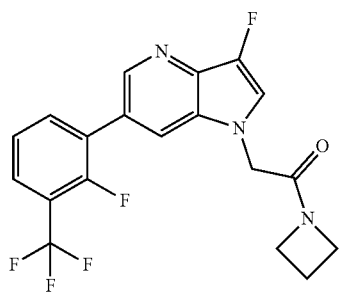 [SMILES: O=C(Cn1cc(F)c2ncc(-c3cccc(C(F)(F)F)c3F)cc21)N1CCC1]

The title compound was prepared in a manner analogous to Example 182. MS (ESI): mass calcd. for $C_{19}H_{14}F_5N_3O$, 395.1. m/z found, 396.0 [M+H]⁺. ¹H NMR (400 MHz, DMSO-d₆) δ 8.56 (t, J=1.8 Hz, 1H), 8.19-8.14 (m, 1H), 7.99-7.93 (m, 1H), 7.89-7.81 (m, 1H), 7.73 (d, J=2.1 Hz, 1H), 7.57 (t, J=7.8 Hz, 1H), 4.96 (s, 2H), 4.22 (t, J=7.7 Hz, 2H), 3.90 (t, J=7.7 Hz, 2H), 2.33-2.21 (m, 2H).

Example 477

1-(Azetidin-1-yl)-2-[3-fluoro-6-(2,3,4-trifluorophenyl)pyrrolo[3,2-b]pyridin-1-yl]ethanone

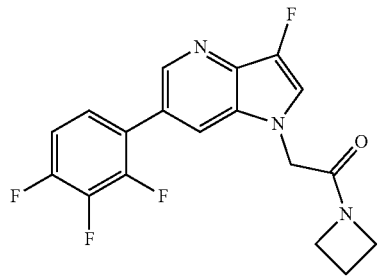 [SMILES: O=C(Cn1cc(F)c2ncc(-c3ccc(F)c(F)c3F)cc21)N1CCC1]

The title compound was prepared in a manner analogous to Example 182. MS (ESI): mass calcd. for $C_{18}H_{13}F_4N_3O$, 363.1. m/z found, 364.0 [M+H]⁺. ¹H NMR (400 MHz, DMSO-d₆) δ 8.54 (t, J=1.8 Hz, 1H), 8.14-8.10 (m, 1H), 7.73 (d, J=2.2 Hz, 1H), 7.52-7.45 (m, 2H), 4.95 (s, 2H), 4.22 (t, J=7.7 Hz, 2H), 3.89 (t, J=7.7 Hz, 2H), 2.30-2.20 (m, 2H).

Example 478

1-(Azetidin-1-yl)-2-[6-(3-chlorophenyl)-3-fluoropyrrolo[3,2-b]pyridin-1-yl]ethanone

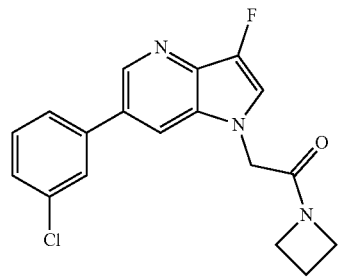 [SMILES: O=C(Cn1cc(F)c2ncc(-c3cccc(Cl)c3)cc21)N1CCC1]

The title compound was prepared in a manner analogous to Example 182. MS (ESI): mass calcd. for $C_{18}H_{15}ClFN_3O$, 343.1. m/z found, 344.0 [M+H]⁺. ¹H NMR (400 MHz, CD₃OD) δ 8.62 (d, J=1.8 Hz, 1H), 8.13 (t, J=2.1 Hz, 1H), 7.75 (t, J=1.9 Hz, 1H), 7.68-7.62 (m, 1H), 7.52-7.45 (m, 2H), 7.44-7.38 (m, 1H), 4.97 (s, 2H), 4.32 (t, J=7.7 Hz, 2H), 4.07 (t, J=7.8 Hz, 2H), 2.44-2.33 (m, 2H).

Example 479

1-(Azetidin-1-yl)-2-[6-(3-chloro-2-fluoro-phenyl)-3-fluoro-pyrrolo[3,2-b]pyridin-1-yl]ethanone

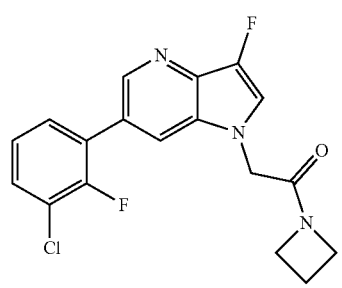 [SMILES: O=C(Cn1cc(F)c2ncc(-c3cccc(Cl)c3F)cc21)N1CCC1]

The title compound was prepared in a manner analogous to Example 182. MS (ESI): mass calcd. for $C_{18}H_{14}ClF_2N_3O$, 361.1. m/z found, 362.0 [M+H]⁺. ¹H NMR (400 MHz, MeOD) δ 8.90-8.81 (m, 2H), 8.09 (d, J=2.2 Hz, 1H), 7.69-7.57 (m, 2H), 7.45-7.31 (m, 1H), 5.20 (s, 2H), 4.41 (t, J=7.7 Hz, 2H), 4.14-4.02 (m, 2H), 2.50-2.36 (m, 2H).

Example 480

1-(Azetidin-1-yl)-2-[6-(2,4-difluoro-3-methyl-phenyl)-3-fluoro-Pyrrolo[3,2-b]pyridin-1-yl]ethanone

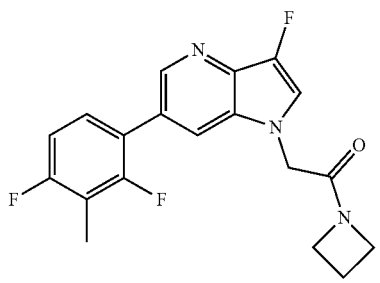

The title compound was prepared in a manner analogous to Example 182. MS (ESI): mass calcd. for $C_{19}H_{18}F_3N_3O$, 359.1. m/z found, 360.0 [M+H]⁺. ¹H NMR (400 MHz, CD₃OD) δ 8.94-8.90 (m, 1H), 8.87 (s, 1H), 8.15 (d, J=2.2 Hz, 1H), 7.63-7.51 (m, 1H), 7.20-7.12 (m, 1H), 5.25 (s, 2H), 4.44 (t, J=7.7 Hz, 2H), 4.09 (t, J=7.8 Hz, 2H), 2.49-2.36 (m, 2H), 2.34-2.27 (m, 3H).

Example 481

1-(Azetidin-1-yl)-2-[6-(3-chloro-4-fluoro-phenyl)-3-fluoro-pyrrolo[3,2-b]pyridin-1-yl]ethanone

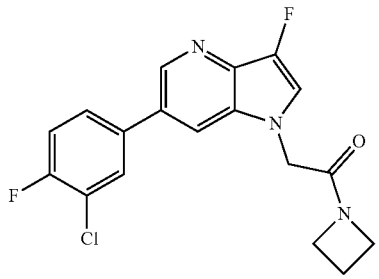 [SMILES: O=C(Cn1cc(F)c2ncc(-c3ccc(F)c(Cl)c3)cc21)N1CCC1]

The title compound was prepared in a manner analogous to Example 182. MS (ESI): mass calcd. for $C_{18}H_{14}ClF_2N_3O$, 361.1. m/z found, 362.0 [M+H]⁺. ¹H NMR (400 MHz, CD₃OD) δ 8.58 (d, J=1.7 Hz, 1H), 8.14 (t, J=2.1 Hz, 1H), 7.81 (dd, J=7.0, 2.3 Hz, 1H), 7.66-7.59 (m, 1H), 7.53 (d, J=2.3 Hz, 1H), 7.34 (t, J=8.8 Hz, 1H), 4.95 (s, 2H), 4.32 (t, J=7.8 Hz, 2H), 4.06 (t, J=7.7 Hz, 2H), 2.44-2.32 (m, 2H).

Example 482

1-(3-Fluoroazetidin-1-yl)-2-(3-fluoro-6-phenyl-pyrrolo[3,2-b]pyridin-1-yl)ethanone

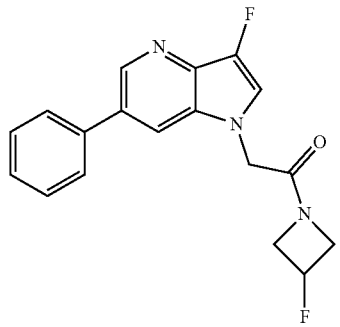 [SMILES: O=C(Cn1cc(F)c2ncc(-c3ccccc3)cc21)N1CC(F)C1]

The title compound was prepared in a manner analogous to Example 182. MS (ESI): mass calcd. for $C_{18}H_{16}F_2N_3O$, 327.1. m/z found, 328.0 [M+H]⁺. ¹H NMR (500 MHz, DMSO-d₆) δ 8.70 (d, J=1.8 Hz, 1H), 8.19 (t, J=2.2 Hz, 1H), 7.78-7.74 (m, 2H), 7.65 (d, J=2.2 Hz, 1H), 7.55-7.49 (m, 2H), 7.44-7.38 (m, 1H), 5.55-5.37 (m, 1H), 5.03 (d, J=2.7 Hz, 2H), 4.61-4.50 (m, 1H), 4.38-4.18 (m, 2H), 4.02-3.91 (m, 1H).

Example 483

1-(3-Fluoroazetidin-1-yl)-2-[3-fluoro-6-(2-fluoro-3-methyl-phenyl)pyrrolo[3,2-b]pyridin-1-yl]ethanone

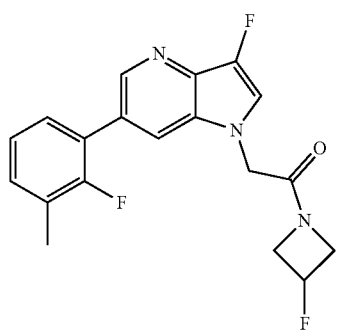 [SMILES: Cc1cccc(-c2cnc3c(F)cn(CC(=O)N4CC(F)C4)c3c2)c1F]

The title compound was prepared in a manner analogous to Example 182. MS (ESI): mass calcd. for $C_{19}H_{18}F_3N_3O$, 359.1. m/z found, 360.0 [M+H]⁺. ¹H NMR (500 MHz, CD₃OD) δ 8.52 (t, J=1.8 Hz, 1H), 8.03 (s, 1H), 7.51 (d, J=2.3 Hz, 1H), 7.37 (td, J=7.5, 1.7 Hz, 1H), 7.32-7.26 (m, 1H), 7.19 (t, J=7.6 Hz, 1H), 5.47-5.30 (m, 1H), 5.00 (d, J=2.1 Hz, 2H), 4.61-4.50 (m, 1H), 4.41-4.28 (m, 2H), 4.15-4.04 (m, 1H), 2.36 (d, J=2.3 Hz, 3H).

Example 484

1-(3-Fluoroazetidin-1-yl)-2-[3-fluoro-6-[3-(trifluoromethyl)phenyl]pyrrolo[3,2-b]pyridin-1-yl]ethanone

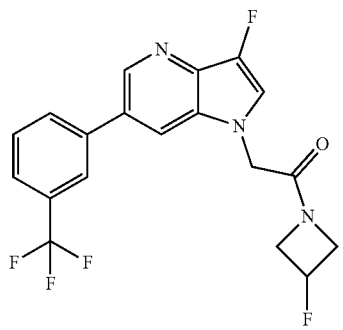 [SMILES: O=C(Cn1cc(F)c2ncc(-c3cccc(C(F)(F)F)c3)cc21)N1CC(F)C1]

The title compound was prepared in a manner analogous to Example 182. MS (ESI): mass calcd. for $C_{19}H_{14}F_6N_3O$, 395.1. m/z found, 396.0 [M+H]$^+$. $^1$H NMR (500 MHz, DMSO-d$_6$) δ 8.77 (d, J=1.9 Hz, 1H), 8.31 (t, J=2.1 Hz, 1H), 8.12-8.05 (m, 2H), 7.80-7.72 (m, 2H), 7.70 (d, J=2.1 Hz, 1H), 5.55-5.37 (m, 1H), 5.09-5.00 (m, 2H), 4.62-4.50 (m, 1H), 4.40-4.17 (m, 2H), 4.04-3.91 (m, 1H).

Example 485

1-(3-Fluoroazetidin-1-yl)-2-[3-fluoro-6-[2-fluoro-3-(trifluoromethyl)phenyl]pyrrolo[3,2-b]pyridin-1-yl]ethanone

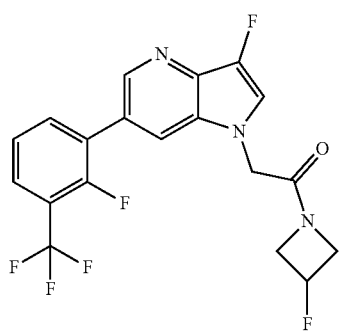 [SMILES: O=C(Cn1cc(F)c2ncc(-c3cccc(C(F)(F)F)c3F)cc21)N1CC(F)C1]

The title compound was prepared in a manner analogous to Example 182. MS (ESI): mass calcd. for $C_{19}H_{13}F_6N_3O$, 413.1. m/z found, 414.0 [M+H]$^+$. $^1$H NMR (500 MHz, DMSO-d$_6$) δ 8.56 (s, 1H), 8.18 (s, 1H), 7.95 (t, J=7.3 Hz, 1H), 7.85 (t, J=7.3 Hz, 1H), 7.74 (s, 1H), 7.63-7.52 (m, 1H), 5.57-5.35 (m, 1H), 5.03 (s, 2H), 4.64-4.48 (m, 1H), 4.41-4.16 (m, 2H), 4.03-3.89 (m, 1H).

Example 486

1-(3-Fluoroazetidin-1-yl)-2-[3-fluoro-6-(2,3,4-trifluorophenyl)pyrrolo[3,2-b]pyridin-1-yl]ethanone

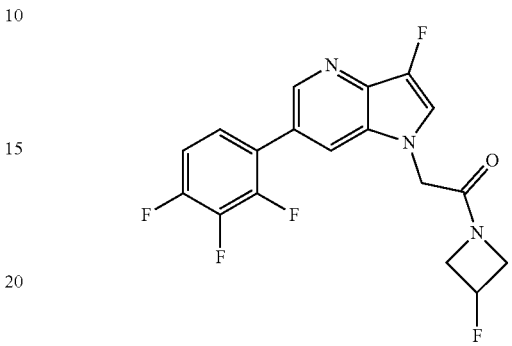

The title compound was prepared in a manner analogous to Example 182. MS (ESI): mass calcd. for $C_{16}H_{12}F_6N_3O$, 381.1. m/z found, 382.0 [M+H]$^+$. $^1$H NMR (500 MHz, DMSO-d$_6$) δ 8.54 (t, J=1.8 Hz, 1H), 8.13 (s, 1H), 7.73 (d, J=2.2 Hz, 1H), 7.53-7.44 (m, 2H), 5.55-5.35 (m, 1H), 5.01 (d, J=3.9 Hz, 2H), 4.62-4.49 (m, 1H), 4.39-4.17 (m, 2H), 4.01-3.90 (m, 1H).

Example 487

2-[6-(3,5-Difluorophenyl)-3-fluoro-pyrrolo[3,2-b]pyridin-1-yl]-1-(3-fluoroazetidin-1-yl)ethanone

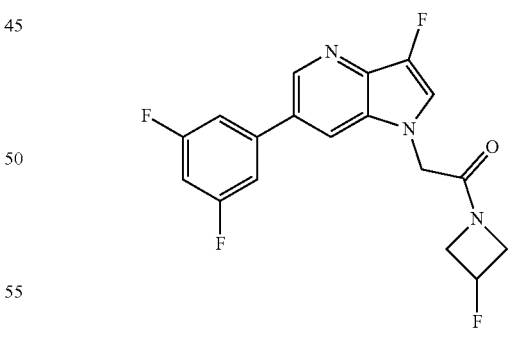

The title compound was prepared in a manner analogous to Example 182. MS (ESI): mass calcd. for $C_{18}H_{13}F_4N_3O$, 363.1. m/z found, 364.0 [M+H]$^+$. $^1$H NMR (500 MHz, DMSO-d$_6$) δ 8.79 (d, J=1.9 Hz, 1H), 8.32 (t, J=2.2 Hz, 1H), 7.71 (d, J=2.2 Hz, 1H), 7.61-7.54 (m, 2H), 7.30-7.24 (m, 1H), 5.56-5.38 (m, 1H), 5.03 (d, J=1.8 Hz, 2H), 4.61-4.49 (m, 1H), 4.39-4.18 (m, 2H), 4.03-3.89 (m, 1H).

Example 488

2-[6-(2,4-Difluoro-3-methyl-phenyl)-3-fluoro-pyrrolo[3,2-b]pyridin-1-yl]-1-(3-fluoroazetidin-1-yl)ethanone

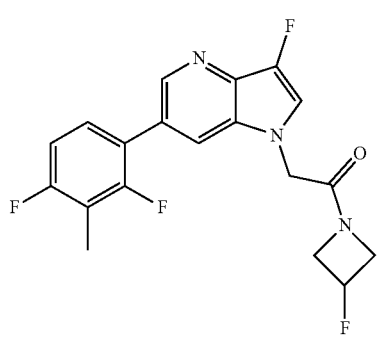 [SMILES: Cc1c(F)ccc(-c2cnc3c(F)cn(CC(=O)N4CC(F)C4)c3c2)c1F]

The title compound was prepared in a manner analogous to Example 182. MS (ESI): mass calcd. for $C_{19}H_{18}F_4N_3O$, 377.1. m/z found, 378.0 [M+H]$^+$. $^1$H NMR (500 MHz, DMSO-d$_6$) δ 8.52-8.45 (m, 1H), 8.06 (s, 1H), 7.69 (d, J=2.1 Hz, 1H), 7.51-7.41 (m, 1H), 7.22 (t, J=8.7 Hz, 1H), 5.55-5.36 (m, 1H), 5.00 (d, J=4.0 Hz, 2H), 4.61-4.47 (m, 1H), 4.37-4.17 (m, 2H), 4.01-3.87 (m, 1H), 2.25 (s, 3H).

Example 489

2-[6-(3-Chlorophenyl)-3-fluoro-pyrrolo[3,2-b]pyridin-1-yl]-1-(3-fluoroazetidin-1-yl)ethanone

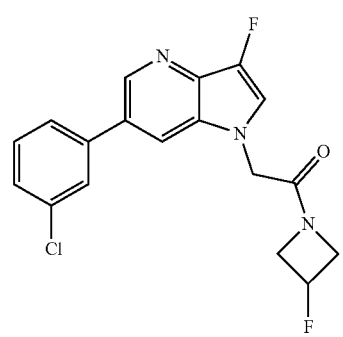 [SMILES: O=C(Cn1cc(F)c2ncc(-c3cccc(Cl)c3)cc21)N1CC(F)C1]

The title compound was prepared in a manner analogous to Example 182. MS (ESI): mass calcd. for $C_{16}H_{14}ClF_2N_3O$, 361.1. m/z found, 362.0 [M+H]$^+$. $^1$H NMR (500 MHz, DMSO-d$_6$) δ 8.73 (d, J=1.9 Hz, 1H), 8.26 (t, J=2.2 Hz, 1H), 7.84 (t, J=1.9 Hz, 1H), 7.78-7.72 (m, 1H), 7.68 (d, J=2.2 Hz, 1H), 7.54 (t, J=7.9 Hz, 1H), 7.50-7.44 (m, 1H), 5.55-5.38 (m, 1H), 5.03 (d, J=1.9 Hz, 2H), 4.61-4.50 (m, 1H), 4.37-4.20 (m, 2H), 4.02-3.92 (m, 1H).

Example 490

2-[6-(3-Chloro-2-fluoro-phenyl)-3-fluoro-pyrrolo[3,2-b]pyridin-1-yl]-1-(3-fluoroazetidin-1-yl)ethanone

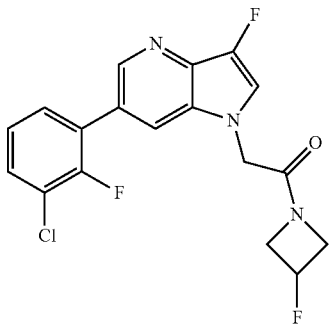 [SMILES: O=C(Cn1cc(F)c2ncc(-c3cccc(Cl)c3F)cc21)N1CC(F)C1]

The title compound was prepared in a manner analogous to Example 182. MS (ESI): mass calcd. for $C_{16}H_{13}ClF_3N_3O$, 379.1. m/z found, 380.0 [M+H]$^+$. $^1$H NMR (500 MHz, DMSO-d$_6$) δ 8.55 (t, J=1.8 Hz, 1H), 8.15 (s, 1H), 7.72 (d, J=2.2 Hz, 1H), 7.68-7.63 (m, 1H), 7.61-7.56 (m, 1H), 7.41-7.34 (m, 1H), 5.55-5.36 (m, 1H), 5.02 (d, J=3.5 Hz, 2H), 4.61-4.50 (m, 1H), 4.39-4.17 (m, 2H), 4.02-3.88 (m, 1H).

Example 491

2-[6-(3-Ethylphenyl)-3-fluoro-pyrrolo[3,2-b]pyridin-1-yl]-1-(3-fluoroazetidin-1-yl)ethanone

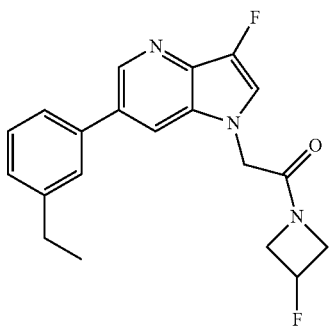 [SMILES: CCc1cccc(-c2cnc3c(F)cn(CC(=O)N4CC(F)C4)c3c2)c1]

The title compound was prepared in a manner analogous to Example 182. MS (ESI): mass calcd. for $C_{20}H_{19}F_2N_3O$, 355.1. m/z found, 356.1 [M+H]$^+$. $^1$H NMR (500 MHz, DMSO-d$_6$) δ 8.69 (d, J=1.8 Hz, 1H), 8.16 (t, J=2.2 Hz, 1H), 7.64 (d, J=2.1 Hz, 1H), 7.59-7.57 (m, 1H), 7.57-7.53 (m, 1H), 7.42 (t, J=7.6 Hz, 1H), 7.25 (d, J=7.6 Hz, 1H), 5.55-5.37 (m, 1H), 5.02 (d, J=3.0 Hz, 2H), 4.61-4.49 (m, 1H), 4.38-4.17 (m, 2H), 4.02-3.90 (m, 1H), 2.71 (q, J=7.6 Hz, 2H), 1.25 (t, J=7.6 Hz, 3H).

Example 492

1-(3-Fluoroazetidin-1-yl)-2-[3-fluoro-6-(3-fluorophenyl)pyrrolo[3,2-b]pyridin-1-yl]ethanone

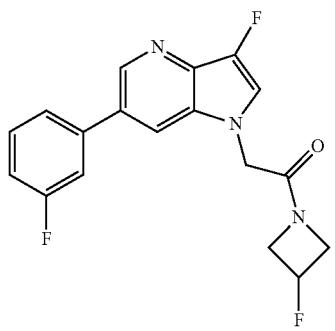 [SMILES: O=C(Cn1cc(F)c2ncc(-c3cccc(F)c3)cc21)N1CC(F)C1]

The title compound was prepared in a manner analogous to Example 182. MS (ESI): mass calcd. for $C_{16}H_{14}F_3N_3O$, 345.1. m/z found, 346.1 [M+H]$^+$. $^1$H NMR (500 MHz, DMSO-d$_6$) δ 8.75 (d, J=1.9 Hz, 1H), 8.26 (t, J=2.2 Hz, 1H), 7.68 (d, J=2.2 Hz, 1H), 7.66-7.60 (m, 2H), 7.59-7.52 (m, 1H), 7.28-7.19 (m, 1H), 5.56-5.38 (m, 1H), 5.03 (d, J=2.2 Hz, 2H), 4.62-4.49 (m, 1H), 4.39-4.18 (m, 2H), 4.02-3.92 (m, 1H).

Example 493

2-[3-Fluoro-6-(2-fluorophenyl)pyrrolo[3,2-b]pyridin-1-yl]-N,N-dimethyl-acetamide

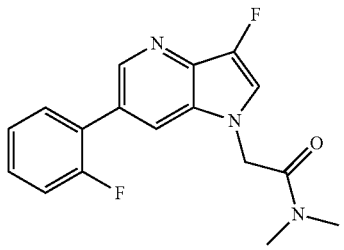 [SMILES: CN(C)C(=O)Cn1cc(F)c2ncc(-c3ccccc3F)cc21]

The title compound was prepared in a manner analogous to Example 92. MS (ESI): mass calcd. for $C_{17}H_{15}F_2N_3O$, 315.1. m/z found, 316.0 [M+H]$^+$. $^1$H NMR (500 MHz, DMSO-d$_6$) δ 8.55-8.50 (m, 1H), 8.09 (s, 1H), 7.65 (d, J=2.1 Hz, 1H), 7.63-7.56 (m, 1H), 7.51-7.44 (m, 1H), 7.40-7.33 (m, 2H), 5.20 (s, 2H), 3.08 (s, 3H), 2.84 (s, 3H).

Example 494

2-[3-Fluoro-6-(2-fluoro-3-methyl-phenyl)pyrrolo[3,2-b]pyridin-1-yl]-N,N-dimethyl-acetamide

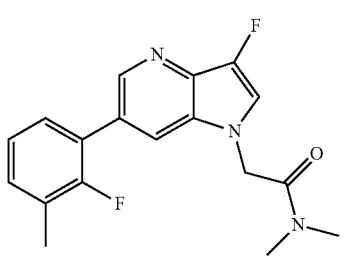

The title compound was prepared in a manner analogous to Example 92. MS (ESI): mass calcd. for $C_{16}H_{17}F_2N_3O$, 329.1. m/z found, 330.0 [M+H]$^+$. $^1$H NMR (500 MHz, DMSO-d$_6$) δ 8.50 (t, J=1.9 Hz, 1H), 8.09-8.02 (m, 1H), 7.64 (d, J=2.1 Hz, 1H), 7.42-7.36 (m, 1H), 7.34 (t, J=7.4 Hz, 1H), 7.23 (t, J=7.6 Hz, 1H), 5.20 (s, 2H), 3.08 (s, 3H), 2.84 (s, 3H), 2.32 (d, J=2.1 Hz, 3H).

Example 495

2-(3-Fluoro-6-phenyl-pyrrolo[3,2-b]pyridin-1-yl)-N,N-dimethyl-acetamide

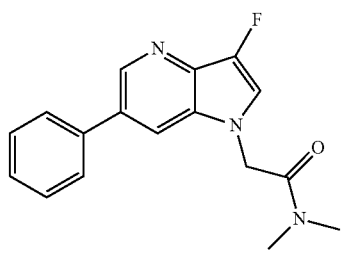 [SMILES: CN(C)C(=O)Cn1cc(F)c2ncc(-c3ccccc3)cc21]

The title compound was prepared in a manner analogous to Example 92. MS (ESI): mass calcd. for $C_{17}H_{16}FN_3O$, 297.1. m/z found, 298.1 [M+H]$^+$. $^1$H NMR (500 MHz, DMSO-d$_6$) δ 8.69 (d, J=1.8 Hz, 1H), 8.19 (t, J=2.2 Hz, 1H), 7.78-7.72 (m, 2H), 7.61 (d, J=2.2 Hz, 1H), 7.54-7.48 (m, 2H), 7.43-7.37 (m, 1H), 5.21 (s, 2H), 3.10 (s, 3H), 2.85 (s, 3H).

Example 496

2-[3-Fluoro-6-(m-tolyl)pyrrolo[3,2-b]pyridin-1-yl]-N,N-dimethyl-acetamide

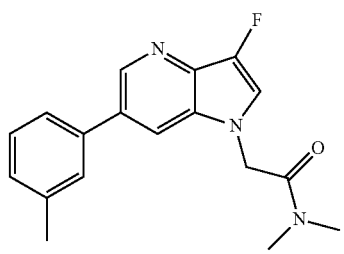 [SMILES: Cc1cccc(-c2cnc3c(F)cn(CC(=O)N(C)C)c3c2)c1]

The title compound was prepared in a manner analogous to Example 92. MS (ESI): mass calcd. for $C_{16}H_{16}FN_3O$, 311.1. m/z found, 312.1 [M+H]$^+$. $^1$H NMR (500 MHz, CD$_3$OD) δ 8.59 (d, J=1.8 Hz, 1H), 8.05 (t, J=2.1 Hz, 1H), 7.53-7.50 (m, 1H), 7.49-7.45 (m, 1H), 7.43 (d, J=2.3 Hz, 1H), 7.36 (t, J=7.7 Hz, 1H), 7.24-7.19 (m, 1H), 5.22 (s, 2H), 3.19 (s, 3H), 2.98 (s, 3H), 2.43 (s, 3H).

Example 497

1-(Azetidin-1-yl)-2-(3-fluoro-6-phenyl-pyrrolo[3,2-b]pyridin-1-yl)ethanone

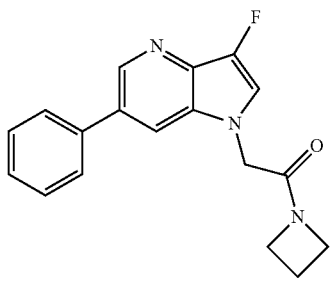 [SMILES: O=C(Cn1cc(F)c2ncc(-c3ccccc3)cc21)N1CCC1]

The title compound was prepared in a manner analogous to Example 182. MS (ESI): mass calcd. for $C_{18}H_{16}FN_3O$, 309.1. m/z found, 310.0 [M+H]$^+$. $^1$H NMR (400 MHz, DMSO-d$_6$) δ 8.70 (d, J=1.9 Hz, 1H), 8.18 (t, J=2.2 Hz, 1H), 7.81-7.72 (m, 2H), 7.65 (d, J=2.3 Hz, 1H), 7.56-7.48 (m, 2H), 7.45-7.38 (m, 1H), 4.96 (s, 2H), 4.22 (t, J=7.7 Hz, 2H), 3.90 (t, J=7.7 Hz, 2H), 2.34-2.22 (m, 2H).

Example 498

1-(Azetidin-1-yl)-2-[6-(3-ethylphenyl)-3-fluoro-pyrrolo[3,2-b]pyridin-1-yl]ethanone

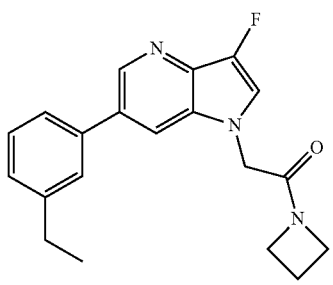 [SMILES: CCc1cccc(-c2cnc3c(F)cn(CC(=O)N4CCC4)c3c2)c1]

The title compound was prepared in a manner analogous to Example 182. MS (ESI): mass calcd. for $C_{20}H_{20}FN_3O$, 337.2. m/z found, 338.1 [M+H]$^+$. $^1$H NMR (400 MHz, CD$_3$OD) δ 7.80 (d, J=1.7 Hz, 1H), 7.26 (t, J=2.1 Hz, 1H), 6.74-6.67 (m, 2H), 6.66 (d, J=2.3 Hz, 1H), 6.59 (t, J=7.6 Hz, 1H), 6.47-6.41 (m, 1H), 4.15 (s, 2H), 3.49 (t, J=7.7 Hz, 2H), 3.26 (t, J=7.8 Hz, 2H), 1.94 (q, J=7.6 Hz, 2H), 1.62-1.52 (m, 2H), 0.49 (t, J=7.6 Hz, 3H).

Example 499

2-[3-Fluoro-6-[3-(trifluoromethyl)phenyl]pyrrolo[3,2-b]pyridin-1-yl]-N,N-dimethyl-acetamide

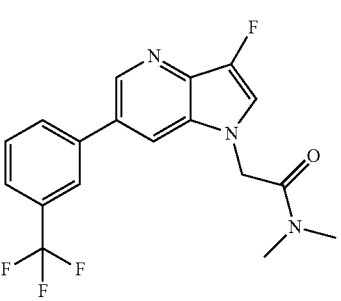

The title compound was prepared in a manner analogous to Example 92. MS (ESI): mass calcd. for $C_{18}H_{16}F_4N_3O$, 365.1. m/z found, 366.0 [M+H]$^+$. $^1$H NMR (400 MHz, DMSO-d$_6$) δ 8.75 (d, J=1.9 Hz, 1H), 8.30 (t, J=2.2 Hz, 1H), 8.12-8.05 (m, 2H), 7.80-7.73 (m, 2H), 7.66 (d, J=2.2 Hz, 1H), 5.24 (s, 2H), 3.11 (s, 3H), 2.85 (s, 3H).

Example 500

2-[3-Fluoro-6-[2-fluoro-3-(trifluoromethyl)phenyl]pyrrolo[3,2-b]pyridin-1-yl]-N,N-dimethyl-acetamide

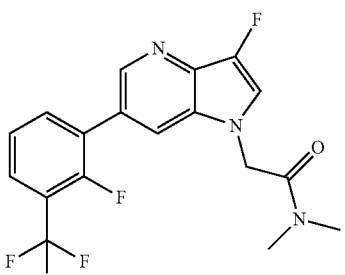

The title compound was prepared in a manner analogous to Example 92. MS (ESI): mass calcd. for $C_{16}H_{14}F_6N_3O$, 383.1. m/z found, 384.0 [M+H]$^+$. $^1$H NMR (500 MHz, DMSO-d$_6$) δ 8.54 (d, J=1.8 Hz, 1H), 8.17 (s, 1H), 7.98-7.91 (m, 1H), 7.88-7.82 (m, 1H), 7.70 (s, 1H), 7.60-7.53 (m, 1H), 5.22 (s, 2H), 3.08 (s, 3H), 2.84 (s, 3H).

Example 501

2-[3-Fluoro-6-(2,3,4-trifluorophenyl)pyrrolo[3,2-b]pyridin-1-yl]-N,N-dimethyl-acetamide

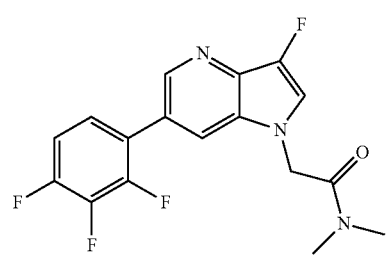

The title compound was prepared in a manner analogous to Example 92. MS (ESI): mass calcd. for $C_{17}H_{13}F_4N_3O$, 351.1. m/z found, 352.0 [M+H]$^+$. $^1$H NMR (500 MHz, DMSO-d$_6$) δ 8.52 (t, J=1.9 Hz, 1H), 8.14-8.11 (m, 1H), 7.69 (d, J=2.2 Hz, 1H), 7.52-7.43 (m, 2H), 5.20 (s, 2H), 3.08 (s, 3H), 2.84 (s, 3H).

Example 502

2-[6-(2,4-Difluoro-3-methyl-phenyl)-3-fluoro-pyrrolo[3,2-b]pyridin-1-yl]-N,N-dimethyl-acetamide

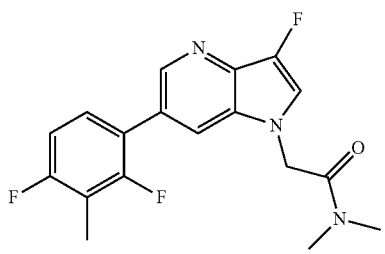 [SMILES: Cc1c(F)ccc(-c2cnc3c(F)cn(CC(=O)N(C)C)c3c2)c1F]

The title compound was prepared in a manner analogous to Example 92. MS (ESI): mass calcd. for $C_{16}H_{16}F_3N_3O$, 347.1. m/z found, 348.1 [M+H]+. 1H NMR (500 MHz, DMSO-$d_6$) δ 8.48 (t, J=1.9 Hz, 1H), 8.05 (s, 1H), 7.65 (d, J=2.2 Hz, 1H), 7.50-7.41 (m, 1H), 7.21 (t, J=8.7 Hz, 1H), 5.19 (s, 2H), 3.08 (s, 3H), 2.84 (s, 3H), 2.24 (s, 3H).

Example 503

2-[6-(3-Chlorophenyl)-3-fluoro-pyrrolo[3,2-b]pyridin-1-yl]-N,N-dimethyl-acetamide

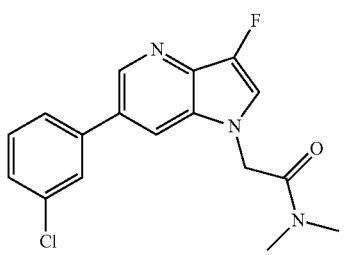

The title compound was prepared in a manner analogous to Example 92. MS (ESI): mass calcd. for $C_{17}H_{15}ClFN_3O$, 331.1. m/z found, 332.0 [M+H]+. 1H NMR (500 MHz, DMSO-$d_6$) δ 8.72 (d, J=1.9 Hz, 1H), 8.26 (t, J=2.2 Hz, 1H), 7.83 (t, J=1.9 Hz, 1H), 7.77-7.73 (m, 1H), 7.64 (d, J=2.2 Hz, 1H), 7.53 (t, J=7.9 Hz, 1H), 7.48-7.43 (m, 1H), 5.22 (s, 2H), 3.10 (s, 3H), 2.85 (s, 3H).

Example 504

2-[6-(3-Chloro-4-fluoro-phenyl)-3-fluoro-pyrrolo[3,2-b]pyridin-1-yl]-N,N-dimethyl-acetamide

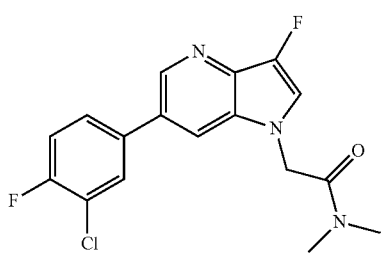

The title compound was prepared in a manner analogous to Example 92. MS (ESI): mass calcd. for $C_{17}H_{14}ClF_2N_3O$, 349.1. m/z found, 350.0 [M+H]+. 1H NMR (500 MHz, DMSO-$d_6$) δ 8.71 (d, J=1.9 Hz, 1H), 8.25 (t, J=2.2 Hz, 1H), 7.99 (dd, J=7.1, 2.3 Hz, 1H), 7.82-7.76 (m, 1H), 7.64 (d, J=2.2 Hz, 1H), 7.56 (t, J=9.0 Hz, 1H), 5.21 (s, 2H), 3.10 (s, 3H), 2.85 (s, 3H).

Example 505

2-[6-(3-Ethylphenyl)-3-fluoro-pyrrolo[3,2-b]pyridin-1-yl]-N,N-dimethyl-acetamide

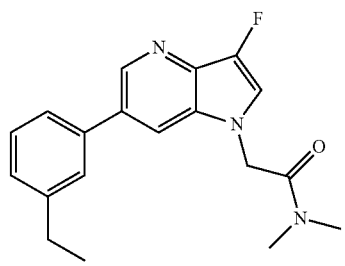

The title compound was prepared in a manner analogous to Example 92. MS (ESI): mass calcd. for $C_{19}H_{20}FN_3O$, 325.2. m/z found, 326.1 [M+H]+. 1H NMR (500 MHz, DMSO-$d_6$) δ 8.67 (d, J=1.9 Hz, 1H), 8.15 (t, J=2.2 Hz, 1H), 7.60 (d, J=2.2 Hz, 1H), 7.58-7.56 (m, 1H), 7.54 (d, J=8.0 Hz, 1H), 7.41 (t, J=7.6 Hz, 1H), 7.25 (d, J=7.6 Hz, 1H), 5.21 (s, 2H), 3.10 (s, 3H), 2.85 (s, 3H), 2.70 (q, J=7.5 Hz, 2H), 1.25 (t, J=7.6 Hz, 3H).

Example 506

1-(Azetidin-1-yl)-2-[3-fluoro-6-(3-fluorophenyl)pyrrolo[3,2-b]pyridin-1-yl]ethanone

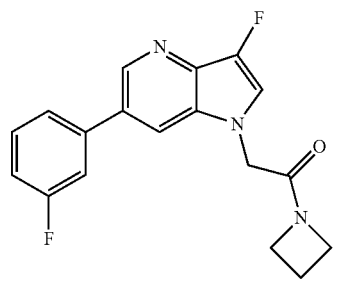 [SMILES: O=C(Cn1cc(F)c2ncc(-c3cccc(F)c3)cc21)N1CCC1]

The title compound was prepared in a manner analogous to Example 182. MS (ESI): mass calcd. for $C_{18}H_{15}F_2N_3O$, 327.1. m/z found, 328.0 [M+H]+. 1H NMR (500 MHz, DMSO-$d_6$) δ 8.77-8.71 (m, 1H), 8.26 (s, 1H), 7.70-7.62 (m, 3H), 7.59-7.53 (m, 1H), 7.27-7.20 (m, 1H), 4.96 (s, 2H), 4.23 (t, J=7.7 Hz, 2H), 3.91 (t, J=7.7 Hz, 2H), 2.34-2.22 (m, 2H).

Example 507

1-(3-Fluoroazetidin-1-yl)-2-[3-fluoro-6-(2-fluorophenyl)pyrrolo[3,2-b]pyridin-1-yl]ethanone

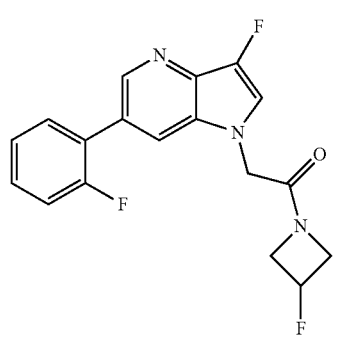 [SMILES: O=C(Cn1cc(F)c2ncc(-c3ccccc3F)cc21)N1CC(F)C1]

The title compound was prepared in a manner analogous to Example 182. MS (ESI): mass calcd. for $C_{16}H_{14}F_3N_3O$, 345.1. m/z found, 346.1 [M+H]$^+$. $^1$H NMR (500 MHz, CD$_3$OD) δ 8.54 (t, J=1.8 Hz, 1H), 8.08-8.02 (m, 1H), 7.62-7.55 (m, 1H), 7.52 (d, J=2.3 Hz, 1H), 7.47-7.41 (m, 1H), 7.35-7.29 (m, 1H), 7.29-7.22 (m, 1H), 5.48-5.30 (m, 1H), 5.00 (d, J=2.2 Hz, 2H), 4.61-4.51 (m, 1H), 4.42-4.28 (m, 2H), 4.14-4.03 (m, 1H).

Example 508

1-(3-Fluoroazetidin-1-yl)-2-[3-fluoro-6-[4-fluoro-3-(trifluoromethyl)phenyl]pyrrolo[3,2-b]pyridin-1-yl]ethanone

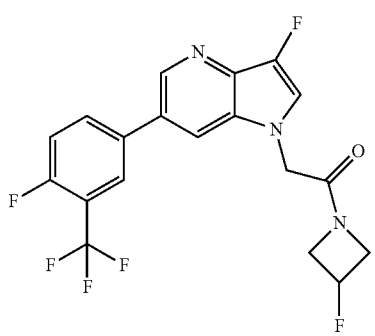 [SMILES: O=C(Cn1cc(F)c2ncc(-c3ccc(F)c(C(F)(F)F)c3)cc21)N1CC(F)C1]

The title compound was prepared in a manner analogous to Example 182. MS (ESI): mass calcd. for $C_{19}H_{13}F_6N_3O$, 413.1. m/z found, 414.0 [M+H]$^+$. $^1$H NMR (500 MHz, DMSO-d$_6$) δ 8.75 (d, J=1.9 Hz, 1H), 8.29 (t, J=2.2 Hz, 1H), 8.17-8.11 (m, 1H), 8.09 (dd, J=6.9, 2.4 Hz, 1H), 7.70 (d, J=2.1 Hz, 1H), 7.69-7.65 (m, 1H), 5.55-5.37 (m, 1H), 5.03 (d, J=2.1 Hz, 2H), 4.60-4.49 (m, 2H), 4.37-4.19 (m, 2H), 4.03-3.90 (m, 1H).

Example 509

2-[6-(3,5-Difluorophenyl)-3-fluoro-pyrrolo[3,2-b]pyridin-1-yl]-N,N-dimethyl-acetamide

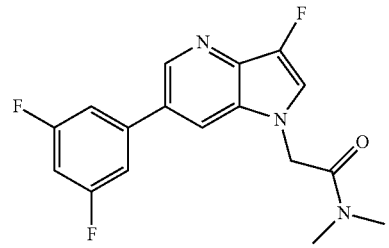

The title compound was prepared in a manner analogous to Example 92. MS (ESI): mass calcd. for $C_{17}H_{14}F_3N_3O$, 333.1. m/z found, 334.0 [M+H]$^+$. $^1$H NMR (500 MHz, DMSO-d$_6$) δ 8.78 (d, J=1.9 Hz, 1H), 8.32 (t, J=2.2 Hz, 1H), 7.67 (d, J=2.1 Hz, 1H), 7.61-7.54 (m, 2H), 7.29-7.21 (m, 1H), 5.21 (s, 2H), 3.11 (s, 3H), 2.86 (s, 3H).

Example 510

2-[3-Fluoro-6-(3-fluorophenyl)pyrrolo[3,2-b]pyridin-1-yl]-N,N-dimethyl-acetamide

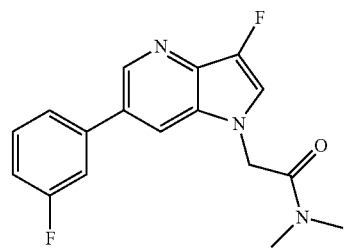

The title compound was prepared in a manner analogous to Example 92. MS (ESI): mass calcd. for $C_{17}H_{16}F_2N_3O$, 315.1. m/z found, 316.0 [M+H]$^+$. $^1$H NMR (500 MHz, CD$_3$OD) δ 8.62 (d, J=1.8 Hz, 1H), 8.12 (t, J=2.1 Hz, 1H), 7.56-7.44 (m, 4H), 7.16-7.10 (m, 1H), 5.23 (s, 2H), 3.19 (s, 3H), 2.98 (s, 3H).

Example 511

2-[3-Chloro-6-(4-fluorophenyl)pyrrolo[3,2-b]pyridin-1-yl]-N,N-dimethyl-acetamide

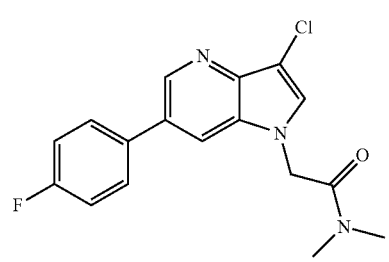

The title compound was prepared in a manner analogous to Example 146. MS (ESI): mass calcd. for $C_{17}H_{15}ClFN_3O$, 331.1. m/z found, 332.0 [M+H]$^+$. $^1$H NMR (500 MHz, DMSO-d$_6$) δ 8.70 (d, J=1.9 Hz, 1H), 8.21 (d, J=1.9 Hz, 1H), 7.83-7.76 (m, 2H), 7.75 (s, 1H), 7.38-7.32 (m, 2H), 5.26 (s, 2H), 3.11 (s, 3H), 2.86 (s, 3H).

Example 512

2-[3-Chloro-6-(2-fluorophenyl)pyrrolo[3,2-b]pyridin-1-yl]-N,N-dimethyl-acetamide

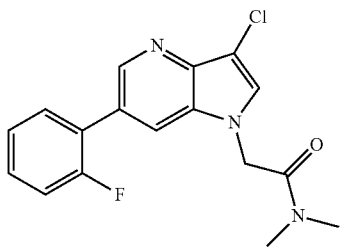 [SMILES: CN(C)C(=O)Cn1cc(Cl)c2ncc(-c3ccccc3F)cc21]

The title compound was prepared in a manner analogous to Example 146. MS (ESI): mass calcd. for $C_{17}H_{15}ClFN_3O$, 331.1. m/z found, 332.0 [M+H]$^+$. $^1$H NMR (500 MHz, DMSO-$d_6$) δ 8.56 (t, J=1.9 Hz, 1H), 8.12 (dd, J=1.9, 1.1 Hz, 1H), 7.79 (s, 1H), 7.63-7.56 (m, 1H), 7.51-7.44 (m, 1H), 7.40-7.33 (m, 2H), 5.26 (s, 2H), 3.09 (s, 3H), 2.85 (s, 3H).

Example 513

2-[3-Chloro-6-(2-fluoro-3-methyl-phenyl)pyrrolo[3,2-b]pyridin-1-yl]-N,N-dimethyl-acetamide

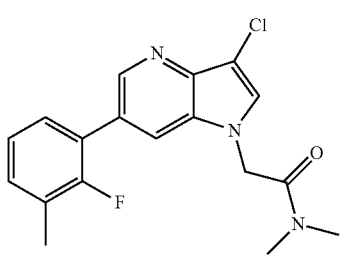

The title compound was prepared in a manner analogous to Example 146. MS (ESI): mass calcd. for $C_{18}H_{17}ClFN_3O$, 345.1. m/z found, 346.0 [M+H]$^+$. $^1$H NMR (500 MHz, CD$_3$OD) δ 8.54 (t, J=1.9 Hz, 1H), 8.03 (t, J=1.4 Hz, 1H), 7.62 (s, 1H), 7.39-7.33 (m, 1H), 7.32-7.25 (m, 1H), 7.18 (t, J=7.6 Hz, 1H), 5.26 (s, 2H), 3.18 (s, 3H), 2.97 (s, 3H), 2.35 (d, J=2.3 Hz, 3H).

Example 514

2-(3-Chloro-6-phenyl-pyrrolo[3,2-b]pyridin-1-yl)-N,N-dimethyl-acetamide

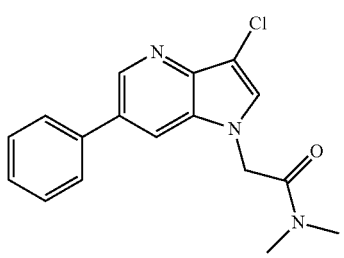 [SMILES: CN(C)C(=O)Cn1cc(Cl)c2ncc(-c3ccccc3)cc21]

Example 514

The title compound was prepared in a manner analogous to Example 146. MS (ESI): mass calcd. for $C_{17}H_{16}ClN_3O$, 313.1. m/z found, 314.0 [M+H]$^+$. $^1$H NMR (500 MHz, DMSO-$d_6$) δ 8.72 (d, J=1.9 Hz, 1H), 8.22 (d, J=1.9 Hz, 1H), 7.79-7.71 (m, 3H), 7.55-7.48 (m, 2H), 7.44-7.37 (m, 1H), 5.27 (s, 2H), 3.11 (s, 3H), 2.86 (s, 3H).

Example 515

2-[3-Chloro-6-(m-tolyl)pyrrolo[3,2-b]pyridin-1-yl]-N,N-dimethyl-acetamide

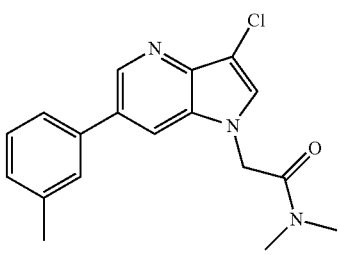

The title compound was prepared in a manner analogous to Example 146. MS (ESI): mass calcd. for $C_{18}H_{18}ClN_3O$, 327.1. m/z found, 328.1 [M+H]$^+$. $^1$H NMR (500 MHz, DMSO-$d_6$) δ 8.70 (d, J=1.9 Hz, 1H), 8.19 (d, J=1.9 Hz, 1H), 7.74 (s, 1H), 7.57 (s, 1H), 7.53 (d, J=7.8 Hz, 1H), 7.39 (t, J=7.6 Hz, 1H), 7.22 (d, J=7.5 Hz, 1H), 5.27 (s, 2H), 3.11 (s, 3H), 2.86 (s, 3H), 2.41 (s, 3H).

Example 516

2-[3-Chloro-6-[4-fluoro-3-(trifluoromethyl)phenyl]pyrrolo[3,2-b]pyridin-1-yl]-N,N-dimethyl-acetamide

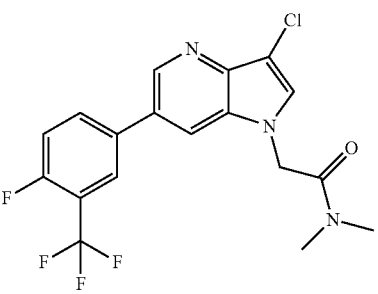

The title compound was prepared in a manner analogous to Example 146. MS (ESI): mass calcd. for $C_{18}H_{14}ClF_4N_3O$, 399.1. m/z found, 400.0 [M+H]$^+$. $^1$H NMR (500 MHz, DMSO-$d_6$) δ 8.77 (d, J=1.9 Hz, 1H), 8.31 (d, J=1.9 Hz, 1H), 8.17-8.10 (m, 1H), 8.08 (dd, J=6.8, 2.4 Hz, 1H), 7.80 (s, 1H), 7.71-7.63 (m, 1H), 5.28 (s, 2H), 3.11 (s, 3H), 2.86 (s, 3H).

Example 517

2-[3-Chloro-6-[2-fluoro-3-(trifluoromethyl)phenyl]pyrrolo[3,2-b]pyridin-1-yl]-N,N-dimethyl-acetamide

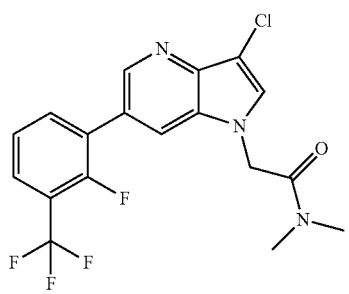

The title compound was prepared in a manner analogous to Example 146. MS (ESI): mass calcd. for C$_{16}$H$_{14}$ClF$_4$N$_3$O, 399.1. m/z found, 400.0 [M+H]$^+$. $^1$H NMR (500 MHz, DMSO-d$_6$) δ 8.58 (t, J=1.8 Hz, 1H), 8.21-8.18 (m, 1H), 7.94 (t, J=7.3 Hz, 1H), 7.89-7.82 (m, 2H), 7.57 (t, J=7.8 Hz, 1H), 5.28 (s, 2H), 3.09 (s, 3H), 2.85 (s, 3H).

Example 518

2-[3-Chloro-6-(2,3,4-trifluorophenyl)pyrrolo[3,2-b]pyridin-1-yl]-N,N-dimethyl-acetamide

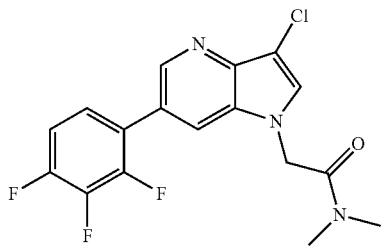

The title compound was prepared in a manner analogous to Example 146. MS (ESI): mass calcd. for C$_{17}$H$_{13}$ClF$_3$N$_3$O, 367.1. m/z found, 368.0 [M+H]$^+$. $^1$H NMR (500 MHz, DMSO-d$_6$) δ 8.56 (t, J=1.9 Hz, 1H), 8.19-8.12 (m, 1H), 7.83 (s, 1H), 7.53-7.43 (m, 2H), 5.26 (s, 2H), 3.09 (s, 3H), 2.85 (s, 3H).

Example 519

2-[3-Chloro-6-(2,4-difluoro-3-methyl-phenyl)pyrrolo[3,2-b]pyridin-1-yl]-N,N-dimethyl-acetamide

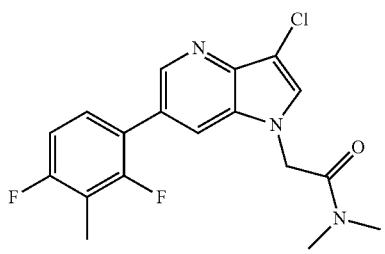 [SMILES: Cc1c(F)ccc(-c2cnc3c(Cl)cn(CC(=O)N(C)C)c3c2)c1F]

The title compound was prepared in a manner analogous to Example 146. MS (ESI): mass calcd. for C$_{18}$H$_{16}$ClF$_2$N$_3$O, 363.1. m/z found, 364.0 [M+H]$^+$. $^1$H NMR (500 MHz, DMSO-d$_6$) δ 8.52 (d, J=1.8 Hz, 1H), 8.09 (d, J=1.8 Hz, 1H), 7.79 (s, 1H), 7.50-7.41 (m, 1H), 7.22 (t, J=9.2 Hz, 1H), 5.25 (s, 2H), 3.09 (s, 3H), 2.85 (s, 3H), 2.25 (s, 3H).

Example 520

2-[3-Chloro-6-(3-chloro-4-fluoro-phenyl)pyrrolo[3,2-b]pyridin-1-yl]-N,N-dimethyl-acetamide

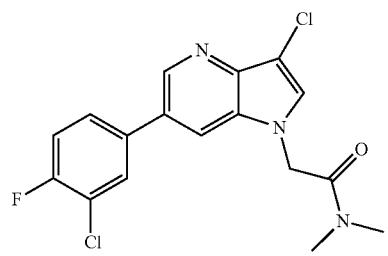 [SMILES: CN(C)C(=O)Cn1cc(Cl)c2ncc(-c3ccc(F)c(Cl)c3)cc21]

The title compound was prepared in a manner analogous to Example 146. MS (ESI): mass calcd. for C$_{17}$H$_{14}$Cl$_2$FN$_3$O, 365.0. m/z found, 366.0 [M+H]$^+$. $^1$H NMR (500 MHz, DMSO-d$_6$) δ 8.74 (d, J=1.9 Hz, 1H), 8.28 (d, J=1.9 Hz, 1H), 7.99 (dd, J=7.1, 2.4 Hz, 1H), 7.82-7.78 (m, 1H), 7.78 (s, 1H), 7.56 (t, J=9.0 Hz, 1H), 5.27 (s, 2H), 3.11 (s, 3H), 2.86 (s, 3H).

Example 521

1-(Azetidin-1-yl)-2-[3-chloro-6-(2-fluorophenyl)pyrrolo[3,2-b]pyridin-1-yl]ethanone

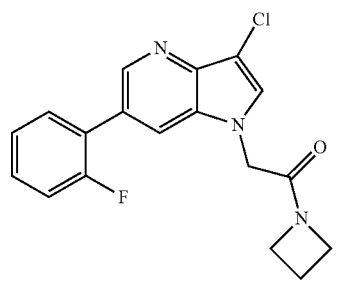 [SMILES: O=C(Cn1cc(Cl)c2ncc(-c3ccccc3F)cc21)N1CCC1]

The title compound was prepared in a manner analogous to Example 146. MS (ESI): mass calcd. for C$_{18}$H$_{15}$ClFN$_3$O, 343.1. m/z found, 344.0 [M+H]$^+$. $^1$H NMR (500 MHz, DMSO-d$_6$) δ 8.58 (t, J=1.9 Hz, 1H), 8.12 (s, 1H), 7.82 (s, 1H), 7.64-7.58 (m, 1H), 7.52-7.45 (m, 1H), 7.41-7.34 (m, 2H), 5.00 (s, 2H), 4.24 (t, J=7.6 Hz, 2H), 3.90 (t, J=7.7 Hz, 2H), 2.32-2.23 (m, 2H).

Example 522

1-(Azetidin-1-yl)-2-[3-chloro-6-(2-fluoro-3-methyl-phenyl)pyrrolo[3,2-b]pyridin-1-yl]ethanone

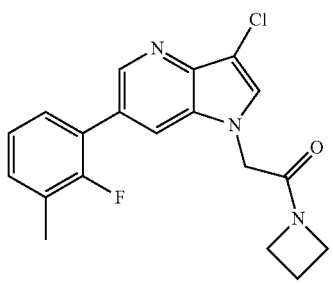

The title compound was prepared in a manner analogous to Example 146. MS (ESI): mass calcd. for $C_{19}H_{17}ClFN_3O$, 357.1. m/z found, 358.0 [M+H]$^+$. $^1$H NMR (500 MHz, DMSO-d$_6$) δ 8.55 (t, J=1.9 Hz, 1H), 8.10 (dd, J=1.9, 1.1 Hz, 1H), 7.81 (s, 1H), 7.43-7.37 (m, 1H), 7.37-7.32 (m, 1H), 7.24 (t, J=7.6 Hz, 1H), 5.00 (s, 2H), 4.23 (t, J=7.7 Hz, 2H), 3.90 (t, J=7.7 Hz, 2H), 2.33 (d, J=2.1 Hz, 3H), 2.31-2.23 (m, 2H).

Example 523

1-(Azetidin-1-yl)-2-[3-chloro-6-[4-fluoro-3-(trifluoromethyl)phenyl]pyrrolo[3,2-b]pyridin-1-yl]ethanone

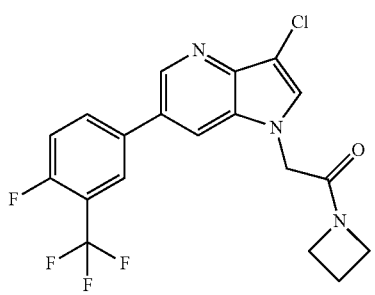 [SMILES: O=C(Cn1cc(Cl)c2ncc(-c3ccc(F)c(C(F)(F)F)c3)cc21)N1CCC1]

The title compound was prepared in a manner analogous to Example 146. MS (ESI): mass calcd. for $C_{19}H_{14}ClF_4N_3O$, 411.1. m/z found, 412.0 [M+H]$^+$. $^1$H NMR (500 MHz, DMSO-d$_6$) δ 8.78 (d, J=1.9 Hz, 1H), 8.32 (d, J=1.9 Hz, 1H), 8.17-8.12 (m, 1H), 8.10 (dd, J=6.8, 2.4 Hz, 1H), 7.83 (s, 1H), 7.72-7.65 (m, 1H), 5.03 (s, 2H), 4.24 (t, J=7.7 Hz, 2H), 3.91 (t, J=7.7 Hz, 2H), 2.33-2.24 (m, 2H).

Example 524

1-(Azetidin-1-yl)-2-[3-chloro-6-[2-fluoro-3-(trifluoromethyl)phenyl]pyrrolo[3,2-b]pyridin-1-yl]ethanone

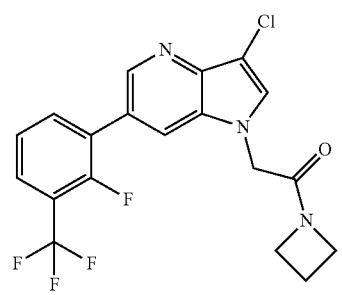 [SMILES: O=C(Cn1cc(Cl)c2ncc(-c3cccc(C(F)(F)F)c3F)cc21)N1CCC1]

The title compound was prepared in a manner analogous to Example 146. MS (ESI): mass calcd. for $C_{19}H_{14}ClF_4N_3O$, 411.1. m/z found, 412.0 [M+H]$^+$. $^1$H NMR (500 MHz, DMSO-d$_6$) δ 8.59 (t, J=1.8 Hz, 1H), 8.20 (t, J=1.5 Hz, 1H), 7.99-7.93 (m, 1H), 7.89-7.83 (m, 2H), 7.58 (t, J=7.9 Hz, 1H), 5.02 (s, 2H), 4.24 (t, J=7.7 Hz, 2H), 3.90 (t, J=7.7 Hz, 2H), 2.32-2.23 (m, 2H).

Example 525

1-(Azetidin-1-yl)-2-[3-chloro-6-(2,4-difluoro-3-methyl-phenyl)pyrrolo[3,2-b]pyridin-1-yl]ethanone

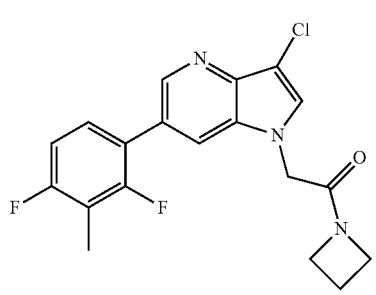 [SMILES: Cc1c(F)ccc(-c2cnc3c(Cl)cn(CC(=O)N4CCC4)c3c2)c1F]

The title compound was prepared in a manner analogous to Example 146. MS (ESI): mass calcd. for $C_{19}H_{16}ClF_2N_3O$, 375.1. m/z found, 376.0 [M+H]$^+$. $^1$H NMR (500 MHz, DMSO-d$_6$) δ 8.53 (t, J=1.9 Hz, 1H), 8.09 (t, J=1.4 Hz, 1H), 7.82 (s, 1H), 7.50-7.43 (m, 1H), 7.23 (t, J=8.5 Hz, 1H), 4.99 (s, 2H), 4.23 (t, J=7.7 Hz, 2H), 3.90 (t, J=7.7 Hz, 2H), 2.32-2.22 (m, 5H).

Example 526

1-(Azetidin-1-yl)-2-[3-chloro-6-(3-chlorophenyl)pyrrolo[3,2-b]pyridin-1-yl]ethanone

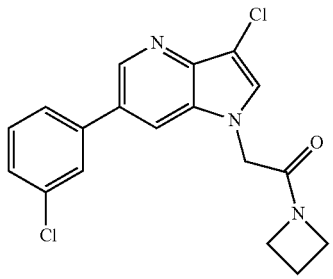

The title compound was prepared in a manner analogous to Example 146. MS (ESI): mass calcd. for C$_{18}$H$_{15}$Cl$_2$N$_3$O, 359.1. m/z found, 360.0 [M+H]$^+$. $^1$H NMR (500 MHz, DMSO-d$_6$) δ 8.76 (d, J=1.9 Hz, 1H), 8.29 (d, J=1.9 Hz, 1H), 7.85 (t, J=1.9 Hz, 1H), 7.81 (s, 1H), 7.78-7.72 (m, 1H), 7.55 (t, J=7.8 Hz, 1H), 7.51-7.45 (m, 1H), 5.03 (s, 2H), 4.25 (t, J=7.7 Hz, 2H), 3.91 (t, J=7.7 Hz, 2H), 2.34-2.23 (m, 2H).

Example 527

1-(Azetidin-1-yl)-2-[3-chloro-6-(3-chloro-4-fluorophenyl)pyrrolo[3,2-b]pyridin-1-yl]ethanone

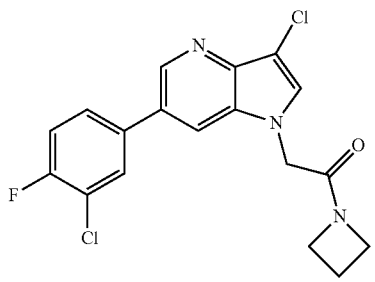

The title compound was prepared in a manner analogous to Example 146. MS (ESI): mass calcd. for C$_{18}$H$_{14}$Cl$_2$FN$_3$O, 377.0. m/z found, 378.0 [M+H]$^+$. $^1$H NMR (500 MHz, DMSO-d$_6$) δ 8.75 (d, J=1.9 Hz, 1H), 8.28 (d, J=2.0 Hz, 1H), 8.01 (dd, J=7.1, 2.3 Hz, 1H), 7.83-7.78 (m, 2H), 7.61-7.54 (m, 1H), 5.02 (s, 2H), 4.24 (t, J=7.7 Hz, 2H), 3.91 (t, J=7.7 Hz, 2H), 2.33-2.24 (m, 2H).

Example 528

1-(Azetidin-1-yl)-2-[3-chloro-6-(3-chloro-2-fluorophenyl)pyrrolo[3,2-b]pyridin-1-yl]ethanone

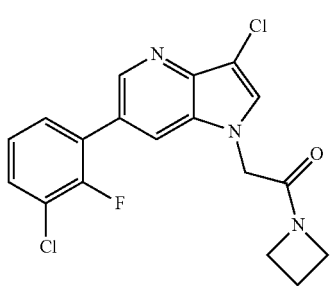 [SMILES: O=C(Cn1cc(Cl)c2ncc(-c3cccc(Cl)c3F)cc21)N1CCC1]

The title compound was prepared in a manner analogous to Example 146. MS (ESI): mass calcd. for C$_{18}$H$_{14}$Cl$_2$FN$_3$O, 377.0. m/z found, 378.0 [M+H]$^+$. $^1$H NMR (500 MHz, DMSO-d$_6$) δ 8.58 (s, 1H), 8.17 (s, 1H), 7.85 (s, 1H), 7.66 (t, J=7.4 Hz, 1H), 7.58 (t, J=7.5 Hz, 1H), 7.38 (t, J=7.9 Hz, 1H), 5.01 (s, 2H), 4.24 (t, J=7.7 Hz, 2H), 3.90 (t, J=7.7 Hz, 2H), 2.32-2.23 (m, 2H).

Example 529

1-(Azetidin-1-yl)-2-[3-chloro-6-[3-(difluoromethyl)phenyl]pyrrolo[3,2-b]pyridin-1-yl]ethanone

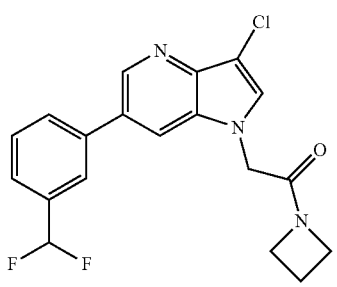 [SMILES: O=C(Cn1cc(Cl)c2ncc(-c3cccc(C(F)F)c3)cc21)N1CCC1]

The title compound was prepared in a manner analogous to Example 146. MS (ESI): mass calcd. for C$_{19}$H$_{16}$ClF$_2$N$_3$O, 375.1. m/z found, 376.0 [M+H]$^+$. $^1$H NMR (500 MHz, CD$_3$OD) δ 8.69 (d, J=1.7 Hz, 1H), 8.18 (d, J=1.8 Hz, 1H), 7.92-7.84 (m, 2H), 7.68-7.56 (m, 3H), 6.87 (t, J=56.2 Hz, 1H), 5.03 (s, 2H), 4.33 (t, J=7.7 Hz, 2H), 4.07 (t, J=7.9 Hz, 2H), 2.44-2.34 (m, 2H).

Example 530

1-(Azetidin-1-yl)-2-[3-chloro-6-(3-fluorophenyl)pyrrolo[3,2-b]pyridin-1-yl]ethanone

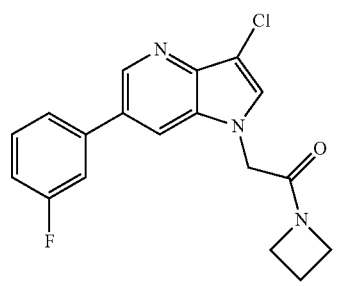 [SMILES: O=C(Cn1cc(Cl)c2ncc(-c3cccc(F)c3)cc21)N1CCC1]

The title compound was prepared in a manner analogous to Example 146. MS (ESI): mass calcd. for C$_{18}$H$_{15}$ClFN$_3$O, 343.1. m/z found, 344.0 [M+H]$^+$. $^1$H NMR (500 MHz, DMSO-d$_6$) δ 8.79-8.75 (m, 1H), 8.31-8.27 (m, 1H), 7.81 (d, J=2.1 Hz, 1H), 7.68-7.61 (m, 2H), 7.60-7.52 (m, 1H), 7.24 (t, J=8.2 Hz, 1H), 5.02 (d, J=2.3 Hz, 2H), 4.25 (t, J=7.7 Hz, 2H), 3.91 (t, J=7.5 Hz, 2H), 2.33-2.25 (m, 2H).

Example 531

2-[3-Chloro-6-(3-fluorophenyl)pyrrolo[3,2-b]pyridin-1-yl]-N,N-dimethyl-acetamide

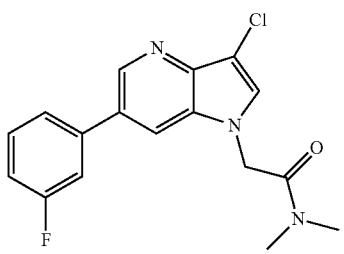 [SMILES: CN(C)C(=O)Cn1cc(Cl)c2ncc(-c3cccc(F)c3)cc21]

The title compound was prepared in a manner analogous to Example 146. MS (ESI): mass calcd. for $C_{17}H_{15}ClFN_3O$, 331.1. m/z found, 332.0 [M+H]⁺. ¹H NMR (500 MHz, CD₃OD) δ 8.66 (d, J=1.9 Hz, 1H), 8.15 (d, J=1.9 Hz, 1H), 7.62 (s, 1H), 7.57-7.46 (m, 3H), 7.17-7.09 (m, 1H), 5.29 (s, 2H), 3.20 (s, 3H), 2.98 (s, 3H).

Example 532

1-(Azetidin-1-yl)-2-[3-chloro-6-(3,5-difluorophenyl)pyrrolo[3,2-b]pyridin-1-yl]ethanone

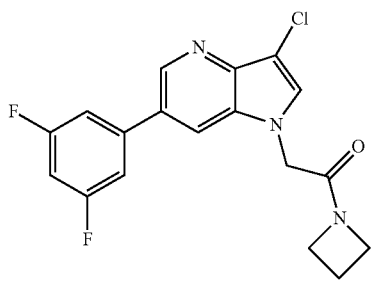 [SMILES: O=C(Cn1cc(Cl)c2ncc(-c3cc(F)cc(F)c3)cc21)N1CCC1]

The title compound was prepared in a manner analogous to Example 146. MS (ESI): mass calcd. for $C_{18}H_{14}ClF_2N_3O$, 361.1. m/z found, 362.0 [M+H]⁺. ¹H NMR (500 MHz, CD₃OD) δ 8.68 (d, J=1.9 Hz, 1H), 8.20 (d, J=1.9 Hz, 1H), 7.68 (s, 1H), 7.39 (dd, J=8.7, 2.2 Hz, 2H), 7.03-6.96 (m, 1H), 5.03 (s, 2H), 4.39-4.30 (m, 2H), 4.08 (t, J=7.8 Hz, 2H), 2.44-2.35 (m, 2H).

Example 533

1-(Azetidin-1-yl)-2-[3-chloro-6-(3-ethylphenyl)pyrrolo[3,2-b]pyridin-1-yl]ethanone

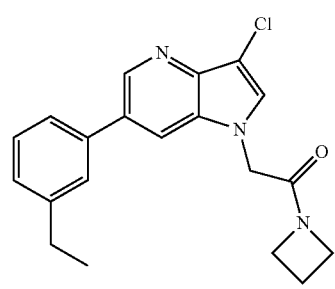 [SMILES: CCc1cccc(-c2cnc3c(Cl)cn(CC(=O)N4CCC4)c3c2)c1]

The title compound was prepared in a manner analogous to Example 146. MS (ESI): mass calcd. for $C_{20}H_{20}ClN_3O$, 353.1. m/z found, 354.0 [M+H]⁺. ¹H NMR (500 MHz, DMSO-d₆) δ 8.72 (d, J=1.9 Hz, 1H), 8.19 (d, J=1.9 Hz, 1H), 7.78 (s, 1H), 7.60-7.57 (m, 1H), 7.58-7.53 (m, 1H), 7.43 (t, J=7.6 Hz, 1H), 7.26 (d, J=7.5 Hz, 1H), 5.02 (s, 2H), 4.24 (t, J=7.7 Hz, 2H), 3.91 (t, J=7.7 Hz, 2H), 2.71 (q, J=7.6 Hz, 2H), 2.32-2.23 (m, 2H), 1.26 (t, J=7.6 Hz, 3H).

Example 534

2-[3-Chloro-6-(3-chlorophenyl)pyrrolo[3,2-b]pyridin-1-yl]-N,N-dimethyl-acetamide

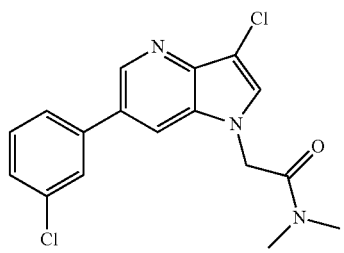 [SMILES: CN(C)C(=O)Cn1cc(Cl)c2ncc(-c3cccc(Cl)c3)cc21]

The title compound was prepared in a manner analogous to Example 146. MS (ESI): mass calcd. for $C_{17}H_{15}Cl_2N_3O$, 347.1. m/z found, 348.0 [M+H]⁺. ¹H NMR (500 MHz, DMSO-d₆) δ 8.75 (d, J=1.9 Hz, 1H), 8.30 (d, J=1.9 Hz, 1H), 7.84 (t, J=1.9 Hz, 1H), 7.78 (s, 1H), 7.77-7.73 (m, 1H), 7.54 (t, J=7.8 Hz, 1H), 7.49-7.45 (m, 1H), 5.28 (s, 2H), 3.12 (s, 3H), 2.86 (s, 3H).

Example 535

2-[3-Chloro-6-(2-fluorophenyl)pyrrolo[3,2-b]pyridin-1-yl]-1-(3-fluoroazetidin-1-yl)ethanone

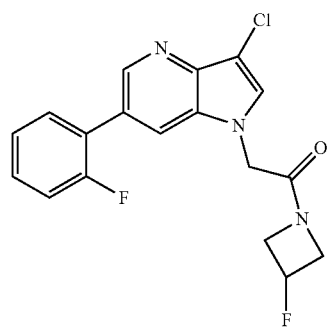 [SMILES: O=C(Cn1cc(Cl)c2ncc(-c3ccccc3F)cc21)N1CC(F)C1]

The title compound was prepared in a manner analogous to Example 146. MS (ESI): mass calcd. for $C_{18}H_{14}ClF_2N_3O$, 361.1. m/z found, 362.0 [M+H]⁺. ¹H NMR (500 MHz, DMSO-d₆) δ 8.58 (t, J=1.9 Hz, 1H), 8.14 (dd, J=1.9, 1.1 Hz, 1H), 7.83 (s, 1H), 7.64-7.57 (m, 1H), 7.51-7.45 (m, 1H), 7.41-7.34 (m, 2H), 5.55-5.37 (m, 1H), 5.07 (d, J=3.7 Hz, 2H), 4.63-4.52 (m, 1H), 4.40-4.29 (m, 1H), 4.29-4.16 (m, 1H), 4.02-3.89 (m, 1H).

Example 536

2-[3-Chloro-6-(2-fluoro-3-methyl-phenyl)pyrrolo[3,2-b]pyridin-1-yl]-1-(3-fluoroazetidin-1-yl)ethanone

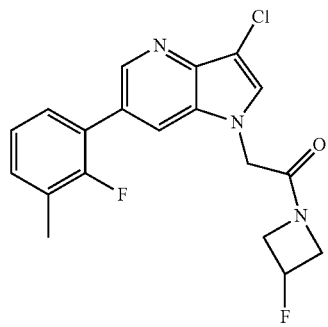 [SMILES: Cc1cccc(-c2cnc3c(Cl)cn(CC(=O)N4CC(F)C4)c3c2)c1F]

The title compound was prepared in a manner analogous to Example 146. MS (ESI): mass calcd. for $C_{19}H_{16}ClF_2N_3O$, 375.1. m/z found, 376.0 [M+H]$^+$. $^1$H NMR (500 MHz, DMSO-d$_6$) δ 8.58-8.54 (m, 1H), 8.11 (s, 1H), 7.82 (d, J=1.6 Hz, 1H), 7.40 (t, J=7.5 Hz, 1H), 7.35 (t, J=7.4 Hz, 1H), 7.24 (t, J=7.7 Hz, 1H), 5.55-5.38 (m, 1H), 5.07 (d, J=3.9 Hz, 2H), 4.64-4.51 (m, 1H), 4.41-4.29 (m, 1H), 4.29-4.19 (m, 1H), 4.02-3.90 (m, 1H), 2.33 (s, 3H).

Example 537

2-[3-Chloro-6-(3,5-difluorophenyl)pyrrolo[3,2-b]pyridin-1-yl]-1-(3-fluoroazetidin-1-yl)ethanone

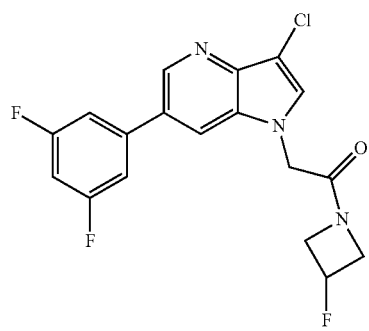 [SMILES: O=C(Cn1cc(Cl)c2ncc(-c3cc(F)cc(F)c3)cc21)N1CC(F)C1]

The title compound was prepared in a manner analogous to Example 146. MS (ESI): mass calcd. for $C_{18}H_{13}ClF_3N_3O$, 379.1. m/z found, 380.0 [M+H]$^+$. $^1$H NMR (500 MHz, DMSO-d$_6$) δ 8.82 (d, J=1.9 Hz, 1H), 8.35 (d, J=2.0 Hz, 1H), 7.84 (s, 1H), 7.61-7.55 (m, 2H), 7.31-7.23 (m, 1H), 5.57-5.40 (m, 1H), 5.08 (s, 2H), 4.65-4.53 (m, 1H), 4.41-4.31 (m, 1H), 4.31-4.20 (m, 1H), 4.04-3.93 (m, 1H).

Example 538

2-[3-Chloro-6-[2-fluoro-3-(trifluoromethyl)phenyl]pyrrolo[3,2-b]pyridin-1-yl]-1-(3-fluoroazetidin-1-yl)ethanone

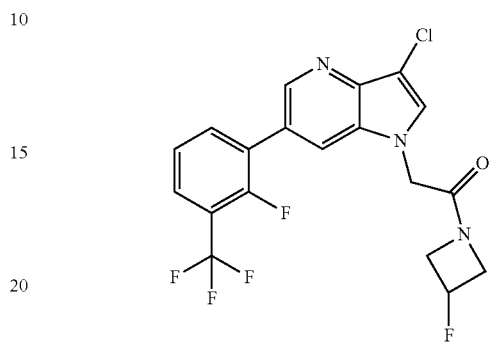

The title compound was prepared in a manner analogous to Example 146. MS (ESI): mass calcd. for $C_{19}H_{13}ClF_6N_3O$, 429.1. m/z found, 430.0 [M+H]$^+$. $^1$H NMR (500 MHz, DMSO-d$_6$) δ 8.60 (t, J=1.7 Hz, 1H), 8.22-8.20 (m, 1H), 7.98-7.93 (m, 1H), 7.89-7.83 (m, 2H), 7.58 (t, J=7.8 Hz, 1H), 5.55-5.38 (m, 1H), 5.08 (d, J=3.5 Hz, 2H), 4.63-4.52 (m, 1H), 4.40-4.30 (m, 1H), 4.29-4.18 (m, 1H), 4.02-3.91 (m, 1H).

Example 539

2-[3-Chloro-6-(2,4-difluoro-3-methyl-phenyl)pyrrolo[3,2-b]pyridin-1-yl]-1-(3-fluoroazetidin-1-yl)ethanone

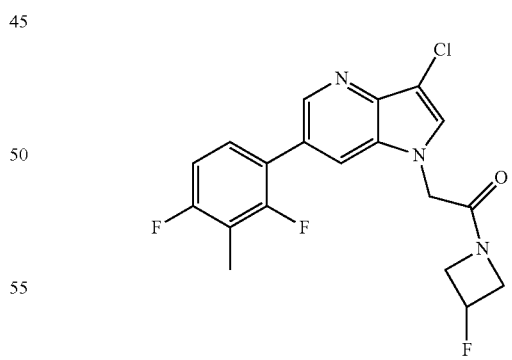

The title compound was prepared in a manner analogous to Example 146. MS (ESI): mass calcd. for $C_{19}H_{15}ClF_3N_3O$, 393.1. m/z found, 394.0 [M+H]$^+$. $^1$H NMR (500 MHz, DMSO-d$_6$) δ 8.53 (d, J=2.1 Hz, 1H), 8.10 (s, 1H), 7.82 (s, 1H), 7.50-7.42 (m, 1H), 7.22 (t, J=8.9 Hz, 1H), 5.57-5.36 (m, 1H), 5.06 (d, J=4.1 Hz, 2H), 4.63-4.50 (m, 1H), 4.42-4.17 (m, 2H), 4.06-3.89 (m, 1H), 2.25 (s, 3H).

Example 540

2-[3-Chloro-6-(3-chloro-4-fluoro-phenyl)pyrrolo[3,2-b]pyridin-1-yl]-1-(3-fluoroazetidin-1-yl)ethanone

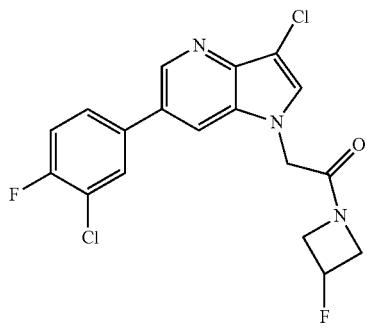 [SMILES: O=C(Cn1cc(Cl)c2ncc(-c3ccc(F)c(Cl)c3)cc21)N1CC(F)C1]

The title compound was prepared in a manner analogous to Example 146. MS (ESI): mass calcd. for $C_{18}H_{13}Cl_2F_2N_3O$, 395.0. m/z found, 396.0 [M+H]+. 1H NMR (500 MHz, DMSO-$d_6$) δ 8.75 (d, J=1.9 Hz, 1H), 8.28 (d, J=1.9 Hz, 1H), 8.00 (dd, J=7.1, 2.3 Hz, 1H), 7.82 (s, 1H), 7.81-7.77 (m, 1H), 7.61-7.52 (m, 1H), 5.57-5.39 (m, 1H), 5.08 (d, J=2.1 Hz, 2H), 4.64-4.52 (m, 1H), 4.40-4.30 (m, 1H), 4.30-4.20 (m, 1H), 4.03-3.90 (m, 1H).

Example 541

2-[3-Chloro-6-(3-chloro-2-fluoro-phenyl)pyrrolo[3,2-b]pyridin-1-yl]-1-(3-fluoroazetidin-1-yl)ethanone

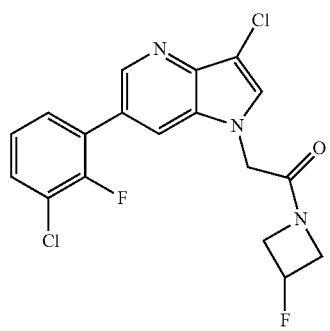 [SMILES: O=C(Cn1cc(Cl)c2ncc(-c3cccc(Cl)c3F)cc21)N1CC(F)C1]

The title compound was prepared in a manner analogous to Example 146. MS (ESI): mass calcd. for $C_{18}H_{13}Cl_2F_2N_3O$, 395.0. m/z found, 396.0 [M+H]+. 1H NMR (500 MHz, DMSO-$d_6$) δ 8.59 (t, J=1.8 Hz, 1H), 8.19 (t, J=1.5 Hz, 1H), 7.86 (s, 1H), 7.69-7.63 (m, 1H), 7.61-7.56 (m, 1H), 7.42-7.35 (m, 1H), 5.55-5.38 (m, 1H), 5.07 (d, J=3.6 Hz, 2H), 4.63-4.52 (m, 1H), 4.40-4.30 (m, 1H), 4.29-4.19 (m, 1H), 4.02-3.90 (m, 1H).

Example 542

2-[3-Chloro-6-(3-ethylphenyl)pyrrolo[3,2-b]pyridin-1-yl]-1-(3-fluoroazetidin-1-yl)ethanone

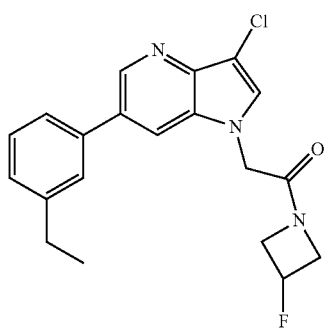 [SMILES: CCc1cccc(-c2cnc3c(Cl)cn(CC(=O)N4CC(F)C4)c3c2)c1]

The title compound was prepared in a manner analogous to Example 146. MS (ESI): mass calcd. for $C_{20}H_{19}ClFN_3O$, 371.1. m/z found, 372.0 [M+H]+. 1H NMR (500 MHz, DMSO-$d_6$) δ 8.72 (d, J=1.9 Hz, 1H), 8.20 (d, J=1.9 Hz, 1H), 7.78 (5, 1 H), 7.60-7.52 (m, 2H), 7.43 (t, J=7.6 Hz, 1H), 7.26 (d, J=7.5 Hz, 1H), 5.56-5.39 (m, 1H), 5.08 (d, J=3.0 Hz, 2H), 4.63-4.53 (m, 1H), 4.41-4.30 (m, 1H), 4.30-4.20 (m, 1H), 4.03-3.90 (m, 1H), 2.71 (q, J=7.6 Hz, 2H), 1.26 (t, J=7.6 Hz, 3H).

Example 543

2-[3-Chloro-6-(3-fluorophenyl)pyrrolo[3,2-b]pyridin-1-yl]-1-(3-fluoroazetidin-1-yl)ethanone

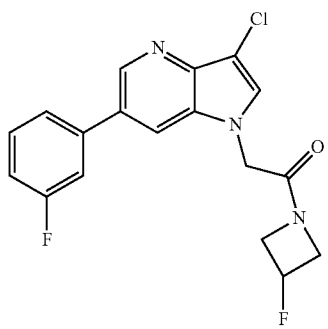 [SMILES: O=C(Cn1cc(Cl)c2ncc(-c3cccc(F)c3)cc21)N1CC(F)C1]

The title compound was prepared in a manner analogous to Example 146. MS (ESI): mass calcd. for $C_{18}H_{14}ClF_2N_3O$, 361.1. m/z found, 362.0 [M+H]+. 1H NMR (500 MHz, DMSO-$d_6$) δ 8.78 (d, J=1.9 Hz, 1H), 8.29 (d, J=1.9 Hz, 1H), 7.82 (5, 1 H), 7.66-7.61 (m, 2H), 7.59-7.53 (m, 1H), 7.28-7.20 (m, 1H), 5.57-5.39 (m, 1H), 5.08 (d, J=2.3 Hz, 2H), 4.64-4.53 (m, 1H), 4.40-4.30 (m, 1H), 4.30-4.20 (m, 1H), 4.04-3.91 (m, 1H).

Example 544

2-[3-Chloro-6-(3-chloro-2-fluoro-phenyl)pyrrolo[3,2-b]pyridin-1-yl]-N,N-dimethyl-acetamide

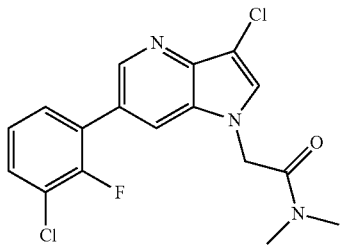

The title compound was prepared in a manner analogous to Example 146. MS (ESI): mass calcd. for $C_{17}H_{14}Cl_2FN_3O$, 365.0. m/z found, 366.0 [M+H]$^+$. $^1$H NMR (400 MHz, CD$_3$OD) δ 8.55 (t, J=1.9 Hz, 1H), 8.08 (t, J=1.5 Hz, 1H), 7.66 (s, 1H), 7.57-7.48 (m, 2H), 7.34-7.26 (m, 1H), 5.28 (s, 2H), 3.18 (s, 3H), 2.97 (s, 3H).

Example 545

2-[3-Chloro-6-(3-chlorophenyl)pyrrolo[3,2-b]pyridin-1-yl]-1-(3-fluoroazetidin-1-yl)ethanone

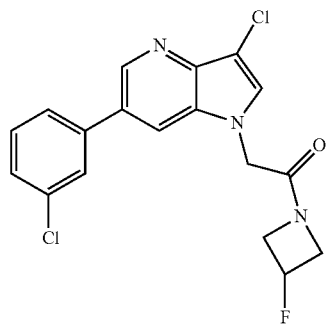 [SMILES: O=C(Cn1cc(Cl)c2ncc(-c3cccc(Cl)c3)cc21)N1CC(F)C1]

The title compound was prepared in a manner analogous to Example 146. MS (ESI): mass calcd. for $C_{18}H_{14}Cl_2FN_3O$, 377.0. m/z found, 378.0 [M+H]$^+$. $^1$H NMR (500 MHz, DMSO-d$_6$) δ 8.76 (d, J=1.9 Hz, 1H), 8.30 (d, J=1.9 Hz, 1H), 7.84 (t, J=1.9 Hz, 1H), 7.82 (s, 1H), 7.78-7.73 (m, 1H), 7.55 (t, J=7.9 Hz, 1H), 7.49-7.45 (m, 1H), 5.56-5.39 (m, 1H), 5.09 (d, J=2.0 Hz, 2H), 4.64-4.53 (m, 1H), 4.42-4.30 (m, 1H), 4.30-4.20 (m, 1H), 4.04-3.92 (m, 1H).

Example 546

2-[3-Chloro-6-[3-(difluoromethyl)phenyl]pyrrolo[3,2-b]pyridin-1-yl]-1-(3-fluoroazetidin-1-yl)ethanone

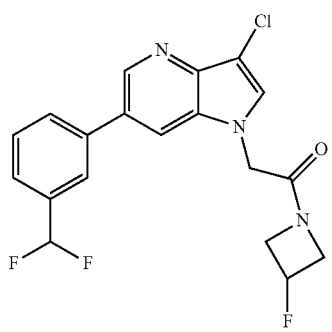 [SMILES: O=C(Cn1cc(Cl)c2ncc(-c3cccc(C(F)F)c3)cc21)N1CC(F)C1]

The title compound was prepared in a manner analogous to Example 146. MS (ESI): mass calcd. for $C_{19}H_{15}ClF_3N_3O$, 393.1. m/z found, 394.0 [M+H]$^+$. $^1$H NMR (400 MHz, DMSO-d$_6$) δ 8.76 (s, 1H), 8.28 (s, 1H), 7.96-7.92 (m, 2H), 7.82 (s, 1H), 7.73-7.56 (m, 2H), 7.30-6.95 (m, 1H), 5.60-5.36 (m, 1H), 5.10 (s, 2H), 4.66-4.50 (m, 1H), 4.43-4.17 (m, 2H), 4.05-3.89 (m, 1H).

Example 547

1-(Azetidin-1-yl)-2-[3-fluoro-2-methyl-6-(m-tolyl)pyrrolo[3,2-b]pyridin-1-yl]ethanone

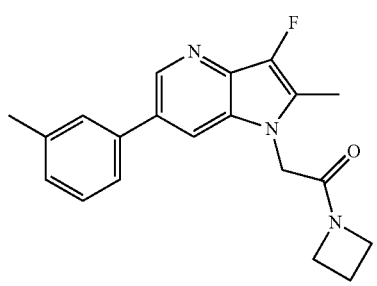 [SMILES: Cc1cccc(-c2cnc3c(F)c(C)n(CC(=O)N4CCC4)c3c2)c1]

To a solution of compound of 1-(azetidin-1-yl)-2-[2-methyl-6-(m-tolyl)pyrrolo[3,2-b]pyridin-1-yl]ethanone (Example 41,104 mg, 0.32 mmol) and Selectfluor® (135 mg, 0.38 mmol) in ACN (0.63 mL) was added pyridine (0.18 mL, 2.34 mmol). The reaction mixture was stirred at room temperature for 12 hours, concentrated under reduced pressure. Purification (FCC, SiO$_2$, 50-100% EtOAc in hexanes) afforded the title compound (6.4 mg, 6%). MS (ESI): mass calcd. for $C_{20}H_{20}FN_3O$, 337.2. m/z found, 338.1 [M+H]$^+$. $^1$H NMR (500 MHz, CD$_3$OD) δ 8.52 (d, J=1.7 Hz, 1H), 8.01 (dd, J=2.4, 1.8 Hz, 1H), 7.50 (s, 1H), 7.48-7.44 (m, 1H), 7.36 (t, J=7.6 Hz, 1H), 7.23-7.18 (m, 1H), 4.94 (s, 2H), 4.32 (t, J=7.7 Hz, 2H), 4.07 (t, J=7.8 Hz, 2H), 2.43 (s, 3H), 2.41 (d, J=2.0 Hz, 3H), 2.41-2.34 (m, 2H).

Example 548

1-(Azetidin-1-yl)-2-[6-(3,4-difluorophenyl)-3-methyl-pyrrolo[3,2-b]pyridin-1-yl]ethanone

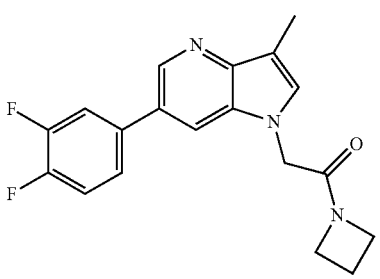 [SMILES: Cc1cn(CC(=O)N2CCC2)c2cc(-c3ccc(F)c(F)c3)cnc12]

The title compound was prepared in a manner analogous to Example 27. MS (ESI): mass calcd. for $C_{19}H_{17}F_2N_3O$, 341.1. m/z found, 342.0 [M+H]$^+$. $^1$H NMR (300 MHz, CDCl$_3$) δ 8.61 (s, 1H), 7.83 (s, 1H), 7.47-7.37 (m, 1H), 7.37-7.29 (m, 1H), 7.29-7.18 (m, 2H), 4.77 (s, 2H), 4.09 (t, J=7.7 Hz, 2H), 4.00 (t, J=7.6 Hz, 2H), 2.45 (s, 3H), 2.38-2.21 (m, 2H).

Example 549

2-[6-(3,4-Difluorophenyl)-3-methyl-pyrrolo[3,2-b]pyridin-1-yl]-N,N-dimethyl-acetamide

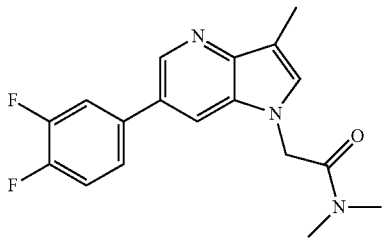 [SMILES: Cc1cn(CC(=O)N(C)C)c2cc(-c3ccc(F)c(F)c3)cnc12]

The title compound was prepared in a manner analogous to Example 27. MS (ESI): mass calcd. for $C_{18}H_{17}F_2N_3O$, 329.1. m/z found, 330.0 [M+H]$^+$. $^1$H NMR (300 MHz, CDCl$_3$) δ 8.50 (s, 1H), 8.05 (s, 1H), 7.41-7.21 (m, 4H), 5.09 (s, 2H), 3.14 (s, 3H), 2.96 (s, 3H), 2.47 (s, 3H).

Example 550

1-(3-Fluoroazetidin-1-yl)-2-[3-methyl-6-(m-tolyl)pyrrolo[3,2-b]pyridin-1-yl]ethanone

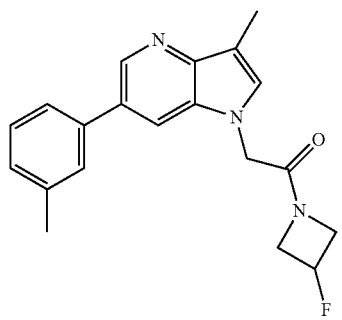 [SMILES: Cc1cccc(-c2cnc3c(C)cn(CC(=O)N4CC(F)C4)c3c2)c1]

The title compound was prepared in a manner analogous to Example 27. MS (ESI): mass calcd. for $C_{20}H_{20}FN_3O$, 337.2. m/z found, 338.0 [M+H]$^+$. $^1$H NMR (300 MHz, DMSO-d$_6$) δ 8.61 (d, J=1.8 Hz, 1H), 8.02 (d, J=1.8 Hz, 1H), 7.57-7.47 (m, 2H), 7.43-7.34 (m, 2H), 7.19 (d, J=7.6 Hz, 1H), 5.58-5.44 (m, 1H), 5.00 (s, 2H), 4.61-4.42 (m, 1H), 4.37-4.14 (m, 2H), 4.04-3.86 (m, 1H), 2.41 (s, 3H), 2.30 (s, 3H).

Example 551

2-[6-(3,4-Difluorophenyl)-3-methyl-pyrrolo[3,2-b]pyridin-1-yl]-1-(3-fluoroazetidin-1-yl)ethanone

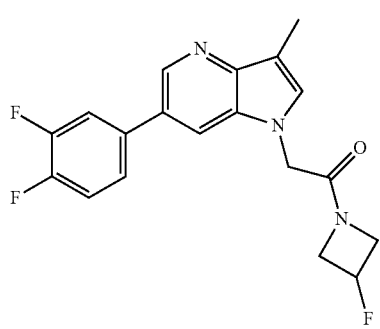 [SMILES: Cc1cn(CC(=O)N2CC(F)C2)c2cc(-c3ccc(F)c(F)c3)cnc12]

The title compound was prepared in a manner analogous to Example 27. MS (ESI): mass calcd. for $C_{19}H_{18}F_3N_3O$, 359.1. m/z found, 360.0 [M+H]$^+$. $^1$H NMR (300 MHz, DMSO-d$_6$) δ 8.65 (d, J=1.7 Hz, 1H), 8.10 (d, J=1.7 Hz, 1H), 7.89-7.79 (m, 1H), 7.64-7.50 (m, 2H), 7.40 (s, 1H), 5.59-5.30 (m, 1H), 4.99 (s, 2H), 4.61-4.43 (m, 1H), 4.35-4.15 (m, 2H), 4.04-3.87 (m, 1H), 2.30 (s, 3H).

Example 552

1-(Azetidin-1-yl)-2-[3-methyl-6-[3-(trifluoromethyl)phenyl]pyrrolo[3,2-b]pyridin-1-yl]ethanone

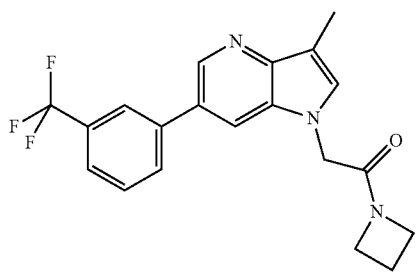 [SMILES: Cc1cn(CC(=O)N2CCC2)c2cc(-c3cccc(C(F)(F)F)c3)cnc12]

The title compound was prepared in a manner analogous to Example 27. MS (ESI): mass calcd. for $C_{20}H_{18}F_3N_3O$, 373.1. m/z found, 374.0 [M+H]$^+$. $^1$H NMR (300 MHz, CDCl$_3$) δ 8.71 (s, 1H), 8.25 (br. s, 1H), 7.89-7.78 (m, 2H), 7.76-7.57 (m, 2H), 7.45 (s, 1H), 4.89 (s, 2H), 4.34-4.22 (m, 2H), 4.13 (t, J=7.8 Hz, 2H), 2.59 (s, 3H), 2.50-2.32 (m, 2H).

Example 553

N,N-Dimethyl-2-[3-methyl-6-[3-(trifluoromethyl)phenyl]pyrrolo[3,2-b]pyridin-1-yl]acetamide

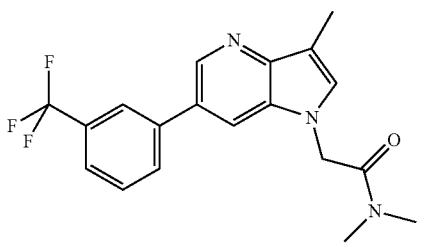 [SMILES: Cc1cn(CC(=O)N(C)C)c2cc(-c3cccc(C(F)(F)F)c3)cnc12]

The title compound was prepared in a manner analogous to Example 27. MS (ESI): mass calcd. for $C_{19}H_{18}F_3N_3O$, 361.1. m/z found, 362.0 [M+H]$^+$. $^1$H NMR (300 MHz, CDCl$_3$) δ 8.67 (s, 1H), 7.86-7.74 (m, 3H), 7.67-7.54 (m, 2H), 7.22 (s, 1H), 4.98 (s, 2H), 3.15 (s, 3H), 3.01 (s, 3H), 2.47 (s, 3H).

Example 554

1-(3-Fluoroazetidin-1-yl)-2-[3-methyl-6-[3-(trifluoromethyl)phenyl]pyrrolo[3,2-b]pyridin-1-yl]ethanone

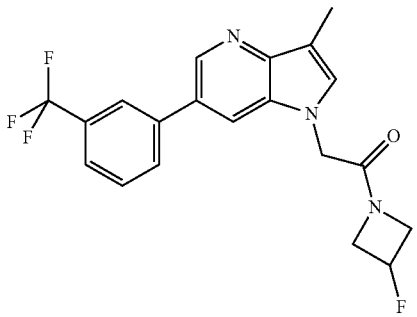 [SMILES: Cc1cn(CC(=O)N2CC(F)C2)c2cc(-c3cccc(C(F)(F)F)c3)cnc12]

The title compound was prepared in a manner analogous to Example 27. MS (ESI): mass calcd. for $C_{20}H_{17}F_4N_3O$, 391.1. m/z found, 392.0 [M+H]$^+$. $^1$H NMR (300 MHz, DMSO-d$_6$) δ 8.69 (d, J=1.9 Hz, 1H), 8.17 (d, J=1.9 Hz, 1H), 8.10-7.99 (m, 2H), 7.74 (d, J=4.7 Hz, 2H), 7.42 (s, 1H), 5.59-5.28 (m, 1H), 5.02 (s, 2H), 4.61-4.42 (m, 1H), 4.37-4.15 (m, 2H), 4.04-3.87 (m, 1H), 2.31 (s, 3H).

Example 555

2-[6-(3,5-Difluorophenyl)-3-methyl-pyrrolo[3,2-b]pyridin-1-yl]-N,N-dimethyl-acetamide

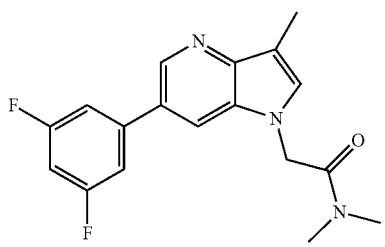 [SMILES: Cc1cn(CC(=O)N(C)C)c2cc(-c3cc(F)cc(F)c3)cnc12]

The title compound was prepared in a manner analogous to Example 27. MS (ESI): mass calcd. for $C_{16}H_{17}F_2N_3O$, 329.1. m/z found, 330.0 [M+H]$^+$. $^1$H NMR (300 MHz, DMSO-d$_6$) δ 8.70 (d, J=1.9 Hz, 1H), 8.18 (d, J=2.0 Hz, 1H), 7.59-7.48 (m, 2H), 7.38 (s, 1H), 7.28-7.15 (m, 1H), 5.19 (s, 2H), 3.12 (s, 3H), 2.86 (s, 3H), 2.30 (s, 3H).

Example 556

1-(Azetidin-1-yl)-2-[6-(3,5-difluorophenyl)-3-methyl-pyrrolo[3,2-b]pyridin-1-yl]ethanone

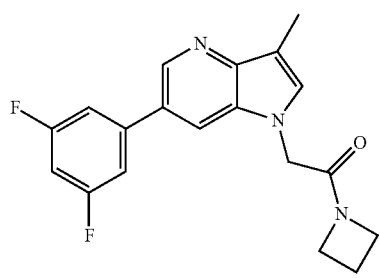 [SMILES: Cc1cn(CC(=O)N2CCC2)c2cc(-c3cc(F)cc(F)c3)cnc12]

The title compound was prepared in a manner analogous to Example 27. MS (ESI): mass calcd. for $C_{19}H_{17}F_2N_3O$, 341.1. m/z found, 342.0 [M+H]$^+$. $^1$H NMR (300 MHz, DMSO-d$_6$) δ 8.71 (d, J=2.0 Hz, 1H), 8.18 (d, J=2.0 Hz, 1H), 7.60-7.49 (m, 2H), 7.42 (s, 1H), 7.30-7.15 (m, 1H), 4.94 (s, 2H), 4.20 (t, J=7.7 Hz, 2H), 3.90 (t, J=7.7 Hz, 2H), 2.34-2.19 (m, 5H).

Example 557

2-[6-(3,5-Difluorophenyl)-3-methyl-pyrrolo[3,2-b]pyridin-1-yl]-N-ethyl-N-methyl-acetamide

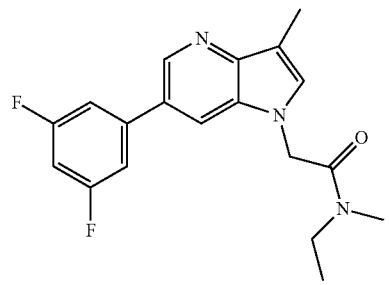 [SMILES: CCN(C)C(=O)Cn1cc(C)c2ncc(-c3cc(F)cc(F)c3)cc21]

The title compound was prepared in a manner analogous to Example 27. MS (ESI): mass calcd. for $C_{19}H_{19}F_2N_3O$, 343.1. m/z found, 344.0 [M+H]$^+$. $^1$H NMR (300 MHz, DMSO-d$_6$) δ 8.70 (s, 1H), 8.23-8.07 (m, 1H), 7.60-7.46 (m, 2H), 7.45-7.35 (m, 1H), 7.27-7.15 (m, 1H), 5.20 (s, 0.8H), 5.17 (s, 1.2H), 3.48 (q, J=7.0 Hz, 1.2H), 3.32-3.20 (m, 0.8H), 3.09 (s, 1.8H), 2.82 (s, 1.2H), 2.30 (s, 3H), 1.24 (t, J=7.0 Hz, 1.2H), 1.03 (t, J=7.1 Hz, 1.8H).

Example 558

2-[6-(4-Fluorophenyl)-3-methyl-pyrrolo[3,2-b]pyridin-1-yl]-N,N-dimethyl-acetamide

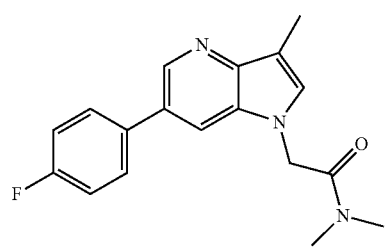 [SMILES: Cc1cn(CC(=O)N(C)C)c2cc(-c3ccc(F)cc3)cnc12]

The title compound was prepared in a manner analogous to Example 27. MS (ESI): mass calcd. for $C_{16}H_{16}FN_3O$, 311.1. m/z found, 312.0 [M+H]$^+$. $^1$H NMR (300 MHz, DMSO-d$_6$) δ 8.59 (d, J=1.9 Hz, 1H), 8.02 (d, J=1.9 Hz, 1H), 7.80-7.70 (m, 2H), 7.39-7.27 (m, 3H), 5.18 (s, 2H), 3.11 (s, 3H), 2.85 (s, 3H), 2.30 (s, 3H).

Example 559

N-Ethyl-2-[6-(4-fluorophenyl)-3-methyl-pyrrolo[3,2-b]pyridin-1-yl]-N-methyl-acetamide

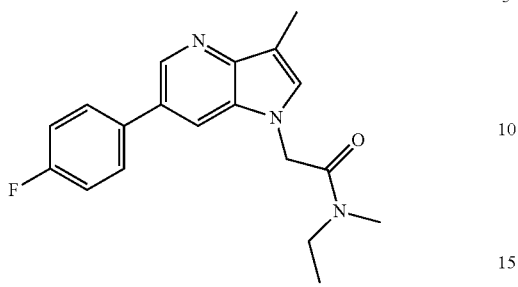

The title compound was prepared in a manner analogous to Example 27. MS (ESI): mass calcd. for $C_{19}H_{20}FN_3O$, 325.2. m/z found, 326.0 [M+H]$^+$. $^1$H NMR (300 MHz, CDCl$_3$) δ 8.65 (s, 1H), 7.65-7.51 (m, 3H), 7.21-7.09 (m, 3H), 4.89 (d, J=9.2 Hz, 2H), 3.53-3.38 (m, 2H), 3.07-2.90 (m, 3H), 2.44 (s, 3H), 1.29-1.05 (m, 3H).

Example 560

N-Ethyl-2-[6-(2-fluoro-3-methyl-phenyl)-3-methyl-pyrrolo[3,2-b]pyridin-1-yl]-N-methyl-acetamide

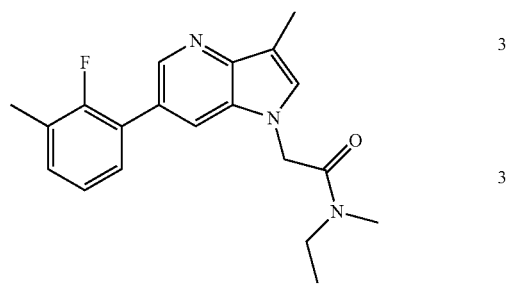

The title compound was prepared in a manner analogous to Example 27. MS (ESI): mass calcd. for $C_{20}H_{22}FN_3O$, 339.2. m/z found, 340.0 [M+H]$^+$. 1H NMR (300 MHz, DMSO-d$_6$) δ 8.44 (s, 1H), 7.93-7.84 (m, 1H), 7.42-7.26 (m, 3H), 7.25-7.16 (m, 1H), 5.18 (s, 0.8H), 5.14 (s, 1.2H), 3.45 (d, J=7.1 Hz, 1.2H), 3.32-3.21 (m, 0.8H), 3.06 (s, 1.8H), 2.81 (s, 1.2H), 2.32 (s, 3H), 2.30 (s, 3H), 1.20 (t, J=7.1 Hz, 1.2H), 1.01 (t, J=7.0 Hz, 1.8H).

Example 561

1-(Azetidin-1-yl)-2-[6-(2-fluoro-3-methyl-phenyl)-3-methyl-pyrrolo[3,2-b]pyridin-1-yl]ethanone

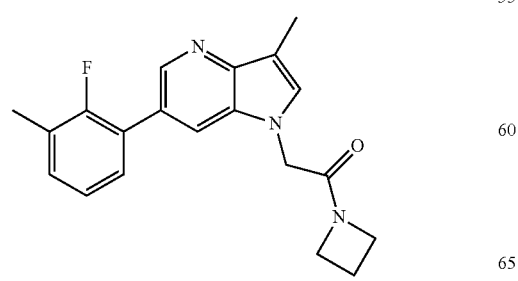

The title compound was prepared in a manner analogous to Example 27. MS (ESI): mass calcd. for $C_{20}H_{20}FN_3O$, 337.2. m/z found, 337.0 [M+H]$^+$. $^1$H NMR (300 MHz, DMSO-d$_6$) δ 8.45 (s, 1H), 7.91 (s, 1H), 7.42-7.27 (m, 3H), 7.22 (t, J=7.5 Hz, 1H), 4.91 (s, 2H), 4.18 (t, J=7.6 Hz, 2H), 3.89 (t, J=7.7 Hz, 2H), 2.36-2.17 (m, 8H).

Example 562

2-[6-(2-Fluoro-3-methyl-phenyl)-3-methyl-pyrrolo[3,2-b]pyridin-1-yl]-N,N-dimethyl-acetamide

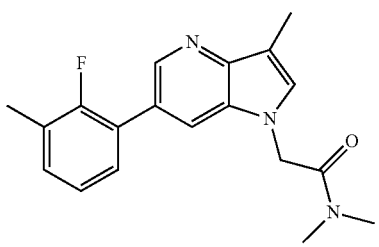

The title compound was prepared in a manner analogous to Example 27. MS (ESI): mass calcd. for $C_{19}H_{20}FN_3O$, 325.2. m/z found, 326.0 [M+H]$^+$. $^1$H NMR (300 MHz, DMSO-d$_6$) δ 8.47-8.42 (m, 1H), 7.92-7.88 (m, 1H), 7.42-7.26 (m, 3H), 7.26-7.16 (m, 1H), 5.17 (s, 2H), 3.09 (s, 3H), 2.84 (s, 3H), 2.35-2.27 (m, 6H).

Example 563

1-(3-Fluoroazetidin-1-yl)-2-[6-(2-fluoro-3-methyl-phenyl)-3-methyl-pyrrolo[3,2-b]pyridin-1-yl]ethanone

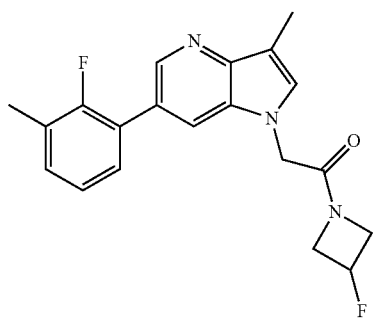 [SMILES: Cc1cccc(-c2cnc3c(C)cn(CC(=O)N4CC(F)C4)c3c2)c1F]

The title compound was prepared in a manner analogous to Example 27. MS (ESI): mass calcd. for $C_{20}H_{19}F_2N_3O$, 355.1. m/z found, 356.0 [M+H]$^+$. $^1$H NMR (300 MHz, CDCl$_3$) δ 8.66 (s, 1H), 7.74 (s, 1H), 7.38-7.10 (m, 4H), 5.33-5.02 (m, 1H), 4.77 (s, 2H), 4.41-4.06 (m, 2H), 3.91-3.74 (m, 2H), 2.45 (s, 3H), 2.36 (s, 3H).

Example 564

1-(3,3-Difluoroazetidin-1-yl)-2-[6-(2-fluoro-3-methyl-phenyl)-3-methyl-pyrrolo[3,2-b]pyridin-1-yl]ethanone

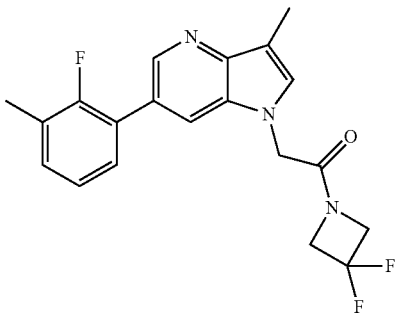 [SMILES: Cc1cccc(-c2cnc3c(C)cn(CC(=O)N4CC(F)(F)C4)c3c2)c1F]

The title compound was prepared in a manner analogous to Example 27. MS (ESI): mass calcd. for $C_{20}H_{18}F_3N_3O$, 373.1. m/z found, 373.0 [M+H]$^+$. $^1$H NMR (300 MHz, DMSO-d$_6$) δ 8.48-8.44 (m, 1H), 7.97-7.93 (m, 1H), 7.42-7.27 (m, 3H), 7.26-7.18 (m, 1H), 5.05 (s, 2H), 4.70 (t, J=12.5 Hz, 2H), 4.35 (t, J=12.6 Hz, 2H), 2.36-2.26 (m, 6H).

Example 565

2-[6-(2-Fluoro-3-methyl-phenyl)-3-methyl-pyrrolo[3,2-b]pyridin-1-yl]-1-pyrrolidin-1-yl-ethanone

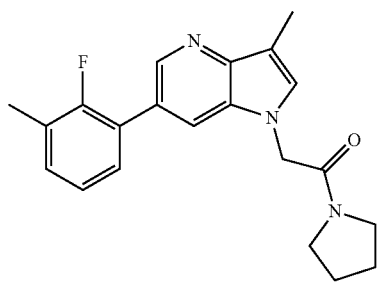 [SMILES: Cc1cccc(-c2cnc3c(C)cn(CC(=O)N4CCCC4)c3c2)c1F]

The title compound was prepared in a manner analogous to Example 27. MS (ESI): mass calcd. for $C_{21}H_{22}FN_3O$, 351.2. m/z found, 352.0 [M+H]$^+$. $^1$H NMR (300 MHz, CDCl$_3$) δ 8.60 (s, 1H), 7.75 (s, 1H), 7.49-7.06 (m, 4H), 4.83 (s, 2H), 3.51 (t, J=6.9 Hz, 2H), 3.42 (t, J=6.7 Hz, 2H), 2.42 (s, 3H), 2.35 (s, 3H), 2.06-1.95 (m, 2H), 1.92-1.82 (m, 2H).

Example 566

2-[6-(4-Fluoro-3-methyl-phenyl)-3-methyl-pyrrolo[3,2-b]pyridin-1-yl]-N,N-dimethyl-acetamide

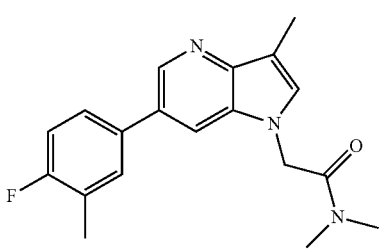 [SMILES: Cc1cc(-c2cnc3c(C)cn(CC(=O)N(C)C)c3c2)ccc1F]

The title compound was prepared in a manner analogous to Example 27. MS (ESI): mass calcd. for $C_{19}H_{20}FN_3O$, 325.2. m/z found, 326.0 [M+H]$^+$. $^1$H NMR (300 MHz, DMSO-d$_6$) δ 8.58 (d, J=1.8 Hz, 1H), 8.01 (d, J=1.9 Hz, 1H), 7.67-7.60 (m, 1H), 7.59-7.51 (m, 1H), 7.33 (s, 1H), 7.25 (t, J=9.1 Hz, 1H), 5.18 (s, 2H), 3.11 (s, 3H), 2.85 (s, 3H), 2.33 (s, 3H), 2.29 (s, 3H).

Example 567

2-[3-Methyl-6-[3-(trifluoromethyl)phenyl]pyrrolo[3,2-b]pyridin-1-yl]-1-pyrrolidin-1-yl-ethanone

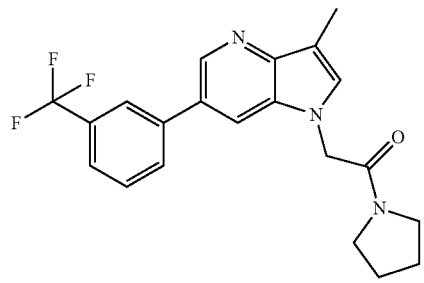 [SMILES: Cc1cn(CC(=O)N2CCCC2)c2cc(-c3cccc(C(F)(F)F)c3)cnc12]

The title compound was prepared in a manner analogous to Example 27. MS (ESI): mass calcd. for $C_{21}H_{20}F_3N_3O$, 387.2. m/z found, 388.0 [M+H]$^+$. $^1$H NMR (300 MHz, CDCl$_3$) δ 8.68 (s, 1H), 7.91-7.76 (m, 2H), 7.70 (s, 1H), 7.65-7.50 (m, 2H), 7.20 (s, 1H), 4.85 (s, 2H), 3.64-3.41 (m, 4H), 2.43 (s, 3H), 2.15-1.97 (m, 2H), 1.97-1.81 (m, 2H).

Example 568

N-Ethyl-N-methyl-2-[3-methyl-6-[3-(trifluoromethyl)phenyl]pyrrolo[3,2-b]pyridin-1-yl]acetamide

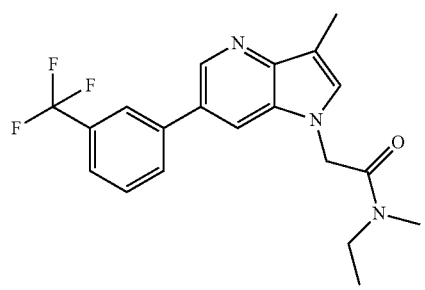 [SMILES: CCN(C)C(=O)Cn1cc(C)c2ncc(-c3cccc(C(F)(F)F)c3)cc21]

The title compound was prepared in a manner analogous to Example 27. MS (ESI): mass calcd. for $C_{20}H_{20}F_3N_3O$, 375.2. m/z found, 376.0 [M+H]$^+$. $^1$H NMR (300 MHz, CDCl$_3$) δ 8.68 (s, 1H), 7.88-7.76 (m, 2H), 7.69-7.51 (m, 3H), 7.18 (s, 1H), 4.92 (d, J=8.7 Hz, 2H), 3.59-3.34 (m, 2H), 3.08 (s, 1.5H), 2.98 (s, 1.5H), 2.44 (s, 3H), 1.25 (t, J=7.2 Hz, 1.5H), 1.14 (t, J=7.1 Hz, 1.5H).

Example 569

1-(3,3-Difluoroazetidin-1-yl)-2-[3-methyl-6-[3-(trifluoromethyl)phenyl]pyrrolo[3,2-b]pyridin-1-yl]ethanone

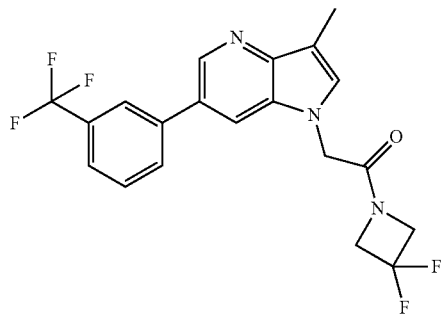 [SMILES: Cc1cn(CC(=O)N2CC(F)(F)C2)c2cc(-c3cccc(C(F)(F)F)c3)cnc12]

The title compound was prepared in a manner analogous to Example 27. MS (ESI): mass calcd. for $C_{20}H_{16}F_5N_3O$, 409.1. m/z found, 410.0 [M+H]$^+$. $^1$H NMR (300 MHz, CDCl$_3$) δ 8.75 (s, 1H), 7.89-7.78 (m, 2H), 7.72-7.57 (m, 3H), 7.16 (s, 1H), 4.85 (s, 2H), 4.39 (t, J=12.0 Hz, 2H), 4.00 (t, J=11.5 Hz, 2H), 2.46 (s, 3H).

Example 570

1-(Azetidin-1-yl)-2-[3-methyl-6-(3,4,5-trifluorophenyl)pyrrolo[3,2-b]pyridin-1-yl]ethanone

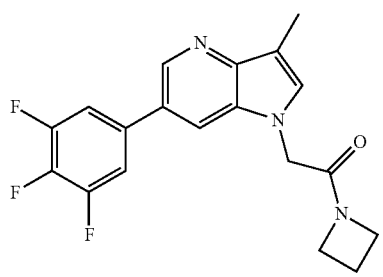 [SMILES: Cc1cn(CC(=O)N2CCC2)c2cc(-c3cc(F)c(F)c(F)c3)cnc12]

The title compound was prepared in a manner analogous to Example 27. MS (ESI): mass calcd. for $C_{19}H_{16}F_3N_3O$, 359.1. m/z found, 360.0 [M+H]$^+$. $^1$H NMR (300 MHz, DMSO-d$_6$) δ 8.69 (d, J=1.7 Hz, 1H), 8.16 (d, J=1.7 Hz, 1H), 7.79 (dd, J=9.6, 6.8 Hz, 2H), 7.42 (s, 1H), 4.93 (s, 2H), 4.19 (t, J=7.6 Hz, 2H), 3.90 (t, J=7.6 Hz, 2H), 2.38-2.15 (m, 5H).

Example 571

N,N-Dimethyl-2-[3-methyl-6-(3,4,5-trifluorophenyl)pyrrolo[3,2-b]pyridin-1-yl]acetamide

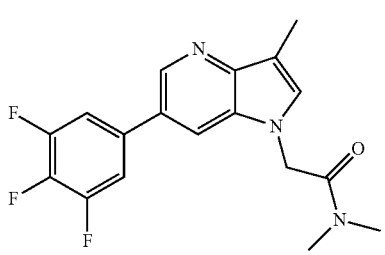 [SMILES: Cc1cn(CC(=O)N(C)C)c2cc(-c3cc(F)c(F)c(F)c3)cnc12]

The title compound was prepared in a manner analogous to Example 27. MS (ESI): mass calcd. for $C_{18}H_{16}F_3N_3O$, 347.1. m/z found, 348.0 [M+H]$^+$. $^1$H NMR (300 MHz, DMSO-d$_6$) δ 8.69 (d, J=1.6 Hz, 1H), 8.15 (d, J=1.5 Hz, 1H), 7.77 (dd, J=9.5, 6.8 Hz, 2H), 7.41 (d, J=17.8 Hz, 1H), 5.18 (s, 2H), 3.12 (s, 3H), 2.86 (s, 3H), 2.30 (s, 3H).

Example 572

N,N-Dimethyl-2-[3-methyl-6-(m-tolyl)pyrrolo[3,2-b]pyridin-1-yl]acetamide

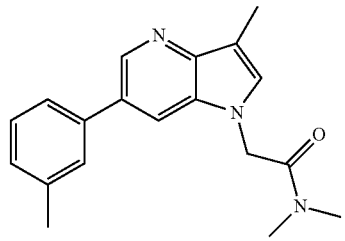 [SMILES: Cc1cccc(-c2cnc3c(C)cn(CC(=O)N(C)C)c3c2)c1]

The title compound was prepared in a manner analogous to Example 27. MS (ESI): mass calcd. for $C_{19}H_{21}N_3O$, 307.2. m/z found, 308.0 [M+H]$^+$. $^1$H NMR (300 MHz, CDCl$_3$) δ 8.57 (s, 1H), 7.96 (s, 1H), 7.42-7.18 (m, 5H), 5.06 (s, 2H), 3.16 (s, 3H), 3.01 (s, 3H), 2.44 (s, 3H), 2.42 (s, 3H).

Example 573

N,N-Dimethyl-2-[3-methyl-6-(4-methyl-2-thienyl)pyrrolo[3,2-b]pyridin-1-yl]acetamide

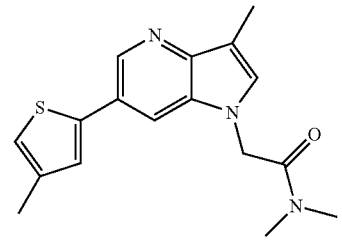 [SMILES: Cc1csc(-c2cnc3c(C)cn(CC(=O)N(C)C)c3c2)c1]

The title compound was prepared in a manner analogous to Example 27. MS (ESI): mass calcd. for $C_{17}H_{19}N_3OS$, 313.1. m/z found, 314.0 [M+H]$^+$. $^1$H NMR (300 MHz, CDCl$_3$) δ 8.68 (d, J=1.6 Hz, 1H), 7.68 (s, 1H), 7.14 (d, J=3.8 Hz, 2H), 6.88 (s, 1H), 4.90 (s, 2H), 3.11 (s, 3H), 3.00 (s, 3H), 2.41 (s, 3H), 2.30 (s, 3H).

Example 574

1-(Azetidin-1-yl)-2-[3-methyl-6-(4-methyl-2-thienyl)pyrrolo[3,2-b]pyridin-1-yl]ethanone

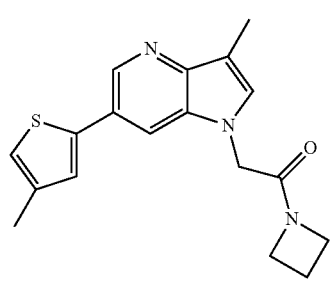 [SMILES: Cc1csc(-c2cnc3c(C)cn(CC(=O)N4CCC4)c3c2)c1]

The title compound was prepared in a manner analogous to Example 27. MS (ESI): mass calcd. for C₁₈H₁₉N₃OS, 325.1. m/z found, 326.0 [M+H]⁺. ¹H NMR (300 MHz, CDCl₃) δ 8.70 (s, 1H), 7.73 (s, 1H), 7.18 (s, 1H), 7.14 (s, 1H), 6.89 (s, 1H), 4.72 (s, 2H), 4.09 (t, J=7.7 Hz, 2H), 3.85 (t, J=7.7 Hz, 2H), 2.39 (s, 3H), 2.31 (s, 3H), 2.27-2.21 (m, 2H).

Example 575

1-(3-Fluoroazetidin-1-yl)-2-[3-methyl-6-(4-methyl-2-thienyl)pyrrolo[3,2-b]pyridin-1-yl]ethanone

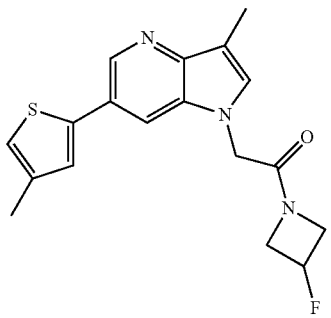 [SMILES: Cc1csc(-c2cnc3c(C)cn(CC(=O)N4CC(F)C4)c3c2)c1]

The title compound was prepared in a manner analogous to Example 27. MS (ESI): mass calcd. for C₁₈H₁₈FN₃OS, 343.1. m/z found, 344.0 [M+H]⁺. ¹H NMR (300 MHz, CDCl₃) δ 8.76 (d, J=1.7 Hz, 1H), 7.65 (s, 1H), 7.18 (s, 1H), 7.10 (s, 1H), 6.90 (s, 1H), 5.29-5.04 (m, 1H), 4.76 (s, 2H), 4.40-4.09 (m, 2H), 3.82 (dd, J=21.7, 4.4 Hz, 2H), 2.42 (s, 3H), 2.32 (s, 3H).

Example 576

N,N-Dimethyl-2-(3-methyl-6-phenyl-pyrrolo[3,2-b]pyridin-1-yl)acetamide

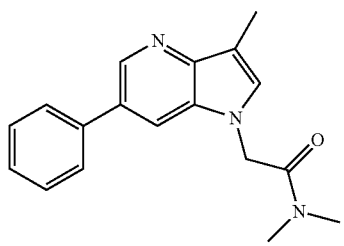 [SMILES: Cc1cn(CC(=O)N(C)C)c2cc(-c3ccccc3)cnc12]

The title compound was prepared in a manner analogous to Example 27. MS (ESI): mass calcd. for C₁₈H₁₉N₃O, 293.2. m/z found, 294.0 [M+H]⁺. ¹H NMR (300 MHz, DMSO-d₆) δ 8.62 (d, J=1.9 Hz, 1H), 8.04 (d, J=1.9 Hz, 1H), 7.77-7.70 (m, 2H), 7.49 (t, J=7.6 Hz, 2H), 7.38 (d, J=7.3 Hz, 1H), 7.33 (s, 1H), 5.18 (s, 2H), 3.11 (s, 3H), 2.85 (s, 3H), 2.30 (s, 3H).

Example 577

N-Ethyl-N-methyl-2-(3-methyl-6-phenyl-pyrrolo[3,2-b]pyridin-1-yl)acetamide

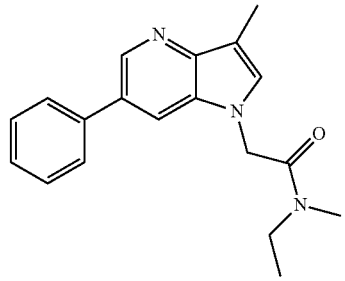 [SMILES: CCN(C)C(=O)Cn1cc(C)c2ncc(-c3ccccc3)cc21]

The title compound was prepared in a manner analogous to Example 27. MS (ESI): mass calcd. for C₁₉H₂₁N₃O, 307.2. m/z found, 308.0 [M+H]⁺. ¹H NMR (300 MHz, DMSO-d₆) δ 8.62 (d, J=2.0 Hz, 1H), 8.01 (dd, J=9.3, 2.0 Hz, 1H), 7.72 (d, J=7.6 Hz, 2H), 7.49 (t, J=7.6 Hz, 2H), 7.42-7.30 (m, 2H), 5.20 (s, 0.8H), 5.16 (s, 1.2H), 3.53-3.41 (m, 0.8H), 3.33-3.26 (m, 1.2H), 3.08 (s, 1.8H), 2.82 (s, 1.2H), 2.30 (s, 3H), 1.22 (t, J=7.0 Hz, 1.2H), 1.02 (t, J=7.1 Hz, 1.8H).

Example 578

1-(3-Fluoroazetidin-1-yl)-2-(3-methyl-6-phenyl-pyrrolo[3,2-b]pyridin-1-yl)ethanone

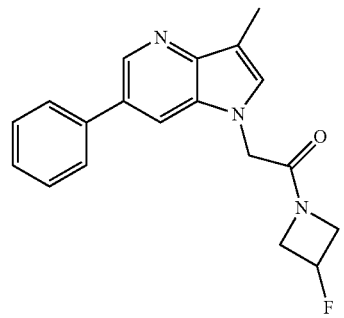 [SMILES: Cc1cn(CC(=O)N2CC(F)C2)c2cc(-c3ccccc3)cnc12]

The title compound was prepared in a manner analogous to Example 27. MS (ESI): mass calcd. for C₁₉H₁₈FN₃O, 323.1. m/z found, 324.0 [M+H]⁺. ¹H NMR (300 MHz, DMSO-d₆) δ 8.64 (d, J=1.9 Hz, 1H), 8.06 (d, J=1.9 Hz, 1H), 7.77-7.68 (m, 2H), 7.57-7.46 (m, 2H), 7.43-7.33 (m, 2H), 5.59-5.29 (m, 1H), 5.00 (s, 2H), 4.61-4.42 (m, 1H), 4.38-4.15 (m, 2H), 4.05-3.85 (m, 1H), 2.30 (s, 3H).

Example 579

1-(3,3-Difluoroazetidin-1-yl)-2-(3-methyl-6-phenyl-pyrrolo[3,2-b]pyridin-1-yl)ethanone

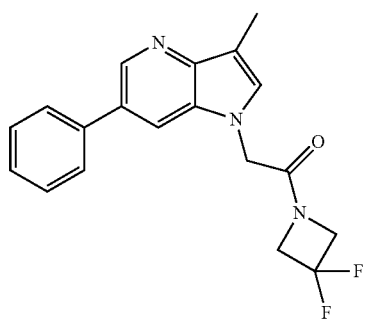 [SMILES: Cc1cn(CC(=O)N2CC(F)(F)C2)c2cc(-c3ccccc3)cnc12]

The title compound was prepared in a manner analogous to Example 27. MS (ESI): mass calcd. for $C_{19}H_{17}F_2N_3O$, 341.1. m/z found, 342.0 [M+H]$^+$. $^1$H NMR (300 MHz, DMSO-d$_6$) δ 8.63 (d, J=1.9 Hz, 1H), 8.06 (d, J=1.9 Hz, 1H), 7.73 (d, J=7.6 Hz, 2H), 7.50 (t, J=7.6 Hz, 2H), 7.43-7.32 (m, 2H), 5.07 (s, 2H), 4.71 (t, J=12.5 Hz, 2H), 4.36 (t, J=12.7 Hz, 2H), 2.30 (s, 3H).

Example 580

1-(3-Fluoroazetidin-1-yl)-2-[6-(4-fluoro-3-methyl-phenyl)-3-methyl-pyrrolo[3,2-b]pyridin-1-yl]ethanone

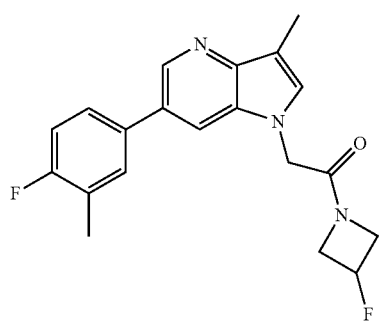 [SMILES: Cc1cc(-c2cnc3c(C)cn(CC(=O)N4CC(F)C4)c3c2)ccc1F]

The title compound was prepared in a manner analogous to Example 27. MS (ESI): mass calcd. for $C_{20}H_{19}F_2N_3O$, 355.1. m/z found, 356.0 [M+H]$^+$. $^1$H NMR (300 MHz, CDCl$_3$) δ 8.60 (s, 1H), 7.89 (s, 1H), 7.40 (d, J=6.2 Hz, 2H), 7.23 (s, 1H), 7.10 (t, J=8.8 Hz, 1H), 5.27-5.01 (m, 1H), 5.01-4.76 (m, 2H), 4.47-3.95 (m, 4H), 2.44 (s, 3H), 2.35 (s, 3H).

Example 581

1-(Azetidin-1-yl)-2-[3-methyl-6-(m-tolyl)pyrrolo[3,2-b]pyridin-1-yl]ethanone

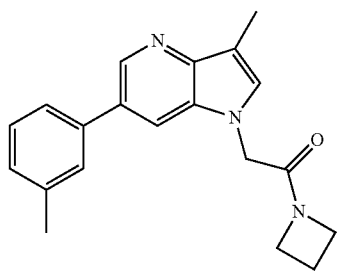 [SMILES: Cc1cccc(-c2cnc3c(C)cn(CC(=O)N4CCC4)c3c2)c1]

The title compound was prepared in a manner analogous to Example 27. MS (ESI): mass calcd. for $C_{20}H_{21}N_3O$, 319.2. m/z found, 320.0 [M+H]$^+$. $^1$H NMR (300 MHz, DMSO-d$_6$) δ 8.61 (d, J=1.7 Hz, 1H), 8.01 (d, J=1.7 Hz, 1H), 7.53 (d, J=12.9 Hz, 2H), 7.37 (d, J=7.7 Hz, 2H), 7.19 (d, J=7.4 Hz, 1H), 4.93 (s, 2H), 4.18 (t, J=7.6 Hz, 2H), 3.89 (t, J=7.6 Hz, 2H), 2.41 (s, 3H), 2.33-2.17 (m, 5H).

Example 582

1-(Azetidin-1-yl)-2-[3-methyl-6-(2,3,4-trifluorophenyl)pyrrolo[3,2-b]pyridin-1-yl]ethanone

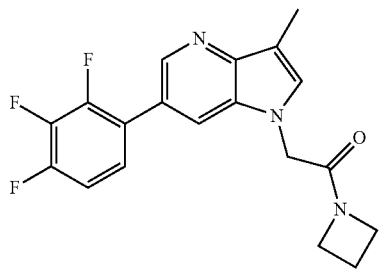 [SMILES: Cc1cn(CC(=O)N2CCC2)c2cc(-c3ccc(F)c(F)c3F)cnc12]

The title compound was prepared in a manner analogous to Example 27. MS (ESI): mass calcd. for $C_{19}H_{16}F_3N_3O$, 359.1. m/z found, 360.0 [M+H]$^+$. $^1$H NMR (300 MHz, DMSO-d$_6$) δ 8.47 (s, 1H), 7.97 (s, 1H), 7.56-7.39 (m, 3H), 4.92 (s, 2H), 4.19 (t, J=7.6 Hz, 2H), 3.89 (t, J=7.7 Hz, 2H), 2.30 (s, 3H), 2.28-2.18 (m, 2H).

Example 583

N,N-Dimethyl-2-[3-methyl-6-(2,3,4-trifluorophenyl)pyrrolo[3,2-b]pyridin-1-yl]acetamide

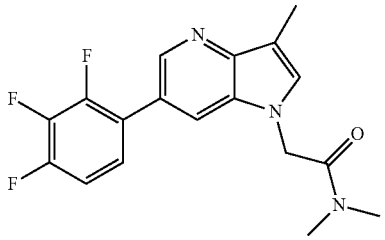 [SMILES: Cc1cn(CC(=O)N(C)C)c2cc(-c3ccc(F)c(F)c3F)cnc12]

The title compound was prepared in a manner analogous to Example 27. MS (ESI): mass calcd. for $C_{18}H_{16}F_3N_3O$, 347.1. m/z found, 348.0 [M+H]$^+$. $^1$H NMR (300 MHz, DMSO-d$_6$) δ 8.46 (s, 1H), 7.96 (s, 1H), 7.54-7.37 (m, 3H), 5.18 (s, 2H), 3.09 (s, 3H), 2.84 (s, 3H), 2.31 (s, 3H).

Example 584

N-Ethyl-N-methyl-2-[3-methyl-6-(2,3,4-trifluorophenyl)pyrrolo[3,2-b]pyridin-1-yl]acetamide

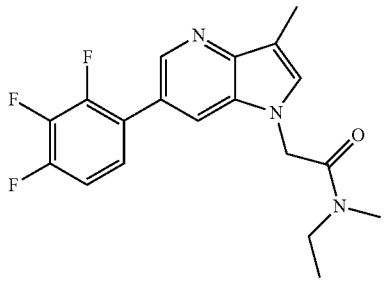 [SMILES: CCN(C)C(=O)Cn1cc(C)c2ncc(-c3ccc(F)c(F)c3F)cc21]

The title compound was prepared in a manner analogous to Example 27. MS (ESI): mass calcd. for $C_{19}H_{18}F_3N_3O$, 361.1. m/z found, 362.0 [M+H]$^+$. $^1$H NMR (300 MHz, DMSO-d$_6$) δ 8.46 (s, 1H), 7.99-7.90 (m, 1H), 7.53-7.38 (m, 3H), 5.19 (s, 0.8H), 5.15 (s, 1.2H), 3.45 (q, J=7.0 Hz, 0.8H), 3.30-3.25 (m, 1.2H), 3.06 (s, 1.8H), 2.81 (s, 1.2H), 2.31 (s, 3H), 1.21 (t, J=7.1 Hz, 1.2H), 1.01 (t, J=7.1 Hz, 1.8H).

Example 585

1-(Azetidin-1-yl)-2-[6-[2-fluoro-3-(trifluoromethyl)phenyl]-3-methyl-pyrrolo[3,2-b]pyridin-1-yl]ethanone

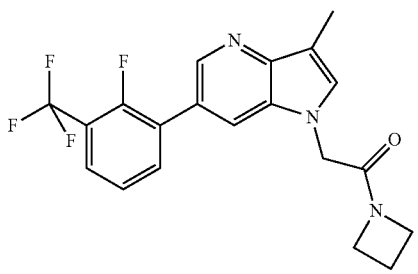 [SMILES: Cc1cn(CC(=O)N2CCC2)c2cc(-c3cccc(C(F)(F)F)c3F)cnc12]

The title compound was prepared in a manner analogous to Example 27. MS (ESI): mass calcd. for $C_{20}H_{17}F_4N_3O$, 391.1. m/z found, 392.0 [M+H]$^+$. $^1$H NMR (300 MHz, DMSO-d$_6$) δ 8.49 (s, 1H), 8.02 (s, 1H), 7.93 (t, J=7.6 Hz, 1H), 7.82 (t, J=6.9 Hz, 1H), 7.56 (t, J=7.8 Hz, 1H), 7.45 (s, 1H), 4.93 (s, 2H), 4.19 (t, J=7.6 Hz, 2H), 3.89 (t, J=7.6 Hz, 2H), 2.31 (s, 3H), 2.29-2.21 (m, 2H).

Example 586

2-[6-[2-Fluoro-3-(trifluoromethyl)phenyl]-3-methyl-pyrrolo[3,2-b]pyridin-1-yl]-N,N-dimethyl-acetamide

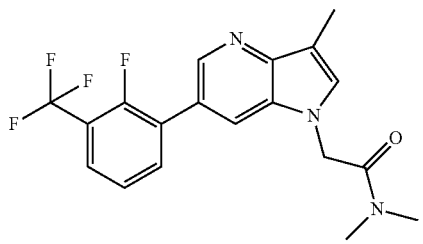 [SMILES: Cc1cn(CC(=O)N(C)C)c2cc(-c3cccc(C(F)(F)F)c3F)cnc12]

The title compound was prepared in a manner analogous to Example 27. MS (ESI): mass calcd. for $C_{19}H_{17}F_4N_3O$, 379.1. m/z found, 380.0 [M+H]$^+$. $^1$H NMR (300 MHz, DMSO-d$_6$) δ 8.50-8.45 (m, 1H), 8.03-7.99 (m, 1H), 7.92 (t, J=7.6 Hz, 1H), 7.81 (t, J=7.2 Hz, 1H), 7.54 (t, J=7.8 Hz, 1H), 7.41 (s, 1H), 5.19 (s, 2H), 3.09 (s, 3H), 2.84 (s, 3H), 2.31 (s, 3H).

Example 587

N-Ethyl-2-[6-[2-fluoro-3-(trifluoromethyl)phenyl]-3-methyl-pyrrolo[3,2-b]pyridin-1-yl]-N-methyl-acetamide

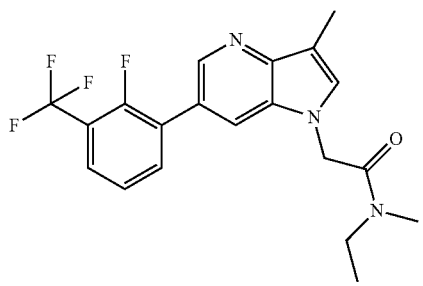 [SMILES: CCN(C)C(=O)Cn1cc(C)c2ncc(-c3cccc(C(F)(F)F)c3F)cc21]

The title compound was prepared in a manner analogous to Example 27. MS (ESI): mass calcd. for $C_{20}H_{19}F_4N_3O$, 393.1. m/z found, 394.0 [M+H]$^+$. $^1$H NMR (300 MHz, DMSO-d$_6$) δ 8.47 (s, 1H), 8.03-7.96 (m, 1H), 7.92 (t, J=7.5 Hz, 1H), 7.81 (t, J=7.1 Hz, 1H), 7.54 (t, J=7.8 Hz, 1H), 7.47-7.39 (m, 1H), 5.20 (s, 0.8H), 5.17 (s, 1.2H), 3.45 (q, J=7.1 Hz, 0.8H), 3.33-3.25 (m, 1.2H), 3.06 (s, 1.8H), 2.81 (s, 1.2H), 2.31 (s, 3H), 1.21 (t, J=7.1 Hz, 1.2H), 1.01 (t, J=7.1 Hz, 1.8H).

Example 588

1-(3-Fluoroazetidin-1-yl)-2-[3-methyl-6-(2,3,4-trifluorophenyl)pyrrolo[3,2-b]pyridin-1-yl]ethanone

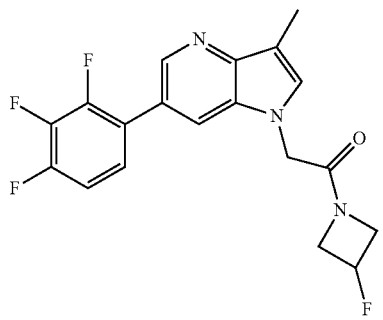 [SMILES: Cc1cn(CC(=O)N2CC(F)C2)c2cc(-c3ccc(F)c(F)c3F)cnc12]

The title compound was prepared in a manner analogous to Example 27. MS (ESI): mass calcd. for $C_{19}H_{15}F_4N_3O$, 377.1. m/z found, 378.0 [M+H]$^+$. $^1$H NMR (300 MHz, DMSO-d$_6$) δ 8.51-8.43 (m, 1H), 7.98 (s, 1H), 7.52-7.40 (m, 3H), 5.59-5.30 (m, 1H), 4.99 (s, 2H), 4.62-4.41 (m, 1H), 4.40-4.12 (m, 2H), 4.04-3.83 (m, 1H), 2.31 (s, 3H).

Example 589

1-(3-Fluoroazetidin-1-yl)-2-[6-[2-fluoro-3-(trifluoromethyl)phenyl]-3-methyl-pyrrolo[3,2-b]pyridin-1-yl]ethanone

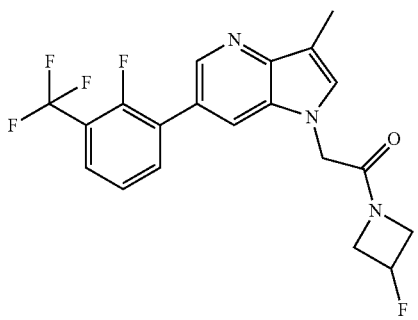 [SMILES: Cc1cn(CC(=O)N2CC(F)C2)c2cc(-c3cccc(C(F)(F)F)c3F)cnc12]

The title compound was prepared in a manner analogous to Example 27. MS (ESI): mass calcd. for $C_{20}H_{18}F_6N_3O$, 409.1. m/z found, 410.0 [M+H]$^+$. $^1$H NMR (300 MHz, DMSO-d$_6$) δ 8.52-8.46 (m, 1H), 8.05-8.00 (m, 1H), 7.97-7.89 (m, 1H), 7.87-7.77 (m, 1H), 7.55 (t, J=7.8 Hz, 1H), 7.46-7.43 (m, 1H), 5.58-5.29 (m, 1H), 5.00 (s, 2H), 4.61-4.41 (m, 1H), 4.38-4.12 (m, 2H), 4.04-3.86 (m, 1H), 2.31 (s, 3H).

Example 590

2-[6-[2-Fluoro-3-(trifluoromethyl)phenyl]-3-methyl-pyrrolo[3,2-b]pyridin-1-yl]-1-pyrrolidin-1-yl-ethanone

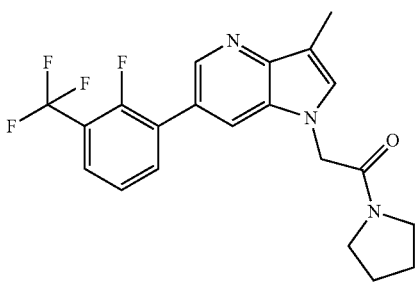 [SMILES: Cc1cn(CC(=O)N2CCCC2)c2cc(-c3cccc(C(F)(F)F)c3F)cnc12]

The title compound was prepared in a manner analogous to Example 27. MS (ESI): mass calcd. for $C_{21}H_{19}F_4N_3O$, 405.1. m/z found, 406.0 [M+H]$^+$. $^1$H NMR (300 MHz, DMSO-d$_6$) δ 8.50-8.45 (m, 1H), 8.04-8.00 (m, 1H), 7.92 (t, J=7.7 Hz, 1H), 7.82 (t, J=7.1 Hz, 1H), 7.55 (t, J=7.8 Hz, 1H), 7.45-7.42 (m, 1H), 5.10 (s, 2H), 3.56 (t, J=6.8 Hz, 2H), 3.34-3.25 (m, 2H), 2.32 (s, 3H), 2.01-1.89 (m, 2H), 1.85-1.72 (m, 2H).

Example 591

2-[3-Methyl-6-(2,3,4-trifluorophenyl)pyrrolo[3,2-b]pyridin-1-yl]-1-pyrrolidin-1-yl-ethanone

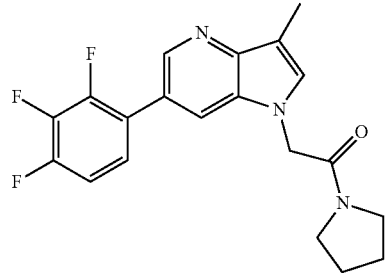 [SMILES: Cc1cn(CC(=O)N2CCCC2)c2cc(-c3ccc(F)c(F)c3F)cnc12]

The title compound was prepared in a manner analogous to Example 27. MS (ESI): mass calcd. for $C_{20}H_{18}F_3N_3O$, 373.1. m/z found, 374.0 [M+H]$^+$. $^1$H NMR (300 MHz, DMSO-d$_6$) δ 8.48-8.43 (m, 1H), 8.00-7.96 (m, 1H), 7.51-7.38 (m, 3H), 5.09 (s, 2H), 3.56 (t, J=6.8 Hz, 2H), 3.34-3.25 (m, 2H), 2.31 (s, 3H), 2.00-1.89 (m, 2H), 1.86-1.72 (m, 2H).

Example 592

1-(Azetidin-1-yl)-2-[6-(2-fluorophenyl)-3-methyl-pyrrolo[3,2-b]pyridin-1-yl]ethanone

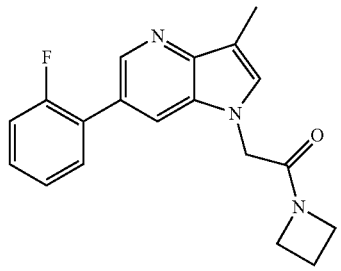 [SMILES: Cc1cn(CC(=O)N2CCC2)c2cc(-c3ccccc3F)cnc12]

The title compound was prepared in a manner analogous to Example 27. MS (ESI): mass calcd. for $C_{19}H_{18}FN_3O$, 323.1. m/z found, 324.0 [M+H]$^+$. $^1$H NMR (300 MHz, DMSO-d$_6$) δ 8.50-8.44 (m, 1H), 7.96-7.91 (m, 1H), 7.63-7.55 (m, 1H), 7.49-7.27 (m, 4H), 4.91 (s, 2H), 4.19 (t, J=7.7 Hz, 2H), 3.89 (t, J=7.7 Hz, 2H), 2.30 (s, 3H), 2.29-2.18 (m, 2H).

Example 593

2-[6-(2-Fluorophenyl)-3-methyl-pyrrolo[3,2-b]pyridin-1-yl]-N,N-dimethyl-acetamide

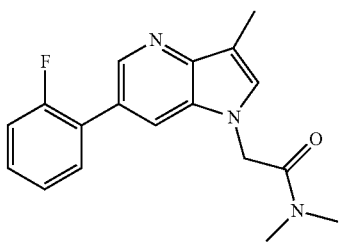 [SMILES: Cc1cn(CC(=O)N(C)C)c2cc(-c3ccccc3F)cnc12]

The title compound was prepared in a manner analogous to Example 27. MS (ESI): mass calcd. for $C_{18}H_{18}FN_3O$, 311.1. m/z found, 312.0 [M+H]⁺. ¹H NMR (300 MHz, DMSO-d₆) δ 8.53-8.46 (m, 1H), 8.02 (s, 1H), 7.63-7.51 (m, 1H), 7.50-7.39 (m, 2H), 7.39-7.30 (m, 2H), 5.19 (s, 2H), 3.09 (s, 3H), 2.84 (s, 3H), 2.31 (s, 3H).

Example 594

N-Ethyl-2-[6-(2-fluorophenyl)-3-methyl-pyrrolo[3,2-b]pyridin-1-yl]-N-methyl-acetamide

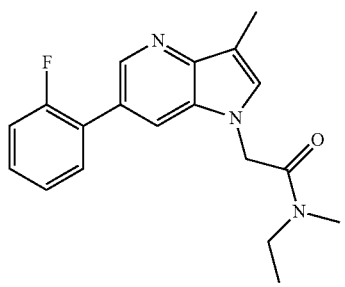 [SMILES: CCN(C)C(=O)Cn1cc(C)c2ncc(-c3ccccc3F)cc21]

The title compound was prepared in a manner analogous to Example 27. MS (ESI): mass calcd. for C₁₉H₂₀FN₃O, 325.2. m/z found, 326.0 [M+H]⁺. ¹H NMR (300 MHz, DMSO-d₆) δ 8.49-8.44 (m, 1H), 7.91 (d, J=7.9 Hz, 1H), 7.62-7.53 (m, 1H), 7.49-7.29 (m, 4H), 5.18 (s, 0.8H), 5.15 (s, 1.2H), 3.45 (q, J=7.2 Hz, 0.8H), 3.33 (s, 1.2H), 3.06 (s, 1.8H), 2.81 (s, 1.2H), 2.31 (s, 3H), 1.20 (t, J=7.1 Hz, 1.2H), 1.01 (t, J=7.1 Hz, 1.8H).

Example 595

1-(3,3-Difluoroazetidin-1-yl)-2-[6-[2-fluoro-3-(trifluoromethyl)phenyl]-3-methyl-pyrrolo[3,2-b]pyridin-1-yl]ethanone

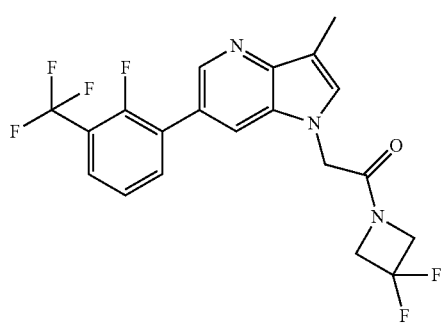 [SMILES: Cc1cn(CC(=O)N2CC(F)(F)C2)c2cc(-c3cccc(C(F)(F)F)c3F)cnc12]

The title compound was prepared in a manner analogous to Example 27. MS (ESI): mass calcd. for C₂₀H₁₅F₆N₃O, 427.1. m/z found, 428.0 [M+H]⁺. ¹H NMR (300 MHz, DMSO-d₆) δ 8.51-8.47 (m, 1H), 8.06-8.01 (m, 1H), 7.93 (t, J=7.6 Hz, 1H), 7.82 (t, J=7.3 Hz, 1H), 7.55 (t, J=7.9 Hz, 1H), 7.44 (s, 1H), 5.07 (s, 2H), 4.71 (t, J=12.6 Hz, 2H), 4.35 (t, J=12.6 Hz, 2H), 2.32 (s, 3H).

Example 596

1-(3,3-Difluoroazetidin-1-yl)-2-[3-methyl-6-(2,3,4-trifluorophenyl)pyrrolo[3,2-b]pyridin-1-yl]ethanone

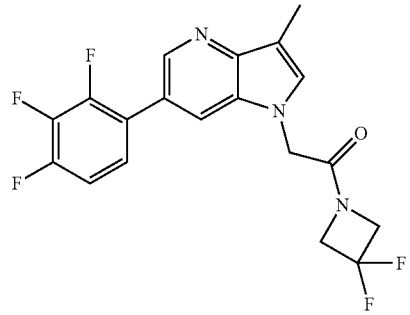 [SMILES: Cc1cn(CC(=O)N2CC(F)(F)C2)c2cc(-c3ccc(F)c(F)c3F)cnc12]

The title compound was prepared in a manner analogous to Example 27. MS (ESI): mass calcd. for C₁₉H₁₄F₆N₃O, 395.1. m/z found, 396.0 [M+H]⁺. ¹H NMR (300 MHz, DMSO-d₆) δ 8.50-8.45 (m, 1H), 8.01-7.98 (m, 1H), 7.52-7.40 (m, 3H), 5.06 (s, 2H), 4.71 (t, J=12.6 Hz, 2H), 4.35 (t, J=12.7 Hz, 2H), 2.31 (s, 3H).

Example 597

1-(3,3-Difluoroazetidin-1-yl)-2-[6-(2-fluorophenyl)-3-methyl-pyrrolo[3,2-b]pyridin-1-yl]ethanone

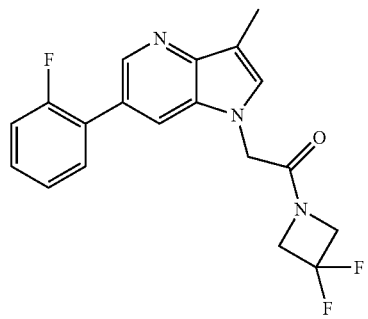 [SMILES: Cc1cn(CC(=O)N2CC(F)(F)C2)c2cc(-c3ccccc3F)cnc12]

The title compound was prepared in a manner analogous to Example 27. MS (ESI): mass calcd. for C₁₉H₁₆F₃N₃O, 359.1. m/z found, 360.0 [M+H]⁺. ¹H NMR (300 MHz, DMSO-d₆) δ 8.51-8.46 (m, 1H), 8.00-7.93 (m, 1H), 7.63-7.54 (m, 1H), 7.51-7.29 (m, 4H), 5.06 (s, 2H), 4.71 (t, J=12.4 Hz, 2H), 4.35 (t, J=12.7 Hz, 2H), 2.31 (s, 3H).

Example 598

1-(3-Fluoroazetidin-1-yl)-2-[3-methyl-6-(3,4,5-trifluorophenyl)pyrrolo[3,2-b]pyridin-1-yl]ethanone

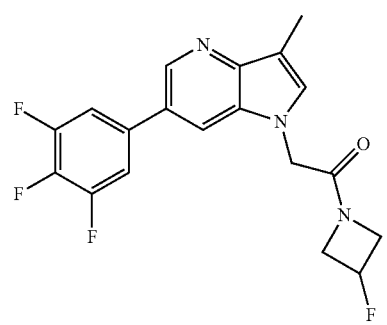 [SMILES: Cc1cn(CC(=O)N2CC(F)C2)c2cc(-c3cc(F)c(F)c(F)c3)cnc12]

The title compound was prepared in a manner analogous to Example 27. MS (ESI): mass calcd. for $C_{19}H_{15}F_4N_3O$, 377.1. m/z found, 378.0 [M+H]$^+$. $^1$H NMR (300 MHz, DMSO-d$_6$) δ 8.70 (s, 1H), 8.16 (s, 1H), 7.95-7.68 (m, 2H), 7.42 (s, 1H), 5.82-5.17 (m, 1H), 4.99 (s, 2H), 4.65-4.40 (m, 1H), 4.40-4.11 (m, 2H), 4.11-3.76 (m, 1H), 2.30 (s, 3H).

Example 599

2-[3-Chloro-6-(2,5-dimethyl-3-thienyl)pyrrolo[3,2-b]pyridin-1-yl]-N,N-dimethyl-acetamide

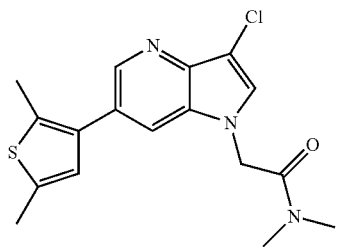 [SMILES: Cc1cc(-c2cnc3c(Cl)cn(CC(=O)N(C)C)c3c2)c(C)s1]

The title compound was prepared in a manner analogous to Example 146. MS (ESI): mass calcd. for $C_{17}H_{18}ClN_3OS$, 347.1. m/z found, 348.0 [M+H]$^+$. $^1$H NMR (400 MHz, CDCl$_3$) δ 8.56 (d, J=1.7 Hz, 1H), 7.50 (d, J=1.7 Hz, 1H), 7.32 (s, 1H), 6.71 (s, 1H), 4.87 (s, 2H), 3.10 (s, 3H), 3.00 (s, 3H), 2.46 (s, 3H), 2.43 (s, 3H).

Example 600

2-[3-Chloro-6-[3-(trifluoromethyl)phenyl]pyrrolo[3,2-b]pyridin-1-yl]-N,N-dimethyl-acetamide

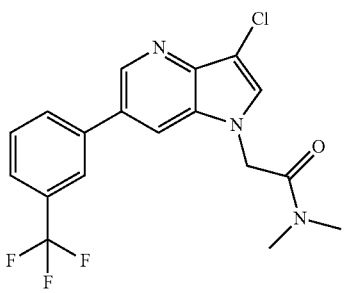

The title compound was prepared in a manner analogous to Example 146. MS (ESI): mass calcd. for $C_{18}H_{15}ClF_3N_3O$, 381.1. m/z found, 382.0 [M+H]$^+$. $^1$H NMR (400 MHz, CDCl$_3$) δ 8.75 (d, J=1.8 Hz, 1H), 7.84-7.81 (m, 1H), 7.81-7.76 (m, 1H), 7.69 (d, J=1.8 Hz, 1H), 7.67-7.55 (m, 2H), 7.36 (s, 1H), 4.95 (s, 2H), 3.15 (s, 3H), 3.01 (s, 3H).

Example 601

2-[3-Chloro-6-[6-(trifluoromethyl)-2-pyridyl]pyrrolo[3,2-b]pyridin-1-yl]-N,N-dimethyl-acetamide

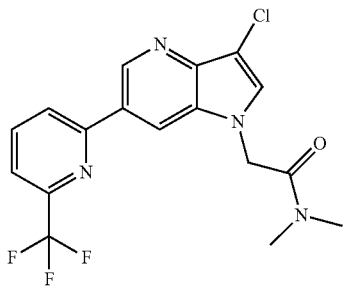 [SMILES: CN(C)C(=O)Cn1cc(Cl)c2ncc(-c3cccc(C(F)(F)F)n3)cc21]

The title compound was prepared in a manner analogous to Example 146. MS (ESI): mass calcd. for $C_{17}H_{14}ClF_3N_4O$, 382.1. m/z found, 383.0 [M+H]$^+$. $^1$H NMR (400 MHz, CDCl$_3$) δ 9.07 (d, J=1.8 Hz, 1H), 8.37 (d, J=1.8 Hz, 1H), 8.01 (d, J=8.0 Hz, 1H), 7.95 (t, J=7.8 Hz, 1H), 7.66-7.60 (m, 1H), 7.42 (s, 1H), 4.99 (s, 2H), 3.17 (s, 3H), 3.01 (s, 3H).

Example 602

2-[3-Chloro-6-(5-chloro-4-methyl-2-thienyl)pyrrolo[3,2-b]pyridin-1-yl]-N,N-dimethyl-acetamide

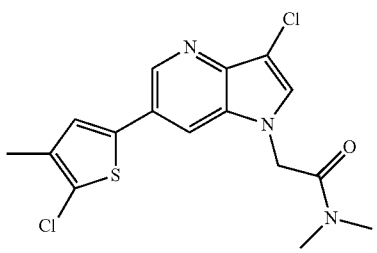

The title compound was prepared in a manner analogous to Example 146. MS (ESI): mass calcd. for $C_{16}H_{15}Cl_2N_3OS$, 367.0. m/z found, 368.0 [M+H]$^+$. $^1$H NMR (500 MHz, DMSO-d$_6$) δ 8.63 (d, J=1.9 Hz, 1H), 8.12 (d, J=2.0 Hz, 1H), 7.74 (s, 1H), 7.41 (s, 1H), 5.23 (s, 2H), 3.09 (s, 3H), 2.85 (s, 3H), 2.19 (s, 3H).

Example 603

2-[3-Chloro-6-[5-(trifluoromethyl)-2-thienyl]pyrrolo[3,2-b]pyridin-1-yl]-N,N-dimethyl-acetamide

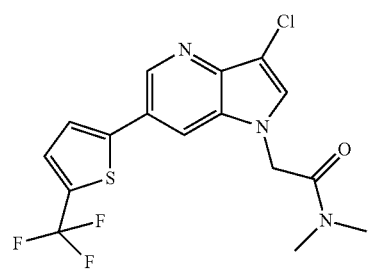 [SMILES: CN(C)C(=O)Cn1cc(Cl)c2ncc(-c3ccc(C(F)(F)F)s3)cc21]

The title compound was prepared in a manner analogous to Example 146. MS (ESI): mass calcd. for $C_{16}H_{13}ClF_3N_3OS$, 387.0. m/z found, 388.0 [M+H]$^+$. $^1$H NMR (500 MHz, DMSO-d$_6$) δ 8.79 (d, J=1.9 Hz, 1H), 8.30 (d, J=1.9 Hz, 1H), 7.80 (s, 1H), 7.79-7.74 (m, 1H), 7.69-7.64 (m, 1H), 5.26 (s, 2H), 3.10 (s, 3H), 2.85 (s, 3H).

Example 604

2-[6-(Benzothiophen-2-yl)pyrrolo[3,2-b]pyridin-1-yl]-N,N-dimethyl-acetamide

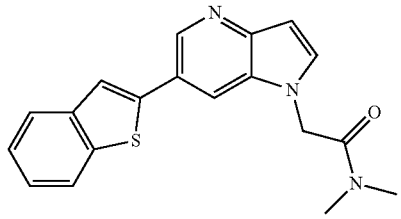 [SMILES: CN(C)C(=O)Cn1ccc2ncc(-c3cc4ccccc4s3)cc21]

The title compound was prepared in a manner analogous to Example 106. $^1$H NMR (400 MHz, CDCl$_3$) δ 8.85 (d, J=2.0 Hz, 1H), 7.82 (d, J=7.9 Hz, 1H), 7.80-7.74 (m, 2H), 7.56 (s, 1H), 7.40-7.28 (m, 3H), 6.78 (d, J=3.3 Hz, 1H), 4.92 (s, 2H), 3.10 (s, 3H), 3.00 (s, 3H).

Example 605

2-[3-Fluoro-6-[4-fluoro-3-(trifluoromethyl)phenyl]pyrrolo[3,2-b]pyridin-1-yl]-N,N-dimethyl-acetamide

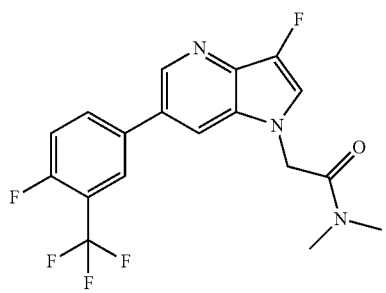 [SMILES: CN(C)C(=O)Cn1cc(F)c2ncc(-c3ccc(F)c(C(F)(F)F)c3)cc21]

The title compound was prepared in a manner analogous to Example 92. MS (ESI): mass calcd. for $C_{18}H_{14}F_6N_3O$, 383.1. m/z found, 384.0 [M+H]$^+$. $^1$H NMR (500 MHz, DMSO-d$_6$) δ 8.73 (d, J=1.9 Hz, 1H), 8.30-8.26 (m, 1H), 8.17-8.04 (m, 2H), 7.72-7.63 (m, 2H), 5.22 (s, 2H), 3.10 (s, 3H), 2.85 (s, 3H).

Example 606

2-[6-(3-Chloro-2-fluoro-phenyl)-3-fluoro-pyrrolo[3,2-b]pyridin-1-yl]-N,N-dimethyl-acetamide

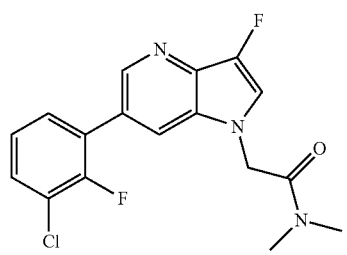 [SMILES: CN(C)C(=O)Cn1cc(F)c2ncc(-c3cccc(Cl)c3F)cc21]

The title compound was prepared in a manner analogous to Example 92. MS (ESI): mass calcd. for $C_{17}H_{14}ClF_2N_3O$, 349.1. m/z found, 350.0 [M+H]$^+$. $^1$H NMR (500 MHz, DMSO-d$_6$) δ 8.54-8.51 (m, 1H), 8.14 (s, 1H), 7.68 (d, J=2.2 Hz, 1H), 7.67-7.62 (m, 1H), 7.59-7.54 (m, 1H), 7.40-7.34 (m, 1H), 5.21 (s, 2H), 3.08 (s, 3H), 2.84 (s, 3H).

Example 607

1-(3-Fluoroazetidin-1-yl)-2-[3-fluoro-6-(m-tolyl)pyrrolo[3,2-b]pyridin-1-yl]ethanone

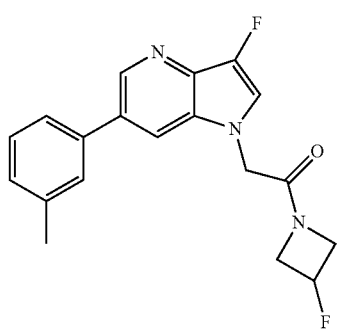 [SMILES: Cc1cccc(-c2cnc3c(F)cn(CC(=O)N4CC(F)C4)c3c2)c1]

The title compound was prepared in a manner analogous to Example 92. MS (ESI): mass calcd. for $C_{19}H_{17}F_2N_3O$, 341.1. m/z found, 342.1 [M+H]$^+$. $^1$H NMR (400 MHz, DMSO-d$_6$) δ 8.68 (d, J=1.8 Hz, 1H), 8.16 (t, J=2.2 Hz, 1H), 7.64 (d, J=2.2 Hz, 1H), 7.57 (s, 1H), 7.54 (d, J=8.1 Hz, 1H), 7.40 (t, J=7.6 Hz, 1H), 7.22 (d, J=7.5 Hz, 1H), 5.58-5.35 (m, 1H), 5.03 (s, 2H), 4.64-4.47 (m, 1H), 4.40-4.16 (m, 2H), 4.04-3.89 (m, 1H), 2.41 (s, 3H).

Example 608

2-[6-(3-Chloro-4-fluoro-phenyl)-3-fluoro-pyrrolo[3,2-b]pyridin-1-yl]-1-(3-fluoroazetidin-1-yl)ethanone

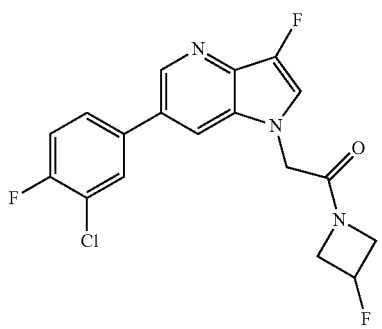 [SMILES: O=C(Cn1cc(F)c2ncc(-c3ccc(F)c(Cl)c3)cc21)N1CC(F)C1]

The title compound was prepared in a manner analogous to Example 92. MS (ESI): mass calcd. for $C_{18}H_{13}ClF_3N_3O$, 379.1. m/z found, 380.0 [M+H]$^+$. $^1$H NMR (400 MHz, DMSO-d$_6$) δ 8.72 (d, J=1.9 Hz, 1H), 8.25 (t, J=2.2 Hz, 1H), 8.00 (dd, J=7.1, 2.3 Hz, 1H), 7.84-7.74 (m, 1H), 7.68 (d, J=2.2 Hz, 1H), 7.57 (t, J=9.0 Hz, 1H), 5.58-5.35 (m, 1H), 5.02 (s, 2H), 4.63-4.48 (m, 1H), 4.40-4.15 (m, 2H), 4.07-3.87 (m, 1H).

Example 609

1-(Azetidin-1-yl)-2-(3-[³H]-6-(4-fluoro-3-methyl-phenyl)-1H-pyrrolo[3,2-b]pyridin-1-yl)ethanone

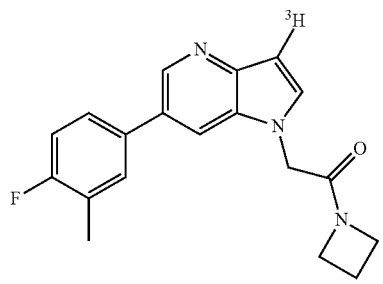 [SMILES: [3H]c1cn(CC(=O)N2CCC2)c2cc(-c3ccc(F)c(C)c3)cnc12]

The title compound was prepared in a manner analogous to Example 349 substituting tritium gas for $H_2$ gas. ³H NMR (300 MHz, $CD_3OD$) δ 6.97 (s, 1H).

Example 610

2-[2-Deuterio-6-(4-fluoro-3-methyl-phenyl)pyrrolo[3,2-b]pyridin-1-yl]-N,N-dimethyl-acetamide

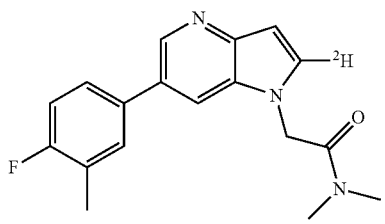 [SMILES: [2H]c1cc2ncc(-c3ccc(F)c(C)c3)cc2n1CC(=O)N(C)C]

Step A: tert-Butyl 6-(4-fluoro-3-methylphenyl)-1H-pyrrolo[3,2-b]pyridine-1-carboxylate To a solution of 6-(4-fluoro-3-methylphenyl)-1H-pyrrolo[3,2-b]pyridine (500 mg, 2.21 mmol) in DCM (10 mL) was added $(Boc)_2O$ (0.57 mL, 2.65 mmol) and DMAP (27 mg, 0.22 mmol) and the reaction mixture was stirred at rt for 1 hour. Water was added and the resulting mixture was extracted with EtOAc. The organic layers were combined, dried, concentrated and purified by FCC (0-100% EtOAc in hexanes) to provide tert-butyl 6-(4-fluoro-3-methylphenyl)-1H-pyrrolo[3,2-b]pyridine-1-carboxylate (78%, 564 mg).

Step B: 6-(4-Fluoro-3-methylphenyl)-2-duetero-1H-pyrrolo[3,2-b]pyridine

To a solution of tert-butyl 6-(4-fluoro-3-methylphenyl)-1H-pyrrolo[3,2-b]pyridine-1-carboxylate (400 mg, 1.23 mmol) in THF at −78° C. was added tBuLi (2.89 mL, 4.91 mmol, 1.7 M in hexanes) and the reaction mixture was stirred for 15 minutes. To the reaction mixture was added $CD_3CO_2D$ (0.75 mL, 12.3 mmol) and the reaction mixture was slowly warmed to rt. The reaction mixture was diluted with EtOAc and washed with water. The organic phase was dried, concentrated and purified by FCC (0-100% EtOAc in hexanes) to provide 6-(4-fluoro-3-methylphenyl)-2-duetero-1H-pyrrolo[3,2-b]pyridine (89%, 251 mg).

Step C: 2-(6-(4-Fluoro-3-methylphenyl)-2-duetero-1H-pyrrolo[3,2-b]pyridin-1-yl)-N,N-dimethylacetamide.

The title compound was prepared in a manner analogous to Example 66. MS (ESI): mass calcd. for $C_{18}H_{17}DFN_3O$, 312.1. m/z found, [M+H]⁺.

Example 611

2-[6-(3,5-Difluorophenyl)-3-(trifluoromethyl)pyrrolo[3,2-b]pyridin-1-yl]-N,N-dimethyl-acetamide

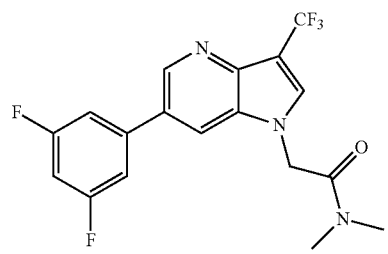 [SMILES: CN(C)C(=O)Cn1cc(C(F)(F)F)c2ncc(-c3cc(F)cc(F)c3)cc21]

Step A: 6-(3,5-Difluorophenyl)-3-iodo-1H-pyrrolo[3,2-b]pyridine

To a solution of 6-(3,5-difluorophenyl)-1H-pyrrolo[3,2-b]pyridine (Intermediate 9, 750 mg, 3.5 mmol) in DMF (10 mL) at room temperature was added NIS (1.1 g, 4.4 mmol). The solution was stirred overnight and water (20 mL) was added in the morning. The reaction mixture was concentrated directly onto silica gel and purified (FCC, $SiO_2$, 0-100% EtOAc in hexanes) to afford the title compound (1.1 g, 97%). ¹H NMR (400 MHz, DMSO) δ 11.96 (s, 1H), 8.82-8.66 (d, J=2.0 Hz, 1H), 8.19-8.02 (d, J=2.0 Hz, 1H), 8.02-7.80 (d, J=2.8 Hz, 1H), 7.70-7.45 (m, 2H), 7.33-7.14 (m, 1H).

Step B: tert-Butyl 6-(3,5-difluorophenyl)-3-iodo-1H-pyrrolo[3,2-b]pyridine-1-carboxylate To a solution 6-(3,5-difluorophenyl)-3-iodo-1H-pyrrolo[3,2-b]pyridine (1.13 g, 3.2 mmol) in DCM (10 mL) was added DMAP (39 mg, 0.32 mmol) followed by BOC-anhydride (0.82 mL, 3.8 mmol). The reaction mixture was stirred for one hour. Water (25 mL) and EtOAc (25 mL) were added. The organics were extracted, combined, dried ($MgSO_4$), filtered and concentrated under reduced pressure. Purification ($SiO_2$, 0-100% EtOAc in hexanes) afforded the title compound (946 mg, 65%). MS(ESI): mass calcd. for $C_{18}H_{15}F_2IN_2O_2$, 456.04. m/z found, 457.05.

Step C: 6-(3,5-Difluorophenyl)-3-(trifluoromethyl)-1H-pyrrolo[3,2-b]pyridine.

To a solution of tert-butyl 6-(3,5-difluorophenyl)-3-iodo-1H-pyrrolo[3,2-b]pyridine-1-carboxylate (500 mg, 1.1 mmol) in DMF (5 mL) was added copper (208 mg, 3.3 mmol) and diphenyl(trifluoromethyl)sulfonium trifluoromethanesulfonate (886 mg, 2.2 mmol). The mixture was refluxed at 90° C. for 12 hours. The reaction was diluted with water (5 mL) and concentrated onto silica gel. Purification (FCC, $SiO_2$, 0-100% EtOAc in hexanes) afforded the title compound (177 mg, 54%). MS(ESI): mass calcd. for $C_{14}H_7F_5N_2$, 298.2. m/z found, 299.1.

Step D: 2-(6-(3,5-Difluorophenyl)-3-(trifluoromethyl)-1H-pyrrolo[3,2-b]pyridin-1-yl)-N,N-dimethylacetamide To a solution of 6-(3,5-difluorophenyl)-3-(trifluoromethyl)-1H-pyrrolo[3,2-b]pyridine (15 mg, 0.05 mmol) in DMF (0.5 mL) at 0° C. was added NaH (6.0 mg, 0.15 mmol, 60% dispersion in oil). The reaction mixture was warmed to room temperature and stirred for 30 minutes and then cooled to 0° C. followed by the addition of a solution of 1-(azetidin-1-yl)-2-bromoethanone (10 mg, 0.06 mmol) in DMF (0.5 mL). The reaction mixture was warmed to room temperature and stirred for 12 hours. Water was added and the mixture was extracted with EtOAc. The combined organic layers were dried (MgSO$_4$), filtered and concentrated under reduced pressure. HPLC purification via Method A afforded the title compound (1.7 mg, 8.8%). MS (ESI): mass calcd. for $C_{18}H_{14}F_5N_3O$, 383.1. m/z found, [M+H]$^+$. $^1$H NMR (400 MHz, CD$_3$OD) δ 8.82-8.50 (d, 1H), 8.34-8.15 (d, 1H), 8.03 (s, 1H), 7.51-7.29 (d, J=8.4 Hz, 3H), 7.11-6.91 (m, 1H), 5.37 (s, 2H), 3.22 (s, 2H), 2.99 (s, 2H).

Example 612

3-Chloro-1-(3-pyridylmethyl)-6-[3-(trifluoromethyl)phenyl]pyrrolo[3,2-b]pyridine

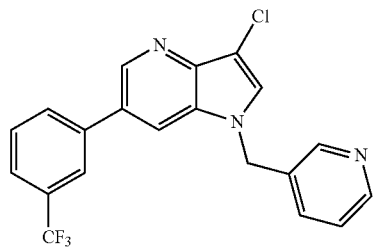

The title compound was prepared in a manner analogous to Example 1, using 3-chloro-6-(3-(trifluoromethyl)phenyl)-1H-pyrrolo[3,2-b]pyridine and 3-(bromomethyl)pyridine hydrobromide in step C. MS (ESI): mass calcd. for $C_{20}H_{13}ClF_3N_3$, 387.1. m/z found, 388.0 [M+H]$^+$. $^1$H NMR (400 MHz, CDCl$_3$) δ 5.40 (s, 2H) 7.27-7.32 (m, 1H) 7.36-7.44 (m, 2H) 7.56-7.69 (m, 2H) 7.72 (d, J=1.85 Hz, 1H) 7.76 (d, J=7.63 Hz, 1H) 7.80 (s, 1H) 8.49-8.67 (m, 2H) 8.79 (d, J=1.85 Hz, 1H)

Example 613

1-(Pyridazin-3-ylmethyl)-6-[3-(trifluoromethyl)phenyl]pyrrolo[3,2-b]pyridine

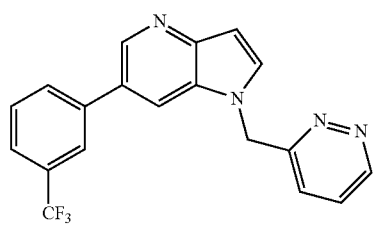 [SMILES: FC(F)(F)c1cccc(-c2cnc3ccn(Cc4cccnn4)c3c2)c1]

The title compound was prepared in a manner analogous to Example 1, using 6-(3-(trifluoromethyl)phenyl)-1H-pyrrolo[3,2-b]pyridine and 3-(chloromethyl)pyridazine in step C. MS (ESI): mass calcd. for $C_{19}H_{13}F_3N_4$, 354.1. m/z found, 355.1 [M+H]$^+$. $^1$H NMR (400 MHz, CDCl$_3$) δ 5.77 (s, 2H) 6.88 (dd, J=3.24, 0.69 Hz, 1H) 6.98 (dd, J=8.55, 1.39 Hz, 1H) 7.28-7.44 (m, 1H) 7.50-7.65 (m, 3H) 7.72-7.84 (m, 3H) 8.74 (d, J=1.85 Hz, 1H) 9.15 (dd, J=4.97, 1.50 Hz, 1H)

Example 614

3-Chloro-6-(4-fluoro-3-methyl-phenyl)-1-(pyridazin-3-ylmethyl)pyrrolo[3,2-b]pyridine

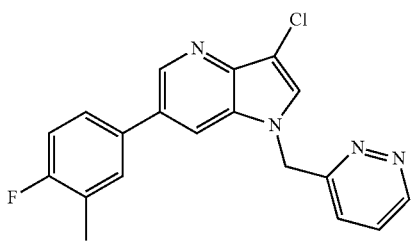 [SMILES: Cc1cc(-c2cnc3c(Cl)cn(Cc4cccnn4)c3c2)ccc1F]

The title compound was prepared in a manner analogous to Example 1, using 3-chloro-6-(4-fluoro-3-methylphenyl)-1H-pyrrolo[3,2-b]pyridine and 3-(chloromethyl)pyridazine hydrochloride in step C. MS (ESI): mass calcd. for $C_{19}H_{14}ClFN_4$, 352.1. m/z found, 353.1 [M+H]$^+$. $^1$H NMR (400 MHz, CDCl$_3$) δ 2.35 (d, J=1.16 Hz, 3H) 5.71 (s, 2H) 7.09 (s, 2H) 7.28-7.38 (m, 2H) 7.39-7.45 (m, 1H) 7.49 (s, 1H) 7.72 (d, J=1.62 Hz, 1H) 8.75 (d, J=1.16 Hz, 1H) 9.16 (d, J=4.86 Hz, 1H)

Example 615

3-Chloro-1-(pyridazin-3-ylmethyl)-6-[3-(trifluoromethyl)phenyl]pyrrolo[3,2-b]pyridine

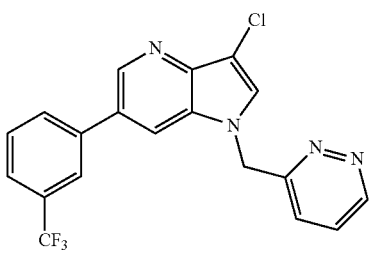 [SMILES: FC(F)(F)c1cccc(-c2cnc3c(Cl)cn(Cc4cccnn4)c3c2)c1]

The title compound was prepared in a manner analogous to Example 1, using 3-chloro-6-(3-(trifluoromethyl)phenyl)-1H-pyrrolo[3,2-b]pyridine and 3-(chloromethyl)pyridazine hydrochloride in step C. MS (ESI): mass calcd. for $C_{19}H_{12}ClF_3N_4$, 388.1. m/z found, 389.1 [M+H]$^+$. $^1$H NMR (400 MHz, CDCl₃) δ 5.74 (s, 2H) 7.09 (dd, J=8.55, 1.62 Hz, 1H) 7.45 (dd, J=8.55, 5.09 Hz, 1H) 7.54 (s, 1H) 7.56-7.70 (m, 2H) 7.75 (s, 1H) 7.78-7.86 (m, 2H) 8.80 (d, J=1.85 Hz, 1H) 9.18 (dd, J=4.85, 1.62 Hz, 1H)

Example 616

2-[6-(4-Fluoro-3-methyl-phenyl)-3-methyl-pyrrolo[3,2-b]pyridin-1-yl]-1-pyrrolidin-1-yl-ethanone

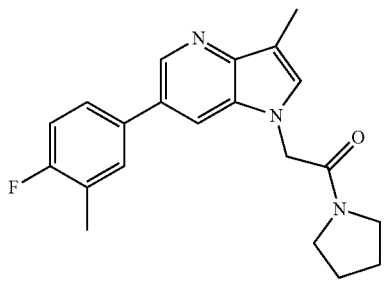 [SMILES: Cc1cc(-c2cnc3c(C)cn(CC(=O)N4CCCC4)c3c2)ccc1F]

The title compound was prepared in a manner analogous to Example 27, substituting (4-fluoro-3-methylphenyl)boronic acid for (4-fluorophenyl)boronic acid in step A. MS (ESI): mass calcd. for C₂₁H₂₂FN₃O, 351.2. m/z found, 352 [M+H]⁺. ¹H NMR (300 MHz, DMSO-d₆) δ 8.58 (s, 1H), 8.01 (s, 1H), 7.64 (d, J=7.4 Hz, 1H), 7.60-7.48 (m, 1H), 7.34 (s, 1H), 7.25 (t, J=9.1 Hz, 1H), 5.09 (s, 2H), 3.58 (t, J=6.7 Hz, 2H), 3.31-3.25 (m, 3H), 2.33 (s, 3H), 2.29 (s, 3H), 2.05-1.88 (m, 2H), 1.86-1.72 (m, 2H).

Example 617

N-Ethyl-2-[6-(4-fluoro-3-methyl-phenyl)-3-methyl-pyrrolo[3,2-b]pyridin-1-yl]-N-methyl-acetamide

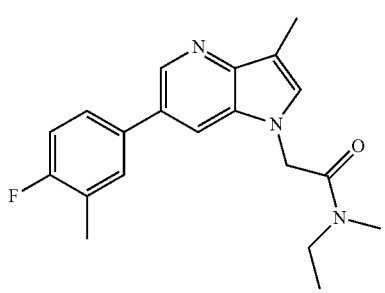 [SMILES: CCN(C)C(=O)Cn1cc(C)c2ncc(-c3ccc(F)c(C)c3)cc21]

The title compound was prepared in a manner analogous to Example 27. MS (ESI): mass calcd. for C₂₀H₂₂FN₃O, 339.2. m/z found, 340 [M+H]⁺. ¹H NMR (300 MHz, DMSO-d₆) δ 8.58 (s, 1H), 7.98 (d, J=5.5 Hz, 1H), 7.63 (d, J=6.9 Hz, 1H), 7.59-7.48 (m, 1H), 7.35 (d, J=8.4 Hz, 1H), 7.25 (t, J=9.1 Hz, 1H), 5.19 (s, 0.8H), 5.15 (s, 1.2H), 3.52-3.42 (m, 1.2H), 3.30-3.24 (m, 0.8H), 3.08 (s, 1.8H), 2.82 (s, 1.2H), 2.33 (s, 3H), 2.29 (s, 3H), 1.22 (t, 1.2H), 1.02 (t, J=7.1 Hz, 1.8H).

Example 618

1-(3,3-Difluoroazetidin-1-yl)-2-[6-(4-fluoro-3-methyl-phenyl)-3-methyl-pyrrolo[3,2-b]pyridin-1-yl]ethanone

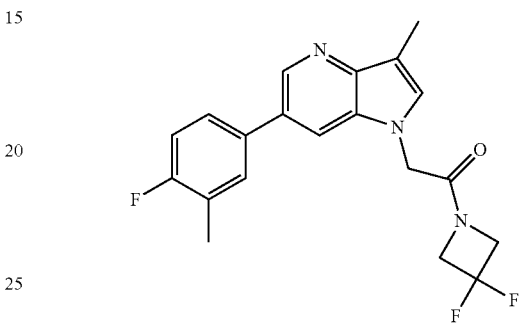

The title compound was prepared in a manner analogous to Example 27. The title compound was prepared in a manner analogous to Example 27. MS (ESI): mass calcd. for C₂₀H₁₈F₃N₃O, 373.1. m/z found, 374 [M+H]⁺. ¹H NMR (300 MHz, DMSO-d₆) δ 8.60 (s, 1H), 8.03 (s, 1H), 7.64 (d, J=7.4 Hz, 1H), 7.60-7.51 (m, 1H), 7.36 (s, 1H), 7.26 (t, J=9.1 Hz, 1H), 5.06 (s, 2H), 4.70 (t, J=12.5 Hz, 2H), 4.36 (t, J=12.5 Hz, 2H), 2.33 (s, 3H), 2.30 (s, 3H).

Example 619

2-[6-(3,4-Difluorophenyl)-3-methyl-pyrrolo[3,2-b]pyridin-1-yl]-1-pyrrolidin-1-yl-ethanone

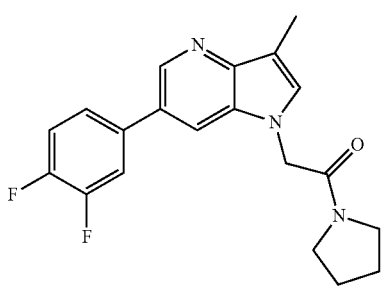 [SMILES: Cc1cn(CC(=O)N2CCCC2)c2cc(-c3ccc(F)c(F)c3)cnc12]

The title compound was prepared in a manner analogous to Example 27. MS (ESI): mass calcd. for C₂₀H₁₉F₂N₃O, 355.1. m/z found, 356 [M+H]⁺. ¹H NMR (300 MHz, DMSO-d₆) δ 8.64 (s, 1H), 8.10 (s, 1H), 7.90-7.76 (m, 1H), 7.65-7.47 (m, 2H), 7.38 (s, 1H), 5.09 (s, 2H), 3.58 (t, J=6.7 Hz, 2H), 3.30-3.21 (m, 2H), 2.30 (s, 3H), 2.03-1.89 (m, 2H), 1.87-1.70 (m, 2H).

Example 620

2-[6-(3,4-Difluorophenyl)-3-methyl-pyrrolo[3,2-b]pyridin-1-yl]-N-ethyl-N-methyl-acetamide

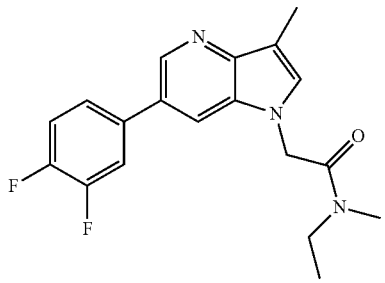 [SMILES: CCN(C)C(=O)Cn1cc(C)c2ncc(-c3ccc(F)c(F)c3)cc21]

The title compound was prepared in a manner analogous to Example 27. MS (ESI): mass calcd. for $C_{19}H_{19}F_2N_3O$, 343.1. m/z found, 344 [M+H]$^+$. $^1$H NMR (300 MHz, DMSO-d$_6$) δ 8.63 (s, 1H), 8.07 (d, J=8.8 Hz, 1H), 7.89-7.77 (m, 1H), 7.64-7.47 (m, 2H), 7.38 (d, J=8.3 Hz, 1H), 5.19 (s, 0.9H), 5.16 (s, 1.1H), 3.54-3.41 (m, 1.1H), 3.30-3.24 (m, 0.9H), 3.09 (s, 1.7H), 2.82 (s, 1.3H), 2.29 (s, 3H), 1.23 (t, J=7.0 Hz, 1.3H), 1.02 (t, J=7.0 Hz, 1.7H).

Example 621

1-(3,3-Difluoroazetidin-1-yl)-2-[6-(3,4-difluorophenyl)-3-methyl-pyrrolo[3,2-b]pyridin-1-yl]ethanone

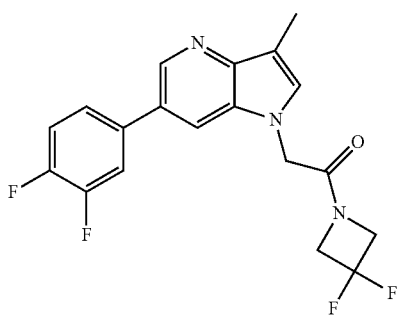 [SMILES: Cc1cn(CC(=O)N2CC(F)(F)C2)c2cc(-c3ccc(F)c(F)c3)cnc12]

The title compound was prepared in a manner analogous to Example 27. MS (ESI): mass calcd. for $C_{19}H_{15}F_4N_3O$, 377.1. m/z found, 378 [M+H]$^+$. $^1$H NMR (300 MHz, DMSO-d$_6$) δ 8.65 (s, 1H), 8.10 (s, 1H), 7.91-7.76 (m, 1H), 7.65-7.47 (m, 2H), 7.39 (s, 1H), 5.06 (s, 2H), 4.70 (t, J=12.2 Hz, 2H), 4.36 (t, J=12.6 Hz, 2H), 2.30 (s, 3H).

Example 622

2-[6-(2,4-Difluoro-3-methyl-phenyl)-3-methyl-pyrrolo[3,2-b]pyridin-1-yl]-N,N-dimethyl-acetamide

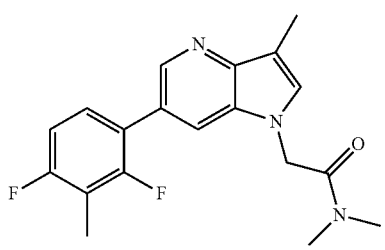 [SMILES: Cc1c(F)ccc(-c2cnc3c(C)cn(CC(=O)N(C)C)c3c2)c1F]

The title compound was prepared in a manner analogous to Example 27. MS (ESI): mass calcd. for $C_{19}H_{19}F_2N_3O$, 343.1; 343 [M+H]$^+$. $^1$H NMR (300 MHz, DMSO-d$_6$) δ 8.41 (s, 1H), 7.89 (s, 1H), 7.48-7.32 (m, 2H), 7.19 (t, J=8.7 Hz, 1H), 5.16 (s, 2H), 3.08 (s, 3H), 2.84 (s, 3H), 2.30 (s, 3H), 2.24 (s, 3H).

Example 623

2-[6-(3,5-Difluorophenyl)-3-methyl-pyrrolo[3,2-b]pyridin-1-yl]-1-pyrrolidin-1-yl-ethanone

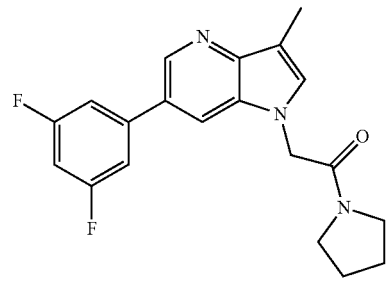 [SMILES: Cc1cn(CC(=O)N2CCCC2)c2cc(-c3cc(F)cc(F)c3)cnc12]

The title compound was prepared in a manner analogous to Example 27. MS (ESI): mass calcd. for $C_{20}H_{19}F_2N_3O$, 355.1. m/z found, 356 [M+H]$^+$. $^1$H NMR (300 MHz, CDCl$_3$) δ 8.66 (d, J=1.8 Hz, 1H), 7.66 (d, J=1.8 Hz, 1H), 7.23-7.08 (m, 3H), 6.85-6.74 (m, 1H), 4.83 (s, 2H), 3.58-3.42 (m, 4H), 2.44 (s, 3H), 2.12-1.97 (m, 2H), 1.96-1.82 (m, 2H).

Example 624

2-[6-(2,4-Difluoro-3-methyl-phenyl)-3-methyl-pyrrolo[3,2-b]pyridin-1-yl]-1-pyrrolidin-1-yl-ethanone

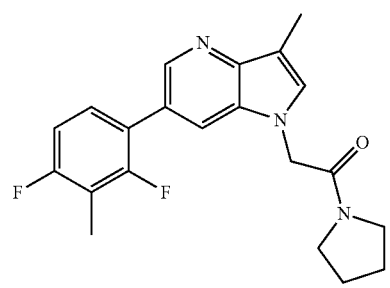 [SMILES: Cc1c(F)ccc(-c2cnc3c(C)cn(CC(=O)N4CCCC4)c3c2)c1F]

The title compound was prepared in a manner analogous to Example 27. MS (ESI): mass calcd. for $C_{21}H_{21}F_2N_3O$, 369.2. m/z found, 370 [M+H]+. $^1$H NMR (300 MHz, DMSO-d$_6$) δ 8.45 (s, 1H), 7.98 (s, 1H), 7.50-7.37 (m, 2H), 7.20 (t, J=8.8 Hz, 1H), 5.09 (s, 2H), 3.56 (t, J=6.7 Hz, 2H), 3.29-3.17 (m, 2H), 2.31 (s, 3H), 2.24 (s, 3H), 2.03-1.86 (m, 2H), 1.86-1.70 (m, 2H).

Example 625

2-[6-(2,4-Difluoro-3-methyl-phenyl)-3-methyl-pyrrolo[3,2-b]pyridin-1-yl]-N-ethyl-N-methyl-acetamide

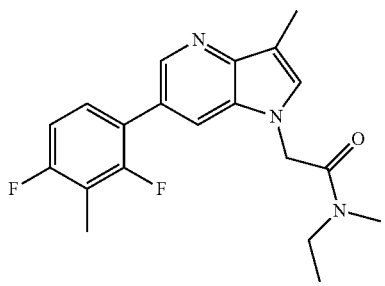 [SMILES: CCN(C)C(=O)Cn1cc(C)c2ncc(-c3ccc(F)c(C)c3F)cc21]

The title compound was prepared in a manner analogous to Example 27. MS (ESI): mass calcd. for $C_{20}H_{21}F_2N_3O$, 357.2. m/z found, 358 [M+H]$^+$. $^1$H NMR (300 MHz, DMSO-d$_6$) δ 8.42 (s, 1H), 7.89 (d, J=6.9 Hz, 1H), 7.49-7.34 (m, 2H), 7.19 (t, J=8.7 Hz, 1H), 5.18 (s, 0.8H), 5.14 (s, 1.2H), 3.52-3.38 (m, 2H), 3.06 (s, 1.8H), 2.81 (s, 1.2H), 2.30 (s, 3H), 2.24 (s, 3H), 1.20 (t, J=6.9 Hz, 1.2H), 1.01 (t, J=7.0 Hz, 1.8H).

Example 626

1-(3,3-Difluoroazetidin-1-yl)-2-[6-(2,4-difluoro-3-methyl-phenyl)-3-methyl-pyrrolo[3,2-b]pyridin-1-yl]ethanone

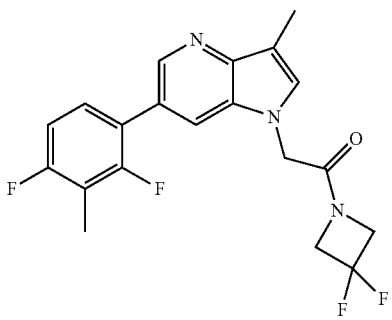 [SMILES: Cc1c(F)ccc(-c2cnc3c(C)cn(CC(=O)N4CC(F)(F)C4)c3c2)c1F]

The title compound was prepared in a manner analogous to Example 27. MS (ESI): mass calcd. for $C_{20}H_{17}F_4N_3O$, 391.1. m/z found, 392 [M+H]$^+$. $^1$H NMR (300 MHz, DMSO-d$_6$) δ 8.44 (s, 1H), 7.93 (s, 1H), 7.54-7.34 (m, 2H), 7.20 (s, 1H), 5.05 (s, 2H), 4.82-4.61 (m, 2H), 4.45-4.24 (m, 2H), 2.30 (s, 3H), 2.24 (s, 3H).

Example 627

1-(Azetidin-1-yl)-2-[6-(2,4-difluoro-3-methyl-phenyl)-3-methyl-pyrrolo[3,2-b]pyridin-1-yl]ethanone

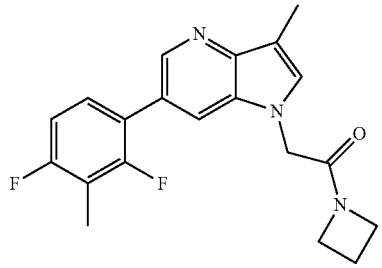 [SMILES: Cc1c(F)ccc(-c2cnc3c(C)cn(CC(=O)N4CCC4)c3c2)c1F]

The title compound was prepared in a manner analogous to Example 27. MS (ESI): mass calcd. for $C_{20}H_{19}F_2N_3O$, 355.1; 356 [M+H]$^+$. $^1$H NMR (300 MHz, DMSO-d$_6$) δ 8.43 (s, 1H), 7.90 (s, 1H), 7.50-7.35 (m, 2H), 7.20 (t, J=8.7 Hz, 1H), 4.90 (s, 2H), 4.18 (t, J=7.4 Hz, 2H), 3.88 (t, J=7.5 Hz, 2H), 2.30 (s, 3H), 2.28-2.18 (m, 5H).

Example 628

2-[6-(5-Chloro-2-thienyl)-3-methyl-pyrrolo[3,2-b]pyridin-1-yl]-N,N-dimethyl-acetamide

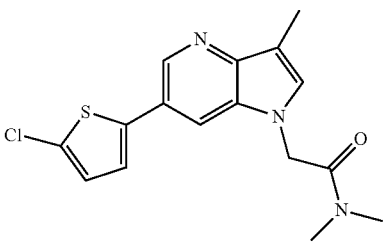 [SMILES: Cc1cn(CC(=O)N(C)C)c2cc(-c3ccc(Cl)s3)cnc12]

The title compound was prepared in a manner analogous to Example 27. MS (ESI): mass calcd. for $C_{16}H_{16}ClN_3OS$, 333.1; 334 [M+H]$^+$. $^1$H NMR (300 MHz, DMSO-d$_6$) δ 8.56 (s, 1H), 7.99 (s, 1H), 7.40 (d, J=3.9 Hz, 1H), 7.36 (s, 1H), 7.18 (d, J=3.9 Hz, 1H), 5.16 (s, 2H), 3.11 (s, 3H), 2.86 (s, 3H), 2.27 (s, 3H).

Example 629

2-[6-(2,4-Difluoro-3-methyl-phenyl)-3-methyl-pyrrolo[3,2-b]pyridin-1-yl]-1-(3-fluoroazetidin-1-yl)ethanone

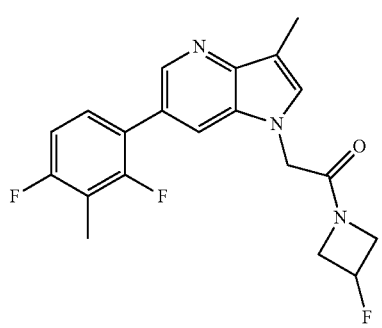 [SMILES: Cc1c(F)ccc(-c2cnc3c(C)cn(CC(=O)N4CC(F)C4)c3c2)c1F]

The title compound was prepared in a manner analogous to Example 27. MS (ESI): mass calcd. for C₂₀H₁₈F₃N₃O, 373.1. m/z found, 374 [M+H]⁺. ¹H NMR (300 MHz, CDCl₃) δ 8.61 (s, 1H), 7.68 (s, 1H), 7.38-7.27 (m, 1H), 7.15 (s, 1H), 6.96 (t, J=8.5 Hz, 1H), 5.42-5.21 (m, 1H), 4.76 (s, 2H), 4.42-4.07 (m, 2H), 3.99-3.74 (m, 2H), 2.45 (s, 3H), 2.28 (s, 3H), 1.60 (s, 3H).

Example 630

N-Ethyl-N-methyl-2-[3-methyl-6-(5-methyl-2-thienyl)pyrrolo[3,2-b]pyridin-1-yl]acetamide

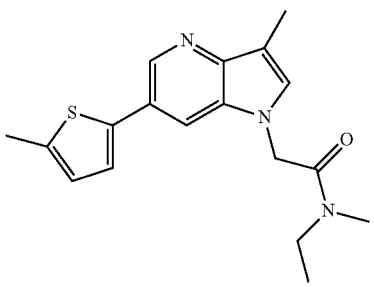

The title compound was prepared in a manner analogous to Example 27. MS (ESI): mass calcd. for C₁₈H₂₁N₃OS, 327.1. m/z found, 328 [M+H]⁺. ¹H NMR (300 MHz, DMSO-d₆) δ 8.55 (s, 1H), 7.88 (d, J=7.7 Hz, 1H), 7.37-7.26 (m, 2H), 6.84 (d, J=2.4 Hz, 1H), 5.16 (s, 0.8H), 5.13 (s, 1.2H), 3.52-3.40 (m, 2H), 3.08 (s, 1.8H), 2.82 (s, 1.2H), 2.48 (s, 3H), 2.27 (s, 3H), 1.22 (t, J=7.0 Hz, 1.2H), 1.02 (t, J=7.1 Hz, 1.8H).

Example 631

2-[3-Methyl-6-(5-methyl-2-thienyl)pyrrolo[3,2-b]pyridin-1-yl]-1-pyrrolidin-1-yl-ethanone

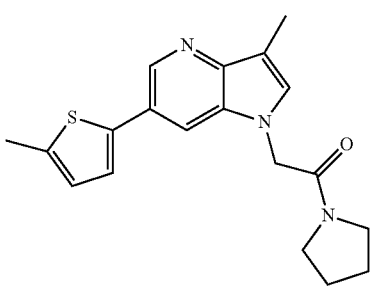 [SMILES: Cc1ccc(-c2cnc3c(C)cn(CC(=O)N4CCCC4)c3c2)s1]

The title compound was prepared in a manner analogous to Example 27. MS (ESI): mass calcd. for C₁₉H₂₁N₃OS, 339.1. m/z found, 340 [M+H]⁺. ¹H NMR (300 MHz, DMSO-d₆) δ 8.55 (s, 1H), 7.94 (s, 1H), 7.36-7.27 (m, 2H), 6.84 (d, J=2.4 Hz, 1H), 5.07 (s, 2H), 3.58 (t, J=6.7 Hz, 2H), 3.30-3.24 (m, 2H), 2.48 (s, 3H), 2.27 (s, 3H), 1.95 (dd, J=13.3, 6.7 Hz, 2H), 1.82 (dd, J=13.4, 6.7 Hz, 2H).

Example 632

1-(3,3-Difluoroazetidin-1-yl)-2-[3-methyl-6-(5-methyl-2-thienyl)pyrrolo[3,2-b]pyridin-1-yl]ethanone

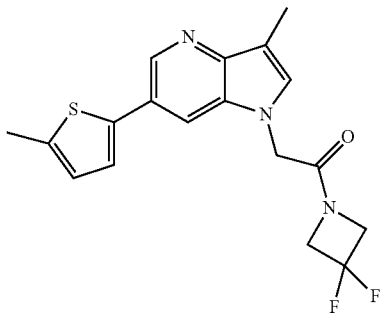 [SMILES: Cc1ccc(-c2cnc3c(C)cn(CC(=O)N4CC(F)(F)C4)c3c2)s1]

The title compound was prepared in a manner analogous to Example 27. MS (ESI): mass calcd. for C₁₈H₁₇F₂N₃OS, 361.1. m/z found, 362 [M+H]⁺. ¹H NMR (300 MHz, CDCl₃) δ 8.69 (s, 1H), 7.70 (s, 1H), 7.17 (d, J=3.4 Hz, 1H), 7.12 (s, 1H), 6.77 (d, J=2.5 Hz, 1H), 4.85 (s, 2H), 4.38 (t, J=11.9 Hz, 2H), 4.03 (t, J=11.3 Hz, 2H), 2.53 (s, 3H), 2.41 (s, 3H).

Example 633

1-(Azetidin-1-yl)-2-[3-methyl-6-(5-methyl-2-thienyl)pyrrolo[3,2-b]pyridin-1-yl]ethanone

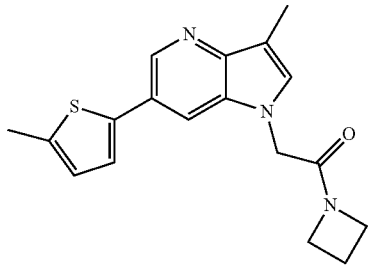 [SMILES: Cc1ccc(-c2cnc3c(C)cn(CC(=O)N4CCC4)c3c2)s1]

The title compound was prepared in a manner analogous to Example 27. MS (ESI): mass calcd. for C₁₈H₁₉N₃OS, 325.1. m/z found, 326 [M+H]⁺. ¹H NMR (300 MHz, CDCl₃) δ 8.72 (s, 1H), 7.64 (s, 1H), 7.20-7.00 (m, 2H), 6.77 (s, 1H), 4.68 (s, 2H), 4.07 (t, J=7.6 Hz, 2H), 3.77 (t, J=7.6 Hz, 2H), 2.53 (s, 3H), 2.41 (s, 3H), 2.22 (dd, J=15.3, 7.7 Hz, 2H).

Example 634

1-(3-Fluoroazetidin-1-yl)-2-[3-methyl-6-(5-methyl-2-thienyl)pyrrolo[3,2-b]pyridin-1-yl]ethanone

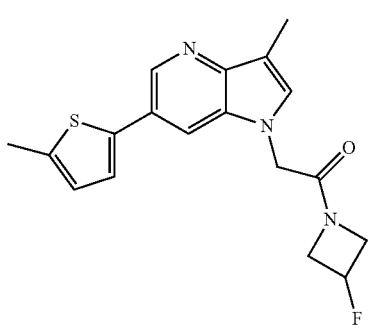 [SMILES: Cc1ccc(-c2cnc3c(C)cn(CC(=O)N4CC(F)C4)c3c2)s1]

The title compound was prepared in a manner analogous to Example 27. MS (ESI): mass calcd. for $C_{18}H_{18}FN_3OS$, 343.1. m/z found, 344 [M+H]+. $^1$H NMR (300 MHz, CDCl$_3$) δ 8.73 (d, J=1.4 Hz, 1H), 7.61 (d, J=1.5 Hz, 1H), 7.15 (d, J=3.4 Hz, 1H), 7.09 (s, 1H), 6.77 (d, J=2.3 Hz, 1H), 5.27 (dd, J=9.7, 5.1 Hz, 0.5H), 5.13-5.01 (m, 0.5H), 4.74 (s, 2H), 4.41-4.08 (m, 2H), 3.85 (d, J=4.2 Hz, 1H), 3.78 (d, J=4.2 Hz, 1H), 2.53 (s, 3H), 2.41 (s, 3H).

Example 635

2-[6-(3,5-Difluorophenyl)-3-methyl-pyrrolo[3,2-b]pyridin-1-yl]-1-(3-fluoroazetidin-1-yl)ethanone

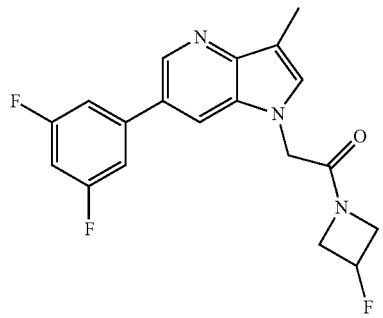 [SMILES: Cc1cn(CC(=O)N2CC(F)C2)c2cc(-c3cc(F)cc(F)c3)cnc12]

The title compound was prepared in a manner analogous to Example 27. MS (ESI): mass calcd. for $C_{19}H_{16}F_3N_3O$, 359.1. m/z found, 360 [M+H]+. $^1$H NMR (300 MHz, DMSO-d$_6$) δ 8.72 (s, 1H), 8.19 (s, 1H), 7.54 (d, J=7.6 Hz, 2H), 7.42 (s, 1H), 7.23 (t, J=9.4 Hz, 1H), 5.60-5.51 (m, 0.5H), 5.41-5.30 (m, 0.5H), 5.00 (s, 2H), 4.62-4.43 (m, 1H), 4.38-4.14 (m, 2H), 4.05-3.86 (m, 1H), 2.30 (s, 3H).

Example 636

2-[6-(5-Chloro-2-thienyl)-3-methyl-pyrrolo[3,2-b]pyridin-1-yl]-1-(3-fluoroazetidin-1-yl)ethanone

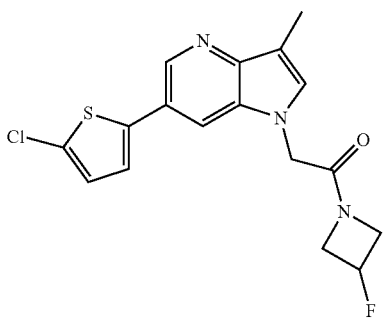 [SMILES: Cc1cn(CC(=O)N2CC(F)C2)c2cc(-c3ccc(Cl)s3)cnc12]

The title compound was prepared in a manner analogous to Example 27. MS (ESI): mass calcd. for $C_{17}H_{15}ClFN_3OS$, 363.1. m/z found, 364 [M+H]+. $^1$H NMR (300 MHz, DMSO-d$_6$) δ 8.59 (d, J=1.4 Hz, 1H), 8.00 (d, J=1.4 Hz, 1H), 7.45-7.35 (m, 2H), 7.19 (d, J=3.9 Hz, 1H), 5.61-5.48 (m, 0.5H), 5.41-5.30 (m, 0.5H), 4.98 (s, 2H), 4.64-4.45 (m, 1H), 4.40-4.15 (m, 2H), 4.06-3.85 (m, 1H), 2.28 (s, 3H).

Example 637

N,N-Dimethyl-2-[3-methyl-6-(5-methyl-2-thienyl)pyrrolo[3,2-b]pyridin-1-yl]acetamide

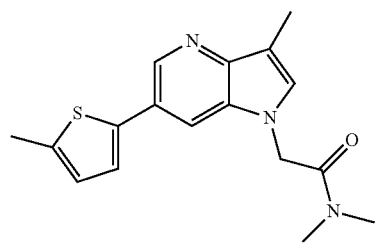

The title compound was prepared in a manner analogous to Example 27. MS (ESI): mass calcd. for $C_{17}H_{19}N_3OS$, 313.1. m/z found, 314 [M+H]+. $^1$H NMR (300 MHz, CDCl$_3$) δ 8.69 (d, J=1.6 Hz, 1H), 7.58 (d, J=1.6 Hz, 1H), 7.13-7.06 (m, 2H), 6.75 (d, J=2.4 Hz, 1H), 4.86 (s, 2H), 3.09 (s, 3H), 3.01 (s, 3H), 2.52 (s, 3H), 2.40 (s, 3H).

Example 638

1-(3-Fluoroazetidin-1-yl)-2-[6-(2-fluorophenyl)-3-methyl-pyrrolo[3,2-b]pyridin-1-yl]ethanone

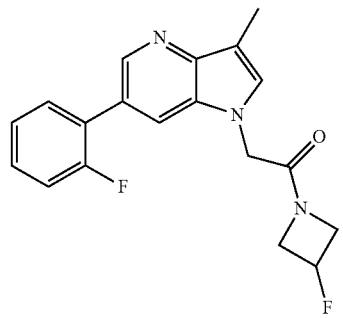 [SMILES: Cc1cn(CC(=O)N2CC(F)C2)c2cc(-c3ccccc3F)cnc12]

The title compound was prepared in a manner analogous to Example 27. MS (ESI): mass calcd. for $C_{19}H_{17}F_2N_3O$, 341.1. m/z found, 342 [M+H]+. $^1$H NMR (300 MHz, DMSO-d$_6$) δ 8.48 (s, 1H), 7.95 (s, 1H), 7.58 (t, J=7.8 Hz, 1H), 7.50-7.27 (m, 4H), 5.53 (s, 0.5H), 5.34 (s, 0.5H), 4.98 (s, 2H), 4.59-4.43 (m, 1H), 4.37-4.13 (m, 2H), 3.95 (dd, J=24.6, 11.6 Hz, 1H), 2.31 (s, 3H).

Example 639

2-[6-[5-(Difluoromethyl)-2-thienyl]pyrrolo[3,2-b]pyridin-1-yl]-N,N-dimethyl-acetamide

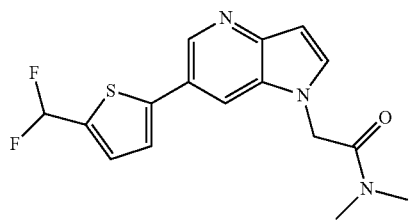 [SMILES: CN(C)C(=O)Cn1ccc2ncc(-c3ccc(C(F)F)s3)cc21]

Step A: 2-(6-Bromo-1H-pyrrolo[3,2-b]pyridin-1-yl)-N,N-dimethylacetamide

The title compound was prepared in an analogous manner to Intermediate 10, using 6-bromo-1H-pyrrolo[3,2-b]pyridine and 2-bromo-N,N-dimethylacetamide. MS (ESI): mass calcd. for $C_{11}H_{12}BrN_3O$, 281.1. m/z found, 282.05 [M+H]+.

Step B: 2-(6-(5-(Difluoromethyl)thiophen-2-yl)-1H-pyrrolo[3,2-b]pyridin-1-yl)-N,N-dimethylacetamide To a solution of 2-bromo-5-(difluoromethyl)thiophene (100 mg, 0.47 mmol) in dioxane (2 mL) was added bis(pinacolato)diboron (143 mg, 0.56 mmol), $PdCl_2(dppf)$·$CH_2Cl_2$ (35 mg, 0.05 mmol), KOAc (138 mg, 1.40 mmol). The resulting reaction mixture was heated to 90° C. in a sealed vessel and stirred for two hours. The reaction mixture was cooled to room temperature then the intermediate from Step A (50 mg, 0.18 mmol) was subsequently added followed by $Cs_2CO_3$ (115 mg, 0.352 mmol) and additional amounts of $PdCl_2(dppf)$·$CH_2Cl_2$ (35 mg, 0.05 mmol) and dioxane (3 mL). The reaction mixture was again heated to 90° C. and stirred for two hours in a sealed vessel. The reaction was cooled to room temperature and washed with saturated $NaHCO_3$ solution. The organic layer was isolated then dried over $Mg_2SO_4$, filtered and conc. into a brown residue which was purified via silica gel chromatography (0-7% 2M $NH_3$/MeOH in DCM) to provide the title compound (45 mg, 30%). MS (ESI): mass calcd. for $C_{16}H_{15}F_2N_3OS$, 335.3; m/z found, 335.9 [M+H]+. $^1H$ NMR (500 MHz, $CDCl_3$) δ 8.76-8.71 (d, J=2.0 Hz, 1H), 7.71-7.66 (m, 1H), 7.37-7.33 (d, J=3.3 Hz, 1H), 7.28-7.23 (m, 2H), 6.97-6.72 (m, 2H), 4.96-4.89 (s, 2H), 3.14-3.09 (s, 3H), 3.04-2.97 (s, 3H).

Biological Assays

Inhibition of Specific Binding to the Rat NR1/NR2B Receptor

The assay depends on the binding of a tracer to the GluN2B subunit-containing NMDA receptors and the ability of the test compounds to displace such binding. 3-[$^3H$] 1-(azetidin-1-yl)-2-[6-(4-fluoro-3-methyl-phenyl)pyrrolo[3,2-b]pyridin-1-yl]ethanone is a high-affinity GluN2B-selective antagonist, which binds to the Ifenprodil binding site located at the interphase between GluN1 and GluN2B subunits. Alternatively, The assay measures binding affinity for ligands that compete for the Ifenprodil binding site in the native NMDA receptors from adult rat cortical membranes.

In brief, rat adult cortex is homogenized in the assay buffer (50 mM Tris; pH 7.4). The resulting cortical membranes containing native NMDA receptors are purified by centrifugation and extensively washed, then re-suspended in the assay buffer. The test compounds, tracer and membranes are mixed together and incubated with shaking for 2 hours at room temperature to reach binding equilibrium. Non-specific binding of the tracer is determined by pre-incubation of brain membranes with 10 μM of CP 101,606. Following the incubation, the bound and unbound tracer is separated by filtration with cell harvester and GF/B filter plates (PerkinElmer) soaked with polyethylenimine.

The extent of binding is measured by counting [3H] radioactivity retained on the filters plates with liquid scintillator counter. Binding affinity (equilibrium dissociation constant Ki) for the test compounds is determined by fitting experimental data with the following model log $EC_{50}$=log (10^ log Ki*(1+[Radioligand]/HotKd)) and Y=Bottom+ (Top−Bottom)/(1+10^(X−Log $EC_{50}$)) where [Radioligand] is the concentration of the tracer, HotKdNM is the equilibrium dissociation constant of the tracer, Top and Bottom are the curve plateaus in the units of Y axis.

HNR2BC: Effects of Test Articles on Cloned Human NR1/NR2B Ion Channels Expressed in Mammalian Cells NMDA receptors are ion channels that are highly permeable to $Ca^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular $Ca^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 137 mM NaCl, 4 mM KCl, 2 mM $CaCl_2$, 0.5 mM $MgCl_2$, 10 mM HEPES and 5 mM D-glucose; pH 7.4. After 1 h incubation at the room temperature, the dye is washed away with the assay buffer (137 mM NaCl, 4 mM KCl, 2 mM $CaCl_2$, 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to ~$EC_{50}$ is used to maximize the assay's signal window and ability to detect NMDA receptor antagonists and negative allosteric modulators. A saturating concentration (10 μM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

TABLE 5

| Example # | Compound Name | $pIC_{50}$ |
|---|---|---|
| 1 | 2-(3-Chloro-6-phenyl-pyrrolo[3,2-b]pyridin-1-yl)-N-cyclopropyl-acetamide; | 6.5 |
| 2 | 2-[3-Chloro-6-(4-fluorophenyl)pyrrolo[3,2-b]pyridin-1-yl]-N-cyclopropyl-acetamide; | 6.9 |
| 3 | 1-(Azetidin-1-yl)-2-[3-chloro-6-(4-fluorophenyl)pyrrolo[3,2-b]pyridin-1-yl]ethanone; | 7.6 |
| 4 | 2-(3-Chloro-6-phenyl-pyrrolo[3,2-b]pyridin-1-yl)-1-pyrrolidin-1-yl-ethanone; | 7.3 |
| 5 | 2-(3-Chloro-6-phenyl-pyrrolo[3,2-b]pyridin-1-yl)-1-morpholino-ethanone; | 6.7 |
| 6 | 1-(Azetidin-1-yl)-2-(3-chloro-6-phenyl-pyrrolo[3,2-b]pyridin-1-yl)ethanone; | 7.3 |
| 7 | 2-[3-Chloro-6-(4-fluorophenyl)pyrrolo[3,2-b]pyridin-1-yl]-1-morpholino-ethanone; | 6.8 |
| 8 | 1-(Azetidin-1-yl)-2-[3-chloro-6-(m-tolyl)pyrrolo[3,2-b]pyridin-1-yl]ethanone; | 7.5 |
| 9 | 2-[3-Chloro-6-(4-fluorophenyl)pyrrolo[3,2-b]pyridin-1-yl]-1-pyrrolidin-1-yl-ethanone; | 7.2 |
| 10 | 2-[3-Chloro-6-(m-tolyl)pyrrolo[3,2-b]pyridin-1-yl]-N-cyclopropyl-acetamide; | 7.3 |
| 11 | 1-(Azetidin-1-yl)-2-(3-bromo-6-phenyl-pyrrolo[3,2-b]pyridin-1-yl)ethanone; | 7.6 |
| 12 | 2-[3-Chloro-6-(m-tolyl)pyrrolo[3,2-b]pyridin-1-yl]-1-pyrrolidin-1-yl-ethanone; | 7.4 |
| 13 | 2-[3-Chloro-6-(m-tolyl)pyrrolo[3,2-b]pyridin-1-yl]-1-morpholino-ethanone; | 7.3 |
| 14 | 2-(3-Bromo-6-phenyl-pyrrolo[3,2-b]pyridin-1-yl)-N-cyclopropyl-acetamide; | 6.9 |

TABLE 5-continued

| Example # | Compound Name | pIC$_{50}$ |
|---|---|---|
| 15 | 2-(3-Bromo-6-phenyl-pyrrolo[3,2-b]pyridin-1-yl)-1-pyrrolidin-1-yl-ethanone; | 7.4 |
| 16 | 2-(3-Bromo-6-phenyl-pyrrolo[3,2-b]pyridin-1-yl)-1-morpholino-ethanone; | 7.1 |
| 17 | 2-[3-Bromo-6-(4-fluorophenyl)pyrrolo[3,2-b]pyridin-1-yl]-N-cyclopropyl-acetamide; | 7.3 |
| 18 | 1-(Azetidin-1-yl)-2-[3-bromo-6-(4-fluorophenyl)pyrrolo[3,2-b]pyridin-1-yl]ethanone; | 7.7 |
| 19 | 2-[3-Bromo-6-(4-fluorophenyl)pyrrolo[3,2-b]pyridin-1-yl]-1-pyrrolidin-1-yl-ethanone; | 7.5 |
| 20 | 2-[3-Bromo-6-(4-fluorophenyl)pyrrolo[3,2-b]pyridin-1-yl]-1-morpholino-ethanone; | 7.3 |
| 21 | 2-[3-Bromo-6-(m-tolyl)pyrrolo[3,2-b]pyridin-1-yl]-N-cyclopropyl-acetamide; | 7.4 |
| 22 | 1-(Azetidin-1-yl)-2-[3-bromo-6-(m-tolyl)pyrrolo[3,2-b]pyridin-1-yl]ethanone; | 7.6 |
| 23 | 2-[3-Bromo-6-(m-tolyl)pyrrolo[3,2-b]pyridin-1-yl]-1-pyrrolidin-1-yl-ethanone; | 7.3 |
| 24 | 2-[3-Bromo-6-(m-tolyl)pyrrolo[3,2-b]pyridin-1-yl]-1-morpholino-ethanone; | 7.0 |
| 25 | 2-[3-Chloro-6-(4-fluoro-3-methyl-phenyl)pyrrolo[3,2-b]pyridin-1-yl]-1-(3,3-difluoroazetidin-1-yl)ethanone; | 7.1 |
| 26 | 2-[3-Chloro-6-(4-fluoro-3-methyl-phenyl)pyrrolo[3,2-b]pyridin-1-yl]-1-(3-fluoroazetidin-1-yl)ethanone; | 7.4 |
| 27 | 2-[6-(4-Fluorophenyl)-3-methyl-pyrrolo[3,2-b]pyridin-1-yl]-1-pyrrolidin-1-yl-ethanone; | 7.3 |
| 28 | 2-[6-(4-Fluorophenyl)-3-methyl-pyrrolo[3,2-b]pyridin-1-yl]-1-morpholino-ethanone; | 6.7 |
| 29 | 1-(Azetidin-1-yl)-2-[3-chloro-6-(3,4-difluorophenyl)pyrrolo[3,2-b]pyridin-1-yl]ethanone; | 7.7 |
| 30 | 2-[3-Chloro-6-(3,4-difluorophenyl)pyrrolo[3,2-b]pyridin-1-yl]-1-(3-fluoroazetidin-1-yl)ethanone; | 7.7 |
| 31 | 2-[6-(4-Fluorophenyl)-2-methyl-pyrrolo[3,2-b]pyridin-1-yl]-1-morpholino-ethanone; | 5.5 |
| 32 | N-Cyclopropyl-2-[6-(4-fluorophenyl)-3-methyl-pyrrolo[3,2-b]pyridin-1-yl]acetamide; | 6.4 |
| 33 | 1-(Azetidin-1-yl)-2-[6-(4-fluorophenyl)-3-methyl-pyrrolo[3,2-b]pyridin-1-yl]ethanone; | 7.2 |
| 34 | 2-[3-Chloro-6-(3,4-difluorophenyl)pyrrolo[3,2-b]pyridin-1-yl]-1-(3,3-difluoroazetidin-1-yl)ethanone; | 7.8 |
| 35 | 2-[3-Chloro-6-[4-fluoro-3-(trifluoromethyl)phenyl]pyrrolo[3,2-b]pyridin-1-yl]-1-(3-fluoroazetidin-1-yl)ethanone; | 6.7 |
| 36 | 2-[3-Chloro-6-[3-(trifluoromethyl)phenyl]pyrrolo[3,2-b]pyridin-1-yl]-1-(3,3-difluoroazetidin-1-yl)ethanone; | 7.0 |
| 37 | 2-[6-(4-Fluorophenyl)-2-methyl-pyrrolo[3,2-b]pyridin-1-yl]-1-pyrrolidin-1-yl-ethanone; | 6.0 |
| 38 | N-Cyclopropyl-2-[6-(4-fluorophenyl)-2-methyl-pyrrolo[3,2-b]pyridin-1-yl]acetamide; | 5.3 |
| 39 | 2-[3-Chloro-6-(3,4,5-trifluorophenyl)pyrrolo[3,2-b]pyridin-1-yl]-1-(3-fluoroazetidin-1-yl)ethanone; | 7.5 |
| 40 | 2-[3-Chloro-6-[4-fluoro-3-(trifluoromethyl)phenyl]pyrrolo[3,2-b]pyridin-1-yl]-1-(3,3-difluoroazetidin-1-yl)ethanone; | 6.3 |
| 41 | 1-(Azetidin-1-yl)-2-[2-methyl-6-(m-tolyl)pyrrolo[3,2-b]pyridin-1-yl]ethanone; | 7.6 |
| 42 | 2-(2-Methyl-6-phenyl-pyrrolo[3,2-b]pyridin-1-yl)-1-pyrrolidin-1-yl-ethanone; | 5.6 |
| 43 | N-Cyclopropyl-2-(2-methyl-6-phenyl-pyrrolo[3,2-b]pyridin-1-yl)acetamide; | NT |
| 44 | 2-[2-Methyl-6-(m-tolyl)pyrrolo[3,2-b]pyridin-1-yl]-1-pyrrolidin-1-yl-ethanone; | 6.7 |
| 45 | 2-[2-Methyl-6-(m-tolyl)pyrrolo[3,2-b]pyridin-1-yl]-1-morpholino-ethanone; | 6.3 |
| 46 | 1-(Azetidin-1-yl)-2-[6-(4-fluorophenyl)-2-methyl-pyrrolo[3,2-b]pyridin-1-yl]ethanone; | 6.3 |
| 47 | 1-(Azetidin-1-yl)-2-(2-methyl-6-phenyl-pyrrolo[3,2-b]pyridin-1-yl)ethanone; | 7.1 |
| 48 | 2-[3-Chloro-6-[3-(trifluoromethyl)phenyl]pyrrolo[3,2-b]pyridin-1-yl]-1-(3-fluoroazetidin-1-yl)ethanone; | 6.2 |
| 49 | 2-[3-Chloro-6-(3,4,5-trifluorophenyl)pyrrolo[3,2-b]pyridin-1-yl]-1-(3,3-difluoroazetidin-1-yl)ethanone; | 6.7 |
| 50 | 2-[3-Chloro-6-(2,3,4-trifluorophenyl)pyrrolo[3,2-b]pyridin-1-yl]-1-(3,3-difluoroazetidin-1-yl)ethanone; | 7.4 |
| 51 | N-Cyclopropyl-2-[2-methyl-6-(m-tolyl)pyrrolo[3,2-b]pyridin-1-yl]acetamide; | 7.2 |
| 52 | 2-(2-Methyl-6-phenyl-pyrrolo[3,2-b]pyridin-1-yl)-1-morpholino-ethanone; | 5.9 |
| 53 | 2-[3-Chloro-6-(m-tolyl)pyrrolo[3,2-b]pyridin-1-yl]-1-(3,3-difluoroazetidin-1-yl)ethanone; | 5.3 |
| 54 | 2-[3-Chloro-6-(m-tolyl)pyrrolo[3,2-b]pyridin-1-yl]-1-(3-fluoroazetidin-1-yl)ethanone; | 7.2 |
| 55 | 2-(3-Chloro-6-phenyl-pyrrolo[3,2-b]pyridin-1-yl)-1-(3,3-difluoroazetidin-1-yl)ethanone; | 7.5 |
| 56 | 2-(3-Chloro-6-phenyl-pyrrolo[3,2-b]pyridin-1-yl)-1-(3-fluoroazetidin-1-yl)ethanone; | 7.3 |
| 57 | 2-[3-Chloro-6-(4-fluorophenyl)pyrrolo[3,2-b]pyridin-1-yl]-1-(3,3-difluoroazetidin-1-yl)ethanone; | 7.5 |
| 58 | 2-[3-Chloro-6-(4-fluorophenyl)pyrrolo[3,2-b]pyridin-1-yl]-1-(3-fluoroazetidin-1-yl)ethanone; | 7.6 |
| 59 | 3-[[6-(4-Fluoro-2-methyl-phenyl)pyrrolo[3,2-b]pyridin-1-yl]methyl]-5-methyl-isoxazole; | 7.4 |
| 60 | 5-Methyl-3-[[6-[3-(trifluoromethyl)phenyl]pyrrolo[3,2-b]pyridin-1-yl]methyl]isoxazole; | 7.0 |
| 61 | 5-Methyl-3-[[6-(m-tolyl)pyrrolo[3,2-b]pyridin-1-yl]methyl]isoxazole trifluoroacetate salt; | 6.4 |
| 62 | 5-Methyl-3-[[6-(o-tolyl)pyrrolo[3,2-b]pyridin-1-yl]methyl]isoxazole trifluoroacetate salt; | 6.9 |
| 63 | 3-[[6-(4-Fluoro-3-methyl-phenyl)pyrrolo[3,2-b]pyridin-1-yl]methyl]-5-methyl-isoxazole trifluoroacetate salt; | 6.7 |
| 64 | 3-[[6-(3,5-Difluorophenyl)pyrrolo[3,2-b]pyridin-1-yl]methyl]-5-methyl-isoxazole trifluoroacetate salt; | 7.2 |
| 65 | 3-[[6-(4-Fluorophenyl)pyrrolo[3,2-b]pyridin-1-yl]methyl]-5-methyl-isoxazole trifluoroacetate salt; | 7.1 |
| 66 | N-Cyclobutyl-2-[6-(4-fluoro-3-methyl-phenyl)pyrrolo[3,2-b]pyridin-1-yl]acetamide trifluoroacetate salt; | 6.7 |
| 67 | 2-[6-(4-Fluoro-3-methyl-phenyl)pyrrolo[3,2-b]pyridin-1-yl]-1-pyrrolidin-1-yl-ethanone trifluoroacetate salt; | 5.3 |
| 68 | 1-(Azetidin-1-yl)-2-[3-bromo-6-(4-fluoro-3-methyl-phenyl)pyrrolo[3,2-b]pyridin-1-yl]ethanone; | 7.4 |
| 69 | 1-(Azetidin-1-yl)-2-[3-fluoro-6-(4-fluoro-3-methyl-phenyl)pyrrolo[3,2-b]pyridin-1-yl]ethanone; | 7.6 |
| 70 | 2-[6-(4-Fluoro-3-methyl-phenyl)pyrrolo[3,2-b]pyridin-1-yl]acetic acid; | 7.3 |
| 71 | 1-(Azetidin-1-yl)-2-[6-(2-fluorophenyl)pyrrolo[3,2-b]pyridin-1-yl]ethanone; | 5.1 |
| 72 | 1-(Azetidin-1-yl)-2-[6-(3-fluorophenyl)pyrrolo[3,2-b]pyridin-1-yl]ethanone; | 6.6 |
| 73 | 1-(Azetidin-1-yl)-2-[6-(p-tolyl)pyrrolo[3,2-b]pyridin-1-yl]ethanone; | 7.4 |
| 74 | 1-(Azetidin-1-yl)-2-[6-(3-ethylphenyl)pyrrolo[3,2-b]pyridin-1-yl]ethanone; | 6.7 |
| 75 | N-Cyclopropyl-2-[6-(2-fluorophenyl)pyrrolo[3,2-b]pyridin-1-yl]acetamide; | 7.3 |
| 76 | N-Cyclopropyl-2-[6-(3-fluorophenyl)pyrrolo[3,2-b]pyridin-1-yl]acetamide; | 6.0 |
| 77 | N-Cyclopropyl-2-[6-(p-tolyl)pyrrolo[3,2-b]pyridin-1-yl]acetamide; | 6.6 |
| 78 | 2-(6-Phenylpyrrolo[3,2-b]pyridin-1-yl)-1-pyrrolidin-1-yl-ethanone; | 5.8 |
| 79 | 2-[6-(2-Fluorophenyl)pyrrolo[3,2-b]pyridin-1-yl]-1-pyrrolidin-1-yl-ethanone; | 7.1 |
| 80 | 2-[6-(4-Fluorophenyl)pyrrolo[3,2-b]pyridin-1-yl]-1-pyrrolidin-1-yl-ethanone; | 6.5 |
| 81 | 2-[6-(m-Tolyl)pyrrolo[3,2-b]pyridin-1-yl]-1-pyrrolidin-1-yl-ethanone; | 6.5 |
| 82 | 2-[6-(p-Tolyl)pyrrolo[3,2-b]pyridin-1-yl]-1-pyrrolidin-1-yl-ethanone; | 7.2 |
| 83 | 2-[6-(3-Ethylphenyl)pyrrolo[3,2-b]pyridin-1-yl]-1-pyrrolidin-1-yl-ethanone; | 6.6 |
| 84 | 2-[6-(3-Fluorophenyl)pyrrolo[3,2-b]pyridin-1-yl]-1-pyrrolidin-1-yl-ethanone; | 7.1 |
| 85 | 1-Morpholino-2-(6-phenylpyrrolo[3,2-b]pyridin-1-yl)ethanone; | 7.2 |
| 86 | 2-[6-(2-Fluorophenyl)pyrrolo[3,2-b]pyridin-1-yl]-1-morpholino-ethanone; | 6.3 |
| 87 | 2-[6-(3-Fluorophenyl)pyrrolo[3,2-b]pyridin-1-yl]-1-morpholino-ethanone; | 6.0 |
| 88 | 2-[6-(4-Fluorophenyl)pyrrolo[3,2-b]pyridin-1-yl]-1-morpholino-ethanone; | 6.6 |
| 89 | 1-Morpholino-2-[6-(m-tolyl)pyrrolo[3,2-b]pyridin-1-yl]ethanone; | 6.7 |

TABLE 5-continued

| Example # | Compound Name | pIC$_{50}$ |
|---|---|---|
| 90 | 1-Morpholino-2-[6-(p-tolyl)pyrrolo[3,2-b]pyridin-1-yl]ethanone; | 7.2 |
| 91 | 2-[6-(3-Ethylphenyl)pyrrolo[3,2-b]pyridin-1-yl]-1-morpholino-ethanone; | 5.8 |
| 92 | 2-[3-Fluoro-6-(4-fluoro-3-methyl-phenyl)pyrrolo[3,2-b]pyridin-1-yl]-N,N-dimethyl-acetamide; | 6.9 |
| 93 | 2-[6-(3,4-Difluorophenyl)-3-fluoro-pyrrolo[3,2-b]pyridin-1-yl]-N,N-dimethyl-acetamide; | 7.4 |
| 94 | 2-[3-Fluoro-6-(3,4,5-trifluorophenyl)pyrrolo[3,2-b]pyridin-1-yl]-N,N-dimethyl-acetamide; | 7.2 |
| 95 | 2-[6-[3-(Difluoromethyl)phenyl]-3-fluoro-pyrrolo[3,2-b]pyridin-1-yl]-N,N-dimethyl-acetamide; | 7.4 |
| 96 | 2-[3-Fluoro-6-(4-methyl-2-thienyl)pyrrolo[3,2-b]pyridin-1-yl]-N,N-dimethyl-acetamide; | 7.3 |
| 97 | 2-[6-(5-Chloro-2-thienyl)-3-fluoro-pyrrolo[3,2-b]pyridin-1-yl]-N,N-dimethyl-acetamide; | 7.2 |
| 98 | 2-[3-Fluoro-6-(4-fluorophenyl)pyrrolo[3,2-b]pyridin-1-yl]-N,N-dimethyl-acetamide; | 7.3 |
| 99 | N-Cyclopropyl-2-[6-[5-(trifluoromethyl)-3-pyridyl]pyrrolo[3,2-b]pyridin-1-yl]acetamide; | 6.2 |
| 100 | N-Cyclopropyl-2-[6-(3,4-difluorophenyl)pyrrolo[3,2-b]pyridin-1-yl]acetamide; | 6.0 |
| 101 | N-Cyclopropyl-2-[6-[4-fluoro-3-(trifluoromethyl)phenyl]pyrrolo[3,2-b]pyridin-1-yl]acetamide; | 6.7 |
| 102 | 1-(Azetidin-1-yl)-2-[6-[5-(trifluoromethyl)-3-pyridyl]pyrrolo[3,2-b]pyridin-1-yl]ethanone; | 6.4 |
| 103 | 1-(Azetidin-1-yl)-2-[6-(3,4-difluorophenyl)pyrrolo[3,2-b]pyridin-1-yl]ethanone; | 6.6 |
| 104 | 1-(Azetidin-1-yl)-2-[6-[4-fluoro-3-(trifluoromethyl)phenyl]pyrrolo[3,2-b]pyridin-1-yl]ethanone; | 7.5 |
| 105 | 2-[6-[4-fluoro-3-(trifluoromethyl)phenyl]pyrrolo[3,2-b]pyridin-1-yl]-1-pyrrolidin-1-yl-ethanone; | 7.4 |
| 106 | 1-(3,3-Difluoroazetidin-1-yl)-2-[6-[4-fluoro-3-(trifluoromethyl)phenyl]pyrrolo[3,2-b]pyridin-1-yl]ethanone; | 6.5 |
| 107 | 2-[6-(3,4-Difluorophenyl)pyrrolo[3,2-b]pyridin-1-yl]-1-morpholino-ethanone; | 6.8 |
| 108 | 2-[6-[4-Fluoro-3-(trifluoromethyl)phenyl]pyrrolo[3,2-b]pyridin-1-yl]-1-morpholino-ethanone; | 6.9 |
| 109 | 1-(Azetidin-1-yl)-2-[6-[2-(trifluoromethyl)-4-pyridyl]pyrrolo[3,2-b]pyridin-1-yl]ethanone; | 6.8 |
| 110 | N-Cyclopropyl-2-[6-[2-(trifluoromethyl)-4-pyridyl]pyrrolo[3,2-b]pyridin-1-yl]acetamide; | 6.6 |
| 111 | N-Cyclopropyl-2-[6-[6-(trifluoromethyl)-2-pyridyl]pyrrolo[3,2-b]pyridin-1-yl]acetamide; | 6.4 |
| 112 | 1-(Azetidin-1-yl)-2-[6-(6-methyl-3-pyridyl)pyrrolo[3,2-b]pyridin-1-yl]ethanone; | 6.3 |
| 113 | 5-[1-[2-(Azetidin-1-yl)-2-oxo-ethyl]pyrrolo[3,2-b]pyridin-6-yl]pyridine-2-carbonitrile; | 5.3 |
| 114 | 6-(3,4-Difluorophenyl)-1-(pyrimidin-5-ylmethyl)pyrrolo[3,2-b]pyridine; | <5 |
| 115 | 6-(3,4-Difluorophenyl)-1-[(5-fluoropyrimidin-2-yl)methyl]pyrrolo[3,2-b]pyridine; | 6.5 |
| 116 | Cyclobutyl-[6-(3,4-difluorophenyl)pyrrolo[3,2-b]pyridin-1-yl]methanone; | 6.1 |
| 117 | 1-(3,3-Difluoroazetidin-1-yl)-2-[6-[6-(trifluoromethyl)-2-pyridyl]pyrrolo[3,2-b]pyridin-1-yl]ethanone; | 5.3 |
| 118 | 1-(Azetidin-1-yl)-2-[6-(2,3,4-trifluorophenyl)pyrrolo[3,2-b]pyridin-1-yl]ethanone; | 7.0 |
| 119 | 2-Cyclopropyl-1-[6-(3,4-difluorophenyl)pyrrolo[3,2-b]pyridin-1-yl]ethanone; | 7.3 |
| 120 | 1-Pyrrolidin-1-yl-2-[6-(2,3,4-trifluorophenyl)pyrrolo[3,2-b]pyridin-1-yl]ethanone; | 6.2 |
| 121 | 1-(3,3-Difluoroazetidin-1-yl)-2-[6-(3,5-difluorophenyl)pyrrolo[3,2-b]pyridin-1-yl]ethanone; | 7.2 |
| 122 | 2-[6-(3,5-Difluorophenyl)pyrrolo[3,2-b]pyridin-1-yl]-1-pyrrolidin-1-yl-ethanone; | 7.4 |
| 123 | 1-Pyrrolidin-1-yl-2-[6-(3,4,5-trifluorophenyl)pyrrolo[3,2-b]pyridin-1-yl]ethanone; | 7.7 |
| 124 | 1-(3,3-Difluoroazetidin-1-yl)-2-[6-(3,4,5-trifluorophenyl)pyrrolo[3,2-b]pyridin-1-yl]ethanone; | 7.5 |
| 125 | 2-[6-(3,5-Difluorophenyl)pyrrolo[3,2-b]pyridin-1-yl]-1-morpholino-ethanone; | 7.5 |
| 126 | 1-Morpholino-2-[6-(2,3,4-trifluorophenyl)pyrrolo[3,2-b]pyridin-1-yl]ethanone; | 7.0 |
| 127 | 1-Morpholino-2-[6-(3,4,5-trifluorophenyl)pyrrolo[3,2-b]pyridin-1-yl]ethanone; | 6.8 |
| 128 | 2-[6-(3,4-Difluorophenyl)pyrrolo[3,2-b]pyridin-1-yl]-1-(3-fluoroazetidin-1-yl)ethanone; | 7.2 |
| 129 | 2-[6-(3,5-Difluorophenyl)pyrrolo[3,2-b]pyridin-1-yl]-1-(3-fluoroazetidin-1-yl)ethanone; | 7.6 |
| 130 | 6-(4-Methyl-2-thienyl)-1-(pyridazin-3-ylmethyl)pyrrolo[3,2-b]pyridine; | 7.7 |
| 131 | 6-(3,4-Difluorophenyl)-1-(pyridazin-3-ylmethyl)pyrrolo[3,2-b]pyridine; | 6.9 |
| 132 | 2-[6-(4-Methyl-2-thienyl)pyrrolo[3,2-b]pyridin-1-yl]-1-morpholino-ethanone; | 6.9 |
| 133 | 1-(Azetidin-1-yl)-2-[6-(2,4-difluorophenyl)pyrrolo[3,2-b]pyridin-1-yl]ethanone; | 7.1 |
| 134 | 1-(Azetidin-1-yl)-2-[6-(2,3-difluorophenyl)pyrrolo[3,2-b]pyridin-1-yl]ethanone; | 7.5 |
| 135 | 1-(Azetidin-1-yl)-2-[6-(2,5-difluorophenyl)pyrrolo[3,2-b]pyridin-1-yl]ethanone; | 7.4 |
| 136 | 1-Cyclopropyl-2-[6-(3,4-difluorophenyl)-3-fluoro-pyrrolo[3,2-b]pyridin-1-yl]ethanone; | 7.2 |
| 137 | 6-(4-Methyl-2-thienyl)-1-[[5-(trifluoromethyl)-2-furyl]methyl]pyrrolo[3,2-b]pyridine; | 7.7 |
| 138 | 6-(3,4-Difluorophenyl)-1-[[5-(trifluoromethyl)-2-furyl]methyl]pyrrolo[3,2-b]pyridine; | NT |
| 139 | N,N-Dimethyl-2-[6-(4-methyl-2-thienyl)pyrrolo[3,2-b]pyridin-1-yl]acetamide; | NT |
| 140 | 1-[6-(3,4-Difluorophenyl)pyrrolo[3,2-b]pyridin-1-yl]-3,3-dimethyl-butan-2-one; | 7.5 |
| 141 | 1-[6-(4-Fluoro-3-methyl-phenyl)pyrrolo[3,2-b]pyridin-1-yl]-3,3-dimethyl-butan-2-one; | 6.4 |
| 142 | 1-[6-(3,5-Difluorophenyl)pyrrolo[3,2-b]pyridin-1-yl]-3,3-dimethyl-butan-2-one; | 6.3 |
| 143 | 3,3-Dimethyl-1-[6-(4-methyl-2-thienyl)pyrrolo[3,2-b]pyridin-1-yl]butan-2-one; | 6.1 |
| 144 | 1-[6-[3-(Difluoromethyl)phenyl]pyrrolo[3,2-b]pyridin-1-yl]-3,3-dimethyl-butan-2-one; | 5.7 |
| 145 | 1-[6-(3-Ethylphenyl)pyrrolo[3,2-b]pyridin-1-yl]-3,3-dimethyl-butan-2-one; | 6.3 |
| 146 | 2-[3-Chloro-6-(4-fluoro-3-methyl-phenyl)pyrrolo[3,2-b]pyridin-1-yl]-N,N-dimethyl-acetamide; | 6.0 |
| 147 | 2-[3-Chloro-6-(3,4-difluorophenyl)pyrrolo[3,2-b]pyridin-1-yl]-N,N-dimethyl-acetamide; | 7.3 |
| 148 | 2-[3-Chloro-6-(3,5-difluorophenyl)pyrrolo[3,2-b]pyridin-1-yl]-N,N-dimethyl-acetamide; | 7.3 |
| 149 | 2-[3-Chloro-6-(4-methyl-2-thienyl)pyrrolo[3,2-b]pyridin-1-yl]-N,N-dimethyl-acetamide; | 7.3 |
| 150 | 2-[3-Chloro-6-[3-(difluoromethyl)phenyl]pyrrolo[3,2-b]pyridin-1-yl]-N,N-dimethyl-acetamide; | 7.3 |
| 151 | 2-[3-Chloro-6-(3-ethylphenyl)pyrrolo[3,2-b]pyridin-1-yl]-N,N-dimethyl-acetamide; | 7.1 |
| 152 | 2-[3-Chloro-6-(3,4,5-trifluorophenyl)pyrrolo[3,2-b]pyridin-1-yl]-N,N-dimethyl-acetamide; | 7.0 |
| 153 | N-Cyclopropyl-2-[6-(4-methyl-2-thienyl)pyrrolo[3,2-b]pyridin-1-yl]acetamide trifluoroacetate salt; | 7.2 |
| 154 | N-Cyclopropyl-2-[6-(2,3-dimethylphenyl)pyrrolo[3,2-b]pyridin-1-yl]acetamide trifluoroacetate salt; | 6.4 |
| 155 | N-Cyclopropyl-2-[6-(m-tolyl)pyrrolo[3,2-b]pyridin-1-yl]acetamide trifluoroacetate salt; | 6.6 |
| 156 | N-Cyclopropyl-2-[6-(3,4-dichlorophenyl)pyrrolo[3,2-b]pyridin-1-yl]acetamide trifluoroacetate salt; | 6.7 |
| 157 | N-Cyclopropyl-2-[6-[2-methyl-3-(trifluoromethyl)phenyl]pyrrolo[3,2-b]pyridin-1-yl]acetamide trifluoroacetate salt; | 6.6 |
| 158 | N-Cyclopropyl-2-[6-(6-phenylpyrrolo[3,2-b]pyridin-1-yl)acetamide trifluoroacetate salt; | 6.2 |
| 159 | N-Cyclopropyl-2-[6-(4-fluoro-2,3-dimethyl-phenyl)pyrrolo[3,2-b]pyridin-1-yl]acetamide trifluoroacetate salt; | 6.6 |
| 160 | N-Cyclopropyl-2-[6-(o-tolyl)pyrrolo[3,2-b]pyridin-1-yl]acetamide; | 6.7 |
| 161 | N-Cyclopropyl-2-[6-(4-fluoro-2-methyl-phenyl)pyrrolo[3,2-b]pyridin-1-yl]acetamide trifluoroacetate salt; | 6.7 |
| 162 | 1-(Azetidin-1-yl)-2-[6-(o-tolyl)pyrrolo[3,2-b]pyridin-1-yl]ethanone trifluoroacetate salt; | 7.0 |

TABLE 5-continued

| Example # | Compound Name | pIC$_{50}$ |
|---|---|---|
| 163 | 1-(Azetidin-1-yl)-2-[6-(4-fluoro-2-methyl-phenyl)pyrrolo[3,2-b]pyridin-1-yl]ethanone trifluoroacetate salt; | 7.1 |
| 164 | 1-(Azetidin-1-yl)-2-[6-(4-fluoro-2,3-dimethyl-phenyl)pyrrolo[3,2-b]pyridin-1-yl]ethanone trifluoroacetate salt; | 7.2 |
| 165 | 1-(Azetidin-1-yl)-2-[6-(2,3-dimethylphenyl)pyrrolo[3,2-b]pyridin-1-yl]ethanone trifluoroacetate salt; | 7.2 |
| 166 | 1-(Azetidin-1-yl)-2-[6-[3-(trifluoromethyl)phenyl]pyrrolo[3,2-b]pyridin-1-yl]ethanone trifluoroacetate salt; | 6.9 |
| 167 | 1-(Azetidin-1-yl)-2-[6-[2-methyl-3-(trifluoromethyl)phenyl]pyrrolo[3,2-b]pyridin-1-yl]ethanone trifluoroacetate salt; | 7.4 |
| 168 | N-Cyclopropyl-2-[6-(4-fluorophenyl)pyrrolo[3,2-b]pyridin-1-yl]acetamide; | 6.6 |
| 169 | 1-(Azetidin-1-yl)-2-[6-(4-fluoro-3-methyl-phenyl)-3-methyl-pyrrolo[3,2-b]pyridin-1-yl]ethanone trifluoroacetate salt; | 6.7 |
| 170 | 1-Butyl-6-(4-fluoro-3-methyl-phenyl)pyrrolo[3,2-b]pyridine trifluoroacetate salt; | 6.5 |
| 171 | 6-(4-Fluoro-3-methyl-phenyl)-1-isopentyl-pyrrolo[3,2-b]pyridine trifluoroacetate salt; | 6.7 |
| 172 | 6-(4-Fluoro-3-methyl-phenyl)-1-(3-pyridylmethyl)pyrrolo[3,2-b]pyridine trifluoroacetate salt; | 6.1 |
| 173 | 1-(Cyclobutylmethyl)-6-(4-fluoro-3-methyl-phenyl)pyrrolo[3,2-b]pyridine trifluoroacetate salt; | 7.2 |
| 174 | 1-(Cyclopropylmethyl)-6-(4-fluoro-3-methyl-phenyl)pyrrolo[3,2-b]pyridine trifluoroacetate salt; | 6.8 |
| 175 | 2-[6-(4-Fluoro-3-methyl-phenyl)pyrrolo[3,2-b]pyridin-1-yl]-N,N-dimethyl-acetamide trifluoroacetate salt; | 6.3 |
| 176 | 2-[3-Chloro-6-(4-fluoro-3-methyl-phenyl)pyrrolo[3,2-b]pyridin-1-yl]-N-cyclopropyl-acetamide trifluoroacetate salt; | 7.5 |
| 177 | 6-(4-Fluoro-3-methyl-phenyl)-1-(2-pyridylmethyl)pyrrolo[3,2-b]pyridine trifluoroacetate salt; | 7.5 |
| 178 | (R/S)-6-(4-Fluoro-3-methyl-phenyl)-1-(tetrahydrofuran-3-ylmethyl)pyrrolo[3,2-b]pyridine trifluoroacetate salt; | 6.5 |
| 179 | 6-(4-Fluoro-3-methyl-phenyl)-1-(4-pyridylmethyl)pyrrolo[3,2-b]pyridine trifluoroacetate salt; | 7.3 |
| 180 | (R/S)-6-(4-Fluoro-3-methyl-phenyl)-1-(oxiran-2-ylmethyl)pyrrolo[3,2-b]pyridine trifluoroacetate salt; | 6.1 |
| 181 | 6-(4-Fluoro-3-methyl-phenyl)-1-(2-pyrazol-1-ylethyl)pyrrolo[3,2-b]pyridine trifluoroacetate salt; | 6.1 |
| 182 | 1-(Azetidin-1-yl)-2-[6-(5-chloro-2-thienyl)-3-fluoro-pyrrolo[3,2-b]pyridin-1-yl]ethanone; | 5.4 |
| 183 | 6-(4-Fluoro-3-methyl-phenyl)-1-(pyrimidin-2-ylmethyl)pyrrolo[3,2-b]pyridine trifluoroacetate salt; | 7.5 |
| 184 | (R/S)-6-(4-Fluoro-3-methyl-phenyl)-1-(oxetan-2-ylmethyl)pyrrolo[3,2-b]pyridine trifluoroacetate salt; | 6.3 |
| 185 | 1-(3,3-Difluoroazetidin-1-yl)-2-[3-fluoro-6-(4-fluoro-3-methyl-phenyl)pyrrolo[3,2-b]pyridin-1-yl]ethanone; | 7.0 |
| 186 | 1-Cyclopropyl-2-[6-(4-fluoro-3-methyl-phenyl)pyrrolo[3,2-b]pyridin-1-yl]ethanone trifluoroacetate salt; | 7.4 |
| 187 | 1-[6-(4-Fluoro-3-methyl-phenyl)pyrrolo[3,2-b]pyridin-1-yl]-3-methyl-butan-2-one trifluoroacetate salt; | 7.3 |
| 188 | 2-[6-(4-Fluoro-3-methyl-phenyl)pyrrolo[3,2-b]pyridin-1-yl]-1-(4-hydroxy-1-piperidyl)ethanone trifluoroacetate salt; | 7.3 |
| 189 | (R/S)-1-(3-Azabicyclo[3.1.0]hexan-3-yl)-2-[6-(4-fluoro-3-methyl-phenyl)pyrrolo[3,2-b]pyridin-1-yl]ethanone trifluoroacetate salt; | 6.9 |
| 190 | 2-[6-(4-Fluoro-3-methyl-phenyl)pyrrolo[3,2-b]pyridin-1-yl]-1-(4-methoxy-1-piperidyl)ethanone trifluoroacetate salt; | 6.6 |
| 191 | 2-[6-(4-Fluoro-3-methyl-phenyl)pyrrolo[3,2-b]pyridin-1-yl]-1-(4-fluoro-1-piperidyl)ethanone trifluoroacetate salt; | 6.5 |
| 192 | 2-[6-(4-Fluoro-3-methyl-phenyl)pyrrolo[3,2-b]pyridin-1-yl]-1-[4-(fluoromethyl)-1-piperidyl]ethanone trifluoroacetate salt; | 7.1 |
| 193 | 2-[6-(4-Fluoro-3-methyl-phenyl)pyrrolo[3,2-b]pyridin-1-yl]-1-(1-piperidyl)ethanone trifluoroacetate salt; | 6.1 |
| 194 | (R/S)-2-[6-(4-Fluoro-3-methyl-phenyl)pyrrolo[3,2-b]pyridin-1-yl]-1-(2-methylmorpholin-4-yl)ethanone trifluoroacetate salt; | 6.8 |
| 195 | (R/S)-2-[6-(4-Fluoro-3-methyl-phenyl)pyrrolo[3,2-b]pyridin-1-yl]-1-[3-(trifluoromethyl)-1-piperidyl]ethanone trifluoroacetate salt; | 6.4 |
| 196 | (R/S)-1-(2-Ethylpyrrolidin-1-yl)-2-[6-(4-fluoro-3-methyl-phenyl)pyrrolo[3,2-b]pyridin-1-yl]ethanone trifluoroacetate salt; | 5.9 |
| 197 | 1-(2,2-Dimethylmorpholin-4-yl)-2-[6-(4-fluoro-3-methyl-phenyl)pyrrolo[3,2-b]pyridin-1-yl]ethanone trifluoroacetate salt; | 5.8 |
| 198 | (R/S)-2-[6-(4-Fluoro-3-methyl-phenyl)pyrrolo[3,2-b]pyridin-1-yl]-1-(3-methoxypyrrolidin-1-yl)ethanone trifluoroacetate salt; | 6.0 |
| 199 | (R/S)-2-[6-(4-Fluoro-3-methyl-phenyl)pyrrolo[3,2-b]pyridin-1-yl]-1-(3-fluoro-1-piperidyl)ethanone trifluoroacetate salt; | 6.7 |
| 200 | 1-(2,2-Dimethylpyrrolidin-1-yl)-2-[6-(4-fluoro-3-methyl-phenyl)pyrrolo[3,2-b]pyridin-1-yl]ethanone trifluoroacetate salt; | 6.6 |
| 201 | 2-[6-(4-Fluoro-3-methyl-phenyl)pyrrolo[3,2-b]pyridin-1-yl]-1-[(3R)-3-fluoropyrrolidin-1-yl]ethanone trifluoroacetate salt; | 5.4 |
| 202 | 2-[6-(4-Fluorophenyl)pyrrolo[3,2-b]pyridin-1-yl]-1-(3-hydroxy-3-methyl-azetidin-1-yl)ethanone; | 6.9 |
| 203 | 2-[6-(4-Fluorophenyl)pyrrolo[3,2-b]pyridin-1-yl]-1-[3-hydroxy-3-(trifluoromethyl)azetidin-1-yl]ethanone; | 6.4 |
| 204 | 1-(3-Fluoroazetidin-1-yl)-2-[6-(4-fluorophenyl)pyrrolo[3,2-b]pyridin-1-yl]ethanone; | 5.8 |
| 205 | N-Cyclopropyl-2-[6-(4-fluorophenyl)pyrrolo[3,2-b]pyridin-1-yl]-N-methyl-acetamide; | 7.3 |
| 206 | 2-[6-(4-Fluorophenyl)pyrrolo[3,2-b]pyridin-1-yl]-1-[3-(hydroxymethyl)azetidin-1-yl]ethanone; | 6.5 |
| 207 | 2-[6-(4-Fluorophenyl)pyrrolo[3,2-b]pyridin-1-yl]-1-(3-methoxyazetidin-1-yl)ethanone; | 6.5 |
| 208 | 1-(5-Azaspiro[2.3]hexan-5-yl)-2-[6-(4-fluoro-3-methyl-phenyl)pyrrolo[3,2-b]pyridin-1-yl]ethanone trifluoroacetate salt; | 6.5 |
| 209 | 2-[6-(4-Fluoro-3-methyl-phenyl)pyrrolo[3,2-b]pyridin-1-yl]-1-(4-hydroxy-4-methyl-1-piperidyl)ethanone trifluoroacetate salt; | 6.7 |
| 210 | (R/S)-2-[6-(4-Fluoro-3-methyl-phenyl)pyrrolo[3,2-b]pyridin-1-yl]-1-(3-methylmorpholin-4-yl)ethanone trifluoroacetate salt; | 6.4 |
| 211 | 2-[6-(4-Fluorophenyl)pyrrolo[3,2-b]pyridin-1-yl]-1-(3-hydroxyazetidin-1-yl)ethanone; | 6.4 |
| 212 | 1-[2-[6-(4-Fluorophenyl)pyrrolo[3,2-b]pyridin-1-yl]acetyl]azetidine-3-carbonitrile; | 6.5 |
| 213 | 1-(3,3-Difluoroazetidin-1-yl)-2-[6-(4-fluorophenyl)pyrrolo[3,2-b]pyridin-1-yl]ethanone; | 6.2 |
| 214 | 2-[6-(4-Fluorophenyl)pyrrolo[3,2-b]pyridin-1-yl]-1-(3-methylazetidin-1-yl)ethanone; | 7.0 |
| 215 | 1-(3,3-Dimethylazetidin-1-yl)-2-[6-(4-fluorophenyl)pyrrolo[3,2-b]pyridin-1-yl]ethanone; | 6.8 |
| 216 | 1-[2-[6-(4-Fluorophenyl)pyrrolo[3,2-b]pyridin-1-yl]acetyl]pyrrolidin-3-one trifluoroacetate salt; | 5.9 |
| 217 | 1-(3,3-Difluoropyrrolidin-1-yl)-2-[6-(4-fluorophenyl)pyrrolo[3,2-b]pyridin-1-yl]ethanone; | 6.5 |
| 218 | (R/S)-2-[6-(4-Fluorophenyl)pyrrolo[3,2-b]pyridin-1-yl]-1-(3-hydroxypyrrolidin-1-yl)ethanone; | 6.4 |
| 219 | 1-Cyclopropyl-2-[6-(m-tolyl)pyrrolo[3,2-b]pyridin-1-yl]ethanone; | 6.3 |
| 220 | 1-Cyclopropyl-2-(6-phenylpyrrolo[3,2-b]pyridin-1-yl)ethanone; | 7.3 |
| 221 | 1-Cyclopropyl-2-[6-(3-fluorophenyl)pyrrolo[3,2-b]pyridin-1-yl]ethanone; | 7.1 |
| 222 | 1-Cyclopropyl-2-[6-(4-fluorophenyl)pyrrolo[3,2-b]pyridin-1-yl]ethanone; | 7.1 |
| 223 | 1-[6-(4-Fluoro-2,3-dimethyl-phenyl)pyrrolo[3,2-b]pyridin-1-yl]-3-methyl-butan-2-one; | 7.1 |
| 224 | 1-[6-(3-Ethylphenyl)pyrrolo[3,2-b]pyridin-1-yl]-3-methyl-butan-2-one; | 6.4 |
| 225 | 1-[6-(2,3-Dimethylphenyl)pyrrolo[3,2-b]pyridin-1-yl]-3-methyl-butan-2-one; | 7.1 |

TABLE 5-continued

| Example # | Compound Name | pIC$_{50}$ |
|---|---|---|
| 226 | 2-[6-(4-Fluorophenyl)pyrrolo[3,2-b]pyridin-1-yl]-1-phenyl-ethanone; | 6.7 |
| 227 | 1-(4-Fluorophenyl)-2-[6-(4-fluorophenyl)pyrrolo[3,2-b]pyridin-1-yl]ethanone; | 6.1 |
| 228 | (R/S)-6-(4-Fluorophenyl)-1-(tetrahydropyran-2-ylmethyl)pyrrolo[3,2-b]pyridine trifluoroacetate salt; | 6.2 |
| 229 | 2-[6-(4-Fluorophenyl)pyrrolo[3,2-b]pyridin-1-yl]-N-isopropyl-acetamide; | 6.3 |
| 230 | 2-[6-(4-Fluorophenyl)pyrrolo[3,2-b]pyridin-1-yl]-N-propyl-acetamide; | 5.3 |
| 231 | (R/S)-2-[6-(4-Fluorophenyl)pyrrolo[3,2-b]pyridin-1-yl]-N-(2,2,2-trifluoro-1-methyl-ethyl)acetamide; | 5.7 |
| 232 | 2-[6-(4-Fluorophenyl)pyrrolo[3,2-b]pyridin-1-yl]-N-(1-methylcyclopropyl)acetamide; | 5.0 |
| 233 | N-(2-Fluoroethyl)-2-[6-(4-fluorophenyl)pyrrolo[3,2-b]pyridin-1-yl]acetamide; | 4.8 |
| 234 | 2-[6-(4-Fluorophenyl)pyrrolo[3,2-b]pyridin-1-yl]-N-isobutyl-acetamide; | 5.6 |
| 235 | 5-[[6-(4-Fluoro-3-methyl-phenyl)pyrrolo[3,2-b]pyridin-1-yl]methyl]-3-methyl-1,2,4-oxadiazole; | 4.9 |
| 236 | 6-(4-Fluoro-3-methyl-phenyl)-1-[(1-methylpyrazol-4-yl)methyl]pyrrolo[3,2-b]pyridine; | 6.7 |
| 237 | N-(Cyclopropylmethyl)-2-[6-(4-fluorophenyl)pyrrolo[3,2-b]pyridin-1-yl]acetamide; | 5.7 |
| 238 | 6-(4-Fluoro-3-methyl-phenyl)-1-[(1-methyltriazol-4-yl)methyl]pyrrolo[3,2-b]pyridine; | 5.5 |
| 239 | 5-[[3-Chloro-6-(4-fluoro-3-methyl-phenyl)pyrrolo[3,2-b]pyridin-1-yl]methyl]-3-methyl-1,2,4-oxadiazole; | 6.8 |
| 240 | 3-Chloro-6-(4-fluoro-3-methyl-phenyl)-1-[(1-methylpyrazol-4-yl)methyl]pyrrolo[3,2-b]pyridine; | 6.3 |
| 241 | 2-[3-Chloro-6-(4-fluoro-3-methyl-phenyl)pyrrolo[3,2-b]pyridin-1-yl]-1-cyclobutyl-ethanone; | 5.3 |
| 242 | 1-Cyclobutyl-2-[6-(4-fluoro-3-methyl-phenyl)pyrrolo[3,2-b]pyridin-1-yl]ethanone; | 6.1 |
| 243 | 1-(Azetidin-1-yl)-2-[3-chloro-6-[5-(trifluoromethyl)-3-pyridyl]pyrrolo[3,2-b]pyridin-1-yl]ethanone trifluoroacetate salt; | 7.0 |
| 244 | 2-[3-Chloro-6-[5-(trifluoromethyl)-3-pyridyl]pyrrolo[3,2-b]pyridin-1-yl]-N-cyclopropyl-acetamide trifluoroacetate salt; | 6.2 |
| 245 | 1-(Azetidin-1-yl)-2-[3-chloro-6-[6-(trifluoromethyl)-2-pyridyl]pyrrolo[3,2-b]pyridin-1-yl]ethanone; | 6.4 |
| 246 | 2-[3-Chloro-6-[6-(trifluoromethyl)-2-pyridyl]pyrrolo[3,2-b]pyridin-1-yl]-N-cyclopropyl-acetamide; | 7.0 |
| 247 | 2-[3-Chloro-6-[6-(trifluoromethyl)-2-pyridyl]pyrrolo[3,2-b]pyridin-1-yl]-1-(3-fluoroazetidin-1-yl)ethanone; | 6.5 |
| 248 | N-Cyclopropyl-2-[6-(3,4,5-trifluorophenyl)pyrrolo[3,2-b]pyridin-1-yl]acetamide; | 7.2 |
| 249 | N-Cyclopropyl-2-[6-(2,3,4-trifluorophenyl)pyrrolo[3,2-b]pyridin-1-yl]acetamide; | 7.1 |
| 250 | N-Cyclopropyl-2-[6-[3-(difluoromethyl)phenyl]pyrrolo[3,2-b]pyridin-1-yl]acetamide; | 6.6 |
| 251 | N-Benzyl-2-[6-(4-fluorophenyl)pyrrolo[3,2-b]pyridin-1-yl]acetamide; | 7.3 |
| 252 | 2-[[6-(4-Fluoro-3-methyl-phenyl)pyrrolo[3,2-b]pyridin-1-yl]methyl]oxazole; | 5.3 |
| 253 | 2-[6-(4-Fluorophenyl)pyrrolo[3,2-b]pyridin-1-yl]-N-(2-hydroxyethyl)acetamide; | 7.1 |
| 254 | 2-[6-(4-Fluorophenyl)pyrrolo[3,2-b]pyridin-1-yl]-N-(2-methoxyethyl)acetamide; | 5.9 |
| 255 | 1-(3,3-Difluoroazetidin-1-yl)-2-[6-[2-fluoro-3-(trifluoromethyl)phenyl]pyrrolo[3,2-b]pyridin-1-yl]ethanone trifluoroacetate salt; | 5.4 |
| 256 | 1-(3,3-Difluoroazetidin-1-yl)-2-[6-(3-fluorophenyl)pyrrolo[3,2-b]pyridin-1-yl]ethanone trifluoroacetate salt; | 7.1 |
| 257 | 1-(3,3-Difluoroazetidin-1-yl)-2-(6-phenylpyrrolo[3,2-b]pyridin-1-yl)ethanone trifluoroacetate salt; | 6.9 |
| 258 | 1-(3,3-Difluoroazetidin-1-yl)-2-[6-(3-ethylphenyl)pyrrolo[3,2-b]pyridin-1-yl]ethanone trifluoroacetate salt; | 6.7 |
| 259 | 1-(3,3-Difluoroazetidin-1-yl)-2-[6-(4-fluoro-3-methyl-phenyl)pyrrolo[3,2-b]pyridin-1-yl]ethanone trifluoroacetate salt; | 7.5 |
| 260 | 1-(3,3-Difluoroazetidin-1-yl)-2-[6-[3-(trifluoromethyl)phenyl]pyrrolo[3,2-b]pyridin-1-yl]ethanone trifluoroacetate salt; | 7.4 |
| 261 | 1-(3,3-Difluoroazetidin-1-yl)-2-[6-(4-fluoro-2-methyl-phenyl)pyrrolo[3,2-b]pyridin-1-yl]ethanone trifluoroacetate salt; | 7.3 |
| 262 | 1-(3-Fluoroazetidin-1-yl)-2-[6-[4-fluoro-3-(trifluoromethyl)phenyl]pyrrolo[3,2-b]pyridin-1-yl]ethanone trifluoroacetate salt; | 7.0 |
| 263 | 1-(3-Fluoroazetidin-1-yl)-2-[6-(3-fluorophenyl)pyrrolo[3,2-b]pyridin-1-yl]ethanone trifluoroacetate salt; | 6.8 |
| 264 | 1-(3-Fluoroazetidin-1-yl)-2-[6-(4-fluoro-2-methyl-phenyl)pyrrolo[3,2-b]pyridin-1-yl]ethanone trifluoroacetate salt; | 7.2 |
| 265 | 1-(3-Fluoroazetidin-1-yl)-2-[6-[3-(trifluoromethyl)phenyl]pyrrolo[3,2-b]pyridin-1-yl]ethanone trifluoroacetate salt; | 7.0 |
| 266 | 1-(3-Fluoroazetidin-1-yl)-2-[6-(m-tolyl)pyrrolo[3,2-b]pyridin-1-yl]ethanone trifluoroacetate salt; | 6.9 |
| 267 | 1-(3-Fluoroazetidin-1-yl)-2-[6-[2-fluoro-3-(trifluoromethyl)phenyl]pyrrolo[3,2-b]pyridin-1-yl]ethanone trifluoroacetate salt; | 7.4 |
| 268 | 2-[6-(3-Ethylphenyl)pyrrolo[3,2-b]pyridin-1-yl]-1-(3-fluoroazetidin-1-yl)ethanone trifluoroacetate salt; | 7.1 |
| 269 | 1-(3,3-Difluoroazetidin-1-yl)-2-[6-(m-tolyl)pyrrolo[3,2-b]pyridin-1-yl]ethanone; | 7.2 |
| 270 | 1-(3-Fluoroazetidin-1-yl)-2-(6-phenylpyrrolo[3,2-b]pyridin-1-yl)ethanone; | 7.4 |
| 271 | 1-(3,3-Difluoroazetidin-1-yl)-2-[6-(2,4-difluoro-3-methyl-phenyl)-3-fluoro-pyrrolo[3,2-b]pyridin-1-yl]ethanone; | 7.1 |
| 272 | (R/S)-1-[6-(3,5-Difluorophenyl)pyrrolo[3,2-b]pyridin-1-yl]-3-methyl-butan-2-ol; | 7.6 |
| 273 | 2-[6-(4-Fluoro-3-methyl-phenyl)pyrrolo[3,2-b]pyridin-1-yl]-1-(3-hydroxyazetidin-1-yl)ethanone; | 6.0 |
| 274 | (R/S)-1-Cyclopropyl-2-[6-(4-fluoro-3-methyl-phenyl)pyrrolo[3,2-b]pyridin-1-yl]ethanol; | 7.2 |
| 275 | (R/S)-2-Cyclopropyl-1-[6-(4-fluoro-3-methyl-phenyl)pyrrolo[3,2-b]pyridin-1-yl]propan-2-ol trifluoroacetate salt; | 6.8 |
| 276 | 1-Cyclopropyl-2-[6-(4-fluoro-3-methyl-phenyl)pyrrolo[3,2-b]pyridin-1-yl]-N-methoxy-ethanimine; | 6.3 |
| 277 | 1-(3-Fluoroazetidin-1-yl)-2-[6-(2-thienyl)pyrrolo[3,2-b]pyridin-1-yl]ethanone; | 5.5 |
| 278 | 1-Pyrrolidin-1-yl-2-[6-(2-thienyl)pyrrolo[3,2-b]pyridin-1-yl]ethanone; | 6.6 |
| 279 | 1-(3,3-Difluoroazetidin-1-yl)-2-[6-(5-methyl-2-thienyl)pyrrolo[3,2-b]pyridin-1-yl]ethanone; | 6.6 |
| 280 | 1-(3-Fluoroazetidin-1-yl)-2-[6-(5-methyl-2-thienyl)pyrrolo[3,2-b]pyridin-1-yl]ethanone; | 7.5 |
| 281 | 2-[6-(5-Ethyl-2-thienyl)pyrrolo[3,2-b]pyridin-1-yl]-1-(3-fluoroazetidin-1-yl)ethanone; | 7.7 |
| 282 | 2-[6-(5-Ethyl-2-thienyl)pyrrolo[3,2-b]pyridin-1-yl]-1-pyrrolidin-1-yl-ethanone; | 7.1 |
| 283 | 2-[6-(5-Methyl-2-thienyl)pyrrolo[3,2-b]pyridin-1-yl]-1-pyrrolidin-1-yl-ethanone; | 6.7 |
| 284 | 1-(3,3-Difluoroazetidin-1-yl)-2-[6-(5-ethyl-2-thienyl)pyrrolo[3,2-b]pyridin-1-yl]ethanone; | 7.0 |
| 285 | 2-[6-(4-Chloro-2-thienyl)pyrrolo[3,2-b]pyridin-1-yl]-1-(3-fluoroazetidin-1-yl)ethanone; | 6.8 |
| 286 | 1-Cyclopropyl-2-[6-(4-fluoro-3-methyl-phenyl)pyrrolo[3,2-b]pyridin-1-yl]ethanone oxime trifluoroacetate salt; | 6.8 |
| 287 | 2-[6-(5-Chloro-2-thienyl)pyrrolo[3,2-b]pyridin-1-yl]-1-pyrrolidin-1-yl-ethanone; | 6.2 |
| 288 | 2-[6-(4-Chloro-2-thienyl)pyrrolo[3,2-b]pyridin-1-yl]-1-pyrrolidin-1-yl-ethanone; | 7.7 |
| 289 | (R/S)-1-(2-Cyclopropyl-2-fluoro-ethyl)-6-(4-fluoro-3-methyl-phenyl)pyrrolo[3,2-b]pyridine; | 7.1 |
| 290 | 2-[6-(4-Fluoro-3-methyl-phenyl)pyrrolo[3,2-b]pyridin-1-yl]-1-(3-methoxyazetidin-1-yl)ethanone; | 6.2 |
| 291 | 6-(4-Fluoro-3-methyl-phenyl)-1-(2-methoxyethyl)pyrrolo[3,2-b]pyridine trifluoroacetate salt; | 7.1 |

TABLE 5-continued

| Example # | Compound Name | pIC$_{50}$ |
|---|---|---|
| 292 | 1-Cyclobutyl-2-[6-(3-fluorophenyl)pyrrolo[3,2-b]pyridin-1-yl]ethanone; | 5.9 |
| 293 | 2-[6-(4-Fluorophenyl)pyrrolo[3,2-b]pyridin-1-yl]-1-[(3R)-3-fluoropyrrolidin-1-yl]ethanone trifluoroacetate salt; | 7.5 |
| 294 | 2-[6-(4-Fluorophenyl)pyrrolo[3,2-b]pyridin-1-yl]-1-[(3S)-3-fluoropyrrolidin-1-yl]ethanone trifluoroacetate salt; | 6.5 |
| 295 | 1-[6-(4-Fluoro-3-methyl-phenyl)pyrrolo[3,2-b]pyridin-1-yl]butan-2-one trifluoroacetate salt; | 6.5 |
| 296 | N-Ethyl-2-[6-(4-fluoro-3-methyl-phenyl)pyrrolo[3,2-b]pyridin-1-yl]-N-methyl-acetamide; | 7.6 |
| 297 | N,N-Diethyl-2-[6-(4-fluoro-3-methyl-phenyl)pyrrolo[3,2-b]pyridin-1-yl]acetamide; | 7.4 |
| 298 | 1-(Azetidin-1-yl)-2-[3-chloro-6-[3-(trifluoromethyl)phenyl]pyrrolo[3,2-b]pyridin-1-yl]ethanone; | 6.3 |
| 299 | 2-[3-Chloro-6-(m-tolyl)pyrrolo[3,2-b]pyridin-1-yl]-1-cyclopropyl-ethanone; | 7.3 |
| 300 | 2-(3-Chloro-6-phenyl-pyrrolo[3,2-b]pyridin-1-yl)-1-cyclopropyl-ethanone; | 7.7 |
| 301 | 1-(Azetidin-1-yl)-2-[3-chloro-6-(3,4,5-trifluorophenyl)pyrrolo[3,2-b]pyridin-1-yl]ethanone; | 7.7 |
| 302 | 1-(Azetidin-1-yl)-2-[3-fluoro-6-(4-fluorophenyl)pyrrolo[3,2-b]pyridin-1-yl]ethanone; | 7.5 |
| 303 | 1-(Azetidin-1-yl)-2-[3-chloro-6-(3,5-dimethylphenyl)pyrrolo[3,2-b]pyridin-1-yl]ethanone; | 7.4 |
| 304 | 2-[3-Fluoro-6-(4-fluoro-3-methyl-phenyl)pyrrolo[3,2-b]pyridin-1-yl]-1-morpholino-ethanone; | 6.8 |
| 305 | 2-[3-Fluoro-6-(4-fluorophenyl)pyrrolo[3,2-b]pyridin-1-yl]-1-morpholino-ethanone; | 7.1 |
| 306 | 1-(3-Fluoroazetidin-1-yl)-2-[3-fluoro-6-(3,4,5-trifluorophenyl)pyrrolo[3,2-b]pyridin-1-yl]ethanone; | 6.4 |
| 307 | 1-(3-Fluoroazetidin-1-yl)-2-[3-fluoro-6-(4-fluoro-3-methyl-phenyl)pyrrolo[3,2-b]pyridin-1-yl]ethanone; | 7.4 |
| 308 | 1-(3-Fluoroazetidin-1-yl)-2-[3-fluoro-6-(4-fluorophenyl)pyrrolo[3,2-b]pyridin-1-yl]ethanone; | 7.2 |
| 309 | 1-(3-Fluoroazetidin-1-yl)-2-[3-fluoro-6-(4-methyl-2-thienyl)pyrrolo[3,2-b]pyridin-1-yl]ethanone; | 6.7 |
| 310 | 2-[6-[3-(Difluoromethyl)phenyl]-3-fluoro-pyrrolo[3,2-b]pyridin-1-yl]-1-(3-fluoroazetidin-1-yl)ethanone; | 7.3 |
| 311 | 2-[6-(3,4-Difluorophenyl)-3-fluoro-pyrrolo[3,2-b]pyridin-1-yl]-1-(3-fluoroazetidin-1-yl)ethanone; | 7.2 |
| 312 | 1-(Azetidin-1-yl)-2-[3-chloro-6-(2,3,4-trifluorophenyl)pyrrolo[3,2-b]pyridin-1-yl]ethanone; | 6.8 |
| 313 | 2-[3-Fluoro-6-(4-fluoro-3-methyl-phenyl)pyrrolo[3,2-b]pyridin-1-yl]-1-pyrrolidin-1-yl-ethanone; | 7.7 |
| 314 | 2-[3-Fluoro-6-(4-fluorophenyl)pyrrolo[3,2-b]pyridin-1-yl]-1-pyrrolidin-1-yl-ethanone; | 7.2 |
| 315 | 2-[3-Fluoro-6-(3,4,5-trifluorophenyl)pyrrolo[3,2-b]pyridin-1-yl]-1-pyrrolidin-1-yl-ethanone; | 7.1 |
| 316 | 1-Cyclopropyl-2-[3-fluoro-6-(4-fluoro-3-methyl-phenyl)pyrrolo[3,2-b]pyridin-1-yl]ethanone; | 7.4 |
| 317 | 1-Cyclopropyl-2-[3-fluoro-6-(4-methyl-2-thienyl)pyrrolo[3,2-b]pyridin-1-yl]ethanone; | 7.4 |
| 318 | 2-[6-(5-Chloro-2-thienyl)-3-fluoro-pyrrolo[3,2-b]pyridin-1-yl]-1-cyclopropyl-ethanone; | 7.7 |
| 319 | 1-Cyclopropyl-2-[3-fluoro-6-(4-fluorophenyl)pyrrolo[3,2-b]pyridin-1-yl]ethanone; | 7.7 |
| 320 | 1-Cyclopropyl-2-[3-fluoro-6-(3,4,5-trifluorophenyl)pyrrolo[3,2-b]pyridin-1-yl]ethanone; | 7.5 |
| 321 | 1-Cyclopropyl-2-[6-[3-(difluoromethyl)phenyl]-3-fluoro-pyrrolo[3,2-b]pyridin-1-yl]ethanone; | 7.7 |
| 322 | 1-(Azetidin-1-yl)-2-[3-fluoro-6-(4-methyl-2-thienyl)pyrrolo[3,2-b]pyridin-1-yl]ethanone; | 7.7 |
| 323 | 1-(Azetidin-1-yl)-2-[6-[3-(difluoromethyl)phenyl]-3-fluoro-pyrrolo[3,2-b]pyridin-1-yl]ethanone; | 7.0 |
| 324 | 1-[3-Fluoro-6-(4-fluoro-3-methyl-phenyl)pyrrolo[3,2-b]pyridin-1-yl]-3-methyl-butan-2-one; | 7.0 |
| 325 | 1-[6-(3-Ethylphenyl)-3-fluoro-pyrrolo[3,2-b]pyridin-1-yl]-3-methyl-butan-2-one; | 6.7 |
| 326 | 1-[6-(3,4-Difluorophenyl)-3-fluoro-pyrrolo[3,2-b]pyridin-1-yl]-3-methyl-butan-2-one; | 6.7 |
| 327 | 1-[3-Fluoro-6-(3-fluorophenyl)pyrrolo[3,2-b]pyridin-1-yl]-3-methyl-butan-2-one; | 7.2 |
| 328 | 1-[3-Fluoro-6-[3-(trifluoromethyl)phenyl]pyrrolo[3,2-b]pyridin-1-yl]-3-methyl-butan-2-one; | 7.2 |
| 329 | 1-[3-Fluoro-6-(m-tolyl)pyrrolo[3,2-b]pyridin-1-yl]-3-methyl-butan-2-one; | 6.3 |
| 330 | 6-(4-Fluoro-3-methyl-phenyl)-1-(methylsulfanylmethyl)pyrrolo[3,2-b]pyridine; | 7.2 |
| 331 | (R/S)-6-(4-Fluoro-3-methyl-phenyl)-1-(methylsulfinylmethyl)pyrrolo[3,2-b]pyridine; | 5.4 |
| 332 | 6-(4-Fluoro-3-methyl-phenyl)-1-(methylsulfonylmethyl)pyrrolo[3,2-b]pyridine; | 5.8 |
| 333 | 1-[3-Fluoro-6-(4-fluorophenyl)pyrrolo[3,2-b]pyridin-1-yl]butan-2-one; | 5.2 |
| 334 | 1-[3-Fluoro-6-(3,4,5-trifluorophenyl)pyrrolo[3,2-b]pyridin-1-yl]butan-2-one; | 7.6 |
| 335 | 1-[3-Fluoro-6-(4-fluoro-3-methyl-phenyl)pyrrolo[3,2-b]pyridin-1-yl]butan-2-one; | 7.9 |
| 336 | 1-[6-(3,4-Difluorophenyl)-3-fluoro-pyrrolo[3,2-b]pyridin-1-yl]butan-2-one; | 7.7 |
| 337 | 1-[6-[3-(Difluoromethyl)phenyl]-3-fluoro-pyrrolo[3,2-b]pyridin-1-yl]butan-2-one; | 7.8 |
| 338 | 1-[6-(5-Chloro-2-thienyl)-3-fluoro-pyrrolo[3,2-b]pyridin-1-yl]butan-2-one; | 7.8 |
| 339 | 1-[3-Fluoro-6-(4-methyl-2-thienyl)pyrrolo[3,2-b]pyridin-1-yl]butan-2-one; | 7.9 |
| 340 | 4-[6-(4-Fluorophenyl)pyrrolo[3,2-b]pyridin-1-yl]butan-2-one; | 7.9 |
| 341 | 1-[3-Fluoro-6-(4-fluorophenyl)pyrrolo[3,2-b]pyridin-1-yl]-3-methyl-butan-2-one; | 6.0 |
| 342 | 1-[6-[3-(Difluoromethyl)phenyl]-3-fluoro-pyrrolo[3,2-b]pyridin-1-yl]-3-methyl-butan-2-one; | 7.3 |
| 343 | 1-[3-Fluoro-6-(4-methyl-2-thienyl)pyrrolo[3,2-b]pyridin-1-yl]-3-methyl-butan-2-one; | 7.2 |
| 344 | 1-[3-Fluoro-6-(3,4,5-trifluorophenyl)pyrrolo[3,2-b]pyridin-1-yl]-3-methyl-butan-2-one; | 7.3 |
| 345 | 1-[6-(5-Chloro-2-thienyl)-3-fluoro-pyrrolo[3,2-b]pyridin-1-yl]-3-methyl-butan-2-one; | 7.5 |
| 346 | 2-[6-(4-Fluoro-3-methyl-phenyl)pyrrolo[3,2-b]pyridin-1-yl]-1-morpholino-ethanone; | 7.4 |
| 347 | 1-(3-Fluoroazetidin-1-yl)-2-[6-(4-fluoro-3-methyl-phenyl)pyrrolo[3,2-b]pyridin-1-yl]ethanone; | 7.3 |
| 348 | N-Cyclopropyl-2-[6-(4-fluoro-3-methyl-phenyl)pyrrolo[3,2-b]pyridin-1-yl]acetamide; | 7.5 |
| 349 | 1-(Azetidin-1-yl)-2-[6-(4-fluoro-3-methyl-phenyl)pyrrolo[3,2-b]pyridin-1-yl]ethanone; | 7.5 |
| 350 | N-Cyclopropyl-2-[6-(3,5-difluorophenyl)pyrrolo[3,2-b]pyridin-1-yl]acetamide trifluoroacetate salt; | 7.8 |
| 351 | N-Cyclopropyl-2-[6-[3-(trifluoromethyl)phenyl]pyrrolo[3,2-b]pyridin-1-yl]acetamide trifluoroacetate salt; | 7.1 |
| 352 | N-Cyclopropyl-2-[6-[2-fluoro-3-(trifluoromethyl)phenyl]pyrrolo[3,2-b]pyridin-1-yl]acetamide trifluoroacetate salt; | 7.4 |
| 353 | 1-(Azetidin-1-yl)-2-[6-(4-fluorophenyl)pyrrolo[3,2-b]pyridin-1-yl]ethanone; | 7.5 |
| 354 | 1-(Azetidin-1-yl)-2-(6-phenylpyrrolo[3,2-b]pyridin-1-yl)ethanone; | 7.5 |
| 355 | 1-(Azetidin-1-yl)-2-[6-(3,5-difluorophenyl)pyrrolo[3,2-b]pyridin-1-yl]ethanone; | 7.3 |
| 356 | 1-(Azetidin-1-yl)-2-[6-(m-tolyl)pyrrolo[3,2-b]pyridin-1-yl]ethanone trifluoroacetate salt; | 7.7 |
| 357 | 1-(Azetidin-1-yl)-2-[6-(3,4-dichlorophenyl)pyrrolo[3,2-b]pyridin-1-yl]ethanone trifluoroacetate salt; | 7.7 |
| 358 | 1-(Azetidin-1-yl)-2-[6-[2-fluoro-3-(trifluoromethyl)phenyl]pyrrolo[3,2-b]pyridin-1-yl]ethanone trifluoroacetate salt; | 7.4 |
| 359 | 1-(Azetidin-1-yl)-2-[6-(4-methyl-2-thienyl)pyrrolo[3,2-b]pyridin-1-yl]ethanone trifluoroacetate salt; | 7.5 |
| 360 | 1-(Azetidin-1-yl)-2-[3-chloro-6-(4-fluoro-3-methyl-phenyl)pyrrolo[3,2-b]pyridin-1-yl]ethanone; | 7.5 |
| 361 | 1-(3,3-Difluoroazetidin-1-yl)-2-[6-(3,4-difluorophenyl)pyrrolo[3,2-b]pyridin-1-yl]ethanone; | 7.6 |
| 362 | 1-(Azetidin-1-yl)-2-[6-(6-(trifluoromethyl)-2-pyridyl]pyrrolo[3,2-b]pyridin-1-yl]ethanone; | 7.5 |
| 363 | 1-(Azetidin-1-yl)-2-[6-(3,4,5-trifluorophenyl)pyrrolo[3,2-b]pyridin-1-yl]ethanone; | 7.1 |
| 364 | 1-[6-(3,5-Difluorophenyl)pyrrolo[3,2-b]pyridin-1-yl]-3-methyl-butan-2-one; | 7.7 |
| 365 | 1-Cyclobutyl-2-[6-(4-fluorophenyl)pyrrolo[3,2-b]pyridin-1-yl]ethanone; | 7.7 |

TABLE 5-continued

| Example # | Compound Name | pIC$_{50}$ |
|---|---|---|
| 366 | N-Cyclopropyl-2-[6-(3-ethylphenyl)pyrrolo[3,2-b]pyridin-1-yl]acetamide; | 7.5 |
| 367 | 2-[6-(3,4-Difluorophenyl)pyrrolo[3,2-b]pyridin-1-yl]-1-pyrrolidin-1-yl-ethanone; | 7.3 |
| 368 | 1-(3,3-Difluoroazetidin-1-yl)-2-[6-(4-methyl-2-thienyl)pyrrolo[3,2-b]pyridin-1-yl]ethanone; | 7.6 |
| 369 | 2-[6-(4-Methyl-2-thienyl)pyrrolo[3,2-b]pyridin-1-yl]-1-pyrrolidin-1-yl-ethanone; | 7.7 |
| 370 | 1-(3-Fluoroazetidin-1-yl)-2-[6-(4-methyl-2-thienyl)pyrrolo[3,2-b]pyridin-1-yl]ethanone; | 7.5 |
| 371 | 1-(3-Fluoroazetidin-1-yl)-2-[6-(3,4,5-trifluorophenyl)pyrrolo[3,2-b]pyridin-1-yl]ethanone; | 7.8 |
| 372 | 2-[6-(5-Chloro-2-thienyl)pyrrolo[3,2-b]pyridin-1-yl]-1-(3-fluoroazetidin-1-yl)ethanone; | 7.8 |
| 373 | 1-(Azetidin-1-yl)-2-[6-(5-chloro-2-thienyl)pyrrolo[3,2-b]pyridin-1-yl]ethanone; | 7.7 |
| 374 | 2-[3-Chloro-6-(2,3,4-trifluorophenyl)pyrrolo[3,2-b]pyridin-1-yl]-1-(3-fluoroazetidin-1-yl)ethanone; | 7.7 |
| 375 | N,N-Dimethyl-2-[6-(3,4,5-trifluorophenyl)pyrrolo[3,2-b]pyridin-1-yl]acetamide; | 7.9 |
| 376 | 2-[6-(3,5-Difluorophenyl)pyrrolo[3,2-b]pyridin-1-yl]-N,N-dimethyl-acetamide; | 7.7 |
| 377 | 2-[6-[3-(Difluoromethyl)phenyl]pyrrolo[3,2-b]pyridin-1-yl]-N,N-dimethyl-acetamide; | 8.0 |
| 378 | 2-[6-(5-Chloro-2-thienyl)pyrrolo[3,2-b]pyridin-1-yl]-N,N-dimethyl-acetamide; | 8.2 |
| 379 | 2-[6-(3,4-Difluorophenyl)pyrrolo[3,2-b]pyridin-1-yl]-N,N-dimethyl-acetamide; | 7.5 |
| 380 | 1-(Azetidin-1-yl)-2-[6-(5-methyl-2-thienyl)pyrrolo[3,2-b]pyridin-1-yl]ethanone; | 8.0 |
| 381 | 1-(Azetidin-1-yl)-2-[3-chloro-6-(5-chloro-2-thienyl)pyrrolo[3,2-b]pyridin-1-yl]ethanone; | 7.8 |
| 382 | 1-(Azetidin-1-yl)-2-[6-(3,4-difluorophenyl)-3-fluoro-pyrrolo[3,2-b]pyridin-1-yl]ethanone; | 7.8 |
| 383 | 1-(Azetidin-1-yl)-2-[3-fluoro-6-(3,4,5-trifluorophenyl)pyrrolo[3,2-b]pyridin-1-yl]ethanone; | 7.8 |
| 384 | 2-[3-Chloro-6-(4-fluorophenyl)pyrrolo[3,2-b]pyridin-1-yl]-1-cyclopropyl-ethanone; | 7.7 |
| 385 | 1-(Azetidin-1-yl)-2-[6-(3-thienyl)pyrrolo[3,2-b]pyridin-1-yl]ethanone trifluoroacetate salt; | 7.7 |
| 386 | N,N-Dimethyl-2-[6-(5-methyl-2-thienyl)pyrrolo[3,2-b]pyridin-1-yl]acetamide trifluoroacetate salt; | 6.4 |
| 387 | 2-[3-Fluoro-6-(2-thienyl)pyrrolo[3,2-b]pyridin-1-yl]-N,N-dimethyl-acetamide; | 7.2 |
| 388 | 2-[6-(5-Ethyl-2-thienyl)pyrrolo[3,2-b]pyridin-1-yl]-N,N-dimethyl-acetamide trifluoroacetate salt; | 6.1 |
| 389 | 1-(Azetidin-1-yl)-2-[3-fluoro-6-(2-thienyl)pyrrolo[3,2-b]pyridin-1-yl]ethanone trifluoroacetate salt; | 6.8 |
| 390 | 2-[3-Fluoro-6-(5-methyl-2-thienyl)pyrrolo[3,2-b]pyridin-1-yl]-N,N-dimethyl-acetamide; | 6.5 |
| 391 | 2-[6-(4-Chloro-2-thienyl)pyrrolo[3,2-b]pyridin-1-yl]-N,N-dimethyl-acetamide trifluoroacetate salt; | 7.3 |
| 392 | 1-(Azetidin-1-yl)-2-[6-(5-ethyl-2-thienyl)pyrrolo[3,2-b]pyridin-1-yl]ethanone trifluoroacetate salt; | 7.2 |
| 393 | 2-[6-(5-Ethyl-2-thienyl)-3-fluoro-pyrrolo[3,2-b]pyridin-1-yl]-N,N-dimethyl-acetamide; | 6.9 |
| 394 | 1-(Azetidin-1-yl)-2-[6-(4-chloro-2-thienyl)pyrrolo[3,2-b]pyridin-1-yl]ethanone trifluoroacetate salt; | 6.8 |
| 395 | 1-(3-Fluoroazetidin-1-yl)-2-[3-fluoro-6-(2-thienyl)pyrrolo[3,2-b]pyridin-1-yl]ethanone trifluoroacetate salt; | 7.3 |
| 396 | 2-[6-(4-Chloro-2-thienyl)-3-fluoro-pyrrolo[3,2-b]pyridin-1-yl]-N,N-dimethyl-acetamide; | 6.3 |
| 397 | 1-(Azetidin-1-yl)-2-[6-(4-chloro-2-thienyl)-3-fluoro-pyrrolo[3,2-b]pyridin-1-yl]ethanone trifluoroacetate salt; | 7.3 |
| 398 | 2-[6-(5-Ethyl-2-thienyl)-3-fluoro-pyrrolo[3,2-b]pyridin-1-yl]-1-(3-fluoroazetidin-1-yl)ethanone trifluoroacetate salt; | 7.4 |
| 399 | 1-(Azetidin-1-yl)-2-[6-(2-thienyl)pyrrolo[3,2-b]pyridin-1-yl]ethanone; | 6.8 |
| 400 | N,N-Dimethyl-2-[6-(2-thienyl)pyrrolo[3,2-b]pyridin-1-yl]acetamide; | 6.3 |
| 401 | 1-(Azetidin-1-yl)-2-[6-(5-ethyl-2-thienyl)-3-fluoro-pyrrolo[3,2-b]pyridin-1-yl]ethanone; | 6.2 |
| 402 | 1-(3-Fluoroazetidin-1-yl)-2-[3-fluoro-6-(5-methyl-2-thienyl)pyrrolo[3,2-b]pyridin-1-yl]ethanone trifluoroacetate salt; | 6.6 |
| 403 | 1-(Azetidin-1-yl)-2-[6-(3-chloro-2-thienyl)pyrrolo[3,2-b]pyridin-1-yl]ethanone; | 7.0 |
| 404 | 1-(Azetidin-1-yl)-2-[6-(2-methylthiazol-5-yl)pyrrolo[3,2-b]pyridin-1-yl]ethanone; | 7.5 |
| 405 | 1-(Azetidin-1-yl)-2-(6-thiazol-5-ylpyrrolo[3,2-b]pyridin-1-yl)ethanone; | 5.0 |
| 406 | 1-(Azetidin-1-yl)-2-[6-(6-fluoro-3-pyridyl)pyrrolo[3,2-b]pyridin-1-yl]ethanone; | NT |
| 407 | 1-(Azetidin-1-yl)-2-[3-chloro-6-(4-methyl-2-thienyl)pyrrolo[3,2-b]pyridin-1-yl]ethanone; | 5.2 |
| 408 | 1-(Azetidin-1-yl)-2-[3-chloro-6-(5-ethyl-2-thienyl)pyrrolo[3,2-b]pyridin-1-yl]ethanone; | 7.4 |
| 409 | 1-(Azetidin-1-yl)-2-[3-chloro-6-(2-thienyl)pyrrolo[3,2-b]pyridin-1-yl]ethanone; | 6.7 |
| 410 | 1-(Azetidin-1-yl)-2-[3-chloro-6-(5-methyl-2-thienyl)pyrrolo[3,2-b]pyridin-1-yl]ethanone; | 6.5 |
| 411 | 2-[6-(4-Fluorophenyl)pyrrolo[3,2-b]pyridin-1-yl]-N-methyl-N-(2,2,2-trifluoroethyl)acetamide; | 7.6 |
| 412 | 2-[3-Chloro-6-(5-methyl-2-thienyl)pyrrolo[3,2-b]pyridin-1-yl]-1-(3-fluoroazetidin-1-yl)ethanone; | 5.1 |
| 413 | 2-[3-Chloro-6-(5-chloro-2-thienyl)pyrrolo[3,2-b]pyridin-1-yl]-1-(3-fluoroazetidin-1-yl)ethanone; | 7.3 |
| 414 | 2-[3-Chloro-6-(4-fluorophenyl)pyrrolo[3,2-b]pyridin-1-yl]-N,N-dimethyl-acetamide; | 7.4 |
| 415 | 2-[6-(4-Fluoro-3-methyl-phenyl)pyrrolo[3,2-b]pyridin-1-yl]-N-methyl-N-(2,2,2-trifluoroethyl)acetamide; | 7.2 |
| 416 | 2-[3-Chloro-6-(4-methyl-2-thienyl)pyrrolo[3,2-b]pyridin-1-yl]-1-(3-fluoroazetidin-1-yl)ethanone; | 5.6 |
| 417 | 2-[3-Chloro-6-(2-thienyl)pyrrolo[3,2-b]pyridin-1-yl]-1-(3-fluoroazetidin-1-yl)ethanone; | 7.2 |
| 418 | 2-[3-Chloro-6-(4-chloro-2-thienyl)pyrrolo[3,2-b]pyridin-1-yl]-1-(3-fluoroazetidin-1-yl)ethanone; | 6.3 |
| 419 | N-Ethyl-2-[6-(4-fluorophenyl)pyrrolo[3,2-b]pyridin-1-yl]-N-methyl-acetamide; | 7.2 |
| 420 | 2-[3-Chloro-6-(2-thienyl)pyrrolo[3,2-b]pyridin-1-yl]-N,N-dimethyl-acetamide; | 6.2 |
| 421 | 2-[3-Chloro-6-(5-ethyl-2-thienyl)pyrrolo[3,2-b]pyridin-1-yl]-N,N-dimethyl-acetamide; | 6.2 |
| 422 | 1-(Azetidin-1-yl)-2-[3-chloro-6-(4-chloro-2-thienyl)pyrrolo[3,2-b]pyridin-1-yl]ethanone; | 6.7 |
| 423 | 2-[3-Chloro-6-(5-chloro-2-thienyl)pyrrolo[3,2-b]pyridin-1-yl]-N,N-dimethyl-acetamide; | 7.4 |
| 424 | 2-[3-Chloro-6-(5-ethyl-2-thienyl)pyrrolo[3,2-b]pyridin-1-yl]-1-(3-fluoroazetidin-1-yl)ethanone; | 7.5 |
| 425 | 2-[6-[2-Fluoro-3-(trifluoromethyl)phenyl]pyrrolo[3,2-b]pyridin-1-yl]-N,N-dimethyl-acetamide; | 6.5 |
| 426 | 2-[6-(5-Chloro-4-methyl-2-thienyl)pyrrolo[3,2-b]pyridin-1-yl]-N,N-dimethyl-acetamide; | 7.1 |
| 427 | 2-[6-(2,5-Dimethyl-3-thienyl)pyrrolo[3,2-b]pyridin-1-yl]-N,N-dimethyl-acetamide; | 7.5 |
| 428 | N,N-Dimethyl-2-[6-(2,4,5-trimethyl-3-thienyl)pyrrolo[3,2-b]pyridin-1-yl]acetamide; | 7.0 |
| 429 | 2-[6-(3-Chlorophenyl)pyrrolo[3,2-b]pyridin-1-yl]-N,N-dimethyl-acetamide; | 6.1 |
| 430 | 2-[6-(4-Fluorophenyl)pyrrolo[3,2-b]pyridin-1-yl]-N,N-dimethyl-acetamide; | 7.2 |
| 431 | 2-[6-(2-Fluorophenyl)pyrrolo[3,2-b]pyridin-1-yl]-N,N-dimethyl-acetamide; | 6.6 |
| 432 | 2-[6-(2-Fluoro-3-methyl-phenyl)pyrrolo[3,2-b]pyridin-1-yl]-N,N-dimethyl-acetamide; | 6.1 |
| 433 | N,N-Dimethyl-2-[6-(6-phenylpyrrolo[3,2-b]pyridin-1-yl)acetamide; | 7.6 |
| 434 | N,N-Dimethyl-2-[6-(m-tolyl)pyrrolo[3,2-b]pyridin-1-yl]acetamide; | 7.0 |
| 435 | N,N-Dimethyl-2-[6-[3-(trifluoromethyl)phenyl]pyrrolo[3,2-b]pyridin-1-yl]acetamide; | 7.3 |
| 436 | 2-[6-[4-Fluoro-3-(trifluoromethyl)phenyl]pyrrolo[3,2-b]pyridin-1-yl]-N,N-dimethyl-acetamide; | 7.1 |
| 437 | N,N-Dimethyl-2-[6-(2,3,4-trifluorophenyl)pyrrolo[3,2-b]pyridin-1-yl]acetamide; | 6.5 |
| 438 | N,N-Dimethyl-2-[6-[5-(trifluoromethyl)-2-thienyl]pyrrolo[3,2-b]pyridin-1-yl]acetamide; | 6.6 |

TABLE 5-continued

| Example # | Compound Name | pIC$_{50}$ |
|---|---|---|
| 439 | 2-[6-(5-Chloro-3-thienyl)pyrrolo[3,2-b]pyridin-1-yl]-N,N-dimethyl-acetamide; | 7.3 |
| 440 | 2-[6-(2,5-Dichloro-3-thienyl)pyrrolo[3,2-b]pyridin-1-yl]-N,N-dimethyl-acetamide; | 6.9 |
| 441 | N,N-Dimethyl-2-[6-[6-(trifluoromethyl)-2-pyridyl]pyrrolo[3,2-b]pyridin-1-yl]acetamide; | 7.0 |
| 442 | N,N-Dimethyl-2-[6-[2-(trifluoromethyl)-4-pyridyl]pyrrolo[3,2-b]pyridin-1-yl]acetamide; | 6.8 |
| 443 | N,N-Dimethyl-2-[6-[5-(trifluoromethyl)-3-pyridyl]pyrrolo[3,2-b]pyridin-1-yl]acetamide; | 6.4 |
| 444 | 2-[6-(2,6-Difluoro-3-methyl-phenyl)pyrrolo[3,2-b]pyridin-1-yl]-N,N-dimethyl-acetamide; | 6.2 |
| 445 | 2-[6-(2-Fluoro-5-methyl-phenyl)pyrrolo[3,2-b]pyridin-1-yl]-N,N-dimethyl-acetamide; | 6.4 |
| 446 | 1-(Azetidin-1-yl)-2-[6-[3-(difluoromethyl)phenyl]pyrrolo[3,2-b]pyridin-1-yl]ethanone; | 7.0 |
| 447 | 2-[6-(2,4-Difluoro-3-methyl-phenyl)pyrrolo[3,2-b]pyridin-1-yl]-N,N-dimethyl-acetamide; | 7.7 |
| 448 | 2-[6-(3-Chloro-2-fluoro-phenyl)pyrrolo[3,2-b]pyridin-1-yl]-N,N-dimethyl-acetamide; | 7.7 |
| 449 | 2-[6-(3-Ethylphenyl)pyrrolo[3,2-b]pyridin-1-yl]-N,N-dimethyl-acetamide; | 7.2 |
| 450 | 2-[6-(3-Fluorophenyl)pyrrolo[3,2-b]pyridin-1-yl]-N,N-dimethyl-acetamide; | 7.4 |
| 451 | 1-(Azetidin-1-yl)-2-[6-(2-fluoro-3-methyl-phenyl)pyrrolo[3,2-b]pyridin-1-yl]ethanone; | 7.3 |
| 452 | 1-(Azetidin-1-yl)-2-[6-(2,4-difluoro-3-methyl-phenyl)pyrrolo[3,2-b]pyridin-1-yl]ethanone; | 7.6 |
| 453 | 1-(Azetidin-1-yl)-2-[6-(3-chloro-2-fluoro-phenyl)pyrrolo[3,2-b]pyridin-1-yl]ethanone; | 7.6 |
| 454 | 1-(3-Fluoroazetidin-1-yl)-2-[6-(2-fluoro-3-methyl-phenyl)pyrrolo[3,2-b]pyridin-1-yl]ethanone; | 7.6 |
| 455 | 1-(3-Fluoroazetidin-1-yl)-2-[6-(2,3,4-trifluorophenyl)pyrrolo[3,2-b]pyridin-1-yl]ethanone; | 7.5 |
| 456 | 1-(Azetidin-1-yl)-2-[6-(3-chloro-4-fluoro-phenyl)pyrrolo[3,2-b]pyridin-1-yl]ethanone; | 7.2 |
| 457 | 1-(3-Fluoroazetidin-1-yl)-2-[6-(2-fluorophenyl)pyrrolo[3,2-b]pyridin-1-yl]ethanone; | 7.8 |
| 458 | 2-[6-[3-(Difluoromethyl)phenyl]pyrrolo[3,2-b]pyridin-1-yl]-1-(3-fluoroazetidin-1-yl)ethanone; | 6.4 |
| 459 | N-Ethyl-N-methyl-2-[6-(m-tolyl)pyrrolo[3,2-b]pyridin-1-yl]acetamide; | 7.4 |
| 460 | 2-[6-(2,4-Difluoro-3-methyl-phenyl)pyrrolo[3,2-b]pyridin-1-yl]-1-(3-fluoroazetidin-1-yl)ethanone; | 7.2 |
| 461 | 2-[6-(3,4-Difluorophenyl)pyrrolo[3,2-b]pyridin-1-yl]-N-ethyl-N-methyl-acetamide; | 7.5 |
| 462 | N-Ethyl-N-methyl-2-[6-(3,4,5-trifluorophenyl)pyrrolo[3,2-b]pyridin-1-yl]acetamide; | 6.9 |
| 463 | 1-(Azetidin-1-yl)-2-[6-(3-chlorophenyl)pyrrolo[3,2-b]pyridin-1-yl]ethanone; | 7.0 |
| 464 | N-Ethyl-2-[6-[2-fluoro-3-(trifluoromethyl)phenyl]pyrrolo[3,2-b]pyridin-1-yl]-N-methyl-acetamide; | 7.9 |
| 465 | 2-[6-(3-Chlorophenyl)pyrrolo[3,2-b]pyridin-1-yl]-1-(3-fluoroazetidin-1-yl)ethanone; | 7.1 |
| 466 | 2-[6-(3-Chloro-2-fluoro-phenyl)pyrrolo[3,2-b]pyridin-1-yl]-1-(3-fluoroazetidin-1-yl)ethanone; | 7.7 |
| 467 | 2-[6-(3-Chloro-4-fluoro-phenyl)pyrrolo[3,2-b]pyridin-1-yl]-1-(3-fluoroazetidin-1-yl)ethanone; | 7.2 |
| 468 | 2-[6-(3-Chloro-4-fluoro-phenyl)pyrrolo[3,2-b]pyridin-1-yl]-N,N-dimethyl-acetamide; | 7.8 |
| 469 | 2-[6-(2,4-Difluoro-3-methyl-phenyl)pyrrolo[3,2-b]pyridin-1-yl]-N-ethyl-N-methyl-acetamide; | 7.8 |
| 470 | N-Ethyl-N-methyl-2-[6-[3-(trifluoromethyl)phenyl]pyrrolo[3,2-b]pyridin-1-yl]acetamide; | 6.7 |
| 471 | 1-(Azetidin-1-yl)-2-[3-fluoro-6-(2-fluorophenyl)pyrrolo[3,2-b]pyridin-1-yl]ethanone; | 7.0 |
| 472 | 1-(Azetidin-1-yl)-2-[3-fluoro-6-(2-fluoro-3-methyl-phenyl)pyrrolo[3,2-b]pyridin-1-yl]ethanone; | 6.7 |
| 473 | 1-(Azetidin-1-yl)-2-[3-fluoro-6-(m-tolyl)pyrrolo[3,2-b]pyridin-1-yl]ethanone; | 7.5 |
| 474 | 1-(Azetidin-1-yl)-2-[6-(3,5-difluorophenyl)-3-fluoro-pyrrolo[3,2-b]pyridin-1-yl]ethanone; | 7.5 |
| 475 | 1-(Azetidin-1-yl)-2-[3-fluoro-6-[3-(trifluoromethyl)phenyl]pyrrolo[3,2-b]pyridin-1-yl]ethanone; | 7.6 |
| 476 | 1-(Azetidin-1-yl)-2-[3-fluoro-6-[2-fluoro-3-(trifluoromethyl)phenyl]pyrrolo[3,2-b]pyridin-1-yl]ethanone; | 7.3 |
| 477 | 1-(Azetidin-1-yl)-2-[3-fluoro-6-(2,3,4-trifluorophenyl)pyrrolo[3,2-b]pyridin-1-yl]ethanone; | 7.3 |
| 478 | 1-(Azetidin-1-yl)-2-[6-(3-chlorophenyl)-3-fluoro-pyrrolo[3,2-b]pyridin-1-yl]ethanone; | 7.4 |
| 479 | 1-(Azetidin-1-yl)-2-[6-(3-chloro-2-fluoro-phenyl)-3-fluoro-pyrrolo[3,2-b]pyridin-1-yl]ethanone; | 7.6 |
| 480 | 1-(Azetidin-1-yl)-2-[6-(2,4-difluoro-3-methyl-phenyl)-3-fluoro-pyrrolo[3,2-b]pyridin-1-yl]ethanone; | 7.4 |
| 481 | 1-(Azetidin-1-yl)-2-[6-(3-chloro-4-fluoro-phenyl)-3-fluoro-pyrrolo[3,2-b]pyridin-1-yl]ethanone; | 7.6 |
| 482 | 1-(3-Fluoroazetidin-1-yl)-2-(3-fluoro-6-phenyl-pyrrolo[3,2-b]pyridin-1-yl)ethanone; | 7.8 |
| 483 | 1-(3-Fluoroazetidin-1-yl)-2-[3-fluoro-6-(2-fluoro-3-methyl-phenyl)pyrrolo[3,2-b]pyridin-1-yl]ethanone; | 7.2 |
| 484 | 1-(3-Fluoroazetidin-1-yl)-2-[3-fluoro-6-[3-(trifluoromethyl)phenyl]pyrrolo[3,2-b]pyridin-1-yl]ethanone; | 7.9 |
| 485 | 1-(3-Fluoroazetidin-1-yl)-2-[3-fluoro-6-[2-fluoro-3-(trifluoromethyl)phenyl]pyrrolo[3,2-b]pyridin-1-yl]ethanone; | 7.4 |
| 486 | 1-(3-Fluoroazetidin-1-yl)-2-[3-fluoro-6-(2,3,4-trifluorophenyl)pyrrolo[3,2-b]pyridin-1-yl]ethanone; | 7.6 |
| 487 | 2-[6-(3,5-Difluorophenyl)-3-fluoro-pyrrolo[3,2-b]pyridin-1-yl]-1-(3-fluoroazetidin-1-yl)ethanone; | 7.3 |
| 488 | 2-[6-(2,4-Difluoro-3-methyl-phenyl)-3-fluoro-pyrrolo[3,2-b]pyridin-1-yl]-1-(3-fluoroazetidin-1-yl)ethanone; | 7.8 |
| 489 | 2-[6-(3-Chlorophenyl)-3-fluoro-pyrrolo[3,2-b]pyridin-1-yl]-1-(3-fluoroazetidin-1-yl)ethanone; | 8.0 |
| 490 | 2-[6-(3-Chloro-2-fluoro-phenyl)-3-fluoro-pyrrolo[3,2-b]pyridin-1-yl]-1-(3-fluoroazetidin-1-yl)ethanone; | 7.7 |
| 491 | 2-[6-(3-Ethylphenyl)-3-fluoro-pyrrolo[3,2-b]pyridin-1-yl]-1-(3-fluoroazetidin-1-yl)ethanone; | 7.8 |
| 492 | 1-(3-Fluoroazetidin-1-yl)-2-[3-fluoro-6-(3-fluorophenyl)pyrrolo[3,2-b]pyridin-1-yl]ethanone; | 7.6 |
| 493 | 2-[3-Fluoro-6-(2-fluorophenyl)pyrrolo[3,2-b]pyridin-1-yl]-N,N-dimethyl-acetamide; | 7.6 |
| 494 | 2-[3-Fluoro-6-(2-fluoro-3-methyl-phenyl)pyrrolo[3,2-b]pyridin-1-yl]-N,N-dimethyl-acetamide; | 6.5 |
| 495 | 2-(3-Fluoro-6-phenyl-pyrrolo[3,2-b]pyridin-1-yl)-N,N-dimethyl-acetamide; | 7.9 |
| 496 | 2-[3-Fluoro-6-(m-tolyl)pyrrolo[3,2-b]pyridin-1-yl]-N,N-dimethyl-acetamide; | 7.1 |
| 497 | 1-(Azetidin-1-yl)-2-(3-fluoro-6-phenyl-pyrrolo[3,2-b]pyridin-1-yl)ethanone; | 7.5 |
| 498 | 1-(Azetidin-1-yl)-2-[6-(3-ethylphenyl)-3-fluoro-pyrrolo[3,2-b]pyridin-1-yl]ethanone; | 7.1 |
| 499 | 2-[3-Fluoro-6-[3-(trifluoromethyl)phenyl]pyrrolo[3,2-b]pyridin-1-yl]-N,N-dimethyl-acetamide; | 7.6 |
| 500 | 2-[3-Fluoro-6-[2-fluoro-3-(trifluoromethyl)phenyl]pyrrolo[3,2-b]pyridin-1-yl]-N,N-dimethyl-acetamide; | 7.5 |
| 501 | 2-[3-Fluoro-6-(2,3,4-trifluorophenyl)pyrrolo[3,2-b]pyridin-1-yl]-N,N-dimethyl-acetamide; | 7.4 |
| 502 | 2-[6-(2,4-Difluoro-3-methyl-phenyl)-3-fluoro-pyrrolo[3,2-b]pyridin-1-yl]-N,N-dimethyl-acetamide; | 7.4 |
| 503 | 2-[6-(3-Chlorophenyl)-3-fluoro-pyrrolo[3,2-b]pyridin-1-yl]-N,N-dimethyl-acetamide; | 7.8 |
| 504 | 2-[6-(3-Chloro-4-fluoro-phenyl)-3-fluoro-pyrrolo[3,2-b]pyridin-1-yl]-N,N-dimethyl-acetamide; | 7.9 |
| 505 | 2-[6-(3-Ethylphenyl)-3-fluoro-pyrrolo[3,2-b]pyridin-1-yl]-N,N-dimethyl-acetamide; | 7.7 |
| 506 | 1-(Azetidin-1-yl)-2-[3-fluoro-6-(3-fluorophenyl)pyrrolo[3,2-b]pyridin-1-yl]ethanone; | 7.8 |
| 507 | 1-(3-Fluoroazetidin-1-yl)-2-[3-fluoro-6-(2-fluorophenyl)pyrrolo[3,2-b]pyridin-1-yl]ethanone; | 7.7 |
| 508 | 1-(3-Fluoroazetidin-1-yl)-2-[3-fluoro-6-[4-fluoro-3-(trifluoromethyl)phenyl]pyrrolo[3,2-b]pyridin-1-yl]ethanone; | 6.9 |
| 509 | 2-[6-(3,5-Difluorophenyl)-3-fluoro-pyrrolo[3,2-b]pyridin-1-yl]-N,N-dimethyl-acetamide; | 7.5 |

TABLE 5-continued

| Example # | Compound Name | pIC$_{50}$ |
|---|---|---|
| 510 | 2-[3-Fluoro-6-(3-fluorophenyl)pyrrolo[3,2-b]pyridin-1-yl]-N,N-dimethyl-acetamide; | 7.4 |
| 46 | 2-[3-Chloro-6-(4-fluorophenyl)pyrrolo[3,2-b]pyridin-1-yl]-N,N-dimethyl-acetamide; | 7.5 |
| 512 | 2-[3-Chloro-6-(2-fluorophenyl)pyrrolo[3,2-b]pyridin-1-yl]-N,N-dimethyl-acetamide; | 6.5 |
| 513 | 2-[3-Chloro-6-(2-fluoro-3-methyl-phenyl)pyrrolo[3,2-b]pyridin-1-yl]-N,N-dimethyl-acetamide; | 7.3 |
| 514 | 2-(3-Chloro-6-phenyl-pyrrolo[3,2-b]pyridin-1-yl)-N,N-dimethyl-acetamide; | 6.9 |
| 515 | 2-[3-Chloro-6-(m-tolyl)pyrrolo[3,2-b]pyridin-1-yl]-N,N-dimethyl-acetamide; | 7.0 |
| 516 | 2-[3-Chloro-6-[4-fluoro-3-(trifluoromethyl)phenyl]pyrrolo[3,2-b]pyridin-1-yl]-N,N-dimethyl-acetamide; | 6.7 |
| 517 | 2-[3-Chloro-6-[2-fluoro-3-(trifluoromethyl)phenyl]pyrrolo[3,2-b]pyridin-1-yl]-N,N-dimethyl-acetamide; | 7.0 |
| 518 | 2-[3-Chloro-6-(2,3,4-trifluorophenyl)pyrrolo[3,2-b]pyridin-1-yl]-N,N-dimethyl-acetamide; | 7.2 |
| 519 | 2-[3-Chloro-6-(2,4-difluoro-3-methyl-phenyl)pyrrolo[3,2-b]pyridin-1-yl]-N,N-dimethyl-acetamide; | 7.2 |
| 520 | 2-[3-Chloro-6-(3-chloro-4-fluoro-phenyl)pyrrolo[3,2-b]pyridin-1-yl]-N,N-dimethyl-acetamide; | 7.1 |
| 521 | 1-(Azetidin-1-yl)-2-[3-chloro-6-(2-fluorophenyl)pyrrolo[3,2-b]pyridin-1-yl]ethanone; | 6.9 |
| 522 | 1-(Azetidin-1-yl)-2-[3-chloro-6-(2-fluoro-3-methyl-phenyl)pyrrolo[3,2-b]pyridin-1-yl]ethanone; | 7.1 |
| 523 | 1-(Azetidin-1-yl)-2-[3-chloro-6-[4-fluoro-3-(trifluoromethyl)phenyl]pyrrolo[3,2-b]pyridin-1-yl]ethanone; | 6.8 |
| 524 | 1-(Azetidin-1-yl)-2-[3-chloro-6-[2-fluoro-3-(trifluoromethyl)phenyl]pyrrolo[3,2-b]pyridin-1-yl]ethanone; | 7.1 |
| 525 | 1-(Azetidin-1-yl)-2-[3-chloro-6-(2,4-difluoro-3-methyl-phenyl)pyrrolo[3,2-b]pyridin-1-yl]ethanone; | 7.3 |
| 526 | 1-(Azetidin-1-yl)-2-[3-chloro-6-(3-chlorophenyl)pyrrolo[3,2-b]pyridin-1-yl]ethanone; | 7.2 |
| 527 | 1-(Azetidin-1-yl)-2-[3-chloro-6-(3-chloro-4-fluoro-phenyl)pyrrolo[3,2-b]pyridin-1-yl]ethanone; | 7.3 |
| 528 | 1-(Azetidin-1-yl)-2-[3-chloro-6-(3-chloro-2-fluoro-phenyl)pyrrolo[3,2-b]pyridin-1-yl]ethanone; | 7.4 |
| 529 | 1-(Azetidin-1-yl)-2-[3-chloro-6-[3-(difluoromethyl)phenyl]pyrrolo[3,2-b]pyridin-1-yl]ethanone; | 7.1 |
| 530 | 1-(Azetidin-1-yl)-2-[3-chloro-6-(3-fluorophenyl)pyrrolo[3,2-b]pyridin-1-yl]ethanone; | 7.4 |
| 531 | 2-[3-Chloro-6-(3-fluorophenyl)pyrrolo[3,2-b]pyridin-1-yl]-N,N-dimethyl-acetamide; | 7.3 |
| 532 | 1-(Azetidin-1-yl)-2-[3-chloro-6-(3,5-difluorophenyl)pyrrolo[3,2-b]pyridin-1-yl]ethanone; | 7.3 |
| 533 | 1-(Azetidin-1-yl)-2-[3-chloro-6-(3-ethylphenyl)pyrrolo[3,2-b]pyridin-1-yl]ethanone; | 7.3 |
| 534 | 2-[3-Chloro-6-(3-chlorophenyl)pyrrolo[3,2-b]pyridin-1-yl]-N,N-dimethyl-acetamide; | 7.5 |
| 535 | 2-[3-Chloro-6-(2-fluorophenyl)pyrrolo[3,2-b]pyridin-1-yl]-1-(3-fluoroazetidin-1-yl)ethanone; | 6.7 |
| 536 | 2-[3-Chloro-6-(2-fluoro-3-methyl-phenyl)pyrrolo[3,2-b]pyridin-1-yl]-1-(3-fluoroazetidin-1-yl)ethanone; | 7.6 |
| 537 | 2-[3-Chloro-6-(3,5-difluorophenyl)pyrrolo[3,2-b]pyridin-1-yl]-1-(3-fluoroazetidin-1-yl)ethanone; | 7.9 |
| 538 | 2-[3-Chloro-6-[2-fluoro-3-(trifluoromethyl)phenyl]pyrrolo[3,2-b]pyridin-1-yl]-1-(3-fluoroazetidin-1-yl)ethanone; | 7.1 |
| 539 | 2-[3-Chloro-6-(2,4-difluoro-3-methyl-phenyl)pyrrolo[3,2-b]pyridin-1-yl]-1-(3-fluoroazetidin-1-yl)ethanone; | 7.6 |
| 540 | 2-[3-Chloro-6-(3-chloro-4-fluoro-phenyl)pyrrolo[3,2-b]pyridin-1-yl]-1-(3-fluoroazetidin-1-yl)ethanone; | 7.6 |
| 541 | 2-[3-Chloro-6-(3-chloro-2-fluoro-phenyl)pyrrolo[3,2-b]pyridin-1-yl]-1-(3-fluoroazetidin-1-yl)ethanone; | 7.4 |
| 542 | 2-[3-Chloro-6-(3-ethylphenyl)pyrrolo[3,2-b]pyridin-1-yl]-1-(3-fluoroazetidin-1-yl)ethanone; | 7.5 |
| 543 | 2-[3-Chloro-6-(3-fluorophenyl)pyrrolo[3,2-b]pyridin-1-yl]-1-(3-fluoroazetidin-1-yl)ethanone; | 7.7 |
| 544 | 2-[3-Chloro-6-(3-chloro-2-fluoro-phenyl)pyrrolo[3,2-b]pyridin-1-yl]-N,N-dimethyl-acetamide; | 7.5 |
| 545 | 2-[3-Chloro-6-(3-chlorophenyl)pyrrolo[3,2-b]pyridin-1-yl]-1-(3-fluoroazetidin-1-yl)ethanone; | 7.9 |
| 546 | 2-[3-Chloro-6-[3-(difluoromethyl)phenyl]pyrrolo[3,2-b]pyridin-1-yl]-1-(3-fluoroazetidin-1-yl)ethanone; | 7.4 |
| 547 | 1-(Azetidin-1-yl)-2-[3-fluoro-2-methyl-6-(m-tolyl)pyrrolo[3,2-b]pyridin-1-yl]ethanone; | 6.4 |
| 548 | 1-(Azetidin-1-yl)-2-[6-(3,4-difluorophenyl)-3-methyl-pyrrolo[3,2-b]pyridin-1-yl]ethanone; | 7.1 |
| 549 | 2-[6-(3,4-Difluorophenyl)-3-methyl-pyrrolo[3,2-b]pyridin-1-yl]-N,N-dimethyl-acetamide; | 7.1 |
| 550 | 1-(3-Fluoroazetidin-1-yl)-2-[3-methyl-6-(m-tolyl)pyrrolo[3,2-b]pyridin-1-yl]ethanone; | 6.9 |
| 551 | 2-[6-(3,4-Difluorophenyl)-3-methyl-pyrrolo[3,2-b]pyridin-1-yl]-1-(3-fluoroazetidin-1-yl)ethanone; | 7.2 |
| 552 | 1-(Azetidin-1-yl)-2-[3-methyl-6-[3-(trifluoromethyl)phenyl]pyrrolo[3,2-b]pyridin-1-yl]ethanone; | 7.1 |
| 553 | N,N-Dimethyl-2-[3-methyl-6-[3-(trifluoromethyl)phenyl]pyrrolo[3,2-b]pyridin-1-yl]acetamide; | 7.1 |
| 554 | 1-(3-Fluoroazetidin-1-yl)-2-[3-methyl-6-[3-(trifluoromethyl)phenyl]pyrrolo[3,2-b]pyridin-1-yl]ethanone; | 6.7 |
| 555 | 2-[6-(3,5-Difluorophenyl)-3-methyl-pyrrolo[3,2-b]pyridin-1-yl]-N,N-dimethyl-acetamide; | 7.2 |
| 556 | 1-(Azetidin-1-yl)-2-[6-(3,5-difluorophenyl)-3-methyl-pyrrolo[3,2-b]pyridin-1-yl]ethanone; | 6.4 |
| 557 | 2-[6-(3,5-Difluorophenyl)-3-methyl-pyrrolo[3,2-b]pyridin-1-yl]-N-ethyl-N-methyl-acetamide; | 6.9 |
| 558 | 2-[6-(4-Fluorophenyl)-3-methyl-pyrrolo[3,2-b]pyridin-1-yl]-N,N-dimethyl-acetamide; | 7.1 |
| 559 | N-Ethyl-2-[6-(4-fluorophenyl)-3-methyl-pyrrolo[3,2-b]pyridin-1-yl]-N-methyl-acetamide; | 6.8 |
| 560 | N-Ethyl-2-[6-(2-fluoro-3-methyl-phenyl)-3-methyl-pyrrolo[3,2-b]pyridin-1-yl]-N-methyl-acetamide; | 6.1 |
| 561 | 1-(Azetidin-1-yl)-2-[6-(2-fluoro-3-methyl-phenyl)-3-methyl-pyrrolo[3,2-b]pyridin-1-yl]ethanone; | 6.4 |
| 562 | 2-[6-(2-Fluoro-3-methyl-phenyl)-3-methyl-pyrrolo[3,2-b]pyridin-1-yl]-N,N-dimethyl-acetamide; | 7.3 |
| 563 | 1-(3-Fluoroazetidin-1-yl)-2-[6-(2-fluoro-3-methyl-phenyl)-3-methyl-pyrrolo[3,2-b]pyridin-1-yl]ethanone; | 7.4 |
| 564 | 1-(3,3-Difluoroazetidin-1-yl)-2-[6-(2-fluoro-3-methyl-phenyl)-3-methyl-pyrrolo[3,2-b]pyridin-1-yl]ethanone; | 7.0 |
| 565 | 2-[6-(2-Fluoro-3-methyl-phenyl)-3-methyl-pyrrolo[3,2-b]pyridin-1-yl]-1-pyrrolidin-1-yl-ethanone; | 6.9 |
| 566 | 2-[6-(4-Fluoro-3-methyl-phenyl)-3-methyl-pyrrolo[3,2-b]pyridin-1-yl]-N,N-dimethyl-acetamide; | 7.3 |
| 567 | 2-[3-Methyl-6-[3-(trifluoromethyl)phenyl]pyrrolo[3,2-b]pyridin-1-yl]-1-pyrrolidin-1-yl-ethanone; | 6.7 |
| 568 | N-Ethyl-N-methyl-2-[3-methyl-6-[3-(trifluoromethyl)phenyl]pyrrolo[3,2-b]pyridin-1-yl]acetamide; | 6.3 |
| 569 | 1-(3,3-Difluoroazetidin-1-yl)-2-[3-methyl-6-[3-(trifluoromethyl)phenyl]pyrrolo[3,2-b]pyridin-1-yl]ethanone; | 6.4 |
| 570 | 1-(Azetidin-1-yl)-2-[3-methyl-6-(3,4,5-trifluorophenyl)pyrrolo[3,2-b]pyridin-1-yl]ethanone; | 7.2 |
| 571 | N,N-Dimethyl-2-[3-methyl-6-(3,4,5-trifluorophenyl)pyrrolo[3,2-b]pyridin-1-yl]acetamide; | 7.3 |
| 572 | N,N-Dimethyl-2-[3-methyl-6-(m-tolyl)pyrrolo[3,2-b]pyridin-1-yl]acetamide; | 7.1 |
| 573 | N,N-Dimethyl-2-[3-methyl-6-(4-methyl-2-thienyl)pyrrolo[3,2-b]pyridin-1-yl]acetamide; | 6.9 |
| 574 | 1-(Azetidin-1-yl)-2-[3-methyl-6-(4-methyl-2-thienyl)pyrrolo[3,2-b]pyridin-1-yl]ethanone; | 7.1 |
| 575 | 1-(3-Fluoroazetidin-1-yl)-2-[3-methyl-6-(4-methyl-2-thienyl)pyrrolo[3,2-b]pyridin-1-yl]ethanone; | 7.1 |
| 576 | N,N-Dimethyl-2-(3-methyl-6-phenyl-pyrrolo[3,2-b]pyridin-1-yl)acetamide; | 7.0 |
| 577 | N-Ethyl-N-methyl-2-(3-methyl-6-phenyl-pyrrolo[3,2-b]pyridin-1-yl)acetamide; | 6.7 |
| 578 | 1-(3-Fluoroazetidin-1-yl)-2-(3-methyl-6-phenyl-pyrrolo[3,2-b]pyridin-1-yl)ethanone; | 6.9 |
| 579 | 1-(3,3-Difluoroazetidin-1-yl)-2-(3-methyl-6-phenyl-pyrrolo[3,2-b]pyridin-1-yl)ethanone; | 7.2 |

TABLE 5-continued

| Example # | Compound Name | pIC$_{50}$ |
|---|---|---|
| 580 | 1-(3-Fluoroazetidin-1-yl)-2-[6-(4-fluoro-3-methyl-phenyl)-3-methyl-pyrrolo[3,2-b]pyridin-1-yl]ethanone; | 7.1 |
| 581 | 1-(Azetidin-1-yl)-2-[3-methyl-6-(m-tolyl)pyrrolo[3,2-b]pyridin-1-yl]ethanone; | 7.1 |
| 582 | 1-(Azetidin-1-yl)-2-[3-methyl-6-(2,3,4-trifluorophenyl)pyrrolo[3,2-b]pyridin-1-yl]ethanone; | 7.4 |
| 583 | N,N-Dimethyl-2-[3-methyl-6-(2,3,4-trifluorophenyl)pyrrolo[3,2-b]pyridin-1-yl]acetamide; | 6.9 |
| 584 | N-Ethyl-N-methyl-2-[3-methyl-6-(2,3,4-trifluorophenyl)pyrrolo[3,2-b]pyridin-1-yl]acetamide; | 6.4 |
| 585 | 1-(Azetidin-1-yl)-2-[6-[2-fluoro-3-(trifluoromethyl)phenyl]-3-methyl-pyrrolo[3,2-b]pyridin-1-yl]ethanone; | 6.6 |
| 586 | 2-[6-[2-Fluoro-3-(trifluoromethyl)phenyl]-3-methyl-pyrrolo[3,2-b]pyridin-1-yl]-N,N-dimethyl-acetamide; | 6.9 |
| 587 | N-Ethyl-2-[6-[2-fluoro-3-(trifluoromethyl)phenyl]-3-methyl-pyrrolo[3,2-b]pyridin-1-yl]-N-methyl-acetamide; | 6.6 |
| 588 | 1-(3-Fluoroazetidin-1-yl)-2-[3-methyl-6-(2,3,4-trifluorophenyl)pyrrolo[3,2-b]pyridin-1-yl]ethanone; | 6.2 |
| 589 | 1-(3-Fluoroazetidin-1-yl)-2-[6-[2-fluoro-3-(trifluoromethyl)phenyl]-3-methyl-pyrrolo[3,2-b]pyridin-1-yl]ethanone; | 6.9 |
| 590 | 2-[6-[2-Fluoro-3-(trifluoromethyl)phenyl]-3-methyl-pyrrolo[3,2-b]pyridin-1-yl]-1-pyrrolidin-1-yl-ethanone; | 6.5 |
| 591 | 2-[3-Methyl-6-(2,3,4-trifluorophenyl)pyrrolo[3,2-b]pyridin-1-yl]-1-pyrrolidin-1-yl-ethanone; | 6.9 |
| 592 | 1-(Azetidin-1-yl)-2-[6-(2-fluorophenyl)-3-methyl-pyrrolo[3,2-b]pyridin-1-yl]ethanone; | 6.9 |
| 593 | 2-[6-(2-Fluorophenyl)-3-methyl-pyrrolo[3,2-b]pyridin-1-yl]-N,N-dimethyl-acetamide; | 6.6 |
| 594 | N-Ethyl-2-[6-(2-fluorophenyl)-3-methyl-pyrrolo[3,2-b]pyridin-1-yl]-N-methyl-acetamide; | 6.1 |
| 595 | 1-(3,3-Difluoroazetidin-1-yl)-2-[6-[2-fluoro-3-(trifluoromethyl)phenyl]-3-methyl-pyrrolo[3,2-b]pyridin-1-yl]ethanone; | 6.6 |
| 596 | 1-(3,3-Difluoroazetidin-1-yl)-2-[3-methyl-6-(2,3,4-trifluorophenyl)pyrrolo[3,2-b]pyridin-1-yl]ethanone; | 7.3 |
| 597 | 1-(3,3-Difluoroazetidin-1-yl)-2-[6-(2-fluorophenyl)-3-methyl-pyrrolo[3,2-b]pyridin-1-yl]ethanone; | 6.5 |
| 598 | 1-(3-Fluoroazetidin-1-yl)-2-[3-methyl-6-(3,4,5-trifluorophenyl)pyrrolo[3,2-b]pyridin-1-yl]ethanone; | 7.4 |
| 599 | 2-[3-Chloro-6-(2,5-dimethyl-3-thienyl)pyrrolo[3,2-b]pyridin-1-yl]-N,N-dimethyl-acetamide; | 7.0 |
| 600 | 2-[3-Chloro-6-[3-(trifluoromethyl)phenyl]pyrrolo[3,2-b]pyridin-1-yl]-N,N-dimethyl-acetamide; | 7.1 |
| 601 | 2-[3-Chloro-6-[6-(trifluoromethyl)-2-pyridyl]pyrrolo[3,2-b]pyridin-1-yl]-N,N-dimethyl-acetamide; | 6.9 |
| 602 | 2-[3-Chloro-6-(5-chloro-4-methyl-2-thienyl)pyrrolo[3,2-b]pyridin-1-yl]-N,N-dimethyl-acetamide; | 8.0 |
| 603 | 2-[3-Chloro-6-[5-(trifluoromethyl)-2-thienyl]pyrrolo[3,2-b]pyridin-1-yl]-N,N-dimethyl-acetamide; | 7.2 |
| 604 | 2-[6-(Benzothiophen-2-yl)pyrrolo[3,2-b]pyridin-1-yl]-N,N-dimethyl-acetamide; | 6.7 |
| 605 | 2-[3-Fluoro-6-[4-fluoro-3-(trifluoromethyl)phenyl]pyrrolo[3,2-b]pyridin-1-yl]-N,N-dimethyl-acetamide; | 7.2 |
| 606 | 2-[6-(3-Chloro-2-fluoro-phenyl)-3-fluoro-pyrrolo[3,2-b]pyridin-1-yl]-N,N-dimethyl-acetamide; | 7.2 |
| 607 | 1-(3-Fluoroazetidin-1-yl)-2-[3-fluoro-6-(m-tolyl)pyrrolo[3,2-b]pyridin-1-yl]ethanone; | 7.4 |
| 608 | 2-[6-(3-Chloro-4-fluoro-phenyl)-3-fluoro-pyrrolo[3,2-b]pyridin-1-yl]-1-(3-fluoroazetidin-1-yl)ethanone; | 7.7 |
| 609 | 1-(Azetidin-1-yl)-2-[3-[³H]-6-(4-fluoro-3-methylphenyl)-1H-pyrrolo[3,2-b]pyridin-1-yl]ethanone; | NT |
| 610 | 2-[2-Deuterio-6-(4-fluoro-3-methyl-phenyl)pyrrolo[3,2-b]pyridin-1-yl]-N,N-dimethyl-acetamide; | 8.7 |
| 611 | 2-[6-(3,5-Difluorophenyl)-3-(trifluoromethyl)pyrrolo[3,2-b]pyridin-1-yl]-N,N-dimethyl-acetamide; | 8.0 |
| 612 | 3-Chloro-1-(3-pyridylmethyl)-6-[3-(trifluoromethyl)phenyl]pyrrolo[3,2-b]pyridine; | 7.5 |
| 613 | 1-(Pyridazin-3-ylmethyl)-6-[3-(trifluoromethyl)phenyl]pyrrolo[3,2-b]pyridine; | 5.6 |
| 614 | 3-Chloro-6-(4-fluoro-3-methyl-phenyl)-1-(pyridazin-3-ylmethyl)pyrrolo[3,2-b]pyridine; | 7.5 |
| 615 | 3-Chloro-1-(pyridazin-3-ylmethyl)-6-[3-(trifluoromethyl)phenyl]pyrrolo[3,2-b]pyridine; | 7.6 |
| 616 | 2-[6-(4-Fluoro-3-methyl-phenyl)-3-methyl-pyrrolo[3,2-b]pyridin-1-yl]-1-pyrrolidin-1-yl-ethanone; | 7.5 |
| 617 | N-Ethyl-2-[6-(4-fluoro-3-methyl-phenyl)-3-methyl-pyrrolo[3,2-b]pyridin-1-yl]-N-methyl-acetamide; | 7.3 |
| 618 | 1-(3,3-Difluoroazetidin-1-yl)-2-[6-(4-fluoro-3-methyl-phenyl)-3-methyl-pyrrolo[3,2-b]pyridin-1-yl]ethanone; | 7.5 |
| 619 | 2-[6-(3,4-Difluorophenyl)-3-methyl-pyrrolo[3,2-b]pyridin-1-yl]-1-pyrrolidin-1-yl-ethanone; | 7.4 |
| 620 | 2-[6-(3,4-Difluorophenyl)-3-methyl-pyrrolo[3,2-b]pyridin-1-yl]-N-ethyl-N-methyl-acetamide; | 7.6 |
| 621 | 1-(3,3-Difluoroazetidin-1-yl)-2-[6-(3,4-difluorophenyl)-3-methyl-pyrrolo[3,2-b]pyridin-1-yl]ethanone; | 6.2 |
| 622 | 2-[6-(2,4-Difluoro-3-methyl-phenyl)-3-methyl-pyrrolo[3,2-b]pyridin-1-yl]-N,N-dimethyl-acetamide; | 7.0 |
| 623 | 2-[6-(3,5-Difluorophenyl)-3-methyl-pyrrolo[3,2-b]pyridin-1-yl]-1-pyrrolidin-1-yl-ethanone; | 7.8 |
| 624 | 2-[6-(2,4-Difluoro-3-methyl-phenyl)-3-methyl-pyrrolo[3,2-b]pyridin-1-yl]-1-pyrrolidin-1-yl-ethanone; | 7.1 |
| 625 | 2-[6-(2,4-Difluoro-3-methyl-phenyl)-3-methyl-pyrrolo[3,2-b]pyridin-1-yl]-N-ethyl-N-methyl-acetamide; | 7.0 |
| 626 | 1-(3,3-Difluoroazetidin-1-yl)-2-[6-(2,4-difluoro-3-methyl-phenyl)-3-methyl-pyrrolo[3,2-b]pyridin-1-yl]ethanone; | 6.2 |
| 627 | 1-(Azetidin-1-yl)-2-[6-(2,4-difluoro-3-methyl-phenyl)-3-methyl-pyrrolo[3,2-b]pyridin-1-yl]ethanone; | 6.8 |
| 628 | 2-[6-(5-Chloro-2-thienyl)-3-methyl-pyrrolo[3,2-b]pyridin-1-yl]-N,N-dimethyl-acetamide; | 7.0 |
| 629 | 2-[6-(2,4-Difluoro-3-methyl-phenyl)-3-methyl-pyrrolo[3,2-b]pyridin-1-yl]-1-(3-fluoroazetidin-1-yl)ethanone; | 7.4 |
| 630 | N-Ethyl-N-methyl-2-[3-methyl-6-(5-methyl-2-thienyl)pyrrolo[3,2-b]pyridin-1-yl]acetamide; | 6.6 |
| 631 | 2-[3-Methyl-6-(5-methyl-2-thienyl)pyrrolo[3,2-b]pyridin-1-yl]-1-pyrrolidin-1-yl-ethanone; | 6.8 |
| 632 | 1-(3,3-Difluoroazetidin-1-yl)-2-[3-methyl-6-(5-methyl-2-thienyl)pyrrolo[3,2-b]pyridin-1-yl]ethanone; | 6.7 |
| 633 | 1-(Azetidin-1-yl)-2-[3-methyl-6-(5-methyl-2-thienyl)pyrrolo[3,2-b]pyridin-1-yl]ethanone; | 7.3 |
| 634 | 1-(3-Fluoroazetidin-1-yl)-2-[3-methyl-6-(5-methyl-2-thienyl)pyrrolo[3,2-b]pyridin-1-yl]ethanone; | 6.2 |
| 635 | 2-[6-(3,5-Difluorophenyl)-3-methyl-pyrrolo[3,2-b]pyridin-1-yl]-1-(3-fluoroazetidin-1-yl)ethanone; | 6.5 |
| 636 | 2-[6-(5-Chloro-2-thienyl)-3-methyl-pyrrolo[3,2-b]pyridin-1-yl]-1-(3-fluoroazetidin-1-yl)ethanone; | 6.8 |
| 637 | N,N-Dimethyl-2-[3-methyl-6-(5-methyl-2-thienyl)pyrrolo[3,2-b]pyridin-1-yl]acetamide; | 6.5 |
| 638 | 1-(3-Fluoroazetidin-1-yl)-2-[6-(2-fluorophenyl)-3-methyl-pyrrolo[3,2-b]pyridin-1-yl]ethanone; and | 6.9 |
| 639 | 2-[6-[5-(Difluoromethyl)-2-thienyl]pyrrolo[3,2-b]pyridin-1-yl]-N,N-dimethyl-acetamide; | 6.7 |

*NT means not tested.

What is claimed:

1. A compound, and pharmaceutically acceptable salts, solvates, or N-oxides thereof, having the structure of Formula (I):

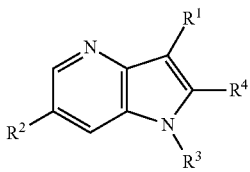

(I)

wherein:
$R^1$ is selected from the group consisting of: H, $^3$H, halo, $C_{1-3}$alkyl, and $C_{1-3}$haloalkyl;
$R^2$ is selected from the group consisting of: phenyl optionally substituted with one, two, or three members independently selected from: halo, $C_{1-5}$alkyl, and $C_{1-5}$haloalkyl; pyridinyl optionally substituted with halo, $C_{1-5}$alkyl, $C_{1-5}$haloalkyl; and —CN; thiazolyl optionally substituted with $C_{1-5}$alkyl; benzothiophenyl; and thienyl optionally substituted with one, two or three members independently selected from: halo, $C_{1-5}$alkyl; and $C_{1-5}$haloalkyl;
$R^3$ is selected from the group consisting of:
(a)

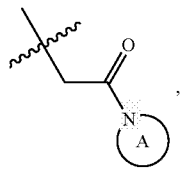

wherein ring A is a wherein ring A is a 4-7 membered heterocycloalkyl optionally containing an additional oxygen heteroatom selected from the group consisting of: azetidinyl optionally substituted with one or two members independently selected from the group consisting of: halo, $C_{1-5}$alkyl, $C_{1-5}$haloalkyl, $CH_2OH$, $C_{1-5}$alkoxy, OH, and CN; pyrrolidinyl optionally substituted one or two members independently selected from the group consisting of: halo, $C_{1-5}$alkyl, $C_{1-5}$alkoxy, and OH; morpholino optionally substituted one or two $C_{1-5}$alkyl members; piperidinyl optionally substituted with one or two members independently selected from the group consisting of: halo, $C_{1-5}$alkyl, $C_{1-5}$haloalkyl, $C_{1-5}$alkoxy, and OH; 3-azabicyclo[3.1.0]hexan-3-yl; 5-azaspiro[2.3]hexan-5-yl; and pyrrolidin-3-one; or
(b)

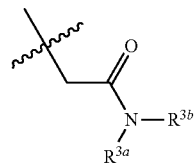

wherein $R^{3a}$ is H, or $C_{1-5}$alkyl;
and $R^{3b}$ is selected from the group consisting of: $C_{1-5}$alkyl optionally substituted with OH, halo, or $OCH_3$; $C_{1-5}$haloalkyl; benzyl; $CH_2$cyclopropyl; cyclopropyl optionally substituted with $C_{1-5}$alkyl; and cyclobutyl; or (c)

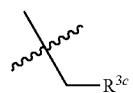

wherein $R^{3c}$ is selected from the group consisting of: cyclopropyl; cyclobutyl; pyrimidinyl optionally substituted with halo; pyridinyl; pyridazinyl; furanyl optionally substituted with $C_{1-5}$haloalkyl; oxazolyl; isoxazolyl optionally substituted with $C_{1-5}$alkyl; oxadiazolyl optionally substituted with $C_{1-5}$alkyl; pyrazolyl optionally substituted with $C_{1-5}$alkyl; triazolyl optionally substituted with $C_{1-5}$alkyl; tetrahydrofuranyl; tetrahydropyranyl; oxetanyl; and oxiranyl; or (d)

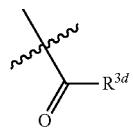

wherein $R^{3d}$ is $CH_2$-cyclopropyl or cyclobutyl; or (e)

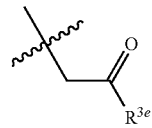

wherein $R^{3e}$ is selected from the group consisting of: OH, $C_{1-5}$alkyl, cyclopropyl, cyclobutyl, and phenyl optionally substituted with one halo substituent; or (f) $C_{1-5}$alkyl optionally substituted with OH or $C_{1-5}$alkoxy; $CH_2S(CH_3)$; $CH_2(S=O)CH_3$; $CH_2(SO_2)CH_3$; and $CH_2CH_2(C=O)CH_3$; or (g)

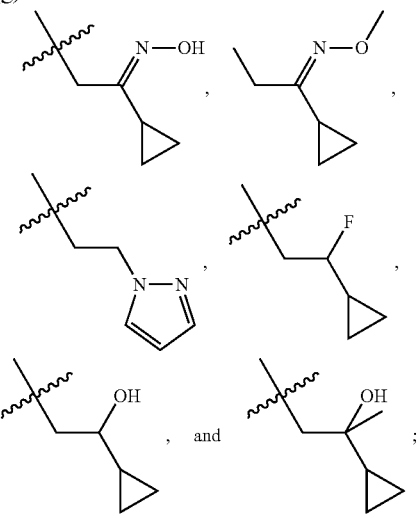

and
$R^4$ is H, $^2$H or $C_{1-3}$alkyl.

2. The compound of claim 1, wherein $R^1$ is H, Cl, Br, F, or $CH_3$.
3. The compound of claim 1, wherein $R^1$ is H.
4. The compound of claim 1, wherein $R^1$ is Cl.
5. The compound of claim 1, wherein $R^1$ is $CH_3$.

6. The compound of claim 1, wherein $R^2$ is phenyl optionally substituted with one, two, or three members independently selected from: Cl, F, $CH_3$, $CH_2CH_3$, $CF_2H$, and $CF_3$, pyridinyl optionally substituted with F, CN, $CH_3$ and $CF_3$, thiazolyl optionally substituted with $CH_3$, benzothiophenyl; and thienyl optionally substituted with one, two or three members independently selected from: Cl, $CH_3$, $CH_2CH_3$, $CHF_2$ and $CF_3$.

7. The compound of claim 1, wherein $R^2$ is phenyl, 2-methylphenyl, 3-methylphenyl, 4-methylphenyl, 3-ethylphenyl, 3-(difluoromethyl)phenyl, 3-(trifluoromethyl)phenyl, 3,5-dimethylphenyl, 2,3-dimethylphenyl, 2-fluorophenyl, 3-fluorophenyl, 3-chlorophenyl, 4-fluorophenyl, 2,3-difluorophenyl, 2,4-difluorophenyl, 3,4-difluorophenyl, 3,4-dichlorophenyl, 2,5-difluorophenyl, 3,5-difluorophenyl, 3-chloro-2-fluoro-phenyl, 3-chloro-4-fluoro-phenyl, 2-fluoro-3-methyl-phenyl, 4-fluoro-2-methyl-phenyl, 2-methyl-3-(trifluoromethyl)phenyl, 2-fluoro-3-(trifluoromethyl)phenyl, 4-fluoro-3-(trifluoromethyl)phenyl, 4-fluoro-3-methyl-phenyl, 2-fluoro-5-methyl-phenyl, 4-fluoro-2,3-dimethyl-phenyl, 2,4-difluoro-3-methyl-phenyl, 2,6-difluoro-3-methyl-phenyl, 2,3,4-trifluorophenyl, 3,4,5-trifluorophenyl, 2-thienyl, 3-thienyl, 5-methyl-2-thienyl, 4-methyl-2-thienyl, 5-ethyl-2-thienyl, 5-chloro-2-thienyl, 3-chloro-2-thienyl, 4-chloro-2-thienyl, 5-chloro-3-thienyl, 5-(difluoromethyl)-2-thienyl, 5-(trifluoromethyl)-2-thienyl, 2,5-dimethyl-3-thienyl, 2,5-dichloro-3-thienyl, 5-chloro-4-methyl-2-thienyl, 2,4,5-trimethyl-3-thienyl, 6-thiazol-5-yl, 2-methylthiazol-5-yl, 6-methyl-3-pyridyl, 6-fluoro-3-pyridyl, pyridine-2-carbonitrile, 2-(trifluoromethyl)-4-pyridyl, 5-(trifluoromethyl)-3-pyridyl, 6-(trifluoromethyl)-2-pyridyl, or benzothiophen-2-yl.

8. The compound of claim 1, wherein $R^2$ is phenyl or thienyl, wherein the phenyl or thienyl is optionally substituted with one, two, or three members independently selected from: halo, $C_{1-5}$alkyl, and $C_{1-5}$haloalkyl.

9. The compound of claim 1, wherein $R^3$ is

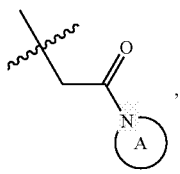

wherein ring A is

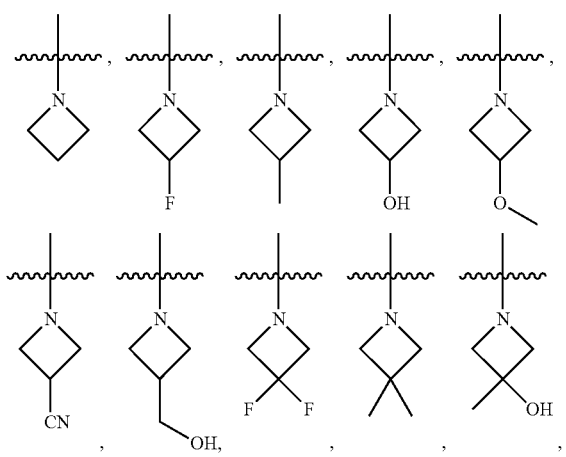

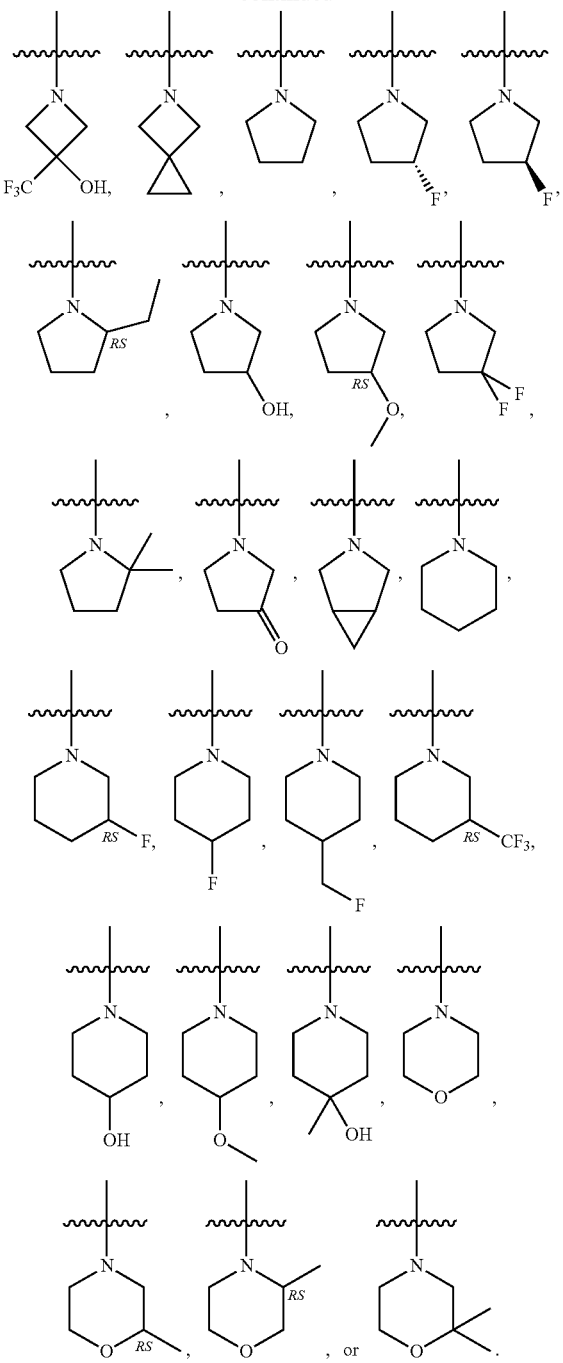

10. The compound of claim 1, wherein $R^3$ is

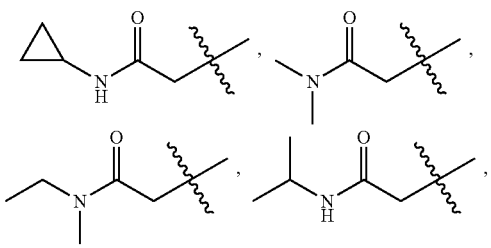

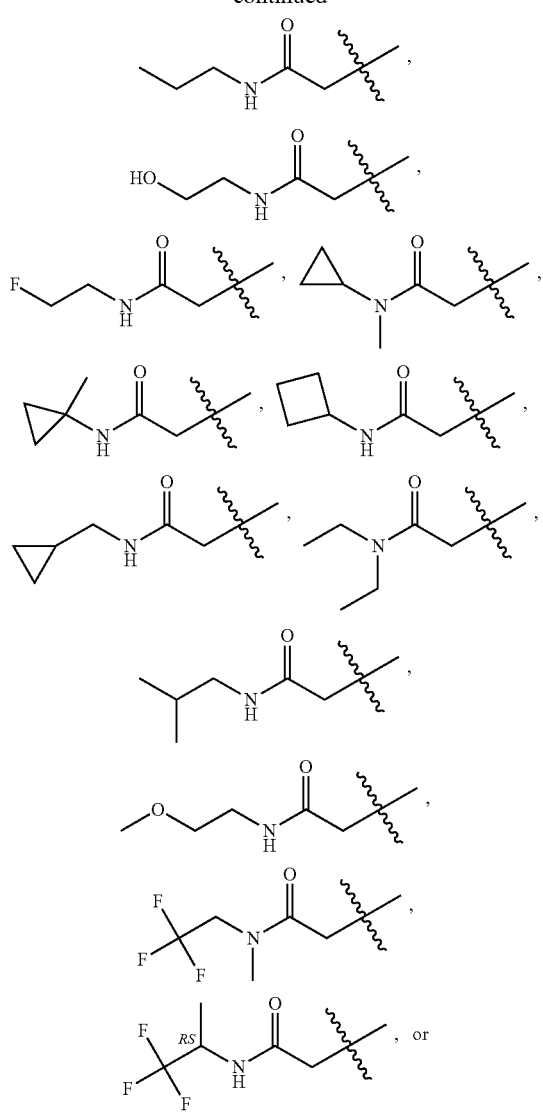
11. The compound of claim 1, wherein R³ is
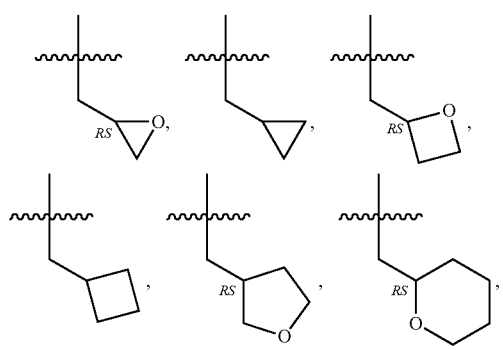
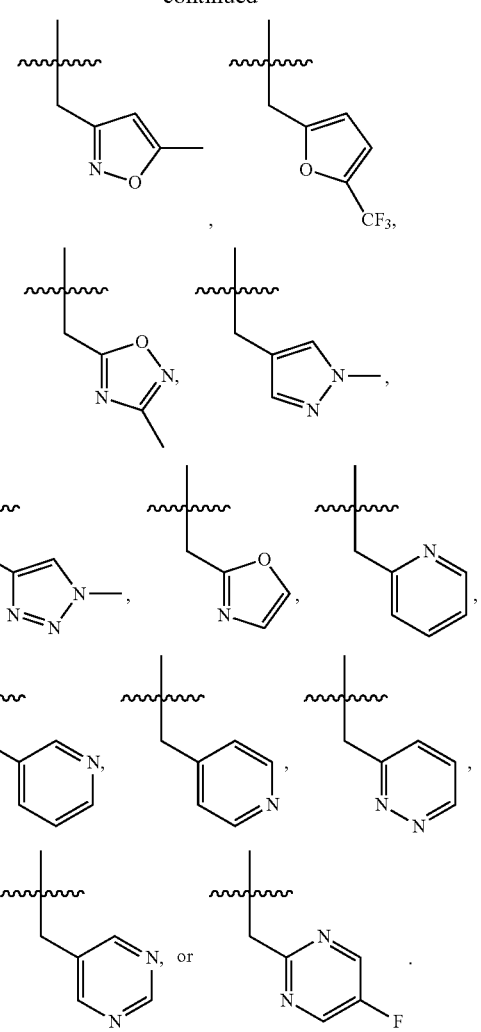
12. The compound of claim 1, wherein R³ is
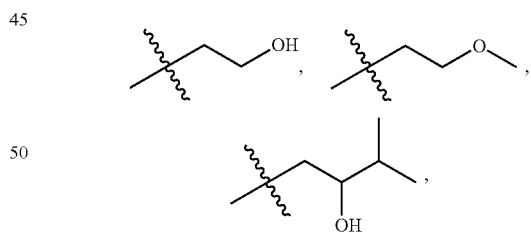
$CH_2S(CH_3)$, $CH_2(S=O)CH_3$, $CH_2(SO_2)CH_3$, or $CH_2CH_2(C=O)CH_3$.
13. The compound of claim 1, wherein R³ is
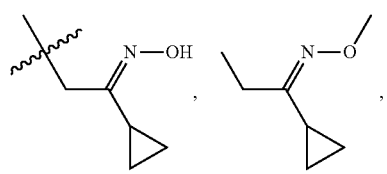

-continued

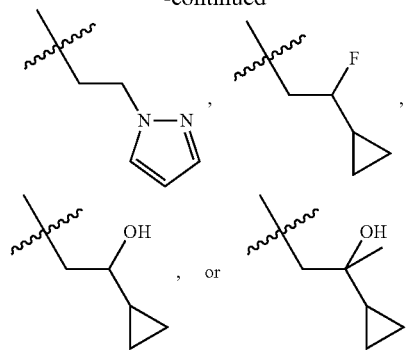

14. The compound of claim 1, wherein R³ is

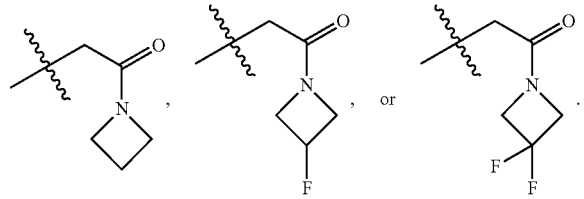 [SMILES: *CC(=O)N1CCC1 ; *CC(=O)N1CC(F)C1 ; *CC(=O)N1CC(F)(F)C1]

15. The compound of claim 1, wherein R⁴ is H.

16. The compound of claim 1, wherein R⁴ is CH₃.

17. The compound of claim 1, and pharmaceutically acceptable salts, solvates, or N-oxides thereof, having the structure of Formula (II):

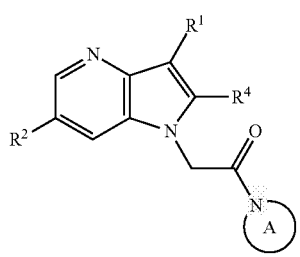

(II)

wherein
R¹ is selected from the group consisting of: H, ³H, halo and $C_{1-3}$alkyl,
R² is selected from the group consisting of: phenyl optionally substituted with one, two, or three members independently selected from: halo, $C_{1-5}$alkyl, and $C_{1-5}$haloalkyl; pyridinyl optionally substituted with halo, $C_{1-5}$alkyl, $C_{1-5}$haloalkyl, and CN; thiazolyl optionally substituted with $C_{1-5}$alkyl; and thienyl optionally substituted with halo, or $C_{1-5}$alkyl;
ring A is selected from the group consisting of:

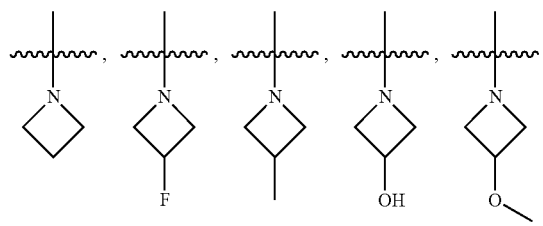

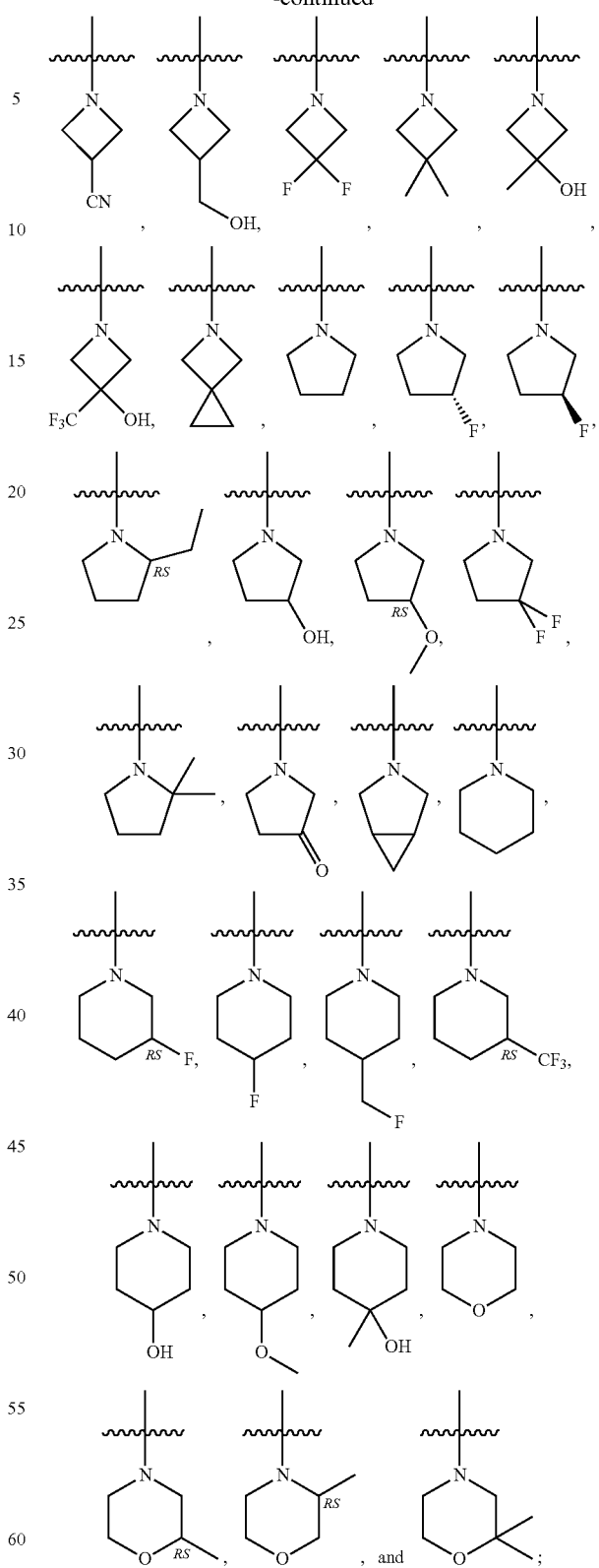

and R⁴ is H, ²H, or CH₃.

18. The compound of claim 1, and pharmaceutically acceptable salts, solvates, or N-oxides thereof, having the structure of Formula (IIA):

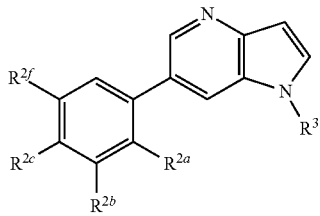

wherein
 $R^{2a}$ is H, or F;
 $R^{2b}$ is H, F, $CH_3$ or $CH_2CH_3$;
 $R^{2c}$ is H, F or $CH_3$;
 $R^{2f}$ is H, F, or $CH_3$; and
 $R^3$ is

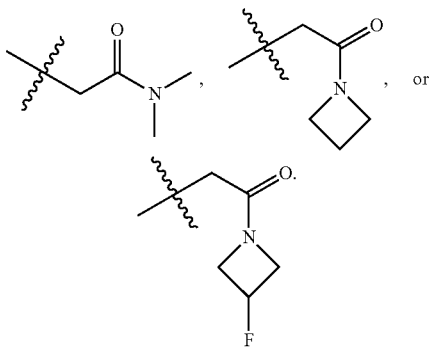

19. The compound of claim 1, and pharmaceutically acceptable salts, solvates, or N-oxides thereof, having the structure of Formula (IIB):

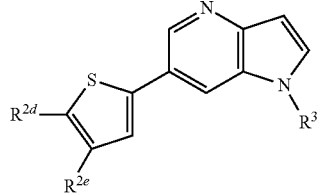

wherein
 $R^{2d}$ is H, Cl, $CH_3$ or $CF_3$;
 $R^{2e}$ is H or $CH_3$; and
 $R^3$ is

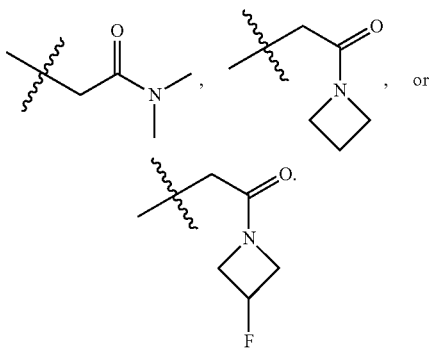

20. The compound of claim 1, and pharmaceutically acceptable salts, solvates, or N-oxides thereof, having the structure of Formula (III):

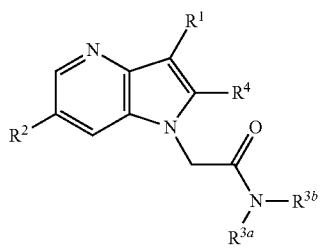

wherein
 $R^1$ is H, $^3$H, halo, $C_{1-3}$alkyl, or $C_{1-3}$haloalkyl;
 $R^2$ is selected from the group consisting of: phenyl optionally substituted with one, two, or three members independently selected from: halo, $C_{1-5}$alkyl, and $C_{1-5}$haloalkyl; pyridinyl optionally substituted with $C_{1-5}$haloalkyl; benzothiophenyl; and thienyl optionally substituted with one, two, or three members independently selected from halo, $C_{1-5}$alkyl, or
 $R^{3a}$ is H, or $C_{1-5}$alkyl;
 $R^{3b}$ is selected from the group consisting of: $C_{1-5}$alkyl optionally substituted with OH or $OCH_3$; $C_{1-5}$haloalkyl; benzyl; $CH_2$cyclopropyl; cyclopropyl optionally substituted with $C_{1-5}$alkyl; and cyclobutyl; and
 $R^4$ is H, $H^2$, or $CH_3$.

21. The compound of claim 1, and pharmaceutically acceptable salts, solvates, or N-oxides thereof, having the structure of Formula (IV):

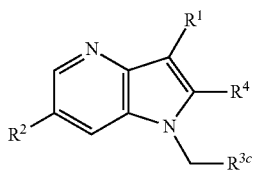

$R^1$ is H, or halo;
$R^2$ is phenyl optionally substituted with one, or two members independently selected from: halo, $C_{1-5}$alkyl, and $C_{1-5}$haloalkyl; or thienyl substituted with $C_{1-5}$alkyl;
$R^{3c}$ is

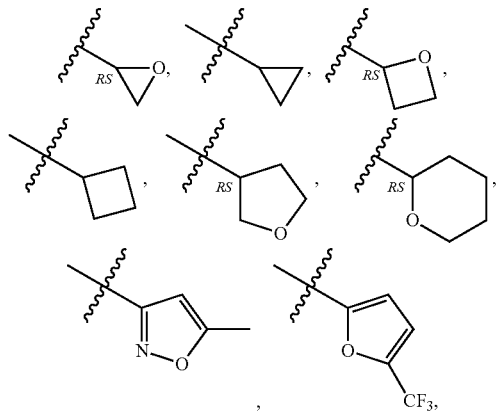

-continued

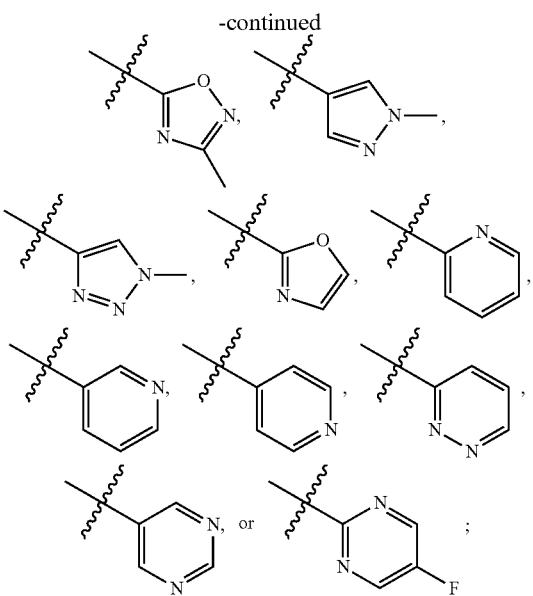

and R⁴ is H.

22. The compound of claim 1, and pharmaceutically acceptable salts, solvates, or N-oxides thereof, having the structure of Formula (V):

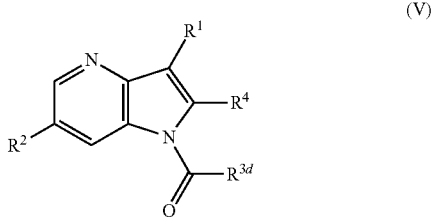

wherein
R¹ and R⁴ are H;
R² is phenyl optionally substituted with two halo; and
R$^{3d}$ is cyclobutyl, or CH$_2$-cyclopropyl.

23. The compound of claim 1, and pharmaceutically acceptable salts, solvates, or N-oxides thereof, having the structure of Formula (VI):

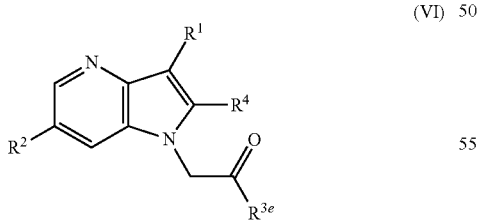

R¹ is H or halo;
R² is phenyl optionally substituted with one, two, or three members independently selected from: halo, C$_{1-5}$alkyl, and C$_{1-5}$haloalkyl; or thienyl substituted with halo or C$_{1-5}$alkyl;
R$^{3e}$ is selected from the group consisting of: OH, C$_{1-5}$alkyl, cyclopropyl, cyclobutyl, and phenyl optionally substituted with one halo substituent;

and
R⁴ is H or CH$_3$.

24. A compound selected from the group consisting of:
2-(3-Chloro-6-phenyl-pyrrolo[3,2-b]pyridin-1-yl)-N-cyclopropyl-acetamide;
2-[3-Chloro-6-(4-fluorophenyl)pyrrolo[3,2-b]pyridin-1-yl]-N-cyclopropyl-acetamide;
1-(Azetidin-1-yl)-2-[3-chloro-6-(4-fluorophenyl)pyrrolo[3,2-b]pyridin-1-yl]ethanone;
2-(3-Chloro-6-phenyl-pyrrolo[3,2-b]pyridin-1-yl)-1-pyrrolidin-1-yl-ethanone;
2-(3-Chloro-6-phenyl-pyrrolo[3,2-b]pyridin-1-yl)-1-morpholino-ethanone;
1-(Azetidin-1-yl)-2-(3-chloro-6-phenyl-pyrrolo[3,2-b]pyridin-1-yl)ethanone;
2-[3-Chloro-6-(4-fluorophenyl)pyrrolo[3,2-b]pyridin-1-yl]-1-morpholino-ethanone;
1-(Azetidin-1-yl)-2-[3-chloro-6-(m-tolyl)pyrrolo[3,2-b]pyridin-1-yl]ethanone;
2-[3-Chloro-6-(4-fluorophenyl)pyrrolo[3,2-b]pyridin-1-yl]-1-pyrrolidin-1-yl-ethanone;
2-[3-Chloro-6-(m-tolyl)pyrrolo[3,2-b]pyridin-1-yl]-N-cyclopropyl-acetamide;
1-(Azetidin-1-yl)-2-(3-bromo-6-phenyl-pyrrolo[3,2-b]pyridin-1-yl)ethanone;
2-[3-Chloro-6-(m-tolyl)pyrrolo[3,2-b]pyridin-1-yl]-1-pyrrolidin-1-yl-ethanone;
2-[3-Chloro-6-(m-tolyl)pyrrolo[3,2-b]pyridin-1-yl]-1-morpholino-ethanone;
2-(3-Bromo-6-phenyl-pyrrolo[3,2-b]pyridin-1-yl)-N-cyclopropyl-acetamide;
2-(3-Bromo-6-phenyl-pyrrolo[3,2-b]pyridin-1-yl)-1-pyrrolidin-1-yl-ethanone;
2-(3-Bromo-6-phenyl-pyrrolo[3,2-b]pyridin-1-yl)-1-morpholino-ethanone;
2-[3-Bromo-6-(4-fluorophenyl)pyrrolo[3,2-b]pyridin-1-yl]-N-cyclopropyl-acetamide;
1-(Azetidin-1-yl)-2-[3-bromo-6-(4-fluorophenyl)pyrrolo[3,2-b]pyridin-1-yl]ethanone;
2-[3-Bromo-6-(4-fluorophenyl)pyrrolo[3,2-b]pyridin-1-yl]-1-pyrrolidin-1-yl-ethanone;
2-[3-Bromo-6-(4-fluorophenyl)pyrrolo[3,2-b]pyridin-1-yl]-1-morpholino-ethanone;
2-[3-Bromo-6-(m-tolyl)pyrrolo[3,2-b]pyridin-1-yl]-N-cyclopropyl-acetamide;
1-(Azetidin-1-yl)-2-[3-bromo-6-(m-tolyl)pyrrolo[3,2-b]pyridin-1-yl]ethanone;
2-[3-Bromo-6-(m-tolyl)pyrrolo[3,2-b]pyridin-1-yl]-1-pyrrolidin-1-yl-ethanone;
2-[3-Bromo-6-(m-tolyl)pyrrolo[3,2-b]pyridin-1-yl]-1-morpholino-ethanone;
2-[3-Chloro-6-(4-fluoro-3-methyl-phenyl)pyrrolo[3,2-b]pyridin-1-yl]-1-(3,3-difluoroazetidin-1-yl)ethanone;
2-[3-Chloro-6-(4-fluoro-3-methyl-phenyl)pyrrolo[3,2-b]pyridin-1-yl]-1-(3-fluoroazetidin-1-yl)ethanone;
2-[6-(4-Fluorophenyl)-3-methyl-pyrrolo[3,2-b]pyridin-1-yl]-1-pyrrolidin-1-yl-ethanone;
2-[6-(4-Fluorophenyl)-3-methyl-pyrrolo[3,2-b]pyridin-1-yl]-1-morpholino-ethanone;
1-(Azetidin-1-yl)-2-[3-chloro-6-(3,4-difluorophenyl)pyrrolo[3,2-b]pyridin-1-yl]ethanone;
2-[3-Chloro-6-(3,4-difluorophenyl)pyrrolo[3,2-b]pyridin-1-yl]-1-(3-fluoroazetidin-1-yl)ethanone;
2-[6-(4-Fluorophenyl)-2-methyl-pyrrolo[3,2-b]pyridin-1-yl]-1-morpholino-ethanone;
N-Cyclopropyl-2-[6-(4-fluorophenyl)-3-methyl-pyrrolo[3,2-b]pyridin-1-yl]acetamide;

1-(Azetidin-1-yl)-2-[6-(4-fluorophenyl)-3-methyl-pyrrolo[3,2-b]pyridin-1-yl]ethanone;
2-[3-Chloro-6-(3,4-difluorophenyl)pyrrolo[3,2-b]pyridin-1-yl]-1-(3,3-difluoroazetidin-1-yl)ethanone;
2-[3-Chloro-6-[4-fluoro-3-(trifluoromethyl)phenyl]pyrrolo[3,2-b]pyridin-1-yl]-1-(3-fluoroazetidin-1-yl)ethanone;
2-[3-Chloro-6-[3-(trifluoromethyl)phenyl]pyrrolo[3,2-b]pyridin-1-yl]-1-(3,3-difluoroazetidin-1-yl)ethanone;
2-[6-(4-Fluorophenyl)-2-methyl-pyrrolo[3,2-b]pyridin-1-yl]-1-pyrrolidin-1-yl-ethanone;
N-Cyclopropyl-2-[6-(4-fluorophenyl)-2-methyl-pyrrolo[3,2-b]pyridin-1-yl]acetamide;
2-[3-Chloro-6-(3,4,5-trifluorophenyl)pyrrolo[3,2-b]pyridin-1-yl]-1-(3-fluoroazetidin-1-yl)ethanone;
2-[3-Chloro-6-[4-fluoro-3-(trifluoromethyl)phenyl]pyrrolo[3,2-b]pyridin-1-yl]-1-(3,3-difluoroazetidin-1-yl)ethanone;
1-(Azetidin-1-yl)-2-[2-methyl-6-(m-tolyl)pyrrolo[3,2-b]pyridin-1-yl]ethanone;
2-(2-Methyl-6-phenyl-pyrrolo[3,2-b]pyridin-1-yl)-1-pyrrolidin-1-yl-ethanone;
N-Cyclopropyl-2-(2-methyl-6-phenyl-pyrrolo[3,2-b]pyridin-1-yl)acetamide;
2-[2-Methyl-6-(m-tolyl)pyrrolo[3,2-b]pyridin-1-yl]-1-pyrrolidin-1-yl-ethanone;
2-[2-Methyl-6-(m-tolyl)pyrrolo[3,2-b]pyridin-1-yl]-1-morpholino-ethanone;
1-(Azetidin-1-yl)-2-[6-(4-fluorophenyl)-2-methyl-pyrrolo[3,2-b]pyridin-1-yl]ethanone;
1-(Azetidin-1-yl)-2-(2-methyl-6-phenyl-pyrrolo[3,2-b]pyridin-1-yl)ethanone;
2-[3-Chloro-6-[3-(trifluoromethyl)phenyl]pyrrolo[3,2-b]pyridin-1-yl]-1-(3-fluoroazetidin-1-yl)ethanone;
2-[3-Chloro-6-(3,4,5-trifluorophenyl)pyrrolo[3,2-b]pyridin-1-yl]-1-(3,3-difluoroazetidin-1-yl)ethanone;
2-[3-Chloro-6-(2,3,4-trifluorophenyl)pyrrolo[3,2-b]pyridin-1-yl]-1-(3,3-difluoroazetidin-1-yl)ethanone;
N-Cyclopropyl-2-[2-methyl-6-(m-tolyl)pyrrolo[3,2-b]pyridin-1-yl]acetamide;
2-(2-Methyl-6-phenyl-pyrrolo[3,2-b]pyridin-1-yl)-1-morpholino-ethanone;
2-[3-Chloro-6-(m-tolyl)pyrrolo[3,2-b]pyridin-1-yl]-1-(3,3-difluoroazetidin-1-yl)ethanone;
2-[3-Chloro-6-(m-tolyl)pyrrolo[3,2-b]pyridin-1-yl]-1-(3-fluoroazetidin-1-yl)ethanone;
2-(3-Chloro-6-phenyl-pyrrolo[3,2-b]pyridin-1-yl)-1-(3,3-difluoroazetidin-1-yl)ethanone;
2-(3-Chloro-6-phenyl-pyrrolo[3,2-b]pyridin-1-yl)-1-(3-fluoroazetidin-1-yl)ethanone;
2-[3-Chloro-6-(4-fluorophenyl)pyrrolo[3,2-b]pyridin-1-yl]-1-(3,3-difluoroazetidin-1-yl)ethanone;
2-[3-Chloro-6-(4-fluorophenyl)pyrrolo[3,2-b]pyridin-1-yl]-1-(3-fluoroazetidin-1-yl)ethanone;
3-[[6-(4-Fluoro-2-methyl-phenyl)pyrrolo[3,2-b]pyridin-1-yl]methyl]-5-methyl-isoxazole;
5-Methyl-3-[[6-[3-(trifluoromethyl)phenyl]pyrrolo[3,2-b]pyridin-1-yl]methyl]isoxazole;
5-Methyl-3-[[6-(m-tolyl)pyrrolo[3,2-b]pyridin-1-yl]methyl]isoxazole trifluoroacetate salt;
5-Methyl-3-[[6-(o-tolyl)pyrrolo[3,2-b]pyridin-1-yl]methyl]isoxazole trifluoroacetate salt;
3-[[6-(4-Fluoro-3-methyl-phenyl)pyrrolo[3,2-b]pyridin-1-yl]methyl]-5-methyl-isoxazole trifluoroacetate salt;
3-[[6-(3,5-Difluorophenyl)pyrrolo[3,2-b]pyridin-1-yl]methyl]-5-methyl-isoxazole trifluoroacetate salt;
3-[[6-(4-Fluorophenyl)pyrrolo[3,2-b]pyridin-1-yl]methyl]-5-methyl-isoxazole trifluoroacetate salt;
N-Cyclobutyl-2-[6-(4-fluoro-3-methyl-phenyl)pyrrolo[3,2-b]pyridin-1-yl]acetamide trifluoroacetate salt;
2-[6-(4-Fluoro-3-methyl-phenyl)pyrrolo[3,2-b]pyridin-1-yl]-1-pyrrolidin-1-yl-ethanone trifluoroacetate salt;
1-(Azetidin-1-yl)-2-[3-bromo-6-(4-fluoro-3-methyl-phenyl)pyrrolo[3,2-b]pyridin-1-yl]ethanone;
1-(Azetidin-1-yl)-2-[3-fluoro-6-(4-fluoro-3-methyl-phenyl)pyrrolo[3,2-b]pyridin-1-yl]ethanone;
2-[6-(4-Fluoro-3-methyl-phenyl)pyrrolo[3,2-b]pyridin-1-yl]acetic acid;
1-(Azetidin-1-yl)-2-[6-(2-fluorophenyl)pyrrolo[3,2-b]pyridin-1-yl]ethanone;
1-(Azetidin-1-yl)-2-[6-(3-fluorophenyl)pyrrolo[3,2-b]pyridin-1-yl]ethanone;
1-(Azetidin-1-yl)-2-[6-(p-tolyl)pyrrolo[3,2-b]pyridin-1-yl]ethanone;
1-(Azetidin-1-yl)-2-[6-(3-ethylphenyl)pyrrolo[3,2-b]pyridin-1-yl]ethanone;
N-Cyclopropyl-2-[6-(2-fluorophenyl)pyrrolo[3,2-b]pyridin-1-yl]acetamide;
N-Cyclopropyl-2-[6-(3-fluorophenyl)pyrrolo[3,2-b]pyridin-1-yl]acetamide;
N-Cyclopropyl-2-[6-(p-tolyl)pyrrolo[3,2-b]pyridin-1-yl]acetamide;
2-(6-Phenylpyrrolo[3,2-b]pyridin-1-yl)-1-pyrrolidin-1-yl-ethanone;
2-[6-(2-Fluorophenyl)pyrrolo[3,2-b]pyridin-1-yl]-1-pyrrolidin-1-yl-ethanone;
2-[6-(4-Fluorophenyl)pyrrolo[3,2-b]pyridin-1-yl]-1-pyrrolidin-1-yl-ethanone;
2-[6-(m-Tolyl)pyrrolo[3,2-b]pyridin-1-yl]-1-pyrrolidin-1-yl-ethanone;
2-[6-(p-Tolyl)pyrrolo[3,2-b]pyridin-1-yl]-1-pyrrolidin-1-yl-ethanone;
2-[6-(3-Ethylphenyl)pyrrolo[3,2-b]pyridin-1-yl]-1-pyrrolidin-1-yl-ethanone;
2-[6-(3-Fluorophenyl)pyrrolo[3,2-b]pyridin-1-yl]-1-pyrrolidin-1-yl-ethanone;
1-Morpholino-2-(6-phenylpyrrolo[3,2-b]pyridin-1-yl)ethanone;
2-[6-(2-Fluorophenyl)pyrrolo[3,2-b]pyridin-1-yl]-1-morpholino-ethanone;
2-[6-(3-Fluorophenyl)pyrrolo[3,2-b]pyridin-1-yl]-1-morpholino-ethanone;
2-[6-(4-Fluorophenyl)pyrrolo[3,2-b]pyridin-1-yl]-1-morpholino-ethanone;
1-Morpholino-2-[6-(m-tolyl)pyrrolo[3,2-b]pyridin-1-yl]ethanone;
1-Morpholino-2-[6-(p-tolyl)pyrrolo[3,2-b]pyridin-1-yl]ethanone;
2-[6-(3-Ethylphenyl)pyrrolo[3,2-b]pyridin-1-yl]-1-morpholino-ethanone;
2-[3-Fluoro-6-(4-fluoro-3-methyl-phenyl)pyrrolo[3,2-b]pyridin-1-yl]-N,N-dimethyl-acetamide;
2-[6-(3,4-Difluorophenyl)-3-fluoro-pyrrolo[3,2-b]pyridin-1-yl]-N,N-dimethyl-acetamide;
2-[3-Fluoro-6-(3,4,5-trifluorophenyl)pyrrolo[3,2-b]pyridin-1-yl]-N,N-dimethyl-acetamide;
2-[6-[3-(Difluoromethyl)phenyl]-3-fluoro-pyrrolo[3,2-b]pyridin-1-yl]-N,N-dimethyl-acetamide;
2-[3-Fluoro-6-(4-methyl-2-thienyl)pyrrolo[3,2-b]pyridin-1-yl]-N,N-dimethyl-acetamide;
2-[6-(5-Chloro-2-thienyl)-3-fluoro-pyrrolo[3,2-b]pyridin-1-yl]-N,N-dimethyl-acetamide;

2-[3-Fluoro-6-(4-fluorophenyl)pyrrolo[3,2-b]pyridin-1-yl]-N, N-dimethyl-acetamide;
N-Cyclopropyl-2-[6-[5-(trifluoromethyl)-3-pyridyl]pyrrolo[3,2-b]pyridin-1-yl]acetamide;
N-Cyclopropyl-2-[6-(3,4-difluorophenyl)pyrrolo[3,2-b]pyridin-1-yl]acetamide;
N-Cyclopropyl-2-[6-[4-fluoro-3-(trifluoromethyl)phenyl]pyrrolo[3,2-b]pyridin-1-yl]acetamide;
1-(Azetidin-1-yl)-2-[6-[5-(trifluoromethyl)-3-pyridyl]pyrrolo[3,2-b]pyridin-1-yl]ethanone;
1-(Azetidin-1-yl)-2-[6-(3,4-difluorophenyl)pyrrolo[3,2-b]pyridin-1-yl]ethanone;
1-(Azetidin-1-yl)-2-[6-[4-fluoro-3-(trifluoromethyl)phenyl]pyrrolo[3,2-b]pyridin-1-yl]ethanone;
2-[6-[4-fluoro-3-(trifluoromethyl)phenyl]pyrrolo[3,2-b]pyridin-1-yl]-1-pyrrolidin-1-yl-ethanone;
1-(3,3-Difluoroazetidin-1-yl)-2-[6-[4-fluoro-3-(trifluoromethyl)phenyl]pyrrolo[3,2-b]pyridin-1-yl]ethanone;
2-[6-(3,4-Difluorophenyl)pyrrolo[3,2-b]pyridin-1-yl]-1-morpholino-ethanone;
2-[6-[4-Fluoro-3-(trifluoromethyl)phenyl]pyrrolo[3,2-b]pyridin-1-yl]-1-morpholino-ethanone;
1-(Azetidin-1-yl)-2-[6-[2-(trifluoromethyl)-4-pyridyl]pyrrolo[3,2-b]pyridin-1-yl]ethanone;
N-Cyclopropyl-2-[6-[2-(trifluoromethyl)-4-pyridyl]pyrrolo[3,2-b]pyridin-1-yl]acetamide;
N-Cyclopropyl-2-[6-[6-(trifluoromethyl)-2-pyridyl]pyrrolo[3,2-b]pyridin-1-yl]acetamide;
1-(Azetidin-1-yl)-2-[6-(6-methyl-3-pyridyl)pyrrolo[3,2-b]pyridin-1-yl]ethanone;
5-[1-[2-(Azetidin-1-yl)-2-oxo-ethyl]pyrrolo[3,2-b]pyridin-6-yl]pyridine-2-carbonitrile;
6-(3,4-Difluorophenyl)-1-(pyrimidin-5-ylmethyl)pyrrolo[3,2-b]pyridine;
6-(3,4-Difluorophenyl)-1-[(5-fluoropyrimidin-2-yl)methyl]pyrrolo[3,2-b]pyridine;
Cyclobutyl-[6-(3,4-difluorophenyl)pyrrolo[3,2-b]pyridin-1-yl]methanone;
1-(3,3-Difluoroazetidin-1-yl)-2-[6-[6-(trifluoromethyl)-2-pyridyl]pyrrolo[3,2-b]pyridin-1-yl]ethanone;
1-(Azetidin-1-yl)-2-[6-(2,3,4-trifluorophenyl)pyrrolo[3,2-b]pyridin-1-yl]ethanone;
2-Cyclopropyl-1-[6-(3,4-difluorophenyl)pyrrolo[3,2-b]pyridin-1-yl]ethanone;
1-Pyrrolidin-1-yl-2-[6-(2,3,4-trifluorophenyl)pyrrolo[3,2-b]pyridin-1-yl]ethanone;
1-(3,3-Difluoroazetidin-1-yl)-2-[6-(3,5-difluorophenyl)pyrrolo[3,2-b]pyridin-1-yl]ethanone;
2-[6-(3,5-Difluorophenyl)pyrrolo[3,2-b]pyridin-1-yl]-1-pyrrolidin-1-yl-ethanone;
1-Pyrrolidin-1-yl-2-[6-(3,4,5-trifluorophenyl)pyrrolo[3,2-b]pyridin-1-yl]ethanone;
1-(3,3-Difluoroazetidin-1-yl)-2-[6-(3,4,5-trifluorophenyl)pyrrolo[3,2-b]pyridin-1-yl]ethanone;
2-[6-(3,5-Difluorophenyl)pyrrolo[3,2-b]pyridin-1-yl]-1-morpholino-ethanone;
1-Morpholino-2-[6-(2,3,4-trifluorophenyl)pyrrolo[3,2-b]pyridin-1-yl]ethanone;
1-Morpholino-2-[6-(3,4,5-trifluorophenyl)pyrrolo[3,2-b]pyridin-1-yl]ethanone;
2-[6-(3,4-Difluorophenyl)pyrrolo[3,2-b]pyridin-1-yl]-1-(3-fluoroazetidin-1-yl)ethanone;
2-[6-(3,5-Difluorophenyl)pyrrolo[3,2-b]pyridin-1-yl]-1-(3-fluoroazetidin-1-yl)ethanone;
6-(4-Methyl-2-thienyl)-1-(pyridazin-3-ylmethyl)pyrrolo[3,2-b]pyridine;
6-(3,4-Difluorophenyl)-1-(pyridazin-3-ylmethyl)pyrrolo[3,2-b]pyridine;
2-[6-(4-Methyl-2-thienyl)pyrrolo[3,2-b]pyridin-1-yl]-1-morpholino-ethanone;
1-(Azetidin-1-yl)-2-[6-(2,4-difluorophenyl)pyrrolo[3,2-b]pyridin-1-yl]ethanone;
1-(Azetidin-1-yl)-2-[6-(2,3-difluorophenyl)pyrrolo[3,2-b]pyridin-1-yl]ethanone;
1-(Azetidin-1-yl)-2-[6-(2,5-difluorophenyl)pyrrolo[3,2-b]pyridin-1-yl]ethanone;
1-Cyclopropyl-2-[6-(3,4-difluorophenyl)-3-fluoro-pyrrolo[3,2-b]pyridin-1-yl]ethanone;
6-(4-Methyl-2-thienyl)-1-[[5-(trifluoromethyl)-2-furyl]methyl]pyrrolo[3,2-b]pyridine;
6-(3,4-Difluorophenyl)-1-[[5-(trifluoromethyl)-2-furyl]methyl]pyrrolo[3,2-b]pyridine;
N,N-Dimethyl-2-[6-(4-methyl-2-thienyl)pyrrolo[3,2-b]pyridin-1-yl]acetamide;
1-[6-(3,4-Difluorophenyl)pyrrolo[3,2-b]pyridin-1-yl]-3,3-dimethyl-butan-2-one;
1-[6-(4-Fluoro-3-methyl-phenyl)pyrrolo[3,2-b]pyridin-1-yl]-3,3-dimethyl-butan-2-one;
1-[6-(3,5-Difluorophenyl)pyrrolo[3,2-b]pyridin-1-yl]-3,3-dimethyl-butan-2-one;
3,3-Dimethyl-1-[6-(4-methyl-2-thienyl)pyrrolo[3,2-b]pyridin-1-yl]butan-2-one;
1-[6-[3-(Difluoromethyl)phenyl]pyrrolo[3,2-b]pyridin-1-yl]-3,3-dimethyl-butan-2-one;
1-[6-(3-Ethylphenyl)pyrrolo[3,2-b]pyridin-1-yl]-3,3-dimethyl-butan-2-one;
2-[3-Chloro-6-(4-fluoro-3-methyl-phenyl)pyrrolo[3,2-b]pyridin-1-yl]-N,N-dimethyl-acetamide;
2-[3-Chloro-6-(3,4-difluorophenyl)pyrrolo[3,2-b]pyridin-1-yl]-N,N-dimethyl-acetamide;
2-[3-Chloro-6-(3,5-difluorophenyl)pyrrolo[3,2-b]pyridin-1-yl]-N,N-dimethyl-acetamide;
2-[3-Chloro-6-(4-methyl-2-thienyl)pyrrolo[3,2-b]pyridin-1-yl]-N, N-dimethyl-acetamide;
2-[3-Chloro-6-[3-(difluoromethyl)phenyl]pyrrolo[3,2-b]pyridin-1-yl]-N,N-dimethyl-acetamide;
2-[3-Chloro-6-(3-ethylphenyl)pyrrolo[3,2-b]pyridin-1-yl]-N,N-dimethyl-acetamide;
2-[3-Chloro-6-(3,4,5-trifluorophenyl)pyrrolo[3,2-b]pyridin-1-yl]-N,N-dimethyl-acetamide;
N-Cyclopropyl-2-[6-(4-methyl-2-thienyl)pyrrolo[3,2-b]pyridin-1-yl]acetamide trifluoroacetate salt;
N-Cyclopropyl-2-[6-(2,3-dimethylphenyl)pyrrolo[3,2-b]pyridin-1-yl]acetamide trifluoroacetate salt;
N-Cyclopropyl-2-[6-(m-tolyl)pyrrolo[3,2-b]pyridin-1-yl]acetamide trifluoroacetate salt;
N-Cyclopropyl-2-[6-(3,4-dichlorophenyl)pyrrolo[3,2-b]pyridin-1-yl]acetamide trifluoroacetate salt;
N-Cyclopropyl-2-[6-[2-methyl-3-(trifluoromethyl)phenyl]pyrrolo[3,2-b]pyridin-1-yl]acetamide trifluoroacetate salt;
N-Cyclopropyl-2-(6-phenylpyrrolo[3,2-b]pyridin-1-yl)acetamide trifluoroacetate salt;
N-Cyclopropyl-2-[6-(4-fluoro-2,3-dimethyl-phenyl)pyrrolo[3,2-b]pyridin-1-yl]acetamide trifluoroacetate salt;
N-Cyclopropyl-2-[6-(o-tolyl)pyrrolo[3,2-b]pyridin-1-yl]acetamide;
N-Cyclopropyl-2-[6-(4-fluoro-2-methyl-phenyl)pyrrolo[3,2-b]pyridin-1-yl]acetamide trifluoroacetate salt;
1-(Azetidin-1-yl)-2-[6-(o-tolyl)pyrrolo[3,2-b]pyridin-1-yl]ethanone trifluoroacetate salt;
1-(Azetidin-1-yl)-2-[6-(4-fluoro-2-methyl-phenyl)pyrrolo[3,2-b]pyridin-1-yl]ethanone trifluoroacetate salt;

1-(Azetidin-1-yl)-2-[6-(4-fluoro-2,3-dimethyl-phenyl)pyrrolo[3,2-b]pyridin-1-yl]ethanone trifluoroacetate salt;
1-(Azetidin-1-yl)-2-[6-(2,3-dimethylphenyl)pyrrolo[3,2-b]pyridin-1-yl]ethanone trifluoroacetate salt;
1-(Azetidin-1-yl)-2-[6-[3-(trifluoromethyl)phenyl]pyrrolo[3,2-b]pyridin-1-yl]ethanone trifluoroacetate salt;
1-(Azetidin-1-yl)-2-[6-[2-methyl-3-(trifluoromethyl)phenyl]pyrrolo[3,2-b]pyridin-1-yl]ethanone trifluoroacetate salt;
N-Cyclopropyl-2-[6-(4-fluorophenyl)pyrrolo[3,2-b]pyridin-1-yl]acetamide;
1-(Azetidin-1-yl)-2-[6-(4-fluoro-3-methyl-phenyl)-3-methyl-pyrrolo[3,2-b]pyridin-1-yl]ethanone trifluoroacetate salt;
1-Butyl-6-(4-fluoro-3-methyl-phenyl)pyrrolo[3,2-b]pyridine trifluoroacetate salt;
6-(4-Fluoro-3-methyl-phenyl)-1-isopentyl-pyrrolo[3,2-b]pyridine trifluoroacetate salt;
6-(4-Fluoro-3-methyl-phenyl)-1-(3-pyridylmethyl)pyrrolo[3,2-b]pyridine trifluoroacetate salt;
1-(Cyclobutylmethyl)-6-(4-fluoro-3-methyl-phenyl)pyrrolo[3,2-b]pyridine trifluoroacetate salt;
1-(Cyclopropylmethyl)-6-(4-fluoro-3-methyl-phenyl)pyrrolo[3,2-b]pyridine trifluoroacetate salt;
2-[6-(4-Fluoro-3-methyl-phenyl)pyrrolo[3,2-b]pyridin-1-yl]-N,N-dimethyl-acetamide trifluoroacetate salt;
2-[3-Chloro-6-(4-fluoro-3-methyl-phenyl)pyrrolo[3,2-b]pyridin-1-yl]-N-cyclopropyl-acetamide trifluoroacetate salt;
6-(4-Fluoro-3-methyl-phenyl)-1-(2-pyridylmethyl)pyrrolo[3,2-b]pyridine trifluoroacetate salt;
(R/S)-6-(4-Fluoro-3-methyl-phenyl)-1-(tetrahydrofuran-3-ylmethyl)pyrrolo[3,2-b]pyridine trifluoroacetate salt;
6-(4-Fluoro-3-methyl-phenyl)-1-(4-pyridylmethyl)pyrrolo[3,2-b]pyridine trifluoroacetate salt;
(R/S)-6-(4-Fluoro-3-methyl-phenyl)-1-(oxiran-2-ylmethyl)pyrrolo[3,2-b]pyridine trifluoroacetate salt;
6-(4-Fluoro-3-methyl-phenyl)-1-(2-pyrazol-1-ylethyl)pyrrolo[3,2-b]pyridine trifluoroacetate salt;
1-(Azetidin-1-yl)-2-[6-(5-chloro-2-thienyl)-3-fluoro-pyrrolo[3,2-b]pyridin-1-yl]ethanone;
6-(4-Fluoro-3-methyl-phenyl)-1-(pyrimidin-2-ylmethyl)pyrrolo[3,2-b]pyridine trifluoroacetate salt;
(R/S)-6-(4-Fluoro-3-methyl-phenyl)-1-(oxetan-2-ylmethyl)pyrrolo[3,2-b]pyridine trifluoroacetate salt;
1-(3,3-Difluoroazetidin-1-yl)-2-[3-fluoro-6-(4-fluoro-3-methyl-phenyl)pyrrolo[3,2-b]pyridin-1-yl]ethanone;
1-Cyclopropyl-2-[6-(4-fluoro-3-methyl-phenyl)pyrrolo[3,2-b]pyridin-1-yl]ethanone trifluoroacetate salt;
1-[6-(4-Fluoro-3-methyl-phenyl)pyrrolo[3,2-b]pyridin-1-yl]-3-methyl-butan-2-one trifluoroacetate salt;
2-[6-(4-Fluoro-3-methyl-phenyl)pyrrolo[3,2-b]pyridin-1-yl]-1-(4-hydroxy-1-piperidyl)ethanone trifluoroacetate salt;
(R/S)-1-(3-Azabicyclo[3.1.0]hexan-3-yl)-2-[6-(4-fluoro-3-methyl-phenyl)pyrrolo[3,2-b]pyridin-1-yl]ethanone trifluoroacetate salt;
2-[6-(4-Fluoro-3-methyl-phenyl)pyrrolo[3,2-b]pyridin-1-yl]-1-(4-methoxy-1-piperidyl)ethanone trifluoroacetate salt;
2-[6-(4-Fluoro-3-methyl-phenyl)pyrrolo[3,2-b]pyridin-1-yl]-1-(4-fluoro-1-piperidyl)ethanone trifluoroacetate salt;
2-[6-(4-Fluoro-3-methyl-phenyl)pyrrolo[3,2-b]pyridin-1-yl]-1-[4-(fluoromethyl)-1-piperidyl]ethanone trifluoroacetate salt;
2-[6-(4-Fluoro-3-methyl-phenyl)pyrrolo[3,2-b]pyridin-1-yl]-1-(1-piperidyl)ethanone trifluoroacetate salt;
(R/S)-2-[6-(4-Fluoro-3-methyl-phenyl)pyrrolo[3,2-b]pyridin-1-yl]-1-(2-methylmorpholin-4-yl)ethanone trifluoroacetate salt;
(R/S)-2-[6-(4-Fluoro-3-methyl-phenyl)pyrrolo[3,2-b]pyridin-1-yl]-1-[3-(trifluoromethyl)-1-piperidyl]ethanone trifluoroacetate salt;
(R/S)-1-(2-Ethylpyrrolidin-1-yl)-2-[6-(4-fluoro-3-methyl-phenyl)pyrrolo[3,2-b]pyridin-1-yl]ethanone trifluoroacetate salt;
1-(2,2-Dimethylmorpholin-4-yl)-2-[6-(4-fluoro-3-methyl-phenyl)pyrrolo[3,2-b]pyridin-1-yl]ethanone trifluoroacetate salt;
(R/S)-2-[6-(4-Fluoro-3-methyl-phenyl)pyrrolo[3,2-b]pyridin-1-yl]-1-(3-methoxypyrrolidin-1-yl)ethanone trifluoroacetate salt;
(R/S)-2-[6-(4-Fluoro-3-methyl-phenyl)pyrrolo[3,2-b]pyridin-1-yl]-1-(3-fluoro-1-piperidyl)ethanone trifluoroacetate salt;
1-(2,2-Dimethylpyrrolidin-1-yl)-2-[6-(4-fluoro-3-methyl-phenyl)pyrrolo[3,2-b]pyridin-1-yl]ethanone trifluoroacetate salt;
2-[6-(4-Fluoro-3-methyl-phenyl)pyrrolo[3,2-b]pyridin-1-yl]-1-[(3R)-3-fluoropyrrolidin-1-yl]ethanone trifluoroacetate salt;
2-[6-(4-Fluorophenyl)pyrrolo[3,2-b]pyridin-1-yl]-1-(3-hydroxy-3-methyl-azetidin-1-yl)ethanone;
2-[6-(4-Fluorophenyl)pyrrolo[3,2-b]pyridin-1-yl]-1-[3-hydroxy-3-(trifluoromethyl)azetidin-1-yl]ethanone;
1-(3-Fluoroazetidin-1-yl)-2-[6-(4-fluorophenyl)pyrrolo[3,2-b]pyridin-1-yl]ethanone;
N-Cyclopropyl-2-[6-(4-fluorophenyl)pyrrolo[3,2-b]pyridin-1-yl]-N-methyl-acetamide;
2-[6-(4-Fluorophenyl)pyrrolo[3,2-b]pyridin-1-yl]-1-[3-(hydroxymethyl)azetidin-1-yl]ethanone;
2-[6-(4-Fluorophenyl)pyrrolo[3,2-b]pyridin-1-yl]-1-(3-methoxyazetidin-1-yl)ethanone;
1-(5-Azaspiro[2.3]hexan-5-yl)-2-[6-(4-fluoro-3-methyl-phenyl)pyrrolo[3,2-b]pyridin-1-yl]ethanone trifluoroacetate salt;
2-[6-(4-Fluoro-3-methyl-phenyl)pyrrolo[3,2-b]pyridin-1-yl]-1-(4-hydroxy-4-methyl-1-piperidyl)ethanone trifluoroacetate salt;
(R/S)-2-[6-(4-Fluoro-3-methyl-phenyl)pyrrolo[3,2-b]pyridin-1-yl]-1-(3-methylmorpholin-4-yl)ethanone trifluoroacetate salt;
2-[6-(4-Fluorophenyl)pyrrolo[3,2-b]pyridin-1-yl]-1-(3-hydroxyazetidin-1-yl)ethanone;
1-[2-[6-(4-Fluorophenyl)pyrrolo[3,2-b]pyridin-1-yl]acetyl]azetidine-3-carbonitrile;
1-(3,3-Difluoroazetidin-1-yl)-2-[6-(4-fluorophenyl)pyrrolo[3,2-b]pyridin-1-yl]ethanone;
2-[6-(4-Fluorophenyl)pyrrolo[3,2-b]pyridin-1-yl]-1-(3-methylazetidin-1-yl)ethanone;
1-(3,3-Dimethylazetidin-1-yl)-2-[6-(4-fluorophenyl)pyrrolo[3,2-b]pyridin-1-yl]ethanone;
1-[2-[6-(4-Fluorophenyl)pyrrolo[3,2-b]pyridin-1-yl]acetyl]pyrrolidin-3-one trifluoroacetate salt;
1-(3,3-Difluoropyrrolidin-1-yl)-2-[6-(4-fluorophenyl)pyrrolo[3,2-b]pyridin-1-yl]ethanone;
(R/S)-2-[6-(4-Fluorophenyl)pyrrolo[3,2-b]pyridin-1-yl]-1-(3-hydroxypyrrolidin-1-yl)ethanone;
1-Cyclopropyl-2-[6-(m-tolyl)pyrrolo[3,2-b]pyridin-1-yl]ethanone;
1-Cyclopropyl-2-(6-phenylpyrrolo[3,2-b]pyridin-1-yl)ethanone;

1-Cyclopropyl-2-[6-(3-fluorophenyl)pyrrolo[3,2-b]pyridin-1-yl]ethanone;
1-Cyclopropyl-2-[6-(4-fluorophenyl)pyrrolo[3,2-b]pyridin-1-yl]ethanone;
1-[6-(4-Fluoro-2,3-dimethyl-phenyl)pyrrolo[3,2-b]pyridin-1-yl]-3-methyl-butan-2-one;
1-[6-(3-Ethylphenyl)pyrrolo[3,2-b]pyridin-1-yl]-3-methyl-butan-2-one;
1-[6-(2,3-Dimethylphenyl)pyrrolo[3,2-b]pyridin-1-yl]-3-methyl-butan-2-one;
2-[6-(4-Fluorophenyl)pyrrolo[3,2-b]pyridin-1-yl]-1-phenyl-ethanone;
1-(4-Fluorophenyl)-2-[6-(4-fluorophenyl)pyrrolo[3,2-b]pyridin-1-yl]ethanone;
(R/S)-6-(4-Fluorophenyl)-1-(tetrahydropyran-2-ylmethyl)pyrrolo[3,2-b]pyridine trifluoroacetate salt;
2-[6-(4-Fluorophenyl)pyrrolo[3,2-b]pyridin-1-yl]-N-isopropyl-acetamide;
2-[6-(4-Fluorophenyl)pyrrolo[3,2-b]pyridin-1-yl]-N-propyl-acetamide;
(R/S)-2-[6-(4-Fluorophenyl)pyrrolo[3,2-b]pyridin-1-yl]-N-(2,2,2-trifluoro-1-methyl-ethyl)acetamide;
2-[6-(4-Fluorophenyl)pyrrolo[3,2-b]pyridin-1-yl]-N-(1-methylcyclopropyl)acetamide;
N-(2-Fluoroethyl)-2-[6-(4-fluorophenyl)pyrrolo[3,2-b]pyridin-1-yl]acetamide;
2-[6-(4-Fluorophenyl)pyrrolo[3,2-b]pyridin-1-yl]-N-isobutyl-acetamide;
5-[[6-(4-Fluoro-3-methyl-phenyl)pyrrolo[3,2-b]pyridin-1-yl]methyl]-3-methyl-1,2,4-oxadiazole;
6-(4-Fluoro-3-methyl-phenyl)-1-[(1-methylpyrazol-4-yl)methyl]pyrrolo[3,2-b]pyridine;
N-(Cyclopropylmethyl)-2-[6-(4-fluorophenyl)pyrrolo[3,2-b]pyridin-1-yl]acetamide;
6-(4-Fluoro-3-methyl-phenyl)-1-[(1-methyltriazol-4-yl)methyl]pyrrolo[3,2-b]pyridine;
5-[[3-Chloro-6-(4-fluoro-3-methyl-phenyl)pyrrolo[3,2-b]pyridin-1-yl]methyl]-3-methyl-1,2,4-oxadiazole;
3-Chloro-6-(4-fluoro-3-methyl-phenyl)-1-[(1-methylpyrazol-4-yl)methyl]pyrrolo[3,2-b]pyridine;
2-[3-Chloro-6-(4-fluoro-3-methyl-phenyl)pyrrolo[3,2-b]pyridin-1-yl]-1-cyclobutyl-ethanone;
1-Cyclobutyl-2-[6-(4-fluoro-3-methyl-phenyl)pyrrolo[3,2-b]pyridin-1-yl]ethanone;
1-(Azetidin-1-yl)-2-[3-chloro-6-[5-(trifluoromethyl)-3-pyridyl]pyrrolo[3,2-b]pyridin-1-yl]ethanone trifluoroacetate salt;
2-[3-Chloro-6-[5-(trifluoromethyl)-3-pyridyl]pyrrolo[3,2-b]pyridin-1-yl]-N-cyclopropyl-acetamide trifluoroacetate salt;
1-(Azetidin-1-yl)-2-[3-chloro-6-[6-(trifluoromethyl)-2-pyridyl]pyrrolo[3,2-b]pyridin-1-yl]ethanone;
2-[3-Chloro-6-[6-(trifluoromethyl)-2-pyridyl]pyrrolo[3,2-b]pyridin-1-yl]-N-cyclopropyl-acetamide;
2-[3-Chloro-6-[6-(trifluoromethyl)-2-pyridyl]pyrrolo[3,2-b]pyridin-1-yl]-1-(3-fluoroazetidin-1-yl)ethanone;
N-Cyclopropyl-2-[6-(3,4,5-trifluorophenyl)pyrrolo[3,2-b]pyridin-1-yl]acetamide;
N-Cyclopropyl-2-[6-(2,3,4-trifluorophenyl)pyrrolo[3,2-b]pyridin-1-yl]acetamide;
N-Cyclopropyl-2-[6-[3-(difluoromethyl)phenyl]pyrrolo[3,2-b]pyridin-1-yl]acetamide;
N-Benzyl-2-[6-(4-fluorophenyl)pyrrolo[3,2-b]pyridin-1-yl]acetamide;
2-[[6-(4-Fluoro-3-methyl-phenyl)pyrrolo[3,2-b]pyridin-1-yl]methyl]oxazole;
2-[6-(4-Fluorophenyl)pyrrolo[3,2-b]pyridin-1-yl]-N-(2-hydroxyethyl)acetamide;
2-[6-(4-Fluorophenyl)pyrrolo[3,2-b]pyridin-1-yl]-N-(2-methoxyethyl)acetamide;
1-(3,3-Difluoroazetidin-1-yl)-2-[6-[2-fluoro-3-(trifluoromethyl)phenyl]pyrrolo[3,2-b]pyridin-1-yl]ethanone trifluoroacetate salt;
1-(3,3-Difluoroazetidin-1-yl)-2-[6-(3-fluorophenyl)pyrrolo[3,2-b]pyridin-1-yl]ethanone trifluoroacetate salt;
1-(3,3-Difluoroazetidin-1-yl)-2-(6-phenyl pyrrolo[3,2-b]pyridin-1-yl)ethanone trifluoroacetate salt;
1-(3,3-Difluoroazetidin-1-yl)-2-[6-(3-ethylphenyl)pyrrolo[3,2-b]pyridin-1-yl]ethanone trifluoroacetate salt;
1-(3,3-Difluoroazetidin-1-yl)-2-[6-(4-fluoro-3-methylphenyl)pyrrolo[3,2-b]pyridin-1-yl]ethanone trifluoroacetate salt;
1-(3,3-Difluoroazetidin-1-yl)-2-[6-[3-(trifluoromethyl)phenyl]pyrrolo[3,2-b]pyridin-1-yl]ethanone trifluoroacetate salt;
1-(3,3-Difluoroazetidin-1-yl)-2-[6-(4-fluoro-2-methylphenyl)pyrrolo[3,2-b]pyridin-1-yl]ethanone trifluoroacetate salt;
1-(3-Fluoroazetidin-1-yl)-2-[6-[4-fluoro-3-(trifluoromethyl)phenyl]pyrrolo[3,2-b]pyridin-1-yl]ethanone trifluoroacetate salt;
1-(3-Fluoroazetidin-1-yl)-2-[6-(3-fluorophenyl)pyrrolo[3,2-b]pyridin-1-yl]ethanone trifluoroacetate salt;
1-(3-Fluoroazetidin-1-yl)-2-[6-(4-fluoro-2-methyl-phenyl)pyrrolo[3,2-b]pyridin-1-yl]ethanone trifluoroacetate salt;
1-(3-Fluoroazetidin-1-yl)-2-[6-[3-(trifluoromethyl)phenyl]pyrrolo[3,2-b]pyridin-1-yl]ethanone trifluoroacetate salt;
1-(3-Fluoroazetidin-1-yl)-2-[6-(m-tolyl)pyrrolo[3,2-b]pyridin-1-yl]ethanone trifluoroacetate salt;
1-(3-Fluoroazetidin-1-yl)-2-[6-[2-fluoro-3-(trifluoromethyl)phenyl]pyrrolo[3,2-b]pyridin-1-yl]ethanone trifluoroacetate salt;
2-[6-(3-Ethylphenyl)pyrrolo[3,2-b]pyridin-1-yl]-1-(3-fluoroazetidin-1-yl)ethanone trifluoroacetate salt;
1-(3,3-Difluoroazetidin-1-yl)-2-[6-(m-tolyl)pyrrolo[3,2-b]pyridin-1-yl]ethanone;
1-(3-Fluoroazetidin-1-yl)-2-(6-phenylpyrrolo[3,2-b]pyridin-1-yl)ethanone;
1-(3,3-Difluoroazetidin-1-yl)-2-[6-(2,4-difluoro-3-methyl-phenyl)-3-fluoro-pyrrolo[3,2-b]pyridin-1-yl]ethanone;
(R/S)-1-[6-(3,5-Difluorophenyl)pyrrolo[3,2-b]pyridin-1-yl]-3-methyl-butan-2-ol;
2-[6-(4-Fluoro-3-methyl-phenyl)pyrrolo[3,2-b]pyridin-1-yl]-1-(3-hydroxyazetidin-1-yl)ethanone;
(R/S)-1-Cyclopropyl-2-[6-(4-fluoro-3-methyl-phenyl)pyrrolo[3,2-b]pyridin-1-yl]ethanol;
(R/S)-2-Cyclopropyl-1-[6-(4-fluoro-3-methyl-phenyl)pyrrolo[3,2-b]pyridin-1-yl]propan-2-ol trifluoroacetate salt;
1-Cyclopropyl-2-[6-(4-fluoro-3-methyl-phenyl)pyrrolo[3,2-b]pyridin-1-yl]-N-methoxy-ethanimine;
1-(3-Fluoroazetidin-1-yl)-2-[6-(2-thienyl)pyrrolo[3,2-b]pyridin-1-yl]ethanone;
1-Pyrrolidin-1-yl-2-[6-(2-thienyl)pyrrolo[3,2-b]pyridin-1-yl]ethanone;
1-(3,3-Difluoroazetidin-1-yl)-2-[6-(5-methyl-2-thienyl)pyrrolo[3,2-b]pyridin-1-yl]ethanone;
1-(3-Fluoroazetidin-1-yl)-2-[6-(5-methyl-2-thienyl)pyrrolo[3,2-b]pyridin-1-yl]ethanone;

2-[6-(5-Ethyl-2-thienyl)pyrrolo[3,2-b]pyridin-1-yl]-1-(3-fluoroazetidin-1-yl)ethanone;
2-[6-(5-Ethyl-2-thienyl)pyrrolo[3,2-b]pyridin-1-yl]-1-pyrrolidin-1-yl-ethanone;
2-[6-(5-Methyl-2-thienyl)pyrrolo[3,2-b]pyridin-1-yl]-1-pyrrolidin-1-yl-ethanone;
1-(3,3-Difluoroazetidin-1-yl)-2-[6-(5-ethyl-2-thienyl)pyrrolo[3,2-b]pyridin-1-yl]ethanone;
2-[6-(4-Chloro-2-thienyl)pyrrolo[3,2-b]pyridin-1-yl]-1-(3-fluoroazetidin-1-yl)ethanone;
1-Cyclopropyl-2-[6-(4-fluoro-3-methyl-phenyl)pyrrolo[3,2-b]pyridin-1-yl]ethanone oxime trifluoroacetate salt;
2-[6-(5-Chloro-2-thienyl)pyrrolo[3,2-b]pyridin-1-yl]-1-pyrrolidin-1-yl-ethanone;
2-[6-(4-Chloro-2-thienyl)pyrrolo[3,2-b]pyridin-1-yl]-1-pyrrolidin-1-yl-ethanone;
(R/S)-1-(2-Cyclopropyl-2-fluoro-ethyl)-6-(4-fluoro-3-methyl-phenyl)pyrrolo[3,2-b]pyridine;
2-[6-(4-Fluoro-3-methyl-phenyl)pyrrolo[3,2-b]pyridin-1-yl]-1-(3-methoxyazetidin-1-yl)ethanone;
6-(4-Fluoro-3-methyl-phenyl)-1-(2-methoxyethyl)pyrrolo[3,2-b]pyridine trifluoroacetate salt;
1-Cyclobutyl-2-[6-(3-fluorophenyl)pyrrolo[3,2-b]pyridin-1-yl]ethanone;
2-[6-(4-Fluorophenyl)pyrrolo[3,2-b]pyridin-1-yl]-1-[(3R)-3-fluoropyrrolidin-1-yl]ethanone trifluoroacetate salt;
2-[6-(4-Fluorophenyl)pyrrolo[3,2-b]pyridin-1-yl]-1-[(3S)-3-fluoropyrrolidin-1-yl]ethanone trifluoroacetate salt;
1-[6-(4-Fluoro-3-methyl-phenyl)pyrrolo[3,2-b]pyridin-1-yl]butan-2-one trifluoroacetate salt;
N-Ethyl-2-[6-(4-fluoro-3-methyl-phenyl)pyrrolo[3,2-b]pyridin-1-yl]-N-methyl-acetamide;
N,N-Diethyl-2-[6-(4-fluoro-3-methyl-phenyl)pyrrolo[3,2-b]pyridin-1-yl]acetamide;
1-(Azetidin-1-yl)-2-[3-chloro-6-[3-(trifluoromethyl)phenyl]pyrrolo[3,2-b]pyridin-1-yl]ethanone;
2-[3-Chloro-6-(m-tolyl)pyrrolo[3,2-b]pyridin-1-yl]-1-cyclopropyl-ethanone;
2-(3-Chloro-6-phenyl-pyrrolo[3,2-b]pyridin-1-yl)-1-cyclopropyl-ethanone;
1-(Azetidin-1-yl)-2-[3-chloro-6-(3,4,5-trifluorophenyl)pyrrolo[3,2-b]pyridin-1-yl]ethanone;
1-(Azetidin-1-yl)-2-[3-fluoro-6-(4-fluorophenyl)pyrrolo[3,2-b]pyridin-1-yl]ethanone;
1-(Azetidin-1-yl)-2-[3-chloro-6-(3,5-dimethylphenyl)pyrrolo[3,2-b]pyridin-1-yl]ethanone;
2-[3-Fluoro-6-(4-fluoro-3-methyl-phenyl)pyrrolo[3,2-b]pyridin-1-yl]-1-morpholino-ethanone;
2-[3-Fluoro-6-(4-fluorophenyl)pyrrolo[3,2-b]pyridin-1-yl]-1-morpholino-ethanone;
1-(3-Fluoroazetidin-1-yl)-2-[3-fluoro-6-(3,4,5-trifluorophenyl)pyrrolo[3,2-b]pyridin-1-yl]ethanone;
1-(3-Fluoroazetidin-1-yl)-2-[3-fluoro-6-(4-fluoro-3-methyl-phenyl)pyrrolo[3,2-b]pyridin-1-yl]ethanone;
1-(3-Fluoroazetidin-1-yl)-2-[3-fluoro-6-(4-fluorophenyl)pyrrolo[3,2-b]pyridin-1-yl]ethanone;
1-(3-Fluoroazetidin-1-yl)-2-[3-fluoro-6-(4-methyl-2-thienyl)pyrrolo[3,2-b]pyridin-1-yl]ethanone;
2-[6-[3-(Difluoromethyl)phenyl]-3-fluoro-pyrrolo[3,2-b]pyridin-1-yl]-1-(3-fluoroazetidin-1-yl)ethanone;
2-[6-(3,4-Difluorophenyl)-3-fluoro-pyrrolo[3,2-b]pyridin-1-yl]-1-(3-fluoroazetidin-1-yl)ethanone;
1-(Azetidin-1-yl)-2-[3-chloro-6-(2,3,4-trifluorophenyl)pyrrolo[3,2-b]pyridin-1-yl]ethanone;
2-[3-Fluoro-6-(4-fluoro-3-methyl-phenyl)pyrrolo[3,2-b]pyridin-1-yl]-1-pyrrolidin-1-yl-ethanone;
2-[3-Fluoro-6-(4-fluorophenyl)pyrrolo[3,2-b]pyridin-1-yl]-1-pyrrolidin-1-yl-ethanone;
2-[3-Fluoro-6-(3,4,5-trifluorophenyl)pyrrolo[3,2-b]pyridin-1-yl]-1-pyrrolidin-1-yl-ethanone;
1-Cyclopropyl-2-[3-fluoro-6-(4-fluoro-3-methyl-phenyl)pyrrolo[3,2-b]pyridin-1-yl]ethanone;
1-Cyclopropyl-2-[3-fluoro-6-(4-methyl-2-thienyl)pyrrolo[3,2-b]pyridin-1-yl]ethanone;
2-[6-(5-Chloro-2-thienyl)-3-fluoro-pyrrolo[3,2-b]pyridin-1-yl]-1-cyclopropyl-ethanone;
1-Cyclopropyl-2-[3-fluoro-6-(4-fluorophenyl)pyrrolo[3,2-b]pyridin-1-yl]ethanone;
1-Cyclopropyl-2-[3-fluoro-6-(3,4,5-trifluorophenyl)pyrrolo[3,2-b]pyridin-1-yl]ethanone;
1-Cyclopropyl-2-[6-[3-(difluoromethyl)phenyl]-3-fluoro-pyrrolo[3,2-b]pyridin-1-yl]ethanone;
1-(Azetidin-1-yl)-2-[3-fluoro-6-(4-methyl-2-thienyl)pyrrolo[3,2-b]pyridin-1-yl]ethanone;
1-(Azetidin-1-yl)-2-[6-[3-(difluoromethyl)phenyl]-3-fluoro-pyrrolo[3,2-b]pyridin-1-yl]ethanone;
1-[3-Fluoro-6-(4-fluoro-3-methyl-phenyl)pyrrolo[3,2-b]pyridin-1-yl]-3-methyl-butan-2-one;
1-[6-(3-Ethylphenyl)-3-fluoro-pyrrolo[3,2-b]pyridin-1-yl]-3-methyl-butan-2-one;
1-[6-(3,4-Difluorophenyl)-3-fluoro-pyrrolo[3,2-b]pyridin-1-yl]-3-methyl-butan-2-one;
1-[3-Fluoro-6-(3-fluorophenyl)pyrrolo[3,2-b]pyridin-1-yl]-3-methyl-butan-2-one;
1-[3-Fluoro-6-[3-(trifluoromethyl)phenyl]pyrrolo[3,2-b]pyridin-1-yl]-3-methyl-butan-2-one;
1-[3-Fluoro-6-(m-tolyl)pyrrolo[3,2-b]pyridin-1-yl]-3-methyl-butan-2-one;
6-(4-Fluoro-3-methyl-phenyl)-1-(methylsulfanylmethyl)pyrrolo[3,2-b]pyridine;
(R/S)-6-(4-Fluoro-3-methyl-phenyl)-1-(methylsulfinylmethyl)pyrrolo[3,2-b]pyridine;
6-(4-Fluoro-3-methyl-phenyl)-1-(methylsulfonylmethyl)pyrrolo[3,2-b]pyridine;
1-[3-Fluoro-6-(4-fluorophenyl)pyrrolo[3,2-b]pyridin-1-yl]butan-2-one;
1-[3-Fluoro-6-(3,4,5-trifluorophenyl)pyrrolo[3,2-b]pyridin-1-yl]butan-2-one;
1-[6-(4-fluoro-3-methyl-phenyl)pyrrolo[3,2-b]pyridin-1-yl]butan-2-one;
1-[6-(3,4-Difluorophenyl)-3-fluoro-pyrrolo[3,2-b]pyridin-1-yl]butan-2-one;
1-[6-[3-(Difluoromethyl)phenyl]-3-fluoro-pyrrolo[3,2-b]pyridin-1-yl]butan-2-one;
1-[6-(5-Chloro-2-thienyl)-3-fluoro-pyrrolo[3,2-b]pyridin-1-yl]butan-2-one;
1-[3-Fluoro-6-(4-methyl-2-thienyl)pyrrolo[3,2-b]pyridin-1-yl]butan-2-one;
4-[6-(4-Fluorophenyl)pyrrolo[3,2-b]pyridin-1-yl]butan-2-one;
1-[3-Fluoro-6-(4-fluorophenyl)pyrrolo[3,2-b]pyridin-1-yl]-3-methyl-butan-2-one;
1-[6-[3-(Difluoromethyl)phenyl]-3-fluoro-pyrrolo[3,2-b]pyridin-1-yl]-3-methyl-butan-2-one;
1-[3-Fluoro-6-(4-methyl-2-thienyl)pyrrolo[3,2-b]pyridin-1-yl]-3-methyl-butan-2-one;
1-[3-Fluoro-6-(3,4,5-trifluorophenyl)pyrrolo[3,2-b]pyridin-1-yl]-3-methyl-butan-2-one;
1-[6-(5-Chloro-2-thienyl)-3-fluoro-pyrrolo[3,2-b]pyridin-1-yl]-3-methyl-butan-2-one;

2-[6-(4-Fluoro-3-methyl-phenyl)pyrrolo[3,2-b]pyridin-1-yl]-1-morpholino-ethanone;
1-(3-Fluoroazetidin-1-yl)-2-[6-(4-fluoro-3-methyl-phenyl)pyrrolo[3,2-b]pyridin-1-yl]ethanone;
N-Cyclopropyl-2-[6-(4-fluoro-3-methyl-phenyl)pyrrolo[3,2-b]pyridin-1-yl]acetamide;
1-(Azetidin-1-yl)-2-[6-(4-fluoro-3-methyl-phenyl)pyrrolo[3,2-b]pyridin-1-yl]ethanone;
N-Cyclopropyl-2-[6-(3,5-difluorophenyl)pyrrolo[3,2-b]pyridin-1-yl]acetamide trifluoroacetate salt;
N-Cyclopropyl-2-[6-[3-(trifluoromethyl)phenyl]pyrrolo[3,2-b]pyridin-1-yl]acetamide trifluoroacetate salt;
N-Cyclopropyl-2-[6-[2-fluoro-3-(trifluoromethyl)phenyl]pyrrolo[3,2-b]pyridin-1-yl]acetamide trifluoroacetate salt;
1-(Azetidin-1-yl)-2-[6-(4-fluorophenyl)pyrrolo[3,2-b]pyridin-1-yl]ethanone;
1-(Azetidin-1-yl)-2-(6-phenylpyrrolo[3,2-b]pyridin-1-yl)ethanone;
1-(Azetidin-1-yl)-2-[6-(3,5-difluorophenyl)pyrrolo[3,2-b]pyridin-1-yl]ethanone;
1-(Azetidin-1-yl)-2-[6-(m-tolyl)pyrrolo[3,2-b]pyridin-1-yl]ethanone trifluoroacetate salt;
1-(Azetidin-1-yl)-2-[6-(3,4-dichlorophenyl)pyrrolo[3,2-b]pyridin-1-yl]ethanone trifluoroacetate salt;
1-(Azetidin-1-yl)-2-[6-[2-fluoro-3-(trifluoromethyl)phenyl]pyrrolo[3,2-b]pyridin-1-yl]ethanone trifluoroacetate salt;
1-(Azetidin-1-yl)-2-[6-(4-methyl-2-thienyl)pyrrolo[3,2-b]pyridin-1-yl]ethanone trifluoroacetate salt;
1-(Azetidin-1-yl)-2-[3-chloro-6-(4-fluoro-3-methyl-phenyl)pyrrolo[3,2-b]pyridin-1-yl]ethanone;
1-(3,3-Difluoroazetidin-1-yl)-2-[6-(3,4-difluorophenyl)pyrrolo[3,2-b]pyridin-1-yl]ethanone;
1-(Azetidin-1-yl)-2-[6-[6-(trifluoromethyl)-2-pyridyl]pyrrolo[3,2-b]pyridin-1-yl]ethanone;
1-(Azetidin-1-yl)-2-[6-(3,4,5-trifluorophenyl)pyrrolo[3,2-b]pyridin-1-yl]ethanone;
1-[6-(3,5-Difluorophenyl)pyrrolo[3,2-b]pyridin-1-yl]-3-methyl-butan-2-one;
1-Cyclobutyl-2-[6-(4-fluorophenyl)pyrrolo[3,2-b]pyridin-1-yl]ethanone;
N-Cyclopropyl-2-[6-(3-ethylphenyl)pyrrolo[3,2-b]pyridin-1-yl]acetamide;
2-[6-(3,4-Difluorophenyl)pyrrolo[3,2-b]pyridin-1-yl]-1-pyrrolidin-1-yl-ethanone;
1-(3,3-Difluoroazetidin-1-yl)-2-[6-(4-methyl-2-thienyl)pyrrolo[3,2-b]pyridin-1-yl]ethanone;
2-[6-(4-Methyl-2-thienyl)pyrrolo[3,2-b]pyridin-1-yl]-1-pyrrolidin-1-yl-ethanone;
1-(3-Fluoroazetidin-1-yl)-2-[6-(4-methyl-2-thienyl)pyrrolo[3,2-b]pyridin-1-yl]ethanone;
1-(3-Fluoroazetidin-1-yl)-2-[6-(3,4,5-trifluorophenyl)pyrrolo[3,2-b]pyridin-1-yl]ethanone;
2-[6-(5-Chloro-2-thienyl)pyrrolo[3,2-b]pyridin-1-yl]-1-(3-fluoroazetidin-1-yl)ethanone;
1-(Azetidin-1-yl)-2-[6-(5-chloro-2-thienyl)pyrrolo[3,2-b]pyridin-1-yl]ethanone;
2-[3-Chloro-6-(2,3,4-trifluorophenyl)pyrrolo[3,2-b]pyridin-1-yl]-1-(3-fluoroazetidin-1-yl)ethanone;
N,N-Dimethyl-2-[6-(3,4,5-trifluorophenyl)pyrrolo[3,2-b]pyridin-1-yl]acetamide;
2-[6-(3,5-Difluorophenyl)pyrrolo[3,2-b]pyridin-1-yl]-N,N-dimethyl-acetamide;
2-[6-[3-(Difluoromethyl)phenyl]pyrrolo[3,2-b]pyridin-1-yl]-N, N-dimethyl-acetamide;
2-[6-(5-Chloro-2-thienyl)pyrrolo[3,2-b]pyridin-1-yl]-N, N-dimethyl-acetamide;
2-[6-(3,4-Difluorophenyl)pyrrolo[3,2-b]pyridin-1-yl]-N, N-dimethyl-acetamide;
1-(Azetidin-1-yl)-2-[6-(5-methyl-2-thienyl)pyrrolo[3,2-b]pyridin-1-yl]ethanone;
1-(Azetidin-1-yl)-2-[3-chloro-6-(5-chloro-2-thienyl)pyrrolo[3,2-b]pyridin-1-yl]ethanone;
1-(Azetidin-1-yl)-2-[6-(3,4-difluorophenyl)-3-fluoro-pyrrolo[3,2-b]pyridin-1-yl]ethanone;
1-(Azetidin-1-yl)-2-[3-fluoro-6-(3,4,5-trifluorophenyl)pyrrolo[3,2-b]pyridin-1-yl]ethanone;
2-[3-Chloro-6-(4-fluorophenyl)pyrrolo[3,2-b]pyridin-1-yl]-1-cyclopropyl-ethanone;
1-(Azetidin-1-yl)-2-[6-(3-thienyl)pyrrolo[3,2-b]pyridin-1-yl]ethanone trifluoroacetate salt;
N,N-Dimethyl-2-[6-(5-methyl-2-thienyl)pyrrolo[3,2-b]pyridin-1-yl]acetamide trifluoroacetate salt;
2-[3-Fluoro-6-(2-thienyl)pyrrolo[3,2-b]pyridin-1-yl]-N, N-dimethyl-acetamide;
2-[6-(5-Ethyl-2-thienyl)pyrrolo[3,2-b]pyridin-1-yl]-N,N-dimethyl-acetamide trifluoroacetate salt;
1-(Azetidin-1-yl)-2-[3-fluoro-6-(2-thienyl)pyrrolo[3,2-b]pyridin-1-yl]ethanone trifluoroacetate salt;
2-[3-Fluoro-6-(5-methyl-2-thienyl)pyrrolo[3,2-b]pyridin-1-yl]-N,N-dimethyl-acetamide;
2-[6-(4-Chloro-2-thienyl)pyrrolo[3,2-b]pyridin-1-yl]-N, N-dimethyl-acetamide trifluoroacetate salt;
1-(Azetidin-1-yl)-2-[6-(5-ethyl-2-thienyl)pyrrolo[3,2-b]pyridin-1-yl]ethanone trifluoroacetate salt;
2-[6-(5-Ethyl-2-thienyl)-3-fluoro-pyrrolo[3,2-b]pyridin-1-yl]-N,N-dimethyl-acetamide;
1-(Azetidin-1-yl)-2-[6-(4-chloro-2-thienyl)pyrrolo[3,2-b]pyridin-1-yl]ethanone trifluoroacetate salt;
1-(3-Fluoroazetidin-1-yl)-2-[3-fluoro-6-(2-thienyl)pyrrolo[3,2-b]pyridin-1-yl]ethanone trifluoroacetate salt;
2-[6-(4-Chloro-2-thienyl)-3-fluoro-pyrrolo[3,2-b]pyridin-1-yl]-N,N-dimethyl-acetamide;
1-(Azetidin-1-yl)-2-[6-(4-chloro-2-thienyl)-3-fluoro-pyrrolo[3,2-b]pyridin-1-yl]ethanone trifluoroacetate salt;
2-[6-(5-Ethyl-2-thienyl)-3-fluoro-pyrrolo[3,2-b]pyridin-1-yl]-1-(3-fluoroazetidin-1-yl)ethanone trifluoroacetate salt;
1-(Azetidin-1-yl)-2-[6-(2-thienyl)pyrrolo[3,2-b]pyridin-1-yl]ethanone;
N,N-Dimethyl-2-[6-(2-thienyl)pyrrolo[3,2-b]pyridin-1-yl]acetamide;
1-(Azetidin-1-yl)-2-[6-(5-ethyl-2-thienyl)-3-fluoro-pyrrolo[3,2-b]pyridin-1-yl]ethanone;
1-(3-Fluoroazetidin-1-yl)-2-[3-fluoro-6-(5-methyl-2-thienyl)pyrrolo[3,2-b]pyridin-1-yl]ethanone trifluoroacetate salt;
1-(Azetidin-1-yl)-2-[6-(3-chloro-2-thienyl)pyrrolo[3,2-b]pyridin-1-yl]ethanone;
1-(Azetidin-1-yl)-2-[6-(2-methylthiazol-5-yl)pyrrolo[3,2-b]pyridin-1-yl]ethanone;
1-(Azetidin-1-yl)-2-(6-thiazol-5-ylpyrrolo[3,2-b]pyridin-1-yl)ethanone;
1-(Azetidin-1-yl)-2-[6-(6-fluoro-3-pyridyl)pyrrolo[3,2-b]pyridin-1-yl]ethanone;
1-(Azetidin-1-yl)-2-[3-chloro-6-(4-methyl-2-thienyl)pyrrolo[3,2-b]pyridin-1-yl]ethanone;
1-(Azetidin-1-yl)-2-[3-chloro-6-(5-ethyl-2-thienyl)pyrrolo[3,2-b]pyridin-1-yl]ethanone,
1-(Azetidin-1-yl)-2-[3-chloro-6-(2-thienyl)pyrrolo[3,2-b]pyridin-1-yl]ethanone;

1-(Azetidin-1-yl)-2-[3-chloro-6-(5-methyl-2-thienyl)pyrrolo[3,2-b]pyridin-1-yl]ethanone;
2-[6-(4-Fluorophenyl)pyrrolo[3,2-b]pyridin-1-yl]-N-methyl-N-(2,2,2-trifluoroethyl)acetamide;
2-[3-Chloro-6-(5-methyl-2-thienyl)pyrrolo[3,2-b]pyridin-1-yl]-1-(3-fluoroazetidin-1-yl)ethanone;
2-[3-Chloro-6-(5-chloro-2-thienyl)pyrrolo[3,2-b]pyridin-1-yl]-1-(3-fluoroazetidin-1-yl)ethanone;
2-[3-Chloro-6-(4-chloro-2-thienyl)pyrrolo[3,2-b]pyridin-1-yl]-N,N-dimethyl-acetamide;
2-[6-(4-Fluoro-3-methyl-phenyl)pyrrolo[3,2-b]pyridin-1-yl]-N-methyl-N-(2,2,2-trifluoroethyl)acetamide;
2-[3-Chloro-6-(4-methyl-2-thienyl)pyrrolo[3,2-b]pyridin-1-yl]-1-(3-fluoroazetidin-1-yl)ethanone;
2-[3-Chloro-6-(2-thienyl)pyrrolo[3,2-b]pyridin-1-yl]-1-(3-fluoroazetidin-1-yl)ethanone;
2-[3-Chloro-6-(4-chloro-2-thienyl)pyrrolo[3,2-b]pyridin-1-yl]-1-(3-fluoroazetidin-1-yl)ethanone;
N-Ethyl-2-[6-(4-fluorophenyl)pyrrolo[3,2-b]pyridin-1-yl]-N-methyl-acetamide;
2-[3-Chloro-6-(2-thienyl)pyrrolo[3,2-b]pyridin-1-yl]-N,N-dimethyl-acetamide;
2-[3-Chloro-6-(5-ethyl-2-thienyl)pyrrolo[3,2-b]pyridin-1-yl]-N,N-dimethyl-acetamide;
1-(Azetidin-1-yl)-2-[3-chloro-6-(4-chloro-2-thienyl)pyrrolo[3,2-b]pyridin-1-yl]ethanone;
2-[3-Chloro-6-(5-chloro-2-thienyl)pyrrolo[3,2-b]pyridin-1-yl]-N,N-dimethyl-acetamide;
2-[3-Chloro-6-(5-ethyl-2-thienyl)pyrrolo[3,2-b]pyridin-1-yl]-1-(3-fluoroazetidin-1-yl)ethanone;
2-[6-[2-Fluoro-3-(trifluoromethyl)phenyl]pyrrolo[3,2-b]pyridin-1-yl]-N,N-dimethyl-acetamide;
2-[6-(5-Chloro-4-methyl-2-thienyl)pyrrolo[3,2-b]pyridin-1-yl]-N,N-dimethyl-acetamide;
2-[6-(2,5-Dimethyl-3-thienyl)pyrrolo[3,2-b]pyridin-1-yl]-N,N-dimethyl-acetamide;
N,N-Dimethyl-2-[6-(2,4,5-trimethyl-3-thienyl)pyrrolo[3,2-b]pyridin-1-yl]acetamide;
2-[6-(3-Chlorophenyl)pyrrolo[3,2-b]pyridin-1-yl]-N,N-dimethyl-acetamide;
2-[6-(4-Fluorophenyl)pyrrolo[3,2-b]pyridin-1-yl]-N,N-dimethyl-acetamide;
2-[6-(2-Fluorophenyl)pyrrolo[3,2-b]pyridin-1-yl]-N,N-dimethyl-acetamide;
2-[6-(2-Fluoro-3-methyl-phenyl)pyrrolo[3,2-b]pyridin-1-yl]-N,N-dimethyl-acetamide;
N,N-Dimethyl-2-(6-phenylpyrrolo[3,2-b]pyridin-1-yl)acetamide;
N,N-Dimethyl-2-[6-(m-tolyl)pyrrolo[3,2-b]pyridin-1-yl]acetamide;
N,N-Dimethyl-2-[6-[3-(trifluoromethyl)phenyl]pyrrolo[3,2-b]pyridin-1-yl]acetamide;
2-[6-[4-Fluoro-3-(trifluoromethyl)phenyl]pyrrolo[3,2-b]pyridin-1-yl]-N,N-dimethyl-acetamide;
N,N-Dimethyl-2-[6-(2,3,4-trifluorophenyl)pyrrolo[3,2-b]pyridin-1-yl]acetamide;
N,N-Dimethyl-2-[6-[5-(trifluoromethyl)-2-thienyl]pyrrolo[3,2-b]pyridin-1-yl]acetamide;
2-[6-(5-Chloro-3-thienyl)pyrrolo[3,2-b]pyridin-1-yl]-N,N-dimethyl-acetamide;
2-[6-(2,5-Dichloro-3-thienyl)pyrrolo[3,2-b]pyridin-1-yl]-N,N-dimethyl-acetamide;
N,N-Dimethyl-2-[6-[6-(trifluoromethyl)-2-pyridyl]pyrrolo[3,2-b]pyridin-1-yl]acetamide;
N,N-Dimethyl-2-[6-[2-(trifluoromethyl)-4-pyridyl]pyrrolo[3,2-b]pyridin-1-yl]acetamide;
N,N-Dimethyl-2-[6-[5-(trifluoromethyl)-3-pyridyl]pyrrolo[3,2-b]pyridin-1-yl]acetamide;
2-[6-(2,6-Difluoro-3-methyl-phenyl)pyrrolo[3,2-b]pyridin-1-yl]-N,N-dimethyl-acetamide;
2-[6-(2-Fluoro-5-methyl-phenyl)pyrrolo[3,2-b]pyridin-1-yl]-N,N-dimethyl-acetamide;
1-(Azetidin-1-yl)-2-[6-[3-(difluoromethyl)phenyl]pyrrolo[3,2-b]pyridin-1-yl]ethanone;
2-[6-(2,4-Difluoro-3-methyl-phenyl)pyrrolo[3,2-b]pyridin-1-yl]-N,N-dimethyl-acetamide;
2-[6-(3-Chloro-2-fluoro-phenyl)pyrrolo[3,2-b]pyridin-1-yl]-N,N-dimethyl-acetamide;
2-[6-(3-Ethylphenyl)pyrrolo[3,2-b]pyridin-1-yl]-N,N-dimethyl-acetamide;
2-[6-(3-Fluorophenyl)pyrrolo[3,2-b]pyridin-1-yl]-N,N-dimethyl-acetamide;
1-(Azetidin-1-yl)-2-[6-(2-fluoro-3-methyl-phenyl)pyrrolo[3,2-b]pyridin-1-yl]ethanone;
1-(Azetidin-1-yl)-2-[6-(2,4-difluoro-3-methyl-phenyl)pyrrolo[3,2-b]pyridin-1-yl]ethanone;
1-(Azetidin-1-yl)-2-[6-(3-chloro-2-fluoro-phenyl)pyrrolo[3,2-b]pyridin-1-yl]ethanone;
1-(3-Fluoroazetidin-1-yl)-2-[6-(2-fluoro-3-methyl-phenyl)pyrrolo[3,2-b]pyridin-1-yl]ethanone;
1-(3-Fluoroazetidin-1-yl)-2-[6-(2,3,4-trifluorophenyl)pyrrolo[3,2-b]pyridin-1-yl]ethanone;
1-(Azetidin-1-yl)-2-[6-(3-chloro-4-fluoro-phenyl)pyrrolo[3,2-b]pyridin-1-yl]ethanone;
1-(3-Fluoroazetidin-1-yl)-2-[6-(2-fluorophenyl)pyrrolo[3,2-b]pyridin-1-yl]ethanone;
2-[6-[3-(Difluoromethyl)phenyl]pyrrolo[3,2-b]pyridin-1-yl]-1-(3-fluoroazetidin-1-yl)ethanone;
N-Ethyl-N-methyl-2-[6-(m-tolyl)pyrrolo[3,2-b]pyridin-1-yl]acetamide;
2-[6-(2,4-Difluoro-3-methyl-phenyl)pyrrolo[3,2-b]pyridin-1-yl]-1-(3-fluoroazetidin-1-yl)ethanone;
2-[6-(3,4-Difluorophenyl)pyrrolo[3,2-b]pyridin-1-yl]-N-ethyl-N-methyl-acetamide;
N-Ethyl-N-methyl-2-[6-(3,4,5-trifluorophenyl)pyrrolo[3,2-b]pyridin-1-yl]acetamide;
1-(Azetidin-1-yl)-2-[6-(3-chlorophenyl)pyrrolo[3,2-b]pyridin-1-yl]ethanone;
N-Ethyl-2-[6-[2-fluoro-3-(trifluoromethyl)phenyl]pyrrolo[3,2-b]pyridin-1-yl]-N-methyl-acetamide;
2-[6-(3-Chlorophenyl)pyrrolo[3,2-b]pyridin-1-yl]-1-(3-fluoroazetidin-1-yl)ethanone;
2-[6-(3-Chloro-2-fluoro-phenyl)pyrrolo[3,2-b]pyridin-1-yl]-1-(3-fluoroazetidin-1-yl)ethanone;
2-[6-(3-Chloro-4-fluoro-phenyl)pyrrolo[3,2-b]pyridin-1-yl]-1-(3-fluoroazetidin-1-yl)ethanone;
2-[6-(3-Chloro-4-fluoro-phenyl)pyrrolo[3,2-b]pyridin-1-yl]-N,N-dimethyl-acetamide;
2-[6-(2,4-Difluoro-3-methyl-phenyl)pyrrolo[3,2-b]pyridin-1-yl]-N-ethyl-N-methyl-acetamide;
N-Ethyl-N-methyl-2-[6-[3-(trifluoromethyl)phenyl]pyrrolo[3,2-b]pyridin-1-yl]acetamide;
1-(Azetidin-1-yl)-2-[3-fluoro-6-(2-fluorophenyl)pyrrolo[3,2-b]pyridin-1-yl]ethanone;
1-(Azetidin-1-yl)-2-[3-fluoro-6-(2-fluoro-3-methyl-phenyl)pyrrolo[3,2-b]pyridin-1-yl]ethanone;
1-(Azetidin-1-yl)-2-[3-fluoro-6-(m-tolyl)pyrrolo[3,2-b]pyridin-1-yl]ethanone;
1-(Azetidin-1-yl)-2-[6-(3,5-difluorophenyl)-3-fluoro-pyrrolo[3,2-b]pyridin-1-yl]ethanone;
1-(Azetidin-1-yl)-2-[3-fluoro-6-[3-(trifluoromethyl)phenyl]pyrrolo[3,2-b]pyridin-1-yl]ethanone;

1-(Azetidin-1-yl)-2-[3-fluoro-6-[2-fluoro-3-(trifluoromethyl)phenyl]pyrrolo[3,2-b]pyridin-1-yl]ethanone;
1-(Azetidin-1-yl)-2-[3-fluoro-6-(2,3,4-trifluorophenyl)pyrrolo[3,2-b]pyridin-1-yl]ethanone;
1-(Azetidin-1-yl)-2-[6-(3-chlorophenyl)-3-fluoro-pyrrolo[3,2-b]pyridin-1-yl]ethanone;
1-(Azetidin-1-yl)-2-[6-(3-chloro-2-fluoro-phenyl)-3-fluoro-pyrrolo[3,2-b]pyridin-1-yl]ethanone;
1-(Azetidin-1-yl)-2-[6-(2,4-difluoro-3-methyl-phenyl)-3-fluoro-pyrrolo[3,2-b]pyridin-1-yl]ethanone;
1-(Azetidin-1-yl)-2-[6-(3-chloro-4-fluoro-phenyl)-3-fluoro-pyrrolo[3,2-b]pyridin-1-yl]ethanone;
1-(3-Fluoroazetidin-1-yl)-2-(3-fluoro-6-phenyl-pyrrolo[3,2-b]pyridin-1-yl)ethanone;
1-(3-Fluoroazetidin-1-yl)-2-[3-fluoro-6-(2-fluoro-3-methyl-phenyl)pyrrolo[3,2-b]pyridin-1-yl]ethanone;
1-(3-Fluoroazetidin-1-yl)-2-[3-fluoro-6-[3-(trifluoromethyl)phenyl]pyrrolo[3,2-b]pyridin-1-yl]ethanone;
1-(3-Fluoroazetidin-1-yl)-2-[3-fluoro-6-[2-fluoro-3-(trifluoromethyl)phenyl]pyrrolo[3,2-b]pyridin-1-yl]ethanone;
1-(3-Fluoroazetidin-1-yl)-2-[3-fluoro-6-(2,3,4-trifluorophenyl)pyrrolo[3,2-b]pyridin-1-yl]ethanone;
2-[6-(3,5-Difluorophenyl)-3-fluoro-pyrrolo[3,2-b]pyridin-1-yl]-1-(3-fluoroazetidin-1-yl)ethanone;
2-[6-(2,4-Difluoro-3-methyl-phenyl)-3-fluoro-pyrrolo[3,2-b]pyridin-1-yl]-1-(3-fluoroazetidin-1-yl)ethanone;
2-[6-(3-Chlorophenyl)-3-fluoro-pyrrolo[3,2-b]pyridin-1-yl]-1-(3-fluoroazetidin-1-yl)ethanone;
2-[6-(3-Chloro-2-fluoro-phenyl)-3-fluoro-pyrrolo[3,2-b]pyridin-1-yl]-1-(3-fluoroazetidin-1-yl)ethanone;
2-[6-(3-Ethylphenyl)-3-fluoro-pyrrolo[3,2-b]pyridin-1-yl]-1-(3-fluoroazetidin-1-yl)ethanone;
1-(3-Fluoroazetidin-1-yl)-2-[3-fluoro-6-(3-fluorophenyl)pyrrolo[3,2-b]pyridin-1-yl]ethanone;
2-[3-Fluoro-6-(2-fluorophenyl)pyrrolo[3,2-b]pyridin-1-yl]-N,N-dimethyl-acetamide;
2-[3-Fluoro-6-(2-fluoro-3-methyl-phenyl)pyrrolo[3,2-b]pyridin-1-yl]-N,N-dimethyl-acetamide;
2-(3-Fluoro-6-phenyl-pyrrolo[3,2-b]pyridin-1-yl)-N,N-dimethyl-acetamide;
2-[3-Fluoro-6-(m-tolyl)pyrrolo[3,2-b]pyridin-1-yl]-N,N-dimethyl-acetamide;
1-(Azetidin-1-yl)-2-(3-fluoro-6-phenyl-pyrrolo[3,2-b]pyridin-1-yl)ethanone;
1-(Azetidin-1-yl)-2-[6-(3-ethylphenyl)-3-fluoro-pyrrolo[3,2-b]pyridin-1-yl]ethanone;
2-[3-Fluoro-6-[3-(trifluoromethyl)phenyl]pyrrolo[3,2-b]pyridin-1-yl]-N,N-dimethyl-acetamide;
2-[3-Fluoro-6-[2-fluoro-3-(trifluoromethyl)phenyl]pyrrolo[3,2-b]pyridin-1-yl]-N,N-dimethyl-acetamide;
2-[3-Fluoro-6-(2,3,4-trifluorophenyl)pyrrolo[3,2-b]pyridin-1-yl]-N,N-dimethyl-acetamide;
2-[6-(2,4-Difluoro-3-methyl-phenyl)-3-fluoro-pyrrolo[3,2-b]pyridin-1-yl]-N,N-dimethyl-acetamide;
2-[6-(3-Chlorophenyl)-3-fluoro-pyrrolo[3,2-b]pyridin-1-yl]-N,N-dimethyl-acetamide;
2-[6-(3-Chloro-4-fluoro-phenyl)-3-fluoro-pyrrolo[3,2-b]pyridin-1-yl]-N,N-dimethyl-acetamide;
2-[6-(3-Ethylphenyl)-3-fluoro-pyrrolo[3,2-b]pyridin-1-yl]-N,N-dimethyl-acetamide;
1-(Azetidin-1-yl)-2-[3-fluoro-6-(3-fluorophenyl)pyrrolo[3,2-b]pyridin-1-yl]ethanone;
1-(3-Fluoroazetidin-1-yl)-2-[3-fluoro-6-(2-fluorophenyl)pyrrolo[3,2-b]pyridin-1-yl]ethanone;
1-(3-Fluoroazetidin-1-yl)-2-[3-fluoro-6-[4-fluoro-3-(trifluoromethyl)phenyl]pyrrolo[3,2-b]pyridin-1-yl]ethanone;
2-[6-(3,5-Difluorophenyl)-3-fluoro-pyrrolo[3,2-b]pyridin-1-yl]-N,N-dimethyl-acetamide;
2-[3-Fluoro-6-(3-fluorophenyl)pyrrolo[3,2-b]pyridin-1-yl]-N,N-dimethyl-acetamide;
2-[3-Chloro-6-(4-fluorophenyl)pyrrolo[3,2-b]pyridin-1-yl]-N,N-dimethyl-acetamide;
2-[3-Chloro-6-(2-fluorophenyl)pyrrolo[3,2-b]pyridin-1-yl]-N,N-dimethyl-acetamide;
2-[3-Chloro-6-(2-fluoro-3-methyl-phenyl)pyrrolo[3,2-b]pyridin-1-yl]-N,N-dimethyl-acetamide;
2-(3-Chloro-6-phenyl-pyrrolo[3,2-b]pyridin-1-yl)-N,N-dimethyl-acetamide;
2-[3-Chloro-6-(m-tolyl)pyrrolo[3,2-b]pyridin-1-yl]-N,N-dimethyl-acetamide;
2-[3-Chloro-6-[4-fluoro-3-(trifluoromethyl)phenyl]pyrrolo[3,2-b]pyridin-1-yl]-N,N-dimethyl-acetamide;
2-[3-Chloro-6-[2-fluoro-3-(trifluoromethyl)phenyl]pyrrolo[3,2-b]pyridin-1-yl]-N,N-dimethyl-acetamide;
2-[3-Chloro-6-(2,3,4-trifluorophenyl)pyrrolo[3,2-b]pyridin-1-yl]-N,N-dimethyl-acetamide;
2-[3-Chloro-6-(2,4-difluoro-3-methyl-phenyl)pyrrolo[3,2-b]pyridin-1-yl]-N,N-dimethyl-acetamide;
2-[3-Chloro-6-(3-chloro-4-fluoro-phenyl)pyrrolo[3,2-b]pyridin-1-yl]-N,N-dimethyl-acetamide;
1-(Azetidin-1-yl)-2-[3-chloro-6-(2-fluorophenyl)pyrrolo[3,2-b]pyridin-1-yl]ethanone;
1-(Azetidin-1-yl)-2-[3-chloro-6-(2-fluoro-3-methyl-phenyl)pyrrolo[3,2-b]pyridin-1-yl]ethanone;
1-(Azetidin-1-yl)-2-[3-chloro-6-[4-fluoro-3-(trifluoromethyl)phenyl]pyrrolo[3,2-b]pyridin-1-yl]ethanone;
1-(Azetidin-1-yl)-2-[3-chloro-6-[2-fluoro-3-(trifluoromethyl)phenyl]pyrrolo[3,2-b]pyridin-1-yl]ethanone;
1-(Azetidin-1-yl)-2-[3-chloro-6-(2, 4-difluoro-3-methyl-phenyl)pyrrolo[3,2-b]pyridin-1-yl]ethanone;
1-(Azetidin-1-yl)-2-[3-chloro-6-(3-chlorophenyl)pyrrolo[3,2-b]pyridin-1-yl]ethanone;
1-(Azetidin-1-yl)-2-[3-chloro-6-(3-chloro-4-fluoro-phenyl)pyrrolo[3,2-b]pyridin-1-yl]ethanone;
1-(Azetidin-1-yl)-2-[3-chloro-6-(3-chloro-2-fluoro-phenyl)pyrrolo[3,2-b]pyridin-1-yl]ethanone;
1-(Azetidin-1-yl)-2-[3-chloro-6-[3-(difluoromethyl)phenyl]pyrrolo[3,2-b]pyridin-1-yl]ethanone;
1-(Azetidin-1-yl)-2-[3-chloro-6-(3-fluorophenyl)pyrrolo[3,2-b]pyridin-1-yl]ethanone;
2-[3-Chloro-6-(3-fluorophenyl)pyrrolo[3,2-b]pyridin-1-yl]-N,N-dimethyl-acetamide;
1-(Azetidin-1-yl)-2-[3-chloro-6-(3,5-difluorophenyl)pyrrolo[3,2-b]pyridin-1-yl]ethanone;
1-(Azetidin-1-yl)-2-[3-chloro-6-(3-ethylphenyl)pyrrolo[3,2-b]pyridin-1-yl]ethanone;
2-[3-Chloro-6-(3-chlorophenyl)pyrrolo[3,2-b]pyridin-1-yl]-N, N-dimethyl-acetamide;
2-[3-Chloro-6-(2-fluorophenyl)pyrrolo[3,2-b]pyridin-1-yl]-1-(3-fluoroazetidin-1-yl)ethanone;
2-[3-Chloro-6-(2-fluoro-3-methyl-phenyl)pyrrolo[3,2-b]pyridin-1-yl]-1-(3-fluoroazetidin-1-yl)ethanone;
2-[3-Chloro-6-(3,5-difluorophenyl)pyrrolo[3,2-b]pyridin-1-yl]-1-(3-fluoroazetidin-1-yl)ethanone;
2-[3-Chloro-6-[2-fluoro-3-(trifluoromethyl)phenyl]pyrrolo[3,2-b]pyridin-1-yl]-1-(3-fluoroazetidin-1-yl)ethanone;
2-[3-Chloro-6-(2,4-difluoro-3-methyl-phenyl)pyrrolo[3,2-b]pyridin-1-yl]-1-(3-fluoroazetidin-1-yl)ethanone;

2-[3-Chloro-6-(3-chloro-4-fluoro-phenyl)pyrrolo[3,2-b]
   pyridin-1-yl]-1-(3-fluoroazetidin-1-yl)ethanone;
2-[3-Chloro-6-(3-chloro-2-fluoro-phenyl)pyrrolo[3,2-b]
   pyridin-1-yl]-1-(3-fluoroazetidin-1-yl)ethanone;
2-[3-Chloro-6-(3-ethylphenyl)pyrrolo[3,2-b]pyridin-1-
   yl]-1-(3-fluoroazetidin-1-yl)ethanone;
2-[3-Chloro-6-(3-fluorophenyl)pyrrolo[3,2-b]pyridin-1-
   yl]-1-(3-fluoroazetidin-1-yl)ethanone;
2-[3-Chloro-6-(3-chloro-2-fluoro-phenyl)pyrrolo[3,2-b]
   pyridin-1-yl]-N, N-dimethyl-acetamide;
2-[3-Chloro-6-(3-chlorophenyl)pyrrolo[3,2-b]pyridin-1-
   yl]-1-(3-fluoroazetidin-1-yl)ethanone;
2-[3-Chloro-6-[3-(difluoromethyl)phenyl]pyrrolo[3,2-b]
   pyridin-1-yl]-1-(3-fluoroazetidin-1-yl)ethanone;
1-(Azetidin-1-yl)-2-[3-fluoro-2-methyl-6-(m-tolyl)pyr-
   rolo[3,2-b]pyridin-1-yl]ethanone;
1-(Azetidin-1-yl)-2-[6-(3,4-difluorophenyl)-3-methyl-
   pyrrolo[3,2-b]pyridin-1-yl]ethanone;
2-[6-(3,4-Difluorophenyl)-3-methyl-pyrrolo[3,2-b]pyri-
   din-1-yl]-N, N-dimethyl-acetamide;
1-(3-Fluoroazetidin-1-yl)-2-[3-methyl-6-(m-tolyl)pyrrolo
   [3,2-b]pyridin-1-yl]ethanone;
2-[6-(3,4-Difluorophenyl)-3-methyl-pyrrolo[3,2-b]pyri-
   din-1-yl]-1-(3-fluoroazetidin-1-yl)ethanone;
1-(Azetidin-1-yl)-2-[3-methyl-6-[3-(trifluoromethyl)phe-
   nyl]pyrrolo[3,2-b]pyridin-1-yl]ethanone;
N,N-Dimethyl-2-[3-methyl-6-[3-(trifluoromethyl)phe-
   nyl]pyrrolo[3,2-b]pyridin-1-yl]acetamide;
1-(3-Fluoroazetidin-1-yl)-2-[3-methyl-6-[3-(trifluorom-
   ethyl)phenyl]pyrrolo[3,2-b]pyridin-1-yl]ethanone;
2-[6-(3,5-Difluorophenyl)-3-methyl-pyrrolo[3,2-b]pyri-
   din-1-yl]-N, N-dimethyl-acetamide;
1-(Azetidin-1-yl)-2-[6-(3,5-difluorophenyl)-3-methyl-
   pyrrolo[3,2-b]pyridin-1-yl]ethanone;
2-[6-(3,5-Difluorophenyl)-3-methyl-pyrrolo[3,2-b]pyri-
   din-1-yl]-N-ethyl-N-methyl-acetamide;
2-[6-(4-Fluorophenyl)-3-methyl-pyrrolo[3,2-b]pyridin-1-
   yl]-N, N-dimethyl-acetamide;
N-Ethyl-2-[6-(4-fluorophenyl)-3-methyl-pyrrolo[3,2-b]
   pyridin-1-yl]-N-methyl-acetamide;
N-Ethyl-2-[6-(2-fluoro-3-methyl-phenyl)-3-methyl-pyr-
   rolo[3,2-b]pyridin-1-yl]-N-methyl-acetamide;
1-(Azetidin-1-yl)-2-[6-(2-fluoro-3-methyl-phenyl)-3-
   methyl-pyrrolo[3,2-b]pyridin-1-yl]ethanone;
2-[6-(2-Fluoro-3-methyl-phenyl)-3-methyl-pyrrolo[3,2-
   b]pyridin-1-yl]-N,N-dimethyl-acetamide;
1-(3-Fluoroazetidin-1-yl)-2-[6-(2-fluoro-3-methyl-phe-
   nyl)-3-methyl-pyrrolo[3,2-b]pyridin-1-yl]ethanone;
1-(3,3-Difluoroazetidin-1-yl)-2-[6-(2-fluoro-3-methyl-
   phenyl)-3-methyl-pyrrolo[3,2-b]pyridin-1-yl]etha-
   none;
2-[6-(2-Fluoro-3-methyl-phenyl)-3-methyl-pyrrolo[3,2-
   b]pyridin-1-yl]-1-pyrrolidin-1-yl-ethanone;
2-[6-(4-Fluoro-3-methyl-phenyl)-3-methyl-pyrrolo[3,2-
   b]pyridin-1-yl]-N,N-dimethyl-acetamide;
2-[3-Methyl-6-[3-(trifluoromethyl)phenyl]pyrrolo[3,2-b]
   pyridin-1-yl]-1-pyrrolidin-1-yl-ethanone;
N-Ethyl-N-methyl-2-[3-methyl-6-[3-(trifluoromethyl)
   phenyl]pyrrolo[3,2-b]pyridin-1-yl]acetamide;
1-(3,3-Difluoroazetidin-1-yl)-2-[3-methyl-6-[3-(trifluo-
   romethyl)phenyl]pyrrolo[3,2-b]pyridin-1-yl]ethanone;
1-(Azetidin-1-yl)-2-[3-methyl-6-(3,4,5-trifluorophenyl)
   pyrrolo[3,2-b]pyridin-1-yl]ethanone;
N,N-Dimethyl-2-[3-methyl-6-(3,4,5-trifluorophenyl)pyr-
   rolo[3,2-b]pyridin-1-yl]acetamide;
N,N-Dimethyl-2-[3-methyl-6-(m-tolyl)pyrrolo[3,2-b]
   pyridin-1-yl]acetamide;
N,N-Dimethyl-2-[3-methyl-6-(4-methyl-2-thienyl)pyr-
   rolo[3,2-b]pyridin-1-yl]acetamide;
1-(Azetidin-1-yl)-2-[3-methyl-6-(4-methyl-2-thienyl)
   pyrrolo[3,2-b]pyridin-1-yl]ethanone;
1-(3-Fluoroazetidin-1-yl)-2-[3-methyl-6-(4-methyl-2-
   thienyl)pyrrolo[3,2-b]pyridin-1-yl]ethanone;
N,N-Dimethyl-2-(3-methyl-6-phenyl-pyrrolo[3,2-b]pyri-
   din-1-yl)acetamide;
N-Ethyl-N-methyl-2-(3-methyl-6-phenyl-pyrrolo[3,2-b]
   pyridin-1-yl)acetamide;
1-(3-Fluoroazetidin-1-yl)-2-(3-methyl-6-phenyl-pyrrolo
   [3,2-b]pyridin-1-yl)ethanone;
1-(3,3-Difluoroazetidin-1-yl)-2-(3-methyl-6-phenyl-pyr-
   rolo[3,2-b]pyridin-1-yl)ethanone;
1-(3-Fluoroazetidin-1-yl)-2-[6-(4-fluoro-3-methyl-phe-
   nyl)-3-methyl-pyrrolo[3,2-b]pyridin-1-yl]ethanone;
1-(Azetidin-1-yl)-2-[3-methyl-6-(m-tolyl)pyrrolo[3,2-b]
   pyridin-1-yl]ethanone;
1-(Azetidin-1-yl)-2-[3-methyl-6-(2,3,4-trifluorophenyl)
   pyrrolo[3,2-b]pyridin-1-yl]ethanone;
N, N-Dimethyl-2-[3-methyl-6-(2,3,4-trifluorophenyl)pyr-
   rolo[3,2-b]pyridin-1-yl]acetamide;
N-Ethyl-N-methyl-2-[3-methyl-6-(2,3,4-trifluorophenyl)
   pyrrolo[3,2-b]pyridin-1-yl]acetamide;
1-(Azetidin-1-yl)-2-[6-[2-fluoro-3-(trifluoromethyl)phe-
   nyl]-3-methyl-pyrrolo[3,2-b]pyridin-1-yl]ethanone;
2-[6-[2-Fluoro-3-(trifluoromethyl)phenyl]-3-methyl-pyr-
   rolo[3,2-b]pyridin-1-yl]-N,N-dimethyl-acetamide;
N-Ethyl-2-[6-[2-fluoro-3-(trifluoromethyl)phenyl]-3-
   methyl-pyrrolo[3,2-b]pyridin-1-yl]-N-methyl-acet-
   amide;
1-(3-Fluoroazetidin-1-yl)-2-[3-methyl-6-(2,3,4-trifluoro-
   phenyl)pyrrolo[3,2-b]pyridin-1-yl]ethanone;
1-(3-Fluoroazetidin-1-yl)-2-[6-[2-fluoro-3-(trifluorom-
   ethyl)phenyl]-3-methyl-pyrrolo[3,2-b]pyridin-1-yl]
   ethanone;
2-[6-[2-Fluoro-3-(trifluoromethyl)phenyl]-3-methyl-pyr-
   rolo[3,2-b]pyridin-1-yl]-1-pyrrolidin-1-yl-ethanone;
2-[3-Methyl-6-(2,3,4-trifluorophenyl)pyrrolo[3,2-b]pyri-
   din-1-yl]-1-pyrrolidin-1-yl-ethanone;
1-(Azetidin-1-yl)-2-[6-(2-fluorophenyl)-3-methyl-pyr-
   rolo[3,2-b]pyridin-1-yl]ethanone;
2-[6-(2-Fluorophenyl)-3-methyl-pyrrolo[3,2-b]pyridin-1-
   yl]-N, N-dimethyl-acetamide;
N-Ethyl-2-[6-(2-fluorophenyl)-3-methyl-pyrrolo[3,2-b]
   pyridin-1-yl]-N-methyl-acetamide;
1-(3,3-Difluoroazetidin-1-yl)-2-[6-[2-fluoro-3-(trifluo-
   romethyl)phenyl]-3-methyl-pyrrolo[3,2-b]pyridin-1-
   yl]ethanone;
1-(3,3-Difluoroazetidin-1-yl)-2-[3-methyl-6-(2,3,4-trif-
   luorophenyl)pyrrolo[3,2-b]pyridin-1-yl]ethanone;
1-(3,3-Difluoroazetidin-1-yl)-2-[6-(2-fluorophenyl)-3-
   methyl-pyrrolo[3,2-b]pyridin-1-yl]ethanone;
1-(3-Fluoroazetidin-1-yl)-2-[3-methyl-6-(3,4,5-trifluoro-
   phenyl)pyrrolo[3,2-b]pyridin-1-yl]ethanone;
2-[3-Chloro-6-(2,5-dimethyl-3-thienyl)pyrrolo[3,2-b]
   pyridin-1-yl]-N, N-dimethyl-acetamide;
2-[3-Chloro-6-[3-(trifluoromethyl)phenyl]pyrrolo[3,2-b]
   pyridin-1-yl]-N,N-dimethyl-acetamide;
2-[3-Chloro-6-[6-(trifluoromethyl)-2-pyridyl]pyrrolo[3,
   2-b]pyridin-1-yl]-N,N-dimethyl-acetamide;
2-[3-Chloro-6-(5-chloro-4-methyl-2-thienyl)pyrrolo[3,2-
   b]pyridin-1-yl]-N, N-dimethyl-acetamide;
2-[3-Chloro-6-[5-(trifluoromethyl)-2-thienyl]pyrrolo[3,
   2-b]pyridin-1-yl]-N, N-dimethyl-acetamide;
2-[6-(Benzothiophen-2-yl)pyrrolo[3,2-b]pyridin-1-yl]-N,
   N-dimethyl-acetamide;
2-[3-Fluoro-6-[4-fluoro-3-(trifluoromethyl)phenyl]pyr-
   rolo[3,2-b]pyridin-1-yl]-N,N-dimethyl-acetamide;

2-[6-(3-Chloro-2-fluoro-phenyl)-3-fluoro-pyrrolo[3,2-b]pyridin-1-yl]-N, N-dimethyl-acetamide;
1-(3-Fluoroazetidin-1-yl)-2-[3-fluoro-6-(m-tolyl)pyrrolo[3,2-b]pyridin-1-yl]ethanone;
2-[6-(3-Chloro-4-fluoro-phenyl)-3-fluoro-pyrrolo[3,2-b]pyridin-1-yl]-1-(3-fluoroazetidin-1-yl)ethanone;
1-(Azetidin-1-yl)-2-(3-[3H]-6-(4-fluoro-3-methylphenyl)-1H-pyrrolo[3,2-b]pyridin-1-yl)ethanone;
2-[2-Deuterio-6-(4-fluoro-3-methyl-phenyl)pyrrolo[3,2-b]pyridin-1-yl]-N, N-dimethyl-acetamide;
2-[6-(3,5-Difluorophenyl)-3-(trifluoromethyl)pyrrolo[3,2-b]pyridin-1-yl]-N, N-dimethyl-acetamide;
3-Chloro-1-(3-pyridylmethyl)-6-[3-(trifluoromethyl)phenyl]pyrrolo[3,2-b]pyridine;
1-(Pyridazin-3-ylmethyl)-6-[3-(trifluoromethyl)phenyl]pyrrolo[3,2-b]pyridine;
3-Chloro-6-(4-fluoro-3-methyl-phenyl)-1-(pyridazin-3-ylmethyl)pyrrolo[3,2-b]pyridine;
3-Chloro-1-(pyridazin-3-ylmethyl)-6-[3-(trifluoromethyl)phenyl]pyrrolo[3,2-b]pyridine;
2-[6-(4-Fluoro-3-methyl-phenyl)-3-methyl-pyrrolo[3,2-b]pyridin-1-yl]-1-pyrrolidin-1-yl-ethanone;
N-Ethyl-2-[6-(4-fluoro-3-methyl-phenyl)-3-methyl-pyrrolo[3,2-b]pyridin-1-yl]-N-methyl-acetamide;
1-(3,3-Difluoroazetidin-1-yl)-2-[6-(4-fluoro-3-methyl-phenyl)-3-methyl-pyrrolo[3,2-b]pyridin-1-yl]ethanone;
2-[6-(3,4-Difluorophenyl)-3-methyl-pyrrolo[3,2-b]pyridin-1-yl]-1-pyrrolidin-1-yl-ethanone;
2-[6-(3,4-Difluorophenyl)-3-methyl-pyrrolo[3,2-b]pyridin-1-yl]-N-ethyl-N-methyl-acetamide;
1-(3,3-Difluoroazetidin-1-yl)-2-[6-(3,4-difluorophenyl)-3-methyl-pyrrolo[3,2-b]pyridin-1-yl]ethanone;
2-[6-(2,4-Difluoro-3-methyl-phenyl)-3-methyl-pyrrolo[3,2-b]pyridin-1-yl]-N,N-dimethyl-acetamide;
2-[6-(3,5-Difluorophenyl)-3-methyl-pyrrolo[3,2-b]pyridin-1-yl]-1-pyrrolidin-1-yl-ethanone;
2-[6-(2,4-Difluoro-3-methyl-phenyl)-3-methyl-pyrrolo[3,2-b]pyridin-1-yl]-1-pyrrolidin-1-yl-ethanone;
2-[6-(2,4-Difluoro-3-methyl-phenyl)-3-methyl-pyrrolo[3,2-b]pyridin-1-yl]-N-ethyl-N-methyl-acetamide;
1-(3,3-Difluoroazetidin-1-yl)-2-[6-(2,4-difluoro-3-methyl-phenyl)-3-methyl-pyrrolo[3,2-b]pyridin-1-yl]ethanone;
1-(Azetidin-1-yl)-2-[6-(2,4-difluoro-3-methyl-phenyl)-3-methyl-pyrrolo[3,2-b]pyridin-1-yl]ethanone;
2-[6-(5-Chloro-2-thienyl)-3-methyl-pyrrolo[3,2-b]pyridin-1-yl]-N,N-dimethyl-acetamide;
2-[6-(2,4-Difluoro-3-methyl-phenyl)-3-methyl-pyrrolo[3,2-b]pyridin-1-yl]-1-(3-fluoroazetidin-1-yl)ethanone;
N-Ethyl-N-methyl-2-[3-methyl-6-(5-methyl-2-thienyl)pyrrolo[3,2-b]pyridin-1-yl]acetamide;
2-[3-Methyl-6-(5-methyl-2-thienyl)pyrrolo[3,2-b]pyridin-1-yl]-1-pyrrolidin-1-yl-ethanone;
1-(3,3-Difluoroazetidin-1-yl)-2-[3-methyl-6-(5-methyl-2-thienyl)pyrrolo[3,2-b]pyridin-1-yl]ethanone;
1-(Azetidin-1-yl)-2-[3-methyl-6-(5-methyl-2-thienyl)pyrrolo[3,2-b]pyridin-1-yl]ethanone;
1-(3-Fluoroazetidin-1-yl)-2-[3-methyl-6-(5-methyl-2-thienyl)pyrrolo[3,2-b]pyridin-1-yl]ethanone;
2-[6-(3,5-Difluorophenyl)-3-methyl-pyrrolo[3,2-b]pyridin-1-yl]-1-(3-fluoroazetidin-1-yl)ethanone;
2-[6-(5-Chloro-2-thienyl)-3-methyl-pyrrolo[3,2-b]pyridin-1-yl]-1-(3-fluoroazetidin-1-yl)ethanone;
N,N-Dimethyl-2-[3-methyl-6-(5-methyl-2-thienyl)pyrrolo[3,2-b]pyridin-1-yl]acetamide;
1-(3-Fluoroazetidin-1-yl)-2-[6-(2-fluorophenyl)-3-methyl-pyrrolo[3,2-b]pyridin-1-yl]ethanone; and
2-[6-[5-(Difluoromethyl)-2-thienyl]pyrrolo[3,2-b]pyridin-1-yl]-N, N-dimethyl-acetamide; and pharmaceutically acceptable salts, N-oxides or solvates thereof.

25. A pharmaceutical composition comprising:
(A) an effective amount of at least one compound selected from compounds of Formula (I) wherein:

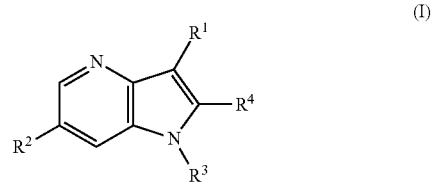

wherein
R$^1$ is selected from the group consisting of: H, $^3$H, halo, C$_{1-3}$alkyl, and C$_{1-3}$haloalkyl;
R$^2$ is selected from the group consisting of: phenyl optionally substituted with one, two, or three members independently selected from: halo, C$_{1-5}$alkyl, and C$_{1-5}$haloalkyl; pyridinyl optionally substituted with halo, C$_{1-5}$alkyl, C$_{1-5}$haloalkyl; and —CN; thiazolyl optionally substituted with C$_{1-5}$alkyl; benzothiophenyl; and thienyl optionally substituted with one, two or three members independently selected from: halo, C$_{1-5}$alkyl, and C$_{1-5}$haloalkyl;
R$^3$ is selected from the group consisting of:
(a)

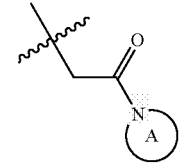

wherein ring A is a 4-6 membered heterocycle optionally containing an additional oxygen heteroatom selected from the group consisting of: azetidinyl optionally substituted with one or two members independently selected from the group consisting of: halo, C$_{1-5}$alkyl, C$_{1-5}$haloalkyl, CH$_2$OH, C$_{1-5}$alkoxy, OH, and CN; pyrrolidinyl optionally substituted one or two members independently selected from the group consisting of: halo, C$_{1-5}$alkyl, C$_{1-5}$alkoxy, and OH; morpholino optionally substituted one or two C$_{1-5}$alkyl members; piperidinyl optionally substituted with one or two members independently selected from the group consisting of: halo, C$_{1-5}$alkyl, C$_{1-5}$haloalkyl, C$_{1-5}$alkoxy, and OH; 3-azabicyclo[3.1.0]hexan-3-yl; 5-azaspiro[2.3]hexan-5-yl; and pyrrolidin-3-one; or
(b)

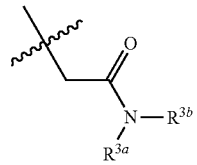

wherein R$^{3a}$ is H, or C$_{1-5}$alkyl;
and R$^{3b}$ is selected from the group consisting of: C$_{1-5}$alkyl optionally substituted with OH, halo, or OCH$_3$; C$_{1-5}$haloalkyl; benzyl; CH$_2$cyclopropyl; cyclopropyl optionally substituted with C$_{1-5}$alkyl; and cyclobutyl; or (c)

wherein $R^{3c}$ is selected from the group consisting of: cyclopropyl; cyclobutyl; pyrimidinyl optionally substituted with halo; pyridinyl; pyridazinyl; furanyl optionally substituted with $C_{1-5}$haloalkyl; oxazolyl; isoxazolyl optionally substituted with $C_{1-5}$alkyl; oxadiazolyl optionally substituted with $C_{1-5}$alkyl; pyrazolyl optionally substituted with $C_{1-5}$alkyl; triazolyl optionally substituted with $C_{1-5}$alkyl; tetrahydrofuranyl; tetrahydropyranyl; oxetanyl; and oxiranyl; or (d)

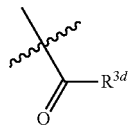

wherein $R^{3d}$ is $CH_2$-cyclopropyl or cyclobutyl; or (e)

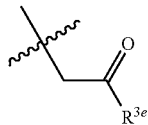

wherein $R^{3e}$ is selected from the group consisting of: OH, $C_{1-5}$alkyl, cyclopropyl, cyclobutyl, and phenyl optionally substituted with one halo substituent; or (f) $C_{1-5}$alkyl optionally substituted with OH or $C_{1-5}$alkoxy; $CH_2S(CH_3)$; $CH_2(S=O)CH_3$; $CH_2(SO_2)CH_3$; and $CH_2CH_2(C=O)CH_3$; or (g)

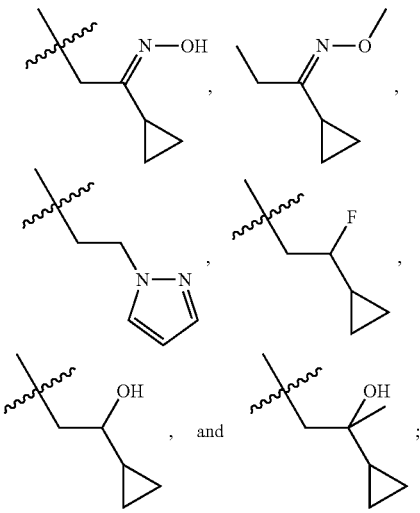

and $R^4$ is H, $^2$H or $C_{1-3}$alkyl;

and pharmaceutically acceptable salts, N-oxides or solvates of compounds of Formula (I); and (B) at least one pharmaceutically acceptable excipient.

26. A pharmaceutical composition comprising an effective amount of at least one compound of claim 24 and at least one pharmaceutically acceptable excipient.

* * * * *